US009393297B2

(12) United States Patent
Marshall et al.

(10) Patent No.: US 9,393,297 B2

(45) Date of Patent: Jul. 19, 2016

(54) INFLUENZA HEMAGGLUTININ PROTEINS AND METHODS OF USE THEREOF

(71) Applicants: Christopher Patrick Marshall, New York, NY (US); Peter Joseph Alff, New York, NY (US); Claudio Bertuccioli, New York, NY (US); Mark Andrew Yondola, Medford, NY (US)

(72) Inventors: Christopher Patrick Marshall, New York, NY (US); Peter Joseph Alff, New York, NY (US); Claudio Bertuccioli, New York, NY (US); Mark Andrew Yondola, Medford, NY (US)

(73) Assignee: AVATAR MEDICAL, LLC, New York, NY (US)

( * ) Notice: Subject to any disclaimer, the term of this patent is extended or adjusted under 35 U.S.C. 154(b) by 0 days.

(21) Appl. No.: 14/450,236

(22) Filed: Aug. 2, 2014

(65) Prior Publication Data

US 2015/0056233 A1 Feb. 26, 2015

Related U.S. Application Data

(60) Provisional application No. 61/861,989, filed on Aug. 3, 2013.

(51) Int. Cl.

| | |
|---|---|
| ***A61K 39/145*** | (2006.01) |
| ***C12N 7/00*** | (2006.01) |
| ***A61K 45/06*** | (2006.01) |
| ***C07K 14/005*** | (2006.01) |

(52) U.S. Cl.

CPC ............... *A61K 39/145* (2013.01); *A61K 45/06* (2013.01); *C07K 14/005* (2013.01); *C12N 7/00* (2013.01); *C07K 2319/50* (2013.01); *C07K 2319/735* (2013.01); *C07K 2319/90* (2013.01); *C12N 2760/16034* (2013.01); *C12N 2760/16071* (2013.01); *C12N 2760/16122* (2013.01); *C12N 2760/16134* (2013.01); *C12N 2760/16151* (2013.01)

(58) Field of Classification Search

None

See application file for complete search history.

(56) References Cited

U.S. PATENT DOCUMENTS

| | | | |
|---|---|---|---|
| 5,589,174 | A | 12/1996 | Okuno |
| 5,631,350 | A | 5/1997 | Okuno |
| 6,337,070 | B1 | 1/2002 | Okuno |
| 6,720,409 | B2 | 4/2004 | Okuno |
| 7,037,894 | B2 | 5/2006 | Marshall |
| 2002/0054882 | A1 | 5/2002 | Okuno |
| 2005/0054572 | A1 | 3/2005 | Marshall |
| 2010/0297174 | A1 | 11/2010 | Garcia-Sastre |
| 2011/0123556 | A1 | 5/2011 | Phogat |
| 2013/0236905 | A1 | 9/2013 | Marshall |
| 2013/0317205 | A1 | 11/2013 | Marshall |
| 2015/0030622 | A1 | 1/2015 | Marshall |

FOREIGN PATENT DOCUMENTS

| | | | |
|---|---|---|---|
| WO | 0129247 | A1 | 4/2001 |
| WO | 2009079259 | A2 | 6/2009 |
| WO | 2013079473 | A1 | 6/2013 |

OTHER PUBLICATIONS

Genbank AFF26485 (Mar. 23, 2012).*
Genbank CY109931 (Mar. 23, 2012).*
Mallajosyula, et al., Influenza hemagglutinin stem-fragment immunogen elicits broadly neutralizing antibodies and confers heterologous protection, Proceedings of the National Academy of Sciences (PNAS), Jun. 9, 2014, E2514-E2523, published on-line.
Sagawa, et al, The immunological activity of a deletion mutant of influenza virus haemagglutinin lacking the globular region, Journal of General Virology, 1996, p. 1483-1487, vol. 77, Great Britain.
Steel, et al, Influenza Virus Vaccine Based on the Conserved Hemagglutinin Stalk Domain, mBIO, May 18, 2010, p. E00018-10, v. 1-1, published on-line.
Okuno, Hemagglutinin [Influenza A virus (A/Suita/1/1989 (H1 N1 )),Feb. 16, 2008, Database EMBL [Online] E.B.I. Hinxton U.K.; 1, Database accession No. BAA02768.
Okuno, A Common Neutralizing Epitope Conserved between the Hemagglutinins of Influenza A Virus Hi and H2 Strains, Journal of Virology, May 1993, p. 2552-2558, v. 67, American Society for Microbiology, US.
International Search Report and Written Opinion received in PCT/US2014/049509 mailed on Feb. 9, 2015.
Yondola, A Universal Flu Vaccine Based on Conformationally Locked Soluble Headless HA, NIH/SBIR Grant Award R43AI118087; Feb. 15, 2015; Published on-line; https://sbirsource.com/sbir/awards/153234-a-universal-flu-vaccine-based-on-conformationally-locked-soluble-headless-ha.

* cited by examiner

*Primary Examiner* — Shanon A Foley
*Assistant Examiner* — Myron Hill
(74) *Attorney, Agent, or Firm* — Grimes & Yvon LLP

(57) ABSTRACT

In some embodiments the present invention provides influenza hemagglutinin ("HA") polypeptides, proteins, and protein complexes that comprise a stalk domain that is engineered to facilitate maintenance of its native trimeric conformation, even if the head domain of the HA protein is removed or disrupted. In some embodiments, the present invention provides compositions comprising such polypeptides, proteins, and protein complexes, and methods of use of such proteins and compositions, for example as vaccine immunogens.

22 Claims, 107 Drawing Sheets

Figure 9

(SEQ ID NO.1)

MKANLLVLLSALAAADADTICIGYHANNSTDTVDTVLEKNVTVTHSVNLLEDSHNGKLCRLKGIAPLQLG

KCNIAGWLLGNPECDPLLPVRSWSYIVETPNSENGICYPGDFIDYEELREQLSSVSSFERFEIFPKESSW

PNHNTNGVTAACSHEGKSSFYRNLLWLTEKEGSYPKLKNSYVNKKGKEVLVLWGIHHPPNSKEQQNIYQN

ENAYVSVVTSNYNRRFTPEIAERPKVRDQAGRMNYYWTLLKPGDTIIFEANGNLIAPMYAFALSRGFGSG

IITSNASMHECNTKCQTPLGAINSSLPYQNIHPVTIGECPKYVRSAKLRMVTGLRNTPSIQSRGLFGAIA

GFIEGGWTGMIDGWYGYHHQNEQGSGYAADQKSTQNAINGITNKVNTVIEKMNIQFTAVGKEFNKLEKRM

ENLNKKVDDGFLDIWTYNAELLVLLENERTLDFHDSNVKNLYEKVKSQLKNNAKEIGNGCFEFYHKCDNE

CMESVRNGTYDYPKYSEESKLNREKVDGVKLESMGIYQILAIYSTVASSLVLLVSLGAISFWMCSNGSLQ

Figure 1:
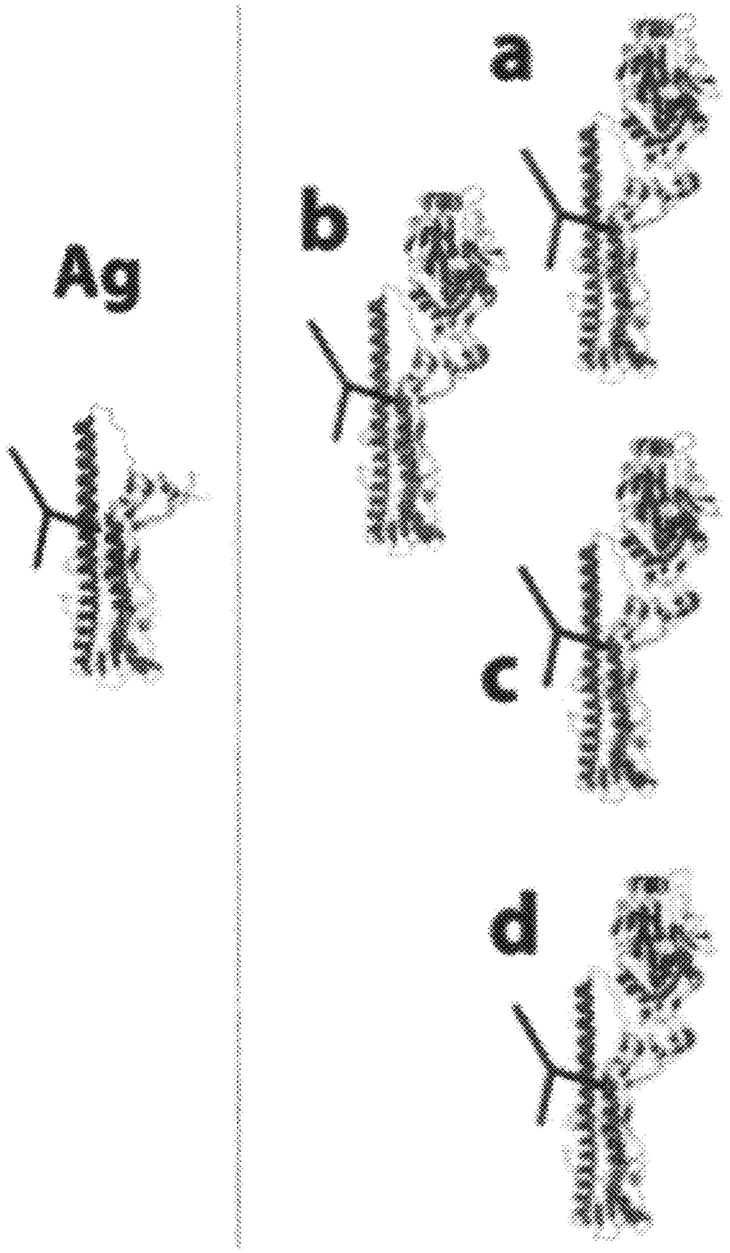

CRICI gi|21693169|gb|AAM75158.1|AF389118_1 hemagglutinin HA [Influenza A virus (A/Puerto Rico/8/34/Mount Sinai(H1N1))]

Figure 10

(SEQ ID NO.2)

ATGAAGGCAAACCTACTGGTCCTGTTAAGTGCACTTGCAGCTGCAGATGCAGACACAATATGTATAGGCT
ACCATGCGAACAATTCAACCGACACTGTTGACACAGTACTCGAGAAGAATGTGACAGTGACACACTCTGT
TAACCTGCTCGAAGACAGCCACAACGGAAAACTATGTAGATTAAAAGGAATAGCCCCACTACAATTGGGG
AAATGTAACATCGCCGGATGGCTCTTGGGAAACCCAGAATGCGACCCACTGCTTCCAGTGAGATCATGGT
CCTACATTGTAGAAACACCAAACTCTGAGAATGGAATATGTTATCCAGGAGATTTCATCGACTATGAGGA
GCTGAGGGAGCAATTGAGCTCAGTGTCATCATTCGAAAGATTCGAAATATTTCCCAAAGAAAGCTCATGG
CCCAACCACAACACAAACGGAGTAACGGCAGCATGCTCCCATGAGGGGAAAAGCAGTTTTTACAGAAATT
TGCTATGGCTGACGGAGAAGGAGGGCTCATACCCAAAGCTGAAAAATTCTTATGTGAACAAAAAAGGGAA
AGAAGTCCTTGTACTGTGGGGTATTCATCACCCGCCTAACAGTAAGGAACAACAGAATATCTATCAGAAT
GAAAATGCTTATGTCTCTGTAGTGACTTCAAATTATAACAGGAGATTTACCCCGGAAATAGCAGAAAGAC
CCAAAGTAAGAGATCAAGCTGGGAGGATGAACTATTACTGGACCTTGCTAAAACCCGGAGACACAATAAT
ATTTGAGGCAAATGGAAATCTAATAGCACCAATGTATGCTTTCGCACTGAGTAGAGGCTTTGGGTCCGGC
ATCATCACCTCAAACGCATCAATGCATGAGTGTAACACGAAGTGTCAAACACCGCTCGGAGCTATAAACA
GCAGTCTCCCTTACCAGAATATACACCCAGTCACAATAGGAGAGTGCCCAAAATACGTCAGGAGTGCCAA
ATTGAGGATGGTTACAGGACTAAGGAACACTCCGTCCATTCAATCCAGAGGTCTATTTGGAGCCATTGCC
GGTTTTATTGAAGGGGGATGGACTGGAATGATAGATGGATGGTATGGTTATCATCATCAGAATGAACAGG
GATCAGGCTATGCAGCGGATCAAAAAAGCACACAAAATGCCATTAACGGGATTACAAACAAGGTGAACAC
TGTTATCGAGAAAATGAACATTCAATTCACAGCTGTGGGTAAAGAATTCAACAAATTAGAAAAAAGGATG
GAAAATTTAAATAAAAAAGTTGATGATGGATTTCTGGACATTTGGACATATAATGCAGAATTGTTAGTTC
TACTGGAAAATGAAAGGACTCTGGATTTCCATGACTCAAATGTGAAGAATCTGTATGAGAAAGTAAAAAG
CCAATTAAAGAATAATGCCAAAGAAATCGGAAATGGATGTTTTGAGTTCTACCACAAGTGTGACAATGAA
TGCATGGAAAGTGTAAGAAATGGGACTTATGATTATCCCAAATATTCAGAAGAGTCAAAGTTGAACAGGG
AAAAGGTAGATGGAGTGAAATTGGAATCAATGGGGATCTATCAGATTCTGGCGATCTACTCAACTGTCGC
CAGTTCACTGGTGCTTTTGGTCTCCCTGGGGGCAATCAGTTTCTGGATGTGTTCTAATGGATCTTTGCAG
TGCAGAATATGCATCTGA

Influenza A virus (A/Puerto Rico/8/34/Mount Sinai(H1N1))

Figure 11

(SEQ ID NO.3)

>PR8HA-63G278S-403Y433Y.pro

MKANLLVLLSALAAADADTICIGYHANNSTDTVDTVLEKNVTVTHSVNLLEDSHNGKLCRLKGENLYFQGKCNIAGWLLG

NPECDPLLPVRSWSYIVETPNSENGICYPGDFIDYEELREQLSSVSSFERFEIFPKESSWPNHNTNGVTAACSHEGKSSF

YRNLLWLTEKEGSYPKLKNSYVNKKGKEVLVLWGIHHPPNSKEQQNIYQNENAYVSVVTSNYNRRFTPEIAERPKVRDQA

GRMNYYWTLLKPGDTIIFEANGNLIAPMYAFALSRGFGENLYFQSNASMHECNTKCQTPLGAINSSLPYQNIHPVTIGEC

PKYVRSAKLRMVTGLRNTPSIQSRGLFGAIAGFIEGGWTGMIDGWYGYHHQNEQGSGYAADQKSTQNAINGITNKVNTVI

EKMYIQFTAVGKEFNKLEKRMENLNKKVDDGFLYIWTYNAELLVLLENERTLDFHDSNVKNLYEKVKSQLKNNAKEIGNG

CFEFYHKCDNECMESVRNGTYDYPKYSEESKLNREKVDGVKLESMGIYQILAIYSTVASSLVLLVSLGAISFWMCSNGSL

QCRICI

Figure 12

(SEQ ID NO.4)

>PR8HA-63G278S-411Y422Y.pro

MKANLLVLLSALAAADADTICIGYHANNSTDTVDTVLEKNVTVTHSVNLLEDSHNGKLCRLKGENLYFQGKCNIAGWLLG

NPECDPLLPVRSWSYIVETPNSENGICYPGDFIDYEELREQLSSVSSFERFEIFPKESSWPNHNTNGVTAACSHEGKSSF

YRNLLWLTEKEGSYPKLKNSYVNKKGKEVLVLWGIHHPPNSKEQQNIYQNENAYVSVVTSNYNRRFTPEIAERPKVRDQA

GRMNYYWTLLKPGDTIIFEANGNLIAPMYAFALSRGFGENLYFQSNASMHECNTKCQTPLGAINSSLPYQNIHPVTIGEC

PKYVRSAKLRMVTGLRNTPSIQSRGLFGAIAGFIEGGWTGMIDGWYGYHHQNEQGSGYAADQKSTQNAINGITNKVNTVI

EKMNIQFTAVGYEFNKLEKRMEYLNKKVDDGFLDIWTYNAELLVLLENERTLDFHDSNVKNLYEKVKSQLKNNAKEIGNG

CFEFYHKCDNECMESVRNGTYDYPKYSEESKLNREKVDGVKLESMGIYQILAIYSTVASSLVLLVSLGAISFWMCSNGSL

QCRICI

Figure 13

(SEQ ID NO.5)

>PR8HA-63G278S-403Y411Y422Y433Y.pro

MKANLLVLLSALAAADADTICIGYHANNSTDTVDTVLEKNVTVTHSVNLLEDSHNGKLCRLKGENLYFQGKCNIAGWLLG

NPECDPLLPVRSWSYIVETPNSENGICYPGDFIDYEELREQLSSVSSFERFEIFPKESSWPNHNTNGVTAACSHEGKSSF

YRNLLWLTEKEGSYPKLKNSYVNKKGKEVLVLWGIHHPPNSKEQQNIYQNENAYVSVVTSNYNRRFTPEIAERPKVRDQA

GRMNYYWTLLKPGDTIIFEANGNLIAPMYAFALSRGFGENLYFQSNASMHECNTKCQTPLGAINSSLPYQNIHPVTIGEC

PKYVRSAKLRMVTGLRNTPSIQSRGLFGAIAGFIEGGWTGMIDGWYGYHHQNEQGSGYAADQKSTQNAINGITNKVNTVI

EKMYIQFTAVGYEFNKLEKRMEYLNKKVDDGFLYIWTYNAELLVLLENERTLDFHDSNVKNLYEKVKSQLKNNAKEIGNG

CFEFYHKCDNECMESVRNGTYDYPKYSEESKLNREKVDGVKLESMGIYQILAIYSTVASSLVLLVSLGAISFWMCSNGSL

QCRICI

Figure 14

(SEQ ID NO.6)

>PR8HA-63G282S-403Y433Y.pro

MKANLLVLLSALAAADADTICIGYHANNSTDTVDTVLEKNVTVTHSVNLLEDSHNGKLCRLKGENLYFQGKCNIAGWLLG

NPECDPLLPVRSWSYIVETPNSENGICYPGDFIDYEELREQLSSVSSFERFEIFPKESSWPNHNTNGVTAACSHEGKSSF

YRNLLWLTEKEGSYPKLKNSYVNKKGKEVLVLWGIHHPPNSKEQQNIYQNENAYVSVVTSNYNRRFTPEIAERPKVRDQA

GRMNYYWTLLKPGDTIIFEANGNLIAPMYAFALSRGFGSGIIENLYFQSTSNASMHECNTKCQTPLGAINSSLPYQNIHP

VTIGECPKYVRSAKLRMVTGLRNTPSIQSRGLFGAIAGFIEGGWTGMIDGWYGYHHQNEQGSGYAADQKSTQNAINGITN

KVNTVIEKMYIQFTAVGKEFNKLEKRMENLNKKVDDGFLYIWTYNAELLVLLENERTLDFHDSNVKNLYEKVKSQLKNNA

KEIGNGCFEFYHKCDNECMESVRNGTYDYPKYSEESKLNREKVDGVKLESMGIYQILAIYSTVASSLVLLVSLGAISFWM

CSNGSLQCRICI

Figure 15

(SEQ ID NO.7)

>PR8HA-63G282S-411Y422Y.pro

MKANLLVLLSALAAADADTICIGYHANNSTDTVDTVLEKNVTVTHSVNLLEDSHNGKLCRLKGENLYFQGKCNIAGWLLG

NPECDPLLPVRSWSYIVETPNSENGICYPGDFIDYEELREQLSSVSSFERFEIFPKESSWPNHNTNGVTAACSHEGKSSF

YRNLLWLTEKEGSYPKLKNSYVNKKGKEVLVLWGIHHPPNSKEQQNIYQNENAYVSVVTSNYNRRFTPEIAERPKVRDQA

GRMNYYWTLLKPGDTIIFEANGNLIAPMYAFALSRGFGSGIIENLYFQSTSNASMHECNTKCQTPLGAINSSLPYQNIHP

VTIGECPKYVRSAKLRMVTGLRNTPSIQSRGLFGAIAGFIEGGWTGMIDGWYGYHHQNEQGSGYAADQKSTQNAINGITN

KVNTVIEKMNIQFTAVGYEFNKLEKRMEYLNKKVDDGFLDIWTYNAELLVLLENERTLDFHDSNVKNLYEKVKSQLKNNA

KEIGNGCFEFYHKCDNECMESVRNGTYDYPKYSEESKLNREKVDGVKLESMGIYQILAIYSTVASSLVLLVSLGAISFWM

CSNGSLQCRICI

Figure 16

(SEQ ID NO.8)

>PR8HA-63G282S-403Y411Y422Y433Y.pro

MKANLLVLLSALAAADADTICIGYHANNSTDTVDTVLEKNVTVTHSVNLLEDSHNGKLCRLKGENLYFQGKCNIAGWLLG

NPECDPLLPVRSWSYIVETPNSENGICYPGDFIDYEELREQLSSVSSFERFEIFPKESSWPNHNTNGVTAACSHEGKSSF

YRNLLWLTEKEGSYPKLKNSYVNKKGKEVLVLWGIHHPPNSKEQQNIYQNENAYVSVVTSNYNRRFTPEIAERPKVRDQA

GRMNYYWTLLKPGDTIIFEANGNLIAPMYAFALSRGFGSGIIENLYFQSTSNASMHECNTKCQTPLGAINSSLPYQNIHP

VTIGECPKYVRSAKLRMVTGLRNTPSIQSRGLFGAIAGFIEGGWTGMIDGWYGYHHQNEQGSGYAADQKSTQNAINGITN

KVNTVIEKMYIQFTAVGYEFNKLEKRMEYLNKKVDDGFLYIWTYNAELLVLLENERTLDFHDSNVKNLYEKVKSQLKNNA

KEIGNGCFEFYHKCDNECMESVRNGTYDYPKYSEESKLNREKVDGVKLESMGIYQILAIYSTVASSLVLLVSLGAISFWM

CSNGSLQCRICI

Figure 17

(SEQ ID NO.9)

>PR8HA-63G283G-403Y433Y.pro

MKANLLVLLSALAAADADTICIGYHANNSTDTVDTVLEKNVTVTHSVNLLEDSHNGKLCRLKGENLYFQGKCNIAGWLLG
NPECDPLLPVRSWSYIVETPNSENGICYPGDFIDYEELREQLSSVSSFERFEIFPKESSWPNHNTNGVTAACSHEGKSSF
YRNLLWLTEKEGSYPKLKNSYVNKKGKEVLVLWGIHHPPNSKEQQNIYQNENAYVSVVTSNYNRRFTPEIAERPKVRDQA
GRMNYYWTLLKPGDTIIFEANGNLIAPMYAFALSRGFGSGIITENLYFQGSNASMHECNTKCQTPLGAINSSLPYQNIHP
VTIGECPKYVRSAKLRMVTGLRNTPSIQSRGLFGAIAGFIEGGWTGMIDGWYGYHHQNEQGSGYAADQKSTQNAINGITN
KVNTVIEKMYIQFTAVGKEFNKLEKRMENLNKKVDDGFLYIWTYNAELLVLLENERTLDFHDSNVKNLYEKVKSQLKNNA
KEIGNGCFEFYHKCDNECMESVRNGTYDYPKYSEESKLNREKVDGVKLESMGIYQILAIYSTVASSLVLLVSLGAISFWM
CSNGSLQCRICI

Figure 18

(SEQ ID NO.10)

>PR8HA-63G283G-411Y422Y.pro

MKANLLVLLSALAAADADTICIGYHANNSTDTVDTVLEKNVTVTHSVNLLEDSHNGKLCRLKGENLYFQGKCNIAGWLLG

NPECDPLLPVRSWSYIVETPNSENGICYPGDFIDYEELREQLSSVSSFERFEIFPKESSWPNHNTNGVTAACSHEGKSSF

YRNLLWLTEKEGSYPKLKNSYVNKKGKEVLVLWGIHHPPNSKEQQNIYQNENAYVSVVTSNYNRRFTPEIAERPKVRDQA

GRMNYYWTLLKPGDTIIFEANGNLIAPMYAFALSRGFGSGIITENLYFQGSNASMHECNTKCQTPLGAINSSLPYQNIHP

VTIGECPKYVRSAKLRMVTGLRNTPSIQSRGLFGAIAGFIEGGWTGMIDGWYGYHHQNEQGSGYAADQKSTQNAINGITN

KVNTVIEKMNIQFTAVGYEFNKLEKRMEYLNKKVDDGFLDIWTYNAELLVLLENERTLDFHDSNVKNLYEKVKSQLKNNA

KEIGNGCFEFYHKCDNECMESVRNGTYDYPKYSEESKLNREKVDGVKLESMGIYQILAIYSTVASSLVLLVSLGAISFWM

CSNGSLQCRICI

Figure 19

(SEQ ID NO.11)

>PR8HA-63G283G-403Y411Y422Y433Y.pro

MKANLLVLLSALAAADADTICIGYHANNSTDTVDTVLEKNVTVTHSVNLLEDSHNGKLCRLKGENLYFQGKCNIAGWLLG

NPECDPLLPVRSWSYIVETPNSENGICYPGDFIDYEELREQLSSVSSFERFEIFPKESSWPNHNTNGVTAACSHEGKSSF

YRNLLWLTEKEGSYPKLKNSYVNKKGKEVLVLWGIHHPPNSKEQQNIYQNENAYVSVVTSNYNRRFTPEIAERPKVRDQA

GRMNYYWTLLKPGDTIIFEANGNLIAPMYAFALSRGFGSGIITENLYFQGSNASMHECNTKCQTPLGAINSSLPYQNIHP

VTIGECPKYVRSAKLRMVTGLRNTPSIQSRGLFGAIAGFIEGGWTGMIDGWYGYHHQNEQGSGYAADQKSTQNAINGITN

KVNTVIEKMYIQFTAVGYEFNKLEKRMEYLNKKVDDGFLYIWTYNAELLVLLENERTLDFHDSNVKNLYEKVKSQLKNNA

KEIGNGCFEFYHKCDNECMESVRNGTYDYPKYSEESKLNREKVDGVKLESMGIYQILAIYSTVASSLVLLVSLGAISFWM

CSNGSLQCRICI

Figure 20

(SEQ ID NO.12)

>PR8HA-48G291G-403Y433Y.pro

MKANLLVLLSALAAADADTICIGYHANNSTDTVDTVLEKNVTVTHSV<u>ENLYFQG</u>NLLEDSHNGKLCRLKGIAPLQLGKCN

IAGWLLGNPECDPLLPVRSWSYIVETPNSENGICYPGDFIDYEELREQLSSVSSFERFEIFPKESSWPNHNTNGVTAACS

HEGKSSFYRNLLWLTEKEGSYPKLKNSYVNKKGKEVLVLWGIHHPPNSKEQQNIYQNENAYVSVVTSNYNRRFTPEIAER

PKVRDQAGRMNYYWTLLKPGDTIIFEANGNLIAPMYAFALSRGFGSGIITSNASMHEC<u>ENLYFQG</u>NTKCQTPLGAINSSL

PYQNIHPVTIGECPKYVRSAKLRMVTGLRNTPSIQSRGLFGAIAGFIEGGWTGMIDGWYGYHHQNEQGSGYAADQKSTQN

AINGITNKVNTVIEKM<u>Y</u>IQFTAVGKEFNKLEKRMENLNKKVDDGFL<u>Y</u>IWTYNAELLVLLENERTLDFHDSNVKNLYEKVK

SQLKNNAKEIGNGCFEFYHKCDNECMESVRNGTYDYPKYSEESKLNREKVDGVKLESMGIYQILAIYSTVASSLVLLVSL

GAISFWMCSNGSLQCRICI

Figure 21

(SEQ ID NO.13)

>PR8HA-48G291G-411Y422Y.pro

MKANLLVLLSALAAADADTICIGYHANNSTDTVDTVLEKNVTVTHSVENLYFQGNLLEDSHNGKLCRLKGIAPLQLGKCN

IAGWLLGNPECDPLLPVRSWSYIVETPNSENGICYPGDFIDYEELREQLSSVSSFERFEIFPKESSWPNHNTNGVTAACS

HEGKSSFYRNLLWLTEKEGSYPKLKNSYVNKKGKEVLVLWGIHHPPNSKEQQNIYQNENAYVSVVTSNYNRRFTPEIAER

PKVRDQAGRMNYYWTLLKPGDTIIFEANGNLIAPMYAFALSRGFGSGIITSNASMHECENLYFQGNTKCQTPLGAINSSL

PYQNIHPVTIGECPKYVRSAKLRMVTGLRNTPSIQSRGLFGAIAGFIEGGWTGMIDGWYGYHHQNEQGSGYAADQKSTQN

AINGITNKVNTVIEKMNIQFTAVGYEFNKLEKRMEYLNKKVDDGFLDIWTYNAELLVLLENERTLDFHDSNVKNLYEKVK

SQLKNNAKEIGNGCFEFYHKCDNECMESVRNGTYDYPKYSEESKLNREKVDGVKLESMGIYQILAIYSTVASSLVLLVSL

GAISFWMCSNGSLQCRICI

Figure 22

(SEQ ID NO.14)

>PR8HA-48G291G-403Y411Y422Y433Y.pro

MKANLLVLLSALAAADADTICIGYHANNSTDTVDTVLEKNVTVTHSV<u>ENLYFQG</u>NLLEDSHNGKLCRLKGIAPLQLGKCN

IAGWLLGNPECDPLLPVRSWSYIVETPNSENGICYPGDFIDYEELREQLSSVSSFERFEIFPKESSWPNHNTNGVTAACS

HEGKSSFYRNLLWLTEKEGSYPKLKNSYVNKKGKEVLVLWGIHHPPNSKEQQNIYQNENAYVSVVTSNYNRRFTPEIAER

PKVRDQAGRMNYYWTLLKPGDTIIFEANGNLIAPMYAFALSRGFGSGIITSNASMHEC<u>ENLYFQG</u>NTKCQTPLGAINSSL

PYQNIHPVTIGECPKYVRSAKLRMVTGLRNTPSIQSRGLFGAIAGFIEGGWTGMIDGWYGYHHQNEQGSGYAADQKSTQN

AINGITNKVNTVIEKM<u>Y</u>IQFTAVG<u>Y</u>EFNKLEKRME<u>Y</u>LNKKVDDGFL<u>Y</u>IWTYNAELLVLLENERTLDFHDSNVKNLYEKVK

SQLKNNAKEIGNGCFEFYHKCDNECMESVRNGTYDYPKYSEESKLNREKVDGVKLESMGIYQILAIYSTVASSLVLLVSL

GAISFWMCSNGSLQCRICI

Figure 23

(SEQ ID NO.15)

>PR8HA-48G291S-403Y433Y.pro

MKANLLVLLSALAAADADTICIGYHANNSTDTVDTVLEKNVTVTHSVENLYFQGNLLEDSHNGKLCRLKGIAPLQLGKCN

IAGWLLGNPECDPLLPVRSWSYIVETPNSENGICYPGDFIDYEELREQLSSVSSFERFEIFPKESSWPNHNTNGVTAACS

HEGKSSFYRNLLWLTEKEGSYPKLKNSYVNKKGKEVLVLWGIHHPPNSKEQQNIYQNENAYVSVVTSNYNRRFTPEIAER

PKVRDQAGRMNYYWTLLKPGDTIIFEANGNLIAPMYAFALSRGFGSGIITSNASMHECENLYFQSNTKCQTPLGAINSSL

PYQNIHPVTIGECPKYVRSAKLRMVTGLRNTPSIQSRGLFGAIAGFIEGGWTGMIDGWYGYHHQNEQGSGYAADQKSTQN

AINGITNKVNTVIEKMYIQFTAVGKEFNKLEKRMENLNKKVDDGFLYIWTYNAELLVLLENERTLDFHDSNVKNLYEKVK

SQLKNNAKEIGNGCFEFYHKCDNECMESVRNGTYDYPKYSEESKLNREKVDGVKLESMGIYQILAIYSTVASSLVLLVSL

GAISFWMCSNGSLQCRICI

Figure 24

(SEQ ID NO.16)

>PR8HA-48G291S-411Y422Y.pro

MKANLLVLLSALAAADADTICIGYHANNSTDTVDTVLEKNVTVTHSVENLYFQGNLLEDSHNGKLCRLKGIAPLQLGKCN

IAGWLLGNPECDPLLPVRSWSYIVETPNSENGICYPGDFIDYEELREQLSSVSSFERFEIFPKESSWPNHNTNGVTAACS

HEGKSSFYRNLLWLTEKEGSYPKLKNSYVNKKGKEVLVLWGIHHPPNSKEQQNIYQNENAYVSVVTSNYNRRFTPEIAER

PKVRDQAGRMNYYWTLLKPGDTIIFEANGNLIAPMYAFALSRGFGSGIITSNASMHECENLYFQSNTKCQTPLGAINSSL

PYQNIHPVTIGECPKYVRSAKLRMVTGLRNTPSIQSRGLFGAIAGFIEGGWTGMIDGWYGYHHQNEQGSGYAADQKSTQN

AINGITNKVNTVIEKMNIQFTAVGYEFNKLEKRMEYLNKKVDDGFLDIWTYNAELLVLLENERTLDFHDSNVKNLYEKVK

SQLKNNAKEIGNGCFEFYHKCDNECMESVRNGTYDYPKYSEESKLNREKVDGVKLESMGIYQILAIYSTVASSLVLLVSL

GAISFWMCSNGSLQCRICI

Figure 25

(SEQ ID NO.17)

>PR8HA-48G291S-403Y411Y422Y433Y.pro

MKANLLVLLSALAAADADTICIGYHANNSTDTVDTVLEKNVTVTHSVENLYFQGNLLEDSHNGKLCRLKGIAPLQLGKCN

IAGWLLGNPECDPLLPVRSWSYIVETPNSENGICYPGDFIDYEELREQLSSVSSFERFEIFPKESSWPNHNTNGVTAACS

HEGKSSFYRNLLWLTEKEGSYPKLKNSYVNKKGKEVLVLWGIHHPPNSKEQQNIYQNENAYVSVVTSNYNRRFTPEIAER

PKVRDQAGRMNYYWTLLKPGDTIIFEANGNLIAPMYAFALSRGFGSGIITSNASMHECENLYFQSNTKCQTPLGAINSSL

PYQNIHPVTIGECPKYVRSAKLRMVTGLRNTPSIQSRGLFGAIAGFIEGGWTGMIDGWYGYHHQNEQGSGYAADQKSTQN

AINGITNKVNTVIEKMYIQFTAVGYEFNKLEKRMEYLNKKVDDGFLYIWTYNAELLVLLENERTLDFHDSNVKNLYEKVK

SQLKNNAKEIGNGCFEFYHKCDNECMESVRNGTYDYPKYSEESKLNREKVDGVKLESMGIYQILAIYSTVASSLVLLVSL

GAISFWMCSNGSLQCRICI

Figure 26 A

```
PR8HA-291G_    MKANLLVLLSALAAADADTICIGYHANNSTDTVDTVLEKNVTVTHSVN-LLEDSHNGKLC 59
PR8HA-291S_    MKANLLVLLSALAAADADTICIGYHANNSTDTVDTVLEKNVTVTHSVN-LLEDSHNGKLC 59
PR8HA-WT_      MKANLLVLLSALAAADADTICIGYHANNSTDTVDTVLEKNVTVTHSVN-LLEDSHNGKLC 59
PR8HA-48G_     MKANLLVLLSALAAADADTICIGYHANNSTDTVDTVLEKNVTVTHSVENLYFQGHNGKLC 60
PR8HA-286S_    MKANLLVLLSALAAADADTICIGYHANNSTDTVDTVLEKNVTVTHSVN-LLEDSHNGKLC 59
PR8HA-278S_    MKANLLVLLSALAAADADTICIGYHANNSTDTVDTVLEKNVTVTHSVN-LLEDSHNGKLC 59
PR8HA-282S_    MKANLLVLLSALAAADADTICIGYHANNSTDTVDTVLEKNVTVTHSVN-LLEDSHNGKLC 59
PR8HA-63G_     MKANLLVLLSALAAADADTICIGYHANNSTDTVDTVLEKNVTVTHSVN-LLEDSHNGKLC 59
PR8HA-283G_    MKANLLVLLSALAAADADTICIGYHANNSTDTVDTVLEKNVTVTHSVN-LLEDSHNGKLC 59
               ***********************************************: *  :.******

PR8HA-291G_    RLKGIAPLQLGKCNIAGWLLGNPECDPLLPVRSWSYIVETPNSENGICYPGDFIDYEELR 119
PR8HA-291S_    RLKGIAPLQLGKCNIAGWLLGNPECDPLLPVRSWSYIVETPNSENGICYPGDFIDYEELR 119
PR8HA-WT_      RLKGIAPLQLGKCNIAGWLLGNPECDPLLPVRSWSYIVETPNSENGICYPGDFIDYEELR 119
PR8HA-48G_     RLKGIAPLQLGKCNIAGWLLGNPECDPLLPVRSWSYIVETPNSENGICYPGDFIDYEELR 120
PR8HA-286S_    RLKGIAPLQLGKCNIAGWLLGNPECDPLLPVRSWSYIVETPNSENGICYPGDFIDYEELR 119
PR8HA-278S_    RLKGIAPLQLGKCNIAGWLLGNPECDPLLPVRSWSYIVETPNSENGICYPGDFIDYEELR 119
PR8HA-282S_    RLKGIAPLQLGKCNIAGWLLGNPECDPLLPVRSWSYIVETPNSENGICYPGDFIDYEELR 119
PR8HA-63G_     RLKGENLYFQGKCNIAGWLLGNPECDPLLPVRSWSYIVETPNSENGICYPGDFIDYEELR 119
PR8HA-283G_    RLKGIAPLQLGKCNIAGWLLGNPECDPLLPVRSWSYIVETPNSENGICYPGDFIDYEELR 119
               ****       *************************************************

PR8HA-291G_    EQLSSVSSFERFEIFPKESSWPNHNTNGVTAACSHEGKSSFYRNLLWLTEKEGSYPKLKN 179
PR8HA-291S_    EQLSSVSSFERFEIFPKESSWPNHNTNGVTAACSHEGKSSFYRNLLWLTEKEGSYPKLKN 179
PR8HA-WT_      EQLSSVSSFERFEIFPKESSWPNHNTNGVTAACSHEGKSSFYRNLLWLTEKEGSYPKLKN 179
PR8HA-48G_     EQLSSVSSFERFEIFPKESSWPNHNTNGVTAACSHEGKSSFYRNLLWLTEKEGSYPKLKN 180
PR8HA-286S_    EQLSSVSSFERFEIFPKESSWPNHNTNGVTAACSHEGKSSFYRNLLWLTEKEGSYPKLKN 179
PR8HA-278S_    EQLSSVSSFERFEIFPKESSWPNHNTNGVTAACSHEGKSSFYRNLLWLTEKEGSYPKLKN 179
PR8HA-282S_    EQLSSVSSFERFEIFPKESSWPNHNTNGVTAACSHEGKSSFYRNLLWLTEKEGSYPKLKN 179
PR8HA-63G_     EQLSSVSSFERFEIFPKESSWPNHNTNGVTAACSHEGKSSFYRNLLWLTEKEGSYPKLKN 179
PR8HA-283G_    EQLSSVSSFERFEIFPKESSWPNHNTNGVTAACSHEGKSSFYRNLLWLTEKEGSYPKLKN 179
               ************************************************************

PR8HA-291G_    SYVNKKGKEVLVLWGIHHPPNSKEQQNIYQNENAYVSVVTSNYNRRFTPEIAERPKVRDQ 239
PR8HA-291S_    SYVNKKGKEVLVLWGIHHPPNSKEQQNIYQNENAYVSVVTSNYNRRFTPEIAERPKVRDQ 239
PR8HA-WT_      SYVNKKGKEVLVLWGIHHPPNSKEQQNIYQNENAYVSVVTSNYNRRFTPEIAERPKVRDQ 239
PR8HA-48G_     SYVNKKGKEVLVLWGIHHPPNSKEQQNIYQNENAYVSVVTSNYNRRFTPEIAERPKVRDQ 240
PR8HA-286S_    SYVNKKGKEVLVLWGIHHPPNSKEQQNIYQNENAYVSVVTSNYNRRFTPEIAERPKVRDQ 239
PR8HA-278S_    SYVNKKGKEVLVLWGIHHPPNSKEQQNIYQNENAYVSVVTSNYNRRFTPEIAERPKVRDQ 239
PR8HA-282S_    SYVNKKGKEVLVLWGIHHPPNSKEQQNIYQNENAYVSVVTSNYNRRFTPEIAERPKVRDQ 239
PR8HA-63G_     SYVNKKGKEVLVLWGIHHPPNSKEQQNIYQNENAYVSVVTSNYNRRFTPEIAERPKVRDQ 239
PR8HA-283G_    SYVNKKGKEVLVLWGIHHPPNSKEQQNIYQNENAYVSVVTSNYNRRFTPEIAERPKVRDQ 239
               ************************************************************

PR8HA-291G_    AGRMNYYWTLLKPGDTIIFEANGNLIAPMYAFALSRGFGSGIITSNAS-------MHECE 292
PR8HA-291S_    AGRMNYYWTLLKPGDTIIFEANGNLIAPMYAFALSRGFGSGIITSNAS-------MHECE 292
PR8HA-WT_      AGRMNYYWTLLKPGDTIIFEANGNLIAPMYAFALSRGFGSGIITSNAS-------MHECN 292
PR8HA-48G_     AGRMNYYWTLLKPGDTIIFEANGNLIAPMYAFALSRGFGSGIITSNAS-------MHECN 293
PR8HA-286S_    AGRMNYYWTLLKPGDTIIFEANGNLIAPMYAFALSRGFGSGIITSNAENLYFQSSMHECN 299
PR8HA-278S_    AGRMNYYWTLLKPGDTIIFEANGNLIAPMYAFALSRGFG----ENLYFQS--NASMHECN 293
PR8HA-282S_    AGRMNYYWTLLKPGDTIIFEANGNLIAPMYAFALSRGFGSGIIENLYFQSTSNASMHECN 299
PR8HA-63G_     AGRMNYYWTLLKPGDTIIFEANGNLIAPMYAFALSRGFGSGIITS-------NASMHECN 292
PR8HA-283G_    AGRMNYYWTLLKPGDTIIFEANGNLIAPMYAFALSRGFGSGIITENLYFQGSNASMHECN 299
               ***************************************       .        ****:
```

Figure 26 B

```
PR8HA-291G_     NLYFQGNTKCQTPLGAINSSLPYQNIHPVTIGECPKYVRSAKLRMVTGLRNTPSIQSRGL 352
PR8HA-291S_     NLYFQSNTKCQTPLGAINSSLPYQNIHPVTIGECPKYVRSAKLRMVTGLRNTPSIQSRGL 352
PR8HA-WT_       -------TKCQTPLGAINSSLPYQNIHPVTIGECPKYVRSAKLRMVTGLRNTPSIQSRGL 345
PR8HA-48G_      -------TKCQTPLGAINSSLPYQNIHPVTIGECPKYVRSAKLRMVTGLRNTPSIQSRGL 346
PR8HA-286S_     -------TKCQTPLGAINSSLPYQNIHPVTIGECPKYVRSAKLRMVTGLRNTPSIQSRGL 352
PR8HA-278S_     -------TKCQTPLGAINSSLPYQNIHPVTIGECPKYVRSAKLRMVTGLRNTPSIQSRGL 346
PR8HA-282S_     -------TKCQTPLGAINSSLPYQNIHPVTIGECPKYVRSAKLRMVTGLRNTPSIQSRGL 352
PR8HA-63G_      -------TKCQTPLGAINSSLPYQNIHPVTIGECPKYVRSAKLRMVTGLRNTPSIQSRGL 345
PR8HA-283G_     -------TKCQTPLGAINSSLPYQNIHPVTIGECPKYVRSAKLRMVTGLRNTPSIQSRGL 352
                       *****************************************************

PR8HA-291G_     FGAIAGFIEGGWTGMIDGWYGYHHQNEQGSGYAADQKSTQNAINGITNKVNTVIEKMNIQ 412
PR8HA-291S_     FGAIAGFIEGGWTGMIDGWYGYHHQNEQGSGYAADQKSTQNAINGITNKVNTVIEKMNIQ 412
PR8HA-WT_       FGAIAGFIEGGWTGMIDGWYGYHHQNEQGSGYAADQKSTQNAINGITNKVNTVIEKMNIQ 405
PR8HA-48G_      FGAIAGFIEGGWTGMIDGWYGYHHQNEQGSGYAADQKSTQNAINGITNKVNTVIEKMNIQ 406
PR8HA-286S_     FGAIAGFIEGGWTGMIDGWYGYHHQNEQGSGYAADQKSTQNAINGITNKVNTVIEKMNIQ 412
PR8HA-278S_     FGAIAGFIEGGWTGMIDGWYGYHHQNEQGSGYAADQKSTQNAINGITNKVNTVIEKMNIQ 406
PR8HA-282S_     FGAIAGFIEGGWTGMIDGWYGYHHQNEQGSGYAADQKSTQNAINGITNKVNTVIEKMNIQ 412
PR8HA-63G_      FGAIAGFIEGGWTGMIDGWYGYHHQNEQGSGYAADQKSTQNAINGITNKVNTVIEKMNIQ 405
PR8HA-283G_     FGAIAGFIEGGWTGMIDGWYGYHHQNEQGSGYAADQKSTQNAINGITNKVNTVIEKMNIQ 412
                ************************************************************

PR8HA-291G_     FTAVGKEFNKLEKRMENLNKKVDDGFLDIWTYNAELLVLLENERTLDFHDSNVKNLYEKV 472
PR8HA-291S_     FTAVGKEFNKLEKRMENLNKKVDDGFLDIWTYNAELLVLLENERTLDFHDSNVKNLYEKV 472
PR8HA-WT_       FTAVGKEFNKLEKRMENLNKKVDDGFLDIWTYNAELLVLLENERTLDFHDSNVKNLYEKV 465
PR8HA-48G_      FTAVGKEFNKLEKRMENLNKKVDDGFLDIWTYNAELLVLLENERTLDFHDSNVKNLYEKV 466
PR8HA-286S_     FTAVGKEFNKLEKRMENLNKKVDDGFLDIWTYNAELLVLLENERTLDFHDSNVKNLYEKV 472
PR8HA-278S_     FTAVGKEFNKLEKRMENLNKKVDDGFLDIWTYNAELLVLLENERTLDFHDSNVKNLYEKV 466
PR8HA-282S_     FTAVGKEFNKLEKRMENLNKKVDDGFLDIWTYNAELLVLLENERTLDFHDSNVKNLYEKV 472
PR8HA-63G_      FTAVGKEFNKLEKRMENLNKKVDDGFLDIWTYNAELLVLLENERTLDFHDSNVKNLYEKV 465
PR8HA-283G_     FTAVGKEFNKLEKRMENLNKKVDDGFLDIWTYNAELLVLLENERTLDFHDSNVKNLYEKV 472
                ************************************************************

PR8HA-291G_     KSQLKNNAKEIGNGCFEFYHKCDNECMESVRNGTYDYPKYSEESKLNREKVDGVKLESMG 532
PR8HA-291S_     KSQLKNNAKEIGNGCFEFYHKCDNECMESVRNGTYDYPKYSEESKLNREKVDGVKLESMG 532
PR8HA-WT_       KSQLKNNAKEIGNGCFEFYHKCDNECMESVRNGTYDYPKYSEESKLNREKVDGVKLESMG 525
PR8HA-48G_      KSQLKNNAKEIGNGCFEFYHKCDNECMESVRNGTYDYPKYSEESKLNREKVDGVKLESMG 526
PR8HA-286S_     KSQLKNNAKEIGNGCFEFYHKCDNECMESVRNGTYDYPKYSEESKLNREKVDGVKLESMG 532
PR8HA-278S_     KSQLKNNAKEIGNGCFEFYHKCDNECMESVRNGTYDYPKYSEESKLNREKVDGVKLESMG 526
PR8HA-282S_     KSQLKNNAKEIGNGCFEFYHKCDNECMESVRNGTYDYPKYSEESKLNREKVDGVKLESMG 532
PR8HA-63G_      KSQLKNNAKEIGNGCFEFYHKCDNECMESVRNGTYDYPKYSEESKLNREKVDGVKLESMG 525
PR8HA-283G_     KSQLKNNAKEIGNGCFEFYHKCDNECMESVRNGTYDYPKYSEESKLNREKVDGVKLESMG 532
                ************************************************************

PR8HA-291G_     IYQILAIYSTVASSLVLLVSLGAISFWMCSNGSLQCRICI 572 (SEQ ID NO. 18)
PR8HA-291S_     IYQILAIYSTVASSLVLLVSLGAISFWMCSNGSLQCRICI 572 (SEQ ID NO. 19)
PR8HA-WT_       IYQILAIYSTVASSLVLLVSLGAISFWMCSNGSLQCRICI 565 (SEQ ID NO. 1)
PR8HA-48G_      IYQILAIYSTVASSLVLLVSLGAISFWMCSNGSLQCRICI 566 (SEQ ID NO. 20)
PR8HA-286S_     IYQILAIYSTVASSLVLLVSLGAISFWMCSNGSLQCRICI 572 (SEQ ID NO. 21)
PR8HA-278S_     IYQILAIYSTVASSLVLLVSLGAISFWMCSNGSLQCRICI 566 (SEQ ID NO. 22)
PR8HA-282S_     IYQILAIYSTVASSLVLLVSLGAISFWMCSNGSLQCRICI 572 (SEQ ID NO. 23)
PR8HA-63G_      IYQILAIYSTVASSLVLLVSLGAISFWMCSNGSLQCRICI 565 (SEQ ID NO. 24)
PR8HA-283G_     IYQILAIYSTVASSLVLLVSLGAISFWMCSNGSLQCRICI 572 (SEQ ID NO. 25)
```

Figure 27 A

```
PR8HA-63G278S    MKANLLVLLSALAAADADTICIGYHANNSTDTVDTVLEKNVTVTHSVN-------LLEDS 53
PR8HA-63G282S    MKANLLVLLSALAAADADTICIGYHANNSTDTVDTVLEKNVTVTHSVN-------LLEDS 53
PR8HA-63G283G    MKANLLVLLSALAAADADTICIGYHANNSTDTVDTVLEKNVTVTHSVN-------LLEDS 53
PR8HA-48G291G    MKANLLVLLSALAAADADTICIGYHANNSTDTVDTVLEKNVTVTHSVENLYFQGNLLEDS 60
PR8HA-48G291S    MKANLLVLLSALAAADADTICIGYHANNSTDTVDTVLEKNVTVTHSVENLYFQGNLLEDS 60
PR8HA-WT         MKANLLVLLSALAAADADTICIGYHANNSTDTVDTVLEKNVTVTHSVN-------LLEDS 53
                 ***********************************************:       *****

PR8HA-63G278S    HNGKLCRLKGENLYFQGKCNIAGWLLGNPECDPLLPVRSWSYIVETPNSENGICYPGDFI 113
PR8HA-63G282S    HNGKLCRLKGENLYFQGKCNIAGWLLGNPECDPLLPVRSWSYIVETPNSENGICYPGDFI 113
PR8HA-63G283G    HNGKLCRLKGENLYFQGKCNIAGWLLGNPECDPLLPVRSWSYIVETPNSENGICYPGDFI 113
PR8HA-48G291G    HNGKLCRLKGIAPLQLGKCNIAGWLLGNPECDPLLPVRSWSYIVETPNSENGICYPGDFI 120
PR8HA-48G291S    HNGKLCRLKGIAPLQLGKCNIAGWLLGNPECDPLLPVRSWSYIVETPNSENGICYPGDFI 120
PR8HA-WT         HNGKLCRLKGIAPLQLGKCNIAGWLLGNPECDPLLPVRSWSYIVETPNSENGICYPGDFI 113
                 **********      ********************************************

PR8HA-63G278S    DYEELREQLSSVSSFERFEIFPKESSWPNHNTNGVTAACSHEGKSSFYRNLLWLTEKEGS 173
PR8HA-63G282S    DYEELREQLSSVSSFERFEIFPKESSWPNHNTNGVTAACSHEGKSSFYRNLLWLTEKEGS 173
PR8HA-63G283G    DYEELREQLSSVSSFERFEIFPKESSWPNHNTNGVTAACSHEGKSSFYRNLLWLTEKEGS 173
PR8HA-48G291G    DYEELREQLSSVSSFERFEIFPKESSWPNHNTNGVTAACSHEGKSSFYRNLLWLTEKEGS 180
PR8HA-48G291S    DYEELREQLSSVSSFERFEIFPKESSWPNHNTNGVTAACSHEGKSSFYRNLLWLTEKEGS 180
PR8HA-WT         DYEELREQLSSVSSFERFEIFPKESSWPNHNTNGVTAACSHEGKSSFYRNLLWLTEKEGS 173
                 ************************************************************

PR8HA-63G278S    YPKLKNSYVNKKGKEVLVLWGIHHPPNSKEQQNIYQNENAYVSVVTSNYNRRFTPEIAER 233
PR8HA-63G282S    YPKLKNSYVNKKGKEVLVLWGIHHPPNSKEQQNIYQNENAYVSVVTSNYNRRFTPEIAER 233
PR8HA-63G283G    YPKLKNSYVNKKGKEVLVLWGIHHPPNSKEQQNIYQNENAYVSVVTSNYNRRFTPEIAER 233
PR8HA-48G291G    YPKLKNSYVNKKGKEVLVLWGIHHPPNSKEQQNIYQNENAYVSVVTSNYNRRFTPEIAER 240
PR8HA-48G291S    YPKLKNSYVNKKGKEVLVLWGIHHPPNSKEQQNIYQNENAYVSVVTSNYNRRFTPEIAER 240
PR8HA-WT         YPKLKNSYVNKKGKEVLVLWGIHHPPNSKEQQNIYQNENAYVSVVTSNYNRRFTPEIAER 233
                 ************************************************************

PR8HA-63G278S    PKVRDQAGRMNYYWTLLKPGDTIIFEANGNLIAPMYAFALSRGFG-----ENLYFQS--N 286
PR8HA-63G282S    PKVRDQAGRMNYYWTLLKPGDTIIFEANGNLIAPMYAFALSRGFGSGII-ENLYFQSTSN 292
PR8HA-63G283G    PKVRDQAGRMNYYWTLLKPGDTIIFEANGNLIAPMYAFALSRGFGSGIITENLYFQG-SN 292
PR8HA-48G291G    PKVRDQAGRMNYYWTLLKPGDTIIFEANGNLIAPMYAFALSRGFGSG------IITS--N 292
PR8HA-48G291S    PKVRDQAGRMNYYWTLLKPGDTIIFEANGNLIAPMYAFALSRGFGSG------IITS--N 292
PR8HA-WT         PKVRDQAGRMNYYWTLLKPGDTIIFEANGNLIAPMYAFALSRGFGSG------IITS--N 285
                 *********************************************          : .  *

PR8HA-63G278S    ASMHECN-------TKCQTPLGAINSSLPYQNIHPVTIGECPKYVRSAKLRMVTGLRNTP 339
PR8HA-63G282S    ASMHECN-------TKCQTPLGAINSSLPYQNIHPVTIGECPKYVRSAKLRMVTGLRNTP 345
PR8HA-63G283G    ASMHECN-------TKCQTPLGAINSSLPYQNIHPVTIGECPKYVRSAKLRMVTGLRNTP 345
PR8HA-48G291G    ASMHECENLYFQGNTKCQTPLGAINSSLPYQNIHPVTIGECPKYVRSAKLRMVTGLRNTP 352
PR8HA-48G291S    ASMHECENLYFQSNTKCQTPLGAINSSLPYQNIHPVTIGECPKYVRSAKLRMVTGLRNTP 352
PR8HA-WT         ASMHECN-------TKCQTPLGAINSSLPYQNIHPVTIGECPKYVRSAKLRMVTGLRNTP 338
                 ******:       **********************************************
```

Figure 27 B

```
PR8HA-63G278S    SIQSRGLFGAIAGFIEGGWTGMIDGWYGYHHQNEQGSGYAADQKSTQNAINGITNKVNTV 399
PR8HA-63G282S    SIQSRGLFGAIAGFIEGGWTGMIDGWYGYHHQNEQGSGYAADQKSTQNAINGITNKVNTV 405
PR8HA-63G283G    SIQSRGLFGAIAGFIEGGWTGMIDGWYGYHHQNEQGSGYAADQKSTQNAINGITNKVNTV 405
PR8HA-48G291G    SIQSRGLFGAIAGFIEGGWTGMIDGWYGYHHQNEQGSGYAADQKSTQNAINGITNKVNTV 412
PR8HA-48G291S    SIQSRGLFGAIAGFIEGGWTGMIDGWYGYHHQNEQGSGYAADQKSTQNAINGITNKVNTV 412
PR8HA-WT         SIQSRGLFGAIAGFIEGGWTGMIDGWYGYHHQNEQGSGYAADQKSTQNAINGITNKVNTV 398
                 ************************************************************

PR8HA-63G278S    IEKMNIQFTAVGKEFNKLEKRMENLNKKVDDGFLDIWTYNAELLVLLENERTLDFHDSNV 459
PR8HA-63G282S    IEKMNIQFTAVGKEFNKLEKRMENLNKKVDDGFLDIWTYNAELLVLLENERTLDFHDSNV 465
PR8HA-63G283G    IEKMNIQFTAVGKEFNKLEKRMENLNKKVDDGFLDIWTYNAELLVLLENERTLDFHDSNV 465
PR8HA-48G291G    IEKMNIQFTAVGKEFNKLEKRMENLNKKVDDGFLDIWTYNAELLVLLENERTLDFHDSNV 472
PR8HA-48G291S    IEKMNIQFTAVGKEFNKLEKRMENLNKKVDDGFLDIWTYNAELLVLLENERTLDFHDSNV 472
PR8HA-WT         IEKMNIQFTAVGKEFNKLEKRMENLNKKVDDGFLDIWTYNAELLVLLENERTLDFHDSNV 458
                 ************************************************************

PR8HA-63G278S    KNLYEKVKSQLKNNAKEIGNGCFEFYHKCDNECMESVRNGTYDYPKYSEESKLNREKVDG 519
PR8HA-63G282S    KNLYEKVKSQLKNNAKEIGNGCFEFYHKCDNECMESVRNGTYDYPKYSEESKLNREKVDG 525
PR8HA-63G283G    KNLYEKVKSQLKNNAKEIGNGCFEFYHKCDNECMESVRNGTYDYPKYSEESKLNREKVDG 525
PR8HA-48G291G    KNLYEKVKSQLKNNAKEIGNGCFEFYHKCDNECMESVRNGTYDYPKYSEESKLNREKVDG 532
PR8HA-48G291S    KNLYEKVKSQLKNNAKEIGNGCFEFYHKCDNECMESVRNGTYDYPKYSEESKLNREKVDG 532
PR8HA-WT         KNLYEKVKSQLKNNAKEIGNGCFEFYHKCDNECMESVRNGTYDYPKYSEESKLNREKVDG 518
                 ************************************************************

PR8HA-63G278S    VKLESMGIYQILAIYSTVASSLVLLVSLGAISFWMCSNGSLQCRICI 566 (SEQ ID NO. 26)
PR8HA-63G282S    VKLESMGIYQILAIYSTVASSLVLLVSLGAISFWMCSNGSLQCRICI 572 (SEQ ID NO. 27)
PR8HA-63G283G    VKLESMGIYQILAIYSTVASSLVLLVSLGAISFWMCSNGSLQCRICI 572 (SEQ ID NO. 28)
PR8HA-48G291G    VKLESMGIYQILAIYSTVASSLVLLVSLGAISFWMCSNGSLQCRICI 579 (SEQ ID NO. 29)
PR8HA-48G291S    VKLESMGIYQILAIYSTVASSLVLLVSLGAISFWMCSNGSLQCRICI 579 (SEQ ID NO. 30)
PR8HA-WT         VKLESMGIYQILAIYSTVASSLVLLVSLGAISFWMCSNGSLQCRICI 565 (SEQ ID NO. 1)
                 ***********************************************
```

Figure 28

(SEQ ID NO.31)

>PR8HA-63G278S-403Y433Y.seq

ATGAAGGCAAACCTACTGGTCCTGTTAAGTGCACTTGCAGCTGCAGATGCAGACACAATATGTATAGGCTACCATGCGAA

CAATTCAACCGACACTGTTGACACAGTACTCGAGAAGAATGTGACAGTGACACACTCTGTTAACCTGCTCGAAGACAGCC

ACAACGGAAAACTATGTAGATTAAAAGGAgagaatctgtacttccagggaAAATGTAACATCGCCGGATGGCTCTTGGGA

AACCCAGAATGCGACCCACTGCTTCCAGTGAGATCATGGTCCTACATTGTAGAAACACCAAACTCTGAGAATGGAATATG

TTATCCAGGAGATTTCATCGACTATGAGGAGCTGAGGGAGCAATTGAGCTCAGTGTCATCATTCGAAAGATTCGAAATAT

TTCCCAAAGAAAGCTCATGGCCCAACCACAACACAAACGGAGTAACGGCAGCATGCTCCCATGAGGGGAAAAGCAGTTTT

TACAGAAATTTGCTATGGCTGACGGAGAAGGAGGGCTCATACCCAAAGCTGAAAAATTCTTATGTGAACAAAAAAGGGAA

AGAAGTCCTTGTACTGTGGGGTATTCATCACCCGCCTAACAGTAAGGAACAACAGAATATCTATCAGAATGAAAATGCTT

ATGTCTCTGTAGTGACTTCAAATTATAACAGGAGATTTACCCCGGAAATAGCAGAAAGACCCAAAGTAAGAGATCAAGCT

GGGAGGATGAACTATTACTGGACCTTGCTAAAACCCGGAGACACAATAATATTTGAGGCAAATGGAAATCTAATAGCACC

AATGTATGCTTTCGCACTGAGTAGAGGCTTTGGGgagaatctgtacttccagTCAAACGCATCAATGCATGAGTGTAACA

CGAAGTGTCAAACACCGCTCGGAGCTATAAACAGCAGTCTCCCTTACCAGAATATACACCCAGTCACAATAGGAGAGTGC

CCAAAATACGTCAGGAGTGCCAAATTGAGGATGGTTACAGGACTAAGGAACACTCCGTCCATTCAATCCAGAGGTCTATT

TGGAGCCATTGCCGGTTTTATTGAAGGGGGATGGACTGGAATGATAGATGGATGGTATGGTTATCATCATCAGAATGAAC

AGGGATCAGGCTATGCAGCGGATCAAAAAAGCACACAAAATGCCATTAACGGGATTACAAACAAGGTGAACACTGTTATC

GAGAAAATGtACATTCAATTCACAGCTGTCGGTAAAGAATTCAACAAATTACAAAAAACGATGCAAAATTTAAATAAAAA

AGTTGATGATGGATTTCTGtACATTTGGACATATAATGCAGAATTGTTAGTTCTACTGGAAAATGAAAGGACTCTGGATT

TCCATGACTCAAATGTGAAGAATCTGTATGAGAAAGTAAAAAGCCAATTAAAGAATAATGCCAAAGAAATCGGAAATGGA

TGTTTTGAGTTCTACCACAAGTGTGACAATGAATGCATGGAAAGTGTAAGAAATGGGACTTATGATTATCCCAAATATTC

AGAAGAGTCAAAGTTGAACAGGGAAAAGGTAGATGGAGTGAAATTGGAATCAATGGGGATCTATCAGATTCTGGCGATCT

ACTCAACTGTCGCCAGTTCACTGGTGCTTTTGGTCTCCCTGGGGGCAATCAGTTTCTGGATGTGTTCTAATGGATCTTTG

CAGTGCAGAATATGCATCTGA

Figure 29

(SEQ ID NO.32)

>PR8HA-63G278S-411Y422Y.seq

ATGAAGGCAAACCTACTGGTCCTGTTAAGTGCACTTGCAGCTGCAGATGCAGACACAATATGTATAGGCTACCATGCGAA

CAATTCAACCGACACTGTTGACACAGTACTCGAGAAGAATGTGACAGTGACACACTCTGTTAACCTGCTCGAAGACAGCC

ACAACGGAAAACTATGTAGATTAAAAGGAgagaatctgtacttccagggaAAATGTAACATCGCCGGATGGCTCTTGGGA

AACCCAGAATGCGACCCACTGCTTCCAGTGAGATCATGGTCCTACATTGTAGAAACACCAAACTCTGAGAATGGAATATG

TTATCCAGGAGATTTCATCGACTATGAGGAGCTGAGGGAGCAATTGAGCTCAGTGTCATCATTCGAAAGATTCGAAATAT

TTCCCAAAGAAAGCTCATGGCCCAACCACAACACAAACGGAGTAACGGCAGCATGCTCCCATGAGGGGAAAAGCAGTTTT

TACACAAATTTGCTATGGCTGACGGAGAAGGAGGGCTCATACCCAAAGCTGAAAAATTCTTATGTGAACAAAAAAGGGAA

AGAAGTCCTTGTACTGTGGGGTATTCATCACCCGCCTAACAGTAAGGAACAACAGAATATCTATCAGAATGAAAATGCTT

ATGTCTCTGTAGTGACTTCAAATTATAACAGGAGATTTACCCCGGAAATAGCAGAAAGACCCAAAGTAAGAGATCAAGCT

GGGAGGATGAACTATTACTGGACCTTGCTAAAACCCGGAGACACAATAATATTTGAGGCAAATGGAAATCTAATAGCACC

AATGTATGCTTTCGCACTGAGTAGAGGCTTTGGGgagaatctgtacttccagTCAAACGCATCAATGCATGAGTGTAACA

CGAAGTGTCAAACACCGCTCGGAGCTATAAACAGCAGTCTCCCTTACCAGAATATACACCCAGTCACAATAGGAGAGTGC

CCAAAATACGTCAGGAGTGCCAAATTGAGGATGGTTACAGGACTAAGGAACACTCCGTCCATTCAATCCAGAGGTCTATT

TGGAGCCATTGCCGGTTTTATTGAAGGGGGATGGACTGGAATGATAGATGGATGGTATGGTTATCATCATCAGAATGAAC

AGGGATCAGGCTATGCAGCGGATCAAAAAAGCACACAAAATGCCATTAACGGGATTACAAACAAGGTGAACACTGTTATC

GAGAAAATGAACATTCAATTCACAGCTGTGGGTtAcGAATTCAACAAATTAGAAAAAAGGATGGAAtAcTTAAATAAAAA

AGTTGATGATGGATTTCTGGACATTTGGACATATAATGCAGAATTGTTAGTTCTACTGGAAAATGAAAGGACTCTGGATT

TCCATGACTCAAATGTGAAGAATCTGTATGAGAAAGTAAAAAGCCAATTAAAGAATAATGCCAAAGAAATCGGAAATGGA

TGTTTTGAGTTCTACCACAAGTGTGACAATGAATGCATGGAAAGTGTAAGAAATGGGACTTATGATTATCCCAAATATTC

AGAAGAGTCAAAGTTGAACAGGGAAAAGGTAGATGGAGTGAAATTGGAATCAATGGGGATCTATCAGATTCTGGCGATCT

ACTCAACTGTCGCCAGTTCACTGGTGCTTTTGGTCTCCCTGGGGGCAATCAGTTTCTGGATGTGTTCTAATGGATCTTTG

CAGTGCAGAATATGCATCTGA

Figure 30

(SEQ ID NO.33)

>PR8HA-63G278S-403Y411Y422Y433Y.seq

ATGAAGGCAAACCTACTGGTCCTGTTAAGTGCACTTGCAGCTGCAGATGCAGACACAATATGTATAGGCTACCATGCGAA

CAATTCAACCGACACTGTTGACACAGTACTCGAGAAGAATGTGACAGTGACACACTCTGTTAACCTGCTCGAAGACAGCC

ACAACGGAAAACTATGTAGATTAAAAGGAgagaatctgtacttccagggaAAATGTAACATCGCCGGATGGCTCTTGGGA

AACCCAGAATGCGACCCACTGCTTCCAGTGAGATCATGGTCCTACATTGTAGAAACACCAAACTCTGAGAATGGAATATG

TTATCCAGGAGATTTCATCGACTATGAGGAGCTGAGGGAGCAATTGAGCTCAGTGTCATCATTCGAAAGATTCGAAATAT

TTCCCAAAGAAAGCTCATGGCCCAACCACAACACAAACGGAGTAACGGCAGCATGCTCCCATGAGGGGAAAAGCAGTTTT

TACAGAAATTTGCTATGGCTGACGGAGAAGGAGGGCTCATACCCAAAGCTGAAAAATTCTTATGTGAACAAAAAAGGGAA

AGAAGTCCTTGTACTGTGGGGTATTCATCACCCGCCTAACAGTAAGGAACAACAGAATATCTATCAGAATGAAAATGCTT

ATGTCTCTGTAGTGACTTCAAATTATAACAGGAGATTTACCCCGGAAATAGCAGAAAGACCCAAAGTAAGAGATCAAGCT

GGGAGGATGAACTATTACTGGACCTTGCTAAAACCCGGAGACACAATAATATTTGAGGCAAATGGAAATCTAATAGCACC

AATGTATGCTTTCGCACTGAGTAGAGGCTTTGGGgagaatctgtacttccagTCAAACGCATCAATGCATGAGTGTAACA

CGAAGTGTCAAACACCGCTCGGAGCTATAAACAGCAGTCTCCCTTACCAGAATATACACCCAGTCACAATAGGAGAGTGC

CCAAAATACGTCAGGAGTGCCAAATTGAGGATGGTTACAGGACTAAGGAACACTCCGTCCATTCAATCCAGAGGTCTATT

TGGAGCCATTGCCGGTTTTATTGAAGGGGGATGGACTGGAATGATAGATGGATGGTATGGTTATCATCATCAGAATGAAC

AGGGATCAGGCTATGCAGCGGATCAAAAAAGCACACAAAATGCCATTAACGGGATTACAAACAAGGTGAACACTGTTATC

GAGAAAATGtACATTCAATTCACAGCTGTGGGTtAcGAATTCAACAAATTAGAAAAAAGGATGGAAtAcTTAAATAAAAA

AGTTGATGATGGATTTCTGtACATTTGGACATATAATGCAGAATTGTTAGTTCTACTGGAAAATGAAAGGACTCTGGATT

TCCATGACTCAAATGTGAAGAATCTGTATGAGAAAGTAAAAAGCCAATTAAAGAATAATGCCAAAGAAATCGGAAATGGA

TGTTTTGAGTTCTACCACAAGTGTGACAATGAATGCATGGAAAGTGTAAGAAATGGGACTTATGATTATCCCAAATATTC

AGAAGAGTCAAAGTTGAACAGGGAAAAGGTAGATGGAGTGAAATTGGAATCAATGGGGATCTATCAGATTCTGGCGATCT

ACTCAACTGTCGCCAGTTCACTGGTGCTTTTGGTCTCCCTGGGGGCAATCAGTTTCTGGATGTGTTCTAATGGATCTTTG

CAGTGCAGAATATGCATCTGA

Figure 31

(SEQ ID NO.34)

>PR8HA-63G282S-403Y433Y.seq

ATGAAGGCAAACCTACTGGTCCTGTTAAGTGCACTTGCAGCTGCAGATGCAGACACAATATGTATAGGCTACCATGCGAA

CAATTCAACCGACACTGTTGACACAGTACTCGAGAAGAATGTGACAGTGACACACTCTGTTAACCTGCTCGAAGACAGCC

ACAACGGAAAACTATGTAGATTAAAAGGAgagaatctgtacttccagggaAAATGTAACATCGCCGGATGGCTCTTGGGA

AACCCAGAATGCGACCCACTGCTTCCAGTGAGATCATGGTCCTACATTGTAGAAACACCAAACTCTGAGAATGGAATATG

TTATCCAGGAGATTTCATCGACTATGAGGAGCTGAGGGAGCAATTGAGCTCAGTGTCATCATTCGAAAGATTCGAAATAT

TTCCCAAAGAAAGCTCATGGCCCAACCACAACACAAACGGAGTAACGGCAGCATGCTCCCATGAGGGGAAAAGCAGTTTT

TACAGAAATTTGCTATGGCTGACGGAGAAGGAGGGCTCATACCCAAAGCTGAAAAATTCTTATGTGAACAAAAAAGGGAA

AGAAGTCCTTGTACTGTGGGGTATTCATCACCCGCCTAACAGTAAGGAACAACAGAATATCTATCAGAATGAAAATGCTT

ATGTCTCTGTAGTGACTTCAAATTATAACAGGAGATTTACCCCGGAAATAGCAGAAAGACCCAAAGTAAGAGATCAAGCT

GGGAGGATGAACTATTACTGGACCTTGCTAAAACCCGGAGACACAATAATATTTGAGGCAAATGGAAATCTAATAGCACC

AATGTATGCTTTCGCACTGAGTAGAGGCTTTGGGTCCGGCATCATCgagaatctgtacttccagagcACCTCAAACGCAT CAATGCATGAGTGTAACACGAAGTGTCAAACACCgCTcGGAGCTATAAACAGCAGTCTCCCTTACCAGAATATACACCCA

GTCACAATAGGAGAGTGCCCAAAATACGTCAGGAGTGCCAAATTGAGGATGGTTACAGGACTAAGGAACACTCCGTCCAT

TCAATCCAGAGGTCTATTTGGAGCCATTGCCGGTTTTATTGAAGGGGGATGGACTGGAATGATAGATGGATGGTATGGTT

ATCATCATCAGAATGAACAGGGATCAGGCTATGCAGCGGATCAAAAAAGCACACAAAATGCCATTAACGGGATTACAAAC

AAGGTGAACACTGTTATCGAGAAAATGtACATTCAATTCACAGCTGTGGGTAAAGAATTCAACAAATTAGAAAAAAGGAT

GGAAAATTTAAATAAAAAAGTTGATGATGGATTTCTGtACATTTGGACATATAATGCAGAATTGTTAGTTCTACTGGAAA

ATGAAAGGACTCTGGATTTCCATGACTCAAATGTGAAGAATCTGTATGAGAAAGTAAAAAGCCAATTAAAGAATAATGCC

AAACAAATCGGAAATGCATGTTTTGAGTTCTACCACAAGTGTGACAATGAATGCATGGAAAGTGTAAGAAATGGGACTTA

TGATTATCCCAAATATTCAGAAGAGTCAAAGTTGAACAGGGAAAAGGTAGATGGAGTGAAATTGGAATCAATGGGGATCT

ATCAGATTCTGGCGATCTACTCAACTGTCGCCAGTTCACTGGTGCTTTTGGTCTCCCTGGGGGCAATCAGTTTCTGGATG

TGTTCTAATGGATCTTTGCAGTGCAGAATATGCATCTGA

Figure 32

(SEQ ID NO.35)

>PR8HA-63G282S-411Y422Y.seq

ATGAAGGCAAACCTACTGGTCCTGTTAAGTGCACTTGCAGCTGCAGATGCAGACACAATATGTATAGGCTACCATGCGAA

CAATTCAACCGACACTGTTGACACAGTACTCGAGAAGAATGTGACAGTGACACACTCTGTTAACCTGCTCGAAGACAGCC

ACAACGGAAAACTATGTAGATTAAAAGGAgagaatctgtacttccagggaAAATGTAACATCGCCGGATGGCTCTTGGGA

AACCCAGAATGCGACCCACTGCTTCCAGTGAGATCATGGTCCTACATTGTAGAAACACCAAACTCTGAGAATGGAATATG

TTATCCAGGAGATTTCATCGACTATGAGGAGCTGAGGGAGCAATTGAGCTCAGTGTCATCATTCGAAAGATTCGAAATAT

TTCCCAAAGAAAGCTCATGGCCCAACCACAACACAAACGGAGTAACGGCAGCATGCTCCCATGAGGGGAAAAGCAGTTTT

TACAGAAATTTGCTATGGCTGACGGAGAAGGAGGGCTCATACCCAAAGCTGAAAAATTCTTATGTGAACAAAAAAGGAA

AGAAGTCCTTGTACTGTGGGGTATTCATCACCCGCCTAACAGTAAGGAACAACAGAATATCTATCAGAATGAAAATGCTT

ATGTCTCTGTAGTGACTTCAAATTATAACAGGAGATTTACCCCGGAAATAGCAGAAAGACCCAAAGTAAGAGATCAAGCT

GGGAGGATGAACTATTACTGGACCTTGCTAAAACCCGGAGACACAATAATATTTGAGGCAAATGGAAATCTAATAGCACC

AATGTATGCTTTCGCACTGAGTAGAGGCTTTGGGTCCGGCATCATCgagaatctgtacttccagagcACCTCAAACGCAT CAATGCATGAGTGTAACACGAAGTGTCAAACACCgCTcGGAGCTATAAACAGCAGTCTCCCTTACCAGAATATACACCCA

GTCACAATAGGAGAGTGCCCAAAATACGTCAGGAGTGCCAAATTGAGGATGGTTACAGGACTAAGGAACACTCCGTCCAT

TCAATCCAGAGGTCTATTTGGAGCCATTGCCGGTTTTATTGAAGGGGGATGGACTGGAATGATAGATGGATGGTATGGTT

ATCATCATCAGAATGAACAGGGATCAGGCTATGCAGCGGATCAAAAAAGCACACAAAATGCCATTAACGGGATTACAAAC

AAGGTGAACACTGTTATCGAGAAAATGAACATTCAATTCACAGCTGTGGGTtAcGAATTCAACAAATTAGAAAAAAGGAT

GGAAtAcTTAAATAAAAAAGTTGATGATGGATTTCTGGACATTTGGACATATAATGCAGAATTGTTAGTTCTACTGGAAA

ATGAAAGGACTCTGGATTTCCATGACTCAAATGTGAAGAATCTGTATGAGAAAGTAAAAAGCCAATTAAAGAATAATGCC

AAAGAAATCGGAAATGGATGTTTTGAGTTCTACCACAAGTGTGACAATGAATGCATGGAAAGTGTAAGAAATGGGACTTA

TGATTATCCCAAATATTCAGAAGAGTCAAAGTTGAACAGGGAAAAGGTAGATGGAGTGAAATTGGAATCAATGGGGATCT

ATCAGATTCTGGCGATCTACTCAACTGTCGCCAGTTCACTGGTGCTTTTGGTCTCCCTGGGGGCAATCAGTTTCTGGATG

TGTTCTAATGGATCTTTGCAGTGCAGAATATGCATCTGA

Figure 33

(SEQ ID NO.36)

>PR8HA-63G282S-403Y411Y422Y433Y.seq

ATGAAGGCAAACCTACTGGTCCTGTTAAGTGCACTTGCAGCTGCAGATGCAGACACAATATGTATAGGCTACCATGCGAA

CAATTCAACCGACACTGTTGACACAGTACTCGAGAAGAATGTGACAGTGACACACTCTGTTAACCTGCTCGAAGACAGCC

ACAACGGAAAACTATGTAGATTAAAAGGAgagaatctgtacttccagggaAAATGTAACATCGCCGGATGGCTCTTGGGA

AACCCAGAATGCGACCCACTGCTTCCAGTGAGATCATGGTCCTACATTGTAGAAACACCAAACTCTGAGAATGGAATATG

TTATCCAGGAGATTTCATCGACTATGAGGAGCTGAGGGAGCAATTGAGCTCAGTGTCATCATTCGAAAGATTCGAAATAT

TTCCCAAAGAAAGCTCATGGCCCAACCACAACACAAACGGAGTAACGGCAGCATGCTCCCATGAGGGGAAAAGCAGTTTT

TACAGAAATTTGCTATGGCTGACGGAGAAGGAGGGCTCATACCCAAAGCTGAAAAATTCTTATGTGAACAAAAAAGGGAA

AGAAGTCCTTGTACTGTGGGGTATTCATCACCCGCCTAACAGTAAGGAACAACAGAATATCTATCAGAATGAAAATGCTT

ATGTCTCTGTAGTGACTTCAAATTATAACAGGAGATTTACCCCGGAAATAGCAGAAAGACCCAAAGTAAGAGATCAAGCT

GGGAGGATGAACTATTACTGGACCTTGCTAAAACCCGGAGACACAATAATATTTGAGGCAAATGGAAATCTAATAGCACC

AATGTATGCTTTCGCACTGAGTAGAGGCTTTGGGTCCGGCATCATCgagaatctgtacttccagagcACCTCAAACGCAT CAATGCATGAGTGTAACACGAAGTGTCAAACACCgCTcGGAGCTATAAACAGCAGTCTCCCTTACCAGAATATACACCCA

GTCACAATAGGAGAGTGCCCAAAATACGTCAGGAGTGCCAAATTGAGGATGGTTACAGGACTAAGGAACACTCCGTCCAT

TCAATCCAGAGGTCTATTTGGAGCCATTGCCGGTTTTATTGAAGGGGGATGGACTGGAATGATAGATGGATGGTATGGTT

ATCATCATCAGAATGAACAGGGATCAGGCTATGCAGCGGATCAAAAAAGCACACAAAATGCCATTAACGGGATTACAAAC

AAGGTGAACACTGTTATCGAGAAAATGtACATTCAATTCACAGCTGTGGGTtAcGAATTCAACAAATTAGAAAAAAGGAT

GGAAtAcTTAAATAAAAAAGTTGATGATGGATTTCTGtACATTTGGACATATAATGCAGAATTGTTAGTTCTACTGGAAA

ATGAAAGGACTCTGGATTTCCATGACTCAAATGTGAAGAATCTGTATGAGAAAGTAAAAAGCCAATTAAAGAATAATGCC

AAAGAAATCGGAAATGGATGTTTTGAGTTCTACCACAAGTGTGACAATGAATGCATGGAAAGTGTAAGAAATGGGACTTA

TGATTATCCCAAATATTCAGAAGAGTCAAAGTTGAACAGGGAAAAGGTAGATGGAGTGAAATTGGAATCAATGGGGATCT

ATCAGATTCTGGCGATCTACTCAACTGTCGCCAGTTCACTGGTGCTTTTGGTCTCCCTGGGGGCAATCAGTTTCTGGATG

TGTTCTAATGGATCTTTGCAGTGCAGAATATGCATCTGA

Figure 34

(SEQ ID NO.37)

>PR8HA-63G283G-403Y433Y.seq

ATGAAGGCTAACCTGCTGGTGCTGCTGAGCGCCCTGGCTGCCGCTGATGCCGATACCATCTGCATCGGCTACCACGCCAA

CAACAGCACCGACACCGTGGATACCGTGCTGGAAAAGAACGTGACCGTGACCCACAGCGTGAACCTGCTGGAAGATAGCC

ACAACGGCAAGCTGTGCCGGCTGAAGGGCgagaacctgtattttcaaggcAAGTGCAATATCGCCGGCTGGCTGCTGGGC

AACCCCGAGTGTGATCCTCTGCTGCCTGTGCGGAGCTGGTCCTACATCGTGGAAACCCCCAACAGCGAGAACGGCATCTG

CTACCCCGGCGACTTCATCGACTACGAGGAACTGCGCGAGCAGCTGAGCAGCGTGTCCAGCTTCGAGAGATTCGAGATCT

TCCCCAAAGAGAGCAGCTGGCCCAACCACAACACCAACGGCGTGACAGCCGCCTGTAGCCACGAGGGCAAGAGCAGCTTC

TACAGAAACCTGCTGTGGCTGACCGAGAAAGAGGGCAGCTACCCCAAGCTGAAGAACAGCTACGTGAACAAGAAAGGCAA

AGAGGTGCTGGTGCTGTGGGGCATCCACCACCCCCCCAACTCTAAAGAGCAGCAGAACATCTACCAGAACGAGAACGCCT

ACGTGTCCGTCGTGACCAGCAACTACAACCGGCGGTTCACCCCCGAGATCGCCGAGAGGCCTAAAGTGCGGGATCAGGCC

GGCAGAATGAACTACTACTGGACCCTGCTGAAGCCCGGCGACACCATCATCTTCGAGGCCAACGGCAACCTGATCGCCCC

TATGTACGCCTTCGCCCTGAGCAGAGGCTTCGGCAGCGGCATCATCACCgaaaacctgtacttccaaggatccAACGCCA

GCATGCACGAGTGCAACACCAAGTGCCAGACCCCGCTCGGAGCTATAAACAGCAGTCTCCCTTACCAGAATATACACCCA

GTCACAATAGGAGAGTGCCCAAAATACGTCAGGAGTGCCAAATTGAGGATGGTTACAGGACTAAGGAACACTCCGTCCAT

TCAATCCAGAGGTCTATTTGGAGCCATTGCCGGTTTTATTGAAGGGGGATGGACTGGAATGATAGATGGATGGTATGGTT

ATCATCATCAGAATGAACAGGGATCAGGCTATGCAGCGGATCAAAAAAGCACACAAAATGCCATTAACGGGATTACAAAC

AAGGTGAACACTGTTATCGAGAAAATGtACATTCAATTCACAGCTGTGGGTAAAGAATTCAACAAATTAGAAAAAAGGAT

GGAAAATTTAAATAAAAAAGTTGATGATGGATTTCTGtACATTTGGACATATAATGCAGAATTGTTAGTTCTACTGGAAA

ATGAAAGGACTCTGGATTTCCATGACTCAAATGTGAAGAATCTGTATGAGAAAGTAAAAAGCCAATTAAAGAATAATGCC

AAAGAAATCGGAAATGGATGTTTTGAGTTCTACCACAAGTGTGACAATGAATGCATGGAAAGTGTAAGAAATGGGACTTA

TGATTATCCCAAATATTCAGAAGAGTCAAAGTTGAACAGGGAAAAGGTAGATGGAGTGAAATTGGAATCAATGGGGATCT

ATCAGATTCTGGCGATCTACTCAACTGTCGCCAGTTCACTGGTGCTTTTGGTCTCCCTGGGGGCAATCAGTTTCTGGATG

TGTTCTAATGGATCTTTGCAGTGCAGAATATGCATCTGA

Figure 35

(SEQ ID NO.38)

>PR8HA-63G283G-411Y422Y.seq

ATGAAGGCTAACCTGCTGGTGCTGCTGAGCGCCCTGGCTGCCGCTGATGCCGATACCATCTGCATCGGCTACCACGCCAA

CAACAGCACCGACACCGTGGATACCGTGCTGGAAAAGAACGTGACCGTGACCCACAGCGTGAACCTGCTGGAAGATAGCC

ACAACGGCAAGCTGTGCCGGCTGAAGGGCgagaacctgtattttcaaggcAAGTGCAATATCGCCGGCTGGCTGCTGGGC

AACCCCGAGTGTGATCCTCTGCTGCCTGTGCGGAGCTGGTCCTACATCGTGGAAACCCCCAACAGCGAGAACGGCATCTG

CTACCCCGGCGACTTCATCGACTACGAGGAACTGCGCGAGCAGCTGAGCAGCGTGTCCAGCTTCGAGAGATTCGAGATCT

TCCCCAAAGAGAGCAGCTGGCCCAACCACAACACCAACGGCGTGACAGCCGCCTGTAGCCACGAGGGCAAGAGCAGCTTC

TACAGAAACCTGCTGTGGCTGACCGAGAAAGAGGGCAGCTACCCCAAGCTGAAGAACAGCTACGTGAACAAGAAAGGCAA

AGAGGTGCTGGTGCTGTGGGGCATCCACCACCCCCCCAACTCTAAAGAGCAGCAGAACATCTACCAGAACGAGAACGCCT

ACGTGTCCGTCGTGACCAGCAACTACAACCGGCGGTTCACCCCCGAGATCGCCGAGAGGCCTAAAGTGCGGGATCAGGCC

GGCAGAATGAACTACTACTGGACCCTGCTGAAGCCCGGCGACACCATCATCTTCGAGGCCAACGGCAACCTGATCGCCCC

TATGTACGCCTTCGCCCTGAGCAGAGGCTTCGGCAGCGGCATCATCACCgaaaacctgtacttccaaggatccAACGCCA

GCATGCACGAGTGCAACACCAAGTGCCAGACCCCGCTCGGAGCTATAAACAGCAGTCTCCCTTACCAGAATATACACCCA

GTCACAATAGGAGAGTGCCCAAAATACGTCAGGAGTGCCAAATTGAGGATGGTTACAGGACTAAGGAACACTCCGTCCAT

TCAATCCAGAGGTCTATTTGGAGCCATTGCCGGTTTTATTGAAGGGGGATGGACTGGAATGATAGATGGATGGTATGGTT

ATCATCATCAGAATGAACAGGGATCAGGCTATGCAGCGGATCAAAAAAGCACACAAAATGCCATTAACGGGATTACAAAC

AAGGTGAACACTGTTATCGAGAAAATGAACATTCAATTCACAGCTGTGGGTtAcGAATTCAACAAATTAGAAAAAAGGAT

GGAAtAcTTAAATAAAAAAGTTGATGATGGATTTCTGGACATTTGGACATATAATGCAGAATTGTTAGTTCTACTGGAAA

ATGAAAGGACTCTGGATTTCCATGACTCAAATGTGAAGAATCTGTATGAGAAAGTAAAAAGCCAATTAAAGAATAATGCC

AAAGAAATCGGAAATGGATGTTTTGAGTTCTACCACAAGTGTGACAATGAATGCATGGAAAGTGTAAGAAATGGGACTTA

TGATTATCCCAAATATTCAGAAGAGTCAAAGTTGAACAGGGAAAAGGTAGATGGAGTGAAATTGGAATCAATGGGGATCT

ATCAGATTCTGGCGATCTACTCAACTGTCGCCAGTTCACTGGTGCTTTTGGTCTCCCTGGGGGCAATCAGTTTCTGGATG

TGTTCTAATGGATCTTTGCAGTGCAGAATATGCATCTGA

Figure 36

(SEQ ID NO.39)

>PR8HA-63G283G-403Y411Y422Y433Y.seq

ATGAAGGCTAACCTGCTGGTGCTGCTGAGCGCCCTGGCTGCCGCTGATGCCGATACCATCTGCATCGGCTACCACGCCAA

CAACAGCACCGACACCGTGGATACCGTGCTGGAAAAGAACGTGACCGTGACCCACAGCGTGAACCTGCTGGAAGATAGCC

ACAACGGCAAGCTGTGCCGGCTGAAGGGCgagaacctgtattttcaaggcAAGTGCAATATCGCCGGCTGGCTGCTGGGC

AACCCCGAGTGTGATCCTCTGCTGCCTGTGCGGAGCTGGTCCTACATCGTGGAAACCCCCAACAGCGAGAACGGCATCTG

CTACCCCGGCGACTTCATCGACTACGAGGAACTGCGCGAGCAGCTGAGCAGCGTGTCCAGCTTCGAGAGATTCGAGATCT

TCCCCAAAGAGAGCAGCTGGCCCAACCACAACACCAACGGCGTGACAGCCGCCTGTAGCCACGAGGGCAAGAGCAGCTTC

TACAGAAACCTGCTGTGGCTGACCGAGAAAGAGGGCAGCTACCCCAAGCTGAAGAACAGCTACGTGAACAAGAAAGGCAA

AGAGGTGCTGGTGCTGTGGGGCATCCACCACCCCCCCAACTCTAAAGAGCAGCAGAACATCTACCAGAACGAGAACGCCT

ACGTGTCCGTCGTGACCAGCAACTACAACCGGCGGTTCACCCCCGAGATCGCCGAGAGGCCTAAAGTGCGGGATCAGGCC

GGCAGAATGAACTACTACTGGACCCTGCTGAAGCCCGGCGACACCATCATCTTCGAGGCCAACGGCAACCTGATCGCCCC

TATGTACGCCTTCGCCCTGAGCAGAGGCTTCGGCAGCGGCATCATCACCgaaaacctgtacttccaaggatccAACGCCA

GCATGCACGAGTGCAACACCAAGTGCCAGACCCCGCTCGGAGCTATAAACAGCAGTCTCCCTTACCAGAATATACACCCA

GTCACAATAGGAGAGTGCCCAAAATACGTCAGGAGTGCCAAATTGAGGATGGTTACAGGACTAAGGAACACTCCGTCCAT

TCAATCCAGAGGTCTATTTGGAGCCATTGCCGGTTTTATTGAAGGGGGATGGACTGGAATGATAGATGGATGGTATGGTT

ATCATCATCAGAATGAACAGGGATCAGGCTATGCAGCGGATCAAAAAAGCACACAAAATGCCATTAACGGGATTACAAAC

AAGGTGAACACTGTTATCGAGAAAATGtACATTCAATTCACAGCTGTGGGTtAcGAATTCAACAAATTAGAAAAAAGGAT

GGAAtAcTTAAATAAAAAAGTTGATGATGGATTTCTGtACATTTGGACATATAATGCAGAATTGTTAGTTCTACTGGAAA

ATGAAAGGACTCTGGATTTCCATGACTCAAATGTGAAGAATCTGTATGAGAAAGTAAAAAGCCAATTAAAGAATAATGCC

AAAGAAATCGGAAATGGATGTTTTGAGTTCTACCACAAGTGTGACAATGAATGCATGGAAAGTGTAAGAAATGGGACTTA

TGATTATCCCAAATATTCAGAAGAGTCAAAGTTGAACAGGGAAAAGGTAGATGGAGTGAAATTGGAATCAATGGGGATCT

ATCAGATTCTGGCGATCTACTCAACTGTCGCCAGTTCACTGGTGCTTTTGGTCTCCCTGGGGGCAATCAGTTTCTGGATG

TGTTCTAATGGATCTTTGCAGTGCAGAATATGCATCTGA

Figure 37

(SEQ ID NO.40)

>PR8HA-63G286S-403Y433Y.seq

ATGAAGGCAAACCTACTGGTCCTGTTAAGTGCACTTGCAGCTGCAGATGCAGACACAATATGTATAGGCTACCATGCGAA

CAATTCAACCGACACTGTTGACACAGTACTCGAGAAGAATGTGACAGTGACACACTCTGTTAACCTGCTCGAAGACAGCC

ACAACGGAAAACTATGTAGATTAAAAGGAgagaatctgtacttccagggaAAATGTAACATCGCCGGATGGCTCTTGGGA

AACCCAGAATGCGACCCACTGCTTCCAGTGAGATCATGGTCCTACATTGTAGAAACACCAAACTCTGAGAATGGAATATG

TTATCCAGGAGATTTCATCGACTATGAGGAGCTGAGGGAGCAATTGAGCTCAGTGTCATCATTCGAAAGATTCGAAATAT

TTCCCAAAGAAAGCTCATGGCCCAACCACAACACAAACGGAGTAACGGCAGCATGCTCCCATGAGGGGAAAAGCAGTTTT

TACAGAAATTTGCTATGGCTGACGGAGAAGGAGGGCTCATACCCAAAGCTGAAAAATTCTTATGTGAACAAAAAAGGGAA

AGAAGTCCTTGTACTGTGGGGTATTCATCACCCGCCTAACAGTAAGGAACAACAGAATATCTATCAGAATGAAAATGCTT

ATGTCTCTGTAGTGACTTCAAATTATAACAGGAGATTTACCCCGGAAATAGCAGAAAGACCCAAAGTAAGAGATCAAGCT

GGGAGGATGAACTATTACTGGACCTTGCTAAAACCCGGAGACACAATAATATTTGAGGCAAATGGAAATCTAATAGCACC

AATGTATGCTTTCGCACTGAGTAGAGGCTTTGGGTCCGGCATCATCACCTCAAACGCAgagaatctgtacttccagagcT CAATGCATGAGTGTAACACGAAGTGTCAAACACCgCTcGGAGCTATAAACAGCAGTCTCCCTTACCAGAATATACACCCA

GTCACAATAGGAGAGTGCCCAAAATACGTCAGGAGTGCCAAATTGAGGATGGTTACAGGACTAAGGAACACTCCGTCCAT

TCAATCCAGAGGTCTATTTGGAGCCATTGCCGGTTTTATTGAAGGGGGATGGACTGGAATGATAGATGGATGGTATGGTT

ATCATCATCAGAATGAACAGGGATCAGGCTATGCAGCGGATCAAAAAAGCACACAAAATGCCATTAACGGGATTACAAAC

AAGGTGAACACTGTTATCGAGAAAATGtACATTCAATTCACAGCTGTGGGTAAAGAATTCAACAAATTAGAAAAAAGGAT

GGAAAATTTAAATAAAAAAGTTGATGATGGATTTCTGtACATTTGGACATATAATGCAGAATTGTTAGTTCTACTGGAAA

ATGAAAGGACTCTGGATTTCCATGACTCAAATGTGAAGAATCTGTATGAGAAAGTAAAAAGCCAATTAAAGAATAATGCC

AAAGAAATCGGAAATGGATGTTTTGAGTTCTACCACAAGTGTGACAATGAATGCATGGAAAGTGTAAGAAATGGGACTTA

TGATTATCCCAAATATTCAGAAGAGTCAAAGTTGAACAGGGAAAAGGTAGATGGAGTGAAATTGGAATCAATGGGGATCT

ATCAGATTCTGGCGATCTACTCAACTGTCGCCAGTTCACTGGTGCTTTTGGTCTCCCTGGGGGCAATCAGTTTCTGGATG

TGTTCTAATGGATCTTTGCAGTGCAGAATATGCATCTGA

Figure 38

(SEQ ID NO.41)

>PR8HA-63G286S-411Y422Y.seq

ATGAAGGCAAACCTACTGGTCCTGTTAAGTGCACTTGCAGCTGCAGATGCAGACACAATATGTATAGGCTACCATGCGAA

CAATTCAACCGACACTGTTGACACAGTACTCGAGAAGAATGTGACAGTGACACACTCTGTTAACCTGCTCGAAGACAGCC

ACAACGGAAAACTATGTAGATTAAAAGGAgagaatctgtacttccagggaAAATGTAACATCGCCGGATGGCTCTTGGGA

AACCCAGAATGCGACCCACTGCTTCCAGTGAGATCATGGTCCTACATTGTAGAAACACCAAACTCTGAGAATGGAATATG

TTATCCAGGAGATTTCATCGACTATGAGGAGCTGAGGGAGCAATTGAGCTCAGTGTCATCATTCGAAAGATTCGAAATAT

TTCCCAAAGAAAGCTCATGGCCCAACCACAACACAAACGGAGTAACGGCAGCATGCTCCCATGAGGGGAAAAGCAGTTTT

TACAGAAATTTGCTATGGCTGACGGAGAAGGAGGGCTCATACCCAAAGCTGAAAAATTCTTATGTGAACAAAAAAGGGAA

AGAAGTCCTTGTACTGTGGGGTATTCATCACCCGCCTAACAGTAAGGAACAACAGAATATCTATCAGAATGAAAATGCTT

ATGTCTCTGTAGTGACTTCAAATTATAACAGGAGATTTACCCCGGAAATAGCAGAAAGACCCAAAGTAAGAGATCAAGCT

GGGAGGATGAACTATTACTGGACCTTGCTAAAACCCGGAGACACAATAATATTTGAGGCAAATGGAAATCTAATAGCACC

AATGTATGCTTTCGCACTGAGTAGAGGCTTTGGGTCCGGCATCATCACCTCAAACGCAgagaatctgtacttccagagcT CAATGCATGAGTGTAACACGAAGTGTCAAACACCgCTcGGAGCTATAAACAGCAGTCTCCCTTACCAGAATATACACCCA

GTCACAATAGGAGAGTGCCCAAAATACGTCAGGAGTGCCAAATTGAGGATGGTTACAGGACTAAGGAACACTCCGTCCAT

TCAATCCAGAGGTCTATTTGGAGCCATTGCCGGTTTTATTGAAGGGGGATGGACTGGAATGATAGATGGATGGTATGGTT

ATCATCATCAGAATGAACAGGGATCAGGCTATGCAGCGGATCAAAAAAGCACACAAAATGCCATTAACGGGATTACAAAC

AAGGTGAACACTGTTATCGAGAAAATGAACATTCAATTCACAGCTGTGGGTtAcGAATTCAACAAATTAGAAAAAAGGAT

GGAAtAcTTAAATAAAAAAGTTGATGATGGATTTCTGGACATTTGGACATATAATGCAGAATTGTTAGTTCTACTGGAAA

ATGAAAGGACTCTGGATTTCCATGACTCAAATGTGAAGAATCTGTATGAGAAAGTAAAAAGCCAATTAAAGAATAATGCC

AAAGAAATCGGAAATGGATGTTTTGAGTTCTACCACAAGTGTGACAATGAATGCATGGAAAGTGTAAGAAATGGGACTTA

TGATTATCCCAAATATTCAGAAGAGTCAAAGTTGAACAGGGAAAAGGTAGATGGAGTGAAATTGGAATCAATGGGGATCT

ATCAGATTCTGGCGATCTACTCAACTGTCGCCAGTTCACTGGTGCTTTTGGTCTCCCTGGGGGCAATCAGTTTCTGGATG

TGTTCTAATGGATCTTTGCAGTGCAGAATATGCATCTGA

Figure 39

(SEQ ID NO.42)

>PR8HA-63G286S-403Y411Y422Y433Y.seq

ATGAAGGCAAACCTACTGGTCCTGTTAAGTGCACTTGCAGCTGCAGATGCAGACACAATATGTATAGGCTACCATGCGAA

CAATTCAACCGACACTGTTGACACAGTACTCGAGAAGAATGTGACAGTGACACACTCTGTTAACCTGCTCGAAGACAGCC

ACAACGGAAAACTATGTAGATTAAAAGGAgagaatctgtacttccagggaAAATGTAACATCGCCGGATGGCTCTTGGGA

AACCCAGAATGCGACCCACTGCTTCCAGTGAGATCATGGTCCTACATTGTAGAAACACCAAACTCTGAGAATGGAATATG

TTATCCAGGAGATTTCATCGACTATGAGGAGCTGAGGGAGCAATTGAGCTCAGTGTCATCATTCGAAAGATTCGAAATAT

TTCCCAAAGAAAGCTCATGGCCCAACCACAACACAAACGGAGTAACGGCAGCATGCTCCCATGAGGGGAAAAGCAGTTTT

TACAGAAATTTGCTATGGCTGACGGAGAAGGAGGGCTCATACCCAAAGCTGAAAAATTCTTATGTGAACAAAAAAGGGAA

AGAAGTCCTTGTACTGTGGGGTATTCATCACCCGCCTAACAGTAAGGAACAACAGAATATCTATCAGAATGAAAATGCTT

ATGTCTCTGTAGTGACTTCAAATTATAACAGGAGATTTACCCCGGAAATAGCAGAAAGACCCAAAGTAAGAGATCAAGCT

GGGAGGATGAACTATTACTGGACCTTGCTAAAACCCGGAGACACAATAATATTTGAGGCAAATGGAAATCTAATAGCACC

AATGTATGCTTTCGCACTGAGTAGAGGCTTTGGGTCCGGCATCATCACCTCAAACGCAgagaatctgtacttccagagcT CAATGCATGAGTGTAACACGAAGTGTCAAACACCgCTcGGAGCTATAAACAGCAGTCTCCCTTACCAGAATATACACCCA

GTCACAATAGGAGAGTGCCCAAAATACGTCAGGAGTGCCAAATTGAGGATGGTTACAGGACTAAGGAACACTCCGTCCAT

TCAATCCAGAGGTCTATTTGGAGCCATTGCCGGTTTTATTGAAGGGGGATGGACTGGAATGATAGATGGATGGTATGGTT

ATCATCATCAGAATGAACAGGGATCAGGCTATGCAGCGGATCAAAAAAGCACACAAAATGCCATTAACGGGATTACAAAC

AAGGTGAACACTGTTATCGAGAAAATGtACATTCAATTCACAGCTGTGGGTtAcGAATTCAACAAATTAGAAAAAAGGAT

GGAAtAcTTAAATAAAAAAGTTGATGATGGATTTCTGtACATTTGGACATATAATGCAGAATTGTTAGTTCTACTGGAAA

ATGAAAGGACTCTGGATTTCCATGACTCAAATGTGAAGAATCTGTATGAGAAAGTAAAAAGCCAATTAAAGAATAATGCC

AAAGAAATCGGAAATGGATGTTTTGAGTTCTACCACAAGTGTGACAATGAATGCATGGAAAGTGTAAGAAATGGGACTTA

TGATTATCCCAAATATTCAGAAGAGTCAAAGTTGAACAGGGAAAAGGTAGATGGAGTGAAATTGGAATCAATGGGGATCT

ATCAGATTCTGGCGATCTACTCAACTGTCGCCAGTTCACTGGTGCTTTTGGTCTCCCTGGGGGCAATCAGTTTCTGGATG

TGTTCTAATGGATCTTTGCAGTGCAGAATATGCATCTGA

Figure 40

(SEQ ID NO.43)

>PR8HA-48G291G-403Y433Y.seq

ATGAAGGCTAACCTGCTGGTGCTGCTGAGCGCCCTGGCTGCCGCTGATGCCGATACCATCTGCATCGGCTACCACGCCAA

CAACAGCACCGACACCGTGGATACCGTGCTGGAAAAGAACGTGACCGTGACCCACAGCGTGGAAAACCTGTATTTTCAAG

GCAATCTGCTGGAAGATAGCCACAACGGCAAGCTGTGCCGGCTGAAGGGAATCGCCCCTCTGCAGCTGGGCAAGTGCAAT

ATCGCCGGCTGGCTGCTGGGCAACCCCGAGTGTGATCCTCTGCTGCCTGTGCGGAGCTGGTCCTACATCGTGGAAACCCC

CAACAGCGAGAACGGCATCTGCTACCCCGGCGACTTCATCGACTACGAGGAACTGCGCGAGCAGCTGAGCAGCGTGTCCA

GCTTCgaaAGATTCGAGATCTTCCCCAAAGAGAGCAGCTGGCCCAACCACAACACCAACGGCGTGACAGCCGCCTGTAGC

CACGAGGGCAAGAGCAGCTTCTACCGGAACCTGCTGTGGCTGACCGAGAAAGAGGGCAGCTACCCCAAGCTGAAGAACAG

CTACGTGAACAAGAAAGGCAAAGAGGTGCTGGTGCTGTGGGGCATCCACCACCCCCCCAACTCTAAAGAGCAGCAGAACA

TCTACCAGAACGAGAACGCCTACGTGTCCGTCGTGACCAGCAACTACAACCGGCGGTTCACCCCCGAGATCGCCGAGAGG

CCTAAAGTGCGGGATCAGGCCGGCAGAATGAACTACTACTGGACCCTGCTGAAGCCCGGCGACACCATCATCTTCGAGGC

CAACGGCAACCTGATCGCCCCTATGTACGCCTTCGCCCTGAGCAGAGGCTTCGGCAGCGGCATCATCACCAGCAACGCCA

GCATGCACGAGTGCGAGAACCTGTACTTCCAAGGGAACACCAAGTGCCAGACCCCGCTCGGAGCTATAAACAGCAGTCTC

CCTTACCAGAATATACACCCAGTCACAATAGGAGAGTGCCCAAAATACGTCAGGAGTGCCAAATTGAGGATGGTTACAGG

ACTAAGGAACACTCCGTCCATTCAATCCAGAGGTCTATTTGGAGCCATTGCCGGTTTTATTGAAGGCGGATGGACTGGAA

TGATAGATGGATGGTATGGTTATCATCATCAGAATGAACAGGGATCAGGCTATGCAGCGGATCAAAAAAGCACACAAAAT

GCCATTAACGGGATTACAAACAAGGTGAACACTGTTATCGAGAAAATGtACATTCAATTCACAGCTGTGGGTAAAGAATT

CAACAAATTAGAAAAAAGGATGGAAAATTTAAATAAAAAAGTTGATGATGGATTTCTGtACATTTGGACATATAATGCAG

AATTGTTAGTTCTACTGGAAAATGAAAGGACTCTGGATTTCCATGACTCAAATGTGAAGAATCTGTATGAGAAAGTAAAA

AGCCAATTAAAGAATAATGCCAAAGAAATCGGAAATGGATGTTTTGAGTTCTACCACAAGTGTGACAATGAATGCATGGA

AAGTGTAAGAAATGGGACTTATGATTATCCCAAATATTCAGAAGAGTCAAAGTTGAACAGGGAAAAGGTAGATGGAGTGA

AATTGGAATCAATGGGGATCTATCAGATTCTGGCGATCTACTCAACTGTCGCCAGTTCACTGGTGCTTTTGGTCTCCCTG

GGGGCAATCAGTTTCTGGATGTGTTCTAATGGATCTTTGCAGTGCAGAATATGCATCTGA

Figure 41

(SEQ ID NO.44)

>PR8HA-48G291G-411Y422Y.seq

ATGAAGGCTAACCTGCTGGTGCTGCTGAGCGCCCTGGCTGCCGCTGATGCCGATACCATCTGCATCGGCTACCACGCCAA

CAACAGCACCGACACCGTGGATACCGTGCTGGAAAAGAACGTGACCGTGACCCACAGCGTGGAAAACCTGTATTTTCAAG

GCAATCTGCTGGAAGATAGCCACAACGGCAAGCTGTGCCGGCTGAAGGGAATCGCCCCTCTGCAGCTGGGCAAGTGCAAT

ATCGCCGGCTGGCTGCTGGGCAACCCCGAGTGTGATCCTCTGCTGCCTGTGCGGAGCTGGTCCTACATCGTGGAAACCCC

CAACAGCGAGAACGGCATCTGCTACCCCGGCGACTTCATCGACTACGAGGAACTGCGCGAGCAGCTGAGCAGCGTGTCCA

GCTTCgaaAGATTCGAGATCTTCCCCAAAGAGAGCAGCTGGCCCAACCACAACACCAACGGCGTGACAGCCGCCTGTAGC

CACGAGGGCAAGAGCAGCTTCTACCGGAACCTGCTGTGGCTGACCGAGAAAGAGGGCAGCTACCCCAAGCTGAAGAACAG

CTACGTGAACAAGAAAGGCAAAGAGGTGCTGGTGCTGTGGGGCATCCACCACCCCCCCAACTCTAAAGAGCAGCAGAACA

TCTACCAGAACGAGAACGCCTACGTGTCCGTCGTGACCAGCAACTACAACCGGCGGTTCACCCCCGAGATCGCCGAGAGG

CCTAAAGTGCGGGATCAGGCCGGCAGAATGAACTACTACTGGACCCTGCTGAAGCCCGGCGACACCATCATCTTCGAGGC

CAACGGCAACCTGATCGCCCCTATGTACGCCTTCGCCCTGAGCAGAGGCTTCGGCAGCGGCATCATCACCAGCAACGCCA

GCATGCACGAGTGCGAGAACCTGTACTTCCAAGGGAACACCAAGTGCCAGACCCCGCTCGGAGCTATAAACAGCAGTCTC

CCTTACCAGAATATACACCCAGTCACAATAGGAGAGTGCCCAAAATACGTCAGGAGTGCCAAATTGAGGATGGTTACAGG

ACTAAGGAACACTCCGTCCATTCAATCCAGAGGTCTATTTGGAGCCATTGCCGGTTTTATTGAAGGGGGATGGACTGGAA

TGATAGATGGATGGTATGGTTATCATCATCAGAATGAACAGGGATCAGGCTATGCAGCGGATCAAAAAAGCACACAAAAT

GCCATTAACGGGATTACAAACAAGGTGAACACTGTTATCGAGAAAATGAACATTCAATTCACAGCTGTGGGTtAcGAATT

CAACAAATTAGAAAAAAGGATGGAAtAcTTAAATAAAAAAGTTGATGATGGATTTCTGGACATTTGGACATATAATGCAG

AATTGTTAGTTCTACTGGAAAATGAAAGGACTCTGGATTTCCATGACTCAAATGTGAAGAATCTGTATGAGAAAGTAAAA

AGCCAATTAAAGAATAATGCCAAAGAAATCGGAAATGGATGTTTTGAGTTCTACCACAAGTGTGACAATGAATGCATGGA

AAGTGTAAGAAATGGGACTTATGATTATCCCAAATATTCAGAAGAGTCAAAGTTGAACAGGGAAAAGGTAGATGGAGTGA

AATTGGAATCAATGGGGATCTATCAGATTCTGGCGATCTACTCAACTGTCGCCAGTTCACTGGTGCTTTTGGTCTCCCTG

GGGGCAATCAGTTTCTGGATGTGTTCTAATGGATCTTTGCAGTGCAGAATATGCATCTGA

Figure 42

(SEQ ID NO.45)

>PR8HA-48G291G-403Y411Y422Y433Y.seq

ATGAAGGCTAACCTGCTGGTGCTGCTGAGCGCCCTGGCTGCCGCTGATGCCGATACCATCTGCATCGGCTACCACGCCAA

CAACAGCACCGACACCGTGGATACCGTGCTGGAAAAGAACGTGACCGTGACCCACAGCGTGGAAAACCTGTATTTTCAAG

GCAATCTGCTGGAAGATAGCCACAACGGCAAGCTGTGCCGGCTGAAGGGAATCGCCCCTCTGCAGCTGGGCAAGTGCAAT

ATCGCCGGCTGGCTGCTGGGCAACCCCGAGTGTGATCCTCTGCTGCCTGTGCGGAGCTGGTCCTACATCGTGGAAACCCC

CAACAGCGAGAACGGCATCTGCTACCCCGGCGACTTCATCGACTACGAGGAACTGCGCGAGCAGCTGAGCAGCGTGTCCA

GCTTCgaaAGATTCGAGATCTTCCCCAAAGAGAGCAGCTGGCCCAACCACAACACCAACGGCGTGACAGCCGCCTGTAGC

CACGAGGGCAAGAGCAGCTTCTACCGGAACCTGCTGTGGCTGACCGAGAAAGAGGGCAGCTACCCCAAGCTGAAGAACAG

CTACGTGAACAAGAAAGGCAAAGAGGTGCTGGTGCTGTGGGGCATCCACCACCCCCCCAACTCTAAAGAGCAGCAGAACA

TCTACCAGAACGAGAACGCCTACGTGTCCGTCGTGACCAGCAACTACAACCGGCGGTTCACCCCCGAGATCGCCGAGAGG

CCTAAAGTGCGGGATCAGGCCGGCAGAATGAACTACTACTGGACCCTGCTGAAGCCCGGCGACACCATCATCTTCGAGGC

CAACGGCAACCTGATCGCCCCTATGTACGCCTTCGCCCTGAGCAGAGGCTTCGGCAGCGGCATCATCACCAGCAACGCCA

GCATGCACGAGTGCGAGAACCTGTACTTCCAAGGGAACACCAAGTGCCAGACCCCGCTCGGAGCTATAAACAGCAGTCTC

CCTTACCAGAATATACACCCAGTCACAATAGGAGAGTGCCCAAAATACGTCAGGAGTGCCAAATTGAGGATGGTTACAGG

ACTAAGGAACACTCCGTCCATTCAATCCAGAGGTCTATTTGGAGCCATTGCCGGTTTTATTGAAGGGGGATGGACTGGAA

TGATAGATGGATGGTATGGTTATCATCATCAGAATGAACAGGGATCAGGCTATGCAGCGGATCAAAAAAGCACACAAAAT

GCCATTAACGGGATTACAAACAAGGTGAACACTGTTATCGAGAAAATGtACATTCAATTCACAGCTGTGGGTtAcGAATT

CAACAAATTAGAAAAAAGGATGGAAtAcTTAAATAAAAAAGTTGATGATGGATTTCTGtACATTTGGACATATAATGCAG

AATTGTTAGTTCTACTGGAAAATGAAAGGACTCTGGATTTCCATGACTCAAATGTGAAGAATCTGTATGAGAAAGTAAAA

AGCCAATTAAAGAATAATGCCAAAGAAATCGGAAATGGATGTTTTGAGTTCTACCACAAGTGTGACAATGAATGCATGGA

AAGTGTAAGAAATGGGACTTATGATTATCCCAAATATTCAGAAGAGTCAAAGTTGAACAGGGAAAAGGTAGATGGAGTGA

AATTGGAATCAATGGGGATCTATCAGATTCTGGCGATCTACTCAACTGTCGCCAGTTCACTGGTGCTTTTGGTCTCCCTG

GGGGCAATCAGTTTCTGGATGTGTTCTAATGGATCTTTGCAGTGCAGAATATGCATCTGA

Figure 43

(SEQ ID NO.46)

>PR8HA-48G291S-403Y433Y.seq

ATGAAGGCTAACCTGCTGGTGCTGCTGAGCGCCCTGGCTGCCGCTGATGCCGATACCATCTGCATCGGCTACCACGCCAA

CAACAGCACCGACACCGTGGATACCGTGCTGGAAAAGAACGTGACCGTGACCCACAGCGTGGAAAACCTGTATTTTCAAG

GCAATCTGCTGGAAGATAGCCACAACGGCAAGCTGTGCCGGCTGAAGGGAATCGCCCCTCTGCAGCTGGGCAAGTGCAAT

ATCGCCGGCTGGCTGCTGGGCAACCCCGAGTGTGATCCTCTGCTGCCTGTGCGGAGCTGGTCCTACATCGTGGAAACCCC

CAACAGCGAGAACGGCATCTGCTACCCCGGCGACTTCATCGACTACGAGGAACTGCGCGAGCAGCTGAGCAGCGTGTCCA

GCTTCgaaAGATTCGAGATCTTCCCCAAAGAGAGCAGCTGGCCCAACCACAACACCAACGGCGTGACAGCCGCCTGTAGC

CACGAGGGCAAGAGCAGCTTCTACCGGAACCTGCTGTGGCTGACCGAGAAAGAGGGCAGCTACCCCAAGCTGAAGAACAG

CTACGTGAACAAGAAAGGCAAAGAGGTGCTGGTGCTGTGGGGCATCCACCACCCCCCCAACTCTAAAGAGCAGCAGAACA

TCTACCAGAACGAGAACGCCTACGTGTCCGTCGTGACCAGCAACTACAACCGGCGGTTCACCCCCGAGATCGCCGAGAGG

CCTAAAGTGCGGGATCAGGCCGGCAGAATGAACTACTACTGGACCCTGCTGAAGCCCGGCGACACCATCATCTTCGAGGC

CAACGGCAACCTGATCGCCCCTATGTACGCCTTCGCCCTGAGCAGAGGCTTCGGCAGCGGCATCATCACCAGCAACGCCA

GCATGCACGAGTGCGAGAACCTGTACTTCCAAAGCAACACCAAGTGCCAGACCCCGCTCGGAGCTATAAACAGCAGTCTC

CCTTACCAGAATATACACCCAGTCACAATAGGAGAGTGCCCAAAATACGTCAGGAGTGCCAAATTGAGGATGGTTACAGG

ACTAAGGAACACTCCGTCCATTCAATCCAGAGGTCTATTTGGAGCCATTGCCGGTTTTATTGAAGGCGGATGGACTGGAA

TGATAGATGGATGGTATGGTTATCATCATCAGAATGAACAGGGATCAGGCTATGCAGCGGATCAAAAAAGCACACAAAAT

GCCATTAACGGGATTACAAACAAGGTGAACACTGTTATCGAGAAAATGtACATTCAATTCACAGCTGTGGGTAAAGAATT

CAACAAATTAGAAAAAAGGATGGAAAATTTAAATAAAAAAGTTGATGATGGATTTCTGtACATTTGGACATATAATGCAG

AATTGTTAGTTCTACTGGAAAATGAAAGGACTCTGGATTTCCATGACTCAAATGTGAAGAATCTGTATGAGAAAGTAAAA

AGCCAATTAAAGAATAATGCCAAAGAAATCGGAAATGGATGTTTTGAGTTCTACCACAAGTGTGACAATGAATGCATGGA

AAGTGTAAGAAATGGGACTTATCATTATCCCAAATATTCAGAAGAGTCAAAGTTGAACAGGGAAAAGGTAGATGGACTCA

AATTGGAATCAATGGGGATCTATCAGATTCTGGCGATCTACTCAACTGTCGCCAGTTCACTGGTGCTTTTGGTCTCCCTG

GGGGCAATCAGTTTCTGGATGTGTTCTAATGGATCTTTGCAGTGCAGAATATGCATCTGA

Figure 44

(SEQ ID NO.47)

>PR8HA-48G291S-411Y422Y.seq

ATGAAGGCTAACCTGCTGGTGCTGCTGAGCGCCCTGGCTGCCGCTGATGCCGATACCATCTGCATCGGCTACCACGCCAA

CAACAGCACCGACACCGTGGATACCGTGCTGGAAAAGAACGTGACCGTGACCCACAGCGTGGAAAACCTGTATTTTCAAG

GCAATCTGCTGGAAGATAGCCACAACGGCAAGCTGTGCCGGCTGAAGGGAATCGCCCCTCTGCAGCTGGGCAAGTGCAAT

ATCGCCGGCTGGCTGCTGGGCAACCCCGAGTGTGATCCTCTGCTGCCTGTGCGGAGCTGGTCCTACATCGTGGAAACCCC

CAACAGCGAGAACGGCATCTGCTACCCCGGCGACTTCATCGACTACGAGGAACTGCGCGAGCAGCTGAGCAGCGTGTCCA

GCTTCgaaAGATTCGAGATCTTCCCCAAAGAGAGCAGCTGGCCCAACCACAACACCAACGGCGTGACAGCCGCCTGTAGC

CACGAGGGCAAGAGCAGCTTCTACCGGAACCTGCTGTGGCTGACCGAGAAAGAGGGCAGCTACCCCAAGCTGAAGAACAG

CTACGTGAACAAGAAAGGCAAAGAGGTGCTGGTGCTGTGGGGCATCCACCACCCCCCCAACTCTAAAGAGCAGCAGAACA

TCTACCAGAACGAGAACGCCTACGTGTCCGTCGTGACCAGCAACTACAACCGGCGGTTCACCCCCGAGATCGCCGAGAGG

CCTAAAGTGCGGGATCAGGCCGGCAGAATGAACTACTACTGGACCCTGCTGAAGCCCGGCGACACCATCATCTTCGAGGC

CAACGGCAACCTGATCGCCCCTATGTACGCCTTCGCCCTGAGCAGAGGCTTCGGCAGCGGCATCATCACCAGCAACGCCA

GCATGCACGAGTGCGAGAACCTGTACTTCCAAAGCAACACCAAGTGCCAGACCCCGCTCGGAGCTATAAACAGCAGTCTC

CCTTACCAGAATATACACCCAGTCACAATAGGAGAGTGCCCAAAATACGTCAGGAGTGCCAAATTGAGGATGGTTACAGG

ACTAAGGAACACTCCGTCCATTCAATCCAGAGGTCTATTTGGAGCCATTGCCGGTTTTATTGAAGGGGGATGGACTGGAA

TGATAGATGGATGGTATGGTTATCATCATCAGAATGAACAGGGATCAGGCTATGCAGCGGATCAAAAAAGCACACAAAAT

GCCATTAACGGGATTACAAACAAGGTGAACACTGTTATCGAGAAAATGAACATTCAATTCACAGCTGTGGGTtAcGAATT

CAACAAATTAGAAAAAAGGATGGAAtAcTTAAATAAAAAAGTTGATGATGGATTTCTGGACATTTGGACATATAATGCAG

AATTGTTAGTTCTACTGGAAAATGAAAGGACTCTGGATTTCCATGACTCAAATGTGAAGAATCTGTATGAGAAAGTAAAA

AGCCAATTAAAGAATAATGCCAAAGAAATCGGAAATGGATGTTTTGAGTTCTACCACAAGTGTGACAATGAATGCATGGA

AAGTGTAAGAAATGGGACTTATGATTATCCCAAATATTCAGAAGAGTCAAAGTTGAACAGGGAAAAGGTAGATGGAGTGA

AATTGGAATCAATGGGGATCTATCAGATTCTGGCGATCTACTCAACTGTCGCCAGTTCACTGGTGCTTTTGGTCTCCCTG

GGGGCAATCAGTTTCTGGATGTGTTCTAATGGATCTTTGCAGTGCAGAATATGCATCTCA

Figure 45

(SEQ ID NO.48)

>PR8HA-48G291S-403Y411Y422Y433Y.seq

ATGAAGGCTAACCTGCTGGTGCTGCTGAGCGCCCTGGCTGCCGCTGATGCCGATACCATCTGCATCGGCTACCACGCCAA

CAACAGCACCGACACCGTGGATACCGTGCTGGAAAAGAACGTGACCGTGACCCACAGCGTGGAAAACCTGTATTTTCAAG

GCAATCTGCTGGAAGATAGCCACAACGGCAAGCTGTGCCGGCTGAAGGGAATCGCCCCTCTGCAGCTGGGCAAGTGCAAT

ATCGCCGGCTGGCTGCTGGGCAACCCCGAGTGTGATCCTCTGCTGCCTGTGCGGAGCTGGTCCTACATCGTGGAAACCCC

CAACAGCGAGAACGGCATCTGCTACCCCGGCGACTTCATCGACTACGAGGAACTGCGCGAGCAGCTGAGCAGCGTGTCCA

GCTTCgaaAGATTCGAGATCTTCCCCAAAGAGAGCAGCTGGCCCAACCACAACACCAACGGCGTGACAGCCGCCTGTAGC

CACGAGGGCAAGAGCAGCTTCTACCGGAACCTGCTGTGGCTGACCGAGAAAGAGGGCAGCTACCCCAAGCTGAAGAACAG

CTACGTGAACAAGAAAGGCAAAGAGGTGCTGGTGCTGTGGGGCATCCACCACCCCCCCAACTCTAAAGAGCAGCAGAACA

TCTACCAGAACGAGAACGCCTACGTGTCCGTCGTGACCAGCAACTACAACCGGCGGTTCACCCCCGAGATCGCCGAGAGG

CCTAAAGTGCGGGATCAGGCCGGCAGAATGAACTACTACTGGACCCTGCTGAAGCCCGGCGACACCATCATCTTCGAGGC

CAACGGCAACCTGATCGCCCCTATGTACGCCTTCGCCCTGAGCAGAGGCTTCGGCAGCGGCATCATCACCAGCAACGCCA

GCATGCACGAGTGCGAGAACCTGTACTTCCAAAGCAACACCAAGTGCCAGACCCCGCTCGGAGCTATAAACAGCAGTCTC

CCTTACCAGAATATACACCCAGTCACAATAGGAGAGTGCCCAAAATACGTCAGGAGTGCCAAATTGAGGATGGTTACAGG

ACTAAGGAACACTCCGTCCATTCAATCCAGAGGTCTATTTGGAGCCATTGCCGGTTTTATTGAAGGGGGATGGACTGGAA

TGATAGATGGATGGTATGGTTATCATCATCAGAATGAACAGGGATCAGGCTATGCAGCGGATCAAAAAAGCACACAAAAT

GCCATTAACGGGATTACAAACAAGGTGAACACTGTTATCGAGAAAATGtACATTCAATTCACAGCTGTGGGTtAcGAATT

CAACAAATTAGAAAAAAGGATGGAAtAcTTAAATAAAAAAGTTGATGATGGATTTCTGtACATTTGGACATATAATGCAG

AATTGTTAGTTCTACTGGAAAATGAAAGGACTCTGGATTTCCATGACTCAAATGTGAAGAATCTGTATGAGAAAGTAAAA

AGCCAATTAAAGAATAATGCCAAAGAAATCGGAAATGGATGTTTTGAGTTCTACCACAAGTGTGACAATGAATGCATGGA

AAGTGTAAGAAATGGGACTTATGATTATCCCAAATATTCAGAAGAGTCAAAGTTGAACAGGGAAAAGGTAGATGGAGTGA

AATTGGAATCAATGGGGATCTATCAGATTCTGGCGATCTACTCAACTGTCGCCAGTTCACTGGTGCTTTTGGTCTCCCTG

GGGGCAATCAGTTTCTGGATGTGTTCTAATGGATCTTTGCAGTGCAGAATATGCATCTGA

Figure 46 A

```
PR8HA-291G.seq      ATGAAGGCAAACCTACTGGTCCTGTTAAGTGCACTTGCAGCTGCAGATGCAGACACAATA 60
PR8HA-291S.seq      ATGAAGGCAAACCTACTGGTCCTGTTAAGTGCACTTGCAGCTGCAGATGCAGACACAATA 60
PR8HA-63G.seq       ATGAAGGCAAACCTACTGGTCCTGTTAAGTGCACTTGCAGCTGCAGATGCAGACACAATA 60
PR8HA-WT.seq        ATGAAGGCAAACCTACTGGTCCTGTTAAGTGCACTTGCAGCTGCAGATGCAGACACAATA 60
PR8HA-48G.seq       ATGAAGGCAAACCTACTGGTCCTGTTAAGTGCACTTGCAGCTGCAGATGCAGACACAATA 60
PR8HA-278S.seq      ATGAAGGCAAACCTACTGGTCCTGTTAAGTGCACTTGCAGCTGCAGATGCAGACACAATA 60
PR8HA-282S.seq      ATGAAGGCAAACCTACTGGTCCTGTTAAGTGCACTTGCAGCTGCAGATGCAGACACAATA 60
PR8HA-283G.seq      ATGAAGGCAAACCTACTGGTCCTGTTAAGTGCACTTGCAGCTGCAGATGCAGACACAATA 60
PR8HA-286S.seq      ATGAAGGCAAACCTACTGGTCCTGTTAAGTGCACTTGCAGCTGCAGATGCAGACACAATA 60
                    ************************************************************

PR8HA-291G.seq      TGTATAGGCTACCATGCGAACAATTCAACCGACACTGTTGACACAGTACTCGAGAAGAAT 120
PR8HA-291S.seq      TGTATAGGCTACCATGCGAACAATTCAACCGACACTGTTGACACAGTACTCGAGAAGAAT 120
PR8HA-63G.seq       TGTATAGGCTACCATGCGAACAATTCAACCGACACTGTTGACACAGTACTCGAGAAGAAT 120
PR8HA-WT.seq        TGTATAGGCTACCATGCGAACAATTCAACCGACACTGTTGACACAGTACTCGAGAAGAAT 120
PR8HA-48G.seq       TGTATAGGCTACCATGCGAACAATTCAACCGACACTGTTGACACAGTACTCGAGAAGAAT 120
PR8HA-278S.seq      TGTATAGGCTACCATGCGAACAATTCAACCGACACTGTTGACACAGTACTCGAGAAGAAT 120
PR8HA-282S.seq      TGTATAGGCTACCATGCGAACAATTCAACCGACACTGTTGACACAGTACTCGAGAAGAAT 120
PR8HA-283G.seq      TGTATAGGCTACCATGCGAACAATTCAACCGACACTGTTGACACAGTACTCGAGAAGAAT 120
PR8HA-286S.seq      TGTATAGGCTACCATGCGAACAATTCAACCGACACTGTTGACACAGTACTCGAGAAGAAT 120
                    ************************************************************

PR8HA-291G.seq      GTGACAGTGACACACTCTGTT---------------------AACCTGCTCGAAGACAGC 159
PR8HA-291S.seq      GTGACAGTGACACACTCTGTT---------------------AACCTGCTCGAAGACAGC 159
PR8HA-63G.seq       GTGACAGTGACACACTCTGTT---------------------AACCTGCTCGAAGACAGC 159
PR8HA-WT.seq        GTGACAGTGACACACTCTGTT---------------------AACCTGCTCGAAGACAGC 159
PR8HA-48G.seq       GTGACAGTGACACACTCTGTTGAGAACCTGTACTTCCAGGGAAACCTGCTCGAAGACAGC 180
PR8HA-278S.seq      GTGACAGTGACACACTCTGTT---------------------AACCTGCTCGAAGACAGC 159
PR8HA-282S.seq      GTGACAGTGACACACTCTGTT---------------------AACCTGCTCGAAGACAGC 159
PR8HA-283G.seq      GTGACAGTGACACACTCTGTT---------------------AACCTGCTCGAAGACAGC 159
PR8HA-286S.seq      GTGACAGTGACACACTCTGTT---------------------AACCTGCTCGAAGACAGC 159
                    *********************                     ******************

PR8HA-291G.seq      CACAACGGAAAACTATGTAGATTAAAAGGA-ATAGCCC-CACTACAATTGGGGAAATGTA 217
PR8HA-291S.seq      CACAACGGAAAACTATGTAGATTAAAAGGA-ATAGCCC-CACTACAATTGGGGAAATGTA 217
PR8HA-63G.seq       CACAACGGAAAACTATGTAGATTAAAAGGAGAGAATCTGTACTTCCA--GGGAAAATGTA 217
PR8HA-WT.seq        CACAACGGAAAACTATGTAGATTAAAAGGA-ATAGCCC-CACTACAATTGGGGAAATGTA 217
PR8HA-48G.seq       CACAACGGAAAACTATGTAGATTAAAAGGA-ATAGCCC-CACTACAATTGGGGAAATGTA 238
PR8HA-278S.seq      CACAACGGAAAACTATGTAGATTAAAAGGA-ATAGCCC-CACTACAATTGGGGAAATGTA 217
PR8HA-282S.seq      CACAACGGAAAACTATGTAGATTAAAAGGA-ATAGCCC-CACTACAATTGGGGAAATGTA 217
PR8HA-283G.seq      CACAACGGAAAACTATGTAGATTAAAAGGA-ATAGCCC-CACTACAATTGGGGAAATGTA 217
PR8HA-286S.seq      CACAACGGAAAACTATGTAGATTAAAAGGA-ATAGCCC-CACTACAATTGGGGAAATGTA 217
                    ****************************** * *  *   *** * *  *** *******

PR8HA-291G.seq      ACATCGCCGGATGGCTCTTGGGAAACCCAGAATGCGACCCACTGCTTCCAGTGAGATCAT 277
PR8HA-291S.seq      ACATCGCCGGATGGCTCTTGGGAAACCCAGAATGCGACCCACTGCTTCCAGTGAGATCAT 277
PR8HA-63G.seq       ACATCGCCGGATGGCTCTTGGGAAACCCAGAATGCGACCCACTGCTTCCAGTGAGATCAT 277
PR8HA-WT.seq        ACATCGCCGGATGGCTCTTGGGAAACCCAGAATGCGACCCACTGCTTCCAGTGAGATCAT 277
PR8HA-48G.seq       ACATCGCCGGATGGCTCTTGGGAAACCCAGAATGCGACCCACTGCTTCCAGTGAGATCAT 298
PR8HA-278S.seq      ACATCGCCGGATGGCTCTTGGGAAACCCAGAATGCGACCCACTGCTTCCAGTGAGATCAT 277
PR8HA-282S.seq      ACATCGCCGGATGGCTCTTGGGAAACCCAGAATGCGACCCACTGCTTCCAGTGAGATCAT 277
PR8HA-283G.seq      ACATCGCCGGATGGCTCTTGGGAAACCCAGAATGCGACCCACTGCTTCCAGTGAGATCAT 277
PR8HA-286S.seq      ACATCGCCGGATGGCTCTTGGGAAACCCAGAATGCGACCCACTGCTTCCAGTGAGATCAT 277
                    ************************************************************
```

Figure 46 B

```
PR8HA-291G.seq    GGTCCTACATTGTAGAAACACCAAACTCTGAGAATGGAATATGTTATCCAGGAGATTTCA 337
PR8HA-291S.seq    GGTCCTACATTGTAGAAACACCAAACTCTGAGAATGGAATATGTTATCCAGGAGATTTCA 337
PR8HA-63G.seq     GGTCCTACATTGTAGAAACACCAAACTCTGAGAATGGAATATGTTATCCAGGAGATTTCA 337
PR8HA-WT.seq      GGTCCTACATTGTAGAAACACCAAACTCTGAGAATGGAATATGTTATCCAGGAGATTTCA 337
PR8HA-48G.seq     GGTCCTACATTGTAGAAACACCAAACTCTGAGAATGGAATATGTTATCCAGGAGATTTCA 358
PR8HA-278S.seq    GGTCCTACATTGTAGAAACACCAAACTCTGAGAATGGAATATGTTATCCAGGAGATTTCA 337
PR8HA-282S.seq    GGTCCTACATTGTAGAAACACCAAACTCTGAGAATGGAATATGTTATCCAGGAGATTTCA 337
PR8HA-283G.seq    GGTCCTACATTGTAGAAACACCAAACTCTGAGAATGGAATATGTTATCCAGGAGATTTCA 337
PR8HA-286S.seq    GGTCCTACATTGTAGAAACACCAAACTCTGAGAATGGAATATGTTATCCAGGAGATTTCA 337
                  ************************************************************

PR8HA-291G.seq    TCGACTATGAGGAGCTGAGGGAGCAATTGAGCTCAGTGTCATCATTCGAAAGATTCGAAA 397
PR8HA-291S.seq    TCGACTATGAGGAGCTGAGGGAGCAATTGAGCTCAGTGTCATCATTCGAAAGATTCGAAA 397
PR8HA-63G.seq     TCGACTATGAGGAGCTGAGGGAGCAATTGAGCTCAGTGTCATCATTCGAAAGATTCGAAA 397
PR8HA-WT.seq      TCGACTATGAGGAGCTGAGGGAGCAATTGAGCTCAGTGTCATCATTCGAAAGATTCGAAA 397
PR8HA-48G.seq     TCGACTATGAGGAGCTGAGGGAGCAATTGAGCTCAGTGTCATCATTCGAAAGATTCGAAA 418
PR8HA-278S.seq    TCGACTATGAGGAGCTGAGGGAGCAATTGAGCTCAGTGTCATCATTCGAAAGATTCGAAA 397
PR8HA-282S.seq    TCGACTATGAGGAGCTGAGGGAGCAATTGAGCTCAGTGTCATCATTCGAAAGATTCGAAA 397
PR8HA-283G.seq    TCGACTATGAGGAGCTGAGGGAGCAATTGAGCTCAGTGTCATCATTCGAAAGATTCGAAA 397
PR8HA-286S.seq    TCGACTATGAGGAGCTGAGGGAGCAATTGAGCTCAGTGTCATCATTCGAAAGATTCGAAA 397
                  ************************************************************

PR8HA-291G.seq    TATTTCCCAAAGAAAGCTCATGGCCCAACCACAACACAAACGGAGTAACGGCAGCATGCT 457
PR8HA-291S.seq    TATTTCCCAAAGAAAGCTCATGGCCCAACCACAACACAAACGGAGTAACGGCAGCATGCT 457
PR8HA-63G.seq     TATTTCCCAAAGAAAGCTCATGGCCCAACCACAACACAAACGGAGTAACGGCAGCATGCT 457
PR8HA-WT.seq      TATTTCCCAAAGAAAGCTCATGGCCCAACCACAACACAAACGGAGTAACGGCAGCATGCT 457
PR8HA-48G.seq     TATTTCCCAAAGAAAGCTCATGGCCCAACCACAACACAAACGGAGTAACGGCAGCATGCT 478
PR8HA-278S.seq    TATTTCCCAAAGAAAGCTCATGGCCCAACCACAACACAAACGGAGTAACGGCAGCATGCT 457
PR8HA-282S.seq    TATTTCCCAAAGAAAGCTCATGGCCCAACCACAACACAAACGGAGTAACGGCAGCATGCT 457
PR8HA-283G.seq    TATTTCCCAAAGAAAGCTCATGGCCCAACCACAACACAAACGGAGTAACGGCAGCATGCT 457
PR8HA-286S.seq    TATTTCCCAAAGAAAGCTCATGGCCCAACCACAACACAAACGGAGTAACGGCAGCATGCT 457
                  ************************************************************

PR8HA-291G.seq    CCCATGAGGGGAAAAGCAGTTTTTACAGAAATTTGCTATGGCTGACGGAGAAGGAGGGCT 517
PR8HA-291S.seq    CCCATGAGGGGAAAAGCAGTTTTTACAGAAATTTGCTATGGCTGACGGAGAAGGAGGGCT 517
PR8HA-63G.seq     CCCATGAGGGGAAAAGCAGTTTTTACAGAAATTTGCTATGGCTGACGGAGAAGGAGGGCT 517
PR8HA-WT.seq      CCCATGAGGGGAAAAGCAGTTTTTACAGAAATTTGCTATGGCTGACGGAGAAGGAGGGCT 517
PR8HA-48G.seq     CCCATGAGGGGAAAAGCAGTTTTTACAGAAATTTGCTATGGCTGACGGAGAAGGAGGGCT 538
PR8HA-278S.seq    CCCATGAGGGGAAAAGCAGTTTTTACAGAAATTTGCTATGGCTGACGGAGAAGGAGGGCT 517
PR8HA-282S.seq    CCCATGAGGGGAAAAGCAGTTTTTACAGAAATTTGCTATGGCTGACGGAGAAGGAGGGCT 517
PR8HA-283G.seq    CCCATGAGGGGAAAAGCAGTTTTTACAGAAATTTGCTATGGCTGACGGAGAAGGAGGGCT 517
PR8HA-286S.seq    CCCATGAGGGGAAAAGCAGTTTTTACAGAAATTTGCTATGGCTGACGGAGAAGGAGGGCT 517
                  ************************************************************

PR8HA-291G.seq    CATACCCAAAGCTGAAAAATTCTTATGTGAACAAAAAAGGGAAAGAAGTCCTTGTACTGT 577
PR8HA-291S.seq    CATACCCAAAGCTGAAAAATTCTTATGTGAACAAAAAAGGGAAAGAAGTCCTTGTACTGT 577
PR8HA-63G.seq     CATACCCAAAGCTGAAAAATTCTTATGTGAACAAAAAAGGGAAAGAAGTCCTTGTACTGT 577
PR8HA-WT.seq      CATACCCAAAGCTGAAAAATTCTTATGTGAACAAAAAAGGGAAAGAAGTCCTTGTACTGT 577
PR8HA-48G.seq     CATACCCAAAGCTGAAAAATTCTTATGTGAACAAAAAAGGGAAAGAAGTCCTTGTACTGT 598
PR8HA-278S.seq    CATACCCAAAGCTGAAAAATTCTTATGTGAACAAAAAAGGGAAAGAAGTCCTTGTACTGT 577
PR8HA-282S.seq    CATACCCAAAGCTGAAAAATTCTTATGTGAACAAAAAAGGGAAAGAAGTCCTTGTACTGT 577
PR8HA-283G.seq    CATACCCAAAGCTGAAAAATTCTTATGTGAACAAAAAAGGGAAAGAAGTCCTTGTACTGT 577
PR8HA-286S.seq    CATACCCAAAGCTGAAAAATTCTTATGTGAACAAAAAAGGGAAAGAAGTCCTTGTACTGT 577
                  ************************************************************
```

Figure 46 C

```
PR8HA-291G.seq      GGGGTATTCATCACCCGCCTAACAGTAAGGAACAACAGAATATCTATCAGAATGAAAATG 637
PR8HA-291S.seq      GGGGTATTCATCACCCGCCTAACAGTAAGGAACAACAGAATATCTATCAGAATGAAAATG 637
PR8HA-63G.seq       GGGGTATTCATCACCCGCCTAACAGTAAGGAACAACAGAATATCTATCAGAATGAAAATG 637
PR8HA-WT.seq        GGGGTATTCATCACCCGCCTAACAGTAAGGAACAACAGAATATCTATCAGAATGAAAATG 637
PR8HA-48G.seq       GGGGTATTCATCACCCGCCTAACAGTAAGGAACAACAGAATATCTATCAGAATGAAAATG 658
PR8HA-278S.seq      GGGGTATTCATCACCCGCCTAACAGTAAGGAACAACAGAATATCTATCAGAATGAAAATG 637
PR8HA-282S.seq      GGGGTATTCATCACCCGCCTAACAGTAAGGAACAACAGAATATCTATCAGAATGAAAATG 637
PR8HA-283G.seq      GGGGTATTCATCACCCGCCTAACAGTAAGGAACAACAGAATATCTATCAGAATGAAAATG 637
PR8HA-286S.seq      GGGGTATTCATCACCCGCCTAACAGTAAGGAACAACAGAATATCTATCAGAATGAAAATG 637
                    ************************************************************

PR8HA-291G.seq      CTTATGTCTCTGTAGTGACTTCAAATTATAACAGGAGATTTACCCCGGAAATAGCAGAAA 697
PR8HA-291S.seq      CTTATGTCTCTGTAGTGACTTCAAATTATAACAGGAGATTTACCCCGGAAATAGCAGAAA 697
PR8HA-63G.seq       CTTATGTCTCTGTAGTGACTTCAAATTATAACAGGAGATTTACCCCGGAAATAGCAGAAA 697
PR8HA-WT.seq        CTTATGTCTCTGTAGTGACTTCAAATTATAACAGGAGATTTACCCCGGAAATAGCAGAAA 697
PR8HA-48G.seq       CTTATGTCTCTGTAGTGACTTCAAATTATAACAGGAGATTTACCCCGGAAATAGCAGAAA 718
PR8HA-278S.seq      CTTATGTCTCTGTAGTGACTTCAAATTATAACAGGAGATTTACCCCGGAAATAGCAGAAA 697
PR8HA-282S.seq      CTTATGTCTCTGTAGTGACTTCAAATTATAACAGGAGATTTACCCCGGAAATAGCAGAAA 697
PR8HA-283G.seq      CTTATGTCTCTGTAGTGACTTCAAATTATAACAGGAGATTTACCCCGGAAATAGCAGAAA 697
PR8HA-286S.seq      CTTATGTCTCTGTAGTGACTTCAAATTATAACAGGAGATTTACCCCGGAAATAGCAGAAA 697
                    ************************************************************

PR8HA-291G.seq      GACCCAAAGTAAGAGATCAAGCTGGGAGGATGAACTATTACTGGACCTTGCTAAAACCCG 757
PR8HA-291S.seq      GACCCAAAGTAAGAGATCAAGCTGGGAGGATGAACTATTACTGGACCTTGCTAAAACCCG 757
PR8HA-63G.seq       GACCCAAAGTAAGAGATCAAGCTGGGAGGATGAACTATTACTGGACCTTGCTAAAACCCG 757
PR8HA-WT.seq        GACCCAAAGTAAGAGATCAAGCTGGGAGGATGAACTATTACTGGACCTTGCTAAAACCCG 757
PR8HA-48G.seq       GACCCAAAGTAAGAGATCAAGCTGGGAGGATGAACTATTACTGGACCTTGCTAAAACCCG 778
PR8HA-278S.seq      GACCCAAAGTAAGAGATCAAGCTGGGAGGATGAACTATTACTGGACCTTGCTAAAACCCG 757
PR8HA-282S.seq      GACCCAAAGTAAGAGATCAAGCTGGGAGGATGAACTATTACTGGACCTTGCTAAAACCCG 757
PR8HA-283G.seq      GACCCAAAGTAAGAGATCAAGCTGGGAGGATGAACTATTACTGGACCTTGCTAAAACCCG 757
PR8HA-286S.seq      GACCCAAAGTAAGAGATCAAGCTGGGAGGATGAACTATTACTGGACCTTGCTAAAACCCG 757
                    ************************************************************

PR8HA-291G.seq      GAGACACAATAATATTTGAGGCAAATGGAAATCTAATAGCACCAATGTATGCTTTCGCAC 817
PR8HA-291S.seq      GAGACACAATAATATTTGAGGCAAATGGAAATCTAATAGCACCAATGTATGCTTTCGCAC 817
PR8HA-63G.seq       GAGACACAATAATATTTGAGGCAAATGGAAATCTAATAGCACCAATGTATGCTTTCGCAC 817
PR8HA-WT.seq        GAGACACAATAATATTTGAGGCAAATGGAAATCTAATAGCACCAATGTATGCTTTCGCAC 817
PR8HA-48G.seq       GAGACACAATAATATTTGAGGCAAATGGAAATCTAATAGCACCAATGTATGCTTTCGCAC 838
PR8HA-278S.seq      GAGACACAATAATATTTGAGGCAAATGGAAATCTAATAGCACCAATGTATGCTTTCGCAC 817
PR8HA-282S.seq      GAGACACAATAATATTTGAGGCAAATGGAAATCTAATAGCACCAATGTATGCTTTCGCAC 817
PR8HA-283G.seq      GAGACACAATAATATTTGAGGCAAATGGAAATCTAATAGCACCAATGTATGCTTTCGCAC 817
PR8HA-286S.seq      GAGACACAATAATATTTGAGGCAAATGGAAATCTAATAGCACCAATGTATGCTTTCGCAC 817
                    ************************************************************

PR8HA-291G.seq      TGAGTAGAGGCTTTGGGTCCGGCATC-------------------ATC---ACCTC---- 851
PR8HA-291S.seq      TGAGTAGAGGCTTTGGGTCCGGCATC-------------------ATC---ACCTC---- 851
PR8HA-63G.seq       TGAGTAGAGGCTTTGGGTCCGGCATC-------------------ATC---ACCTC---- 851
PR8HA-WT.seq        TGAGTAGAGGCTTTGGGTCCGGCATC-------------------ATC---ACCTC---- 851
PR8HA-48G.seq       TGAGTAGAGGCTTTGGGTCCGGCATC-------------------ATC---ACCTC---- 872
PR8HA-278S.seq      TGAGTAGAGGCTTTGGG------------------------GAGAATCTGTACTTCCAG- 852
PR8HA-282S.seq      TGAGTAGAGGCTTTGGGTCCGGCATCATC------------GAGAATCTGTACTTCCAGA 865
PR8HA-283G.seq      TGAGTAGAGGCTTTGGGTCCGGCATCATCACC---------GAGAATCTGTACTTCCAGG 868
PR8HA-286S.seq      TGAGTAGAGGCTTTGGGTCCGGCATCATCACCTCAAACGCAGAGAATCTGTACTTCCAG- 876
                    *****************                            ***    ** **
```

Figure 46 D

```
PR8HA-291G.seq     -------AAACGCATCAATGCATGAGTGTGAGAATCTGTACTTCCAGGGAAACACGAAGT 904
PR8HA-291S.seq     -------AAACGCATCAATGCATGACTGTGAGAATCTGTACTTCCAGACCAACACGAAGT 904
PR8HA-63G.seq      -------AAACGCATCAATGCATGAGTGT---------------------AACACGAAGT 883
PR8HA-WT.seq       -------AAACGCATCAATGCATGAGTGT---------------------AACACGAAGT 883
PR8HA-48G.seq      -------AAACGCATCAATGCATGAGTGT---------------------AACACGAAGT 904
PR8HA-278S.seq     -----TCAAACGCATCAATGCATGAGTGT---------------------AACACGAAGT 886
PR8HA-282S.seq     GCACCTCAAACGCATCAATGCATGAGTGT---------------------AACACGAAGT 904
PR8HA-283G.seq     GA---TCAAACGCATCAATGCATGAGTGT---------------------AACACGAAGT 904
PR8HA-286S.seq     --------AGC---TCAATGCATGAGTGT---------------------AACACGAAGT 904
                           * *   ***************                     **********

PR8HA-291G.seq     GTCAAACACCGCTCGGAGCTATAAACAGCAGTCTCCCTTACCAGAATATACACCCAGTCA 964
PR8HA-291S.seq     GTCAAACACCGCTCGGAGCTATAAACAGCAGTCTCCCTTACCAGAATATACACCCAGTCA 964
PR8HA-63G.seq      GTCAAACACCGCTCGGAGCTATAAACAGCAGTCTCCCTTACCAGAATATACACCCAGTCA 943
PR8HA-WT.seq       GTCAAACACCGCTCGGAGCTATAAACAGCAGTCTCCCTTACCAGAATATACACCCAGTCA 943
PR8HA-48G.seq      GTCAAACACCGCTCGGAGCTATAAACAGCAGTCTCCCTTACCAGAATATACACCCAGTCA 964
PR8HA-278S.seq     GTCAAACACCGCTCGGAGCTATAAACAGCAGTCTCCCTTACCAGAATATACACCCAGTCA 946
PR8HA-282S.seq     GTCAAACACCGCTCGGAGCTATAAACAGCAGTCTCCCTTACCAGAATATACACCCAGTCA 964
PR8HA-283G.seq     GTCAAACACCGCTCGGAGCTATAAACAGCAGTCTCCCTTACCAGAATATACACCCAGTCA 964
PR8HA-286S.seq     GTCAAACACCGCTCGGAGCTATAAACAGCAGTCTCCCTTACCAGAATATACACCCAGTCA 964
                   ************************************************************

PR8HA-291G.seq     CAATAGGAGAGTGCCCAAAATACGTCAGGAGTGCCAAATTGAGGATGGTTACAGGACTAA 1024
PR8HA-291S.seq     CAATAGGAGAGTGCCCAAAATACGTCAGGAGTGCCAAATTGAGGATGGTTACAGGACTAA 1024
PR8HA-63G.seq      CAATAGGAGAGTGCCCAAAATACGTCAGGAGTGCCAAATTGAGGATGGTTACAGGACTAA 1003
PR8HA-WT.seq       CAATAGGAGAGTGCCCAAAATACGTCAGGAGTGCCAAATTGAGGATGGTTACAGGACTAA 1003
PR8HA-48G.seq      CAATAGGAGAGTGCCCAAAATACGTCAGGAGTGCCAAATTGAGGATGGTTACAGGACTAA 1024
PR8HA-278S.seq     CAATAGGAGAGTGCCCAAAATACGTCAGGAGTGCCAAATTGAGGATGGTTACAGGACTAA 1006
PR8HA-282S.seq     CAATAGGAGAGTGCCCAAAATACGTCAGGAGTGCCAAATTGAGGATGGTTACAGGACTAA 1024
PR8HA-283G.seq     CAATAGGAGAGTGCCCAAAATACGTCAGGAGTGCCAAATTGAGGATGGTTACAGGACTAA 1024
PR8HA-286S.seq     CAATAGGAGAGTGCCCAAAATACGTCAGGAGTGCCAAATTGAGGATGGTTACAGGACTAA 1024
                   ************************************************************

PR8HA-291G.seq     GGAACACTCCGTCCATTCAATCCAGAGGTCTATTTGGAGCCATTGCCGGTTTTATTGAAG 1084
PR8HA-291S.seq     GGAACACTCCGTCCATTCAATCCAGAGGTCTATTTGGAGCCATTGCCGGTTTTATTGAAG 1084
PR8HA-63G.seq      GGAACACTCCGTCCATTCAATCCAGAGGTCTATTTGGAGCCATTGCCGGTTTTATTGAAG 1063
PR8HA-WT.seq       GGAACACTCCGTCCATTCAATCCAGAGGTCTATTTGGAGCCATTGCCGGTTTTATTGAAG 1063
PR8HA-48G.seq      GGAACACTCCGTCCATTCAATCCAGAGGTCTATTTGGAGCCATTGCCGGTTTTATTGAAG 1084
PR8HA-278S.seq     GGAACACTCCGTCCATTCAATCCAGAGGTCTATTTGGAGCCATTGCCGGTTTTATTGAAG 1066
PR8HA-282S.seq     GGAACACTCCGTCCATTCAATCCAGAGGTCTATTTGGAGCCATTGCCGGTTTTATTGAAG 1084
PR8HA-283G.seq     GGAACACTCCGTCCATTCAATCCAGAGGTCTATTTGGAGCCATTGCCGGTTTTATTGAAG 1084
PR8HA-286S.seq     GGAACACTCCGTCCATTCAATCCAGAGGTCTATTTGGAGCCATTGCCGGTTTTATTGAAG 1084
                   ************************************************************

PR8HA-291G.seq     GGGGATGGACTGGAATGATAGATGGATGGTATGGTTATCATCATCAGAATGAACAGGGAT 1144
PR8HA-291S.seq     GGGGATGGACTGGAATGATAGATGGATGGTATGGTTATCATCATCAGAATGAACAGGGAT 1144
PR8HA-63G.seq      GGGGATGGACTGGAATGATAGATGGATGGTATGGTTATCATCATCAGAATGAACAGGGAT 1123
PR8HA-WT.seq       GGGGATGGACTGGAATGATAGATGGATGGTATGGTTATCATCATCAGAATGAACAGGGAT 1123
PR8HA-48G.seq      GGGGATGGACTGGAATGATAGATGGATGGTATGGTTATCATCATCAGAATGAACAGGGAT 1144
PR8HA-278S.seq     GGGGATGGACTGGAATGATAGATGGATGGTATGGTTATCATCATCAGAATGAACAGGGAT 1126
PR8HA-282S.seq     GGGGATGGACTGGAATGATAGATGGATGGTATGGTTATCATCATCAGAATGAACAGGGAT 1144
PR8HA-283G.seq     GGGGATGGACTGGAATGATAGATGGATGGTATGGTTATCATCATCAGAATGAACAGGGAT 1144
PR8HA-286S.seq     GGGGATGGACTGGAATGATAGATGGATGGTATGGTTATCATCATCAGAATGAACAGGGAT 1144
                   ************************************************************
```

Figure 46 E

```
PR8HA-291G.seq      CAGGCTATGCAGCGGATCAAAAAAGCACACAAAATGCCATTAACGGGATTACAAACAAGG 1204
PR8HA-291S.seq      CAGGCTATGCAGCGGATCAAAAAAGCACACAAAATGCCATTAACGGGATTACAAACAAGG 1204
PR8HA-63G.seq       CAGGCTATGCAGCGGATCAAAAAAGCACACAAAATGCCATTAACGGGATTACAAACAAGG 1183
PR8HA-WT.seq        CAGGCTATGCAGCGGATCAAAAAAGCACACAAAATGCCATTAACGGGATTACAAACAAGG 1183
PR8HA-48G.seq       CAGGCTATGCAGCGGATCAAAAAAGCACACAAAATGCCATTAACGGGATTACAAACAAGG 1204
PR8HA-278S.seq      CAGGCTATGCAGCGGATCAAAAAAGCACACAAAATGCCATTAACGGGATTACAAACAAGG 1186
PR8HA-282S.seq      CAGGCTATGCAGCGGATCAAAAAAGCACACAAAATGCCATTAACGGGATTACAAACAAGG 1204
PR8HA-283G.seq      CAGGCTATGCAGCGGATCAAAAAAGCACACAAAATGCCATTAACGGGATTACAAACAAGG 1204
PR8HA-286S.seq      CAGGCTATGCAGCGGATCAAAAAAGCACACAAAATGCCATTAACGGGATTACAAACAAGG 1204
                    ************************************************************

PR8HA-291G.seq      TGAACACTGTTATCGAGAAAATGAACATTCAATTCACAGCTGTGGGTAAAGAATTCAACA 1264
PR8HA-291S.seq      TGAACACTGTTATCGAGAAAATGAACATTCAATTCACAGCTGTGGGTAAAGAATTCAACA 1264
PR8HA-63G.seq       TGAACACTGTTATCGAGAAAATGAACATTCAATTCACAGCTGTGGGTAAAGAATTCAACA 1243
PR8HA-WT.seq        TGAACACTGTTATCGAGAAAATGAACATTCAATTCACAGCTGTGGGTAAAGAATTCAACA 1243
PR8HA-48G.seq       TGAACACTGTTATCGAGAAAATGAACATTCAATTCACAGCTGTGGGTAAAGAATTCAACA 1264
PR8HA-278S.seq      TGAACACTGTTATCGAGAAAATGAACATTCAATTCACAGCTGTGGGTAAAGAATTCAACA 1246
PR8HA-282S.seq      TGAACACTGTTATCGAGAAAATGAACATTCAATTCACAGCTGTGGGTAAAGAATTCAACA 1264
PR8HA-283G.seq      TGAACACTGTTATCGAGAAAATGAACATTCAATTCACAGCTGTGGGTAAAGAATTCAACA 1264
PR8HA-286S.seq      TGAACACTGTTATCGAGAAAATGAACATTCAATTCACAGCTGTGGGTAAAGAATTCAACA 1264
                    ************************************************************

PR8HA-291G.seq      AATTAGAAAAAAGGATGGAAAATTTAAATAAAAAAGTTGATGATGGATTTCTGGACATTT 1324
PR8HA-291S.seq      AATTAGAAAAAAGGATGGAAAATTTAAATAAAAAAGTTGATGATGGATTTCTGGACATTT 1324
PR8HA-63G.seq       AATTAGAAAAAAGGATGGAAAATTTAAATAAAAAAGTTGATGATGGATTTCTGGACATTT 1303
PR8HA-WT.seq        AATTAGAAAAAAGGATGGAAAATTTAAATAAAAAAGTTGATGATGGATTTCTGGACATTT 1303
PR8HA-48G.seq       AATTAGAAAAAAGGATGGAAAATTTAAATAAAAAAGTTGATGATGGATTTCTGGACATTT 1324
PR8HA-278S.seq      AATTAGAAAAAAGGATGGAAAATTTAAATAAAAAAGTTGATGATGGATTTCTGGACATTT 1306
PR8HA-282S.seq      AATTAGAAAAAAGGATGGAAAATTTAAATAAAAAAGTTGATGATGGATTTCTGGACATTT 1324
PR8HA-283G.seq      AATTAGAAAAAAGGATGGAAAATTTAAATAAAAAAGTTGATGATGGATTTCTGGACATTT 1324
PR8HA-286S.seq      AATTAGAAAAAAGGATGGAAAATTTAAATAAAAAAGTTGATGATGGATTTCTGGACATTT 1324
                    ************************************************************

PR8HA-291G.seq      GGACATATAATGCAGAATTGTTAGTTCTACTGGAAAATGAAAGGACTCTGGATTTCCATG 1384
PR8HA-291S.seq      GGACATATAATGCAGAATTGTTAGTTCTACTGGAAAATGAAAGGACTCTGGATTTCCATG 1384
PR8HA-63G.seq       GGACATATAATGCAGAATTGTTAGTTCTACTGGAAAATGAAAGGACTCTGGATTTCCATG 1363
PR8HA-WT.seq        GGACATATAATGCAGAATTGTTAGTTCTACTGGAAAATGAAAGGACTCTGGATTTCCATG 1363
PR8HA-48G.seq       GGACATATAATGCAGAATTGTTAGTTCTACTGGAAAATGAAAGGACTCTGGATTTCCATG 1384
PR8HA-278S.seq      GGACATATAATGCAGAATTGTTAGTTCTACTGGAAAATGAAAGGACTCTGGATTTCCATG 1366
PR8HA-282S.seq      GGACATATAATGCAGAATTGTTAGTTCTACTGGAAAATGAAAGGACTCTGGATTTCCATG 1384
PR8HA-283G.seq      GGACATATAATGCAGAATTGTTAGTTCTACTGGAAAATGAAAGGACTCTGGATTTCCATG 1384
PR8HA-286S.seq      GGACATATAATGCAGAATTGTTAGTTCTACTGGAAAATGAAAGGACTCTGGATTTCCATG 1384
                    ************************************************************

PR8HA-291G.seq      ACTCAAATGTGAAGAATCTGTATGAGAAAGTAAAAAGCCAATTAAAGAATAATGCCAAAG 1444
PR8HA-291S.seq      ACTCAAATGTGAAGAATCTGTATGAGAAAGTAAAAAGCCAATTAAAGAATAATGCCAAAG 1444
PR8HA-63G.seq       ACTCAAATGTGAAGAATCTGTATGAGAAAGTAAAAAGCCAATTAAAGAATAATGCCAAAG 1423
PR8HA-WT.seq        ACTCAAATGTGAAGAATCTGTATGAGAAAGTAAAAAGCCAATTAAAGAATAATGCCAAAG 1423
PR8HA-48G.seq       ACTCAAATGTGAAGAATCTGTATGAGAAAGTAAAAAGCCAATTAAAGAATAATGCCAAAG 1444
PR8HA-278S.seq      ACTCAAATGTGAAGAATCTGTATGAGAAAGTAAAAAGCCAATTAAAGAATAATGCCAAAG 1426
PR8HA-282S.seq      ACTCAAATGTGAAGAATCTGTATGAGAAAGTAAAAAGCCAATTAAAGAATAATGCCAAAG 1444
PR8HA-283G.seq      ACTCAAATGTGAAGAATCTGTATGAGAAAGTAAAAAGCCAATTAAAGAATAATGCCAAAG 1444
PR8HA-286S.seq      ACTCAAATGTGAAGAATCTGTATGAGAAAGTAAAAAGCCAATTAAAGAATAATGCCAAAG 1444
                    ************************************************************
```

Figure 46 F

```
PR8HA-291G.seq    AAATCGGAAATGGATGTTTTGAGTTCTACCACAAGTGTGACAATGAATGCATGGAAAGTG 1504
PR8HA-291S.seq    AAATCGGAAATGGATGTTTTGAGTTCTACCACAAGTGTGACAATGAATGCATGGAAAGTG 1504
PR8HA-63G.seq     AAATCGGAAATGGATGTTTTGAGTTCTACCACAAGTGTGACAATGAATGCATGGAAAGTG 1483
PR8HA-WT.seq      AAATCGGAAATGGATGTTTTGAGTTCTACCACAAGTGTGACAATGAATGCATGGAAAGTG 1483
PR8HA-48G.seq     AAATCGGAAATGGATGTTTTGAGTTCTACCACAAGTGTGACAATGAATGCATGGAAAGTG 1504
PR8HA-278S.seq    AAATCGGAAATGGATGTTTTGAGTTCTACCACAAGTGTGACAATGAATGCATGGAAAGTG 1486
PR8HA-282S.seq    AAATCGGAAATGGATGTTTTGAGTTCTACCACAAGTGTGACAATGAATGCATGGAAAGTG 1504
PR8HA-283G.seq    AAATCGGAAATGGATGTTTTGAGTTCTACCACAAGTGTGACAATGAATGCATGGAAAGTG 1504
PR8HA-286S.seq    AAATCGGAAATGGATGTTTTGAGTTCTACCACAAGTGTGACAATGAATGCATGGAAAGTG 1504
                  ************************************************************

PR8HA-291G.seq    TAAGAAATGGGACTTATGATTATCCCAAATATTCAGAAGAGTCAAAGTTGAACAGGGAAA 1564
PR8HA-291S.seq    TAAGAAATGGGACTTATGATTATCCCAAATATTCAGAAGAGTCAAAGTTGAACAGGGAAA 1564
PR8HA-63G.seq     TAAGAAATGGGACTTATGATTATCCCAAATATTCAGAAGAGTCAAAGTTGAACAGGGAAA 1543
PR8HA-WT.seq      TAAGAAATGGGACTTATGATTATCCCAAATATTCAGAAGAGTCAAAGTTGAACAGGGAAA 1543
PR8HA-48G.seq     TAAGAAATGGGACTTATGATTATCCCAAATATTCAGAAGAGTCAAAGTTGAACAGGGAAA 1564
PR8HA-278S.seq    TAAGAAATGGGACTTATGATTATCCCAAATATTCAGAAGAGTCAAAGTTGAACAGGGAAA 1546
PR8HA-282S.seq    TAAGAAATGGGACTTATGATTATCCCAAATATTCAGAAGAGTCAAAGTTGAACAGGGAAA 1564
PR8HA-283G.seq    TAAGAAATGGGACTTATGATTATCCCAAATATTCAGAAGAGTCAAAGTTGAACAGGGAAA 1564
PR8HA-286S.seq    TAAGAAATGGGACTTATGATTATCCCAAATATTCAGAAGAGTCAAAGTTGAACAGGGAAA 1564
                  ************************************************************

PR8HA-291G.seq    AGGTAGATGGAGTGAAATTGGAATCAATGGGGATCTATCAGATTCTGGCGATCTACTCAA 1624
PR8HA-291S.seq    AGGTAGATGGAGTGAAATTGGAATCAATGGGGATCTATCAGATTCTGGCGATCTACTCAA 1624
PR8HA-63G.seq     AGGTAGATGGAGTGAAATTGGAATCAATGGGGATCTATCAGATTCTGGCGATCTACTCAA 1603
PR8HA-WT.seq      AGGTAGATGGAGTGAAATTGGAATCAATGGGGATCTATCAGATTCTGGCGATCTACTCAA 1603
PR8HA-48G.seq     AGGTAGATGGAGTGAAATTGGAATCAATGGGGATCTATCAGATTCTGGCGATCTACTCAA 1624
PR8HA-278S.seq    AGGTAGATGGAGTGAAATTGGAATCAATGGGGATCTATCAGATTCTGGCGATCTACTCAA 1606
PR8HA-282S.seq    AGGTAGATGGAGTGAAATTGGAATCAATGGGGATCTATCAGATTCTGGCGATCTACTCAA 1624
PR8HA-283G.seq    AGGTAGATGGAGTGAAATTGGAATCAATGGGGATCTATCAGATTCTGGCGATCTACTCAA 1624
PR8HA-286S.seq    AGGTAGATGGAGTGAAATTGGAATCAATGGGGATCTATCAGATTCTGGCGATCTACTCAA 1624
                  ************************************************************

PR8HA-291G.seq    CTGTCGCCAGTTCACTGGTGCTTTTGGTCTCCCTGGGGGCAATCAGTTTCTGGATGTGTT 1684
PR8HA-291S.seq    CTGTCGCCAGTTCACTGGTGCTTTTGGTCTCCCTGGGGGCAATCAGTTTCTGGATGTGTT 1684
PR8HA-63G.seq     CTGTCGCCAGTTCACTGGTGCTTTTGGTCTCCCTGGGGGCAATCAGTTTCTGGATGTGTT 1663
PR8HA-WT.seq      CTGTCGCCAGTTCACTGGTGCTTTTGGTCTCCCTGGGGGCAATCAGTTTCTGGATGTGTT 1663
PR8HA-48G.seq     CTGTCGCCAGTTCACTGGTGCTTTTGGTCTCCCTGGGGGCAATCAGTTTCTGGATGTGTT 1684
PR8HA-278S.seq    CTGTCGCCAGTTCACTGGTGCTTTTGGTCTCCCTGGGGGCAATCAGTTTCTGGATGTGTT 1666
PR8HA-282S.seq    CTGTCGCCAGTTCACTGGTGCTTTTGGTCTCCCTGGGGGCAATCAGTTTCTGGATGTGTT 1684
PR8HA-283G.seq    CTGTCGCCAGTTCACTGGTGCTTTTGGTCTCCCTGGGGGCAATCAGTTTCTGGATGTGTT 1684
PR8HA-286S.seq    CTGTCGCCAGTTCACTGGTGCTTTTGGTCTCCCTGGGGGCAATCAGTTTCTGGATGTGTT 1684
                  ************************************************************

PR8HA-291G.seq    CTAATGGATCTTTGCAGTGCAGAATATGCATCTGA 1719 (SEQ ID NO: 49)
PR8HA-291S.seq    CTAATGGATCTTTGCAGTGCAGAATATGCATCTGA 1719 (SEQ ID NO: 50)
PR8HA-63G.seq     CTAATGGATCTTTGCAGTGCAGAATATGCATCTGA 1698 (SEQ ID NO: 51)
PR8HA-WT.seq      CTAATGGATCTTTGCAGTGCAGAATATGCATCTGA 1698 (SEQ ID NO: 2)
PR8HA-48G.seq     CTAATGGATCTTTGCAGTGCAGAATATGCATCTGA 1719 (SEQ ID NO: 52)
PR8HA-278S.seq    CTAATGGATCTTTGCAGTGCAGAATATGCATCTGA 1701 (SEQ ID NO: 53)
PR8HA-282S.seq    CTAATGGATCTTTGCAGTGCAGAATATGCATCTGA 1719 (SEQ ID NO: 54)
PR8HA-283G.seq    CTAATGGATCTTTGCAGTGCAGAATATGCATCTGA 1719 (SEQ ID NO: 55)
PR8HA-286S.seq    CTAATGGATCTTTGCAGTGCAGAATATGCATCTGA 1719 (SEQ ID NO: 56)
                  ***********************************
```

Figure 47 A

```
PR8HA-63G278S.seq      ATGAAGGCAAACCTACTGGTCCTGTTAAGTGCACTTGCAGCTGCAGATGCAGACACAATA 60
PR8HA-63G282S.seq      ATGAAGGCAAACCTACTGGTCCTGTTAAGTGCACTTGCAGCTGCAGATGCAGACACAATA 60
PR8HA-63G286S.seq      ATGAAGGCAAACCTACTGGTCCTGTTAAGTGCACTTGCAGCTGCAGATGCAGACACAATA 60
PR8HA-WT.seq           ATGAAGGCAAACCTACTGGTCCTGTTAAGTGCACTTGCAGCTGCAGATGCAGACACAATA 60
PR8HA-48G291G.seq      ATGAAGGCTAACCTGCTGGTGCTGCTGAGCGCCCTGGCTGCCGCTGATGCCGATACCATC 60
PR8HA-48G291S.seq      ATGAAGGCTAACCTGCTGGTGCTGCTGAGCGCCCTGGCTGCCGCTGATGCCGATACCATC 60
PR8HA-63G283G.seq      ATGAAGGCTAACCTGCTGGTGCTGCTGAGCGCCCTGGCTGCCGCTGATGCCGATACCATC 60
                       ******** ***** ***** *** * ** ** ** ** ** ** ***** ** ** **

PR8HA-63G278S.seq      TGTATAGGCTACCATGCGAACAATTCAACCGACACTGTTGACACAGTACTCGAGAAGAAT 120
PR8HA-63G282S.seq      TGTATAGGCTACCATGCGAACAATTCAACCGACACTGTTGACACAGTACTCGAGAAGAAT 120
PR8HA-63G286S.seq      TGTATAGGCTACCATGCGAACAATTCAACCGACACTGTTGACACAGTACTCGAGAAGAAT 120
PR8HA-WT.seq           TGTATAGGCTACCATGCGAACAATTCAACCGACACTGTTGACACAGTACTCGAGAAGAAT 120
PR8HA-48G291G.seq      TGCATCGGCTACCACGCCAACAACAGCACCGACACCGTGGATACCGTGCTGGAAAAGAAC 120
PR8HA-48G291S.seq      TGCATCGGCTACCACGCCAACAACAGCACCGACACCGTGGATACCGTGCTGGAAAAGAAC 120
PR8HA-63G283G.seq      TGCATCGGCTACCACGCCAACAACAGCACCGACACCGTGGATACCGTGCTGGAAAAGAAC 120
                       ** ** ******** ** *****    ******** ** ** ** ** ** ** *****

PR8HA-63G278S.seq      GTGACAGTGACACACTCTGT---------------------TAACCTGCTCGAAGACAGC 159
PR8HA-63G282S.seq      GTGACAGTGACACACTCTGT---------------------TAACCTGCTCGAAGACAGC 159
PR8HA-63G286S.seq      GTGACAGTGACACACTCTGT---------------------TAACCTGCTCGAAGACAGC 159
PR8HA-WT.seq           GTGACAGTGACACACTCTGT---------------------TAACCTGCTCGAAGACAGC 159
PR8HA-48G291G.seq      GTGACCGTGACCCACAGCGTGGAAAACCTGTATTTTCAAGGCAATCTGCTGGAAGATAGC 180
PR8HA-48G291S.seq      GTGACCGTGACCCACAGCGTGGAAAACCTGTATTTTCAAGGCAATCTGCTGGAAGATAGC 180
PR8HA-63G283G.seq      GTGACCGTGACCCACAGCGTG---------------------AACCTGCTGGAAGATAGC 159
                       ***** ***** ***   **                      ** ***** ***** ***

PR8HA-63G278S.seq      CACAACGGAAAACTATGTAGATTAAAAGGAGAGAATCTGTACTTCCA-----GGGAAAT 214
PR8HA-63G282S.seq      CACAACGGAAAACTATGTAGATTAAAAGGAGAGAATCTGTACTTCCA-----GGGAAAT 214
PR8HA-63G286S.seq      CACAACGGAAAACTATGTAGATTAAAAGGAGAGAATCTGTACTTCCA-----GGGAAAT 214
PR8HA-WT.seq           CACAACGGAAAACTATGTAGATTAAAAGGA-ATAGCCC-CACTACAATT----GGGGAAAT 214
PR8HA-48G291G.seq      CACAACGGCAAGCTGTGCCGGCTGAAGGGA-ATCGCCCCT-CTGCAGCT---GGGCAAGT 235
PR8HA-48G291S.seq      CACAACGGCAAGCTGTGCCGGCTGAAGGGA-ATCGCCCCT-CTGCAGCT---GGGCAAGT 235
PR8HA-63G283G.seq      CACAACGGCAAGCTGTGCCGGCTGAAGGG----CGAGAAC-CTGTATTTTCAAGGCAAGT 214
                       ******** ** ** **   *  ** **          **             ** ** *

PR8HA-63G278S.seq      GTAACATCGCCGGATGGCTCTTGGGAAACCCAGAATGCGACCCACTGCTTCCAGTGAGAT 274
PR8HA-63G282S.seq      GTAACATCGCCGGATGGCTCTTGGGAAACCCAGAATGCGACCCACTGCTTCCAGTGAGAT 274
PR8HA-63G286S.seq      GTAACATCGCCGGATGGCTCTTGGGAAACCCAGAATGCGACCCACTGCTTCCAGTGAGAT 274
PR8HA-WT.seq           GTAACATCGCCGGATGGCTCTTGGGAAACCCAGAATGCGACCCACTGCTTCCAGTGAGAT 274
PR8HA-48G291G.seq      GCAATATCGCCGGCTGGCTGCTGGGCAACCCCGAGTGTGATCCTCTGCTGCCTGTGCGGA 295
PR8HA-48G291S.seq      GCAATATCGCCGGCTGGCTGCTGGGCAACCCCGAGTGTGATCCTCTGCTGCCTGTGCGGA 295
PR8HA-63G283G.seq      GCAATATCGCCGGCTGGCTGCTGGGCAACCCCGAGTGTGATCCTCTGCTGCCTGTGCGGA 274
                       * ** ******** *****  **** ***** ** ** ** ** ***** ** *** *

PR8HA-63G278S.seq      CATGGTCCTACATTGTAGAAACACCAAACTCTGAGAATGGAATATGTTATCCAGGAGATT 334
PR8HA-63G282S.seq      CATGGTCCTACATTGTAGAAACACCAAACTCTGAGAATGGAATATGTTATCCAGGAGATT 334
PR8HA-63G286S.seq      CATGGTCCTACATTGTAGAAACACCAAACTCTGAGAATGGAATATGTTATCCAGGAGATT 334
PR8HA-WT.seq           CATGGTCCTACATTGTAGAAACACCAAACTCTGAGAATGGAATATGTTATCCAGGAGATT 334
PR8HA-48G291G.seq      GCTGGTCCTACATCGTGGAAACCCCCAACAGCGAGAACGGCATCTGCTACCCCGGCGACT 355
PR8HA-48G291S.seq      GCTGGTCCTACATCGTGGAAACCCCCAACAGCGAGAACGGCATCTGCTACCCCGGCGACT 355
PR8HA-63G283G.seq      GCTGGTCCTACATCGTGGAAACCCCCAACAGCGAGAACGGCATCTGCTACCCCGGCGACT 334
                         *********** ** ***** ** ***   ***** ** ** ** ** ** ** ** *

PR8HA-63G278S.seq      TCATCGACTATGAGGAGCTGAGGGAGCAATTGAGCTCAGTGTCATCATTCGAAAGATTCG 394
PR8HA-63G282S.seq      TCATCGACTATGAGGAGCTGAGGGAGCAATTGAGCTCAGTGTCATCATTCGAAAGATTCG 394
PR8HA-63G286S.seq      TCATCGACTATGAGGAGCTGAGGGAGCAATTGAGCTCAGTGTCATCATTCGAAAGATTCG 394
PR8HA-WT.seq           TCATCGACTATGAGGAGCTGAGGGAGCAATTGAGCTCAGTGTCATCATTCGAAAGATTCG 394
PR8HA-48G291G.seq      TCATCGACTACGAGGAACTGCGCGAGCAGCTGAGCAGCGTGTCCAGCTTCGAAAGATTCG 415
PR8HA-48G291S.seq      TCATCGACTACGAGGAACTGCGCGAGCAGCTGAGCAGCGTGTCCAGCTTCGAAAGATTCG 415
PR8HA-63G283G.seq      TCATCGACTACGAGGAACTGCGCGAGCAGCTGAGCAGCGTGTCCAGCTTCGAGAGATTCG 394
                       ********** ***** *** * *****  *****   *****    ***** *******
```

Figure 47 B

```
PR8HA-63G278S.seq           AAATATTTCCCAAAGAAAGCTCATGGCCCAACCACAACACAAACGGAGTAACGGCAGCAT 454
PR8HA-63G282S.seq           AAATATTTCCCAAAGAAAGCTCATGGCCCAACCACAACACAAACGGAGTAACGGCAGCAT 454
PR8HA-63G286S.seq           AAATATTTCCCAAAGAAAGCTCATGGCCCAACCACAACACAAACGGAGTAACGGCAGCAT 454
PR8HA-WT.seq                AAATATTTCCCAAAGAAAGCTCATGGCCCAACCACAACACAAACGGAGTAACGGCAGCAT 454
PR8HA-48G291G.seq           AGATCTTCCCCAAAGAGAGCAGCTGGCCCAACCACAACACCAACGGCGTGACAGCCGCCT 475
PR8HA-48G291S.seq           AGATCTTCCCCAAAGAGAGCAGCTGGCCCAACCACAACACCAACGGCGTGACAGCCGCCT 475
PR8HA-63G283G.seq           AGATCTTCCCCAAAGAGAGCAGCTGGCCCAACCACAACACCAACGGCGTGACAGCCGCCT 454
                            * ** ** ******** ***   ***************** ***** ** ** ** ** *

PR8HA-63G278S.seq           GCTCCCATGAGGGGAAAAGCAGTTTTTACAGAAATTTGCTATGGCTGACGGAGAAGGAGG 514
PR8HA-63G282S.seq           GCTCCCATGAGGGGAAAAGCAGTTTTTACAGAAATTTGCTATGGCTGACGGAGAAGGAGG 514
PR8HA-63G286S.seq           GCTCCCATGAGGGGAAAAGCAGTTTTTACAGAAATTTGCTATGGCTGACGGAGAAGGAGG 514
PR8HA-WT.seq                GCTCCCATGAGGGGAAAAGCAGTTTTTACAGAAATTTGCTATGGCTGACGGAGAAGGAGG 514
PR8HA-48G291G.seq           GTAGCCACGAGGGCAAGAGCAGCTTCTACCGGAACCTGCTGTGGCTGACCGAGAAAGAGG 535
PR8HA-48G291S.seq           GTAGCCACGAGGGCAAGAGCAGCTTCTACCGGAACCTGCTGTGGCTGACCGAGAAAGAGG 535
PR8HA-63G283G.seq           GTAGCCACGAGGGCAAGAGCAGCTTCTACAGAAACCTGCTGTGGCTGACCGAGAAAGAGG 514
                            *   *** ***** ** ***** ** *** * **  **** ******** ***** ****

PR8HA-63G278S.seq           GCTCATACCCAAAGCTGAAAAATTCTTATGTGAACAAAAAAGGGAAAGAAGTCCTTGTAC 574
PR8HA-63G282S.seq           GCTCATACCCAAAGCTGAAAAATTCTTATGTGAACAAAAAAGGGAAAGAAGTCCTTGTAC 574
PR8HA-63G286S.seq           GCTCATACCCAAAGCTGAAAAATTCTTATGTGAACAAAAAAGGGAAAGAAGTCCTTGTAC 574
PR8HA-WT.seq                GCTCATACCCAAAGCTGAAAAATTCTTATGTGAACAAAAAAGGGAAAGAAGTCCTTGTAC 574
PR8HA-48G291G.seq           GCAGCTACCCCAAGCTGAAGAACAGCTACGTGAACAAGAAAGGCAAAGAGGTGCTGGTGC 595
PR8HA-48G291S.seq           GCAGCTACCCCAAGCTGAAGAACAGCTACGTGAACAAGAAAGGCAAAGAGGTGCTGGTGC 595
PR8HA-63G283G.seq           GCAGCTACCCCAAGCTGAAGAACAGCTACGTGAACAAGAAAGGCAAAGAGGTGCTGGTGC 574
                            **   ***** ******** **    ** ******** ***** ***** ** ** ** *

PR8HA-63G278S.seq           TGTGGGGTATTCATCACCCGCCTAACAGTAAGGAACAACAGAATATCTATCAGAATGAAA 634
PR8HA-63G282S.seq           TGTGGGGTATTCATCACCCGCCTAACAGTAAGGAACAACAGAATATCTATCAGAATGAAA 634
PR8HA-63G286S.seq           TGTGGGGTATTCATCACCCGCCTAACAGTAAGGAACAACAGAATATCTATCAGAATGAAA 634
PR8HA-WT.seq                TGTGGGGTATTCATCACCCGCCTAACAGTAAGGAACAACAGAATATCTATCAGAATGAAA 634
PR8HA-48G291G.seq           TGTGGGGCATCCACCACCCCCCCAACTCTAAAGAGCAGCAGAACATCTACCAGAACGAGA 655
PR8HA-48G291S.seq           TGTGGGGCATCCACCACCCCCCCAACTCTAAAGAGCAGCAGAACATCTACCAGAACGAGA 655
PR8HA-63G283G.seq           TGTGGGGCATCCACCACCCCCCCAACTCTAAAGAGCAGCAGAACATCTACCAGAACGAGA 634
                            ******* ** ** ***** ** ***  *** ** ** ***** ***** ***** ** *

PR8HA-63G278S.seq           ATGCTTATGTCTCTGTAGTGACTTCAAATTATAACAGGAGATTTACCCCGGAAATAGCAG 694
PR8HA-63G282S.seq           ATGCTTATGTCTCTGTAGTGACTTCAAATTATAACAGGAGATTTACCCCGGAAATAGCAG 694
PR8HA-63G286S.seq           ATGCTTATGTCTCTGTAGTGACTTCAAATTATAACAGGAGATTTACCCCGGAAATAGCAG 694
PR8HA-WT.seq                ATGCTTATGTCTCTGTAGTGACTTCAAATTATAACAGGAGATTTACCCCGGAAATAGCAG 694
PR8HA-48G291G.seq           ACGCCTACGTGTCCGTCGTGACCAGCAACTACAACCGGCGGTTCACCCCCGAGATCGCCG 715
PR8HA-48G291S.seq           ACGCCTACGTGTCCGTCGTGACCAGCAACTACAACCGGCGGTTCACCCCCGAGATCGCCG 715
PR8HA-63G283G.seq           ACGCCTACGTGTCCGTCGTGACCAGCAACTACAACCGGCGGTTCACCCCCGAGATCGCCG 694
                            * ** ** ** ** ** *****    ** ** *** ** * ** ***** ** ** ** *

PR8HA-63G278S.seq           AAAGACCCAAAGTAAGAGATCAAGCTGGGAGGATGAACTATTACTGGACCTTGCTAAAAC 754
PR8HA-63G282S.seq           AAAGACCCAAAGTAAGAGATCAAGCTGGGAGGATGAACTATTACTGGACCTTGCTAAAAC 754
PR8HA-63G286S.seq           AAAGACCCAAAGTAAGAGATCAAGCTGGGAGGATGAACTATTACTGGACCTTGCTAAAAC 754
PR8HA-WT.seq                AAAGACCCAAAGTAAGAGATCAAGCTGGGAGGATGAACTATTACTGGACCTTGCTAAAAC 754
PR8HA-48G291G.seq           AGAGGCCTAAAGTGCGGGATCAGGCCGGCAGAATGAACTACTACTGGACCCTGCTGAAGC 775
PR8HA-48G291S.seq           AGAGGCCTAAAGTGCGGGATCAGGCCGGCAGAATGAACTACTACTGGACCCTGCTGAAGC 775
PR8HA-63G283G.seq           AGAGGCCTAAAGTGCGGGATCAGGCCGGCAGAATGAACTACTACTGGACCCTGCTGAAGC 754
                            * ** ** *****  * ***** ** ** ** ******** ********* **** ** *

PR8HA-63G278S.seq           CCGGAGACACAATAATATTTGAGGCAAATGGAAATCTAATAGCACCAATGTATGCTTTCG 814
PR8HA-63G282S.seq           CCGGAGACACAATAATATTTGAGGCAAATGGAAATCTAATAGCACCAATGTATGCTTTCG 814
PR8HA-63G286S.seq           CCGGAGACACAATAATATTTGAGGCAAATGGAAATCTAATAGCACCAATGTATGCTTTCG 814
PR8HA-WT.seq                CCGGAGACACAATAATATTTGAGGCAAATGGAAATCTAATAGCACCAATGTATGCTTTCG 814
PR8HA-48G291G.seq           CCGGCGACACCATCATCTTCGAGGCCAACGGCAACCTGATCGCCCCTATGTACGCCTTCG 835
PR8HA-48G291S.seq           CCGGCGACACCATCATCTTCGAGGCCAACGGCAACCTGATCGCCCCTATGTACGCCTTCG 835
PR8HA-63G283G.seq           CCGGCGACACCATCATCTTCGAGGCCAACGGCAACCTGATCGCCCCTATGTACGCCTTCG 814
                            **** ***** ** ** ** ***** ** ** ** ** ** ** ** ***** ** ****
```

Figure 47 C

```
PR8HA-63G278S.seq    CACTGAGTAGAGGCTTTGGG------------------------GAGAATCTGTACTTCC 850
PR8HA-63G282S.seq    CACTGAGTAGAGGCTTTGGGTCCGGCATCATC------------GAGAATCTGTACTTCC 862
PR8HA-63G286S.seq    CACTGAGTAGAGGCTTTGGGTCCGGCATCATCACCTCAAACGCAGAGAATCTGTACTTCC 874
PR8HA-WT.seq         CACTGAGTAGAGGCTTTGGGTCC----------------------GGCATCATCACCTC- 851
PR8HA-48G291G.seq    CCCTGAGCAGAGGCTTCGGCAGC----------------------GGCATCATCACCAG- 872
PR8HA-48G291S.seq    CCCTGAGCAGAGGCTTCGGCAGC----------------------GGCATCATCACCAG- 872
PR8HA-63G283G.seq    CCCTGAGCAGAGGCTTCGGCAGC----------------------GGCATCATCACCGA- 851
                     * ***** ******** **                           * ***   **

PR8HA-63G278S.seq    AG------TCAAACGCATCAATGCATGAGT----------------------GTAACACG 882
PR8HA-63G282S.seq    AGAGCACCTCAAACGCATCAATGCATGAGT----------------------GTAACACG 900
PR8HA-63G286S.seq    AG---------AGC---TCAATGCATGAGT----------------------GTAACACG 900
PR8HA-WT.seq         ----------AAACGCATCAATGCATGAGT----------------------GTAACACG 879
PR8HA-48G291G.seq    ----------CAACGCCAGCATGCACGAGTGCGAGAACCTGTACTTCCAAG-GGAACACC 921
PR8HA-48G291S.seq    ----------CAACGCCAGCATGCACGAGTGCGAGAACCTGTACTTCCAAA-GCAACACC 921
PR8HA-63G283G.seq    ----------AAACCTGTACTTCCAAGGATCCAACG-CCAGCATGCACGAGTGCAACACC 900
                                * *       * ** *  *                      * *****

PR8HA-63G278S.seq    AAGTGTCAAACACCGCTCGGAGCTATAAACAGCAGTCTCCCTTACCAGAATATACACCCA 942
PR8HA-63G282S.seq    AAGTGTCAAACACCGCTCGGAGCTATAAACAGCAGTCTCCCTTACCAGAATATACACCCA 960
PR8HA-63G286S.seq    AAGTGTCAAACACCGCTCGGAGCTATAAACAGCAGTCTCCCTTACCAGAATATACACCCA 960
PR8HA-WT.seq         AAGTGTCAAACACCGCTCGGAGCTATAAACAGCAGTCTCCCTTACCAGAATATACACCCA 939
PR8HA-48G291G.seq    AAGTGCCAGACCCCGCTCGGAGCTATAAACAGCAGTCTCCCTTACCAGAATATACACCCA 981
PR8HA-48G291S.seq    AAGTGCCAGACCCCGCTCGGAGCTATAAACAGCAGTCTCCCTTACCAGAATATACACCCA 981
PR8HA-63G283G.seq    AAGTGCCAGACCCCGCTCGGAGCTATAAACAGCAGTCTCCCTTACCAGAATATACACCCA 960
                     ***** ** ** ************************************************

PR8HA-63G278S.seq    GTCACAATAGGAGAGTGCCCAAAATACGTCAGGAGTGCCAAATTGAGGATGGTTACAGGA 1002
PR8HA-63G282S.seq    GTCACAATAGGAGAGTGCCCAAAATACGTCAGGAGTGCCAAATTGAGGATGGTTACAGGA 1020
PR8HA-63G286S.seq    GTCACAATAGGAGAGTGCCCAAAATACGTCAGGAGTGCCAAATTGAGGATGGTTACAGGA 1020
PR8HA-WT.seq         GTCACAATAGGAGAGTGCCCAAAATACGTCAGGAGTGCCAAATTGAGGATGGTTACAGGA 999
PR8HA-48G291G.seq    GTCACAATAGGAGAGTGCCCAAAATACGTCAGGAGTGCCAAATTGAGGATGGTTACAGGA 1041
PR8HA-48G291S.seq    GTCACAATAGGAGAGTGCCCAAAATACGTCAGGAGTGCCAAATTGAGGATGGTTACAGGA 1041
PR8HA-63G283G.seq    GTCACAATAGGAGAGTGCCCAAAATACGTCAGGAGTGCCAAATTGAGGATGGTTACAGGA 1020
                     ************************************************************

PR8HA-63G278S.seq    CTAAGGAACACTCCGTCCATTCAATCCAGAGGTCTATTTGGAGCCATTGCCGGTTTTATT 1062
PR8HA-63G282S.seq    CTAAGGAACACTCCGTCCATTCAATCCAGAGGTCTATTTGGAGCCATTGCCGGTTTTATT 1080
PR8HA-63G286S.seq    CTAAGGAACACTCCGTCCATTCAATCCAGAGGTCTATTTGGAGCCATTGCCGGTTTTATT 1080
PR8HA-WT.seq         CTAAGGAACACTCCGTCCATTCAATCCAGAGGTCTATTTGGAGCCATTGCCGGTTTTATT 1059
PR8HA-48G291G.seq    CTAAGGAACACTCCGTCCATTCAATCCAGAGGTCTATTTGGAGCCATTGCCGGTTTTATT 1101
PR8HA-48G291S.seq    CTAAGGAACACTCCGTCCATTCAATCCAGAGGTCTATTTGGAGCCATTGCCGGTTTTATT 1101
PR8HA-63G283G.seq    CTAAGGAACACTCCGTCCATTCAATCCAGAGGTCTATTTGGAGCCATTGCCGGTTTTATT 1080
                     ************************************************************

PR8HA-63G278S.seq    GAAGGGGGATGGACTGGAATGATAGATGGATGGTATGGTTATCATCATCAGAATGAACAG 1122
PR8HA-63G282S.seq    GAAGGGGGATGGACTGGAATGATAGATGGATGGTATGGTTATCATCATCAGAATGAACAG 1140
PR8HA-63G286S.seq    GAAGGGGGATGGACTGGAATGATAGATGGATGGTATGGTTATCATCATCAGAATGAACAG 1140
PR8HA-WT.seq         GAAGGGGGATGGACTGGAATGATAGATGGATGGTATGGTTATCATCATCAGAATGAACAG 1119
PR8HA-48G291G.seq    GAAGGGGGATGGACTGGAATGATAGATGGATGGTATGGTTATCATCATCAGAATGAACAG 1161
PR8HA-48G291S.seq    GAAGGGGGATGGACTGGAATGATAGATGGATGGTATGGTTATCATCATCAGAATGAACAG 1161
PR8HA-63G283G.seq    GAAGGGGGATGGACTGGAATGATAGATGGATGGTATGGTTATCATCATCAGAATGAACAG 1140
                     ************************************************************

PR8HA-63G278S.seq    GGATCAGGCTATGCAGCGGATCAAAAAAGCACACAAAATGCCATTAACGGGATTACAAAC 1182
PR8HA-63G282S.seq    GGATCAGGCTATGCAGCGGATCAAAAAAGCACACAAAATGCCATTAACGGGATTACAAAC 1200
PR8HA-63G286S.seq    GGATCAGGCTATGCAGCGGATCAAAAAAGCACACAAAATGCCATTAACGGGATTACAAAC 1200
PR8HA-WT.seq         GGATCAGGCTATGCAGCGGATCAAAAAAGCACACAAAATGCCATTAACGGGATTACAAAC 1179
PR8HA-48G291G.seq    GGATCAGGCTATGCAGCGGATCAAAAAAGCACACAAAATGCCATTAACGGGATTACAAAC 1221
PR8HA-48G291S.seq    GGATCAGGCTATGCAGCGGATCAAAAAAGCACACAAAATGCCATTAACGGGATTACAAAC 1221
PR8HA-63G283G.seq    GGATCAGGCTATGCAGCGGATCAAAAAAGCACACAAAATGCCATTAACGGGATTACAAAC 1200
                     ************************************************************
```

Figure 47 D

```
PR8HA-63G278S.seq    AAGGTGAACACTGTTATCGAGAAAATGAACATTCAATTCACAGCTGTGGGTAAAGAATTC 1242
PR8HA-63G282S.seq    AAGGTGAACACTGTTATCGAGAAAATGAACATTCAATTCACAGCTGTGGGTAAAGAATTC 1260
PR8HA-63G286S.seq    AAGGTGAACACTGTTATCGAGAAAATGAACATTCAATTCACAGCTGTGGGTAAAGAATTC 1260
PR8HA-WT.seq         AAGGTGAACACTGTTATCGAGAAAATGAACATTCAATTCACAGCTGTGGGTAAAGAATTC 1239
PR8HA-48G291G.seq    AAGGTGAACACTGTTATCGAGAAAATGAACATTCAATTCACAGCTGTGGGTAAAGAATTC 1281
PR8HA-48G291S.seq    AAGGTGAACACTGTTATCGAGAAAATGAACATTCAATTCACAGCTGTGGGTAAAGAATTC 1281
PR8HA-63G283G.seq    AAGGTGAACACTGTTATCGAGAAAATGAACATTCAATTCACAGCTGTGGGTAAAGAATTC 1260
                     ************************************************************

PR8HA-63G278S.seq    AACAAATTAGAAAAAAGGATGGAAAATTTAAATAAAAAAGTTGATGATGGATTTCTGGAC 1302
PR8HA-63G282S.seq    AACAAATTAGAAAAAAGGATGGAAAATTTAAATAAAAAAGTTGATGATGGATTTCTGGAC 1320
PR8HA-63G286S.seq    AACAAATTAGAAAAAAGGATGGAAAATTTAAATAAAAAAGTTGATGATGGATTTCTGGAC 1320
PR8HA-WT.seq         AACAAATTAGAAAAAAGGATGGAAAATTTAAATAAAAAAGTTGATGATGGATTTCTGGAC 1299
PR8HA-48G291G.seq    AACAAATTAGAAAAAAGGATGGAAAATTTAAATAAAAAAGTTGATGATGGATTTCTGGAC 1341
PR8HA-48G291S.seq    AACAAATTAGAAAAAAGGATGGAAAATTTAAATAAAAAAGTTGATGATGGATTTCTGGAC 1341
PR8HA-63G283G.seq    AACAAATTAGAAAAAAGGATGGAAAATTTAAATAAAAAAGTTGATGATGGATTTCTGGAC 1320
                     ************************************************************

PR8HA-63G278S.seq    ATTTGGACATATAATGCAGAATTGTTAGTTCTACTGGAAAATGAAAGGACTCTGGATTTC 1362
PR8HA-63G282S.seq    ATTTGGACATATAATGCAGAATTGTTAGTTCTACTGGAAAATGAAAGGACTCTGGATTTC 1380
PR8HA-63G286S.seq    ATTTGGACATATAATGCAGAATTGTTAGTTCTACTGGAAAATGAAAGGACTCTGGATTTC 1380
PR8HA-WT.seq         ATTTGGACATATAATGCAGAATTGTTAGTTCTACTGGAAAATGAAAGGACTCTGGATTTC 1359
PR8HA-48G291G.seq    ATTTGGACATATAATGCAGAATTGTTAGTTCTACTGGAAAATGAAAGGACTCTGGATTTC 1401
PR8HA-48G291S.seq    ATTTGGACATATAATGCAGAATTGTTAGTTCTACTGGAAAATGAAAGGACTCTGGATTTC 1401
PR8HA-63G283G.seq    ATTTGGACATATAATGCAGAATTGTTAGTTCTACTGGAAAATGAAAGGACTCTGGATTTC 1380
                     ************************************************************

PR8HA-63G278S.seq    CATGACTCAAATGTGAAGAATCTGTATGAGAAAGTAAAAAGCCAATTAAAGAATAATGCC 1422
PR8HA-63G282S.seq    CATGACTCAAATGTGAAGAATCTGTATGAGAAAGTAAAAAGCCAATTAAAGAATAATGCC 1440
PR8HA-63G286S.seq    CATGACTCAAATGTGAAGAATCTGTATGAGAAAGTAAAAAGCCAATTAAAGAATAATGCC 1440
PR8HA-WT.seq         CATGACTCAAATGTGAAGAATCTGTATGAGAAAGTAAAAAGCCAATTAAAGAATAATGCC 1419
PR8HA-48G291G.seq    CATGACTCAAATGTGAAGAATCTGTATGAGAAAGTAAAAAGCCAATTAAAGAATAATGCC 1461
PR8HA-48G291S.seq    CATGACTCAAATGTGAAGAATCTGTATGAGAAAGTAAAAAGCCAATTAAAGAATAATGCC 1461
PR8HA-63G283G.seq    CATGACTCAAATGTGAAGAATCTGTATGAGAAAGTAAAAAGCCAATTAAAGAATAATGCC 1440
                     ************************************************************

PR8HA-63G278S.seq    AAAGAAATCGGAAATGGATGTTTTGAGTTCTACCACAAGTGTGACAATGAATGCATGGAA 1482
PR8HA-63G282S.seq    AAAGAAATCGGAAATGGATGTTTTGAGTTCTACCACAAGTGTGACAATGAATGCATGGAA 1500
PR8HA-63G286S.seq    AAAGAAATCGGAAATGGATGTTTTGAGTTCTACCACAAGTGTGACAATGAATGCATGGAA 1500
PR8HA-WT.seq         AAAGAAATCGGAAATGGATGTTTTGAGTTCTACCACAAGTGTGACAATGAATGCATGGAA 1479
PR8HA-48G291G.seq    AAAGAAATCGGAAATGGATGTTTTGAGTTCTACCACAAGTGTGACAATGAATGCATGGAA 1521
PR8HA-48G291S.seq    AAAGAAATCGGAAATGGATGTTTTGAGTTCTACCACAAGTGTGACAATGAATGCATGGAA 1521
PR8HA-63G283G.seq    AAAGAAATCGGAAATGGATGTTTTGAGTTCTACCACAAGTGTGACAATGAATGCATGGAA 1500
                     ************************************************************

PR8HA-63G278S.seq    AGTGTAAGAAATGGGACTTATGATTATCCCAAATATTCAGAAGAGTCAAAGTTGAACAGG 1542
PR8HA-63G282S.seq    AGTGTAAGAAATGGGACTTATGATTATCCCAAATATTCAGAAGAGTCAAAGTTGAACAGG 1560
PR8HA-63G286S.seq    AGTGTAAGAAATGGGACTTATGATTATCCCAAATATTCAGAAGAGTCAAAGTTGAACAGG 1560
PR8HA-WT.seq         AGTGTAAGAAATGGGACTTATGATTATCCCAAATATTCAGAAGAGTCAAAGTTGAACAGG 1539
PR8HA-48G291G.seq    AGTGTAAGAAATGGGACTTATGATTATCCCAAATATTCAGAAGAGTCAAAGTTGAACAGG 1581
PR8HA-48G291S.seq    AGTGTAAGAAATGGGACTTATGATTATCCCAAATATTCAGAAGAGTCAAAGTTGAACAGG 1581
PR8HA-63G283G.seq    AGTGTAAGAAATGGGACTTATGATTATCCCAAATATTCAGAAGAGTCAAAGTTGAACAGG 1560
                     ************************************************************

PR8HA-63G278S.seq    GAAAAGGTAGATGGAGTGCGTTCTCTGGTTCCGCGTGGTTCT-CCGGGTTCTGGTTACAT 1601
PR8HA-63G282S.seq    GAAAAGGTAGATGGAGTGCGTTCTCTGGTTCCGCGTGGTTCT-CCGGGTTCTGGTTACAT 1619
PR8HA-63G286S.seq    GAAAAGGTAGATGGAGTGCGTTCTCTGGTTCCGCGTGGTTCT-CCGGGTTCTGGTTACAT 1619
PR8HA-WT.seq         GAAAAGGTAGATGGAGTGAAATTG--GAATCAATGGGGATCTATCAGATTCTGGCGATCT 1597
PR8HA-48G291G.seq    GAAAAGGTAGATGGAGTGCGTTCTCTGGTTCCGCGTGGTTCT-CCGGGTTCTGGTTACAT 1640
PR8HA-48G291S.seq    GAAAAGGTAGATGGAGTGCGTTCTCTGGTTCCGCGTGGTTCT-CCGGGTTCTGGTTACAT 1640
PR8HA-63G283G.seq    GAAAAGGTAGATGGAGTGCGTTCTCTGGTTCCGCGTGGTTCT-CCGGGTTCTGGTTACAT 1619
                     ******************   *    *  **   * ** ***  * * ******  *  *
```

Figure 47 E

```
PR8HA-63G278S.seq    CCCGGAAGCTCCGCGTGACGGTCAG-GCTTACG---TTCGTAAAGACGGT-------GA 1649
PR8HA-63G282S.seq    CCCGGAAGCTCCGCGTGACGGTCAG-GCTTACG---TTCGTAAAGACGGT-------GA 1667
PR8HA-63G286S.seq    CCCGGAAGCTCCGCGTGACGGTCAG-GCTTACG---TTCGTAAAGACGGT-------GA 1667
PR8HA-WT.seq         ACTC-AACTGTCGCCAGTTCACTGGTGCTTTTGGTCTCCCTGGGGCAATCAGTTTCTGG 1656
PR8HA-48G291G.seq    CCCGGAAGCTCCGCGTGACGGTCAG-GCTTACG---TTCGTAAAGACGGT-------GA 1688
PR8HA-48G291S.seq    CCCGGAAGCTCCGCGTGACGGTCAG-GCTTACG---TTCGTAAAGACGGT-------GA 1688
PR8HA-63G283G.seq    CCCGGAAGCTCCGCGTGACGGTCAG-GCTTACG---TTCGTAAAGACGGT-------GA 1667
                      *   **    ***  *         * ****  *    * * *   * *  *        *

PR8HA-63G278S.seq    ATGGGTTCTGCTGTCTACCTTCCTGCACCACCACCACCACCACTGA 1695 (SEQ ID NO: 57)
PR8HA-63G282S.seq    ATGGGTTCTGCTGTCTACCTTCCTGCACCACCACCACCACCACTGA 1713 (SEQ ID NO: 58)
PR8HA-63G286S.seq    ATGGGTTCTGCTGTCTACCTTCCTGCACCACCACCACCACCACTGA 1713 (SEQ ID NO: 59)
PR8HA-WT.seq         ATGTGTTCTAATG--GATCTT--TGCAGTGCAGAATATGCATCTGA 1698 (SEQ ID NO: 2)
PR8HA-48G291G.seq    ATGGGTTCTGCTGTCTACCTTCCTGCACCACCACCACCACCACTGA 1734 (SEQ ID NO: 60)
PR8HA-48G291S.seq    ATGGGTTCTGCTGTCTACCTTCCTGCACCACCACCACCACCACTGA 1734 (SEQ ID NO: 61)
PR8HA-63G283G.seq    ATGGGTTCTGCTGTCTACCTTCCTGCACCACCACCACCACCACTGA 1713 (SEQ ID NO: 62)
                     *** *****  **   * ***  ****   *          *  ****
```

Figure 48

(SEQ ID NO.63)

>PR8HA-WT-Homo-sapiens

ATGAAGGCCAACCTGCTGGTGCTGCTGTCTGCCCTGGCTGCCGCCGATGCCGATACCATCTGTATCGGCT
ACCACGCCAACAACAGCACCGACACCGTGGATACCGTGCTGGAAAAGAACGTGACCGTGACCCACAGCGT
GAACCTGCTGGAAGATAGCCACAACGGCAAGCTGTGCCGGCTGAAGGGAATCGCCCCTCTGCAGCTGGGC
AAGTGCAATATCGCCGGCTGGCTGCTGGGCAACCCCGAGTGTGATCCTCTGCTGCCTGTGCGGAGCTGGT
CCTACATCGTGGAAACCCCCAACAGCGAGAACGGCATCTGCTACCCCGGCGACTTCATCGACTACGAGGA
ACTGCGCGAGCAGCTGAGCAGCGTGTCCAGCTTCGAGAGATTCGAGATCTTCCCCAAAGAGAGCAGCTGG
CCCAACCACAACACCAACGGCGTGACAGCCGCCTGTAGCCACGAGGGCAAGAGCAGCTTCTACAGAAACC
TGCTGTGGCTGACCGAGAAAGAGGGCAGCTACCCCAAGCTGAAGAACAGCTACGTGAACAAGAAAGGCAA
AGAGGTGCTGGTGCTGTGGGGCATCCACCACCCCCCCAACTCTAAAGAGCAGCAGAACATCTACCAGAAC
GAGAACGCCTACGTGTCCGTCGTGACCAGCAACTACAACCGGCGGTTCACCCCCGAGATCGCCGAGAGGC
CTAAAGTGCGGGATCAGGCCGGCAGAATGAACTACTACTGGACCCTGCTGAAGCCCGGCGACACCATCAT
CTTCGAGGCCAACGGCAACCTGATCGCCCCTATGTACGCCTTCGCCCTGAGCAGAGGCTTCGGCAGCGGC
ATCATCACCAGCAACGCCAGCATGCACGAGTGCAACACCAAGTGCCAGACCCCCCTGGGCGCCATCAATA
GCAGCCTGCCCTACCAGAATATCCACCCCGTGACCATCGGCGAGTGCCCCAAATACGTGCGGAGCGCCAA
GCTGCGGATGGTCACCGGCCTGAGAAACACCCCCAGCATCCAGAGCAGGGGCCTGTTTGGAGCCATTGCC
GGCTTTATCGAGGGCGGCTGGACCGGCATGATCGACGGGTGGTACGGCTATCACCACCAGAATGAGCAGG
GCAGCGGCTACGCCGCCGATCAGAAGTCTACCCAGAACGCCATCAACGGCATCACCAACAAAGTGAACAC
CGTGATCGAGAAGATGAACATCCAGTTCACCGCCGTGGGCAAAGAGTTCAACAAGCTGGAAAAACGGATG
GAAAACCTGAACAAAAAGGTGGACGACGGCTTCCTGGACATCTGGACCTACAACGCCGAGCTGCTGGTGC
TGCTGGAAAACGAGCGGACCCTGGACTTCCACGACAGCAACGTGAAGAACCTGTACGAGAAAGTGAAGTC
CCAGCTGAAAAACAACGCCAAAGAGATCGGCAACGGCTGCTTCGAGTTCTACCACAAGTGCGACAACGAG
TGCATGGAAAGCGTGCGGAACGGCACCTACGACTACCCTAAGTACAGCGAGGAAAGCAAGCTGAACCGCG
AAAAAGTGGACGGCGTGAAGCTGGAATCCATGGGCATCTATCAGATCCTGGCCATCTACAGCACCGTGGC
CAGCAGCCTGGTGCTGCTGGTGTCTCTGGGCGCCATCTCATTTTGGATGTGCAGCAACGGCTCCCTGCAG
TGCCGGATCTGCATCTGA

Figure 49

(SEQ ID NO.64)

>PR8HA-WT-Cricetulus-griseus

ATGAAGGCCAACCTGCTGGTGCTGCTGTCTGCCCTGGCTGCCGCTGATGCCGACACCATCTGTATCGGCT
ACCACGCCAACAACTCCACCGACACCGTGGATACCGTGCTGGAAAAGAACGTGACCGTGACCCACTCCGT
GAATCTGCTGGAAGATTCCCACAACGGCAAGCTGTGCCGGCTGAAGGGAATCGCCCCTCTGCAGCTGGGC
AAGTGCAATATCGCTGGCTGGCTGCTGGGCAACCCCGAGTGTGATCCTCTGCTGCCTGTGCGGTCCTGGT
CCTACATCGTGGAAACCCCCAACTCCGAGAACGGCATCTGCTACCCCGGCGACTTCATCGACTACGAGGA
ACTGCGCGAGCAGCTGTCCTCCGTGTCCAGCTTCGAGAGATTCGAGATCTTCCCCAAAGAGTCCTCCTGG
CCCAACCACAACACCAACGGCGTGACCGCCGCCTGTTCTCACGAGGGCAAGAGCAGCTTCTACCGGAACC
TGCTGTGGCTGACCGAGAAAGAGGGCTCCTACCCCAAGCTGAAGAACTCCTACGTGAACAAGAAAGGCAA
AGAGGTGCTGGTGCTGTGGGGCATCCACCACCCCCCTAACTCCAAAGAGCAGCAGAACATCTACCAGAAC
GAGAATGCCTACGTGTCCGTCGTGACCTCCAACTACAACCGGCGGTTCACCCCCGAGATCGCCGAGAGGC
CTAAAGTGCGGGATCAGGCCGGCAGAATGAACTACTACTGGACCCTGCTGAAGCCCGGCGATACCATCAT
CTTCGAGGCCAACGGCAACCTGATCGCCCCTATGTACGCCTTCGCCCTGTCCAGAGGCTTCGGCTCCGGC
ATCATCACCTCCAACGCCTCCATGCACGAGTGCAACACCAAGTGCCAGACCCCCCTGGGCGCCATCAACA
GCTCCCTGCCTTACCAGAACATCCACCCCGTGACCATCGGCGAGTGCCCCAAATATGTGCGGAGCGCCAA
GCTGCGGATGGTCACCGGCCTGAGAAACACCCCCTCCATCCAGTCTAGAGGCCTGTTCGGCGCTATCGCC
GGCTTTATCGAGGGCGGCTGGACCGGCATGATCGACGGGTGGTACGGCTACCATCACCAGAATGAGCAGG
GCTCCGGCTACGCCGCCGACCAGAAGTCTACCCAGAACGCCATCAATGGCATCACCAACAAAGTGAACAC
CGTGATCGAGAAGATGAACATCCAGTTCACCGCCGTGGGCAAAGAGTTCAACAAGCTGGAAAAACGGATG
GAAAACCTGAACAAAAAGGTGGACGACGGCTTCCTGGACATCTGGACCTACAACGCCGAGCTGCTGGTGC
TGCTGGAAAACGAGCGGACCCTGGACTTCCACGACTCCAACGTGAAGAACCTGTACGAGAAAGTGAAGTC
CCAGCTGAAAAACAACGCCAAAGAGATCGGCAACGGCTGCTTCGAGTTCTACCACAAGTGCGACAACGAG
TGCATGGAATCCGTGCGGAACGGCACCTACGACTACCCTAAGTACTCCGAGGAAAGCAAGCTGAACCGCG
AAAAAGTGGACGGCGTGAAGCTGGAATCCATGGGCATCTATCAGATCCTGGCCATCTACTCCACCGTGGC
CTCCAGCCTGGTGCTGCTGGTGTCTCTGGGCGCCATCTCTTTCTGGATGTGCTCCAACGGCTCTCTGCAG
TGCCGGATCTGCATCTGA

Figure 50

(SEQ ID NO.65)

>PR8HA-WT-Nicotiana-benthamiana

ATGAAGGCTAACCTTCTGGTGCTTCTGTCTGCTCTTGCTGCTGCTGATGCTGATACCATCTGCATTGGTT
ACCACGCTAACAACAGCACCGATACTGTGGATACCGTGCTTGAGAAGAATGTGACCGTGACCCACTCTGT
GAACCTGCTTGAGGATTCTCACAACGGTAAGCTGTGCAGGCTTAAGGGTATTGCTCCACTGCAGCTTGGT
AAGTGCAATATCGCTGGTTGGCTTCTGGGTAACCCTGAGTGTGATCCTTTGCTTCCTGTGAGGTCCTGGT
CCTACATTGTGGAAACTCCTAACAGCGAGAACGGTATCTGCTACCCTGGTGATTTCATCGATTACGAGGA
ACTGAGAGAGCAGCTGTCCAGCGTTTCATCTTTTGAGAGGTTCGAGATCTTCCCTAAAGAGTCCTCTTGG
CCTAACCACAACACTAACGGTGTTACCGCTGCTTGCTCTCACGAGGGTAAGAGCAGCTTCTATAGGAACC
TTCTTTGGCTGACCGAGAAAGAGGGAAGCTACCCTAAGCTGAAGAACAGCTACGTGAACAAGAAGGGTAA
AGAGGTTCTGGTTCTTTGGGGTATCCACCACCCTCCAAACTCTAAAGAACAGCAGAACATCTACCAGAAC
GAGAACGCTTACGTGAGCGTGGTGACCAGCAATTACAACAGAAGGTTCACCCCTGAGATCGCTGAGAGGC
CTAAGGTTAGAGATCAGGCTGGTAGGATGAACTACTACTGGACCCTTCTGAAGCCTGGTGATACCATTAT
CTTCGAGGCTAACGGTAACCTGATCGCTCCTATGTACGCTTTCGCTCTGTCTAGGGGTTTCGGTTCTGGT
ATCATCACCAGCAACGCTTCTATGCACGAGTGCAATACCAAGTGCCAGACTCCTCTTGGTGCTATCAACA
GCTCTCTGCCTTACCAGAACATTCACCCTGTGACCATTGGTGAGTGCCCTAAGTATGTGAGGTCTGCTAA
GTTGAGGATGGTGACCGGTCTTAGGAACACCCCTTCTATCCAGTCTAGGGGACTTTTCGGAGCTATCGCT
GGATTCATTGAGGGAGGTTGGACCGGTATGATCGATGGTTGGTACGGTTACCACCATCAGAACGAACAGG
GTTCTGGATACGCTGCTGATCAAAAGTCTACCCAGAACGCTATCAACGGAATCACCAACAAGGTGAACAC
CGTGATCGAGAAGATGAACATCCAGTTCACCGCTGTGGGAAAAGAGTTCAACAAGTTGGAGAAGAGGATG
GAAAACCTTAACAAGAAAGTGGATGATGGTTTCCTGGATATCTGGACCTACAACGCTGAGCTGCTTGTGC
TTCTTGAGAACGAGAGGACCCTGGATTTCCACGATAGCAACGTGAAGAACCTGTACGAGAAGGTGAAGTC
CCAGCTTAAGAACAACGCTAAAGAGATCGGTAACGGTTGCTTCGAGTTCTACCACAAGTGCGATAACGAG
TGCATGGAAAGCGTGAGGAACGGAACCTACGATTACCCTAAGTACAGCGAAGAGTCCAAGCTGAACAGGG
AAAAAGTTGATGGTGTGAAGCTTGAGAGCATGGGAATCTATCAGATCCTGGCTATCTACAGCACCGTGGC
TTCTAGCCTTGTGCTTTTGGTTAGCCTGGGTGCTATCTCCTTCTGGATGTGCTCTAACGGTTCTCTGCAG
TGCAGGATCTGCATCTAG

Figure 51

(SEQ ID NO.66)

>PR8HA-WT-Pichia-pastoris

ATGAAGGCTAACTTGTTGGTTTTGTTGTCCGCTTTGGCTGCTGCTGATGCTGACACTATCTGTATTGGTT
ACCACGCTAACAACTCCACTGACACTGTTGACACAGTTTTGGAGAAGAACGTTACTGTTACTCACTCCGT
TAATTTGTTGGAGGACTCCCACAACGGAAAGTTGTGTAGATTGAAGGGTATCGCTCCATTGCAGTTGGGA
AAGTGTAACATTGCTGGTTGGTTGTTGGGTAACCCAGAGTGTGATCCTTTGTTGCCAGTTAGATCCTGGT
CCTACATCGTTGAGACTCCAAACTCCGAGAACGGTATCTGTTACCCAGGTGACTTCATCGACTACGAAGA
GTTGAGAGAGCAGTTGTCCTCCGTTTCCTCATTCGAGAGATTCGAGATCTTCCCAAAAGAGTCCTCTTGG
CCAAACCACAACACTAACGGTGTTACTGCTGCTTGTTCCCACGAGGGAAAGTCCTCATTCTACAGAAACT
TGTTGTGGTTGACTGAGAAAGAGGGTTCCTACCCAAAGTTGAAGAACTCCTACGTTAACAAGAAGGGTAA
AGAGGTTTTGGTTTTGTGGGGTATCCACCACCCACCAAACTCCAAAGAGCAACAGAACATCTACCAGAAC
GAGAACGCTTACGTTTCTGTTGTTACTTCCAACTACAACAGAAGATTCACTCCAGAGATCGCTGAAAGAC
CAAAGGTTAGAGATCAGGCTGGTAGAATGAACTACTACTGGACTTTGTTGAAGCCAGGTGACACAATCAT
CTTCGAGGCTAACGGTAACTTGATCGCTCCAATGTACGCTTTCGCTTTGTCCAGAGGTTTCGGTTCCGGT
ATCATCACTTCTAACGCTTCCATGCACGAGTGTAACACTAAGTGTCAGACTCCATTGGGTGCTATCAACT
CCTCCTTGCCATACCAAAACATCCACCCAGTTACTATCGGTGAGTGTCCTAAGTACGTTAGATCCGCTAA
GTTGAGAATGGTTACTGGTTTGAGAAACACTCCATCCATCCAGTCTAGAGGTTTGTTCGGTGCTATCGCT
GGTTTCATTGAAGGTGGTTGGACTGGTATGATCGACGGTTGGTACGGTTACCACCACCAAAACGAACAAG
GTTCTGGTTACGCTGCTGACCAAAAGTCCACTCAGAACGCTATCAACGGTATCACTAACAAGGTTAACAC
TGTTATCGAGAAGATGAACATCCAGTTCACTGCTGTTGGTAAAGAGTTCAACAAGTTGGAAAAGAGAATG
GAAAACTTGAACAAGAAAGTTGACGACGGTTTCTTGGACATCTGGACTTACAACGCTGAGTTGTTGGTTT
TGTTGGAGAACGAGAGAACTTTGGACTTCCACGACTCCAACGTTAAGAACTTGTACGAGAAGGTTAAGTC
CCAATTGAAGAACAACGCTAAAGAGATCGGTAACGGTTGTTTCGAGTTCTACCACAAGTGTGACAACGAG
TGTATGGAATCCGTTAGAAACGGTACTTACGACTACCCTAAGTACTCCGAAGAGTCCAAGTTGAACAGAG
AAAAGGTTGATGGTGTTAAGTTGGAATCCATGGGTATCTACCAAATCTTGGCTATCTACTCTACTGTTGC
TTCCTCCTTGGTTTTGTTGGTTTCCTTGGGTGCTATCTCCTTCTGGATGTGTTCCAACGGTTCCTTGCAG
TGTAGAATCTGTATCTAA

Figure 52

(SEQ ID NO.67)

>PR8HA-WT-Saccharomyces-cerevisiae

ATGAAGGCCAACTTGTTGGTTTTGTTGTCTGCTTTGGCTGCTGCTGATGCTGATACAATATGTATTGGTT
ACCATGCCAACAACTCTACCGATACTGTTGATACCGTTTTGGAAAAGAACGTTACCGTTACCCATTCCGT
CAATTTGTTGGAAGATTCCCATAACGGTAAATTGTGCAGATTGAAAGGTATTGCCCCATTGCAATTGGGT
AAATGTAATATTGCTGGTTGGTTGTTGGGTAACCCAGAATGTGATCCATTATTGCCAGTTAGATCTTGGT
CCTACATCGTTGAAACTCCAAATTCCGAAAATGGTATTTGCTACCCAGGTGATTTCATCGACTATGAAGA
ATTGAGAGAACAATTGTCCTCCGTTTCCTCATTCGAAAGATTCGAAATCTTCCCAAAAGAATCCTCTTGG
CCAAACCATAACACTAATGGTGTTACTGCTGCTTGTTCCCATGAAGGTAAAAGTTCTTTCTACAGAAACT
TGTTGTGGTTGACCGAAAAAGAAGGTTCTTACCCAAAGTTGAAGAACTCCTACGTTAACAAGAAGGGTAA
AGAAGTTTTGGTCTTGTGGGGTATTCATCATCCACCAAACTCTAAAGAACAACAAAACATCTACCAAAAC
GAAAACGCCTACGTTTCTGTTGTTACCTCTAACTACAACAGAAGATTCACCCCAGAAATTGCTGAAAGAC
CAAAGGTTAGAGATCAAGCTGGTAGAATGAATTACTACTGGACTTTGTTGAAACCAGGTGACACCATTAT
TTTCGAAGCCAACGGTAATTTGATTGCTCCAATGTATGCTTTCGCTTTGTCTAGAGGTTTTGGTTCCGGT
ATTATTACTTCCAACGCTTCTATGCATGAATGCAACACTAAGTGTCAAACTCCATTGGGTGCTATCAATT
CATCTTTGCCATACCAAAACATCCACCCAGTTACTATTGGTGAATGTCCTAAGTATGTTAGATCCGCCAA
ATTGAGAATGGTTACCGGTTTGAGAAACACCCCATCTATTCAATCAAGAGGTTTGTTTGGTGCTATTGCC
GGTTTTATTGAAGGTGGTTGGACTGGTATGATTGATGGTTGGTATGGTTACCACCATCAAAACGAACAAG
GTTCTGGTTACGCTGCTGATCAAAAGTCTACTCAAAATGCCATTAACGGTATTACCAACAAGGTTAACAC
CGTCATCGAAAAGATGAACATTCAATTCACCGCCGTCGGTAAAGAATTCAACAAGTTAGAAAAGAGAATG
GAAAACTTGAACAAAAAGGTCGACGATGGTTTCTTGGATATTTGGACTTACAACGCCGAATTATTGGTCT
TATTGGAAAACGAAAGAACCTTGGATTTCCACGATTCCAACGTTAAGAACTTGTACGAAAAGGTTAAGTC
CCAATTGAAAAACAACGCCAAAGAAATTGGTAACGGTTGCTTTGAATTCTACCACAAGTGTGATAACGAA
TGCATGGAATCTGTTAGAAACGGTACTTACGATTACCCTAAGTACTCCGAAGAATCCAAGTTGAACAGAG
AAAAAGTTGACGGTGTCAAGTTGGAATCTATGGGTATCTATCAAATCTTGGCCATCTACTCTACTGTTGC
CTCTTCATTAGTTTTGTTGGTTAGTTTGGGTGCCATCTCTTTTTGGATGTGTTCTAATGGTTCCTTGCAA
TGTAGAATCTGTATTTGA

Figure 53

(SEQ ID NO.68)

>PR8HA-WT-Spodoptera-frugiperda

ATGAAGGCTAACCTGCTGGTGCTGCTGTCCGCTCTGGCTGCTGCTGACGCTGACACCATCTGCATCGGTT
ACCACGCTAACAACTCCACCGACACCGTGGACACCGTCCTCGAGAAGAACGTGACCGTGACCCACTCCGT
GAACCTGCTCGAGGACTCCCACAACGGCAAGCTGTGCCGCCTGAAGGGTATCGCTCCTCTGCAGCTGGGC
AAGTGCAACATCGCTGGATGGCTGCTGGGCAACCCCGAGTGCGACCCTCTGCTGCCTGTCCGTTCCTGGT
CCTACATCGTGGAAACCCCCAACTCCGAGAACGGTATCTGCTACCCCGGCGACTTCATCGACTACGAGGA
ACTGCGCGAGCAGCTGTCCTCCGTGTCCAGCTTCGAGCGTTTCGAGATCTTCCCCAAGGAATCCTCCTGG
CCCAACCACAACACCAACGGTGTCACCGCTGCTTGCTCCCACGAGGGCAAGTCATCCTTCTACCGCAACC
TGCTGTGGCTGACCGAGAAGGAAGGCTCCTACCCCAAGCTGAAGAACTCCTACGTGAACAAGAAGGGCAA
GGAAGTCCTCGTCCTCTGGGGTATCCACCACCCCCCTAACTCCAAGGAACAGCAGAACATCTACCAGAAC
GAGAACGCTTACGTGTCCGTGGTCACCTCCAACTACAACCGTCGTTTCACCCCCGAGATCGCTGAGCGTC
CTAAAGTGCGCGACCAGGCTGGCCGTATGAACTACTACTGGACCCTGCTGAAGCCCGGCGACACCATCAT
CTTCGAGGCTAACGGCAACCTGATCGCTCCTATGTACGCTTTCGCTCTGTCCCGTGGTTTCGGTTCCGGT
ATCATCACCTCTAACGCTTCCATGCACGAGTGCAACACCAAGTGCCAGACCCCCCTGGGTGCTATCAACT
CCAGCCTGCCTTACCAGAACATCCACCCCGTGACCATCGGCGAGTGCCCTAAATACGTGCGTTCCGCTAA
GCTGCGTATGGTCACCGGCCTGCGTAACACCCCCTCCATCCAGTCCCGTGGCCTGTTCGGTGCTATCGCT
GGTTTCATCGAGGGCGGCTGGACCGGCATGATCGACGGATGGTACGGCTACCACCACCAAAACGAGCAGG
GTTCCGGTTACGCTGCTGACCAGAAGTCCACCCAGAACGCTATCAACGGTATCACCAACAAAGTGAACAC
CGTGATCGAAAAGATGAACATCCAGTTCACCGCCGTCGGCAAGGAATTCAACAAGCTCGAGAAGCGCATG
GAAAACCTCAACAAGAAGGTGGACGACGGCTTCCTGGACATCTGGACCTACAACGCTGAGCTGCTGGTCC
TGTTGGAGAACGAGCGTACCCTGGACTTCCACGACTCCAACGTGAAGAACCTGTACGAGAAAGTGAAGTC
CCAGCTCAAGAACAACGCCAAGGAAATCGGCAACGGTTGCTTCGAGTTCTACCACAAGTGCGACAACGAA
TGCATGGAATCCGTGCGTAACGGCACCTACGACTACCCTAAGTACTCCGAGGAATCTAAGCTGAACCGCG
AGAAGGTCGACGGCGTGAAGCTCGAGTCCATGGGCATCTACCAAATCCTGGCTATCTACTCTACCGTGGC
TTCCTCCCTGGTGCTCCTGGTGTCTCTGGGCGCTATCTCCTTCTGGATGTGCTCCAACGGTTCCCTGCAG
TGCCGTATCTGCATCTAA

Figure 54 A

```
HA-USSR-77.pro                 -------MKAKLLVLLCALSATD---ADTICIGYHANNSTDTVDTVLEKNV 41
HA-Texas-91.pro                -------MKAKLLVLLCAFTATY---ADTICIGYHANNSTDTVDTVLEKNV 41
WT-PR8-34.pro                  -------MKANLLVLLSALAAAD---ADTICIGYHANNSTDTVDTVLEKNV 41
HA-WSN-33.pro                  -------MKAKLLVLLYAFVATD---ADTICIGYHANNSTDTVDTIFEKNV 41
HA-SouthCarolina-1918.pro      -------MEARLLVLLCAFAATN---ADTICIGYHANNSTDTVDTVLEKNV 41
HA-California-09.pro           -------MKAILVVLLYTFATAN---ADTLCIGYHANNSTDTVDTVLEKNV 41
HA-Singapore-57.pro            ---------MAIIYLILLFTAVR---GDQICIGYHANNSTEKVDTILERNV 39
HA-Vietnam-04.pro              --------MEKIVLLFAIVSLVK---SDQICIGYHANNSTEQVDTIMEKNV 40
HA-Udorn-72.pro                MKTIIALSYIFCLVLGQDFPGNDNSTATLCLGHHAVPNGTLVKTITNDQI 50
HA-HongKong-68.pro             MKTIIALSYIFCLALGQDLPGNDNSTATLCLGHHAVPNGTLVKTITDDQI 50
HA-Panama-99.pro               MKTIIALSYILCLVFAQKLPGNDNSTATLCLGHHAVSNGTLVKTITNDQI 50
HA-Wisconsin-05.pro            MKTIIALSYILCLVFAQKLPGNDNSTATLCLGHHAVPNGTIVKTITNDQI 50
HA-Shanghai-13.pro             MN------TQILVFALIAIIPTN---ADKICLGHHAVSNGTKVNTLTERGV 42
                                         :   :             :*:*:**  .   *.*: :  :

HA-USSR-77.pro                 TVTHSVNLLEDSHNGKLCRLKGIAPLQLGKCSIAGWILGNPECESLVSKK 91
HA-Texas-91.pro                TVTHSVNLLEDSHNGKLCRLKGIAPLQLGNCSVAGWILGNPKCESLFSKE 91
WT-PR8-34.pro                  TVTHSVNLLEDSHNGKLCRLKGIAPLQLGKCNIAGWLLGNPECDPLLPVR 91
HA-WSN-33.pro                  AVTHSVNLLEDRHNGKLCKLKGIAPLQLGKCNIIGWLLGNPECDSLLPAR 91
HA-SouthCarolina-1918.pro      TVTHSVNLLEDSHNGKLCKLKGIAPLQLGKCNIAGWLLGNPECDLLLTAS 91
HA-California-09.pro           TVTHSVNLLEDKHNGKLCKLRGVAPLHLGKCNIAGWILGNPECESLSTAS 91
HA-Singapore-57.pro            TVTHAKDILEKTHNGKLCKLNGIPPLELGDCSIAGWLLGNPECDRLLSVP 89
HA-Vietnam-04.pro              TVTHAQDILEKKHNGKLCDLDGVKPLILRDCSVAGWLLGNPMCDEFINVP 90
HA-Udorn-72.pro                EVTNATELVQSSSTGKICN-NPHRILDGIDCTLIDALLGDPHCDGFQNE- 98
HA-HongKong-68.pro             EVTNATELVQSSSTGKICN-NPHRILDGIDCTLIDALLGDPHCDVFQNE- 98
HA-Panama-99.pro               EVTNATELVQSSSTGRICD-SPHQILDGENCTLIDALLGDPHCDGFQNK- 98
HA-Wisconsin-05.pro            EVTNATELVQSSSTGGICD-SPHQILDGENCTLIDALLGDPQCDGFQNK- 98
HA-Shanghai-13.pro             EVVNATETVERTNIPRICS-KGKRTVDLGQCGLLGTITGPPQCDQFLEF- 90
                                *.:: : ::      :*       :   .* : . : * * *: :

HA-USSR-77.pro                 SWSYIAETPNSENGTCYPGYFADYEELREQLSSVSSFERFEIFPKERSWP 141
HA-Texas-91.pro                SWSYIAETPNPENGTCYPGYFADYEELREQLSSVSSFERFEIFPKESSWP 141
WT-PR8-34.pro                  SWSYIVETPNSENGICYPGDFIDYEELREQLSSVSSFERFEIFPKESSWP 141
HA-WSN-33.pro                  SWSYIVETPNSENGACYPGDFIDYEELREQLSSVSSLERFEIFPKESSWP 141
HA-SouthCarolina-1918.pro      SWSYIVETSNSENGTCYPGDFIDYEELREQLSSVSSFEKFEIFPKTSSWP 141
HA-California-09.pro           SWSYIVETPSSDNGTCYPGDFIDYEELREQLSSVSSFERFEIFPKTSSWP 141
HA-Singapore-57.pro            EWSYIMEKENPRDGLCYPGSFNDYEELKHLLSSVKHFEKVKILPK-DRWT 138
HA-Vietnam-04.pro              EWSYIVEKANPVNDLCYPGDFNDYEELKHLLSRINHFEKIQIIPK-SSWS 139
HA-Udorn-72.pro                TWDLFVERSKAFS-NCYPYDVPDYASLRSLVASSG---TLEFISEGFTWT 144
HA-HongKong-68.pro             TWDLFVERSKAFS-NCYPYDVPDYASLRSLVASSG---TLEFITEGFTWT 144
HA-Panama-99.pro               EWDLFVERSKAYS-NCYPYDVPDYASLRSLVASSG---TLEFNNESFNWT 144
HA-Wisconsin-05.pro            KWDLFVERSKAYS-NCYPYDVPDYASLRSLVASSG---TLEFNDESFNWT 144
HA-Shanghai-13.pro             SADLIIERREGSD-VCYPGKFVNEEALRQILRESG---GIDKEAMGFTYS 136
                                 . : *  .  .  ***  . :   *:  :        ..       :.

HA-USSR-77.pro                 KHNVTRGVTASCSHKGKSSFYRNLLWLTE--KNGSYPNLSKSYVNNKEKE 189
HA-Texas-91.pro                NHTVTKGVTTSCSHNGKSSFYRNLLWLTE--KNGLYPNLSKSYVNNKEKE 189
WT-PR8-34.pro                  NHN-TNGVTAACSHEGKSSFYRNLLWLTE--KEGSYPKLKNSYVNKKGKE 188
HA-WSN-33.pro                  NHT-FNGVTASCSHRGKSSFYRNLLWLTK--KGDSYPKLTNSYVNNKGKE 188
HA-SouthCarolina-1918.pro      NHETTKGVTAACSYAGASSFYRNLLWLTK--KGSSYPKLSKSYVNNKGKE 189
HA-California-09.pro           NHDSNKGVTAACPHAGAKSFYKNLIWLVK--KGNSYPKLSKSYINDKGKE 189
HA-Singapore-57.pro            QHTTTGG-SRACAVSGNPSFFRNMVWLTK--KGSNYPVAKGSYNNTSGEQ 185
HA-Vietnam-04.pro              SHEASLGVSSACPYQGKSSFFRNVVWLIK--KNSTYPTIKRSYNNTNQED 187
HA-Udorn-72.pro                GVT-QNGGSNACKRGPDIGFFSRLNWLYK--SGSTYPVLNVTMPNNDNFD 191
HA-HongKong-68.pro             GVT-QNGGSNACKRGPGNGFFSRLNWLTK--SGSTYPVLNVTMPNNDNFD 191
HA-Panama-99.pro               GVA-QNGTSSACKRRSNNSFFSRLNWLHQ--LKYKYPALNVTMPNNEKFD 191
HA-Wisconsin-05.pro            GVT-QNGTSSSCKRRSNNSFFSRLNWLTH--LKFKYPALNVTMPNNEKFD 191
HA-Shanghai-13.pro             GIR-TNGATSACRR-SGSSFYAEMKWLLSNTDNAAFPQMTKSYKNTRKSP 184
                                     * : :*      .*: .: **        :*  . :  *
```

Figure 54 B

```
HA-USSR-77.pro                VLVLWGVHHPSNIEDQKTIYRKENAYVSVVSSNYNRRFTPEIAERPKVRG 239
HA-Texas-91.pro               VLVLWGVHHPSNIRDQRAIYHTENAYVSVVSSHYSRRFTPEIAKRPKVRD 239
WT-PR8-34.pro                 VLVLWGIHHPPNSKEQQNIYQNENAYVSVVTSNYNRRFTPEIAERPKVRD 238
HA-WSN-33.pro                 VLVLWGVHHPSSSDEQQSLYSNGNAYVSVASSNYNRRFTPEIAARPKVKD 238
HA-SouthCarolina-1918.pro     VLVLWGVHHPPTGTDQQSLYQNADAYVSVGSSKYNRRFTPEIAARPKVRD 239
HA-California-09.pro          VLVLWGIHHPSTSADQQSLYQNADAYVFVGSSRYSKKFKPEIAIRPKVRD 239
HA-Singapore-57.pro           MLIIWGVHHPNDETEQRTLYQNVGTYVSVGTSTLNKRSTPDIATRPKVNG 235
HA-Vietnam-04.pro             LLVLWGIHHPNDAAEQTKLYQNPTTYISVGTSTLNQRLVPRIATRSKVNG 237
HA-Udorn-72.pro               KLYIWGVHHPSTDQEQTSLYVQASGRVTVSTKRSQQTIIPNIGSRPWVRG 241
HA-HongKong-68.pro            KLYIWGVHHPSTNQEQTSLYVQESGRVTVSTRRSQQSIIPNIGSRPWVRG 241
HA-Panama-99.pro              KLYIWGVHHPSTDSDQISIYAQASGRVTVSTKRSQQTVIPNIGSIPWVRG 241
HA-Wisconsin-05.pro           KLYIWGVHHPVTDNDQIFLYAQASGRITVSTKRSQQTVIPNIGSRPRIRN 241
HA-Shanghai-13.pro            ALIVWGIHHSVSTAEQTKLYGSGNKLVTVGSSNYQQSFVPSPGARPQVNG 234
                               * :**:**.    :*  :*      : * :   .:   *  .  . :..

HA-USSR-77.pro                QAGRINYYWTLLEPGDTIIFEANGNLIAPWHAFALNRGFGSGIITSNASM 289
HA-Texas-91.pro               QEGRINYYWTLLEPGDTIIFEANGNLIAPWYAFALSRGFGSGIITSNASM 289
WT-PR8-34.pro                 QAGRMNYYWTLLKPGDTIIFEANGNLIAPMYAFALSRGFGSGIITSNASM 288
HA-WSN-33.pro                 QHGRMNYYWTLLEPGDTIIFEATGNLIAPWYAFALSRGFESGIITSNASM 288
HA-SouthCarolina-1918.pro     QAGRMNYYWTLLEPGDTITFEATGNLIAPWYAFALNRGSGSGIITSDAPV 289
HA-California-09.pro          QEGRMNYYWTLVEPGDKITFEATGNLVVPRYAFAMERNAGSGIIISDTPV 289
HA-Singapore-57.pro           LGSRMEFSWTLLDMWDTINFESTGNLIAPEYGFKISKRGSSGIMKTEGTL 285
HA-Vietnam-04.pro             QSGRMEFFWTILKPNDAINFESNGNFIAPEYAYKIVKKGDSTIMKSELEY 287
HA-Udorn-72.pro               LSSRISIYWTIVKPGDILVINSNGNLIAPRGYFKMRTGKSSIMRSDAPIG 291
HA-HongKong-68.pro            QSSRISIYWTIVKPGDVLVINSNGNLIAPRGYFKMRTGKSSIMSSDAPID 291
HA-Panama-99.pro              VSSRISIYWTIVKPGDILLINSTGNLIAPRGYFKIRSGKSSIMRSDAPIG 291
HA-Wisconsin-05.pro           IPSRISIYWTIVKPGDILLINSTGNLIAPRGYFKIRSGKSSIMRSDAPIG 291
HA-Shanghai-13.pro            LSGRIDFHWLMLNPNDTVTFSFNGAFIAPDRASFLR-GKSMGIQSGVQVD 283
                                .*:.  * ::.  * : :. .* ::.*     :       :

HA-USSR-77.pro                DECDTKCQTPQGAINSSLPFQNIHPVTIGECPKYVRSTKLRMVTGLRNIP 339
HA-Texas-91.pro               DECDAKCQTPQGAINSSLPFQNVHPVTIGECPKYVRSTKLRMVTGLRNIP 339
WT-PR8-34.pro                 HECNTKCQTPLGAINSSLPYQNIHPVTIGECPKYVRSAKLRMVTGLRNTP 338
HA-WSN-33.pro                 HECNTKCQTPQGSINSNLPFQNIHPVTIGECPKYVRSTKLRMVTGLRNIP 338
HA-SouthCarolina-1918.pro     HDCNTKCQTPHGAINSSLPFQNIHPVTIGECPKYVRSTKLRMATGLRNIP 339
HA-California-09.pro          HDCNTTCQTPKGAINTSLPFQNIHPITIGKCPKYVKSTKLRLATGLRNIP 339
HA-Singapore-57.pro           ENCETKCQTPLGAINTTLPFHNVHPLTIGECPKYVKSEKLVLATGLRNVP 335
HA-Vietnam-04.pro             GNCNTKCQTPMGAINSSMPFHNIHPLTIGECPKYVKSNRLVLATGLRNSP 337
HA-Udorn-72.pro               T-CISECITPNGSIPNDKPFQNVNKITYGACPKYVKQNTLKLATGMRNVP 340
HA-HongKong-68.pro            T-CISECITPNGSIPNDKPFQNVNKITYGACPKYVKQNTLKLATGMRNVP 340
HA-Panama-99.pro              K-CNSECITPNGSIPNDKPFQNVNRITYGACPRYVKQNTLKLATGMRNVP 340
HA-Wisconsin-05.pro           K-CNSECITPNGSIPNDKPFQNVNRITYGACPRYVKQNTLKLATGMRNVP 340
HA-Shanghai-13.pro            ANCEGDCYHSGGTIISNLPFQNIDSRAVGKCPRYVKQRSLLLATGMKNVP 333
                                *   *  . *:* .  *::*:.  : * **:**:.  * :.**::* *

HA-USSR-77.pro                SIQ----SRGLFGAIAGFIEGGWTGMIDGWYGYHHQNEQGSGYAADQKST 385
HA-Texas-91.pro               SIQ----SRGLFGAIAGFIEGGWTGMIDGWYGYHHQNEQGSGYAADQKST 385
WT-PR8-34.pro                 SIQ----SRGLFGAIAGFIEGGWTGMIDGWYGYHHQNEQGSGYAADQKST 384
HA-WSN-33.pro                 SIQ----YRGLFGAIAGFIEGGWTGMIDGWYGYHHQNEQGSGYAADQKST 384
HA-SouthCarolina-1918.pro     SIQ----SRGLFGAIAGFIEGGWTGMIDGWYGYHHQNEQGSGYAADQKST 385
HA-California-09.pro          SIQ----SRGLFGAIAGFIEGGWTGMVDGWYGYHHQNEQGSGYAADLKST 385
HA-Singapore-57.pro           QIE----SRGLFGAIAGFIEGGWQGMVDGWYGYHHSNDQGSGYAADKEST 381
HA-Vietnam-04.pro             QRERRRKKRGLFGAIAGFIEGGWQGMVDGWYGYHHSNEQGSGYAADKEST 387
HA-Udorn-72.pro               EK-----QTRGLFSAIAGFIENGWEGMIDGWYGFRHQNSEGTGQAADLKST 386
HA-HongKong-68.pro            EK-----QTRGLFGAIAGFIENGWEGMIDGWYGFRHQNSEGTGQAADLKST 386
HA-Panama-99.pro              EK-----QTRGIFGAIAGFIENGWEGMVDGWYGFRHQNSEGTGQAADLKST 386
HA-Wisconsin-05.pro           EK-----QTRGIFGAIAGFIENGWEGMVDGWYGFRHQNSEGIGQAADLKST 386
HA-Shanghai-13.pro            EIP---KGRGLFGAIAGFIENGWEGLIDGWYGFRHQNAQGEGTAADYKST 380
                              .       **:*.*******.** *::*****::*.* :* * *** :**
```

Figure 54 C

```
HA-USSR-77.pro              QNAINGITNKVNSVIEKMNTQFTAVGKEFNKLEKRMENLNKKVDDGFLDI 435
HA-Texas-91.pro             QNAINGITNKVNSVIEKMNTQFTAVGKEFNKLERRMENLNKKVDDGFLDI 435
WT-PR8-34.pro               QNAINGITNKVNTVIEKMNIQFTAVGKEFNKLEKRMENLNKKVDDGFLDI 434
HA-WSN-33.pro               QNAINGITNKVNSIIEKMNTQFTAVGKEFNNLEKRMENLNKKVDDGFLDI 434
HA-SouthCarolina-1918.pro   QNAIDGITNKVNSVIEKMNTQFTAVGKEFNNLERRIENLNKKVDDGFLDI 435
HA-California-09.pro        QNAIDEITNKVNSVIEKMNTQFTAVGKEFNHLEKRIENLNKKVDDGFLDI 435
HA-Singapore-57.pro         QKAFDGITNKVNSVIEKMNTQFEAVGKEFSNLERRLENLNKKMEDGFLDV 431
HA-Vietnam-04.pro           QKAIDGVTNKVNSIIDKMNTQFEAVGREFNNLERRIENLNKKMEDGFLDV 437
HA-Udorn-72.pro             QAAIDQINGKLNRVIEKTNEKFHQIEKEFSEVEGRIQDLEKYVEDTKIDL 436
HA-HongKong-68.pro          QAAIDQINGKLNRVIEKTNEKFHQIEKEFSEVEGRIQDLEKYVEDTKIDL 436
HA-Panama-99.pro            QAAINQINGKLNRLIEKTNEKFHQIEKEFSEVEGRIQDLEKYVEDTKIDL 436
HA-Wisconsin-05.pro         QAAINQINGKLNRLIGKTNEKFHQIEKEFSEVEGRIQDLEKYVEDTKIDL 436
HA-Shanghai-13.pro          QSAIDQITGKLNRLIEKTNQQFELIDNEFNEVEKQIGNVINWTRDSTIEV 430
                            * *:: :..*:* :* * * :*  : .**..:* :: :: :    *   ::

HA-USSR-77.pro              WTYNAELLVLLENERTLDFHDSNVKNLYEKVKSQLKNNAKEIGNGCFEFY 485
HA-Texas-91.pro             WTYNAELLVLLENGRTLDFHDSNVKNLYEKVKSQLKNNAKEIGNGCFEFY 485
WT-PR8-34.pro               WTYNAELLVLLENERTLDFHDSNVKNLYEKVKSQLKNNAKEIGNGCFEFY 484
HA-WSN-33.pro               WTYNAELLVLLENGRTLDFHDLNVKNLYEKVKSQLKNNAKEIGNGCFEFY 484
HA-SouthCarolina-1918.pro   WTYNAELLVLLENERTLDFHDSNVRNLYEKVKSQLKNNAKEIGNGCFEFY 485
HA-California-09.pro        WTYNAELLVLLENERTLDYHDSNVKNLYEKVRSQLKNNAKEIGNGCFEFY 485
HA-Singapore-57.pro         WTYNAELLVLMENERTLDFHDSNVKNLYDKVRMQLRDNVKELGNGCFEFY 481
HA-Vietnam-04.pro           WTYNAELLVLMENERTLDFHDSNVKNLYDKVRLQLRDNAKELGNGCFEFY 487
HA-Udorn-72.pro             WSYNAELLVALENQHTIDLTDSEMNKLFEKTRRQLRENAEDMGNGCFKIY 486
HA-HongKong-68.pro          WSYNAELLVALENQHTIDLTDSEMNKLFEKTRRQLRENAEDMGNGCFKIY 486
HA-Panama-99.pro            WSYNAELLVALENQHTIDLTDSEMNKLFERTKKQLRENAEDMGNGCFKIY 486
HA-Wisconsin-05.pro         WSYNAELLVALENQHTIDLTDSEMNKLFERTKKQLRENAEDMGNGCFKIY 486
HA-Shanghai-13.pro          WSYNAELLVAMENQHTIDLADSEMDKLYERVKRQLRENAEEDGTGCFEIF 480
                            *:******* :** :*:*  * :: :*:::.: **::*.:: *.***:::

HA-USSR-77.pro              HKCNNECMESVKNGTYDYPKYSEESKLNREKIDGVKLESMGVYQILAIYS 535
HA-Texas-91.pro             HKCNNECMESVKNGTYDYPKYSEESKLNRGKIDGVKLESMGVYQILAIYS 535
WT-PR8-34.pro               HKCDNECMESVRNGTYDYPKYSEESKLNREKVDGVKLESMGIYQILAIYS 534
HA-WSN-33.pro               HKCDNECMESVRNGTYDYPKYSEESKLNREKIDGVKLESMGVYQILAIYS 534
HA-SouthCarolina-1918.pro   HKCDDACMESVRNGTYDYPKYSEESKLNREEIDGVKLESMGVYQILAIYS 535
HA-California-09.pro        HKCDNTCMESVKNGTYDYPKYSEEAKLNREEIDGVKLESTRIYQILAIYS 535
HA-Singapore-57.pro         HKCDDECMNSVKNGTYDYPKYEEESKLNRNEIKGVKLSSMGVYQILAIYA 531
HA-Vietnam-04.pro           HKCDNECMESVRNGTYDYPQYSEEARLKREEISGVKLESIGIYQILSIYS 537
HA-Udorn-72.pro             HKCDNACIGSIRNGTYDHDVYRDEALNNRFQIKGVELKS-GYKDWILWIS 535
HA-HongKong-68.pro          HKCDNACIESIRNGTYDHDVYRDEALNNRFQIKGVELKS-GYKDWILWIS 535
HA-Panama-99.pro            HKCDNACIGSIRNGTYDHDVYRDEALNNRFQIKGVELKS-GYKDWILWIS 535
HA-Wisconsin-05.pro         HKCDNACIGSIRNGTYDHDVYRDEALNNRFQIKGVELKS-GYKDWILWIS 535
HA-Shanghai-13.pro          HKCDDDCMASIRNNTYDHSKYREEAMQNRIQIDPVKLSS-GYKDVILWFS 529
                            ***:: *: *::*.***:  * :*:  :* ::. *:*.*     : :   :

HA-USSR-77.pro              TVASSLVLLVSLGAISFWMCSNGSLQCRICI 566 (SEQ ID NO:111)
HA-Texas-91.pro             TVASSLVLLVSLGAISFWMCSNGSLQCRICI 566 (SEQ ID NO:112)
WT-PR8-34.pro               TVASSLVLLVSLGAISFWMCSNGSLQCRICI 565 (SEQ ID NO:1)
HA-WSN-33.pro               TVASSLVLLVSLGAISFWMCSNGSLQCRICI 565 (SEQ ID NO:113)
HA-SouthCarolina-1918.pro   TVASSLVLLVSLGAISFWMCSNGSLQCRICI 566 (SEQ ID NO:114)
HA-California-09.pro        TVASSLVLVVSLGAISFWMCSNGSLQCRICI 566 (SEQ ID NO:115)
HA-Singapore-57.pro         TVAGSLSLAIMMAGISFWMCSNGSLQCRICI 562 (SEQ ID NO:78)
HA-Vietnam-04.pro           TVASSLALAIMVAGLSLWMCSNGSLQCRICI 568 (SEQ ID NO:79)
HA-Udorn-72.pro             FAISCFLLCVVLLGFIMWACQKGNIRCNICI 566 (SEQ ID NO:73)
HA-HongKong-68.pro          FAISCFLLCVVLLGFIMWACQRGNIRCNICI 566 (SEQ ID NO:74)
HA-Panama-99.pro            FAISCFLLCVVLLGFIMWACQKGNIRCNICI 566 (SEQ ID NO:75)
HA-Wisconsin-05.pro         FAISCFLLCVALLGFIMWACQKGNIRCNICI 566 (SEQ ID NO:76)
HA-Shanghai-13.pro          FGASCFILLAIVMGLVFICVKNGNMRCTICI 560 (SEQ ID NO:77)
                              ..: *   : .: :   ..*.::* ***
```

Figure 55

(SEQ ID NO.80)

>PR8HA-soluble

MKANLLVLLSALAAADADTICIGYHANNSTDTVDTVLEKNVTVTHSVNLLEDSHNGKLCRLKGIAPLQLGKCNIAGWLLG

NPECDPLLPVRSWSYIVETPNSENGICYPGDFIDYEELREQLSSVSSFERFEIFPKESSWPNHNTNGVTAACSHEGKSSF

YRNLLWLTEKEGSYPKLKNSYVNKKGKEVLVLWGIHHPPNSKEQQNIYQNENAYVSVVTSNYNRRFTPEIAERPKVRDQA

GRMNYYWTLLKPGDTIIFEANGNLIAPMYAFALSRGFGSGIITSNASMHECNTKCQTPLGAINSSLPYQNIHPVTIGECP

KYVRSAKLRMVTGLRNTPSIQSRGLFGAIAGFIEGGWTGMIDGWYGYHHQNEQGSGYAADQKSTQNAINGITNKVNTVIE

KMNIQFTAVGKEFNKLEKRMENLNKKVDDGFLDIWTYNAELLVLLENERTLDFHDSNVKNLYEKVKSQLKNNAKEIGNGC

FEFYHKCDNECMESVRNGTYDYPKYSEESKLNREKVDGV<u>RSLVPRGSPGSGYIPEAPRDGQAYVRKDGEWVLLSTFLHHH</u>

<u>HHH</u>

Figure 56

(SEQ ID NO.81)

>HA-HongKong-68-soluble.pro

MKTIIALSYIFCLALGQDLPGNDNSTATLCLGHHAVPNGTLVKTITDDQIEVTNATELVQSSSTGKICNNPHRILDGIDC

TLIDALLGDPHCDVFQNETWDLFVERSKAFSNCYPYDVPDYASLRSLVASSGTLEFITEGFTWTGVTQNGGSNACKRGPG

NGFFSRLNWLTKSGSTYPVLNVTMPNNDNFDKLYIWGVHHPSTNQEQTSLYVQESGRVTVSTRRSQQSIIPNIGSRPWVR

GQSSRISIYWTIVKPGDVLVINSNGNLIAPRGYFKMRTGKSSIMSSDAPIDTCISECITPNGSIPNDKPFQNVNKITYGA

CPKYVKQNTLKLATGMRNVPEKQTRGLFGAIAGFIENGWEGMIDGWYGFRHQNSEGTGQAADLKSTQAAIDQINGKLNRV

IEKTNEKFHQIEKEFSEVEGRIQDLEKYVEDTKIDLWSYNAELLVALENQHTIDLTDSEMNKLFEKTRRQLRENAEDMGN

GCFKIYHKCDNACIESIRNGTYDHDVYRDEALNNRFQIKG<u>VRSLVPRGSPGSGYIPEAPRDGQAYVRKDGEWVLLSTFLH</u>

<u>HHHHH</u>

Figure 57

(SEQ ID NO.82)

>HA-Wisconsin-05-soluble.pro

MKTIIALSYILCLVFAQKLPGNDNSTATLCLGHHAVPNGTIVKTITNDQIEVTNATELVQSSSTGGICDSPHQILDGENC

TLIDALLGDPQCDGFQNKKWDLFVERSKAYSNCYPYDVPDYASLRSLVASSGTLEFNDESFNWTGVTQNGTSSSCKRRSN

NSFFSRLNWLTHLKFKYPALNVTMPNNEKFDKLYIWGVHHPVTDNDQIFLYAQASGRITVSTKRSQQTVIPNIGSRPRIR

NIPSRISIYWTIVKPGDILLINSTGNLIAPRGYFKIRSGKSSIMRSDAPIGKCNSECITPNGSIPNDKPFQNVNRITYGA

CPRYVKQNTLKLATGMRNVPEKQTRGIFGAIAGFIENGWEGMVDGWYGFRHQNSEGIGQAADLKSTQAAINQINGKLNRL

IGKTNEKFHQIEKEFSEVEGRIQDLEKYVEDTKIDLWSYNAELLVALENQHTIDLTDSEMNKLFERTKKQLRENAEDMGN

GCFKIYHKCDNACIGSIRNGTYDHDVYRDEALNNRFQIKG<u>VRSLVPRGSPGSGYIPEAPRDGQAYVRKDGEWVLLSTFLH</u>

<u>HHHHH</u>

Figure 58

(SEQ ID NO.83)

>HA-Vietnam-04-soluble.pro

MEKIVLLFAIVSLVKSDQICIGYHANNSTEQVDTIMEKNVTVTHAQDILEKKHNGKLCDLDGVKPLILRDCSVAGWLLGN

PMCDEFINVPEWSYIVEKANPVNDLCYPGDFNDYEELKHLLSRINHFEKIQIIPKSSWSSHEASLGVSSACPYQGKSSFF

RNVVWLIKKNSTYPTIKRSYNNTNQEDLLVLWGIHHPNDAAEQTKLYQNPTTYISVGTSTLNQRLVPRIATRSKVNGQSG

RMEFFWTILKPNDAINFESNGNFIAPEYAYKIVKKGDSTIMKSELEYGNCNTKCQTPMGAINSSMPFHNIHPLTIGECPK

YVKSNRLVLATGLRNSPQRERRRKKRGLFGAIAGFIEGGWQGMVDGWYGYHHSNEQGSGYAADKESTQKAIDGVTNKVNS

IIDKMNTQFEAVGREFNNLERRIENLNKKMEDGFLDVWTYNAELLVLMENERTLDFHDSNVKNLYDKVRLQLRDNAKELG

NGCFEFYHKCDNECMESVRNGTYDYPQYSEEARLKREEISGVRSLVPRGSPGSGYIPEAPRDGQAYVRKDGEWVLLSTFL

HHHHHH

Figure 59

(SEQ ID NO.84)

>HA-Shanghai-13-soluble.pro

MNTQILVFALIAIIPTNADKICLGHHAVSNGTKVNTLTERGVEVVNATETVERTNIPRICSKGKRTVDLGQCGLLGTITG

PPQCDQFLEFSADLIIERREGSDVCYPGKFVNEEALRQILRESGGIDKEAMGFTYSGIRTNGATSACRRSGSSFYAEMKW

LLSNTDNAAFPQMTKSYKNTRKSPALIVWGIHHSVSTAEQTKLYGSGNKLVTVGSSNYQQSFVPSPGARPQVNGLSGRID

FHWLMLNPNDTVTFSFNGAFIAPDRASFLRGKSMGIQSGVQVDANCEGDCYHSGGTIISNLPFQNIDSRAVGKCPRYVKQ

RSLLLATGMKNVPEIPKGRGLFGAIAGFIENGWEGLIDGWYGFRHQNAQGEGTAADYKSTQSAIDQITGKLNRLIEKTNQ

QFELIDNEFNEVEKQIGNVINWTRDSITEVWSYNAELLVAMENQHTIDLADSEMDKLYERVKRQLRENAEEDGTGCFEIF

HKCDDDCMASIRNNTYDHSKYREEAMQNRIQIDP<u>VRSLVPRGSPGSGYIPEAPRDGQAYVRKDGEWVLLSTFLHHHHHH</u>

Figure 60

(SEQ ID NO.85)

>HA-Singapore-57-soluble.pro

MAIIYLILLFTAVRGDQICIGYHANNSTEKVDTILERNVTVTHAKDILEKTHNGKLCKLNGIPPLELGDCSIAGWLLGNP

ECDRLLSVPEWSYIMEKENPRDGLCYPGSFNDYEELKHLLSSVKHFEKVKILPKDRWTQHTTTGGSRACAVSGNPSFFRN

MVWLTKKGSNYPVAKGSYNNTSGEQMLIIWGVHHPNDETEQRTLYQNVGTYVSVGTSTLNKRSTPDIATRPKVNGLGSRM

EFSWTLLDMWDTINFESTGNLIAPEYGFKISKRGSSGIMKTEGTLENCETKCQTPLGAINTTLPFHNVHPLTIGECPKYV

KSEKLVLATGLRNVPQIESRGLFGAIAGFIEGGWQGMVDGWYGYHHSNDQGSGYAADKESTQKAFDGITNKVNSVIEKMN

TQFEAVGKEFSNLERRLENLNKKMEDGFLDVWTYNAELLVLMENERTLDFHDSNVKNLYDKVRMQLRDNVKELGNGCFEF

YHKCDDECMNSVKNGTYDYPKYEEESKLNRNEIKGVRSLVPRGSPGSGYIPEAPRDGQAYVRKDGEWVLLSTFLHHHHHH

Figure 61

(SEQ ID NO.86)

>PR8HA-403Y429Y

MKANLLVLLSALAAADADTICIGYHANNSTDTVDTVLEKNVTVTHSVNLLEDSHNGKLCRLKGIAPLQLGKCNIAGW

LLGNPECDPLLPVRSWSYIVETPNSENGICYPGDFIDYEELREQLSSVSSFERFEIFPKESSWPNHNTNGVTAACSH

EGKSSFYRNLLWLTEKEGSYPKLKNSYVNKKGKEVLVLWGIHHPPNSKEQQNIYQNENAYVSVVTSNYNRRFTPEIA

ERPKVRDQAGRMNYYWTLLKPGDTIIFEANGNLIAPMYAFALSRGFGSGIITSNASMHECNTKCQTPLGAINSSLPY

QNIHPVTIGECPKYVRSAKLRMVTGLRNTPSIQSRGLFGAIAGFIEGGWTGMIDGWYGYHHQNEQGSGYAADQKSTQ

NAINGITNKVNTVIEKMYIQFTAVGKEFNKLEKRMENLNKKVDYGFLDIWTYNAELLVLLENERTLDFHDSNVKNLY

EKVKSQLKNNAKEIGNGCFEFYHKCDNECMESVRNGTYDYPKYSEESKLNREKVDGVKLESMGIYQILAIYSTVASS

LVLLVSLGAISFWMCSNGSLQCRICI

Figure 62

(SEQ ID NO.87)

>PR8HA-403Y432Y

MKANLLVLLSALAAADADTICIGYHANNSTDTVDTVLEKNVTVTHSVNLLEDSHNGKLCRLKGIAPLQLGKCNIAGW

LLGNPECDPLLPVRSWSYIVETPNSENGICYPGDFIDYEELREQLSSVSSFERFEIFPKESSWPNHNTNGVTAACSH

EGKSSFYRNLLWLTEKEGSYPKLKNSYVNKKGKEVLVLWGIHHPPNSKEQQNIYQNENAYVSVVTSNYNRRFTPEIA

ERPKVRDQAGRMNYYWTLLKPGDTIIFEANGNLIAPMYAFALSRGFGSGIITSNASMHECNTKCQTPLGAINSSLPY

QNIHPVTIGECPKYVRSAKLRMVTGLRNTPSIQSRGLFGAIAGFIEGGWTGMIDGWYGYHHQNEQGSGYAADQKSTQ

NAINGITNKVNTVIEKMYIQFTAVGKEFNKLEKRMENLNKKVDDGFYDIWTYNAELLVLLENERTLDFHDSNVKNLY

EKVKSQLKNNAKEIGNGCFEFYHKCDNECMESVRNGTYDYPKYSEESKLNREKVDGVKLESMGIYQILAIYSTVASS

LVLLVSLGAISFWMCSNGSLQCRICI

Figure 63

(SEQ ID NO.88)

>PR8HA-403Y.pro

MKANLLVLLSALAAADADTICIGYHANNSTDTVDTVLEKNVTVTHSVNLLEDSHNGKLCRLKGIAPLQLGKCNIAGW

LLGNPECDPLLPVRSWSYIVETPNSENGICYPGDFIDYEELREQLSSVSSFERFEIFPKESSWPNHNTNGVTAACSH

EGKSSFYRNLLWLTEKEGSYPKLKNSYVNKKGKEVLVLWGIHHPPNSKEQQNIYQNENAYVSVVTSNYNRRFTPEIA

ERPKVRDQAGRMNYYWTLLKPGDTIIFEANGNLIAPMYAFALSRGFGSGIITSNASMHECNTKCQTPLGAINSSLPY

QNIHPVTIGECPKYVRSAKLRMVTGLRNTPSIQSRGLFGAIAGFIEGGWTGMIDGWYGYHHQNEQGSGYAADQKSTQ

NAINGITNKVNTVIEKMYIQFTAVGKEFNKLEKRMENLNKKVDDGFLDIWTYNAELLVLLENERTLDFHDSNVKNLY

EKVKSQLKNNAKEIGNGCFEFYHKCDNECMESVRNGTYDYPKYSEESKLNREKVDGVKLESMGIYQILAIYSTVASS

LVLLVSLGAISFWMCSNGSLQCRICI

Figure 64

(SEQ ID NO.89)

>PR8HA-403Y433Y.pro

MKANLLVLLSALAAADADTICIGYHANNSTDTVDTVLEKNVTVTHSVNLLEDSHNGKLCRLKGIAPLQLGKCNIAGW

LLGNPECDPLLPVRSWSYIVETPNSENGICYPGDFIDYEELREQLSSVSSFERFEIFPKESSWPNHNTNGVTAACSH

EGKSSFYRNLLWLTEKEGSYPKLKNSYVNKKGKEVLVLWGIHHPPNSKEQQNIYQNENAYVSVVTSNYNRRFTPEIA

ERPKVRDQAGRMNYYWTLLKPGDTIIFEANGNLIAPMYAFALSRGFGSGIITSNASMHECNTKCQTPLGAINSSLPY

QNIHPVTIGECPKYVRSAKLRMVTGLRNTPSIQSRGLFGAIAGFIEGGWTGMIDGWYGYHHQNEQGSGYAADQKSTQ

NAINGITNKVNTVIEKMYIQFTAVGKEFNKLEKRMENLNKKVDDGFLYIWTYNAELLVLLENERTLDFHDSNVKNLY

EKVKSQLKNNAKEIGNGCFEFYHKCDNECMESVRNGTYDYPKYSEESKLNREKVDGVKLESMGIYQILAIYSTVASS

LVLLVSLGAISFWMCSNGSLQCRICI

Figure 65

(SEQ ID NO.90)

>PR8HA-433Y435Y.pro

MKANLLVLLSALAAADADTICIGYHANNSTDTVDTVLEKNVTVTHSVNLLEDSHNGKLCRLKGIAPLQLGKCNIAGW

LLGNPECDPLLPVRSWSYIVETPNSENGICYPGDFIDYEELREQLSSVSSFERFEIFPKESSWPNHNTNGVTAACSH

EGKSSFYRNLLWLTEKEGSYPKLKNSYVNKKGKEVLVLWGIHHPPNSKEQQNIYQNENAYVSVVTSNYNRRFTPEIA

ERPKVRDQAGRMNYYWTLLKPGDTIIFEANGNLIAPMYAFALSRGFGSGIITSNASMHECNTKCQTPLGAINSSLPY

QNIHPVTIGECPKYVRSAKLRMVTGLRNTPSIQSRGLFGAIAGFIEGGWTGMIDGWYGYHHQNEQGSGYAADQKSTQ

NAINGITNKVNTVIEKMNIQFTAVGKEFNKLEKRMENLNKKVDDGFL<u>Y</u>I<u>Y</u>TYNAELLVLLENERTLDFHDSNVKNLY

EKVKSQLKNNAKEIGNGCFEFYHKCDNECMESVRNGTYDYPKYSEESKLNREKVDGVKLESMGIYQILAIYSTVASS

LVLLVSLGAISFWMCSNGSLQCRICI

Figure 66

(SEQ ID NO.91)

>PR8HA-435Y.pro

MKANLLVLLSALAAADADTICIGYHANNSTDTVDTVLEKNVTVTHSVNLLEDSHNGKLCRLKGIAPLQLGKCNIAGW

LLGNPECDPLLPVRSWSYIVETPNSENGICYPGDFIDYEELREQLSSVSSFERFEIFPKESSWPNHNTNGVTAACSH

EGKSSFYRNLLWLTEKEGSYPKLKNSYVNKKGKEVLVLWGIHHPPNSKEQQNIYQNENAYVSVVTSNYNRRFTPEIA

ERPKVRDQAGRMNYYWTLLKPGDTIIFEANGNLIAPMYAFALSRGFGSGIITSNASMHECNTKCQTPLGAINSSLPY

QNIHPVTIGECPKYVRSAKLRMVTGLRNTPSIQSRGLFGAIAGFIEGGWTGMIDGWYGYHHQNEQGSGYAADQKSTQ

NAINGITNKVNTVIEKMNIQFTAVGKEFNKLEKRMENLNKKVDDGFLDIYTYNAELLVLLENERTLDFHDSNVKNLY

EKVKSQLKNNAKEIGNGCFEFYHKCDNECMESVRNGTYDYPKYSEESKLNREKVDGVKLESMGIYQILAIYSTVASS

LVLLVSLGAISFWMCSNGSLQCRICI

Figure 67

(SEQ ID NO.92)

>PR8HA-406Y433Y

MKANLLVLLSALAAADADTICIGYHANNSTDTVDTVLEKNVTVTHSVNLLEDSHNGKLCRLKGIAPLQLGKCNIAGW

LLGNPECDPLLPVRSWSYIVETPNSENGICYPGDFIDYEELREQLSSVSSFERFEIFPKESSWPNHNTNGVTAACSH

EGKSSFYRNLLWLTEKEGSYPKLKNSYVNKKGKEVLVLWGIHHPPNSKEQQNIYQNENAYVSVVTSNYNRRFTPEIA

ERPKVRDQAGRMNYYWTLLKPGDTIIFEANGNLIAPMYAFALSRGFGSGIITSNASMHECNTKCQTPLGAINSSLPY

QNIHPVTIGECPKYVRSAKLRMVTGLRNTPSIQSRGLFGAIAGFIEGGWTGMIDGWYGYHHQNEQGSGYAADQKSTQ

NAINGITNKVNTVIEKMNIQYTAVGKEFNKLEKRMENLNKKVDDGFLYIWTYNAELLVLLENERTLDFHDSNVKNLY

EKVKSQLKNNAKEIGNGCFEFYHKCDNECMESVRNGTYDYPKYSEESKLNREKVDGVKLESMGIYQILAIYSTVASS

LVLLVSLGAISFWMCSNGSLQCRICI

Figure 68

(SEQ ID NO.93)

>PR8HA-411Y422Y.pro

MKANLLVLLSALAAADADTICIGYHANNSTDTVDTVLEKNVTVTHSVNLLEDSHNGKLCRLKGIAPLQLGKCNIAGW

LLGNPECDPLLPVRSWSYIVETPNSENGICYPGDFIDYEELREQLSSVSSFERFEIFPKESSWPNHNTNGVTAACSH

EGKSSFYRNLLWLTEKEGSYPKLKNSYVNKKGKEVLVLWGIHHPPNSKEQQNIYQNENAYVSVVTSNYNRRFTPEIA

ERPKVRDQAGRMNYYWTLLKPGDTIIFEANGNLIAPMYAFALSRGFGSGIITSNASMHECNTKCQTPLGAINSSLPY

QNIHPVTIGECPKYVRSAKLRMVTGLRNTPSIQSRGLFGAIAGFIEGGWTGMIDGWYGYHHQNEQGSGYAADQKSTQ

NAINGITNKVNTVIEKMNIQFTAVGYEFNKLEKRMEYLNKKVDDGFLDIWTYNAELLVLLENERTLDFHDSNVKNLY

EKVKSQLKNNAKEIGNGCFEFYHKCDNECMESVRNGTYDYPKYSEESKLNREKVDGVKLESMGIYQILAIYSTVASS

LVLLVSLGAISFWMCSNGSLQCRICI

Figure 69 A

```
PR8HA-403Y429Y        MKANLLVLLSALAAADADTICIGYHANNSTDTVDTVLEKNVTVTHSVNLLEDSHNGKLCR 60
PR8HA-403Y432Y        MKANLLVLLSALAAADADTICIGYHANNSTDTVDTVLEKNVTVTHSVNLLEDSHNGKLCR 60
PR8HA-403Y.pro        MKANLLVLLSALAAADADTICIGYHANNSTDTVDTVLEKNVTVTHSVNLLEDSHNGKLCR 60
PR8HA-403Y433Y.pro    MKANLLVLLSALAAADADTICIGYHANNSTDTVDTVLEKNVTVTHSVNLLEDSHNGKLCR 60
PR8HA-433Y435Y.pro    MKANLLVLLSALAAADADTICIGYHANNSTDTVDTVLEKNVTVTHSVNLLEDSHNGKLCR 60
PR8HA-435Y.pro        MKANLLVLLSALAAADADTICIGYHANNSTDTVDTVLEKNVTVTHSVNLLEDSHNGKLCR 60
PR8HA-406Y433Y        MKANLLVLLSALAAADADTICIGYHANNSTDTVDTVLEKNVTVTHSVNLLEDSHNGKLCR 60
PR8HA-WT              MKANLLVLLSALAAADADTICIGYHANNSTDTVDTVLEKNVTVTHSVNLLEDSHNGKLCR 60
PR8HA-411Y422Y.pro    MKANLLVLLSALAAADADTICIGYHANNSTDTVDTVLEKNVTVTHSVNLLEDSHNGKLCR 60
                      ************************************************************

PR8HA-403Y429Y        LKGIAPLQLGKCNIAGWLLGNPECDPLLPVRSWSYIVETPNSENGICYPGDFIDYEELRE 120
PR8HA-403Y432Y        LKGIAPLQLGKCNIAGWLLGNPECDPLLPVRSWSYIVETPNSENGICYPGDFIDYEELRE 120
PR8HA-403Y.pro        LKGIAPLQLGKCNIAGWLLGNPECDPLLPVRSWSYIVETPNSENGICYPGDFIDYEELRE 120
PR8HA-403Y433Y.pro    LKGIAPLQLGKCNIAGWLLGNPECDPLLPVRSWSYIVETPNSENGICYPGDFIDYEELRE 120
PR8HA-433Y435Y.pro    LKGIAPLQLGKCNIAGWLLGNPECDPLLPVRSWSYIVETPNSENGICYPGDFIDYEELRE 120
PR8HA-435Y.pro        LKGIAPLQLGKCNIAGWLLGNPECDPLLPVRSWSYIVETPNSENGICYPGDFIDYEELRE 120
PR8HA-406Y433Y        LKGIAPLQLGKCNIAGWLLGNPECDPLLPVRSWSYIVETPNSENGICYPGDFIDYEELRE 120
PR8HA-WT              LKGIAPLQLGKCNIAGWLLGNPECDPLLPVRSWSYIVETPNSENGICYPGDFIDYEELRE 120
PR8HA-411Y422Y.pro    LKGIAPLQLGKCNIAGWLLGNPECDPLLPVRSWSYIVETPNSENGICYPGDFIDYEELRE 120
                      ************************************************************

PR8HA-403Y429Y        QLSSVSSFERFEIFPKESSWPNHNTNGVTAACSHEGKSSFYRNLLWLTEKEGSYPKLKNS 180
PR8HA-403Y432Y        QLSSVSSFERFEIFPKESSWPNHNTNGVTAACSHEGKSSFYRNLLWLTEKEGSYPKLKNS 180
PR8HA-403Y.pro        QLSSVSSFERFEIFPKESSWPNHNTNGVTAACSHEGKSSFYRNLLWLTEKEGSYPKLKNS 180
PR8HA-403Y433Y.pro    QLSSVSSFERFEIFPKESSWPNHNTNGVTAACSHEGKSSFYRNLLWLTEKEGSYPKLKNS 180
PR8HA-433Y435Y.pro    QLSSVSSFERFEIFPKESSWPNHNTNGVTAACSHEGKSSFYRNLLWLTEKEGSYPKLKNS 180
PR8HA-435Y.pro        QLSSVSSFERFEIFPKESSWPNHNTNGVTAACSHEGKSSFYRNLLWLTEKEGSYPKLKNS 180
PR8HA-406Y433Y        QLSSVSSFERFEIFPKESSWPNHNTNGVTAACSHEGKSSFYRNLLWLTEKEGSYPKLKNS 180
PR8HA-WT              QLSSVSSFERFEIFPKESSWPNHNTNGVTAACSHEGKSSFYRNLLWLTEKEGSYPKLKNS 180
PR8HA-411Y422Y.pro    QLSSVSSFERFEIFPKESSWPNHNTNGVTAACSHEGKSSFYRNLLWLTEKEGSYPKLKNS 180
                      ************************************************************

PR8HA-403Y429Y        YVNKKGKEVLVLWGIHHPPNSKEQQNIYQNENAYVSVVTSNYNRRFTPEIAERPKVRDQA 240
PR8HA-403Y432Y        YVNKKGKEVLVLWGIHHPPNSKEQQNIYQNENAYVSVVTSNYNRRFTPEIAERPKVRDQA 240
PR8HA-403Y.pro        YVNKKGKEVLVLWGIHHPPNSKEQQNIYQNENAYVSVVTSNYNRRFTPEIAERPKVRDQA 240
PR8HA-403Y433Y.pro    YVNKKGKEVLVLWGIHHPPNSKEQQNIYQNENAYVSVVTSNYNRRFTPEIAERPKVRDQA 240
PR8HA-433Y435Y.pro    YVNKKGKEVLVLWGIHHPPNSKEQQNIYQNENAYVSVVTSNYNRRFTPEIAERPKVRDQA 240
PR8HA-435Y.pro        YVNKKGKEVLVLWGIHHPPNSKEQQNIYQNENAYVSVVTSNYNRRFTPEIAERPKVRDQA 240
PR8HA-406Y433Y        YVNKKGKEVLVLWGIHHPPNSKEQQNIYQNENAYVSVVTSNYNRRFTPEIAERPKVRDQA 240
PR8HA-WT              YVNKKGKEVLVLWGIHHPPNSKEQQNIYQNENAYVSVVTSNYNRRFTPEIAERPKVRDQA 240
PR8HA-411Y422Y.pro    YVNKKGKEVLVLWGIHHPPNSKEQQNIYQNENAYVSVVTSNYNRRFTPEIAERPKVRDQA 240
                      ************************************************************

PR8HA-403Y429Y        GRMNYYWTLLKPGDTIIFEANGNLIAPMYAFALSRGFGSGIITSNASMHECNTKCQTPLG 300
PR8HA-403Y432Y        GRMNYYWTLLKPGDTIIFEANGNLIAPMYAFALSRGFGSGIITSNASMHECNTKCQTPLG 300
PR8HA-403Y.pro        GRMNYYWTLLKPGDTIIFEANGNLIAPMYAFALSRGFGSGIITSNASMHECNTKCQTPLG 300
PR8HA-403Y433Y.pro    GRMNYYWTLLKPGDTIIFEANGNLIAPMYAFALSRGFGSGIITSNASMHECNTKCQTPLG 300
PR8HA-433Y435Y.pro    GRMNYYWTLLKPGDTIIFEANGNLIAPMYAFALSRGFGSGIITSNASMHECNTKCQTPLG 300
PR8HA-435Y.pro        GRMNYYWTLLKPGDTIIFEANGNLIAPMYAFALSRGFGSGIITSNASMHECNTKCQTPLG 300
PR8HA-406Y433Y        GRMNYYWTLLKPGDTIIFEANGNLIAPMYAFALSRGFGSGIITSNASMHECNTKCQTPLG 300
PR8HA-WT              GRMNYYWTLLKPGDTIIFEANGNLIAPMYAFALSRGFGSGIITSNASMHECNTKCQTPLG 300
PR8HA-411Y422Y.pro    GRMNYYWTLLKPGDTIIFEANGNLIAPMYAFALSRGFGSGIITSNASMHECNTKCQTPLG 300
                      ************************************************************

PR8HA-403Y429Y        AINSSLPYQNIHPVTIGECPKYVRSAKLRMVTGLRNTPSIQSRGLFGAIAGFIEGGWTGM 360
PR8HA-403Y432Y        AINSSLPYQNIHPVTIGECPKYVRSAKLRMVTGLRNTPSIQSRGLFGAIAGFIEGGWTGM 360
PR8HA-403Y.pro        AINSSLPYQNIHPVTIGECPKYVRSAKLRMVTGLRNTPSIQSRGLFGAIAGFIEGGWTGM 360
PR8HA-403Y433Y.pro    AINSSLPYQNIHPVTIGECPKYVRSAKLRMVTGLRNTPSIQSRGLFGAIAGFIEGGWTGM 360
PR8HA-433Y435Y.pro    AINSSLPYQNIHPVTIGECPKYVRSAKLRMVTGLRNTPSIQSRGLFGAIAGFIEGGWTGM 360
PR8HA-435Y.pro        AINSSLPYQNIHPVTIGECPKYVRSAKLRMVTGLRNTPSIQSRGLFGAIAGFIEGGWTGM 360
PR8HA-406Y433Y        AINSSLPYQNIHPVTIGECPKYVRSAKLRMVTGLRNTPSIQSRGLFGAIAGFIEGGWTGM 360
PR8HA-WT              AINSSLPYQNIHPVTIGECPKYVRSAKLRMVTGLRNTPSIQSRGLFGAIAGFIEGGWTGM 360
PR8HA-411Y422Y.pro    AINSSLPYQNIHPVTIGECPKYVRSAKLRMVTGLRNTPSIQSRGLFGAIAGFIEGGWTGM 360
                      ************************************************************
```

Figure 69 B

```
PR8HA-403Y429Y         IDGWYGYHHQNEQGSGYAADQKSTQNAINGITNKVNTVIEKMYIQFTAVGKEFNKLEKRM 420
PR8HA-403Y432Y         IDGWYGYHHQNEQGSGYAADQKSTQNAINGITNKVNTVIEKMYIQFTAVGKEFNKLEKRM 420
PR8HA-403Y.pro         IDGWYGYHHQNEQGSGYAADQKSTQNAINGITNKVNTVIEKMYIQFTAVGKEFNKLEKRM 420
PR8HA-403Y433Y.pro     IDGWYGYHHQNEQGSGYAADQKSTQNAINGITNKVNTVIEKMYIQFTAVGKEFNKLEKRM 420
PR8HA-433Y435Y.pro     IDGWYGYHHQNEQGSGYAADQKSTQNAINGITNKVNTVIEKMNIQFTAVGKEFNKLEKRM 420
PR8HA-435Y.pro         IDGWYGYHHQNEQGSGYAADQKSTQNAINGITNKVNTVIEKMNIQFTAVGKEFNKLEKRM 420
PR8HA-406Y433Y         IDGWYGYHHQNEQGSGYAADQKSTQNAINGITNKVNTVIEKMNIQYTAVGKEFNKLEKRM 420
PR8HA-WT               IDGWYGYHHQNEQGSGYAADQKSTQNAINGITNKVNTVIEKMNIQFTAVGKEFNKLEKRM 420
PR8HA-411Y422Y.pro     IDGWYGYHHQNEQGSGYAADQKSTQNAINGITNKVNTVIEKMNIQFTAVGYEFNKLEKRM 420
                       ****************************************** **:**** *********

PR8HA-403Y429Y         ENLNKKVDYGFLDIWTYNAELLVLLENERTLDFHDSNVKNLYEKVKSQLKNNAKEIGNGC 480
PR8HA-403Y432Y         ENLNKKVDDGFYDIWTYNAELLVLLENERTLDFHDSNVKNLYEKVKSQLKNNAKEIGNGC 480
PR8HA-403Y.pro         ENLNKKVDDGFLDIWTYNAELLVLLENERTLDFHDSNVKNLYEKVKSQLKNNAKEIGNGC 480
PR8HA-403Y433Y.pro     ENLNKKVDDGFLYIWTYNAELLVLLENERTLDFHDSNVKNLYEKVKSQLKNNAKEIGNGC 480
PR8HA-433Y435Y.pro     ENLNKKVDDGFLYIYTYNAELLVLLENERTLDFHDSNVKNLYEKVKSQLKNNAKEIGNGC 480
PR8HA-435Y.pro         ENLNKKVDDGFLDIYTYNAELLVLLENERTLDFHDSNVKNLYEKVKSQLKNNAKEIGNGC 480
PR8HA-406Y433Y         ENLNKKVDDGFLYIWTYNAELLVLLENERTLDFHDSNVKNLYEKVKSQLKNNAKEIGNGC 480
PR8HA-WT               ENLNKKVDDGFLDIWTYNAELLVLLENERTLDFHDSNVKNLYEKVKSQLKNNAKEIGNGC 480
PR8HA-411Y422Y.pro     EYLNKKVDDGFLDIWTYNAELLVLLENERTLDFHDSNVKNLYEKVKSQLKNNAKEIGNGC 480
                       * ****** **    *:*******************************************

PR8HA-403Y429Y         FEFYHKCDNECMESVRNGTYDYPKYSEESKLNREKVDGVKLESMGIYQILAIYSTVASSL 540
PR8HA-403Y432Y         FEFYHKCDNECMESVRNGTYDYPKYSEESKLNREKVDGVKLESMGIYQILAIYSTVASSL 540
PR8HA-403Y.pro         FEFYHKCDNECMESVRNGTYDYPKYSEESKLNREKVDGVKLESMGIYQILAIYSTVASSL 540
PR8HA-403Y433Y.pro     FEFYHKCDNECMESVRNGTYDYPKYSEESKLNREKVDGVKLESMGIYQILAIYSTVASSL 540
PR8HA-433Y435Y.pro     FEFYHKCDNECMESVRNGTYDYPKYSEESKLNREKVDGVKLESMGIYQILAIYSTVASSL 540
PR8HA-435Y.pro         FEFYHKCDNECMESVRNGTYDYPKYSEESKLNREKVDGVKLESMGIYQILAIYSTVASSL 540
PR8HA-406Y433Y         FEFYHKCDNECMESVRNGTYDYPKYSEESKLNREKVDGVKLESMGIYQILAIYSTVASSL 540
PR8HA-WT               FEFYHKCDNECMESVRNGTYDYPKYSEESKLNREKVDGVKLESMGIYQILAIYSTVASSL 540
PR8HA-411Y422Y.pro     FEFYHKCDNECMESVRNGTYDYPKYSEESKLNREKVDGVKLESMGIYQILAIYSTVASSL 540
                       ************************************************************

PR8HA-403Y429Y         VLLVSLGAISFWMCSNGSLQCRICI 565 (SEQ ID NO:86)
PR8HA-403Y432Y         VLLVSLGAISFWMCSNGSLQCRICI 565 (SEQ ID NO:87)
PR8HA-403Y.pro         VLLVSLGAISFWMCSNGSLQCRICI 565 (SEQ ID NO:88)
PR8HA-403Y433Y.pro     VLLVSLGAISFWMCSNGSLQCRICI 565 (SEQ ID NO:89)
PR8HA-433Y435Y.pro     VLLVSLGAISFWMCSNGSLQCRICI 565 (SEQ ID NO:90)
PR8HA-435Y.pro         VLLVSLGAISFWMCSNGSLQCRICI 565 (SEQ ID NO:91)
PR8HA-406Y433Y         VLLVSLGAISFWMCSNGSLQCRICI 565 (SEQ ID NO:92)
PR8HA-WT               VLLVSLGAISFWMCSNGSLQCRICI 565 (SEQ ID NO:1)
PR8HA-411Y422Y.pro     VLLVSLGAISFWMCSNGSLQCRICI 565 (SEQ ID NO:93)
                       *************************
```

Figure 70

>PR8HA-63G278S-N.pro

MKANLLVLLSALAAADADTICIGYHANNSTDTVDTVLEKNVTVTHSVNLLEDSHNGKLCRLKGENLYFQ (SEQ ID NO:94)

>PR8HA-63G278S-C-120Y150Y.pro

SNASMHECNTKCQTPLGAINSSLPYQNIHPVTIGECPKYVRSAKLRMVTGLRNTPSIQSRGLFGAIAGFIEGGWTGMIDGWYGYHHQNEQGSGYAADQKSTQNAINGITNKVNTVIEKMYIQFTAVGKEFNKLEKRMENLNKKVDDGFLYIWTYNAELLVLLENERTLDFHDSNVKNLYEKVKSQLKNNAKEIGNGCFEFYHKCDNECMESVRNGTYDYPKYSEESKLNREKVDGVKLESMGIYQILAIYSTVASSLVLLVSLGAISFWMCSNGSLQCRICI (SEQ ID NO:96)

Figure 71

>PR8HA-63G278S-N.pro

MKANLLVLLSALAAADADTICIGYHANNSTDTVDTVLEKNVTVTHSVNLLEDSHNGKLCRLKGENLYFQ (SEQ ID NO:94)

>PR8HA-63G278S-C-128Y139Y.pro

SNASMHECNTKCQTPLGAINSSLPYQNIHPVTIGECPKYVRSAKLRMVTGLRNTPSIQSRGLFGAIAGFIEGGWTGM
IDGWYGYHHQNEQGSGYAADQKSTQNAINGITNKVNTVIEKMNIQFTAVGYEFNKLEKRMEYLNKKVDDGFLDIWTY
NAELLVLLENERTLDFHDSNVKNLYEKVKSQLKNNAKEIGNGCFEFYHKCDNECMESVRNGTYDYPKYSEESKLNRE
KVDGVKLESMGIYQILAIYSTVASSLVLLVSLGAISFWMCSNGSLQCRICI (SEQ ID NO:97)

Figure 72

>PR8HA-63G278S-N.pro

MKANLLVLLSALAAADADTICIGYHANNSTDTVDTVLEKNVTVTHSVNLLEDSHNGKLCRLKGENLYFQ (SEQ ID NO:94)

>PR8HA-63G278S-C-120Y128Y139Y150Y.pro

SNASMHECNTKCQTPLGAINSSLPYQNIHPVTIGECPKYVRSAKLRMVTGLRNTPSIQSRGLFGAIAGFIEGGWTGM
IDGWYGYHHQNEQGSGYAADQKSTQNAINGITNKVNTVIEKMYIQFTAVGYEFNKLEKRMEYLNKKVDDGFLYIWTY
NAELLVLLENERTLDFHDSNVKNLYEKVKSQLKNNAKEIGNGCFEFYHKCDNECMESVRNGTYDYPKYSEESKLNRE
KVDGVKLESMGIYQILAIYSTVASSLVLLVSLGAISFWMCSNGSLQCRICI (SEQ ID NO:98)

Figure 73

>PR8HA-63G282S-N.pro

MKANLLVLLSALAAADADTICIGYHANNSTDTVDTVLEKNVTVTHSVNLLEDSHNGKLCRLKGENLYFQ (SEQ ID NO:94)

>PR8HA-63G282S-C-122Y152Y.pro

STSNASMHECNTKCQTPLGAINSSLPYQNIHPVTIGECPKYVRSAKLRMVTGLRNTPSIQSRGLFGAIAGFIEGGWTGMIDGWYGYHHQNEQGSGYAADQKSTQNAINGITNKVNTVIEKMYIQFTAVGKEFNKLEKRMENLNKKVDDGFLYIWTYNAELLVLLENERTLDFHDSNVKNLYEKVKSQLKNNAKEIGNGCFEFYHKCDNECMESVRNGTYDYPKYSEESKLNREKVDVKLESMGIYQILAIYSTVASSLVLLVSLGAISFWMCSNGSLQCRICI (SEQ ID NO:99)

Figure 74

>PR8HA-63G282S-N.pro

MKANLLVLLSALAAADADTICIGYHANNSTDTVDTVLEKNVTVTHSVNLLEDSHNGKLCRLKGENLYFQ (SEQ ID NO:94)

>PR8HA-63G282S-C-130Y141Y.pro

STSNASMHECNTKCQTPLGAINSSLPYQNIHPVTIGECPKYVRSAKLRMVTGLRNTPSIQSRGLFGAIAGFIEGGWTGMIDGWYGYHHQNEQGSGYAADQKSTQNAINGITNKVNTVIEKMNIQFTAVGYEFNKLEKRMEYLNKKVDDGFLDIWTYNAELLVLLENERTLDFHDSNVKNLYEKVKSQLKNNAKEIGNGCFEFYHKCDNECMESVRNGTYDYPKYSEESKLNREKVDGVKLESMGIYQILAIYSTVASSLVLLVSLGAISFWMCSNGSLQCRICI (SEQ ID NO:100)

Figure 75

>PR8HA-63G282S-N.pro

MKANLLVLLSALAAADADTICIGYHANNSTDTVDTVLEKNVTVTHSVNLLEDSHNGKLCRLKGENLYFQ (SEQ ID NO:94)

>PR8HA-63G282S-C-122Y130Y141Y152Y.pro

STSNASMHECNTKCQTPLGAINSSLPYQNIHPVTIGECPKYVRSAKLRMVTGLRNTPSIQSRGLFGAIAGFIEGGWTGMIDGWYGYHHQNEQGSGYAADQKSTQNAINGITNKVNTVIEKMYIQFTAVGYEFNKLEKRMEYLNKKVDDGFLYIWTYNAELLVLLENERTLDFHDSNVKNLYEKVKSQLKNNAKEIGNGCFEFYHKCDNECMESVRNGTYDYPKYSEESKLNREKVDGVKLESMGIYQILAIYSTVASSLVLLVSLGAISFWMCSNGSLQCRICI (SEQ ID NO:101)

Figure 76

>PR8HA-63G283G-N.pro

MKANLLVLLSALAAADADTICIGYHANNSTDTVDTVLEKNVTVTHSVNLLEDSHNGKLCRLKGENLYFQ (SEQ ID NO:94)

>PR8HA-63G283G-C-121Y151Y.pro

GSNASMHECNTKCQTPLGAINSSLPYQNIHPVTIGECPKYVRSAKLRMVTGLRNTPSIQSRGLFGAIAGFIEGGWTG
MIDGWYGYHHQNEQGSGYAADQKSTQNAINGITNKVNTVIEKMYIQFTAVGKEFNKLEKRMENLNKKVDDGFLYIWT
YNAELLVLLENERTLDFHDSNVKNLYEKVKSQLKNNAKEIGNGCFEFYHKCDNECMESVRNGTYDYPKYSEESKLNR
EKVDGVKLESMGIYQILAIYSTVASSLVLLVSLGAISFWMCSNGSLQCRICI (SEQ ID NO:102)

Figure 77

>PR8HA-63G283G-N.pro

MKANLLVLLSALAAADADTICIGYHANNSTDTVDTVLEKNVTVTHSVNLLEDSHNGKLCRLKGENLYFQ (SEQ ID NO:94)

>PR8HA-63G283G-C-129Y140Y.pro

GSNASMHECNTKCQTPLGAINSSLPYQNIHPVTIGECPKYVRSAKLRMVTGLRNTPSIQSRGLFGAIAGFIEGGWTG
MIDGWYGYHHQNEQGSGYAADQKSTQNAINGITNKVNTVIEKMNIQFTAVGYEFNKLEKRMEYLNKKVDDGFLDIWT
YNAELLVLLENERTLDFHDSNVKNLYEKVKSQLKNNAKEIGNGCFEFYHKCDNECMESVRNGTYDYPKYSEESKLNR
EKVDGVKLESMGIYQILAIYSTVASSLVLLVSLGAISFWMCSNGSLQCRICI (SEQ ID NO:103)

Figure 78

>PR8HA-63G283G-N.pro

MKANLLVLLSALAAADADTICIGYHANNSTDTVDTVLEKNVTVTHSVNLLEDSHNGKLCRLKGENLYFQ (SEQ ID NO:94)

>PR8HA-63G283G-C-121Y129Y140Y151Y.pro

GSNASMHECNTKCQTPLGAINSSLPYQNIHPVTIGECPKYVRSAKLRMVTGLRNTPSIQSRGLFGAIAGFIEGGWTG
MIDGWYGYHHQNEQGSGYAADQKSTQNAINGITNKVNTVIEKMYIQFTAVGYEFNKLEKRMEYLNKKVDDGFLYIWT
YNAELLVLLENERTLDFHDSNVKNLYEKVKSQLKNNAKEIGNGCFEFYHKCDNECMESVRNGTYDYPKYSEESKLNR
EKVDGVKLESMGIYQILAIYSTVASSLVLLVSLGAISFWMCSNGSLQCRICI (SEQ ID NO:104)

Figure 79

>PR8HA-48G291G-N.pro

MKANLLVLLSALAAADADTICIGYHANNSTDTVDTVLEKNVTVTHSVENLYFQ (SEQ ID NO:95)

>PR8HA-48G291G-C-113Y143Y.pro

GNTKCQTPLGAINSSLPYQNIHPVTIGECPKYVRSAKLRMVTGLRNTPSIQSRGLFGAIAGFIEGGWTGMIDGWYGY

HHQNEQGSGYAADQKSTQNAINGITNKVNTVIEKMYIQFTAVGKEFNKLEKRMENLNKKVDDGFLYIWTYNAELLVL

LENERTLDFHDSNVKNLYEKVKSQLKNNAKEIGNGCFEFYHKCDNECMESVRNGTYDYPKYSEESKLNREKVDGVKL

ESMGIYQILAIYSTVASSLVLLVSLGAISFWMCSNGSLQCRICI (SEQ ID NO:105)

Figure 80

>PR8HA-48G291G-N.pro

MKANLLVLLSALAAADADTICIGYHANNSTDTVDTVLEKNVTVTHSVENLYFQ (SEQ ID NO:95)

>PR8HA-48G291G-C-121Y132Y.pro

GNTKCQTPLGAINSSLPYQNIHPVTIGECPKYVRSAKLRMVTGLRNTPSIQSRGLFGAIAGFIEGGWTGMIDGWYGY
HHQNEQGSGYAADQKSTQNAINGITNKVNTVIEKMNIQFTAVGYEFNKLEKRMEYLNKKVDDGFLDIWTYNAELLVL
LENERTLDFHDSNVKNLYEKVKSQLKNNAKEIGNGCFEFYHKCDNECMESVRNGTYDYPKYSEESKLNREKVDGVKL
ESMGIYQILAIYSTVASSLVLLVSLGAISFWMCSNGSLQCRICI (SEQ ID NO:106)

Figure 81

>PR8HA-48G291G-N.pro

MKANLLVLLSALAAADADTICIGYHANNSTDTVDTVLEKNVTVTHSVENLYFQ (SEQ ID NO:95)

>PR8HA-48G291G-C-113Y121Y132Y143Y.pro

GNTKCQTPLGAINSSLPYQNIHPVTIGECPKYVRSAKLRMVTGLRNTPSIQSRGLFGAIAGFIEGGWTGMIDGWYGY

HHQNEQGSGYAADQKSTQNAINGITNKVNTVIEKM<u>Y</u>IQFTAVG<u>Y</u>EFNKLEKRME<u>Y</u>LNKKVDDGFL<u>Y</u>IWTYNAELLVL

LENERTLDFHDSNVKNLYEKVKSQLKNNAKEIGNGCFEFYHKCDNECMESVRNGTYDYPKYSEESKLNREKVDGVKL

ESMGIYQILAIYSTVASSLVLLVSLGAISFWMCSNGSLQCRICI (SEQ ID NO:107)

Figure 82

>PR8HA-48G291S-N.pro

MKANLLVLLSALAAADADTICIGYHANNSTDTVDTVLEKNVTVTHSVENLYFQ (SEQ ID NO:95)

>PR8HA-48G291S-C-113Y143Y.pro

SNTKCQTPLGAINSSLPYQNIHPVTIGECPKYVRSAKLRMVTGLRNTPSIQSRGLFGAIAGFIEGGWTGMIDGWYGY

HHQNEQGSGYAADQKSTQNAINGITNKVNTVIEKMYIQFTAVGKEFNKLEKRMENLNKKVDDGFLYIWTYNAELLVL

LENERTLDFHDSNVKNLYEKVKSQLKNNAKEIGNGCFEFYHKCDNECMESVRNGTYDYPKYSEESKLNREKVDGVKL

ESMGIYQILAIYSTVASSLVLLVSLGAISFWMCSNGSLQCRICI (SEQ ID NO:108)

Figure 83

>PR8HA-48G291S-N.pro

MKANLLVLLSALAAADADTICIGYHANNSTDTVDTVLEKNVTVTHSVENLYFQ (SEQ ID NO:95)

>PR8HA-48G291S-C-121Y132YY.pro

SNTKCQTPLGAINSSLPYQNIHPVTIGECPKYVRSAKLRMVTGLRNTPSIQSRGLFGAIAGFIEGGWTGMIDGWYGY

HHQNEQGSGYAADQKSTQNAINGITNKVNTVIEKMNIQFTAVGYEFNKLEKRMEYLNKKVDDGFLDIWTYNAELLVL

LENERTLDFHDSNVKNLYEKVKSQLKNNAKEIGNGCFEFYHKCDNECMESVRNGTYDYPKYSEESKLNREKVDGVKL

ESMGIYQILAIYSTVASSLVLLVSLGAISFWMCSNGSLQCRICI (SEQ ID NO:109)

Figure 84

>PR8HA-48G291S-N.pro

MKANLLVLLSALAAADADTICIGYHANNSTDTVDTVLEKNVTVTHSVENLYFQ (SEQ ID NO:95)

>PR8HA-48G291S-C-113Y121Y132Y143Y.pro

SNTKCQTPLGAINSSLPYQNIHPVTIGECPKYVRSAKLRMVTGLRNTPSIQSRGLFGAIAGFIEGGWTGMIDGWYGY

HHQNEQGSGYAADQKSTQNAINGITNKVNTVIEKMYIQFTAVGYEFNKLEKRMEYLNKKVDDGFLYIWTYNAELLVL

LENERTLDFHDSNVKNLYEKVKSQLKNNAKEIGNGCFEFYHKCDNECMESVRNGTYDYPKYSEESKLNREKVDGVKL

ESMGIYQILAIYSTVASSLVLLVSLGAISFWMCSNGSLQCRICI (SEQ ID NO:110)

Figure 88

>PR8HA-C-terminalfragment-core1.pro

SNTKCQTPLGAINSSLPYQNIHPVTIGECPKYVRSAKLRMVTGLRNTPSIQSRGLFGAIAGFIEGGWTGMIDGWYGY
HHQNEQGSGYAADQKSTQNAINGITNKVNTVIEKMYIQFTAVGKEFNKLEKRMENLNKKVDDGFLYIWTYNAELLVL
LENERTLDFHDSNVKNLYEKVKSQLKNNAKEIGNGCFEFYHKCDNECMESVRNGTYDYPKYSEESKLNREKVDGVKL
ESMGIYQILAIYSTVASSLVLLVSLGAISFWMCSNGSLQCRICI (SEQ ID NO:108)

>PR8HA-C-terminalfragment-core2.pro

SNTKCQTPLGAINSSLPYQNIHPVTIGECPKYVRSAKLRMVTGLRNTPSIQSRGLFGAIAGFIEGGWTGMIDGWYGY
HHQNEQGSGYAADQKSTQNAINGITNKVNTVIEKMNIQFTAVGYEFNKLEKRMEYLNKKVDDGFLDIWTYNAELLVL
LENERTLDFHDSNVKNLYEKVKSQLKNNAKEIGNGCFEFYHKCDNECMESVRNGTYDYPKYSEESKLNREKVDGVKL
ESMGIYQILAIYSTVASSLVLLVSLGAISFWMCSNGSLQCRICI (SEQ ID NO:109)

>PR8HA-C-terminalfragment-core3.pro

SNTKCQTPLGAINSSLPYQNIHPVTIGECPKYVRSAKLRMVTGLRNTPSIQSRGLFGAIAGFIEGGWTGMIDGWYGY
HHQNEQGSGYAADQKSTQNAINGITNKVNTVIEKMYIQFTAVGYEFNKLEKRMEYLNKKVDDGFLYIWTYNAELLVL
LENERTLDFHDSNVKNLYEKVKSQLKNNAKEIGNGCFEFYHKCDNECMESVRNGTYDYPKYSEESKLNREKVDGVKL
ESMGIYQILAIYSTVASSLVLLVSLGAISFWMCSNGSLQCRICI (SEQ ID NO:110)

Figure 89

(SEQ ID NO.117)

>PR8HA-C-terminalfragment-core1.pro

NTKCQTPLGAINSSLPYQNIHPVTIGECPKYVRSAKLRMVTGLRNTPSIQSRGLFGAIAGFIEGGWTGMIDGWYGYH

HQNEQGSGYAADQKSTQNAINGITNKVNTVIEKMNIQFTAVGKEFNKLEKRMENLNKKVDDGFLDIWTYNAELLVLL

ENERTLDFHDSNVKNLYEKVKSQLKNNAKEIGNGCFEFYHKCDNECMESVRNGTYDYPKYSEESKLNREKVDGVKLE

SMGIYQILAIYSTVASSLVLLVSLGAISFWMCSNGSLQCRICI

SEQUENCE LISTING

```
<160> NUMBER OF SEQ ID NOS: 118

<210> SEQ ID NO 1
<211> LENGTH: 565
<212> TYPE: PRT
<213> ORGANISM: Influenza A virus

<400> SEQUENCE: 1

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80
```

```
Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495
```

```
Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 2
<211> LENGTH: 1698
<212> TYPE: DNA
<213> ORGANISM: Influenza A virus

<400> SEQUENCE: 2

atgaaggcaa acctactggt cctgttaagt gcacttgcag ctgcagatgc agacacaata      60

tgtataggct accatgcgaa caattcaacc gacactgttg acacagtact cgagaagaat     120

gtgacagtga cacactctgt taacctgctc gaagacagcc acaacggaaa actatgtaga     180

ttaaaaggaa tagccccact acaattgggg aaatgtaaca tcgccggatg gctcttggga     240

aacccagaat gcgacccact gcttccagtg agatcatggt cctacattgt agaaacacca     300

aactctgaga atggaatatg ttatccagga gatttcatcg actatgagga gctgagggag     360

caattgagct cagtgtcatc attcgaaaga ttcgaaatat ttcccaaaga aagctcatgg     420

cccaaccaca acacaaacgg agtaacggca gcatgctccc atgaggggaa aagcagtttt     480

tacagaaatt tgctatggct gacggagaag gagggctcat acccaaagct gaaaaattct     540

tatgtgaaca aaaaagggaa agaagtcctt gtactgtggg gtattcatca cccgcctaac     600

agtaaggaac aacagaatat ctatcagaat gaaaatgctt atgtctctgt agtgacttca     660

aattataaca ggagatttac ccccgaaata gcagaaagac ccaaagtaag agatcaagct     720

gggaggatga actattactg gaccttgcta aaacccggag acacaataat atttgaggca     780

aatggaaatc taatagcacc aatgtatgct ttcgcactga gtagaggctt tgggtccggc     840

atcatcacct caaacgcatc aatgcatgag tgtaacacga agtgtcaaac accgctcgga     900

gctataaaca gcagtctccc ttaccagaat atacacccag tcacaatagg agagtgccca     960

aaatacgtca ggagtgccaa attgaggatg gttacaggac taaggaacac tccgtccatt    1020

caatccagag gtctatttgg agccattgcc ggttttattg aaggggggatg gactggaatg    1080

atagatggat ggtatggtta tcatcatcag aatgaacagg gatcaggcta tgcagcggat    1140

caaaaaagca cacaaaatgc cattaacggg attacaaaca aggtgaacac tgttatcgag    1200

aaaatgaaca ttcaattcac agctgtgggt aaagaattca acaaattaga aaaaaggatg    1260

gaaaatttaa ataaaaaagt tgatgatgga tttctggaca tttggacata taatgcagaa    1320

ttgttagttc tactggaaaa tgaaaggact ctggatttcc atgactcaaa tgtgaagaat    1380

ctgtatgaga aagtaaaaag ccaattaaag aataatgcca aagaaatcgg aaatggatgt    1440

tttgagttct accacaagtg tgacaatgaa tgcatggaaa gtgtaagaaa tgggacttat    1500

gattatccca aatattcaga agagtcaaag ttgaacaggg aaaaggtaga tggagtgaaa    1560

ttggaatcaa tggggatcta tcagattctg gcgatctact caactgtcgc cagttcactg    1620

gtgcttttgg tctccctggg ggcaatcagt ttctggatgt gttctaatgg atctttgcag    1680
```

-continued

```
tgcagaatat gcatctga                                                1698


<210> SEQ ID NO 3
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Glu
    50                  55                  60

Asn Leu Tyr Phe Gln Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Glu Asn Leu Tyr Phe Gln Ser Asn Ala Ser
        275                 280                 285

Met His Glu Cys Asn Thr Lys Cys Gln Thr Pro Leu Gly Ala Ile Asn
    290                 295                 300

Ser Ser Leu Pro Tyr Gln Asn Ile His Pro Val Thr Ile Gly Glu Cys
305                 310                 315                 320

Pro Lys Tyr Val Arg Ser Ala Lys Leu Arg Met Val Thr Gly Leu Arg
                325                 330                 335

Asn Thr Pro Ser Ile Gln Ser Arg Gly Leu Phe Gly Ala Ile Ala Gly
            340                 345                 350
```

```
Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Thr Val Ile
385                 390                 395                 400

Glu Lys Met Tyr Ile Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Tyr Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Lys Val Asp Gly Val Lys Leu Glu Ser Met Gly Ile Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 4
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Glu
    50                  55                  60

Asn Leu Tyr Phe Gln Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140
```

```
Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Glu Asn Leu Tyr Phe Gln Ser Asn Ala Ser
        275                 280                 285

Met His Glu Cys Asn Thr Lys Cys Gln Thr Pro Leu Gly Ala Ile Asn
    290                 295                 300

Ser Ser Leu Pro Tyr Gln Asn Ile His Pro Val Thr Ile Gly Glu Cys
305                 310                 315                 320

Pro Lys Tyr Val Arg Ser Ala Lys Leu Arg Met Val Thr Gly Leu Arg
                325                 330                 335

Asn Thr Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Thr Val Ile
385                 390                 395                 400

Glu Lys Met Asn Ile Gln Phe Thr Ala Val Gly Tyr Glu Phe Asn Lys
                405                 410                 415

Leu Glu Lys Arg Met Glu Tyr Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Lys Val Asp Gly Val Lys Leu Glu Ser Met Gly Ile Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560
```

Gln Cys Arg Ile Cys Ile
565

<210> SEQ ID NO 5
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Met Lys Ala Asn Leu Leu Val Leu Leu Ser Ala Leu Ala Ala Ala Asp
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Arg Leu Lys Gly Glu
50 55 60

Asn Leu Tyr Phe Gln Gly Lys Cys Asn Ile Ala Gly Trp Leu Leu Gly
65 70 75 80

Asn Pro Glu Cys Asp Pro Leu Leu Pro Val Arg Ser Trp Ser Tyr Ile
85 90 95

Val Glu Thr Pro Asn Ser Glu Asn Gly Ile Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Pro Lys Glu Ser Ser Trp Pro Asn His Asn
130 135 140

Thr Asn Gly Val Thr Ala Ala Cys Ser His Glu Gly Lys Ser Ser Phe
145 150 155 160

Tyr Arg Asn Leu Leu Trp Leu Thr Glu Lys Glu Gly Ser Tyr Pro Lys
165 170 175

Leu Lys Asn Ser Tyr Val Asn Lys Lys Gly Lys Glu Val Leu Val Leu
180 185 190

Trp Gly Ile His His Pro Pro Asn Ser Lys Glu Gln Gln Asn Ile Tyr
195 200 205

Gln Asn Glu Asn Ala Tyr Val Ser Val Val Thr Ser Asn Tyr Asn Arg
210 215 220

Arg Phe Thr Pro Glu Ile Ala Glu Arg Pro Lys Val Arg Asp Gln Ala
225 230 235 240

Gly Arg Met Asn Tyr Tyr Trp Thr Leu Leu Lys Pro Gly Asp Thr Ile
245 250 255

Ile Phe Glu Ala Asn Gly Asn Leu Ile Ala Pro Met Tyr Ala Phe Ala
260 265 270

Leu Ser Arg Gly Phe Gly Glu Asn Leu Tyr Phe Gln Ser Asn Ala Ser
275 280 285

Met His Glu Cys Asn Thr Lys Cys Gln Thr Pro Leu Gly Ala Ile Asn
290 295 300

Ser Ser Leu Pro Tyr Gln Asn Ile His Pro Val Thr Ile Gly Glu Cys
305 310 315 320

Pro Lys Tyr Val Arg Ser Ala Lys Leu Arg Met Val Thr Gly Leu Arg
325 330 335

Asn Thr Pro Ser Ile Gln Ser Arg Gly Leu Phe Gly Ala Ile Ala Gly
340 345 350

```
Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Thr Val Ile
385                 390                 395                 400

Glu Lys Met Tyr Ile Gln Phe Thr Ala Val Gly Tyr Glu Phe Asn Lys
                405                 410                 415

Leu Glu Lys Arg Met Glu Tyr Leu Asn Lys Lys Val Asp Asp Gly Phe
            420                 425                 430

Leu Tyr Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Lys Val Asp Gly Val Lys Leu Glu Ser Met Gly Ile Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 6
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Glu
    50                  55                  60

Asn Leu Tyr Phe Gln Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
```

-continued

```
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Glu Asn Leu Tyr Phe Gln
        275                 280                 285

Ser Thr Ser Asn Ala Ser Met His Glu Cys Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Tyr Ile Gln Phe Thr Ala Val
                405                 410                 415

Gly Lys Glu Phe Asn Lys Leu Glu Lys Arg Met Glu Asn Leu Asn Lys
            420                 425                 430

Lys Val Asp Asp Gly Phe Leu Tyr Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560
```

Cys Ser Asn Gly Ser Leu Gln Cys Arg Ile Cys Ile
565 570

<210> SEQ ID NO 7
<211> LENGTH: 572
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Met Lys Ala Asn Leu Leu Val Leu Leu Ser Ala Leu Ala Ala Ala Asp
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Arg Leu Lys Gly Glu
50 55 60

Asn Leu Tyr Phe Gln Gly Lys Cys Asn Ile Ala Gly Trp Leu Leu Gly
65 70 75 80

Asn Pro Glu Cys Asp Pro Leu Leu Pro Val Arg Ser Trp Ser Tyr Ile
85 90 95

Val Glu Thr Pro Asn Ser Glu Asn Gly Ile Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Pro Lys Glu Ser Ser Trp Pro Asn His Asn
130 135 140

Thr Asn Gly Val Thr Ala Ala Cys Ser His Glu Gly Lys Ser Ser Phe
145 150 155 160

Tyr Arg Asn Leu Leu Trp Leu Thr Glu Lys Glu Gly Ser Tyr Pro Lys
165 170 175

Leu Lys Asn Ser Tyr Val Asn Lys Lys Gly Lys Glu Val Leu Val Leu
180 185 190

Trp Gly Ile His His Pro Pro Asn Ser Lys Glu Gln Gln Asn Ile Tyr
195 200 205

Gln Asn Glu Asn Ala Tyr Val Ser Val Val Thr Ser Asn Tyr Asn Arg
210 215 220

Arg Phe Thr Pro Glu Ile Ala Glu Arg Pro Lys Val Arg Asp Gln Ala
225 230 235 240

Gly Arg Met Asn Tyr Tyr Trp Thr Leu Leu Lys Pro Gly Asp Thr Ile
245 250 255

Ile Phe Glu Ala Asn Gly Asn Leu Ile Ala Pro Met Tyr Ala Phe Ala
260 265 270

Leu Ser Arg Gly Phe Gly Ser Gly Ile Ile Glu Asn Leu Tyr Phe Gln
275 280 285

Ser Thr Ser Asn Ala Ser Met His Glu Cys Asn Thr Lys Cys Gln Thr
290 295 300

Pro Leu Gly Ala Ile Asn Ser Ser Leu Pro Tyr Gln Asn Ile His Pro
305 310 315 320

Val Thr Ile Gly Glu Cys Pro Lys Tyr Val Arg Ser Ala Lys Leu Arg
325 330 335

Met Val Thr Gly Leu Arg Asn Thr Pro Ser Ile Gln Ser Arg Gly Leu 340 345 350

Phe Gly Ala Ile Ala Gly Phe Ile Glu Gly Gly Trp Thr Gly Met Ile
355 360 365

Asp Gly Trp Tyr Gly Tyr His His Gln Asn Glu Gln Gly Ser Gly Tyr
370 375 380

Ala Ala Asp Gln Lys Ser Thr Gln Asn Ala Ile Asn Gly Ile Thr Asn
385 390 395 400

Lys Val Asn Thr Val Ile Glu Lys Met Asn Ile Gln Phe Thr Ala Val
405 410 415

Gly Tyr Glu Phe Asn Lys Leu Glu Lys Arg Met Glu Tyr Leu Asn Lys
420 425 430

Lys Val Asp Asp Gly Phe Leu Asp Ile Trp Thr Tyr Asn Ala Glu Leu
435 440 445

Leu Val Leu Leu Glu Asn Glu Arg Thr Leu Asp Phe His Asp Ser Asn
450 455 460

Val Lys Asn Leu Tyr Glu Lys Val Lys Ser Gln Leu Lys Asn Asn Ala
465 470 475 480

Lys Glu Ile Gly Asn Gly Cys Phe Glu Phe Tyr His Lys Cys Asp Asn
485 490 495

Glu Cys Met Glu Ser Val Arg Asn Gly Thr Tyr Asp Tyr Pro Lys Tyr
500 505 510

Ser Glu Glu Ser Lys Leu Asn Arg Glu Lys Val Asp Gly Val Lys Leu
515 520 525

Glu Ser Met Gly Ile Tyr Gln Ile Leu Ala Ile Tyr Ser Thr Val Ala
530 535 540

Ser Ser Leu Val Leu Leu Val Ser Leu Gly Ala Ile Ser Phe Trp Met
545 550 555 560

Cys Ser Asn Gly Ser Leu Gln Cys Arg Ile Cys Ile
565 570

<210> SEQ ID NO 8
<211> LENGTH: 572
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Met Lys Ala Asn Leu Leu Val Leu Leu Ser Ala Leu Ala Ala Ala Asp
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Arg Leu Lys Gly Glu
50 55 60

Asn Leu Tyr Phe Gln Gly Lys Cys Asn Ile Ala Gly Trp Leu Leu Gly
65 70 75 80

Asn Pro Glu Cys Asp Pro Leu Leu Pro Val Arg Ser Trp Ser Tyr Ile
85 90 95

Val Glu Thr Pro Asn Ser Glu Asn Gly Ile Cys Tyr Pro Gly Asp Phe
100 105 110

Ile Asp Tyr Glu Glu Leu Arg Glu Gln Leu Ser Ser Val Ser Ser Phe
115 120 125

```
Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Glu Asn Leu Tyr Phe Gln
        275                 280                 285

Ser Thr Ser Asn Ala Ser Met His Glu Cys Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Tyr Ile Gln Phe Thr Ala Val
                405                 410                 415

Gly Tyr Glu Phe Asn Lys Leu Glu Lys Arg Met Glu Tyr Leu Asn Lys
            420                 425                 430

Lys Val Asp Asp Gly Phe Leu Tyr Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
```

```
545                 550                 555                 560

Cys Ser Asn Gly Ser Leu Gln Cys Arg Ile Cys Ile
                565                 570


<210> SEQ ID NO 9
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Glu
    50                  55                  60

Asn Leu Tyr Phe Gln Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Glu Asn Leu Tyr Phe
        275                 280                 285

Gln Gly Ser Asn Ala Ser Met His Glu Cys Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335
```

-continued

```
Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Tyr Ile Gln Phe Thr Ala Val
                405                 410                 415

Gly Lys Glu Phe Asn Lys Leu Glu Lys Arg Met Glu Asn Leu Asn Lys
            420                 425                 430

Lys Val Asp Asp Gly Phe Leu Tyr Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
                565                 570


<210> SEQ ID NO 10
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Glu
    50                  55                  60

Asn Leu Tyr Phe Gln Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125
```

-continued

```
Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Glu Asn Leu Tyr Phe
        275                 280                 285

Gln Gly Ser Asn Ala Ser Met His Glu Cys Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Asn Ile Gln Phe Thr Ala Val
                405                 410                 415

Gly Tyr Glu Phe Asn Lys Leu Glu Lys Arg Met Glu Tyr Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540
```

```
Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
                565                 570


<210> SEQ ID NO 11
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Glu
    50                  55                  60

Asn Leu Tyr Phe Gln Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Glu Asn Leu Tyr Phe
        275                 280                 285

Gln Gly Ser Asn Ala Ser Met His Glu Cys Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335
```

```
Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Tyr Ile Gln Phe Thr Ala Val
                405                 410                 415

Gly Tyr Glu Phe Asn Lys Leu Glu Lys Arg Met Glu Tyr Leu Asn Lys
            420                 425                 430

Lys Val Asp Asp Gly Phe Leu Tyr Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
                565                 570
```

<210> SEQ ID NO 12
<211> LENGTH: 579
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Glu
        35                  40                  45

Asn Leu Tyr Phe Gln Gly Asn Leu Leu Glu Asp Ser His Asn Gly Lys
    50                  55                  60

Leu Cys Arg Leu Lys Gly Ile Ala Pro Leu Gln Leu Gly Lys Cys Asn
65                  70                  75                  80

Ile Ala Gly Trp Leu Leu Gly Asn Pro Glu Cys Asp Pro Leu Leu Pro
                85                  90                  95

Val Arg Ser Trp Ser Tyr Ile Val Glu Thr Pro Asn Ser Glu Asn Gly
            100                 105                 110

Ile Cys Tyr Pro Gly Asp Phe Ile Asp Tyr Glu Glu Leu Arg Glu Gln
```

```
        115                 120                 125

Leu Ser Ser Val Ser Ser Phe Glu Arg Phe Glu Ile Phe Pro Lys Glu
    130                 135                 140

Ser Ser Trp Pro Asn His Asn Thr Asn Gly Val Thr Ala Ala Cys Ser
145                 150                 155                 160

His Glu Gly Lys Ser Ser Phe Tyr Arg Asn Leu Leu Trp Leu Thr Glu
                165                 170                 175

Lys Glu Gly Ser Tyr Pro Lys Leu Lys Asn Ser Tyr Val Asn Lys Lys
            180                 185                 190

Gly Lys Glu Val Leu Val Leu Trp Gly Ile His His Pro Pro Asn Ser
        195                 200                 205

Lys Glu Gln Gln Asn Ile Tyr Gln Asn Glu Asn Ala Tyr Val Ser Val
    210                 215                 220

Val Thr Ser Asn Tyr Asn Arg Arg Phe Thr Pro Glu Ile Ala Glu Arg
225                 230                 235                 240

Pro Lys Val Arg Asp Gln Ala Gly Arg Met Asn Tyr Tyr Trp Thr Leu
                245                 250                 255

Leu Lys Pro Gly Asp Thr Ile Ile Phe Glu Ala Asn Gly Asn Leu Ile
            260                 265                 270

Ala Pro Met Tyr Ala Phe Ala Leu Ser Arg Gly Phe Gly Ser Gly Ile
        275                 280                 285

Ile Thr Ser Asn Ala Ser Met His Glu Cys Glu Asn Leu Tyr Phe Gln
    290                 295                 300

Gly Asn Thr Lys Cys Gln Thr Pro Leu Gly Ala Ile Asn Ser Ser Leu
305                 310                 315                 320

Pro Tyr Gln Asn Ile His Pro Val Thr Ile Gly Glu Cys Pro Lys Tyr
                325                 330                 335

Val Arg Ser Ala Lys Leu Arg Met Val Thr Gly Leu Arg Asn Thr Pro
            340                 345                 350

Ser Ile Gln Ser Arg Gly Leu Phe Gly Ala Ile Ala Gly Phe Ile Glu
        355                 360                 365

Gly Gly Trp Thr Gly Met Ile Asp Gly Trp Tyr Gly Tyr His His Gln
    370                 375                 380

Asn Glu Gln Gly Ser Gly Tyr Ala Ala Asp Gln Lys Ser Thr Gln Asn
385                 390                 395                 400

Ala Ile Asn Gly Ile Thr Asn Lys Val Asn Thr Val Ile Glu Lys Met
                405                 410                 415

Tyr Ile Gln Phe Thr Ala Val Gly Lys Glu Phe Asn Lys Leu Glu Lys
            420                 425                 430

Arg Met Glu Asn Leu Asn Lys Lys Val Asp Asp Gly Phe Leu Tyr Ile
        435                 440                 445

Trp Thr Tyr Asn Ala Glu Leu Leu Val Leu Leu Glu Asn Glu Arg Thr
    450                 455                 460

Leu Asp Phe His Asp Ser Asn Val Lys Asn Leu Tyr Glu Lys Val Lys
465                 470                 475                 480

Ser Gln Leu Lys Asn Asn Ala Lys Glu Ile Gly Asn Gly Cys Phe Glu
                485                 490                 495

Phe Tyr His Lys Cys Asp Asn Glu Cys Met Glu Ser Val Arg Asn Gly
            500                 505                 510

Thr Tyr Asp Tyr Pro Lys Tyr Ser Glu Glu Ser Lys Leu Asn Arg Glu
        515                 520                 525

Lys Val Asp Gly Val Lys Leu Glu Ser Met Gly Ile Tyr Gln Ile Leu
    530                 535                 540
```

Ala Ile Tyr Ser Thr Val Ala Ser Ser Leu Val Leu Leu Val Ser Leu
545 550 555 560

Gly Ala Ile Ser Phe Trp Met Cys Ser Asn Gly Ser Leu Gln Cys Arg
565 570 575

Ile Cys Ile

<210> SEQ ID NO 13
<211> LENGTH: 579
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Met Lys Ala Asn Leu Leu Val Leu Leu Ser Ala Leu Ala Ala Ala Asp
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Glu
35 40 45

Asn Leu Tyr Phe Gln Gly Asn Leu Leu Glu Asp Ser His Asn Gly Lys
50 55 60

Leu Cys Arg Leu Lys Gly Ile Ala Pro Leu Gln Leu Gly Lys Cys Asn
65 70 75 80

Ile Ala Gly Trp Leu Leu Gly Asn Pro Glu Cys Asp Pro Leu Leu Pro
85 90 95

Val Arg Ser Trp Ser Tyr Ile Val Glu Thr Pro Asn Ser Glu Asn Gly
100 105 110

Ile Cys Tyr Pro Gly Asp Phe Ile Asp Tyr Glu Glu Leu Arg Glu Gln
115 120 125

Leu Ser Ser Val Ser Ser Phe Glu Arg Phe Glu Ile Phe Pro Lys Glu
130 135 140

Ser Ser Trp Pro Asn His Asn Thr Asn Gly Val Thr Ala Ala Cys Ser
145 150 155 160

His Glu Gly Lys Ser Ser Phe Tyr Arg Asn Leu Leu Trp Leu Thr Glu
165 170 175

Lys Glu Gly Ser Tyr Pro Lys Leu Lys Asn Ser Tyr Val Asn Lys Lys
180 185 190

Gly Lys Glu Val Leu Val Leu Trp Gly Ile His His Pro Pro Asn Ser
195 200 205

Lys Glu Gln Gln Asn Ile Tyr Gln Asn Glu Asn Ala Tyr Val Ser Val
210 215 220

Val Thr Ser Asn Tyr Asn Arg Arg Phe Thr Pro Glu Ile Ala Glu Arg
225 230 235 240

Pro Lys Val Arg Asp Gln Ala Gly Arg Met Asn Tyr Tyr Trp Thr Leu
245 250 255

Leu Lys Pro Gly Asp Thr Ile Ile Phe Glu Ala Asn Gly Asn Leu Ile
260 265 270

Ala Pro Met Tyr Ala Phe Ala Leu Ser Arg Gly Phe Gly Ser Gly Ile
275 280 285

Ile Thr Ser Asn Ala Ser Met His Glu Cys Glu Asn Leu Tyr Phe Gln
290 295 300

Gly Asn Thr Lys Cys Gln Thr Pro Leu Gly Ala Ile Asn Ser Ser Leu
305 310 315 320

Pro Tyr Gln Asn Ile His Pro Val Thr Ile Gly Glu Cys Pro Lys Tyr
325 330 335

Val Arg Ser Ala Lys Leu Arg Met Val Thr Gly Leu Arg Asn Thr Pro
340 345 350

Ser Ile Gln Ser Arg Gly Leu Phe Gly Ala Ile Ala Gly Phe Ile Glu
355 360 365

Gly Gly Trp Thr Gly Met Ile Asp Gly Trp Tyr Gly Tyr His His Gln
370 375 380

Asn Glu Gln Gly Ser Gly Tyr Ala Ala Asp Gln Lys Ser Thr Gln Asn
385 390 395 400

Ala Ile Asn Gly Ile Thr Asn Lys Val Asn Thr Val Ile Glu Lys Met
405 410 415

Asn Ile Gln Phe Thr Ala Val Gly Tyr Glu Phe Asn Lys Leu Glu Lys
420 425 430

Arg Met Glu Tyr Leu Asn Lys Lys Val Asp Asp Gly Phe Leu Asp Ile
435 440 445

Trp Thr Tyr Asn Ala Glu Leu Leu Val Leu Leu Glu Asn Glu Arg Thr
450 455 460

Leu Asp Phe His Asp Ser Asn Val Lys Asn Leu Tyr Glu Lys Val Lys
465 470 475 480

Ser Gln Leu Lys Asn Asn Ala Lys Glu Ile Gly Asn Gly Cys Phe Glu
485 490 495

Phe Tyr His Lys Cys Asp Asn Glu Cys Met Glu Ser Val Arg Asn Gly
500 505 510

Thr Tyr Asp Tyr Pro Lys Tyr Ser Glu Glu Ser Lys Leu Asn Arg Glu
515 520 525

Lys Val Asp Gly Val Lys Leu Glu Ser Met Gly Ile Tyr Gln Ile Leu
530 535 540

Ala Ile Tyr Ser Thr Val Ala Ser Ser Leu Val Leu Leu Val Ser Leu
545 550 555 560

Gly Ala Ile Ser Phe Trp Met Cys Ser Asn Gly Ser Leu Gln Cys Arg
565 570 575

Ile Cys Ile

<210> SEQ ID NO 14
<211> LENGTH: 579
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

Met Lys Ala Asn Leu Leu Val Leu Leu Ser Ala Leu Ala Ala Ala Asp
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Glu
35 40 45

Asn Leu Tyr Phe Gln Gly Asn Leu Leu Glu Asp Ser His Asn Gly Lys
50 55 60

Leu Cys Arg Leu Lys Gly Ile Ala Pro Leu Gln Leu Gly Lys Cys Asn
65 70 75 80

Ile Ala Gly Trp Leu Leu Gly Asn Pro Glu Cys Asp Pro Leu Leu Pro
85 90 95

-continued

```
Val Arg Ser Trp Ser Tyr Ile Val Glu Thr Pro Asn Ser Glu Asn Gly
            100                 105                 110

Ile Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Glu
    130                 135                 140

Ser Ser Trp Pro Asn His Asn Thr Asn Gly Val Thr Ala Ala Cys Ser
145                 150                 155                 160

His Glu Gly Lys Ser Ser Phe Tyr Arg Asn Leu Leu Trp Leu Thr Glu
                165                 170                 175

Lys Glu Gly Ser Tyr Pro Lys Leu Lys Asn Ser Tyr Val Asn Lys Lys
            180                 185                 190

Gly Lys Glu Val Leu Val Leu Trp Gly Ile His His Pro Pro Asn Ser
        195                 200                 205

Lys Glu Gln Gln Asn Ile Tyr Gln Asn Glu Asn Ala Tyr Val Ser Val
    210                 215                 220

Val Thr Ser Asn Tyr Asn Arg Arg Phe Thr Pro Glu Ile Ala Glu Arg
225                 230                 235                 240

Pro Lys Val Arg Asp Gln Ala Gly Arg Met Asn Tyr Tyr Trp Thr Leu
                245                 250                 255

Leu Lys Pro Gly Asp Thr Ile Ile Phe Glu Ala Asn Gly Asn Leu Ile
            260                 265                 270

Ala Pro Met Tyr Ala Phe Ala Leu Ser Arg Gly Phe Gly Ser Gly Ile
        275                 280                 285

Ile Thr Ser Asn Ala Ser Met His Glu Cys Glu Asn Leu Tyr Phe Gln
    290                 295                 300

Gly Asn Thr Lys Cys Gln Thr Pro Leu Gly Ala Ile Asn Ser Ser Leu
305                 310                 315                 320

Pro Tyr Gln Asn Ile His Pro Val Thr Ile Gly Glu Cys Pro Lys Tyr
                325                 330                 335

Val Arg Ser Ala Lys Leu Arg Met Val Thr Gly Leu Arg Asn Thr Pro
            340                 345                 350

Ser Ile Gln Ser Arg Gly Leu Phe Gly Ala Ile Ala Gly Phe Ile Glu
        355                 360                 365

Gly Gly Trp Thr Gly Met Ile Asp Gly Trp Tyr Gly Tyr His His Gln
    370                 375                 380

Asn Glu Gln Gly Ser Gly Tyr Ala Ala Asp Gln Lys Ser Thr Gln Asn
385                 390                 395                 400

Ala Ile Asn Gly Ile Thr Asn Lys Val Asn Thr Val Ile Glu Lys Met
                405                 410                 415

Tyr Ile Gln Phe Thr Ala Val Gly Tyr Glu Phe Asn Lys Leu Glu Lys
            420                 425                 430

Arg Met Glu Tyr Leu Asn Lys Lys Val Asp Asp Gly Phe Leu Tyr Ile
        435                 440                 445

Trp Thr Tyr Asn Ala Glu Leu Leu Val Leu Leu Glu Asn Glu Arg Thr
    450                 455                 460

Leu Asp Phe His Asp Ser Asn Val Lys Asn Leu Tyr Glu Lys Val Lys
465                 470                 475                 480

Ser Gln Leu Lys Asn Asn Ala Lys Glu Ile Gly Asn Gly Cys Phe Glu
                485                 490                 495

Phe Tyr His Lys Cys Asp Asn Glu Cys Met Glu Ser Val Arg Asn Gly
            500                 505                 510
```

```
Thr Tyr Asp Tyr Pro Lys Tyr Ser Glu Glu Ser Lys Leu Asn Arg Glu
        515                 520                 525

Lys Val Asp Gly Val Lys Leu Glu Ser Met Gly Ile Tyr Gln Ile Leu
    530                 535                 540

Ala Ile Tyr Ser Thr Val Ala Ser Ser Leu Val Leu Leu Val Ser Leu
545                 550                 555                 560

Gly Ala Ile Ser Phe Trp Met Cys Ser Asn Gly Ser Leu Gln Cys Arg
                565                 570                 575

Ile Cys Ile


<210> SEQ ID NO 15
<211> LENGTH: 579
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Glu
        35                  40                  45

Asn Leu Tyr Phe Gln Gly Asn Leu Leu Glu Asp Ser His Asn Gly Lys
    50                  55                  60

Leu Cys Arg Leu Lys Gly Ile Ala Pro Leu Gln Leu Gly Lys Cys Asn
65                  70                  75                  80

Ile Ala Gly Trp Leu Leu Gly Asn Pro Glu Cys Asp Pro Leu Leu Pro
                85                  90                  95

Val Arg Ser Trp Ser Tyr Ile Val Glu Thr Pro Asn Ser Glu Asn Gly
            100                 105                 110

Ile Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Glu
    130                 135                 140

Ser Ser Trp Pro Asn His Asn Thr Asn Gly Val Thr Ala Ala Cys Ser
145                 150                 155                 160

His Glu Gly Lys Ser Ser Phe Tyr Arg Asn Leu Leu Trp Leu Thr Glu
                165                 170                 175

Lys Glu Gly Ser Tyr Pro Lys Leu Lys Asn Ser Tyr Val Asn Lys Lys
            180                 185                 190

Gly Lys Glu Val Leu Val Leu Trp Gly Ile His His Pro Pro Asn Ser
        195                 200                 205

Lys Glu Gln Gln Asn Ile Tyr Gln Asn Glu Asn Ala Tyr Val Ser Val
    210                 215                 220

Val Thr Ser Asn Tyr Asn Arg Arg Phe Thr Pro Glu Ile Ala Glu Arg
225                 230                 235                 240

Pro Lys Val Arg Asp Gln Ala Gly Arg Met Asn Tyr Tyr Trp Thr Leu
                245                 250                 255

Leu Lys Pro Gly Asp Thr Ile Ile Phe Glu Ala Asn Gly Asn Leu Ile
            260                 265                 270

Ala Pro Met Tyr Ala Phe Ala Leu Ser Arg Gly Phe Gly Ser Gly Ile
        275                 280                 285
```

```
Ile Thr Ser Asn Ala Ser Met His Glu Cys Glu Asn Leu Tyr Phe Gln
    290                 295                 300

Ser Asn Thr Lys Cys Gln Thr Pro Leu Gly Ala Ile Asn Ser Ser Leu
305                 310                 315                 320

Pro Tyr Gln Asn Ile His Pro Val Thr Ile Gly Glu Cys Pro Lys Tyr
                325                 330                 335

Val Arg Ser Ala Lys Leu Arg Met Val Thr Gly Leu Arg Asn Thr Pro
            340                 345                 350

Ser Ile Gln Ser Arg Gly Leu Phe Gly Ala Ile Ala Gly Phe Ile Glu
        355                 360                 365

Gly Gly Trp Thr Gly Met Ile Asp Gly Trp Tyr Gly Tyr His His Gln
    370                 375                 380

Asn Glu Gln Gly Ser Gly Tyr Ala Ala Asp Gln Lys Ser Thr Gln Asn
385                 390                 395                 400

Ala Ile Asn Gly Ile Thr Asn Lys Val Asn Thr Val Ile Glu Lys Met
                405                 410                 415

Tyr Ile Gln Phe Thr Ala Val Gly Lys Glu Phe Asn Lys Leu Glu Lys
            420                 425                 430

Arg Met Glu Asn Leu Asn Lys Lys Val Asp Asp Gly Phe Leu Tyr Ile
        435                 440                 445

Trp Thr Tyr Asn Ala Glu Leu Leu Val Leu Leu Glu Asn Glu Arg Thr
    450                 455                 460

Leu Asp Phe His Asp Ser Asn Val Lys Asn Leu Tyr Glu Lys Val Lys
465                 470                 475                 480

Ser Gln Leu Lys Asn Asn Ala Lys Glu Ile Gly Asn Gly Cys Phe Glu
                485                 490                 495

Phe Tyr His Lys Cys Asp Asn Glu Cys Met Glu Ser Val Arg Asn Gly
            500                 505                 510

Thr Tyr Asp Tyr Pro Lys Tyr Ser Glu Glu Ser Lys Leu Asn Arg Glu
        515                 520                 525

Lys Val Asp Gly Val Lys Leu Glu Ser Met Gly Ile Tyr Gln Ile Leu
    530                 535                 540

Ala Ile Tyr Ser Thr Val Ala Ser Ser Leu Val Leu Leu Val Ser Leu
545                 550                 555                 560

Gly Ala Ile Ser Phe Trp Met Cys Ser Asn Gly Ser Leu Gln Cys Arg
                565                 570                 575

Ile Cys Ile


<210> SEQ ID NO 16
<211> LENGTH: 579
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Glu
        35                  40                  45

Asn Leu Tyr Phe Gln Gly Asn Leu Leu Glu Asp Ser His Asn Gly Lys
    50                  55                  60
```

```
Leu Cys Arg Leu Lys Gly Ile Ala Pro Leu Gln Leu Gly Lys Cys Asn
65                  70                  75                  80

Ile Ala Gly Trp Leu Leu Gly Asn Pro Glu Cys Asp Pro Leu Leu Pro
                85                  90                  95

Val Arg Ser Trp Ser Tyr Ile Val Glu Thr Pro Asn Ser Glu Asn Gly
            100                 105                 110

Ile Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Glu
    130                 135                 140

Ser Ser Trp Pro Asn His Asn Thr Asn Gly Val Thr Ala Ala Cys Ser
145                 150                 155                 160

His Glu Gly Lys Ser Ser Phe Tyr Arg Asn Leu Leu Trp Leu Thr Glu
                165                 170                 175

Lys Glu Gly Ser Tyr Pro Lys Leu Lys Asn Ser Tyr Val Asn Lys Lys
            180                 185                 190

Gly Lys Glu Val Leu Val Leu Trp Gly Ile His His Pro Pro Asn Ser
        195                 200                 205

Lys Glu Gln Gln Asn Ile Tyr Gln Asn Glu Asn Ala Tyr Val Ser Val
    210                 215                 220

Val Thr Ser Asn Tyr Asn Arg Arg Phe Thr Pro Glu Ile Ala Glu Arg
225                 230                 235                 240

Pro Lys Val Arg Asp Gln Ala Gly Arg Met Asn Tyr Tyr Trp Thr Leu
                245                 250                 255

Leu Lys Pro Gly Asp Thr Ile Ile Phe Glu Ala Asn Gly Asn Leu Ile
            260                 265                 270

Ala Pro Met Tyr Ala Phe Ala Leu Ser Arg Gly Phe Gly Ser Gly Ile
        275                 280                 285

Ile Thr Ser Asn Ala Ser Met His Glu Cys Glu Asn Leu Tyr Phe Gln
    290                 295                 300

Ser Asn Thr Lys Cys Gln Thr Pro Leu Gly Ala Ile Asn Ser Ser Leu
305                 310                 315                 320

Pro Tyr Gln Asn Ile His Pro Val Thr Ile Gly Glu Cys Pro Lys Tyr
                325                 330                 335

Val Arg Ser Ala Lys Leu Arg Met Val Thr Gly Leu Arg Asn Thr Pro
            340                 345                 350

Ser Ile Gln Ser Arg Gly Leu Phe Gly Ala Ile Ala Gly Phe Ile Glu
        355                 360                 365

Gly Gly Trp Thr Gly Met Ile Asp Gly Trp Tyr Gly Tyr His His Gln
    370                 375                 380

Asn Glu Gln Gly Ser Gly Tyr Ala Ala Asp Gln Lys Ser Thr Gln Asn
385                 390                 395                 400

Ala Ile Asn Gly Ile Thr Asn Lys Val Asn Thr Val Ile Glu Lys Met
                405                 410                 415

Asn Ile Gln Phe Thr Ala Val Gly Tyr Glu Phe Asn Lys Leu Glu Lys
            420                 425                 430

Arg Met Glu Tyr Leu Asn Lys Lys Val Asp Asp Gly Phe Leu Asp Ile
        435                 440                 445

Trp Thr Tyr Asn Ala Glu Leu Leu Val Leu Leu Glu Asn Glu Arg Thr
    450                 455                 460

Leu Asp Phe His Asp Ser Asn Val Lys Asn Leu Tyr Glu Lys Val Lys
465                 470                 475                 480

Ser Gln Leu Lys Asn Asn Ala Lys Glu Ile Gly Asn Gly Cys Phe Glu
```

```
                485                 490                 495

Phe Tyr His Lys Cys Asp Asn Glu Cys Met Glu Ser Val Arg Asn Gly
            500                 505                 510

Thr Tyr Asp Tyr Pro Lys Tyr Ser Glu Glu Ser Lys Leu Asn Arg Glu
        515                 520                 525

Lys Val Asp Gly Val Lys Leu Glu Ser Met Gly Ile Tyr Gln Ile Leu
    530                 535                 540

Ala Ile Tyr Ser Thr Val Ala Ser Ser Leu Val Leu Leu Val Ser Leu
545                 550                 555                 560

Gly Ala Ile Ser Phe Trp Met Cys Ser Asn Gly Ser Leu Gln Cys Arg
                565                 570                 575

Ile Cys Ile


<210> SEQ ID NO 17
<211> LENGTH: 579
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Glu
        35                  40                  45

Asn Leu Tyr Phe Gln Gly Asn Leu Leu Glu Asp Ser His Asn Gly Lys
    50                  55                  60

Leu Cys Arg Leu Lys Gly Ile Ala Pro Leu Gln Leu Gly Lys Cys Asn
65                  70                  75                  80

Ile Ala Gly Trp Leu Leu Gly Asn Pro Glu Cys Asp Pro Leu Leu Pro
                85                  90                  95

Val Arg Ser Trp Ser Tyr Ile Val Glu Thr Pro Asn Ser Glu Asn Gly
            100                 105                 110

Ile Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Glu
    130                 135                 140

Ser Ser Trp Pro Asn His Asn Thr Asn Gly Val Thr Ala Ala Cys Ser
145                 150                 155                 160

His Glu Gly Lys Ser Ser Phe Tyr Arg Asn Leu Leu Trp Leu Thr Glu
                165                 170                 175

Lys Glu Gly Ser Tyr Pro Lys Leu Lys Asn Ser Tyr Val Asn Lys Lys
            180                 185                 190

Gly Lys Glu Val Leu Val Leu Trp Gly Ile His His Pro Pro Asn Ser
        195                 200                 205

Lys Glu Gln Gln Asn Ile Tyr Gln Asn Glu Asn Ala Tyr Val Ser Val
    210                 215                 220

Val Thr Ser Asn Tyr Asn Arg Arg Phe Thr Pro Glu Ile Ala Glu Arg
225                 230                 235                 240

Pro Lys Val Arg Asp Gln Ala Gly Arg Met Asn Tyr Tyr Trp Thr Leu
                245                 250                 255

Leu Lys Pro Gly Asp Thr Ile Ile Phe Glu Ala Asn Gly Asn Leu Ile
```

-continued

```
            260                 265                 270

Ala Pro Met Tyr Ala Phe Ala Leu Ser Arg Gly Phe Gly Ser Gly Ile
        275                 280                 285

Ile Thr Ser Asn Ala Ser Met His Glu Cys Glu Asn Leu Tyr Phe Gln
    290                 295                 300

Ser Asn Thr Lys Cys Gln Thr Pro Leu Gly Ala Ile Asn Ser Ser Leu
305                 310                 315                 320

Pro Tyr Gln Asn Ile His Pro Val Thr Ile Gly Glu Cys Pro Lys Tyr
                325                 330                 335

Val Arg Ser Ala Lys Leu Arg Met Val Thr Gly Leu Arg Asn Thr Pro
            340                 345                 350

Ser Ile Gln Ser Arg Gly Leu Phe Gly Ala Ile Ala Gly Phe Ile Glu
        355                 360                 365

Gly Gly Trp Thr Gly Met Ile Asp Gly Trp Tyr Gly Tyr His His Gln
    370                 375                 380

Asn Glu Gln Gly Ser Gly Tyr Ala Ala Asp Gln Lys Ser Thr Gln Asn
385                 390                 395                 400

Ala Ile Asn Gly Ile Thr Asn Lys Val Asn Thr Val Ile Glu Lys Met
                405                 410                 415

Tyr Ile Gln Phe Thr Ala Val Gly Tyr Glu Phe Asn Lys Leu Glu Lys
            420                 425                 430

Arg Met Glu Tyr Leu Asn Lys Lys Val Asp Asp Gly Phe Leu Tyr Ile
        435                 440                 445

Trp Thr Tyr Asn Ala Glu Leu Leu Val Leu Leu Glu Asn Glu Arg Thr
    450                 455                 460

Leu Asp Phe His Asp Ser Asn Val Lys Asn Leu Tyr Glu Lys Val Lys
465                 470                 475                 480

Ser Gln Leu Lys Asn Asn Ala Lys Glu Ile Gly Asn Gly Cys Phe Glu
                485                 490                 495

Phe Tyr His Lys Cys Asp Asn Glu Cys Met Glu Ser Val Arg Asn Gly
            500                 505                 510

Thr Tyr Asp Tyr Pro Lys Tyr Ser Glu Glu Ser Lys Leu Asn Arg Glu
        515                 520                 525

Lys Val Asp Gly Val Lys Leu Glu Ser Met Gly Ile Tyr Gln Ile Leu
    530                 535                 540

Ala Ile Tyr Ser Thr Val Ala Ser Ser Leu Val Leu Leu Val Ser Leu
545                 550                 555                 560

Gly Ala Ile Ser Phe Trp Met Cys Ser Asn Gly Ser Leu Gln Cys Arg
                565                 570                 575

Ile Cys Ile


<210> SEQ ID NO 18
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
```

```
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Glu Asn Leu Tyr Phe Gln Gly Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Asn Ile Gln Phe Thr Ala Val
                405                 410                 415

Gly Lys Glu Phe Asn Lys Leu Glu Lys Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460
```

-continued

```
Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
                565                 570


<210> SEQ ID NO 19
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
```

-continued

```
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Glu Asn Leu Tyr Phe Gln Ser Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Asn Ile Gln Phe Thr Ala Val
                405                 410                 415

Gly Lys Glu Phe Asn Lys Leu Glu Lys Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
                565                 570


<210> SEQ ID NO 20
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30
```

```
Val Asp Thr Val Leu Glu Lys Asn Val Thr Val Thr His Ser Val Glu
        35                  40                  45

Asn Leu Tyr Phe Gln Gly His Asn Gly Lys Leu Cys Arg Leu Lys Gly
    50                  55                  60

Ile Ala Pro Leu Gln Leu Gly Lys Cys Asn Ile Ala Gly Trp Leu Leu
65                  70                  75                  80

Gly Asn Pro Glu Cys Asp Pro Leu Leu Pro Val Arg Ser Trp Ser Tyr
                85                  90                  95

Ile Val Glu Thr Pro Asn Ser Glu Asn Gly Ile Cys Tyr Pro Gly Asp
            100                 105                 110

Phe Ile Asp Tyr Glu Glu Leu Arg Glu Gln Leu Ser Ser Val Ser Ser
        115                 120                 125

Phe Glu Arg Phe Glu Ile Phe Pro Lys Glu Ser Ser Trp Pro Asn His
    130                 135                 140

Asn Thr Asn Gly Val Thr Ala Ala Cys Ser His Glu Gly Lys Ser Ser
145                 150                 155                 160

Phe Tyr Arg Asn Leu Leu Trp Leu Thr Glu Lys Glu Gly Ser Tyr Pro
                165                 170                 175

Lys Leu Lys Asn Ser Tyr Val Asn Lys Lys Gly Lys Glu Val Leu Val
            180                 185                 190

Leu Trp Gly Ile His His Pro Pro Asn Ser Lys Glu Gln Gln Asn Ile
        195                 200                 205

Tyr Gln Asn Glu Asn Ala Tyr Val Ser Val Val Thr Ser Asn Tyr Asn
    210                 215                 220

Arg Arg Phe Thr Pro Glu Ile Ala Glu Arg Pro Lys Val Arg Asp Gln
225                 230                 235                 240

Ala Gly Arg Met Asn Tyr Tyr Trp Thr Leu Leu Lys Pro Gly Asp Thr
                245                 250                 255

Ile Ile Phe Glu Ala Asn Gly Asn Leu Ile Ala Pro Met Tyr Ala Phe
            260                 265                 270

Ala Leu Ser Arg Gly Phe Gly Ser Gly Ile Ile Thr Ser Asn Ala Ser
        275                 280                 285

Met His Glu Cys Asn Thr Lys Cys Gln Thr Pro Leu Gly Ala Ile Asn
    290                 295                 300

Ser Ser Leu Pro Tyr Gln Asn Ile His Pro Val Thr Ile Gly Glu Cys
305                 310                 315                 320

Pro Lys Tyr Val Arg Ser Ala Lys Leu Arg Met Val Thr Gly Leu Arg
                325                 330                 335

Asn Thr Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Thr Val Ile
385                 390                 395                 400

Glu Lys Met Asn Ile Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
```

450 455 460

Lys Val Lys Ser Gln Leu Lys Asn Asn Ala Lys Glu Ile Gly Asn Gly
465 470 475 480

Cys Phe Glu Phe Tyr His Lys Cys Asp Asn Glu Cys Met Glu Ser Val
485 490 495

Arg Asn Gly Thr Tyr Asp Tyr Pro Lys Tyr Ser Glu Glu Ser Lys Leu
500 505 510

Asn Arg Glu Lys Val Asp Gly Val Lys Leu Glu Ser Met Gly Ile Tyr
515 520 525

Gln Ile Leu Ala Ile Tyr Ser Thr Val Ala Ser Ser Leu Val Leu Leu
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 21
<211> LENGTH: 572
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Met Lys Ala Asn Leu Leu Val Leu Leu Ser Ala Leu Ala Ala Ala Asp
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Arg Leu Lys Gly Ile
50 55 60

Ala Pro Leu Gln Leu Gly Lys Cys Asn Ile Ala Gly Trp Leu Leu Gly
65 70 75 80

Asn Pro Glu Cys Asp Pro Leu Leu Pro Val Arg Ser Trp Ser Tyr Ile
85 90 95

Val Glu Thr Pro Asn Ser Glu Asn Gly Ile Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Pro Lys Glu Ser Ser Trp Pro Asn His Asn
130 135 140

Thr Asn Gly Val Thr Ala Ala Cys Ser His Glu Gly Lys Ser Ser Phe
145 150 155 160

Tyr Arg Asn Leu Leu Trp Leu Thr Glu Lys Glu Gly Ser Tyr Pro Lys
165 170 175

Leu Lys Asn Ser Tyr Val Asn Lys Lys Gly Lys Glu Val Leu Val Leu
180 185 190

Trp Gly Ile His His Pro Pro Asn Ser Lys Glu Gln Gln Asn Ile Tyr
195 200 205

Gln Asn Glu Asn Ala Tyr Val Ser Val Val Thr Ser Asn Tyr Asn Arg
210 215 220

Arg Phe Thr Pro Glu Ile Ala Glu Arg Pro Lys Val Arg Asp Gln Ala
225 230 235 240

```
Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Glu Asn
        275                 280                 285

Leu Tyr Phe Gln Ser Ser Met His Glu Cys Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Asn Ile Gln Phe Thr Ala Val
                405                 410                 415

Gly Lys Glu Phe Asn Lys Leu Glu Lys Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
                565                 570
```

<210> SEQ ID NO 22
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30
```

-continued

```
Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Glu Asn Leu Tyr Phe Gln Ser Asn Ala Ser
        275                 280                 285

Met His Glu Cys Asn Thr Lys Cys Gln Thr Pro Leu Gly Ala Ile Asn
    290                 295                 300

Ser Ser Leu Pro Tyr Gln Asn Ile His Pro Val Thr Ile Gly Glu Cys
305                 310                 315                 320

Pro Lys Tyr Val Arg Ser Ala Lys Leu Arg Met Val Thr Gly Leu Arg
                325                 330                 335

Asn Thr Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Thr Val Ile
385                 390                 395                 400

Glu Lys Met Asn Ile Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445
```

```
Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Lys Val Asp Gly Val Lys Leu Glu Ser Met Gly Ile Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 23
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240
```

```
Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Glu Asn Leu Tyr Phe Gln
        275                 280                 285

Ser Thr Ser Asn Ala Ser Met His Glu Cys Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Asn Ile Gln Phe Thr Ala Val
                405                 410                 415

Gly Lys Glu Phe Asn Lys Leu Glu Lys Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
                565                 570
```

<210> SEQ ID NO 24
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
```

-continued

```
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Glu
    50                  55                  60

Asn Leu Tyr Phe Gln Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445
```

```
Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 25
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
```

```
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Glu Asn Leu Tyr Phe
        275                 280                 285

Gln Gly Ser Asn Ala Ser Met His Glu Cys Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Asn Ile Gln Phe Thr Ala Val
                405                 410                 415

Gly Lys Glu Phe Asn Lys Leu Glu Lys Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
                565                 570
```

<210> SEQ ID NO 26
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Met Lys Ala Asn Leu Leu Val Leu Leu Ser Ala Leu Ala Ala Ala Asp
1               5                   10                  15
```

```
Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Glu
    50                  55                  60

Asn Leu Tyr Phe Gln Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Glu Asn Leu Tyr Phe Gln Ser Asn Ala Ser
        275                 280                 285

Met His Glu Cys Asn Thr Lys Cys Gln Thr Pro Leu Gly Ala Ile Asn
    290                 295                 300

Ser Ser Leu Pro Tyr Gln Asn Ile His Pro Val Thr Ile Gly Glu Cys
305                 310                 315                 320

Pro Lys Tyr Val Arg Ser Ala Lys Leu Arg Met Val Thr Gly Leu Arg
                325                 330                 335

Asn Thr Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Thr Val Ile
385                 390                 395                 400

Glu Lys Met Asn Ile Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
```

```
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Lys Val Asp Gly Val Lys Leu Glu Ser Met Gly Ile Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 27
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Glu
    50                  55                  60

Asn Leu Tyr Phe Gln Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220
```

```
Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Glu Asn Leu Tyr Phe Gln
        275                 280                 285

Ser Thr Ser Asn Ala Ser Met His Glu Cys Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Asn Ile Gln Phe Thr Ala Val
                405                 410                 415

Gly Lys Glu Phe Asn Lys Leu Glu Lys Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
                565                 570


<210> SEQ ID NO 28
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Lys Ala Asn Leu Leu Val Leu Leu Ser Ala Leu Ala Ala Ala Asp
1               5                   10                  15
```

-continued

```
Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Glu
    50                  55                  60

Asn Leu Tyr Phe Gln Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Glu Asn Leu Tyr Phe
        275                 280                 285

Gln Gly Ser Asn Ala Ser Met His Glu Cys Asn Thr Lys Cys Gln Thr
    290                 295                 300

Pro Leu Gly Ala Ile Asn Ser Ser Leu Pro Tyr Gln Asn Ile His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Thr Pro Ser Ile Gln Ser Arg Gly Leu
            340                 345                 350

Phe Gly Ala Ile Ala Gly Phe Ile Glu Gly Gly Trp Thr Gly Met Ile
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Thr Val Ile Glu Lys Met Asn Ile Gln Phe Thr Ala Val
                405                 410                 415

Gly Lys Glu Phe Asn Lys Leu Glu Lys Arg Met Glu Asn Leu Asn Lys
            420                 425                 430
```

```
Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asp Asn
                485                 490                 495

Glu Cys Met Glu Ser Val Arg Asn Gly Thr Tyr Asp Tyr Pro Lys Tyr
            500                 505                 510

Ser Glu Glu Ser Lys Leu Asn Arg Glu Lys Val Asp Gly Val Lys Leu
        515                 520                 525

Glu Ser Met Gly Ile Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
                565                 570


<210> SEQ ID NO 29
<211> LENGTH: 579
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Glu
        35                  40                  45

Asn Leu Tyr Phe Gln Gly Asn Leu Leu Glu Asp Ser His Asn Gly Lys
    50                  55                  60

Leu Cys Arg Leu Lys Gly Ile Ala Pro Leu Gln Leu Gly Lys Cys Asn
65                  70                  75                  80

Ile Ala Gly Trp Leu Leu Gly Asn Pro Glu Cys Asp Pro Leu Leu Pro
                85                  90                  95

Val Arg Ser Trp Ser Tyr Ile Val Glu Thr Pro Asn Ser Glu Asn Gly
            100                 105                 110

Ile Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Glu
    130                 135                 140

Ser Ser Trp Pro Asn His Asn Thr Asn Gly Val Thr Ala Ala Cys Ser
145                 150                 155                 160

His Glu Gly Lys Ser Ser Phe Tyr Arg Asn Leu Leu Trp Leu Thr Glu
                165                 170                 175

Lys Glu Gly Ser Tyr Pro Lys Leu Lys Asn Ser Tyr Val Asn Lys Lys
            180                 185                 190

Gly Lys Glu Val Leu Val Leu Trp Gly Ile His His Pro Pro Asn Ser
        195                 200                 205

Lys Glu Gln Gln Asn Ile Tyr Gln Asn Glu Asn Ala Tyr Val Ser Val
    210                 215                 220
```

```
Val Thr Ser Asn Tyr Asn Arg Arg Phe Thr Pro Glu Ile Ala Glu Arg
225                 230                 235                 240

Pro Lys Val Arg Asp Gln Ala Gly Arg Met Asn Tyr Tyr Trp Thr Leu
                245                 250                 255

Leu Lys Pro Gly Asp Thr Ile Ile Phe Glu Ala Asn Gly Asn Leu Ile
            260                 265                 270

Ala Pro Met Tyr Ala Phe Ala Leu Ser Arg Gly Phe Gly Ser Gly Ile
        275                 280                 285

Ile Thr Ser Asn Ala Ser Met His Glu Cys Glu Asn Leu Tyr Phe Gln
    290                 295                 300

Gly Asn Thr Lys Cys Gln Thr Pro Leu Gly Ala Ile Asn Ser Ser Leu
305                 310                 315                 320

Pro Tyr Gln Asn Ile His Pro Val Thr Ile Gly Glu Cys Pro Lys Tyr
                325                 330                 335

Val Arg Ser Ala Lys Leu Arg Met Val Thr Gly Leu Arg Asn Thr Pro
            340                 345                 350

Ser Ile Gln Ser Arg Gly Leu Phe Gly Ala Ile Ala Gly Phe Ile Glu
        355                 360                 365

Gly Gly Trp Thr Gly Met Ile Asp Gly Trp Tyr Gly Tyr His His Gln
    370                 375                 380

Asn Glu Gln Gly Ser Gly Tyr Ala Ala Asp Gln Lys Ser Thr Gln Asn
385                 390                 395                 400

Ala Ile Asn Gly Ile Thr Asn Lys Val Asn Thr Val Ile Glu Lys Met
                405                 410                 415

Asn Ile Gln Phe Thr Ala Val Gly Lys Glu Phe Asn Lys Leu Glu Lys
            420                 425                 430

Arg Met Glu Asn Leu Asn Lys Lys Val Asp Asp Gly Phe Leu Asp Ile
        435                 440                 445

Trp Thr Tyr Asn Ala Glu Leu Leu Val Leu Leu Glu Asn Glu Arg Thr
    450                 455                 460

Leu Asp Phe His Asp Ser Asn Val Lys Asn Leu Tyr Glu Lys Val Lys
465                 470                 475                 480

Ser Gln Leu Lys Asn Asn Ala Lys Glu Ile Gly Asn Gly Cys Phe Glu
                485                 490                 495

Phe Tyr His Lys Cys Asp Asn Glu Cys Met Glu Ser Val Arg Asn Gly
            500                 505                 510

Thr Tyr Asp Tyr Pro Lys Tyr Ser Glu Glu Ser Lys Leu Asn Arg Glu
        515                 520                 525

Lys Val Asp Gly Val Lys Leu Glu Ser Met Gly Ile Tyr Gln Ile Leu
    530                 535                 540

Ala Ile Tyr Ser Thr Val Ala Ser Ser Leu Val Leu Leu Val Ser Leu
545                 550                 555                 560

Gly Ala Ile Ser Phe Trp Met Cys Ser Asn Gly Ser Leu Gln Cys Arg
                565                 570                 575

Ile Cys Ile
```

<210> SEQ ID NO 30
<211> LENGTH: 579
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

-continued

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Glu
        35                  40                  45

Asn Leu Tyr Phe Gln Gly Asn Leu Leu Glu Asp Ser His Asn Gly Lys
    50                  55                  60

Leu Cys Arg Leu Lys Gly Ile Ala Pro Leu Gln Leu Gly Lys Cys Asn
65                  70                  75                  80

Ile Ala Gly Trp Leu Leu Gly Asn Pro Glu Cys Asp Pro Leu Leu Pro
                85                  90                  95

Val Arg Ser Trp Ser Tyr Ile Val Glu Thr Pro Asn Ser Glu Asn Gly
            100                 105                 110

Ile Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Glu
    130                 135                 140

Ser Ser Trp Pro Asn His Asn Thr Asn Gly Val Thr Ala Ala Cys Ser
145                 150                 155                 160

His Glu Gly Lys Ser Ser Phe Tyr Arg Asn Leu Leu Trp Leu Thr Glu
                165                 170                 175

Lys Glu Gly Ser Tyr Pro Lys Leu Lys Asn Ser Tyr Val Asn Lys Lys
            180                 185                 190

Gly Lys Glu Val Leu Val Leu Trp Gly Ile His His Pro Pro Asn Ser
        195                 200                 205

Lys Glu Gln Gln Asn Ile Tyr Gln Asn Glu Asn Ala Tyr Val Ser Val
    210                 215                 220

Val Thr Ser Asn Tyr Asn Arg Arg Phe Thr Pro Glu Ile Ala Glu Arg
225                 230                 235                 240

Pro Lys Val Arg Asp Gln Ala Gly Arg Met Asn Tyr Tyr Trp Thr Leu
                245                 250                 255

Leu Lys Pro Gly Asp Thr Ile Ile Phe Glu Ala Asn Gly Asn Leu Ile
            260                 265                 270

Ala Pro Met Tyr Ala Phe Ala Leu Ser Arg Gly Phe Gly Ser Gly Ile
        275                 280                 285

Ile Thr Ser Asn Ala Ser Met His Glu Cys Glu Asn Leu Tyr Phe Gln
    290                 295                 300

Ser Asn Thr Lys Cys Gln Thr Pro Leu Gly Ala Ile Asn Ser Ser Leu
305                 310                 315                 320

Pro Tyr Gln Asn Ile His Pro Val Thr Ile Gly Glu Cys Pro Lys Tyr
                325                 330                 335

Val Arg Ser Ala Lys Leu Arg Met Val Thr Gly Leu Arg Asn Thr Pro
            340                 345                 350

Ser Ile Gln Ser Arg Gly Leu Phe Gly Ala Ile Ala Gly Phe Ile Glu
        355                 360                 365

Gly Gly Trp Thr Gly Met Ile Asp Gly Trp Tyr Gly Tyr His His Gln
    370                 375                 380

Asn Glu Gln Gly Ser Gly Tyr Ala Ala Asp Gln Lys Ser Thr Gln Asn
385                 390                 395                 400

Ala Ile Asn Gly Ile Thr Asn Lys Val Asn Thr Val Ile Glu Lys Met
                405                 410                 415
```

-continued

```
Asn Ile Gln Phe Thr Ala Val Gly Lys Glu Phe Asn Lys Leu Glu Lys
            420                 425                 430

Arg Met Glu Asn Leu Asn Lys Lys Val Asp Asp Gly Phe Leu Asp Ile
        435                 440                 445

Trp Thr Tyr Asn Ala Glu Leu Leu Val Leu Leu Glu Asn Glu Arg Thr
    450                 455                 460

Leu Asp Phe His Asp Ser Asn Val Lys Asn Leu Tyr Glu Lys Val Lys
465                 470                 475                 480

Ser Gln Leu Lys Asn Asn Ala Lys Glu Ile Gly Asn Gly Cys Phe Glu
                485                 490                 495

Phe Tyr His Lys Cys Asp Asn Glu Cys Met Glu Ser Val Arg Asn Gly
            500                 505                 510

Thr Tyr Asp Tyr Pro Lys Tyr Ser Glu Glu Ser Lys Leu Asn Arg Glu
        515                 520                 525

Lys Val Asp Gly Val Lys Leu Glu Ser Met Gly Ile Tyr Gln Ile Leu
    530                 535                 540

Ala Ile Tyr Ser Thr Val Ala Ser Ser Leu Val Leu Leu Val Ser Leu
545                 550                 555                 560

Gly Ala Ile Ser Phe Trp Met Cys Ser Asn Gly Ser Leu Gln Cys Arg
                565                 570                 575

Ile Cys Ile


<210> SEQ ID NO 31
<211> LENGTH: 1701
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

atgaaggcaa acctactggt cctgttaagt gcacttgcag ctgcagatgc agacacaata     60

tgtataggct accatgcgaa caattcaacc gacactgttg acacagtact cgagaagaat    120

gtgacagtga cacactctgt taacctgctc gaagacagcc acaacggaaa actatgtaga    180

ttaaaaggag agaatctgta cttccaggga aaatgtaaca tcgccggatg gctcttggga    240

aacccagaat gcgacccact gcttccagtg agatcatggt cctacattgt agaaacacca    300

aactctgaga atggaatatg ttatccagga gatttcatcg actatgagga gctgagggag    360

caattgagct cagtgtcatc attcgaaaga ttcgaaatat ttcccaaaga aagctcatgg    420

cccaaccaca acacaaacgg agtaacggca gcatgctccc atgaggggaa aagcagtttt    480

tacagaaatt tgctatggct gacggagaag gagggctcat acccaaagct gaaaaattct    540

tatgtgaaca aaaaagggaa agaagtcctt gtactgtggg gtattcatca cccgcctaac    600

agtaaggaac aacagaatat ctatcagaat gaaaatgctt atgtctctgt agtgacttca    660

aattataaca ggagatttac cccggaaata gcagaaagac ccaaagtaag agatcaagct    720

gggaggatga actattactg gaccttgcta aaacccggag acacaataat atttgaggca    780

aatggaaatc taatagcacc aatgtatgct ttcgcactga gtagaggctt tggggagaat    840

ctgtacttcc agtcaaacgc atcaatgcat gagtgtaaca cgaagtgtca aacaccgctc    900

ggagctataa acagcagtct cccttaccag aatatacacc cagtcacaat aggagagtgc    960

ccaaaatacg tcaggagtgc caaattgagg atggttacag gactaaggaa cactccgtcc   1020

attcaatcca gaggtctatt tggagccatt gccggtttta ttgaaggggg atggactgga   1080
```

-continued atgatagatg gatggtatgg ttatcatcat cagaatgaac agggatcagg ctatgcagcg 1140
gatcaaaaaa gcacacaaaa tgccattaac gggattacaa acaaggtgaa cactgttatc 1200
gagaaaatgt acattcaatt cacagctgtg ggtaaagaat tcaacaaatt agaaaaaagg 1260
atggaaaatt taaataaaaa agttgatgat ggatttctgt acatttggac atataatgca 1320
gaattgttag ttctactgga aaatgaaagg actctggatt tccatgactc aaatgtgaag 1380
aatctgtatg agaaagtaaa aagccaatta aagaataatg ccaaagaaat cggaaatgga 1440
tgttttgagt tctaccacaa gtgtgacaat gaatgcatgg aaagtgtaag aaatgggact 1500
tatgattatc ccaaatattc agaagagtca aagttgaaca gggaaaaggt agatggagtg 1560
aaattggaat caatggggat ctatcagatt ctggcgatct actcaactgt cgccagttca 1620
ctggtgcttt tggtctccct gggggcaatc agtttctgga tgtgttctaa tggatctttg 1680
cagtgcagaa tatgcatctg a 1701

<210> SEQ ID NO 32
<211> LENGTH: 1701
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 32
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt taacctgctc gaagacagcc acaacggaaa actatgtaga 180
ttaaaaggag agaatctgta cttccaggga aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420
cccaaccaca acacaaacgg agtaacggca gcatgctccc atgaggggaa aagcagtttt 480
tacagaaatt tgctatggct gacggagaag gagggctcat acccaaagct gaaaaattct 540
tatgtgaaca aaaaagggaa agaagtcctt gtactgtggg gtattcatca cccgcctaac 600
agtaaggaac aacagaatat ctatcagaat gaaaatgctt atgtctctgt agtgacttca 660
aattataaca ggagatttac cccggaaata gcagaaagac ccaaagtaag agatcaagct 720
gggaggatga actattactg gaccttgcta aaacccggag acacaataat atttgaggca 780
aatggaaatc taatagcacc aatgtatgct ttcgcactga gtagaggctt tggggagaat 840
ctgtacttcc agtcaaacgc atcaatgcat gagtgtaaca cgaagtgtca aacaccgctc 900
ggagctataa acagcagtct cccttaccag aatatacacc cagtcacaat aggagagtgc 960
ccaaaatacg tcaggagtgc caaattgagg atggttacag gactaaggaa cactccgtcc 1020
attcaatcca gaggtctatt tggagccatt gccggtttta ttgaaggggg atggactgga 1080
atgatagatg gatggtatgg ttatcatcat cagaatgaac agggatcagg ctatgcagcg 1140
gatcaaaaaa gcacacaaaa tgccattaac gggattacaa acaaggtgaa cactgttatc 1200
gagaaaatga acattcaatt cacagctgtg ggttacgaat tcaacaaatt agaaaaaagg 1260
atggaatact taaataaaaa agttgatgat ggatttctgg acatttggac atataatgca 1320
gaattgttag ttctactgga aaatgaaagg actctggatt tccatgactc aaatgtgaag 1380
aatctgtatg agaaagtaaa aagccaatta aagaataatg ccaaagaaat cggaaatgga 1440
tgttttgagt tctaccacaa gtgtgacaat gaatgcatgg aaagtgtaag aaatgggact 1500
tatgattatc ccaaatattc agaagagtca aagttgaaca gggaaaaggt agatggagtg 1560
aaattggaat caatggggat ctatcagatt ctggcgatct actcaactgt cgccagttca 1620
ctggtgcttt tggtctccct gggggcaatc agtttctgga tgtgttctaa tggatctttg 1680
cagtgcagaa tatgcatctg a 1701

<210> SEQ ID NO 33
<211> LENGTH: 1701
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 33
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt taacctgctc gaagacagcc acaacggaaa actatgtaga 180
ttaaaaggag agaatctgta cttccaggga aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420
cccaaccaca acacaaacgg agtaacggca gcatgctccc atgaggggaa aagcagtttt 480
tacagaaatt tgctatggct gacggagaag gagggctcat acccaaagct gaaaaattct 540
tatgtgaaca aaaaagggaa agaagtcctt gtactgtggg gtattcatca cccgcctaac 600
agtaaggaac aacagaatat ctatcagaat gaaaatgctt atgtctctgt agtgacttca 660
aattataaca ggagatttac cccggaaata gcagaaagac ccaaagtaag agatcaagct 720
gggaggatga actattactg gaccttgcta aaacccggag acacaataat atttgaggca 780
aatggaaatc taatagcacc aatgtatgct ttcgcactga gtagaggctt tggggagaat 840
ctgtacttcc agtcaaacgc atcaatgcat gagtgtaaca cgaagtgtca aacaccgctc 900
ggagctataa acagcagtct cccttaccag aatatacacc cagtcacaat aggagagtgc 960
ccaaaatacg tcaggagtgc caaattgagg atggttacag gactaaggaa cactccgtcc 1020
attcaatcca gaggtctatt tggagccatt gccggtttta ttgaaggggg atggactgga 1080
atgatagatg gatggtatgg ttatcatcat cagaatgaac agggatcagg ctatgcagcg 1140
gatcaaaaaa gcacacaaaa tgccattaac gggattacaa acaaggtgaa cactgttatc 1200
gagaaaatgt acattcaatt cacagctgtg ggttacgaat tcaacaaatt agaaaaaagg 1260
atggaatact taaataaaaa agttgatgat ggatttctgt acatttggac atataatgca 1320
gaattgttag ttctactgga aaatgaaagg actctggatt tccatgactc aaatgtgaag 1380
aatctgtatg agaaagtaaa aagccaatta aagaataatg ccaaagaaat cggaaatgga 1440
tgttttgagt tctaccacaa gtgtgacaat gaatgcatgg aaagtgtaag aaatgggact 1500
tatgattatc ccaaatattc agaagagtca aagttgaaca gggaaaaggt agatggagtg 1560
aaattggaat caatggggat ctatcagatt ctggcgatct actcaactgt cgccagttca 1620
ctggtgcttt tggtctccct gggggcaatc agtttctgga tgtgttctaa tggatctttg 1680
cagtgcagaa tatgcatctg a 1701

<210> SEQ ID NO 34
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt taacctgctc gaagacagcc acaacggaaa actatgtaga 180
ttaaaaggag agaatctgta cttccaggga aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420
cccaaccaca acacaaacgg agtaacggca gcatgctccc atgaggggaa aagcagtttt 480
tacagaaatt tgctatggct gacggagaag gagggctcat acccaaagct gaaaaattct 540
tatgtgaaca aaaaagggaa agaagtcctt gtactgtggg gtattcatca cccgcctaac 600
agtaaggaac aacagaatat ctatcagaat gaaaatgctt atgtctctgt agtgacttca 660
aattataaca ggagatttac cccggaaata gcagaaagac ccaaagtaag agatcaagct 720
gggaggatga actattactg gaccttgcta aaacccggag acacaataat atttgaggca 780
aatggaaatc taatagcacc aatgtatgct ttcgcactga gtagaggctt tgggtccggc 840
atcatcgaga atctgtactt ccagagcacc tcaaacgcat caatgcatga gtgtaacacg 900
aagtgtcaaa caccgctcgg agctataaac agcagtctcc cttaccagaa tatacaccca 960
gtcacaatag gagagtgccc aaaatacgtc aggagtgcca aattgaggat ggttacagga 1020
ctaaggaaca ctccgtccat tcaatccaga ggtctatttg gagccattgc cggttttatt 1080
gaagggggat ggactggaat gatagatgga tggtatggtt atcatcatca gaatgaacag 1140
ggatcaggct atgcagcgga tcaaaaaagc acacaaaatg ccattaacgg gattacaaac 1200
aaggtgaaca ctgttatcga gaaaatgtac attcaattca cagctgtggg taaagaattc 1260
aacaaattag aaaaaaggat ggaaaattta aataaaaaag ttgatgatgg atttctgtac 1320
atttggacat ataatgcaga attgttagtt ctactggaaa atgaaaggac tctggatttc 1380
catgactcaa atgtgaagaa tctgtatgag aaagtaaaaa gccaattaaa gaataatgcc 1440
aaagaaatcg gaaatggatg ttttgagttc taccacaagt gtgacaatga atgcatggaa 1500
agtgtaagaa atgggactta tgattatccc aaatattcag aagagtcaaa gttgaacagg 1560
gaaaaggtag atggagtgaa attggaatca atggggatct atcagattct ggcgatctac 1620
tcaactgtcg ccagttcact ggtgcttttg gtctccctgg gggcaatcag tttctggatg 1680
tgttctaatg gatctttgca gtgcagaata tgcatctga 1719

<210> SEQ ID NO 35
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt taacctgctc gaagacagcc acaacggaaa actatgtaga 180
ttaaaaggag agaatctgta cttccaggga aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420
cccaaccaca acacaaacgg agtaacggca gcatgctccc atgaggggaa aagcagtttt 480
tacagaaatt tgctatggct gacggagaag gagggctcat acccaaagct gaaaaattct 540
tatgtgaaca aaaaagggaa agaagtcctt gtactgtggg gtattcatca cccgcctaac 600
agtaaggaac aacagaatat ctatcagaat gaaaatgctt atgtctctgt agtgacttca 660
aattataaca ggagatttac cccggaaata gcagaaagac ccaaagtaag agatcaagct 720
gggaggatga actattactg gaccttgcta aaacccggag acacaataat atttgaggca 780
aatggaaatc taatagcacc aatgtatgct ttcgcactga gtagaggctt tgggtccggc 840
atcatcgaga atctgtactt ccagagcacc tcaaacgcat caatgcatga gtgtaacacg 900
aagtgtcaaa caccgctcgg agctataaac agcagtctcc cttaccagaa tatacaccca 960
gtcacaatag gagagtgccc aaaatacgtc aggagtgcca aattgaggat ggttacagga 1020
ctaaggaaca ctccgtccat tcaatccaga ggtctatttg gagccattgc cggttttatt 1080
gaagggggat ggactggaat gatagatgga tggtatggtt atcatcatca gaatgaacag 1140
ggatcaggct atgcagcgga tcaaaaaagc acacaaaatg ccattaacgg gattacaaac 1200
aaggtgaaca ctgttatcga gaaaatgaac attcaattca cagctgtggg ttacgaattc 1260
aacaaattag aaaaaaggat ggaatactta aataaaaaag ttgatgatgg atttctggac 1320
atttggacat ataatgcaga attgttagtt ctactggaaa atgaaaggac tctggatttc 1380
catgactcaa atgtgaagaa tctgtatgag aaagtaaaaa gccaattaaa gaataatgcc 1440
aaagaaatcg gaaatggatg ttttgagttc taccacaagt gtgacaatga atgcatggaa 1500
agtgtaagaa atgggactta tgattatccc aaatattcag aagagtcaaa gttgaacagg 1560
gaaaaggtag atggagtgaa attggaatca atggggatct atcagattct ggcgatctac 1620
tcaactgtcg ccagttcact ggtgcttttg gtctccctgg gggcaatcag tttctggatg 1680
tgttctaatg gatctttgca gtgcagaata tgcatctga 1719

<210> SEQ ID NO 36
<211> LENGTH: 1719
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 36
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt taacctgctc gaagacagcc acaacggaaa actatgtaga 180
ttaaaaggag agaatctgta cttccaggga aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420
cccaaccaca acacaaacgg agtaacggca gcatgctccc atgaggggaa aagcagtttt 480
tacagaaatt tgctatggct gacggagaag gagggctcat acccaaagct gaaaaattct 540
tatgtgaaca aaaaagggaa agaagtcctt gtactgtggg gtattcatca cccgcctaac 600
agtaaggaac aacagaatat ctatcagaat gaaaatgctt atgtctctgt agtgacttca 660
aattataaca ggagatttac cccggaaata gcagaaagac ccaaagtaag agatcaagct 720
gggaggatga actattactg gaccttgcta aaacccggag acacaataat atttgaggca 780
aatggaaatc taatagcacc aatgtatgct ttcgcactga gtagaggctt tgggtccggc 840
atcatcgaga atctgtactt ccagagcacc tcaaacgcat caatgcatga gtgtaacacg 900
aagtgtcaaa caccgctcgg agctataaac agcagtctcc cttaccagaa tatacaccca 960
gtcacaatag gagagtgccc aaaatacgtc aggagtgcca aattgaggat ggttacagga 1020
ctaaggaaca ctccgtccat tcaatccaga ggtctatttg gagccattgc cggttttatt 1080
gaagggggat ggactggaat gatagatgga tggtatggtt atcatcatca gaatgaacag 1140
ggatcaggct atgcagcgga tcaaaaaagc acacaaaatg ccattaacgg gattacaaac 1200
aaggtgaaca ctgttatcga gaaaatgtac attcaattca cagctgtggg ttacgaattc 1260
aacaaattag aaaaaaggat ggaatactta aataaaaaag ttgatgatgg atttctgtac 1320
atttggacat ataatgcaga attgttagtt ctactggaaa atgaaaggac tctggatttc 1380
catgactcaa atgtgaagaa tctgtatgag aaagtaaaaa gccaattaaa gaataatgcc 1440
aaagaaatcg gaaatggatg ttttgagttc taccacaagt gtgacaatga atgcatggaa 1500
agtgtaagaa atgggactta tgattatccc aaatattcag aagagtcaaa gttgaacagg 1560
gaaaaggtag atggagtgaa attggaatca atggggatct atcagattct ggcgatctac 1620
tcaactgtcg ccagttcact ggtgcttttg gtctccctgg gggcaatcag tttctggatg 1680
tgttctaatg gatctttgca gtgcagaata tgcatctga 1719

<210> SEQ ID NO 37
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
atgaaggcta acctgctggt gctgctgagc gccctggctg ccgctgatgc cgataccatc 60
tgcatcggct accacgccaa caacagcacc gacaccgtgg ataccgtgct ggaaaagaac 120
gtgaccgtga cccacagcgt gaacctgctg gaagatagcc acaacggcaa gctgtgccgg 180
ctgaagggcg agaacctgta ttttcaaggc aagtgcaata tcgccggctg gctgctgggc 240
aaccccgagt gtgatcctct gctgcctgtg cggagctggt cctacatcgt ggaaaccccc 300
aacagcgaga acggcatctg ctaccccggc gacttcatcg actacgagga actgcgcgag 360
cagctgagca gcgtgtccag cttcgagaga ttcgagatct tccccaaaga gagcagctgg 420
cccaaccaca acaccaacgg cgtgacagcc gcctgtagcc acgagggcaa gagcagcttc 480
tacagaaacc tgctgtggct gaccgagaaa gagggcagct accccaagct gaagaacagc 540

```
tacgtgaaca agaaaggcaa agaggtgctg gtgctgtggg gcatccacca cccccccaac    600

tctaaagagc agcagaacat ctaccagaac gagaacgcct acgtgtccgt cgtgaccagc    660

aactacaacc ggcggttcac cccgagatc gccgagaggc ctaaagtgcg ggatcaggcc    720

ggcagaatga actactactg gaccctgctg aagcccggcg acaccatcat cttcgaggcc    780

aacggcaacc tgatcgcccc tatgtacgcc ttcgccctga gcagaggctt cggcagcggc    840

atcatcaccg aaaacctgta cttccaagga tccaacgcca gcatgcacga gtgcaacacc    900

aagtgccaga ccccgctcgg agctataaac agcagtctcc cttaccagaa tatacaccca    960

gtcacaatag gagagtgccc aaaatacgtc aggagtgcca aattgaggat ggttacagga   1020

ctaaggaaca ctccgtccat tcaatccaga ggtctatttg gagccattgc cggtttttatt   1080

gaagggggat ggactggaat gatagatgga tggtatggtt atcatcatca gaatgaacag   1140

ggatcaggct atgcagcgga tcaaaaaagc acacaaaatg ccattaacgg gattacaaac   1200

aaggtgaaca ctgttatcga gaaaatgtac attcaattca cagctgtggg taaagaattc   1260

aacaaattag aaaaaaggat ggaaaattta aataaaaaag ttgatgatgg atttctgtac   1320

atttggacat ataatgcaga attgttagtt ctactggaaa atgaaaggac tctggatttc   1380

catgactcaa atgtgaagaa tctgtatgag aaagtaaaaa gccaattaaa gaataatgcc   1440

aaagaaatcg gaaatggatg ttttgagttc taccacaagt gtgacaatga atgcatggaa   1500

agtgtaagaa atgggactta tgattatccc aaatattcag aagagtcaaa gttgaacagg   1560

gaaaaggtag atggagtgaa attggaatca atggggatct atcagattct ggcgatctac   1620

tcaactgtcg ccagttcact ggtgcttttg gtctccctgg gggcaatcag tttctggatg   1680

tgttctaatg gatctttgca gtgcagaata tgcatctga                          1719
```

<210> SEQ ID NO 38
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
atgaaggcta acctgctggt gctgctgagc gccctggctg ccgctgatgc cgataccatc     60

tgcatcggct accacgccaa caacagcacc gacaccgtgg ataccgtgct ggaaaagaac    120

gtgaccgtga cccacagcgt gaacctgctg gaagatagcc acaacggcaa gctgtgccgg    180

ctgaagggcg agaacctgta ttttcaaggc aagtgcaata tcgccggctg gctgctgggc    240

aaccccgagt gtgatcctct gctgcctgtg cggagctggt cctacatcgt ggaaaccccc    300

aacagcgaga acggcatctg ctaccccggc gacttcatcg actacgagga actgcgcgag    360

cagctgagca gcgtgtccag cttcgagaga ttcgagatct tccccaaaga gagcagctgg    420

cccaaccaca acaccaacgg cgtgacagcc gcctgtagcc acgagggcaa gagcagcttc    480

tacagaaacc tgctgtggct gaccgagaaa gagggcagct accccaagct gaagaacagc    540

tacgtgaaca agaaaggcaa agaggtgctg gtgctgtggg gcatccacca cccccccaac    600

tctaaagagc agcagaacat ctaccagaac gagaacgcct acgtgtccgt cgtgaccagc    660

aactacaacc ggcggttcac cccgagatc gccgagaggc ctaaagtgcg ggatcaggcc    720

ggcagaatga actactactg gaccctgctg aagcccggcg acaccatcat cttcgaggcc    780

aacggcaacc tgatcgcccc tatgtacgcc ttcgccctga gcagaggctt cggcagcggc    840
```

```
atcatcaccg aaaacctgta cttccaagga tccaacgcca gcatgcacga gtgcaacacc    900
aagtgccaga ccccgctcgg agctataaac agcagtctcc cttaccagaa tatacaccca    960
gtcacaatag gagagtgccc aaaatacgtc aggagtgcca aattgaggat ggttacagga   1020
ctaaggaaca ctccgtccat tcaatccaga ggtctatttg gagccattgc cggttttatt   1080
gaagggggat ggactggaat gatagatgga tggtatggtt atcatcatca gaatgaacag   1140
ggatcaggct atgcagcgga tcaaaaaagc acacaaaatg ccattaacgg gattacaaac   1200
aaggtgaaca ctgttatcga gaaaatgaac attcaattca cagctgtggg ttacgaattc   1260
aacaaattag aaaaaaggat ggaatactta aataaaaaag ttgatgatgg atttctggac   1320
atttggacat ataatgcaga attgttagtt ctactggaaa atgaaaggac tctggatttc   1380
catgactcaa atgtgaagaa tctgtatgag aaagtaaaaa gccaattaaa gaataatgcc   1440
aaagaaatcg gaaatggatg ttttgagttc taccacaagt gtgacaatga atgcatggaa   1500
agtgtaagaa atgggactta tgattatccc aaatattcag aagagtcaaa gttgaacagg   1560
gaaaaggtag atggagtgaa attggaatca atggggatct atcagattct ggcgatctac   1620
tcaactgtcg ccagttcact ggtgcttttg gtctccctgg gggcaatcag tttctggatg   1680
tgttctaatg gatctttgca gtgcagaata tgcatctga                          1719
```

<210> SEQ ID NO 39
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
atgaaggcta acctgctggt gctgctgagc gccctggctg ccgctgatgc cgataccatc     60
tgcatcggct accacgccaa caacagcacc gacaccgtgg ataccgtgct ggaaaagaac    120
gtgaccgtga cccacagcgt gaacctgctg gaagatagcc acaacggcaa gctgtgccgg    180
ctgaagggcg agaacctgta ttttcaaggc aagtgcaata tcgccggctg gctgctgggc    240
aaccccgagt gtgatcctct gctgcctgtg cggagctggt cctacatcgt ggaaaccccc    300
aacagcgaga acggcatctg ctaccccggc gacttcatcg actacgagga actgcgcgag    360
cagctgagca gcgtgtccag cttcgagaga ttcgagatct tccccaaaga gagcagctgg    420
cccaaccaca acaccaacgg cgtgacagcc gcctgtagcc acgagggcaa gagcagcttc    480
tacagaaacc tgctgtggct gaccgagaaa gagggcagct accccaagct gaagaacagc    540
tacgtgaaca agaaaggcaa agaggtgctg gtgctgtggg gcatccacca cccccccaac    600
tctaaagagc agcagaacat ctaccagaac gagaacgcct acgtgtccgt cgtgaccagc    660
aactacaacc ggcggttcac ccccgagatc gccgagaggc ctaaagtgcg ggatcaggcc    720
ggcagaatga actactactg gaccctgctg aagcccggcg acaccatcat cttcgaggcc    780
aacggcaacc tgatcgcccc tatgtacgcc ttcgccctga gcagaggctt cggcagcggc    840
atcatcaccg aaaacctgta cttccaagga tccaacgcca gcatgcacga gtgcaacacc    900
aagtgccaga ccccgctcgg agctataaac agcagtctcc cttaccagaa tatacaccca    960
gtcacaatag gagagtgccc aaaatacgtc aggagtgcca aattgaggat ggttacagga   1020
ctaaggaaca ctccgtccat tcaatccaga ggtctatttg gagccattgc cggttttatt   1080
gaagggggat ggactggaat gatagatgga tggtatggtt atcatcatca gaatgaacag   1140
```

```
ggatcaggct atgcagcgga tcaaaaaagc acacaaaatg ccattaacgg gattacaaac   1200

aaggtgaaca ctgttatcga gaaaatgtac attcaattca cagctgtggg ttacgaattc   1260

aacaaattag aaaaaaggat ggaatactta aataaaaaag ttgatgatgg atttctgtac   1320

atttggacat ataatgcaga attgttagtt ctactggaaa atgaaaggac tctggatttc   1380

catgactcaa atgtgaagaa tctgtatgag aaagtaaaaa gccaattaaa gaataatgcc   1440

aaagaaatcg gaaatggatg ttttgagttc taccacaagt gtgacaatga atgcatggaa   1500

agtgtaagaa atgggactta tgattatccc aaatattcag aagagtcaaa gttgaacagg   1560

gaaaaggtag atggagtgaa attggaatca atggggatct atcagattct ggcgatctac   1620

tcaactgtcg ccagttcact ggtgcttttg gtctccctgg gggcaatcag tttctggatg   1680

tgttctaatg gatctttgca gtgcagaata tgcatctga                          1719
```

```
<210> SEQ ID NO 40
<211> LENGTH: 1719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
```

```
atgaaggcaa acctactggt cctgttaagt gcacttgcag ctgcagatgc agacacaata     60

tgtataggct accatgcgaa caattcaacc gacactgttg acacagtact cgagaagaat    120

gtgacagtga cacactctgt taacctgctc gaagacagcc acaacggaaa actatgtaga    180

ttaaaaggag agaatctgta cttccaggga aaatgtaaca tcgccggatg gctcttggga    240

aacccagaat gcgacccact gcttccagtg agatcatggt cctacattgt agaaacacca    300

aactctgaga atggaatatg ttatccagga gatttcatcg actatgagga gctgagggag    360

caattgagct cagtgtcatc attcgaaaga ttcgaaatat ttcccaaaga aagctcatgg    420

cccaaccaca acacaaacgg agtaacggca gcatgctccc atgaggggaa aagcagtttt    480

tacagaaatt tgctatggct gacggagaag gagggctcat acccaaagct gaaaaattct    540

tatgtgaaca aaaaagggaa agaagtcctt gtactgtggg gtattcatca cccgcctaac    600

agtaaggaac aacagaatat ctatcagaat gaaaatgctt atgtctctgt agtgacttca    660

aattataaca ggagatttac cccggaaata gcagaaagac ccaaagtaag agatcaagct    720

gggaggatga actattactg gaccttgcta aaacccggag acacaataat atttgaggca    780

aatggaaatc taatagcacc aatgtatgct ttcgcactga gtagaggctt tgggtccggc    840

atcatcacct caaacgcaga gaatctgtac ttccagagct caatgcatga gtgtaacacg    900

aagtgtcaaa caccgctcgg agctataaac agcagtctcc cttaccagaa tatacaccca    960

gtcacaatag gagagtgccc aaaatacgtc aggagtgcca aattgaggat ggttacagga   1020

ctaaggaaca ctccgtccat tcaatccaga ggtctatttg gagccattgc cggttttatt   1080

gaagggggat ggactggaat gatagatgga tggtatggtt atcatcatca gaatgaacag   1140

ggatcaggct atgcagcgga tcaaaaaagc acacaaaatg ccattaacgg gattacaaac   1200

aaggtgaaca ctgttatcga gaaaatgtac attcaattca cagctgtggg taaagaattc   1260

aacaaattag aaaaaaggat ggaaaattta aataaaaaag ttgatgatgg atttctgtac   1320

atttggacat ataatgcaga attgttagtt ctactggaaa atgaaaggac tctggatttc   1380

catgactcaa atgtgaagaa tctgtatgag aaagtaaaaa gccaattaaa gaataatgcc   1440
```

```
aaagaaatcg gaaatggatg ttttgagttc taccacaagt gtgacaatga atgcatggaa   1500

agtgtaagaa atgggactta tgattatccc aaatattcag aagagtcaaa gttgaacagg   1560

gaaaaggtag atggagtgaa attggaatca atggggatct atcagattct ggcgatctac   1620

tcaactgtcg ccagttcact ggtgcttttg gtctccctgg gggcaatcag tttctggatg   1680

tgttctaatg gatctttgca gtgcagaata tgcatctga                          1719
```

<210> SEQ ID NO 41
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
atgaaggcaa acctactggt cctgttaagt gcacttgcag ctgcagatgc agacacaata     60

tgtataggct accatgcgaa caattcaacc gacactgttg acacagtact cgagaagaat    120

gtgacagtga cacactctgt taacctgctc gaagacagcc acaacggaaa actatgtaga    180

ttaaaaggag agaatctgta cttccaggga aaatgtaaca tcgccggatg gctcttggga    240

aacccagaat gcgacccact gcttccagtg agatcatggt cctacattgt agaaacacca    300

aactctgaga atggaatatg ttatccagga gatttcatcg actatgagga gctgagggag    360

caattgagct cagtgtcatc attcgaaaga ttcgaaatat ttcccaaaga aagctcatgg    420

cccaaccaca acacaaacgg agtaacggca gcatgctccc atgaggggaa aagcagtttt    480

tacagaaatt tgctatggct gacggagaag gagggctcat acccaaagct gaaaaattct    540

tatgtgaaca aaaaagggaa agaagtcctt gtactgtggg gtattcatca cccgcctaac    600

agtaaggaac aacagaatat ctatcagaat gaaaatgctt atgtctctgt agtgacttca    660

aattataaca ggagatttac cccggaaata gcagaaagac ccaaagtaag agatcaagct    720

gggaggatga actattactg gaccttgcta aaacccggag acacaataat atttgaggca    780

aatggaaatc taatagcacc aatgtatgct ttcgcactga gtagaggctt tgggtccggc    840

atcatcacct caaacgcaga gaatctgtac ttccagagct caatgcatga gtgtaacacg    900

aagtgtcaaa caccgctcgg agctataaac agcagtctcc cttaccagaa tatacaccca    960

gtcacaatag gagagtgccc aaaatacgtc aggagtgcca aattgaggat ggttacagga   1020

ctaaggaaca ctccgtccat tcaatccaga ggtctatttg gagccattgc cggttttatt   1080

gaagggggat ggactggaat gatagatgga tggtatggtt atcatcatca gaatgaacag   1140

ggatcaggct atgcagcgga tcaaaaaagc acacaaaatg ccattaacgg gattacaaac   1200

aaggtgaaca ctgttatcga gaaaatgaac attcaattca cagctgtggg ttacgaattc   1260

aacaaattag aaaaaaggat ggaatactta aataaaaaag ttgatgatgg atttctggac   1320

atttggacat ataatgcaga attgttagtt ctactggaaa atgaaaggac tctggatttc   1380

catgactcaa atgtgaagaa tctgtatgag aaagtaaaaa gccaattaaa gaataatgcc   1440

aaagaaatcg gaaatggatg ttttgagttc taccacaagt gtgacaatga atgcatggaa   1500

agtgtaagaa atgggactta tgattatccc aaatattcag aagagtcaaa gttgaacagg   1560

gaaaaggtag atggagtgaa attggaatca atggggatct atcagattct ggcgatctac   1620

tcaactgtcg ccagttcact ggtgcttttg gtctccctgg gggcaatcag tttctggatg   1680

tgttctaatg gatctttgca gtgcagaata tgcatctga                          1719
```

<210> SEQ ID NO 42
<211> LENGTH: 1719
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 42
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt taacctgctc gaagacagcc acaacggaaa actatgtaga 180
ttaaaaggag agaatctgta cttccaggga aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420
cccaaccaca acacaaacgg agtaacggca gcatgctccc atgaggggaa aagcagtttt 480
tacagaaatt tgctatggct gacggagaag gagggctcat acccaaagct gaaaaattct 540
tatgtgaaca aaaaagggaa agaagtcctt gtactgtggg gtattcatca cccgcctaac 600
agtaaggaac aacagaatat ctatcagaat gaaaatgctt atgtctctgt agtgacttca 660
aattataaca ggagatttac cccggaaata gcagaaagac ccaaagtaag agatcaagct 720
gggaggatga actattactg gaccttgcta aaacccggag acacaataat atttgaggca 780
aatggaaatc taatagcacc aatgtatgct ttcgcactga gtagaggctt tgggtccggc 840
atcatcacct caaacgcaga gaatctgtac ttccagagct caatgcatga gtgtaacacg 900
aagtgtcaaa caccgctcgg agctataaac agcagtctcc cttaccagaa tatacaccca 960
gtcacaatag gagagtgccc aaaatacgtc aggagtgcca aattgaggat ggttacagga 1020
ctaaggaaca ctccgtccat tcaatccaga ggtctatttg gagccattgc cggttttatt 1080
gaagggggat ggactggaat gatagatgga tggtatggtt atcatcatca gaatgaacag 1140
ggatcaggct atgcagcgga tcaaaaaagc acacaaaatg ccattaacgg gattacaaac 1200
aaggtgaaca ctgttatcga gaaaatgtac attcaattca cagctgtggg ttacgaattc 1260
aacaaattag aaaaaaggat ggaatactta aataaaaaag ttgatgatgg atttctgtac 1320
atttggacat ataatgcaga attgttagtt ctactggaaa atgaaaggac tctggatttc 1380
catgactcaa atgtgaagaa tctgtatgag aaagtaaaaa gccaattaaa gaataatgcc 1440
aaagaaatcg gaaatggatg ttttgagttc taccacaagt gtgacaatga atgcatggaa 1500
agtgtaagaa atgggactta tgattatccc aaatattcag aagagtcaaa gttgaacagg 1560
gaaaaggtag atggagtgaa attggaatca atggggatct atcagattct ggcgatctac 1620
tcaactgtcg ccagttcact ggtgcttttg gtctccctgg gggcaatcag tttctggatg 1680
tgttctaatg gatctttgca gtgcagaata tgcatctga 1719

<210> SEQ ID NO 43
<211> LENGTH: 1740
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 43
atgaaggcta acctgctggt gctgctgagc gccctggctg ccgctgatgc cgataccatc 60
tgcatcggct accacgccaa caacagcacc gacaccgtgg ataccgtgct ggaaaagaac 120
gtgaccgtga cccacagcgt ggaaaacctg tattttcaag gcaatctgct ggaagatagc 180
cacaacggca agctgtgccg gctgaaggga atcgcccctc tgcagctggg caagtgcaat 240
atcgccggct ggctgctggg caaccccgag tgtgatcctc tgctgcctgt gcggagctgg 300
tcctacatcg tggaaacccc caacagcgag aacggcatct gctaccccgg cgacttcatc 360
gactacgagg aactgcgcga gcagctgagc agcgtgtcca gcttcgaaag attcgagatc 420
ttccccaaag agagcagctg gcccaaccac aacaccaacg gcgtgacagc cgcctgtagc 480
cacgagggca agagcagctt ctaccggaac ctgctgtggc tgaccgagaa agagggcagc 540
taccccaagc tgaagaacag ctacgtgaac aagaaaggca aagaggtgct ggtgctgtgg 600
ggcatccacc accccccaa ctctaaagag cagcagaaca tctaccagaa cgagaacgcc 660
tacgtgtccg tcgtgaccag caactacaac cggcggttca cccccgagat cgccgagagg 720
cctaaagtgc gggatcaggc cggcagaatg aactactact ggaccctgct gaagcccggc 780
gacaccatca tcttcgaggc caacggcaac ctgatcgccc ctatgtacgc cttcgccctg 840
agcagaggct tcggcagcgg catcatcacc agcaacgcca gcatgcacga gtgcgagaac 900
ctgtacttcc aagggaacac caagtgccag accccgctcg gagctataaa cagcagtctc 960
ccttaccaga atatacaccc agtcacaata ggagagtgcc caaaatacgt caggagtgcc 1020
aaattgagga tggttacagg actaaggaac actccgtcca ttcaatccag aggtctattt 1080
ggagccattg ccggttttat tgaagggggga tggactggaa tgatagatgg atggtatggt 1140
tatcatcatc agaatgaaca gggatcaggc tatgcagcgg atcaaaaaag cacacaaaat 1200
gccattaacg ggattacaaa caaggtgaac actgttatcg agaaaatgta cattcaattc 1260
acagctgtgg gtaaagaatt caacaaatta gaaaaaagga tggaaaattt aaataaaaaa 1320
gttgatgatg gatttctgta catttggaca tataatgcag aattgttagt tctactggaa 1380
aatgaaagga ctctggattt ccatgactca aatgtgaaga atctgtatga gaaagtaaaa 1440
agccaattaa agaataatgc caaagaaatc ggaaatggat gttttgagtt ctaccacaag 1500
tgtgacaatg aatgcatgga aagtgtaaga aatgggactt atgattatcc caaatattca 1560
gaagagtcaa agttgaacag ggaaaaggta gatggagtga aattggaatc aatggggatc 1620
tatcagattc tggcgatcta ctcaactgtc gccagttcac tggtgctttt ggtctccctg 1680
ggggcaatca gtttctggat gtgttctaat ggatctttgc agtgcagaat atgcatctga 1740

<210> SEQ ID NO 44
<211> LENGTH: 1740
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 44
atgaaggcta acctgctggt gctgctgagc gccctggctg ccgctgatgc cgataccatc 60
tgcatcggct accacgccaa caacagcacc gacaccgtgg ataccgtgct ggaaaagaac 120
gtgaccgtga cccacagcgt ggaaaacctg tattttcaag gcaatctgct ggaagatagc 180
cacaacggca agctgtgccg gctgaaggga atcgcccctc tgcagctggg caagtgcaat 240

-continued atcgccggct ggctgctggg caaccccgag tgtgatcctc tgctgcctgt gcggagctgg 300
tcctacatcg tggaaacccc caacagcgag aacggcatct gctaccccgg cgacttcatc 360
gactacgagg aactgcgcga gcagctgagc agcgtgtcca gcttcgaaag attcgagatc 420
ttccccaaag agagcagctg gcccaaccac aacaccaacg gcgtgacagc cgcctgtagc 480
cacgagggca agagcagctt ctaccggaac ctgctgtggc tgaccgagaa agagggcagc 540
taccccaagc tgaagaacag ctacgtgaac aagaaaggca aagaggtgct ggtgctgtgg 600
ggcatccacc acccccccaa ctctaaagag cagcagaaca tctaccagaa cgagaacgcc 660
tacgtgtccg tcgtgaccag caactacaac cggcggttca cccccgagat cgccgagagg 720
cctaaagtgc gggatcaggc cggcagaatg aactactact ggaccctgct gaagcccggc 780
gacaccatca tcttcgaggc caacggcaac ctgatcgccc ctatgtacgc cttcgccctg 840
agcagaggct tcggcagcgg catcatcacc agcaacgcca gcatgcacga gtgcgagaac 900
ctgtacttcc aagggaacac caagtgccag accccgctcg gagctataaa cagcagtctc 960
ccttaccaga atatacaccc agtcacaata ggagagtgcc caaaatacgt caggagtgcc 1020
aaattgagga tggttacagg actaaggaac actccgtcca ttcaatccag aggtctattt 1080
ggagccattg ccggttttat tgaaggggga tggactggaa tgatagatgg atggtatggt 1140
tatcatcatc agaatgaaca gggatcaggc tatgcagcgg atcaaaaaag cacacaaaat 1200
gccattaacg ggattacaaa caaggtgaac actgttatcg agaaaatgaa cattcaattc 1260
acagctgtgg gttacgaatt caacaaatta gaaaaaagga tggaatactt aaataaaaaa 1320
gttgatgatg gatttctgga catttggaca tataatgcag aattgttagt tctactggaa 1380
aatgaaagga ctctggattt ccatgactca aatgtgaaga atctgtatga gaaagtaaaa 1440
agccaattaa agaataatgc caaagaaatc ggaaatggat gttttgagtt ctaccacaag 1500
tgtgacaatg aatgcatgga aagtgtaaga aatgggactt atgattatcc caaatattca 1560
gaagagtcaa agttgaacag ggaaaaggta gatggagtga aattggaatc aatggggatc 1620
tatcagattc tggcgatcta ctcaactgtc gccagttcac tggtgctttt ggtctccctg 1680
ggggcaatca gtttctggat gtgttctaat ggatctttgc agtgcagaat atgcatctga 1740

<210> SEQ ID NO 45
<211> LENGTH: 1740
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45
atgaaggcta acctgctggt gctgctgagc gccctggctg ccgctgatgc cgataccatc 60
tgcatcggct accacgccaa caacagcacc gacaccgtgg ataccgtgct ggaaaagaac 120
gtgaccgtga cccacagcgt ggaaaacctg tattttcaag gcaatctgct ggaagatagc 180
cacaacggca agctgtgccg gctgaaggga atcgcccctc tgcagctggg caagtgcaat 240
atcgccggct ggctgctggg caaccccgag tgtgatcctc tgctgcctgt gcggagctgg 300
tcctacatcg tggaaacccc caacagcgag aacggcatct gctaccccgg cgacttcatc 360
gactacgagg aactgcgcga gcagctgagc agcgtgtcca gcttcgaaag attcgagatc 420
ttccccaaag agagcagctg gcccaaccac aacaccaacg gcgtgacagc cgcctgtagc 480
cacgagggca agagcagctt ctaccggaac ctgctgtggc tgaccgagaa agagggcagc 540

-continued

```
taccccaagc tgaagaacag ctacgtgaac aagaaaggca aagaggtgct ggtgctgtgg    600
ggcatccacc acccccccaa ctctaaagag cagcagaaca tctaccagaa cgagaacgcc    660
tacgtgtccg tcgtgaccag caactacaac cggcggttca cccccgagat cgccgagagg    720
cctaaagtgc gggatcaggc cggcagaatg aactactact ggaccctgct gaagcccggc    780
gacaccatca tcttcgaggc caacggcaac ctgatcgccc ctatgtacgc cttcgccctg    840
agcagaggct tcggcagcgg catcatcacc agcaacgcca gcatgcacga gtgcgagaac    900
ctgtacttcc aagggaacac caagtgccag accccgctcg gagctataaa cagcagtctc    960
ccttaccaga atatacaccc agtcacaata ggagagtgcc caaaatacgt caggagtgcc   1020
aaattgagga tggttacagg actaaggaac actccgtcca ttcaatccag aggtctattt   1080
ggagccattg ccggttttat tgaaggggga tggactggaa tgatagatgg atggtatggt   1140
tatcatcatc agaatgaaca gggatcaggc tatgcagcgg atcaaaaaag cacacaaaat   1200
gccattaacg ggattacaaa caaggtgaac actgttatcg agaaaatgta cattcaattc   1260
acagctgtgg gttacgaatt caacaaatta gaaaaaagga tggaatactt aaataaaaaa   1320
gttgatgatg gatttctgta catttggaca tataatgcag aattgttagt tctactggaa   1380
aatgaaagga ctctggattt ccatgactca aatgtgaaga atctgtatga gaaagtaaaa   1440
agccaattaa agaataatgc caaagaaatc ggaaatggat gttttgagtt ctaccacaag   1500
tgtgacaatg aatgcatgga aagtgtaaga aatgggactt atgattatcc caaatattca   1560
gaagagtcaa agttgaacag ggaaaaggta gatggagtga aattggaatc aatggggatc   1620
tatcagattc tggcgatcta ctcaactgtc gccagttcac tggtgctttt ggtctccctg   1680
ggggcaatca gtttctggat gtgttctaat ggatctttgc agtgcagaat atgcatctga   1740
```

<210> SEQ ID NO 46
<211> LENGTH: 1740
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
atgaaggcta acctgctggt gctgctgagc gccctggctg ccgctgatgc cgataccatc     60
tgcatcggct accacgccaa caacagcacc gacaccgtgg ataccgtgct ggaaaagaac    120
gtgaccgtga cccacagcgt ggaaaacctg tattttcaag gcaatctgct ggaagatagc    180
cacaacggca agctgtgccg gctgaaggga atcgcccctc tgcagctggg caagtgcaat    240
atcgccggct ggctgctggg caaccccgag tgtgatcctc tgctgcctgt gcggagctgg    300
tcctacatcg tggaaacccc caacagcgag aacggcatct gctaccccgg cgacttcatc    360
gactacgagg aactgcgcga gcagctgagc agcgtgtcca gcttcgaaag attcgagatc    420
ttccccaaag agagcagctg gcccaaccac aacaccaacg gcgtgacagc cgcctgtagc    480
cacgagggca agagcagctt ctaccggaac ctgctgtggc tgaccgagaa agagggcagc    540
taccccaagc tgaagaacag ctacgtgaac aagaaaggca aagaggtgct ggtgctgtgg    600
ggcatccacc acccccccaa ctctaaagag cagcagaaca tctaccagaa cgagaacgcc    660
tacgtgtccg tcgtgaccag caactacaac cggcggttca cccccgagat cgccgagagg    720
cctaaagtgc gggatcaggc cggcagaatg aactactact ggaccctgct gaagcccggc    780
gacaccatca tcttcgaggc caacggcaac ctgatcgccc ctatgtacgc cttcgccctg    840
```

agcagaggct tcggcagcgg catcatcacc agcaacgcca gcatgcacga gtgcgagaac 900
ctgtacttcc aaagcaacac caagtgccag accccgctcg gagctataaa cagcagtctc 960
ccttaccaga atatacaccc agtcacaata ggagagtgcc caaaatacgt caggagtgcc 1020
aaattgagga tggttacagg actaaggaac actccgtcca ttcaatccag aggtctattt 1080
ggagccattg ccggttttat tgaaggggga tggactggaa tgatagatgg atggtatggt 1140
tatcatcatc agaatgaaca gggatcaggc tatgcagcgg atcaaaaaag cacacaaaat 1200
gccattaacg ggattacaaa caaggtgaac actgttatcg agaaaatgta cattcaattc 1260
acagctgtgg gtaaagaatt caacaaatta gaaaaaagga tggaaaattt aaataaaaaa 1320
gttgatgatg gatttctgta catttggaca tataatgcag aattgttagt tctactggaa 1380
aatgaaagga ctctggattt ccatgactca aatgtgaaga atctgtatga gaaagtaaaa 1440
agccaattaa agaataatgc caaagaaatc ggaaatggat gttttgagtt ctaccacaag 1500
tgtgacaatg aatgcatgga aagtgtaaga aatgggactt atgattatcc caaatattca 1560
gaagagtcaa agttgaacag ggaaaaggta gatggagtga aattggaatc aatggggatc 1620
tatcagattc tggcgatcta ctcaactgtc gccagttcac tggtgctttt ggtctccctg 1680
ggggcaatca gtttctggat gtgttctaat ggatctttgc agtgcagaat atgcatctga 1740

<210> SEQ ID NO 47
<211> LENGTH: 1740
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47
atgaaggcta acctgctggt gctgctgagc gccctggctg ccgctgatgc cgataccatc 60
tgcatcggct accacgccaa caacagcacc gacaccgtgg ataccgtgct ggaaaagaac 120
gtgaccgtga cccacagcgt ggaaaacctg tattttcaag gcaatctgct ggaagatagc 180
cacaacggca agctgtgccg gctgaaggga atcgcccctc tgcagctggg caagtgcaat 240
atcgccggct ggctgctggg caaccccgag tgtgatcctc tgctgcctgt gcggagctgg 300
tcctacatcg tggaaacccc caacagcgag aacggcatct gctaccccgg cgacttcatc 360
gactacgagg aactgcgcga gcagctgagc agcgtgtcca gcttcgaaag attcgagatc 420
ttccccaaag agagcagctg gcccaaccac aacaccaacg gcgtgacagc cgcctgtagc 480
cacgagggca agagcagctt ctaccggaac ctgctgtggc tgaccgagaa agagggcagc 540
taccccaagc tgaagaacag ctacgtgaac aagaaaggca aagaggtgct ggtgctgtgg 600
ggcatccacc acccccccaa ctctaaagag cagcagaaca tctaccagaa cgagaacgcc 660
tacgtgtccg tcgtgaccag caactacaac cggcggttca cccccgagat cgccgagagg 720
cctaaagtgc gggatcaggc cggcagaatg aactactact ggaccctgct gaagcccggc 780
gacaccatca tcttcgaggc caacggcaac ctgatcgccc ctatgtacgc cttcgccctg 840
agcagaggct tcggcagcgg catcatcacc agcaacgcca gcatgcacga gtgcgagaac 900
ctgtacttcc aaagcaacac caagtgccag accccgctcg gagctataaa cagcagtctc 960
ccttaccaga atatacaccc agtcacaata ggagagtgcc caaaatacgt caggagtgcc 1020
aaattgagga tggttacagg actaaggaac actccgtcca ttcaatccag aggtctattt 1080
ggagccattg ccggttttat tgaaggggga tggactggaa tgatagatgg atggtatggt 1140

-continued

```
tatcatcatc agaatgaaca gggatcaggc tatgcagcgg atcaaaaaag cacacaaaat   1200

gccattaacg ggattacaaa caaggtgaac actgttatcg agaaaatgaa cattcaattc   1260

acagctgtgg gttacgaatt caacaaatta gaaaaaagga tggaatactt aaataaaaaa   1320

gttgatgatg gatttctgga catttggaca tataatgcag aattgttagt tctactggaa   1380

aatgaaagga ctctggattt ccatgactca aatgtgaaga atctgtatga gaaagtaaaa   1440

agccaattaa agaataatgc caaagaaatc ggaaatggat gttttgagtt ctaccacaag   1500

tgtgacaatg aatgcatgga aagtgtaaga aatgggactt atgattatcc caaatattca   1560

gaagagtcaa agttgaacag ggaaaaggta gatggagtga aattggaatc aatggggatc   1620

tatcagattc tggcgatcta ctcaactgtc gccagttcac tggtgctttt ggtctccctg   1680

ggggcaatca gtttctggat gtgttctaat ggatctttgc agtgcagaat atgcatctga   1740
```

<210> SEQ ID NO 48
<211> LENGTH: 1740
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
atgaaggcta acctgctggt gctgctgagc gccctggctg ccgctgatgc cgataccatc     60

tgcatcggct accacgccaa caacagcacc gacaccgtgg ataccgtgct ggaaaagaac    120

gtgaccgtga cccacagcgt ggaaaacctg tattttcaag gcaatctgct ggaagatagc    180

cacaacggca agctgtgccg gctgaaggga atcgcccctc tgcagctggg caagtgcaat    240

atcgccggct ggctgctggg caaccccgag tgtgatcctc tgctgcctgt gcggagctgg    300

tcctacatcg tggaaacccc caacagcgag aacggcatct gctaccccgg cgacttcatc    360

gactacgagg aactgcgcga gcagctgagc agcgtgtcca gcttcgaaag attcgagatc    420

ttccccaaag agagcagctg gcccaaccac aacaccaacg gcgtgacagc cgcctgtagc    480

cacgagggca agagcagctt ctaccggaac ctgctgtggc tgaccgagaa agagggcagc    540

taccccaagc tgaagaacag ctacgtgaac aagaaaggca aagaggtgct ggtgctgtgg    600

ggcatccacc acccccccaa ctctaaagag cagcagaaca tctaccagaa cgagaacgcc    660

tacgtgtccg tcgtgaccag caactacaac cggcggttca cccccgagat cgccgagagg    720

cctaaagtgc gggatcaggc cggcagaatg aactactact ggaccctgct gaagcccggc    780

gacaccatca tcttcgaggc caacggcaac ctgatcgccc ctatgtacgc cttcgccctg    840

agcagaggct tcggcagcgg catcatcacc agcaacgcca gcatgcacga gtgcgagaac    900

ctgtacttcc aaagcaacac caagtgccag accccgctcg gagctataaa cagcagtctc    960

ccttaccaga atatacaccc agtcacaata ggagagtgcc caaaatacgt caggagtgcc   1020

aaattgagga tggttacagg actaaggaac actccgtcca ttcaatccag aggtctattt   1080

ggagccattg ccggttttat tgaagggggga tggactggaa tgatagatgg atggtatggt   1140

tatcatcatc agaatgaaca gggatcaggc tatgcagcgg atcaaaaaag cacacaaaat   1200

gccattaacg ggattacaaa caaggtgaac actgttatcg agaaaatgta cattcaattc   1260

acagctgtgg gttacgaatt caacaaatta gaaaaaagga tggaatactt aaataaaaaa   1320

gttgatgatg gatttctgta catttggaca tataatgcag aattgttagt tctactggaa   1380

aatgaaagga ctctggattt ccatgactca aatgtgaaga atctgtatga gaaagtaaaa   1440
```

-continued

```
agccaattaa agaataatgc caaagaaatc ggaaatggat gttttgagtt ctaccacaag   1500

tgtgacaatg aatgcatgga aagtgtaaga aatgggactt atgattatcc caaatattca   1560

gaagagtcaa agttgaacag ggaaaaggta gatggagtga aattggaatc aatggggatc   1620

tatcagattc tggcgatcta ctcaactgtc gccagttcac tggtgctttt ggtctccctg   1680

ggggcaatca gtttctggat gtgttctaat ggatctttgc agtgcagaat atgcatctga   1740
```

<210> SEQ ID NO 49
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
atgaaggcaa acctactggt cctgttaagt gcacttgcag ctgcagatgc agacacaata     60

tgtataggct accatgcgaa caattcaacc gacactgttg acacagtact cgagaagaat    120

gtgacagtga cacactctgt taacctgctc gaagacagcc acaacggaaa actatgtaga    180

ttaaaaggaa tagccccact acaattgggg aaatgtaaca tcgccggatg gctcttggga    240

aacccagaat gcgacccact gcttccagtg agatcatggt cctacattgt agaaacacca    300

aactctgaga atggaatatg ttatccagga gatttcatcg actatgagga gctgagggag    360

caattgagct cagtgtcatc attcgaaaga ttcgaaatat ttcccaaaga aagctcatgg    420

cccaaccaca acacaaacgg agtaacggca gcatgctccc atgaggggaa aagcagtttt    480

tacagaaatt tgctatggct gacggagaag gagggctcat acccaaagct gaaaaattct    540

tatgtgaaca aaaaagggaa agaagtcctt gtactgtggg gtattcatca cccgcctaac    600

agtaaggaac aacagaatat ctatcagaat gaaaatgctt atgtctctgt agtgacttca    660

aattataaca ggagatttac cccggaaata gcagaaagac ccaaagtaag agatcaagct    720

gggaggatga actattactg gaccttgcta aaacccggag acacaataat atttgaggca    780

aatggaaatc taatagcacc aatgtatgct ttcgcactga gtagaggctt tgggtccggc    840

atcatcacct caaacgcatc aatgcatgag tgtgagaatc tgtacttcca gggaaacacg    900

aagtgtcaaa caccgctcgg agctataaac agcagtctcc cttaccagaa tatacaccca    960

gtcacaatag gagagtgccc aaaatacgtc aggagtgcca aattgaggat ggttacagga   1020

ctaaggaaca ctccgtccat tcaatccaga ggtctatttg gagccattgc cggttttatt   1080

gaagggggat ggactggaat gatagatgga tggtatggtt atcatcatca gaatgaacag   1140

ggatcaggct atgcagcgga tcaaaaaagc acacaaaatg ccattaacgg gattacaaac   1200

aaggtgaaca ctgttatcga gaaaatgaac attcaattca cagctgtggg taaagaattc   1260

aacaaattag aaaaaaggat ggaaaattta aataaaaaag ttgatgatgg atttctggac   1320

atttggacat ataatgcaga attgttagtt ctactggaaa atgaaaggac tctggatttc   1380

catgactcaa atgtgaagaa tctgtatgag aaagtaaaaa gccaattaaa gaataatgcc   1440

aaagaaatcg gaaatggatg ttttgagttc taccacaagt gtgacaatga atgcatggaa   1500

agtgtaagaa atgggactta tgattatccc aaatattcag aagagtcaaa gttgaacagg   1560

gaaaaggtag atggagtgaa attggaatca atggggatct atcagattct ggcgatctac   1620

tcaactgtcg ccagttcact ggtgcttttg gtctccctgg gggcaatcag tttctggatg   1680

tgttctaatg gatctttgca gtgcagaata tgcatctga                           1719
```

<210> SEQ ID NO 50
<211> LENGTH: 1719
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 50

```
atgaaggcaa acctactggt cctgttaagt gcacttgcag ctgcagatgc agacacaata     60
tgtataggct accatgcgaa caattcaacc gacactgttg acacagtact cgagaagaat    120
gtgacagtga cacactctgt taacctgctc gaagacagcc acaacggaaa actatgtaga    180
ttaaaaggaa tagccccact acaattgggg aaatgtaaca tcgccggatg gctcttggga    240
aacccagaat gcgacccact gcttccagtg agatcatggt cctacattgt agaaacacca    300
aactctgaga atggaatatg ttatccagga gatttcatcg actatgagga gctgagggag    360
caattgagct cagtgtcatc attcgaaaga ttcgaaatat ttcccaaaga aagctcatgg    420
cccaaccaca acacaaacgg agtaacggca gcatgctccc atgaggggaa aagcagtttt    480
tacagaaatt tgctatggct gacggagaag gagggctcat acccaaagct gaaaaattct    540
tatgtgaaca aaaaagggaa agaagtcctt gtactgtggg gtattcatca cccgcctaac    600
agtaaggaac aacagaatat ctatcagaat gaaaatgctt atgtctctgt agtgacttca    660
aattataaca ggagatttac cccggaaata gcagaaagac ccaaagtaag agatcaagct    720
gggaggatga actattactg gaccttgcta aaacccggag acacaataat atttgaggca    780
aatggaaatc taatagcacc aatgtatgct ttcgcactga gtagaggctt tgggtccggc    840
atcatcacct caaacgcatc aatgcatgag tgtgagaatc tgtacttcca gagcaacacg    900
aagtgtcaaa caccgctcgg agctataaac agcagtctcc cttaccagaa tatacaccca    960
gtcacaatag gagagtgccc aaaatacgtc aggagtgcca aattgaggat ggttacagga   1020
ctaaggaaca ctccgtccat tcaatccaga ggtctatttg gagccattgc cggttttatt   1080
gaagggggat ggactggaat gatagatgga tggtatggtt atcatcatca gaatgaacag   1140
ggatcaggct atgcagcgga tcaaaaaagc acacaaaatg ccattaacgg gattacaaac   1200
aaggtgaaca ctgttatcga gaaaatgaac attcaattca cagctgtggg taaagaattc   1260
aacaaattag aaaaaaggat ggaaaattta aataaaaaag ttgatgatgg atttctggac   1320
atttggacat ataatgcaga attgttagtt ctactggaaa atgaaaggac tctggatttc   1380
catgactcaa atgtgaagaa tctgtatgag aaagtaaaaa gccaattaaa gaataatgcc   1440
aaagaaatcg gaaatggatg ttttgagttc taccacaagt gtgacaatga atgcatggaa   1500
agtgtaagaa atgggactta tgattatccc aaatattcag aagagtcaaa gttgaacagg   1560
gaaaaggtag atggagtgaa attggaatca atggggatct atcagattct ggcgatctac   1620
tcaactgtcg ccagttcact ggtgcttttg gtctccctgg gggcaatcag tttctggatg   1680
tgttctaatg gatctttgca gtgcagaata tgcatctga                          1719
```

<210> SEQ ID NO 51
<211> LENGTH: 1698
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 51
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt taacctgctc gaagacagcc acaacggaaa actatgtaga 180
ttaaaaggag agaatctgta cttccaggga aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420
cccaaccaca acacaaacgg agtaacggca gcatgctccc atgaggggaa aagcagtttt 480
tacagaaatt tgctatggct gacggagaag gagggctcat acccaaagct gaaaaattct 540
tatgtgaaca aaaaagggaa agaagtcctt gtactgtggg gtattcatca cccgcctaac 600
agtaaggaac aacagaatat ctatcagaat gaaaatgctt atgtctctgt agtgacttca 660
aattataaca ggagatttac cccggaaata gcagaaagac ccaaagtaag agatcaagct 720
gggaggatga actattactg gaccttgcta aaacccggag acacaataat atttgaggca 780
aatggaaatc taatagcacc aatgtatgct ttcgcactga gtagaggctt tgggtccggc 840
atcatcacct caaacgcatc aatgcatgag tgtaacacga agtgtcaaac accgctcgga 900
gctataaaca gcagtctccc ttaccagaat atacacccag tcacaatagg agagtgccca 960
aaatacgtca ggagtgccaa attgaggatg gttacaggac taaggaacac tccgtccatt 1020
caatccagag gtctatttgg agccattgcc ggttttattg aagggggatg gactggaatg 1080
atagatggat ggtatggtta tcatcatcag aatgaacagg gatcaggcta tgcagcggat 1140
caaaaaagca cacaaaatgc cattaacggg attacaaaca aggtgaacac tgttatcgag 1200
aaaatgaaca ttcaattcac agctgtgggt aaagaattca acaaattaga aaaaaggatg 1260
gaaaatttaa ataaaaaagt tgatgatgga tttctggaca tttggacata taatgcagaa 1320
ttgttagttc tactggaaaa tgaaaggact ctggatttcc atgactcaaa tgtgaagaat 1380
ctgtatgaga aagtaaaaag ccaattaaag aataatgcca aagaaatcgg aaatggatgt 1440
tttgagttct accacaagtg tgacaatgaa tgcatggaaa gtgtaagaaa tgggacttat 1500
gattatccca aatattcaga agagtcaaag ttgaacaggg aaaaggtaga tggagtgaaa 1560
ttggaatcaa tggggatcta tcagattctg gcgatctact caactgtcgc cagttcactg 1620
gtgcttttgg tctccctggg ggcaatcagt ttctggatgt gttctaatgg atctttgcag 1680
tgcagaatat gcatctga 1698

<210> SEQ ID NO 52
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt tgagaacctg tacttccagg gaaacctgct cgaagacagc 180
cacaacggaa aactatgtag attaaaagga atagccccac tacaattggg gaaatgtaac 240
atcgccggat ggctcttggg aaacccagaa tgcgacccac tgcttccagt gagatcatgg 300

```
tcctacattg tagaaacacc aaactctgag aatggaatat gttatccagg agatttcatc    360

gactatgagg agctgaggga gcaattgagc tcagtgtcat cattcgaaag attcgaaata    420

tttcccaaag aaagctcatg gcccaaccac aacacaaacg gagtaacggc agcatgctcc    480

catgagggga aaagcagttt ttacagaaat ttgctatggc tgacggagaa ggagggctca    540

tacccaaagc tgaaaaattc ttatgtgaac aaaaaaggga aagaagtcct tgtactgtgg    600

ggtattcatc acccgcctaa cagtaaggaa caacagaata tctatcagaa tgaaaatgct    660

tatgtctctg tagtgacttc aaattataac aggagattta ccccggaaat agcagaaaga    720

cccaaagtaa gagatcaagc tgggaggatg aactattact ggaccttgct aaaacccgga    780

gacacaataa tatttgaggc aaatggaaat ctaatagcac caatgtatgc tttcgcactg    840

agtagaggct ttgggtccgg catcatcacc tcaaacgcat caatgcatga gtgtaacacg    900

aagtgtcaaa caccgctcgg agctataaac agcagtctcc cttaccagaa tatacaccca    960

gtcacaatag gagagtgccc aaaatacgtc aggagtgcca aattgaggat ggttacagga   1020

ctaaggaaca ctccgtccat tcaatccaga ggtctatttg gagccattgc cggttttatt   1080

gaagggggat ggactggaat gatagatgga tggtatggtt atcatcatca gaatgaacag   1140

ggatcaggct atgcagcgga tcaaaaaagc acacaaaatg ccattaacgg gattacaaac   1200

aaggtgaaca ctgttatcga gaaaatgaac attcaattca cagctgtggg taaagaattc   1260

aacaaattag aaaaaaggat ggaaaattta aataaaaaag ttgatgatgg atttctggac   1320

atttggacat ataatgcaga attgttagtt ctactggaaa atgaaaggac tctggatttc   1380

catgactcaa atgtgaagaa tctgtatgag aaagtaaaaa gccaattaaa gaataatgcc   1440

aaagaaatcg gaaatggatg ttttgagttc taccacaagt gtgacaatga atgcatggaa   1500

agtgtaagaa atgggactta tgattatccc aaatattcag aagagtcaaa gttgaacagg   1560

gaaaaggtag atggagtgaa attggaatca atggggatct atcagattct ggcgatctac   1620

tcaactgtcg ccagttcact ggtgcttttg gtctccctgg gggcaatcag tttctggatg   1680

tgttctaatg gatctttgca gtgcagaata tgcatctga                          1719
```

```
<210> SEQ ID NO 53
<211> LENGTH: 1701
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
```

```
atgaaggcaa acctactggt cctgttaagt gcacttgcag ctgcagatgc agacacaata     60

tgtataggct accatgcgaa caattcaacc gacactgttg acacagtact cgagaagaat    120

gtgacagtga cacactctgt taacctgctc gaagacagcc acaacggaaa actatgtaga    180

ttaaaaggaa tagccccact acaattgggg aaatgtaaca tcgccggatg gctcttggga    240

aacccagaat gcgacccact gcttccagtg agatcatggt cctacattgt agaaacacca    300

aactctgaga atggaatatg ttatccagga gatttcatcg actatgagga gctgagggag    360

caattgagct cagtgtcatc attcgaaaga ttcgaaatat ttcccaaaga aagctcatgg    420

cccaaccaca acacaaacgg agtaacggca gcatgctccc atgaggggaa aagcagtttt    480

tacagaaatt tgctatggct gacggagaag gagggctcat acccaaagct gaaaaattct    540

tatgtgaaca aaaaagggaa agaagtcctt gtactgtggg gtattcatca cccgcctaac    600
```

agtaaggaac aacagaatat ctatcagaat gaaaatgctt atgtctctgt agtgacttca 660
aattataaca ggagatttac cccggaaata gcagaaagac ccaaagtaag agatcaagct 720
gggaggatga actattactg gaccttgcta aaacccggag acacaataat atttgaggca 780
aatggaaatc taatagcacc aatgtatgct ttcgcactga gtagaggctt tggggagaat 840
ctgtacttcc agtcaaacgc atcaatgcat gagtgtaaca cgaagtgtca aacaccgctc 900
ggagctataa acagcagtct cccttaccag aatatacacc cagtcacaat aggagagtgc 960
ccaaaatacg tcaggagtgc caaattgagg atggttacag gactaaggaa cactccgtcc 1020
attcaatcca gaggtctatt tggagccatt gccggtttta ttgaaggggg atggactgga 1080
atgatagatg gatggtatgg ttatcatcat cagaatgaac agggatcagg ctatgcagcg 1140
gatcaaaaaa gcacacaaaa tgccattaac gggattacaa acaaggtgaa cactgttatc 1200
gagaaaatga acattcaatt cacagctgtg ggtaaagaat tcaacaaatt agaaaaaagg 1260
atggaaaatt taaataaaaa agttgatgat ggatttctgg acatttggac atataatgca 1320
gaattgttag ttctactgga aaatgaaagg actctggatt tccatgactc aaatgtgaag 1380
aatctgtatg agaaagtaaa aagccaatta aagaataatg ccaaagaaat cggaaatgga 1440
tgttttgagt tctaccacaa gtgtgacaat gaatgcatgg aaagtgtaag aaatgggact 1500
tatgattatc ccaaatattc agaagagtca aagttgaaca gggaaaaggt agatggagtg 1560
aaattggaat caatggggat ctatcagatt ctggcgatct actcaactgt cgccagttca 1620
ctggtgcttt tggtctccct gggggcaatc agtttctgga tgtgttctaa tggatctttg 1680
cagtgcagaa tatgcatctg a 1701

<210> SEQ ID NO 54
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt taacctgctc gaagacagcc acaacggaaa actatgtaga 180
ttaaaaggaa tagccccact acaattgggg aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420
cccaaccaca acacaaacgg agtaacggca gcatgctccc atgaggggaa aagcagtttt 480
tacagaaatt tgctatggct gacggagaag gagggctcat acccaaagct gaaaaattct 540
tatgtgaaca aaaaagggaa agaagtcctt gtactgtggg gtattcatca cccgcctaac 600
agtaaggaac aacagaatat ctatcagaat gaaaatgctt atgtctctgt agtgacttca 660
aattataaca ggagatttac cccggaaata gcagaaagac ccaaagtaag agatcaagct 720
gggaggatga actattactg gaccttgcta aaacccggag acacaataat atttgaggca 780
aatggaaatc taatagcacc aatgtatgct ttcgcactga gtagaggctt tgggtccggc 840
atcatcgaga atctgtactt ccagagcacc tcaaacgcat caatgcatga gtgtaacacg 900

```
aagtgtcaaa caccgctcgg agctataaac agcagtctcc cttaccagaa tatacaccca    960
gtcacaatag gagagtgccc aaaatacgtc aggagtgcca aattgaggat ggttacagga   1020
ctaaggaaca ctccgtccat tcaatccaga ggtctatttg gagccattgc cggttttatt   1080
gaagggggat ggactggaat gatagatgga tggtatggtt atcatcatca gaatgaacag   1140
ggatcaggct atgcagcgga tcaaaaaagc acacaaaatg ccattaacgg gattacaaac   1200
aaggtgaaca ctgttatcga gaaaatgaac attcaattca cagctgtggg taaagaattc   1260
aacaaattag aaaaaaggat ggaaaattta aataaaaaag ttgatgatgg atttctggac   1320
atttggacat ataatgcaga attgttagtt ctactggaaa atgaaaggac tctggatttc   1380
catgactcaa atgtgaagaa tctgtatgag aaagtaaaaa gccaattaaa gaataatgcc   1440
aaagaaatcg gaaatggatg ttttgagttc taccacaagt gtgacaatga atgcatggaa   1500
agtgtaagaa atgggactta tgattatccc aaatattcag aagagtcaaa gttgaacagg   1560
gaaaaggtag atggagtgaa attggaatca atggggatct atcagattct ggcgatctac   1620
tcaactgtcg ccagttcact ggtgcttttg gtctccctgg gggcaatcag tttctggatg   1680
tgttctaatg gatctttgca gtgcagaata tgcatctga                          1719
```

<210> SEQ ID NO 55
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
atgaaggcaa acctactggt cctgttaagt gcacttgcag ctgcagatgc agacacaata     60
tgtataggct accatgcgaa caattcaacc gacactgttg acacagtact cgagaagaat    120
gtgacagtga cacactctgt taacctgctc gaagacagcc acaacggaaa actatgtaga    180
ttaaaaggaa tagccccact acaattgggg aaatgtaaca tcgccggatg gctcttggga    240
aacccagaat gcgacccact gcttccagtg agatcatggt cctacattgt agaaacacca    300
aactctgaga atggaatatg ttatccagga gatttcatcg actatgagga gctgagggag    360
caattgagct cagtgtcatc attcgaaaga ttcgaaatat ttcccaaaga aagctcatgg    420
cccaaccaca acacaaacgg agtaacggca gcatgctccc atgaggggaa aagcagtttt    480
tacagaaatt tgctatggct gacggagaag gagggctcat acccaaagct gaaaaattct    540
tatgtgaaca aaaaagggaa agaagtcctt gtactgtggg gtattcatca cccgcctaac    600
agtaaggaac aacagaatat ctatcagaat gaaaatgctt atgtctctgt agtgacttca    660
aattataaca ggagatttac cccggaaata gcagaaagac ccaaagtaag agatcaagct    720
gggaggatga actattactg gaccttgcta aaacccggag acacaataat atttgaggca    780
aatggaaatc taatagcacc aatgtatgct ttcgcactga gtagaggctt tgggtccggc    840
atcatcaccg agaatctgta cttccaggga tcaaacgcat caatgcatga gtgtaacacg    900
aagtgtcaaa caccgctcgg agctataaac agcagtctcc cttaccagaa tatacaccca    960
gtcacaatag gagagtgccc aaaatacgtc aggagtgcca aattgaggat ggttacagga   1020
ctaaggaaca ctccgtccat tcaatccaga ggtctatttg gagccattgc cggttttatt   1080
gaagggggat ggactggaat gatagatgga tggtatggtt atcatcatca gaatgaacag   1140
ggatcaggct atgcagcgga tcaaaaaagc acacaaaatg ccattaacgg gattacaaac   1200
```

aaggtgaaca ctgttatcga gaaaatgaac attcaattca cagctgtggg taaagaattc 1260
aacaaattag aaaaaaggat ggaaaattta aataaaaaag ttgatgatgg atttctggac 1320
atttggacat ataatgcaga attgttagtt ctactggaaa atgaaaggac tctggatttc 1380
catgactcaa atgtgaagaa tctgtatgag aaagtaaaaa gccaattaaa gaataatgcc 1440
aaagaaatcg gaaatggatg ttttgagttc taccacaagt gtgacaatga atgcatggaa 1500
agtgtaagaa atgggactta tgattatccc aaatattcag aagagtcaaa gttgaacagg 1560
gaaaaggtag atggagtgaa attggaatca atggggatct atcagattct ggcgatctac 1620
tcaactgtcg ccagttcact ggtgcttttg gtctccctgg gggcaatcag tttctggatg 1680
tgttctaatg gatctttgca gtgcagaata tgcatctga 1719

<210> SEQ ID NO 56
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt taacctgctc gaagacagcc acaacggaaa actatgtaga 180
ttaaaaggaa tagccccact acaattgggg aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420
cccaaccaca acacaaacgg agtaacggca gcatgctccc atgaggggaa aagcagtttt 480
tacagaaatt tgctatggct gacggagaag gagggctcat acccaaagct gaaaaattct 540
tatgtgaaca aaaaagggaa agaagtcctt gtactgtggg gtattcatca cccgcctaac 600
agtaaggaac aacagaatat ctatcagaat gaaaatgctt atgtctctgt agtgacttca 660
aattataaca ggagatttac cccggaaata gcagaaagac ccaaagtaag agatcaagct 720
gggaggatga actattactg gaccttgcta aaacccggag acacaataat atttgaggca 780
aatggaaatc taatagcacc aatgtatgct ttcgcactga gtagaggctt tgggtccggc 840
atcatcacct caaacgcaga gaatctgtac ttccagagct caatgcatga gtgtaacacg 900
aagtgtcaaa caccgctcgg agctataaac agcagtctcc cttaccagaa tatacaccca 960
gtcacaatag gagagtgccc aaaatacgtc aggagtgcca aattgaggat ggttacagga 1020
ctaaggaaca ctccgtccat tcaatccaga ggtctatttg gagccattgc cggttttatt 1080
gaagggggat ggactggaat gatagatgga tggtatggtt atcatcatca gaatgaacag 1140
ggatcaggct atgcagcgga tcaaaaaagc acacaaaatg ccattaacgg gattacaaac 1200
aaggtgaaca ctgttatcga gaaaatgaac attcaattca cagctgtggg taaagaattc 1260
aacaaattag aaaaaaggat ggaaaattta aataaaaaag ttgatgatgg atttctggac 1320
atttggacat ataatgcaga attgttagtt ctactggaaa atgaaaggac tctggatttc 1380
catgactcaa atgtgaagaa tctgtatgag aaagtaaaaa gccaattaaa gaataatgcc 1440
aaagaaatcg gaaatggatg ttttgagttc taccacaagt gtgacaatga atgcatggaa 1500

```
agtgtaagaa atgggactta tgattatccc aaatattcag aagagtcaaa gttgaacagg   1560

gaaaaggtag atggagtgaa attggaatca atggggatct atcagattct ggcgatctac   1620

tcaactgtcg ccagttcact ggtgcttttg gtctccctgg gggcaatcag tttctggatg   1680

tgttctaatg gatctttgca gtgcagaata tgcatctga                          1719
```

<210> SEQ ID NO 57
<211> LENGTH: 1695
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
atgaaggcaa acctactggt cctgttaagt gcacttgcag ctgcagatgc agacacaata     60

tgtataggct accatgcgaa caattcaacc gacactgttg acacagtact cgagaagaat    120

gtgacagtga cacactctgt taacctgctc gaagacagcc acaacggaaa actatgtaga    180

ttaaaaggag agaatctgta cttccaggga aaatgtaaca tcgccggatg gctcttggga    240

aacccagaat gcgacccact gcttccagtg agatcatggt cctacattgt agaaacacca    300

aactctgaga atggaatatg ttatccagga gatttcatcg actatgagga gctgagggag    360

caattgagct cagtgtcatc attcgaaaga ttcgaaatat ttcccaaaga aagctcatgg    420

cccaaccaca acacaaacgg agtaacggca gcatgctccc atgaggggaa aagcagtttt    480

tacagaaatt tgctatggct gacggagaag gagggctcat acccaaagct gaaaaattct    540

tatgtgaaca aaaaagggaa agaagtcctt gtactgtggg gtattcatca cccgcctaac    600

agtaaggaac aacagaatat ctatcagaat gaaaatgctt atgtctctgt agtgacttca    660

aattataaca ggagatttac cccggaaata gcagaaagac ccaaagtaag agatcaagct    720

gggaggatga actattactg gaccttgcta aaacccggag acacaataat atttgaggca    780

aatggaaatc taatagcacc aatgtatgct ttcgcactga gtagaggctt tggggagaat    840

ctgtacttcc agtcaaacgc atcaatgcat gagtgtaaca cgaagtgtca aacaccgctc    900

ggagctataa acagcagtct cccttaccag aatatacacc cagtcacaat aggagagtgc    960

ccaaaatacg tcaggagtgc caaattgagg atggttacag gactaaggaa cactccgtcc   1020

attcaatcca gaggtctatt tggagccatt gccggtttta ttgaaggggg atggactgga   1080

atgatagatg gatggtatgg ttatcatcat cagaatgaac agggatcagg ctatgcagcg   1140

gatcaaaaaa gcacacaaaa tgccattaac gggattacaa acaaggtgaa cactgttatc   1200

gagaaaatga acattcaatt cacagctgtg ggtaaagaat tcaacaaatt agaaaaaagg   1260

atggaaaatt taaataaaaa agttgatgat ggatttctgg acatttggac atataatgca   1320

gaattgttag ttctactgga aaatgaaagg actctggatt tccatgactc aaatgtgaag   1380

aatctgtatg agaaagtaaa aagccaatta aagaataatg ccaaagaaat cggaaatgga   1440

tgttttgagt tctaccacaa gtgtgacaat gaatgcatgg aaagtgtaag aaatgggact   1500

tatgattatc ccaaatattc agaagagtca aagttgaaca gggaaaaggt agatggagtg   1560

cgttctctgg ttccgcgtgg ttctccgggt tctggttaca tcccggaagc tccgcgtgac   1620

ggtcaggctt acgttcgtaa agacggtgaa tgggttctgc tgtctacctt cctgcaccac   1680

caccaccacc actga                                                    1695
```

<210> SEQ ID NO 58
<211> LENGTH: 1713
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 58
atgaaggcaa acctactggt cctgttaagt gcacttgcag ctgcagatgc agacacaata 60
tgtataggct accatgcgaa caattcaacc gacactgttg acacagtact cgagaagaat 120
gtgacagtga cacactctgt taacctgctc gaagacagcc acaacggaaa actatgtaga 180
ttaaaaggag agaatctgta cttccaggga aaatgtaaca tcgccggatg gctcttggga 240
aacccagaat gcgacccact gcttccagtg agatcatggt cctacattgt agaaacacca 300
aactctgaga atggaatatg ttatccagga gatttcatcg actatgagga gctgagggag 360
caattgagct cagtgtcatc attcgaaaga ttcgaaatat ttcccaaaga aagctcatgg 420
cccaaccaca acacaaacgg agtaacggca gcatgctccc atgaggggaa aagcagtttt 480
tacagaaatt tgctatggct gacggagaag gagggctcat acccaaagct gaaaaattct 540
tatgtgaaca aaaaagggaa agaagtcctt gtactgtggg gtattcatca cccgcctaac 600
agtaaggaac aacagaatat ctatcagaat gaaaatgctt atgtctctgt agtgacttca 660
aattataaca ggagatttac cccggaaata gcagaaagac ccaaagtaag agatcaagct 720
gggaggatga actattactg gaccttgcta aaacccggag acacaataat atttgaggca 780
aatggaaatc taatagcacc aatgtatgct ttcgcactga gtagaggctt tgggtccggc 840
atcatcgaga atctgtactt ccagagcacc tcaaacgcat caatgcatga gtgtaacacg 900
aagtgtcaaa caccgctcgg agctataaac agcagtctcc cttaccagaa tatacaccca 960
gtcacaatag gagagtgccc aaaatacgtc aggagtgcca aattgaggat ggttacagga 1020
ctaaggaaca ctccgtccat tcaatccaga ggtctatttg gagccattgc cggttttatt 1080
gaagggggat ggactggaat gatagatgga tggtatggtt atcatcatca gaatgaacag 1140
ggatcaggct atgcagcgga tcaaaaaagc acacaaaatg ccattaacgg gattacaaac 1200
aaggtgaaca ctgttatcga gaaaatgaac attcaattca cagctgtggg taaagaattc 1260
aacaaattag aaaaaaggat ggaaaattta aataaaaaag ttgatgatgg atttctggac 1320
atttggacat ataatgcaga attgttagtt ctactggaaa atgaaaggac tctggatttc 1380
catgactcaa atgtgaagaa tctgtatgag aaagtaaaaa gccaattaaa gaataatgcc 1440
aaagaaatcg gaaatggatg ttttgagttc taccacaagt gtgacaatga atgcatggaa 1500
agtgtaagaa atgggactta tgattatccc aaatattcag aagagtcaaa gttgaacagg 1560
gaaaaggtag atggagtgcg ttctctggtt ccgcgtggtt ctccgggttc tggttacatc 1620
ccggaagctc cgcgtgacgg tcaggcttac gttcgtaaag acggtgaatg ggttctgctg 1680
tctaccttcc tgcaccacca ccaccaccac tga 1713

<210> SEQ ID NO 59
<211> LENGTH: 1713
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 59

```
atgaaggcaa acctactggt cctgttaagt gcacttgcag ctgcagatgc agacacaata     60

tgtataggct accatgcgaa caattcaacc gacactgttg acacagtact cgagaagaat    120

gtgacagtga cacactctgt taacctgctc gaagacagcc acaacggaaa actatgtaga    180

ttaaaaggag agaatctgta cttccaggga aaatgtaaca tcgccggatg gctcttggga    240

aacccagaat gcgacccact gcttccagtg agatcatggt cctacattgt agaaacacca    300

aactctgaga atggaatatg ttatccagga gatttcatcg actatgagga gctgagggag    360

caattgagct cagtgtcatc attcgaaaga ttcgaaatat ttcccaaaga aagctcatgg    420

cccaaccaca acacaaacgg agtaacggca gcatgctccc atgaggggaa aagcagtttt    480

tacagaaatt tgctatggct gacggagaag gagggctcat acccaaagct gaaaaattct    540

tatgtgaaca aaaaagggaa agaagtcctt gtactgtggg gtattcatca cccgcctaac    600

agtaaggaac aacagaatat ctatcagaat gaaaatgctt atgtctctgt agtgacttca    660

aattataaca ggagatttac cccggaaata gcagaaagac ccaaagtaag agatcaagct    720

gggaggatga actattactg gaccttgcta aaacccggag acacaataat atttgaggca    780

aatggaaatc taatagcacc aatgtatgct ttcgcactga gtagaggctt tgggtccggc    840

atcatcacct caaacgcaga gaatctgtac ttccagagct caatgcatga gtgtaacacg    900

aagtgtcaaa caccgctcgg agctataaac agcagtctcc cttaccagaa tatacaccca    960

gtcacaatag gagagtgccc aaaatacgtc aggagtgcca aattgaggat ggttacagga   1020

ctaaggaaca ctccgtccat tcaatccaga ggtctatttg gagccattgc cggtttttatt   1080

gaagggggat ggactggaat gatagatgga tggtatggtt atcatcatca gaatgaacag   1140

ggatcaggct atgcagcgga tcaaaaaagc acacaaaatg ccattaacgg gattacaaac   1200

aaggtgaaca ctgttatcga gaaaatgaac attcaattca cagctgtggg taaagaattc   1260

aacaaattag aaaaaaggat ggaaaattta aataaaaaag ttgatgatgg atttctggac   1320

atttggacat ataatgcaga attgttagtt ctactggaaa atgaaaggac tctggatttc   1380

catgactcaa atgtgaagaa tctgtatgag aaagtaaaaa gccaattaaa gaataatgcc   1440

aaagaaatcg gaaatggatg ttttgagttc taccacaagt gtgacaatga atgcatggaa   1500

agtgtaagaa atgggactta tgattatccc aaatattcag aagagtcaaa gttgaacagg   1560

gaaaaggtag atggagtgcg ttctctggtt ccgcgtggtt ctccgggttc tggttacatc   1620

ccggaagctc cgcgtgacgg tcaggcttac gttcgtaaag acggtgaatg ggttctgctg   1680

tctaccttcc tgcaccacca ccaccaccac tga                                1713
```

<210> SEQ ID NO 60
<211> LENGTH: 1734
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

```
atgaaggcta acctgctggt gctgctgagc gccctggctg ccgctgatgc cgataccatc     60

tgcatcggct accacgccaa caacagcacc gacaccgtgg ataccgtgct ggaaaagaac    120

gtgaccgtga cccacagcgt ggaaaacctg tattttcaag gcaatctgct ggaagatagc    180

cacaacggca agctgtgccg gctgaaggga atcgcccctc tgcagctggg caagtgcaat    240

atcgccggct ggctgctggg caaccccgag tgtgatcctc tgctgcctgt gcggagctgg    300
```

```
tcctacatcg tggaaacccc caacagcgag aacggcatct gctaccccgg cgacttcatc    360
gactacgagg aactgcgcga gcagctgagc agcgtgtcca gcttcgaaag attcgagatc    420
ttccccaaag agagcagctg gcccaaccac aacaccaacg gcgtgacagc cgcctgtagc    480
cacgagggca agagcagctt ctaccggaac ctgctgtggc tgaccgagaa agagggcagc    540
taccccaagc tgaagaacag ctacgtgaac aagaaaggca aagaggtgct ggtgctgtgg    600
ggcatccacc acccccccaa ctctaaagag cagcagaaca tctaccagaa cgagaacgcc    660
tacgtgtccg tcgtgaccag caactacaac cggcggttca cccccgagat cgccgagagg    720
cctaaagtgc gggatcaggc cggcagaatg aactactact ggaccctgct gaagcccggc    780
gacaccatca tcttcgaggc caacggcaac ctgatcgccc ctatgtacgc cttcgccctg    840
agcagaggct tcggcagcgg catcatcacc agcaacgcca gcatgcacga gtgcgagaac    900
ctgtacttcc aagggaacac caagtgccag accccgctcg gagctataaa cagcagtctc    960
ccttaccaga atatacaccc agtcacaata ggagagtgcc caaaatacgt caggagtgcc   1020
aaattgagga tggttacagg actaaggaac actccgtcca ttcaatccag aggtctattt   1080
ggagccattg ccggttttat tgaagggggga tggactggaa tgatagatgg atggtatggt   1140
tatcatcatc agaatgaaca gggatcaggc tatgcagcgg atcaaaaaag cacacaaaat   1200
gccattaacg ggattacaaa caaggtgaac actgttatcg agaaaatgaa cattcaattc   1260
acagctgtgg gtaaagaatt caacaaatta gaaaaaagga tggaaaattt aaataaaaaa   1320
gttgatgatg gatttctgga catttggaca tataatgcag aattgttagt tctactggaa   1380
aatgaaagga ctctggattt ccatgactca aatgtgaaga atctgtatga gaaagtaaaa   1440
agccaattaa agaataatgc caaagaaatc ggaaatggat gttttgagtt ctaccacaag   1500
tgtgacaatg aatgcatgga aagtgtaaga aatgggactt atgattatcc caaatattca   1560
gaagagtcaa agttgaacag ggaaaaggta gatggagtgc gttctctggt tccgcgtggt   1620
tctccgggtt ctggttacat cccggaagct ccgcgtgacg gtcaggctta cgttcgtaaa   1680
gacggtgaat gggttctgct gtctaccttc ctgcaccacc accaccacca ctga         1734
```

<210> SEQ ID NO 61
<211> LENGTH: 1734
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
atgaaggcta acctgctggt gctgctgagc gccctggctg ccgctgatgc cgataccatc     60
tgcatcggct accacgccaa caacagcacc gacaccgtgg ataccgtgct ggaaaagaac    120
gtgaccgtga cccacagcgt ggaaaacctg tattttcaag gcaatctgct ggaagatagc    180
cacaacggca agctgtgccg gctgaaggga atcgcccctc tgcagctggg caagtgcaat    240
atcgccggct ggctgctggg caaccccgag tgtgatcctc tgctgcctgt gcggagctgg    300
tcctacatcg tggaaacccc caacagcgag aacggcatct gctaccccgg cgacttcatc    360
gactacgagg aactgcgcga gcagctgagc agcgtgtcca gcttcgaaag attcgagatc    420
ttccccaaag agagcagctg gcccaaccac aacaccaacg gcgtgacagc cgcctgtagc    480
cacgagggca agagcagctt ctaccggaac ctgctgtggc tgaccgagaa agagggcagc    540
taccccaagc tgaagaacag ctacgtgaac aagaaaggca aagaggtgct ggtgctgtgg    600
```

```
ggcatccacc acccccccaa ctctaaagag cagcagaaca tctaccagaa cgagaacgcc    660

tacgtgtccg tcgtgaccag caactacaac cggcggttca cccccgagat cgccgagagg    720

cctaaagtgc gggatcaggc cggcagaatg aactactact ggaccctgct gaagcccggc    780

gacaccatca tcttcgaggc caacggcaac ctgatcgccc ctatgtacgc cttcgccctg    840

agcagaggct tcggcagcgg catcatcacc agcaacgcca gcatgcacga gtgcgagaac    900

ctgtacttcc aaagcaacac caagtgccag accccgctcg gagctataaa cagcagtctc    960

ccttaccaga atatacaccc agtcacaata ggagagtgcc caaaatacgt caggagtgcc   1020

aaattgagga tggttacagg actaaggaac actccgtcca ttcaatccag aggtctattt   1080

ggagccattg ccggttttat tgaagggggga tggactggaa tgatagatgg atggtatggt   1140

tatcatcatc agaatgaaca gggatcaggc tatgcagcgg atcaaaaaag cacacaaaat   1200

gccattaacg ggattacaaa caaggtgaac actgttatcg agaaaatgaa cattcaattc   1260

acagctgtgg gtaaagaatt caacaaatta gaaaaaagga tggaaaattt aaataaaaaa   1320

gttgatgatg gatttctgga catttggaca tataatgcag aattgttagt tctactggaa   1380

aatgaaagga ctctggattt ccatgactca aatgtgaaga atctgtatga gaaagtaaaa   1440

agccaattaa agaataatgc caaagaaatc ggaaatggat gttttgagtt ctaccacaag   1500

tgtgacaatg aatgcatgga aagtgtaaga aatgggactt atgattatcc caaatattca   1560

gaagagtcaa agttgaacag ggaaaaggta gatggagtgc gttctctggt tccgcgtggt   1620

tctccgggtt ctggttacat cccggaagct ccgcgtgacg gtcaggctta cgttcgtaaa   1680

gacggtgaat gggttctgct gtctaccttc ctgcaccacc accaccacca ctga         1734
```

<210> SEQ ID NO 62
<211> LENGTH: 1713
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

```
atgaaggcta acctgctggt gctgctgagc gccctggctg ccgctgatgc cgataccatc     60

tgcatcggct accacgccaa caacagcacc gacaccgtgg ataccgtgct ggaaaagaac    120

gtgaccgtga cccacagcgt gaacctgctg gaagatagcc acaacggcaa gctgtgccgg    180

ctgaagggcg agaacctgta ttttcaaggc aagtgcaata tcgccggctg gctgctgggc    240

aaccccgagt gtgatcctct gctgcctgtg cggagctggt cctacatcgt ggaaaccccc    300

aacagcgaga acggcatctg ctaccccggc gacttcatcg actacgagga actgcgcgag    360

cagctgagca gcgtgtccag cttcgagaga ttcgagatct tccccaaaga gagcagctgg    420

cccaaccaca acaccaacgg cgtgacagcc gcctgtagcc acgagggcaa gagcagcttc    480

tacagaaacc tgctgtggct gaccgagaaa gagggcagct accccaagct gaagaacagc    540

tacgtgaaca agaaaggcaa agaggtgctg gtgctgtggg gcatccacca cccccccaac    600

tctaaagagc agcagaacat ctaccagaac gagaacgcct acgtgtccgt cgtgaccagc    660

aactacaacc ggcggttcac ccccgagatc gccgagaggc ctaaagtgcg ggatcaggcc    720

ggcagaatga actactactg gaccctgctg aagcccggcg acaccatcat cttcgaggcc    780

aacggcaacc tgatcgcccc tatgtacgcc ttcgccctga gcagaggctt cggcagcggc    840

atcatcaccg aaaacctgta cttccaagga tccaacgcca gcatgcacga gtgcaacacc    900
```

-continued

```
aagtgccaga ccccgctcgg agctataaac agcagtctcc cttaccagaa tatacaccca    960
gtcacaatag gagagtgccc aaaatacgtc aggagtgcca aattgaggat ggttacagga   1020
ctaaggaaca ctccgtccat tcaatccaga ggtctatttg gagccattgc cggttttatt   1080
gaagggggat ggactggaat gatagatgga tggtatggtt atcatcatca gaatgaacag   1140
ggatcaggct atgcagcgga tcaaaaaagc acacaaaatg ccattaacgg gattacaaac   1200
aaggtgaaca ctgttatcga gaaaatgaac attcaattca cagctgtggg taaagaattc   1260
aacaaattag aaaaaaggat ggaaaattta aataaaaaag ttgatgatgg atttctggac   1320
atttggacat ataatgcaga attgttagtt ctactggaaa atgaaaggac tctggatttc   1380
catgactcaa atgtgaagaa tctgtatgag aaagtaaaaa gccaattaaa gaataatgcc   1440
aaagaaatcg gaaatggatg ttttgagttc taccacaagt gtgacaatga atgcatggaa   1500
agtgtaagaa atgggactta tgattatccc aaatattcag aagagtcaaa gttgaacagg   1560
gaaaaggtag atggagtgcg ttctctggtt ccgcgtggtt ctccgggttc tggttacatc   1620
ccggaagctc cgcgtgacgg tcaggcttac gttcgtaaag acggtgaatg ggttctgctg   1680
tctaccttcc tgcaccacca ccaccaccac tga                                1713
```

<210> SEQ ID NO 63
<211> LENGTH: 1698
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
atgaaggcca acctgctggt gctgctgtct gccctggctg ccgccgatgc cgataccatc     60
tgtatcggct accacgccaa caacagcacc gacaccgtgg ataccgtgct ggaaaagaac    120
gtgaccgtga cccacagcgt gaacctgctg gaagatagcc acaacggcaa gctgtgccgg    180
ctgaagggaa tcgcccctct gcagctgggc aagtgcaata tcgccggctg gctgctgggc    240
aaccccgagt gtgatcctct gctgcctgtg cggagctggt cctacatcgt ggaaaccccc    300
aacagcgaga acggcatctg ctaccccggc gacttcatcg actacgagga actgcgcgag    360
cagctgagca gcgtgtccag cttcgagaga ttcgagatct tccccaaaga gagcagctgg    420
cccaaccaca acaccaacgg cgtgacagcc gcctgtagcc acgagggcaa gagcagcttc    480
tacagaaacc tgctgtggct gaccgagaaa gagggcagct accccaagct gaagaacagc    540
tacgtgaaca agaaaggcaa agaggtgctg gtgctgtggg gcatccacca cccccccaac    600
tctaaagagc agcagaacat ctaccagaac gagaacgcct acgtgtccgt cgtgaccagc    660
aactacaacc ggcggttcac ccccgagatc gccgagaggc ctaaagtgcg ggatcaggcc    720
ggcagaatga actactactg gaccctgctg aagcccggcg acaccatcat cttcgaggcc    780
aacggcaacc tgatcgcccc tatgtacgcc ttcgccctga gcagaggctt cggcagcggc    840
atcatcacca gcaacgccag catgcacgag tgcaacacca agtgccagac cccccctgggc    900
gccatcaata gcagcctgcc ctaccagaat atccaccccg tgaccatcgg cgagtgcccc    960
aaatacgtgc ggagcgccaa gctgcggatg gtcaccggcc tgagaaacac ccccagcatc   1020
cagagcaggg gcctgtttgg agccattgcc ggctttatcg agggcggctg gaccggcatg   1080
atcgacgggt ggtacggcta tcaccaccag aatgagcagg gcagcggcta cgccgccgat   1140
cagaagtcta cccagaacgc catcaacggc atcaccaaca aagtgaacac cgtgatcgag   1200
```

aagatgaaca tccagttcac cgccgtgggc aaagagttca acaagctgga aaaacggatg 1260
gaaaacctga acaaaaaggt ggacgacggc ttcctggaca tctggaccta caacgccgag 1320
ctgctggtgc tgctggaaaa cgagcggacc ctggacttcc acgacagcaa cgtgaagaac 1380
ctgtacgaga aagtgaagtc ccagctgaaa aacaacgcca aagagatcgg caacggctgc 1440
ttcgagttct accacaagtg cgacaacgag tgcatggaaa gcgtgcggaa cggcacctac 1500
gactacccta agtacagcga ggaaagcaag ctgaaccgcg aaaaagtgga cggcgtgaag 1560
ctggaatcca tgggcatcta tcagatcctg gccatctaca gcaccgtggc cagcagcctg 1620
gtgctgctgg tgtctctggg cgccatctca ttttggatgt gcagcaacgg ctccctgcag 1680
tgccggatct gcatctga 1698

<210> SEQ ID NO 64
<211> LENGTH: 1698
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64
atgaaggcca acctgctggt gctgctgtct gccctggctg ccgctgatgc cgacaccatc 60
tgtatcggct accacgccaa caactccacc gacaccgtgg ataccgtgct ggaaaagaac 120
gtgaccgtga cccactccgt gaatctgctg gaagattccc acaacggcaa gctgtgccgg 180
ctgaagggaa tcgcccctct gcagctgggc aagtgcaata tcgctggctg gctgctgggc 240
aaccccgagt gtgatcctct gctgcctgtg cggtcctggt cctacatcgt ggaaaccccc 300
aactccgaga acggcatctg ctaccccggc gacttcatcg actacgagga actgcgcgag 360
cagctgtcct ccgtgtccag cttcgagaga ttcgagatct tccccaaaga gtcctcctgg 420
cccaaccaca acaccaacgg cgtgaccgcc gcctgttctc acgagggcaa gagcagcttc 480
taccggaacc tgctgtggct gaccgagaaa gagggctcct accccaagct gaagaactcc 540
tacgtgaaca agaaaggcaa agaggtgctg gtgctgtggg gcatccacca ccccccctaac 600 tccaaagagc agcagaacat ctaccagaac gagaatgcct acgtgtccgt cgtgacctcc 660
aactacaacc ggcggttcac ccccgagatc gccgagaggc ctaaagtgcg ggatcaggcc 720
ggcagaatga actactactg gaccctgctg aagcccggcg ataccatcat cttcgaggcc 780
aacggcaacc tgatcgcccc tatgtacgcc ttcgccctgt ccagaggctt cggctccggc 840
atcatcacct ccaacgcctc catgcacgag tgcaacacca agtgccagac cccccctgggc 900 gccatcaaca gctccctgcc ttaccagaac atccaccccg tgaccatcgg cgagtgcccc 960
aaatatgtgc ggagcgccaa gctgcggatg gtcaccggcc tgagaaacac cccctccatc 1020
cagtctagag gcctgttcgg cgctatcgcc ggctttatcg agggcggctg gaccggcatg 1080
atcgacgggt ggtacggcta ccatcaccag aatgagcagg gctccggcta cgccgccgac 1140
cagaagtcta cccagaacgc catcaatggc atcaccaaca aagtgaacac cgtgatcgag 1200
aagatgaaca tccagttcac cgccgtgggc aaagagttca acaagctgga aaaacggatg 1260
gaaaacctga acaaaaaggt ggacgacggc ttcctggaca tctggaccta caacgccgag 1320
ctgctggtgc tgctggaaaa cgagcggacc ctggacttcc acgactccaa cgtgaagaac 1380
ctgtacgaga aagtgaagtc ccagctgaaa aacaacgcca aagagatcgg caacggctgc 1440
ttcgagttct accacaagtg cgacaacgag tgcatggaat ccgtgcggaa cggcacctac 1500
gactacccta agtactccga ggaaagcaag ctgaaccgcg aaaaagtgga cggcgtgaag 1560
ctggaatcca tgggcatcta tcagatcctg gccatctact ccaccgtggc ctccagcctg 1620
gtgctgctgg tgtctctggg cgccatctct ttctggatgt gctccaacgg ctctctgcag 1680
tgccggatct gcatctga 1698

<210> SEQ ID NO 65
<211> LENGTH: 1698
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 65
atgaaggcta accttctggt gcttctgtct gctcttgctg ctgctgatgc tgataccatc 60
tgcattggtt accacgctaa caacagcacc gatactgtgg ataccgtgct tgagaagaat 120
gtgaccgtga cccactctgt gaacctgctt gaggattctc acaacggtaa gctgtgcagg 180
cttaagggta ttgctccact gcagcttggt aagtgcaata tcgctggttg gcttctgggt 240
aaccctgagt gtgatccttt gcttcctgtg aggtcctggt cctacattgt ggaaactcct 300
aacagcgaga acggtatctg ctaccctggt gatttcatcg attacgagga actgagagag 360
cagctgtcca gcgtttcatc ttttgagagg ttcgagatct tccctaaaga gtcctcttgg 420
cctaaccaca acactaacgg tgttaccgct gcttgctctc acgagggtaa gagcagcttc 480
tataggaacc ttctttggct gaccgagaaa gagggaagct accctaagct gaagaacagc 540
tacgtgaaca agaagggtaa agaggttctg gttctttggg gtatccacca ccctccaaac 600
tctaaagaac agcagaacat ctaccagaac gagaacgctt acgtgagcgt ggtgaccagc 660
aattacaaca gaaggttcac ccctgagatc gctgagaggc ctaaggttag agatcaggct 720
ggtaggatga actactactg gacccttctg aagcctggtg ataccattat cttcgaggct 780
aacggtaacc tgatcgctcc tatgtacgct ttcgctctgt ctaggggttt cggttctggt 840
atcatcacca gcaacgcttc tatgcacgag tgcaatacca agtgccagac tcctcttggt 900
gctatcaaca gctctctgcc ttaccagaac attcaccctg tgaccattgg tgagtgccct 960
aagtatgtga ggtctgctaa gttgaggatg gtgaccggtc ttaggaacac cccttctatc 1020
cagtctaggg gacttttcgg agctatcgct ggattcattg agggaggttg gaccggtatg 1080
atcgatggtt ggtacggtta ccaccatcag aacgaacagg gttctggata cgctgctgat 1140
caaaagtcta cccagaacgc tatcaacgga atcaccaaca aggtgaacac cgtgatcgag 1200
aagatgaaca tccagttcac cgctgtggga aaagagttca acaagttgga gaagaggatg 1260
gaaaacctta acaagaaagt ggatgatggt ttcctggata tctggaccta caacgctgag 1320
ctgcttgtgc ttcttgagaa cgagaggacc ctggatttcc acgatagcaa cgtgaagaac 1380
ctgtacgaga aggtgaagtc ccagcttaag aacaacgcta aagagatcgg taacggttgc 1440
ttcgagttct accacaagtg cgataacgag tgcatggaaa gcgtgaggaa cggaacctac 1500
gattacccta agtacagcga agagtccaag ctgaacaggg aaaaagttga tggtgtgaag 1560
cttgagagca tgggaatcta tcagatcctg gctatctaca gcaccgtggc ttctagcctt 1620
gtgcttttgg ttagcctggg tgctatctcc ttctggatgt gctctaacgg ttctctgcag 1680
tgcaggatct gcatctag 1698

<210> SEQ ID NO 66

<211> LENGTH: 1698
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 66
atgaaggcta acttgttggt tttgttgtcc gctttggctg ctgctgatgc tgacactatc 60
tgtattggtt accacgctaa caactccact gacactgttg acacagtttt ggagaagaac 120
gttactgtta ctcactccgt taatttgttg gaggactccc acaacggaaa gttgtgtaga 180
ttgaagggta tcgctccatt gcagttggga aagtgtaaca ttgctggttg gttgttgggt 240
aacccagagt gtgatccttt gttgccagtt agatcctggt cctacatcgt tgagactcca 300
aactccgaga acggtatctg ttacccaggt gacttcatcg actacgaaga gttgagagag 360
cagttgtcct ccgtttcctc attcgagaga ttcgagatct tcccaaaaga gtcctcttgg 420
ccaaaccaca acactaacgg tgttactgct gcttgttccc acgagggaaa gtcctcattc 480
tacagaaact tgttgtggtt gactgagaaa gagggttcct acccaaagtt gaagaactcc 540
tacgttaaca agaagggtaa agaggttttg gttttgtggg gtatccacca cccaccaaac 600
tccaaagagc aacagaacat ctaccagaac gagaacgctt acgtttctgt tgttacttcc 660
aactacaaca gaagattcac tccagagatc gctgaaagac caaaggttag agatcaggct 720
ggtagaatga actactactg gactttgttg aagccaggtg acacaatcat cttcgaggct 780
aacggtaact tgatcgctcc aatgtacgct ttcgctttgt ccagaggttt cggttccggt 840
atcatcactt ctaacgcttc catgcacgag tgtaacacta agtgtcagac tccattgggt 900
gctatcaact cctccttgcc ataccaaaac atccacccag ttactatcgg tgagtgtcct 960
aagtacgtta gatccgctaa gttgagaatg gttactggtt tgagaaacac tccatccatc 1020
cagtctagag gtttgttcgg tgctatcgct ggtttcattg aaggtggttg gactggtatg 1080
atcgacggtt ggtacggtta ccaccaccaa aacgaacaag gttctggtta cgctgctgac 1140
caaaagtcca ctcagaacgc tatcaacggt atcactaaca aggttaacac tgttatcgag 1200
aagatgaaca tccagttcac tgctgttggt aaagagttca acaagttgga aaagagaatg 1260
gaaaacttga acaagaaagt tgacgacggt ttcttggaca tctggactta caacgctgag 1320
ttgttggttt tgttggagaa cgagagaact ttggacttcc acgactccaa cgttaagaac 1380
ttgtacgaga aggttaagtc ccaattgaag aacaacgcta aagagatcgg taacggttgt 1440
ttcgagttct accacaagtg tgacaacgag tgtatggaat ccgttagaaa cggtacttac 1500
gactacccta agtactccga agagtccaag ttgaacagag aaaaggttga tggtgttaag 1560
ttggaatcca tgggtatcta ccaaatcttg gctatctact ctactgttgc ttcctccttg 1620
gttttgttgg tttccttggg tgctatctcc ttctggatgt gttccaacgg ttccttgcag 1680
tgtagaatct gtatctaa 1698

<210> SEQ ID NO 67
<211> LENGTH: 1698
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 67
atgaaggcca acttgttggt tttgttgtct gctttggctg ctgctgatgc tgatacaata 60

```
tgtattggtt accatgccaa caactctacc gatactgttg ataccgtttt ggaaaagaac    120

gttaccgtta cccattccgt caatttgttg gaagattccc ataacggtaa attgtgcaga    180

ttgaaaggta ttgccccatt gcaattgggt aaatgtaata ttgctggttg gttgttgggt    240

aacccagaat gtgatccatt attgccagtt agatcttggt cctacatcgt tgaaactcca    300

aattccgaaa atggtatttg ctacccaggt gatttcatcg actatgaaga attgagagaa    360

caattgtcct ccgtttcctc attcgaaaga ttcgaaatct tcccaaaaga atcctcttgg    420

ccaaaccata acactaatgg tgttactgct gcttgttccc atgaaggtaa aagttctttc    480

tacagaaact tgttgtggtt gaccgaaaaa gaaggttctt acccaaagtt gaagaactcc    540

tacgttaaca agaagggtaa agaagttttg gtcttgtggg gtattcatca tccaccaaac    600

tctaaagaac aacaaaacat ctaccaaaac gaaaacgcct acgtttctgt tgttacctct    660

aactacaaca gaagattcac cccagaaatt gctgaaagac caaaggttag agatcaagct    720

ggtagaatga attactactg gactttgttg aaaccaggtg acaccattat tttcgaagcc    780

aacggtaatt tgattgctcc aatgtatgct ttcgctttgt ctagaggttt tggttccggt    840

attattactt ccaacgcttc tatgcatgaa tgcaacacta agtgtcaaac tccattgggt    900

gctatcaatt catctttgcc ataccaaaac atccacccag ttactattgg tgaatgtcct    960

aagtatgtta gatccgccaa attgagaatg gttaccggtt tgagaaacac cccatctatt   1020

caatcaagag gtttgtttgg tgctattgcc ggttttattg aaggtggttg gactggtatg   1080

attgatggtt ggtatggtta ccaccatcaa aacgaacaag gttctggtta cgctgctgat   1140

caaaagtcta ctcaaaatgc cattaacggt attaccaaca aggttaacac cgtcatcgaa   1200

aagatgaaca ttcaattcac cgccgtcggt aaagaattca acaagttaga aaagagaatg   1260

gaaaacttga acaaaaaggt cgacgatggt ttcttggata tttggactta caacgccgaa   1320

ttattggtct tattggaaaa cgaaagaacc ttggatttcc acgattccaa cgttaagaac   1380

ttgtacgaaa aggttaagtc ccaattgaaa aacaacgcca aagaaattgg taacggttgc   1440

tttgaattct accacaagtg tgataacgaa tgcatggaat ctgttagaaa cggtacttac   1500

gattacccta agtactccga agaatccaag ttgaacagag aaaaagttga cggtgtcaag   1560

ttggaatcta tgggtatcta tcaaatcttg gccatctact ctactgttgc ctcttcatta   1620

gttttgttgg ttagtttggg tgccatctct ttttggatgt gttctaatgg ttccttgcaa   1680

tgtagaatct gtatttga                                                 1698
```

```
<210> SEQ ID NO 68
<211> LENGTH: 1698
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

atgaaggcta acctgctggt gctgctgtcc gctctggctg ctgctgacgc tgacaccatc     60

tgcatcggtt accacgctaa caactccacc gacaccgtgg acaccgtcct cgagaagaac    120

gtgaccgtga cccactccgt gaacctgctc gaggactccc acaacggcaa gctgtgccgc    180

ctgaagggta tcgctcctct gcagctgggc aagtgcaaca tcgctggatg gctgctgggc    240

aaccccgagt gcgaccctct gctgcctgtc cgttcctggt cctacatcgt ggaaaccccc    300

aactccgaga acggtatctg ctaccccggc gacttcatcg actacgagga actgcgcgag    360
```

```
cagctgtcct ccgtgtccag cttcgagcgt ttcgagatct tccccaagga atcctcctgg    420

cccaaccaca acaccaacgg tgtcaccgct gcttgctccc acgagggcaa gtcatccttc    480

taccgcaacc tgctgtggct gaccgagaag gaaggctcct accccaagct gaagaactcc    540

tacgtgaaca agaagggcaa ggaagtcctc gtcctctggg gtatccacca cccccctaac    600

tccaaggaac agcagaacat ctaccagaac gagaacgctt acgtgtccgt ggtcacctcc    660

aactacaacc gtcgtttcac ccccgagatc gctgagcgtc ctaaagtgcg cgaccaggct    720

ggccgtatga actactactg gaccctgctg aagcccggcg acaccatcat cttcgaggct    780

aacggcaacc tgatcgctcc tatgtacgct ttcgctctgt cccgtggttt cggttccggt    840

atcatcacct ctaacgcttc catgcacgag tgcaacacca agtgccagac ccccctgggt    900

gctatcaact ccagcctgcc ttaccagaac atccaccccg tgaccatcgg cgagtgccct    960

aaatacgtgc gttccgctaa gctgcgtatg gtcaccggcc tgcgtaacac cccctccatc   1020

cagtcccgtg gcctgttcgg tgctatcgct ggtttcatcg agggcggctg gaccggcatg   1080

atcgacggat ggtacggcta ccaccaccaa aacgagcagg gttccggtta cgctgctgac   1140

cagaagtcca cccagaacgc tatcaacggt atcaccaaca aagtgaacac cgtgatcgaa   1200

aagatgaaca tccagttcac cgccgtcggc aaggaattca acaagctcga gaagcgcatg   1260

gaaaacctca acaagaaggt ggacgacggc ttcctggaca tctggaccta caacgctgag   1320

ctgctggtcc tgttggagaa cgagcgtacc ctggacttcc acgactccaa cgtgaagaac   1380

ctgtacgaga aagtgaagtc ccagctcaag aacaacgcca aggaaatcgg caacggttgc   1440

ttcgagttct accacaagtg cgacaacgaa tgcatggaat ccgtgcgtaa cggcacctac   1500

gactacccta agtactccga ggaatctaag ctgaaccgcg agaaggtcga cggcgtgaag   1560

ctcgagtcca tgggcatcta ccaaatcctg gctatctact ctaccgtggc ttcctccctg   1620

gtgctcctgg tgtctctggg cgctatctcc ttctggatgt gctccaacgg ttccctgcag   1680

tgccgtatct gcatctaa                                                 1698
```

<210> SEQ ID NO 69
<211> LENGTH: 8
<212> TYPE: PRT
<213> ORGANISM: Unknown
<220> FEATURE:
<223> OTHER INFORMATION: Description of Unknown:
PreScission Protease recognition site peptide

<400> SEQUENCE: 69

```
Leu Glu Val Leu Phe Gln Gly Pro
1               5
```

<210> SEQ ID NO 70
<211> LENGTH: 7
<212> TYPE: PRT
<213> ORGANISM: Unknown
<220> FEATURE:
<221> NAME/KEY: source
<223> OTHER INFORMATION: /note="Description of Unknown:
TEV recognition site peptide"

<400> SEQUENCE: 70

```
Glu Asn Leu Tyr Phe Gln Gly
1               5
```

<210> SEQ ID NO 71
<211> LENGTH: 7

<212> TYPE: PRT
<213> ORGANISM: Unknown
<220> FEATURE:
<221> NAME/KEY: source
<223> OTHER INFORMATION: /note="Description of Unknown:
TEV recognition site peptide"

<400> SEQUENCE: 71

Glu Asn Leu Tyr Phe Gln Ser
1 5

<210> SEQ ID NO 72
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 72
cgttctctgg ttccgcgtgg ttctccgggt tctggttaca tcccggaagc tccgcgtgac 60
ggtcaggctt acgttcgtaa agacggtgaa tgggttctgc tgtctacctt cctgcaccac 120
caccaccacc actga 135

<210> SEQ ID NO 73
<211> LENGTH: 566
<212> TYPE: PRT
<213> ORGANISM: Influenza A virus

<400> SEQUENCE: 73

Met Lys Thr Ile Ile Ala Leu Ser Tyr Ile Phe Cys Leu Val Leu Gly
1 5 10 15

Gln Asp Phe Pro Gly Asn Asp Asn Ser Thr Ala Thr Leu Cys Leu Gly
20 25 30

His His Ala Val Pro Asn Gly Thr Leu Val Lys Thr Ile Thr Asn Asp
35 40 45

Gln Ile Glu Val Thr Asn Ala Thr Glu Leu Val Gln Ser Ser Ser Thr
50 55 60

Gly Lys Ile Cys Asn Asn Pro His Arg Ile Leu Asp Gly Ile Asp Cys
65 70 75 80

Thr Leu Ile Asp Ala Leu Leu Gly Asp Pro His Cys Asp Gly Phe Gln
85 90 95

Asn Glu Thr Trp Asp Leu Phe Val Glu Arg Ser Lys Ala Phe Ser Asn
100 105 110

Cys Tyr Pro Tyr Asp Val Pro Asp Tyr Ala Ser Leu Arg Ser Leu Val
115 120 125

Ala Ser Ser Gly Thr Leu Glu Phe Ile Ser Glu Gly Phe Thr Trp Thr
130 135 140

Gly Val Thr Gln Asn Gly Gly Ser Asn Ala Cys Lys Arg Gly Pro Asp
145 150 155 160

Ile Gly Phe Phe Ser Arg Leu Asn Trp Leu Tyr Lys Ser Gly Ser Thr
165 170 175

Tyr Pro Val Leu Asn Val Thr Met Pro Asn Asn Asp Asn Phe Asp Lys
180 185 190

Leu Tyr Ile Trp Gly Val His His Pro Ser Thr Asp Gln Glu Gln Thr
195 200 205

Ser Leu Tyr Val Gln Ala Ser Gly Arg Val Thr Val Ser Thr Lys Arg
210 215 220

Ser Gln Gln Thr Ile Ile Pro Asn Ile Gly Ser Arg Pro Trp Val Arg
225 230 235 240

Gly Leu Ser Ser Arg Ile Ser Ile Tyr Trp Thr Ile Val Lys Pro Gly
245 250 255

Asp Ile Leu Val Ile Asn Ser Asn Gly Asn Leu Ile Ala Pro Arg Gly
260 265 270

Tyr Phe Lys Met Arg Thr Gly Lys Ser Ser Ile Met Arg Ser Asp Ala
275 280 285

Pro Ile Gly Thr Cys Ile Ser Glu Cys Ile Thr Pro Asn Gly Ser Ile
290 295 300

Pro Asn Asp Lys Pro Phe Gln Asn Val Asn Lys Ile Thr Tyr Gly Ala
305 310 315 320

Cys Pro Lys Tyr Val Lys Gln Asn Thr Leu Lys Leu Ala Thr Gly Met
325 330 335

Arg Asn Val Pro Glu Lys Gln Thr Arg Gly Leu Phe Ser Ala Ile Ala
340 345 350

Gly Phe Ile Glu Asn Gly Trp Glu Gly Met Ile Asp Gly Trp Tyr Gly
355 360 365

Phe Arg His Gln Asn Ser Glu Gly Thr Gly Gln Ala Ala Asp Leu Lys
370 375 380

Ser Thr Gln Ala Ala Ile Asp Gln Ile Asn Gly Lys Leu Asn Arg Val
385 390 395 400

Ile Glu Lys Thr Asn Glu Lys Phe His Gln Ile Glu Lys Glu Phe Ser
405 410 415

Glu Val Glu Gly Arg Ile Gln Asp Leu Glu Lys Tyr Val Glu Asp Thr
420 425 430

Lys Ile Asp Leu Trp Ser Tyr Asn Ala Glu Leu Leu Val Ala Leu Glu
435 440 445

Asn Gln His Thr Ile Asp Leu Thr Asp Ser Glu Met Asn Lys Leu Phe
450 455 460

Glu Lys Thr Arg Arg Gln Leu Arg Glu Asn Ala Glu Asp Met Gly Asn
465 470 475 480

Gly Cys Phe Lys Ile Tyr His Lys Cys Asp Asn Ala Cys Ile Gly Ser
485 490 495

Ile Arg Asn Gly Thr Tyr Asp His Asp Val Tyr Arg Asp Glu Ala Leu
500 505 510

Asn Asn Arg Phe Gln Ile Lys Gly Val Glu Leu Lys Ser Gly Tyr Lys
515 520 525

Asp Trp Ile Leu Trp Ile Ser Phe Ala Ile Ser Cys Phe Leu Leu Cys
530 535 540

Val Val Leu Leu Gly Phe Ile Met Trp Ala Cys Gln Lys Gly Asn Ile
545 550 555 560

Arg Cys Asn Ile Cys Ile
565

<210> SEQ ID NO 74
<211> LENGTH: 566
<212> TYPE: PRT
<213> ORGANISM: Influenza A virus

<400> SEQUENCE: 74

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

```
His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Asn Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Glu Ser Gly Arg Val Thr Val Ser Thr Arg Arg
    210                 215                 220

Ser Gln Gln Ser Ile Ile Pro Asn Ile Gly Ser Arg Pro Trp Val Arg
225                 230                 235                 240

Gly Gln Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Ser Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445
```

```
Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565


<210> SEQ ID NO 75
<211> LENGTH: 566
<212> TYPE: PRT
<213> ORGANISM: Influenza A virus

<400> SEQUENCE: 75

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Ser Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Gln Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Ala Gln Asn Gly Thr Ser Ser Ala Cys Lys Arg Arg Ser Asn
145                 150                 155                 160

Asn Ser Phe Phe Ser Arg Leu Asn Trp Leu His Gln Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Ser Thr Asp Ser Asp Gln Ile
        195                 200                 205

Ser Ile Tyr Ala Gln Ala Ser Gly Arg Val Thr Val Ser Thr Lys Arg
    210                 215                 220

Ser Gln Gln Thr Val Ile Pro Asn Ile Gly Ser Ile Pro Trp Val Arg
225                 230                 235                 240

Gly Val Ser Ser Arg Ile Ser Ile Tyr Trp Thr Ile Val Lys Pro Gly
                245                 250                 255
```

```
Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565
```

<210> SEQ ID NO 76
<211> LENGTH: 566
<212> TYPE: PRT
<213> ORGANISM: Influenza A virus

<400> SEQUENCE: 76

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
```

-continued

```
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asn Trp Thr
    130                 135                 140

Gly Val Thr Gln Asn Gly Thr Ser Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480
```

```
Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 77
<211> LENGTH: 560
<212> TYPE: PRT
<213> ORGANISM: Influenza A virus

<400> SEQUENCE: 77

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
```

-continued

```
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Val Met Gly Leu
    530                 535                 540

Val Phe Ile Cys Val Lys Asn Gly Asn Met Arg Cys Thr Ile Cys Ile
545                 550                 555                 560


<210> SEQ ID NO 78
<211> LENGTH: 562
<212> TYPE: PRT
<213> ORGANISM: Influenza A virus

<400> SEQUENCE: 78

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95
```

-continued

```
Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
```

```
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile


<210> SEQ ID NO 79
<211> LENGTH: 568
<212> TYPE: PRT
<213> ORGANISM: Influenza A virus

<400> SEQUENCE: 79

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
```

```
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Ile Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565
```

<210> SEQ ID NO 80
<211> LENGTH: 563
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110
```

```
Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Arg Ser Leu Val Pro Arg Gly Ser Pro
        515                 520                 525

Gly Ser Gly Tyr Ile Pro Glu Ala Pro Arg Asp Gly Gln Ala Tyr Val
```

530 535 540

Arg Lys Asp Gly Glu Trp Val Leu Leu Ser Thr Phe Leu His His His
545 550 555 560

His His His

<210> SEQ ID NO 81
<211> LENGTH: 565
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Ser Ser Thr
50 55 60

Gly Lys Ile Cys Asn Asn Pro His Arg Ile Leu Asp Gly Ile Asp Cys
65 70 75 80

Thr Leu Ile Asp Ala Leu Leu Gly Asp Pro His Cys Asp Val Phe Gln
85 90 95

Asn Glu Thr Trp Asp Leu Phe Val Glu Arg Ser Lys Ala Phe Ser Asn
100 105 110

Cys Tyr Pro Tyr Asp Val Pro Asp Tyr Ala Ser Leu Arg Ser Leu Val
115 120 125

Ala Ser Ser Gly Thr Leu Glu Phe Ile Thr Glu Gly Phe Thr Trp Thr
130 135 140

Gly Val Thr Gln Asn Gly Gly Ser Asn Ala Cys Lys Arg Gly Pro Gly
145 150 155 160

Asn Gly Phe Phe Ser Arg Leu Asn Trp Leu Thr Lys Ser Gly Ser Thr
165 170 175

Tyr Pro Val Leu Asn Val Thr Met Pro Asn Asn Asp Asn Phe Asp Lys
180 185 190

Leu Tyr Ile Trp Gly Val His His Pro Ser Thr Asn Gln Glu Gln Thr
195 200 205

Ser Leu Tyr Val Gln Glu Ser Gly Arg Val Thr Val Ser Thr Arg Arg
210 215 220

Ser Gln Gln Ser Ile Ile Pro Asn Ile Gly Ser Arg Pro Trp Val Arg
225 230 235 240

Gly Gln Ser Ser Arg Ile Ser Ile Tyr Trp Thr Ile Val Lys Pro Gly
245 250 255

Asp Val Leu Val Ile Asn Ser Asn Gly Asn Leu Ile Ala Pro Arg Gly
260 265 270

Tyr Phe Lys Met Arg Thr Gly Lys Ser Ser Ile Met Ser Ser Asp Ala
275 280 285

Pro Ile Asp Thr Cys Ile Ser Glu Cys Ile Thr Pro Asn Gly Ser Ile
290 295 300

Pro Asn Asp Lys Pro Phe Gln Asn Val Asn Lys Ile Thr Tyr Gly Ala
305 310 315 320

Cys Pro Lys Tyr Val Lys Gln Asn Thr Leu Lys Leu Ala Thr Gly Met

```
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Arg Ser Leu Val Pro Arg Gly
        515                 520                 525

Ser Pro Gly Ser Gly Tyr Ile Pro Glu Ala Pro Arg Asp Gly Gln Ala
    530                 535                 540

Tyr Val Arg Lys Asp Gly Glu Trp Val Leu Leu Ser Thr Phe Leu His
545                 550                 555                 560

His His His His His
                565


<210> SEQ ID NO 82
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110
```

-continued

```
Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asn Trp Thr
    130                 135                 140

Gly Val Thr Gln Asn Gly Thr Ser Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Arg Ser Leu Val Pro Arg Gly
        515                 520                 525

Ser Pro Gly Ser Gly Tyr Ile Pro Glu Ala Pro Arg Asp Gly Gln Ala
```

530 535 540

Tyr Val Arg Lys Asp Gly Glu Trp Val Leu Leu Ser Thr Phe Leu His
545 550 555 560

His His His His His
565

<210> SEQ ID NO 83
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Met Glu Lys Ile Val Leu Leu Phe Ala Ile Val Ser Leu Val Lys Ser
1 5 10 15

Asp Gln Ile Cys Ile Gly Tyr His Ala Asn Asn Ser Thr Glu Gln Val
20 25 30

Asp Thr Ile Met Glu Lys Asn Val Thr Val Thr His Ala Gln Asp Ile
35 40 45

Leu Glu Lys Lys His Asn Gly Lys Leu Cys Asp Leu Asp Gly Val Lys
50 55 60

Pro Leu Ile Leu Arg Asp Cys Ser Val Ala Gly Trp Leu Leu Gly Asn
65 70 75 80

Pro Met Cys Asp Glu Phe Ile Asn Val Pro Glu Trp Ser Tyr Ile Val
85 90 95

Glu Lys Ala Asn Pro Val Asn Asp Leu Cys Tyr Pro Gly Asp Phe Asn
100 105 110

Asp Tyr Glu Glu Leu Lys His Leu Leu Ser Arg Ile Asn His Phe Glu
115 120 125

Lys Ile Gln Ile Ile Pro Lys Ser Ser Trp Ser Ser His Glu Ala Ser
130 135 140

Leu Gly Val Ser Ser Ala Cys Pro Tyr Gln Gly Lys Ser Ser Phe Phe
145 150 155 160

Arg Asn Val Val Trp Leu Ile Lys Lys Asn Ser Thr Tyr Pro Thr Ile
165 170 175

Lys Arg Ser Tyr Asn Asn Thr Asn Gln Glu Asp Leu Leu Val Leu Trp
180 185 190

Gly Ile His His Pro Asn Asp Ala Ala Glu Gln Thr Lys Leu Tyr Gln
195 200 205

Asn Pro Thr Thr Tyr Ile Ser Val Gly Thr Ser Thr Leu Asn Gln Arg
210 215 220

Leu Val Pro Arg Ile Ala Thr Arg Ser Lys Val Asn Gly Gln Ser Gly
225 230 235 240

Arg Met Glu Phe Phe Trp Thr Ile Leu Lys Pro Asn Asp Ala Ile Asn
245 250 255

Phe Glu Ser Asn Gly Asn Phe Ile Ala Pro Glu Tyr Ala Tyr Lys Ile
260 265 270

Val Lys Lys Gly Asp Ser Thr Ile Met Lys Ser Glu Leu Glu Tyr Gly
275 280 285

Asn Cys Asn Thr Lys Cys Gln Thr Pro Met Gly Ala Ile Asn Ser Ser
290 295 300

Met Pro Phe His Asn Ile His Pro Leu Thr Ile Gly Glu Cys Pro Lys
305 310 315 320

```
Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Arg Ser Leu Val Pro Arg
        515                 520                 525

Gly Ser Pro Gly Ser Gly Tyr Ile Pro Glu Ala Pro Arg Asp Gly Gln
    530                 535                 540

Ala Tyr Val Arg Lys Asp Gly Glu Trp Val Leu Leu Ser Thr Phe Leu
545                 550                 555                 560

His His His His His His
                565
```

<210> SEQ ID NO 84
<211> LENGTH: 559
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110
```

-continued

```
Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Arg Ser Leu Val Pro Arg Gly Ser Pro Gly Ser Gly Tyr
        515                 520                 525
```

```
Ile Pro Glu Ala Pro Arg Asp Gly Gln Ala Tyr Val Arg Lys Asp Gly
    530                 535                 540

Glu Trp Val Leu Leu Ser Thr Phe Leu His His His His His His
545                 550                 555


<210> SEQ ID NO 85
<211> LENGTH: 560
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335
```

```
Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Arg Ser Leu Val Pro Arg Gly Ser Pro Gly Ser Gly
        515                 520                 525

Tyr Ile Pro Glu Ala Pro Arg Asp Gly Gln Ala Tyr Val Arg Lys Asp
    530                 535                 540

Gly Glu Trp Val Leu Leu Ser Thr Phe Leu His His His His His His
545                 550                 555                 560
```

<210> SEQ ID NO 86
<211> LENGTH: 565
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 86

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
```

```
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Tyr Ile Gln Phe Thr Ala Val Gly Lys Glu Phe Asn Lys Leu
                405                 410                 415

Glu Lys Arg Met Glu Asn Leu Asn Lys Lys Val Asp Tyr Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560
```

Cys Arg Ile Cys Ile
565

<210> SEQ ID NO 87
<211> LENGTH: 565
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

Met Lys Ala Asn Leu Leu Val Leu Leu Ser Ala Leu Ala Ala Ala Asp
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Arg Leu Lys Gly Ile
50 55 60

Ala Pro Leu Gln Leu Gly Lys Cys Asn Ile Ala Gly Trp Leu Leu Gly
65 70 75 80

Asn Pro Glu Cys Asp Pro Leu Leu Pro Val Arg Ser Trp Ser Tyr Ile
85 90 95

Val Glu Thr Pro Asn Ser Glu Asn Gly Ile Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Pro Lys Glu Ser Ser Trp Pro Asn His Asn
130 135 140

Thr Asn Gly Val Thr Ala Ala Cys Ser His Glu Gly Lys Ser Ser Phe
145 150 155 160

Tyr Arg Asn Leu Leu Trp Leu Thr Glu Lys Glu Gly Ser Tyr Pro Lys
165 170 175

Leu Lys Asn Ser Tyr Val Asn Lys Lys Gly Lys Glu Val Leu Val Leu
180 185 190

Trp Gly Ile His His Pro Pro Asn Ser Lys Glu Gln Gln Asn Ile Tyr
195 200 205

Gln Asn Glu Asn Ala Tyr Val Ser Val Val Thr Ser Asn Tyr Asn Arg
210 215 220

Arg Phe Thr Pro Glu Ile Ala Glu Arg Pro Lys Val Arg Asp Gln Ala
225 230 235 240

Gly Arg Met Asn Tyr Tyr Trp Thr Leu Leu Lys Pro Gly Asp Thr Ile
245 250 255

Ile Phe Glu Ala Asn Gly Asn Leu Ile Ala Pro Met Tyr Ala Phe Ala
260 265 270

Leu Ser Arg Gly Phe Gly Ser Gly Ile Ile Thr Ser Asn Ala Ser Met
275 280 285

His Glu Cys Asn Thr Lys Cys Gln Thr Pro Leu Gly Ala Ile Asn Ser
290 295 300

Ser Leu Pro Tyr Gln Asn Ile His Pro Val Thr Ile Gly Glu Cys Pro
305 310 315 320

Lys Tyr Val Arg Ser Ala Lys Leu Arg Met Val Thr Gly Leu Arg Asn
325 330 335

Thr Pro Ser Ile Gln Ser Arg Gly Leu Phe Gly Ala Ile Ala Gly Phe

-continued

```
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Tyr Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Tyr
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 88
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125
```

```
Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Tyr Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
```

```
545                 550                 555                 560

Cys Arg Ile Cys Ile
                565


<210> SEQ ID NO 89
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335
```

```
Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Tyr Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Tyr Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 90
<211> LENGTH: 565
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125
```

-continued

```
Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Tyr Ile Tyr Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540
```

```
Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 91
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335
```

```
Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Tyr Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 92
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
```

-continued

```
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Tyr Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Tyr Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540
```

```
Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 93
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
```

-continued

```
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Tyr Glu Phe Asn Lys Leu
                405                 410                 415

Glu Lys Arg Met Glu Tyr Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 94
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Glu
    50                  55                  60

Asn Leu Tyr Phe Gln
65


<210> SEQ ID NO 95
<211> LENGTH: 53
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 95

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Glu
        35                  40                  45

Asn Leu Tyr Phe Gln
    50
```

<210> SEQ ID NO 96
<211> LENGTH: 282
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 96

```
Ser Asn Ala Ser Met His Glu Cys Asn Thr Lys Cys Gln Thr Pro Leu
1               5                   10                  15

Gly Ala Ile Asn Ser Ser Leu Pro Tyr Gln Asn Ile His Pro Val Thr
            20                  25                  30

Ile Gly Glu Cys Pro Lys Tyr Val Arg Ser Ala Lys Leu Arg Met Val
        35                  40                  45

Thr Gly Leu Arg Asn Thr Pro Ser Ile Gln Ser Arg Gly Leu Phe Gly
    50                  55                  60

Ala Ile Ala Gly Phe Ile Glu Gly Gly Trp Thr Gly Met Ile Asp Gly
65                  70                  75                  80

Trp Tyr Gly Tyr His His Gln Asn Glu Gln Gly Ser Gly Tyr Ala Ala
                85                  90                  95

Asp Gln Lys Ser Thr Gln Asn Ala Ile Asn Gly Ile Thr Asn Lys Val
            100                 105                 110

Asn Thr Val Ile Glu Lys Met Tyr Ile Gln Phe Thr Ala Val Gly Lys
        115                 120                 125

Glu Phe Asn Lys Leu Glu Lys Arg Met Glu Asn Leu Asn Lys Lys Val
    130                 135                 140

Asp Asp Gly Phe Leu Tyr Ile Trp Thr Tyr Asn Ala Glu Leu Leu Val
145                 150                 155                 160

Leu Leu Glu Asn Glu Arg Thr Leu Asp Phe His Asp Ser Asn Val Lys
                165                 170                 175

Asn Leu Tyr Glu Lys Val Lys Ser Gln Leu Lys Asn Asn Ala Lys Glu
            180                 185                 190

Ile Gly Asn Gly Cys Phe Glu Phe Tyr His Lys Cys Asp Asn Glu Cys
        195                 200                 205

Met Glu Ser Val Arg Asn Gly Thr Tyr Asp Tyr Pro Lys Tyr Ser Glu
    210                 215                 220

Glu Ser Lys Leu Asn Arg Glu Lys Val Asp Gly Val Lys Leu Glu Ser
225                 230                 235                 240

Met Gly Ile Tyr Gln Ile Leu Ala Ile Tyr Ser Thr Val Ala Ser Ser
                245                 250                 255

Leu Val Leu Leu Val Ser Leu Gly Ala Ile Ser Phe Trp Met Cys Ser
            260                 265                 270
```

```
Asn Gly Ser Leu Gln Cys Arg Ile Cys Ile
        275                 280


<210> SEQ ID NO 97
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ser Asn Ala Ser Met His Glu Cys Asn Thr Lys Cys Gln Thr Pro Leu
1               5                   10                  15

Gly Ala Ile Asn Ser Ser Leu Pro Tyr Gln Asn Ile His Pro Val Thr
            20                  25                  30

Ile Gly Glu Cys Pro Lys Tyr Val Arg Ser Ala Lys Leu Arg Met Val
        35                  40                  45

Thr Gly Leu Arg Asn Thr Pro Ser Ile Gln Ser Arg Gly Leu Phe Gly
    50                  55                  60

Ala Ile Ala Gly Phe Ile Glu Gly Gly Trp Thr Gly Met Ile Asp Gly
65                  70                  75                  80

Trp Tyr Gly Tyr His His Gln Asn Glu Gln Gly Ser Gly Tyr Ala Ala
                85                  90                  95

Asp Gln Lys Ser Thr Gln Asn Ala Ile Asn Gly Ile Thr Asn Lys Val
            100                 105                 110

Asn Thr Val Ile Glu Lys Met Asn Ile Gln Phe Thr Ala Val Gly Tyr
        115                 120                 125

Glu Phe Asn Lys Leu Glu Lys Arg Met Glu Tyr Leu Asn Lys Lys Val
    130                 135                 140

Asp Asp Gly Phe Leu Asp Ile Trp Thr Tyr Asn Ala Glu Leu Leu Val
145                 150                 155                 160

Leu Leu Glu Asn Glu Arg Thr Leu Asp Phe His Asp Ser Asn Val Lys
                165                 170                 175

Asn Leu Tyr Glu Lys Val Lys Ser Gln Leu Lys Asn Asn Ala Lys Glu
            180                 185                 190

Ile Gly Asn Gly Cys Phe Glu Phe Tyr His Lys Cys Asp Asn Glu Cys
        195                 200                 205

Met Glu Ser Val Arg Asn Gly Thr Tyr Asp Tyr Pro Lys Tyr Ser Glu
    210                 215                 220

Glu Ser Lys Leu Asn Arg Glu Lys Val Asp Gly Val Lys Leu Glu Ser
225                 230                 235                 240

Met Gly Ile Tyr Gln Ile Leu Ala Ile Tyr Ser Thr Val Ala Ser Ser
                245                 250                 255

Leu Val Leu Leu Val Ser Leu Gly Ala Ile Ser Phe Trp Met Cys Ser
            260                 265                 270

Asn Gly Ser Leu Gln Cys Arg Ile Cys Ile
        275                 280


<210> SEQ ID NO 98
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98
```

```
Ser Asn Ala Ser Met His Glu Cys Asn Thr Lys Cys Gln Thr Pro Leu
1               5                   10                  15

Gly Ala Ile Asn Ser Ser Leu Pro Tyr Gln Asn Ile His Pro Val Thr
            20                  25                  30

Ile Gly Glu Cys Pro Lys Tyr Val Arg Ser Ala Lys Leu Arg Met Val
        35                  40                  45

Thr Gly Leu Arg Asn Thr Pro Ser Ile Gln Ser Arg Gly Leu Phe Gly
    50                  55                  60

Ala Ile Ala Gly Phe Ile Glu Gly Gly Trp Thr Gly Met Ile Asp Gly
65                  70                  75                  80

Trp Tyr Gly Tyr His His Gln Asn Glu Gln Gly Ser Gly Tyr Ala Ala
                85                  90                  95

Asp Gln Lys Ser Thr Gln Asn Ala Ile Asn Gly Ile Thr Asn Lys Val
            100                 105                 110

Asn Thr Val Ile Glu Lys Met Tyr Ile Gln Phe Thr Ala Val Gly Tyr
        115                 120                 125

Glu Phe Asn Lys Leu Glu Lys Arg Met Glu Tyr Leu Asn Lys Lys Val
    130                 135                 140

Asp Asp Gly Phe Leu Tyr Ile Trp Thr Tyr Asn Ala Glu Leu Leu Val
145                 150                 155                 160

Leu Leu Glu Asn Glu Arg Thr Leu Asp Phe His Asp Ser Asn Val Lys
                165                 170                 175

Asn Leu Tyr Glu Lys Val Lys Ser Gln Leu Lys Asn Asn Ala Lys Glu
            180                 185                 190

Ile Gly Asn Gly Cys Phe Glu Phe Tyr His Lys Cys Asp Asn Glu Cys
        195                 200                 205

Met Glu Ser Val Arg Asn Gly Thr Tyr Asp Tyr Pro Lys Tyr Ser Glu
    210                 215                 220

Glu Ser Lys Leu Asn Arg Glu Lys Val Asp Gly Val Lys Leu Glu Ser
225                 230                 235                 240

Met Gly Ile Tyr Gln Ile Leu Ala Ile Tyr Ser Thr Val Ala Ser Ser
                245                 250                 255

Leu Val Leu Leu Val Ser Leu Gly Ala Ile Ser Phe Trp Met Cys Ser
            260                 265                 270

Asn Gly Ser Leu Gln Cys Arg Ile Cys Ile
        275                 280
```

<210> SEQ ID NO 99
<211> LENGTH: 283
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

```
Ser Thr Ser Asn Ala Ser Met His Glu Cys Asn Thr Lys Cys Gln Thr
1               5                   10                  15

Pro Leu Gly Ala Ile Asn Ser Ser Leu Pro Tyr Gln Asn Ile His Pro
            20                  25                  30

Val Thr Ile Gly Glu Cys Pro Lys Tyr Val Arg Ser Ala Lys Leu Arg
        35                  40                  45

Met Val Thr Gly Leu Arg Asn Thr Pro Ser Ile Gln Ser Arg Gly Leu
    50                  55                  60

Phe Gly Ala Ile Ala Gly Phe Ile Glu Gly Gly Trp Thr Gly Met Ile
65                  70                  75                  80
```

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Thr Val Ile Glu Lys Met Tyr Ile Gln Phe Thr Ala Val
115 120 125

Gly Lys Glu Phe Asn Lys Leu Glu Lys Arg Met Glu Asn Leu Asn Lys
130 135 140

Lys Val Asp Asp Gly Phe Leu Tyr Ile Trp Thr Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asp Asn
195 200 205

Glu Cys Met Glu Ser Val Arg Asn Gly Thr Tyr Asp Tyr Pro Lys Tyr
210 215 220

Ser Glu Glu Ser Lys Leu Asn Arg Glu Lys Val Asp Val Lys Leu Glu
225 230 235 240

Ser Met Gly Ile Tyr Gln Ile Leu Ala Ile Tyr Ser Thr Val Ala Ser
245 250 255

Ser Leu Val Leu Leu Val Ser Leu Gly Ala Ile Ser Phe Trp Met Cys
260 265 270

Ser Asn Gly Ser Leu Gln Cys Arg Ile Cys Ile
275 280

<210> SEQ ID NO 100
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

Ser Thr Ser Asn Ala Ser Met His Glu Cys Asn Thr Lys Cys Gln Thr
1 5 10 15

Pro Leu Gly Ala Ile Asn Ser Ser Leu Pro Tyr Gln Asn Ile His Pro
20 25 30

Val Thr Ile Gly Glu Cys Pro Lys Tyr Val Arg Ser Ala Lys Leu Arg
35 40 45

Met Val Thr Gly Leu Arg Asn Thr Pro Ser Ile Gln Ser Arg Gly Leu
50 55 60

Phe Gly Ala Ile Ala Gly Phe Ile Glu Gly Gly Trp Thr Gly Met Ile
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Thr Val Ile Glu Lys Met Asn Ile Gln Phe Thr Ala Val
115 120 125

Gly Tyr Glu Phe Asn Lys Leu Glu Lys Arg Met Glu Tyr Leu Asn Lys
130 135 140

Lys Val Asp Asp Gly Phe Leu Asp Ile Trp Thr Tyr Asn Ala Glu Leu

```
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asp Asn
        195                 200                 205

Glu Cys Met Glu Ser Val Arg Asn Gly Thr Tyr Asp Tyr Pro Lys Tyr
    210                 215                 220

Ser Glu Glu Ser Lys Leu Asn Arg Glu Lys Val Asp Gly Val Lys Leu
225                 230                 235                 240

Glu Ser Met Gly Ile Tyr Gln Ile Leu Ala Ile Tyr Ser Thr Val Ala
                245                 250                 255

Ser Ser Leu Val Leu Leu Val Ser Leu Gly Ala Ile Ser Phe Trp Met
            260                 265                 270

Cys Ser Asn Gly Ser Leu Gln Cys Arg Ile Cys Ile
        275                 280


<210> SEQ ID NO 101
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ser Thr Ser Asn Ala Ser Met His Glu Cys Asn Thr Lys Cys Gln Thr
1               5                   10                  15

Pro Leu Gly Ala Ile Asn Ser Ser Leu Pro Tyr Gln Asn Ile His Pro
            20                  25                  30

Val Thr Ile Gly Glu Cys Pro Lys Tyr Val Arg Ser Ala Lys Leu Arg
        35                  40                  45

Met Val Thr Gly Leu Arg Asn Thr Pro Ser Ile Gln Ser Arg Gly Leu
    50                  55                  60

Phe Gly Ala Ile Ala Gly Phe Ile Glu Gly Gly Trp Thr Gly Met Ile
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Thr Val Ile Glu Lys Met Tyr Ile Gln Phe Thr Ala Val
        115                 120                 125

Gly Tyr Glu Phe Asn Lys Leu Glu Lys Arg Met Glu Tyr Leu Asn Lys
    130                 135                 140

Lys Val Asp Asp Gly Phe Leu Tyr Ile Trp Thr Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asp Asn
        195                 200                 205

Glu Cys Met Glu Ser Val Arg Asn Gly Thr Tyr Asp Tyr Pro Lys Tyr
    210                 215                 220
```

```
Ser Glu Glu Ser Lys Leu Asn Arg Glu Lys Val Asp Gly Val Lys Leu
225                 230                 235                 240

Glu Ser Met Gly Ile Tyr Gln Ile Leu Ala Ile Tyr Ser Thr Val Ala
                245                 250                 255

Ser Ser Leu Val Leu Leu Val Ser Leu Gly Ala Ile Ser Phe Trp Met
            260                 265                 270

Cys Ser Asn Gly Ser Leu Gln Cys Arg Ile Cys Ile
        275                 280


<210> SEQ ID NO 102
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gly Ser Asn Ala Ser Met His Glu Cys Asn Thr Lys Cys Gln Thr Pro
1               5                   10                  15

Leu Gly Ala Ile Asn Ser Ser Leu Pro Tyr Gln Asn Ile His Pro Val
            20                  25                  30

Thr Ile Gly Glu Cys Pro Lys Tyr Val Arg Ser Ala Lys Leu Arg Met
        35                  40                  45

Val Thr Gly Leu Arg Asn Thr Pro Ser Ile Gln Ser Arg Gly Leu Phe
    50                  55                  60

Gly Ala Ile Ala Gly Phe Ile Glu Gly Gly Trp Thr Gly Met Ile Asp
65                  70                  75                  80

Gly Trp Tyr Gly Tyr His His Gln Asn Glu Gln Gly Ser Gly Tyr Ala
                85                  90                  95

Ala Asp Gln Lys Ser Thr Gln Asn Ala Ile Asn Gly Ile Thr Asn Lys
            100                 105                 110

Val Asn Thr Val Ile Glu Lys Met Tyr Ile Gln Phe Thr Ala Val Gly
        115                 120                 125

Lys Glu Phe Asn Lys Leu Glu Lys Arg Met Glu Asn Leu Asn Lys Lys
    130                 135                 140

Val Asp Asp Gly Phe Leu Tyr Ile Trp Thr Tyr Asn Ala Glu Leu Leu
145                 150                 155                 160

Val Leu Leu Glu Asn Glu Arg Thr Leu Asp Phe His Asp Ser Asn Val
                165                 170                 175

Lys Asn Leu Tyr Glu Lys Val Lys Ser Gln Leu Lys Asn Asn Ala Lys
            180                 185                 190

Glu Ile Gly Asn Gly Cys Phe Glu Phe Tyr His Lys Cys Asp Asn Glu
        195                 200                 205

Cys Met Glu Ser Val Arg Asn Gly Thr Tyr Asp Tyr Pro Lys Tyr Ser
    210                 215                 220

Glu Glu Ser Lys Leu Asn Arg Glu Lys Val Asp Gly Val Lys Leu Glu
225                 230                 235                 240

Ser Met Gly Ile Tyr Gln Ile Leu Ala Ile Tyr Ser Thr Val Ala Ser
                245                 250                 255

Ser Leu Val Leu Leu Val Ser Leu Gly Ala Ile Ser Phe Trp Met Cys
            260                 265                 270

Ser Asn Gly Ser Leu Gln Cys Arg Ile Cys Ile
        275                 280


<210> SEQ ID NO 103
```

<211> LENGTH: 283
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 103

Gly Ser Asn Ala Ser Met His Glu Cys Asn Thr Lys Cys Gln Thr Pro
1 5 10 15

Leu Gly Ala Ile Asn Ser Ser Leu Pro Tyr Gln Asn Ile His Pro Val
20 25 30

Thr Ile Gly Glu Cys Pro Lys Tyr Val Arg Ser Ala Lys Leu Arg Met
35 40 45

Val Thr Gly Leu Arg Asn Thr Pro Ser Ile Gln Ser Arg Gly Leu Phe
50 55 60

Gly Ala Ile Ala Gly Phe Ile Glu Gly Gly Trp Thr Gly Met Ile Asp
65 70 75 80

Gly Trp Tyr Gly Tyr His His Gln Asn Glu Gln Gly Ser Gly Tyr Ala
85 90 95

Ala Asp Gln Lys Ser Thr Gln Asn Ala Ile Asn Gly Ile Thr Asn Lys
100 105 110

Val Asn Thr Val Ile Glu Lys Met Asn Ile Gln Phe Thr Ala Val Gly
115 120 125

Tyr Glu Phe Asn Lys Leu Glu Lys Arg Met Glu Tyr Leu Asn Lys Lys
130 135 140

Val Asp Asp Gly Phe Leu Asp Ile Trp Thr Tyr Asn Ala Glu Leu Leu
145 150 155 160

Val Leu Leu Glu Asn Glu Arg Thr Leu Asp Phe His Asp Ser Asn Val
165 170 175

Lys Asn Leu Tyr Glu Lys Val Lys Ser Gln Leu Lys Asn Asn Ala Lys
180 185 190

Glu Ile Gly Asn Gly Cys Phe Glu Phe Tyr His Lys Cys Asp Asn Glu
195 200 205

Cys Met Glu Ser Val Arg Asn Gly Thr Tyr Asp Tyr Pro Lys Tyr Ser
210 215 220

Glu Glu Ser Lys Leu Asn Arg Glu Lys Val Asp Gly Val Lys Leu Glu
225 230 235 240

Ser Met Gly Ile Tyr Gln Ile Leu Ala Ile Tyr Ser Thr Val Ala Ser
245 250 255

Ser Leu Val Leu Leu Val Ser Leu Gly Ala Ile Ser Phe Trp Met Cys
260 265 270

Ser Asn Gly Ser Leu Gln Cys Arg Ile Cys Ile
275 280

<210> SEQ ID NO 104
<211> LENGTH: 283
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 104

Gly Ser Asn Ala Ser Met His Glu Cys Asn Thr Lys Cys Gln Thr Pro
1 5 10 15

Leu Gly Ala Ile Asn Ser Ser Leu Pro Tyr Gln Asn Ile His Pro Val
20 25 30

```
Thr Ile Gly Glu Cys Pro Lys Tyr Val Arg Ser Ala Lys Leu Arg Met
        35                  40                  45

Val Thr Gly Leu Arg Asn Thr Pro Ser Ile Gln Ser Arg Gly Leu Phe
    50                  55                  60

Gly Ala Ile Ala Gly Phe Ile Glu Gly Gly Trp Thr Gly Met Ile Asp
65                  70                  75                  80

Gly Trp Tyr Gly Tyr His His Gln Asn Glu Gln Gly Ser Gly Tyr Ala
                85                  90                  95

Ala Asp Gln Lys Ser Thr Gln Asn Ala Ile Asn Gly Ile Thr Asn Lys
            100                 105                 110

Val Asn Thr Val Ile Glu Lys Met Tyr Ile Gln Phe Thr Ala Val Gly
        115                 120                 125

Tyr Glu Phe Asn Lys Leu Glu Lys Arg Met Glu Tyr Leu Asn Lys Lys
    130                 135                 140

Val Asp Asp Gly Phe Leu Tyr Ile Trp Thr Tyr Asn Ala Glu Leu Leu
145                 150                 155                 160

Val Leu Leu Glu Asn Glu Arg Thr Leu Asp Phe His Asp Ser Asn Val
                165                 170                 175

Lys Asn Leu Tyr Glu Lys Val Lys Ser Gln Leu Lys Asn Asn Ala Lys
            180                 185                 190

Glu Ile Gly Asn Gly Cys Phe Glu Phe Tyr His Lys Cys Asp Asn Glu
        195                 200                 205

Cys Met Glu Ser Val Arg Asn Gly Thr Tyr Asp Tyr Pro Lys Tyr Ser
    210                 215                 220

Glu Glu Ser Lys Leu Asn Arg Glu Lys Val Asp Gly Val Lys Leu Glu
225                 230                 235                 240

Ser Met Gly Ile Tyr Gln Ile Leu Ala Ile Tyr Ser Thr Val Ala Ser
                245                 250                 255

Ser Leu Val Leu Leu Val Ser Leu Gly Ala Ile Ser Phe Trp Met Cys
            260                 265                 270

Ser Asn Gly Ser Leu Gln Cys Arg Ile Cys Ile
        275                 280


<210> SEQ ID NO 105
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gly Asn Thr Lys Cys Gln Thr Pro Leu Gly Ala Ile Asn Ser Ser Leu
1               5                   10                  15

Pro Tyr Gln Asn Ile His Pro Val Thr Ile Gly Glu Cys Pro Lys Tyr
            20                  25                  30

Val Arg Ser Ala Lys Leu Arg Met Val Thr Gly Leu Arg Asn Thr Pro
        35                  40                  45

Ser Ile Gln Ser Arg Gly Leu Phe Gly Ala Ile Ala Gly Phe Ile Glu
    50                  55                  60

Gly Gly Trp Thr Gly Met Ile Asp Gly Trp Tyr Gly Tyr His His Gln
65                  70                  75                  80

Asn Glu Gln Gly Ser Gly Tyr Ala Ala Asp Gln Lys Ser Thr Gln Asn
                85                  90                  95

Ala Ile Asn Gly Ile Thr Asn Lys Val Asn Thr Val Ile Glu Lys Met
```

```
            100                 105                 110

Tyr Ile Gln Phe Thr Ala Val Gly Lys Glu Phe Asn Lys Leu Glu Lys
        115                 120                 125

Arg Met Glu Asn Leu Asn Lys Lys Val Asp Asp Gly Phe Leu Tyr Ile
    130                 135                 140

Trp Thr Tyr Asn Ala Glu Leu Leu Val Leu Leu Glu Asn Glu Arg Thr
145                 150                 155                 160

Leu Asp Phe His Asp Ser Asn Val Lys Asn Leu Tyr Glu Lys Val Lys
                165                 170                 175

Ser Gln Leu Lys Asn Asn Ala Lys Glu Ile Gly Asn Gly Cys Phe Glu
            180                 185                 190

Phe Tyr His Lys Cys Asp Asn Glu Cys Met Glu Ser Val Arg Asn Gly
        195                 200                 205

Thr Tyr Asp Tyr Pro Lys Tyr Ser Glu Glu Ser Lys Leu Asn Arg Glu
    210                 215                 220

Lys Val Asp Gly Val Lys Leu Glu Ser Met Gly Ile Tyr Gln Ile Leu
225                 230                 235                 240

Ala Ile Tyr Ser Thr Val Ala Ser Ser Leu Val Leu Leu Val Ser Leu
                245                 250                 255

Gly Ala Ile Ser Phe Trp Met Cys Ser Asn Gly Ser Leu Gln Cys Arg
            260                 265                 270

Ile Cys Ile
        275


<210> SEQ ID NO 106
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gly Asn Thr Lys Cys Gln Thr Pro Leu Gly Ala Ile Asn Ser Ser Leu
1               5                   10                  15

Pro Tyr Gln Asn Ile His Pro Val Thr Ile Gly Glu Cys Pro Lys Tyr
            20                  25                  30

Val Arg Ser Ala Lys Leu Arg Met Val Thr Gly Leu Arg Asn Thr Pro
        35                  40                  45

Ser Ile Gln Ser Arg Gly Leu Phe Gly Ala Ile Ala Gly Phe Ile Glu
    50                  55                  60

Gly Gly Trp Thr Gly Met Ile Asp Gly Trp Tyr Gly Tyr His His Gln
65                  70                  75                  80

Asn Glu Gln Gly Ser Gly Tyr Ala Ala Asp Gln Lys Ser Thr Gln Asn
                85                  90                  95

Ala Ile Asn Gly Ile Thr Asn Lys Val Asn Thr Val Ile Glu Lys Met
            100                 105                 110

Asn Ile Gln Phe Thr Ala Val Gly Tyr Glu Phe Asn Lys Leu Glu Lys
        115                 120                 125

Arg Met Glu Tyr Leu Asn Lys Lys Val Asp Asp Gly Phe Leu Asp Ile
    130                 135                 140

Trp Thr Tyr Asn Ala Glu Leu Leu Val Leu Leu Glu Asn Glu Arg Thr
145                 150                 155                 160

Leu Asp Phe His Asp Ser Asn Val Lys Asn Leu Tyr Glu Lys Val Lys
                165                 170                 175
```

```
Ser Gln Leu Lys Asn Asn Ala Lys Glu Ile Gly Asn Gly Cys Phe Glu
            180                 185                 190

Phe Tyr His Lys Cys Asp Asn Glu Cys Met Glu Ser Val Arg Asn Gly
        195                 200                 205

Thr Tyr Asp Tyr Pro Lys Tyr Ser Glu Glu Ser Lys Leu Asn Arg Glu
    210                 215                 220

Lys Val Asp Gly Val Lys Leu Glu Ser Met Gly Ile Tyr Gln Ile Leu
225                 230                 235                 240

Ala Ile Tyr Ser Thr Val Ala Ser Ser Leu Val Leu Leu Val Ser Leu
                245                 250                 255

Gly Ala Ile Ser Phe Trp Met Cys Ser Asn Gly Ser Leu Gln Cys Arg
            260                 265                 270

Ile Cys Ile
        275
```

<210> SEQ ID NO 107
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

```
Gly Asn Thr Lys Cys Gln Thr Pro Leu Gly Ala Ile Asn Ser Ser Leu
1               5                   10                  15

Pro Tyr Gln Asn Ile His Pro Val Thr Ile Gly Glu Cys Pro Lys Tyr
            20                  25                  30

Val Arg Ser Ala Lys Leu Arg Met Val Thr Gly Leu Arg Asn Thr Pro
        35                  40                  45

Ser Ile Gln Ser Arg Gly Leu Phe Gly Ala Ile Ala Gly Phe Ile Glu
    50                  55                  60

Gly Gly Trp Thr Gly Met Ile Asp Gly Trp Tyr Gly Tyr His His Gln
65                  70                  75                  80

Asn Glu Gln Gly Ser Gly Tyr Ala Ala Asp Gln Lys Ser Thr Gln Asn
                85                  90                  95

Ala Ile Asn Gly Ile Thr Asn Lys Val Asn Thr Val Ile Glu Lys Met
            100                 105                 110

Tyr Ile Gln Phe Thr Ala Val Gly Tyr Glu Phe Asn Lys Leu Glu Lys
        115                 120                 125

Arg Met Glu Tyr Leu Asn Lys Lys Val Asp Asp Gly Phe Leu Tyr Ile
    130                 135                 140

Trp Thr Tyr Asn Ala Glu Leu Leu Val Leu Leu Glu Asn Glu Arg Thr
145                 150                 155                 160

Leu Asp Phe His Asp Ser Asn Val Lys Asn Leu Tyr Glu Lys Val Lys
                165                 170                 175

Ser Gln Leu Lys Asn Asn Ala Lys Glu Ile Gly Asn Gly Cys Phe Glu
            180                 185                 190

Phe Tyr His Lys Cys Asp Asn Glu Cys Met Glu Ser Val Arg Asn Gly
        195                 200                 205

Thr Tyr Asp Tyr Pro Lys Tyr Ser Glu Glu Ser Lys Leu Asn Arg Glu
    210                 215                 220

Lys Val Asp Gly Val Lys Leu Glu Ser Met Gly Ile Tyr Gln Ile Leu
225                 230                 235                 240

Ala Ile Tyr Ser Thr Val Ala Ser Ser Leu Val Leu Leu Val Ser Leu
                245                 250                 255
```

```
Gly Ala Ile Ser Phe Trp Met Cys Ser Asn Gly Ser Leu Gln Cys Arg
            260                 265                 270

Ile Cys Ile
        275
```

<210> SEQ ID NO 108
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Ser Asn Thr Lys Cys Gln Thr Pro Leu Gly Ala Ile Asn Ser Ser Leu
1               5                   10                  15

Pro Tyr Gln Asn Ile His Pro Val Thr Ile Gly Glu Cys Pro Lys Tyr
            20                  25                  30

Val Arg Ser Ala Lys Leu Arg Met Val Thr Gly Leu Arg Asn Thr Pro
        35                  40                  45

Ser Ile Gln Ser Arg Gly Leu Phe Gly Ala Ile Ala Gly Phe Ile Glu
    50                  55                  60

Gly Gly Trp Thr Gly Met Ile Asp Gly Trp Tyr Gly Tyr His His Gln
65                  70                  75                  80

Asn Glu Gln Gly Ser Gly Tyr Ala Ala Asp Gln Lys Ser Thr Gln Asn
                85                  90                  95

Ala Ile Asn Gly Ile Thr Asn Lys Val Asn Thr Val Ile Glu Lys Met
            100                 105                 110

Tyr Ile Gln Phe Thr Ala Val Gly Lys Glu Phe Asn Lys Leu Glu Lys
        115                 120                 125

Arg Met Glu Asn Leu Asn Lys Lys Val Asp Asp Gly Phe Leu Tyr Ile
    130                 135                 140

Trp Thr Tyr Asn Ala Glu Leu Leu Val Leu Leu Glu Asn Glu Arg Thr
145                 150                 155                 160

Leu Asp Phe His Asp Ser Asn Val Lys Asn Leu Tyr Glu Lys Val Lys
                165                 170                 175

Ser Gln Leu Lys Asn Asn Ala Lys Glu Ile Gly Asn Gly Cys Phe Glu
            180                 185                 190

Phe Tyr His Lys Cys Asp Asn Glu Cys Met Glu Ser Val Arg Asn Gly
        195                 200                 205

Thr Tyr Asp Tyr Pro Lys Tyr Ser Glu Glu Ser Lys Leu Asn Arg Glu
    210                 215                 220

Lys Val Asp Gly Val Lys Leu Glu Ser Met Gly Ile Tyr Gln Ile Leu
225                 230                 235                 240

Ala Ile Tyr Ser Thr Val Ala Ser Ser Leu Val Leu Leu Val Ser Leu
                245                 250                 255

Gly Ala Ile Ser Phe Trp Met Cys Ser Asn Gly Ser Leu Gln Cys Arg
            260                 265                 270

Ile Cys Ile
        275
```

<210> SEQ ID NO 109
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Ser Asn Thr Lys Cys Gln Thr Pro Leu Gly Ala Ile Asn Ser Ser Leu
1 5 10 15

Pro Tyr Gln Asn Ile His Pro Val Thr Ile Gly Glu Cys Pro Lys Tyr
20 25 30

Val Arg Ser Ala Lys Leu Arg Met Val Thr Gly Leu Arg Asn Thr Pro
35 40 45

Ser Ile Gln Ser Arg Gly Leu Phe Gly Ala Ile Ala Gly Phe Ile Glu
50 55 60

Gly Gly Trp Thr Gly Met Ile Asp Gly Trp Tyr Gly Tyr His His Gln
65 70 75 80

Asn Glu Gln Gly Ser Gly Tyr Ala Ala Asp Gln Lys Ser Thr Gln Asn
85 90 95

Ala Ile Asn Gly Ile Thr Asn Lys Val Asn Thr Val Ile Glu Lys Met
100 105 110

Asn Ile Gln Phe Thr Ala Val Gly Tyr Glu Phe Asn Lys Leu Glu Lys
115 120 125

Arg Met Glu Tyr Leu Asn Lys Lys Val Asp Asp Gly Phe Leu Asp Ile
130 135 140

Trp Thr Tyr Asn Ala Glu Leu Leu Val Leu Leu Glu Asn Glu Arg Thr
145 150 155 160

Leu Asp Phe His Asp Ser Asn Val Lys Asn Leu Tyr Glu Lys Val Lys
165 170 175

Ser Gln Leu Lys Asn Asn Ala Lys Glu Ile Gly Asn Gly Cys Phe Glu
180 185 190

Phe Tyr His Lys Cys Asp Asn Glu Cys Met Glu Ser Val Arg Asn Gly
195 200 205

Thr Tyr Asp Tyr Pro Lys Tyr Ser Glu Glu Ser Lys Leu Asn Arg Glu
210 215 220

Lys Val Asp Gly Val Lys Leu Glu Ser Met Gly Ile Tyr Gln Ile Leu
225 230 235 240

Ala Ile Tyr Ser Thr Val Ala Ser Ser Leu Val Leu Leu Val Ser Leu
245 250 255

Gly Ala Ile Ser Phe Trp Met Cys Ser Asn Gly Ser Leu Gln Cys Arg
260 265 270

Ile Cys Ile
275

<210> SEQ ID NO 110
<211> LENGTH: 275
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 110

Ser Asn Thr Lys Cys Gln Thr Pro Leu Gly Ala Ile Asn Ser Ser Leu
1 5 10 15

Pro Tyr Gln Asn Ile His Pro Val Thr Ile Gly Glu Cys Pro Lys Tyr
20 25 30

Val Arg Ser Ala Lys Leu Arg Met Val Thr Gly Leu Arg Asn Thr Pro
35 40 45

Ser Ile Gln Ser Arg Gly Leu Phe Gly Ala Ile Ala Gly Phe Ile Glu

```
    50                  55                  60

Gly Gly Trp Thr Gly Met Ile Asp Gly Trp Tyr Gly Tyr His His Gln
65                  70                  75                  80

Asn Glu Gln Gly Ser Gly Tyr Ala Ala Asp Gln Lys Ser Thr Gln Asn
                85                  90                  95

Ala Ile Asn Gly Ile Thr Asn Lys Val Asn Thr Val Ile Glu Lys Met
            100                 105                 110

Tyr Ile Gln Phe Thr Ala Val Gly Tyr Glu Phe Asn Lys Leu Glu Lys
        115                 120                 125

Arg Met Glu Tyr Leu Asn Lys Lys Val Asp Asp Gly Phe Leu Tyr Ile
    130                 135                 140

Trp Thr Tyr Asn Ala Glu Leu Leu Val Leu Leu Glu Asn Glu Arg Thr
145                 150                 155                 160

Leu Asp Phe His Asp Ser Asn Val Lys Asn Leu Tyr Glu Lys Val Lys
                165                 170                 175

Ser Gln Leu Lys Asn Asn Ala Lys Glu Ile Gly Asn Gly Cys Phe Glu
            180                 185                 190

Phe Tyr His Lys Cys Asp Asn Glu Cys Met Glu Ser Val Arg Asn Gly
        195                 200                 205

Thr Tyr Asp Tyr Pro Lys Tyr Ser Glu Glu Ser Lys Leu Asn Arg Glu
    210                 215                 220

Lys Val Asp Gly Val Lys Leu Glu Ser Met Gly Ile Tyr Gln Ile Leu
225                 230                 235                 240

Ala Ile Tyr Ser Thr Val Ala Ser Ser Leu Val Leu Leu Val Ser Leu
                245                 250                 255

Gly Ala Ile Ser Phe Trp Met Cys Ser Asn Gly Ser Leu Gln Cys Arg
            260                 265                 270

Ile Cys Ile
        275


<210> SEQ ID NO 111
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Val Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125
```

```
Glu Arg Phe Glu Ile Phe Pro Lys Glu Arg Ser Trp Pro Lys His Asn
    130                 135                 140

Val Thr Arg Gly Val Thr Ala Ser Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp His Ala Phe
            260                 265                 270

Ala Leu Asn Arg Gly Phe Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
```

545 550 555 560

Gln Cys Arg Ile Cys Ile
565

<210> SEQ ID NO 112
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

Met Lys Ala Lys Leu Leu Val Leu Leu Cys Ala Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Arg Leu Lys Gly Ile
50 55 60

Ala Pro Leu Gln Leu Gly Asn Cys Ser Val Ala Gly Trp Ile Leu Gly
65 70 75 80

Asn Pro Lys Cys Glu Ser Leu Phe Ser Lys Glu Ser Trp Ser Tyr Ile
85 90 95

Ala Glu Thr Pro Asn Pro Glu Asn Gly Thr Cys Tyr Pro Gly Tyr Phe
100 105 110

Ala Asp Tyr Glu Glu Leu Arg Glu Gln Leu Ser Ser Val Ser Ser Phe
115 120 125

Glu Arg Phe Glu Ile Phe Pro Lys Glu Ser Ser Trp Pro Asn His Thr
130 135 140

Val Thr Lys Gly Val Thr Thr Ser Cys Ser His Asn Gly Lys Ser Ser
145 150 155 160

Phe Tyr Arg Asn Leu Leu Trp Leu Thr Glu Lys Asn Gly Leu Tyr Pro
165 170 175

Asn Leu Ser Lys Ser Tyr Val Asn Asn Lys Glu Lys Glu Val Leu Val
180 185 190

Leu Trp Gly Val His His Pro Ser Asn Ile Arg Asp Gln Arg Ala Ile
195 200 205

Tyr His Thr Glu Asn Ala Tyr Val Ser Val Val Ser Ser His Tyr Ser
210 215 220

Arg Arg Phe Thr Pro Glu Ile Ala Lys Arg Pro Lys Val Arg Asp Gln
225 230 235 240

Glu Gly Arg Ile Asn Tyr Tyr Trp Thr Leu Leu Glu Pro Gly Asp Thr
245 250 255

Ile Ile Phe Glu Ala Asn Gly Asn Leu Ile Ala Pro Trp Tyr Ala Phe
260 265 270

Ala Leu Ser Arg Gly Phe Gly Ser Gly Ile Ile Thr Ser Asn Ala Ser
275 280 285

Met Asp Glu Cys Asp Ala Lys Cys Gln Thr Pro Gln Gly Ala Ile Asn
290 295 300

Ser Ser Leu Pro Phe Gln Asn Val His Pro Val Thr Ile Gly Glu Cys
305 310 315 320

Pro Lys Tyr Val Arg Ser Thr Lys Leu Arg Met Val Thr Gly Leu Arg
325 330 335

-continued

Asn Ile Pro Ser Ile Gln Ser Arg Gly Leu Phe Gly Ala Ile Ala Gly
340 345 350

Phe Ile Glu Gly Gly Trp Thr Gly Met Ile Asp Gly Trp Tyr Gly Tyr
355 360 365

His His Gln Asn Glu Gln Gly Ser Gly Tyr Ala Ala Asp Gln Lys Ser
370 375 380

Thr Gln Asn Ala Ile Asn Gly Ile Thr Asn Lys Val Asn Ser Val Ile
385 390 395 400

Glu Lys Met Asn Thr Gln Phe Thr Ala Val Gly Lys Glu Phe Asn Lys
405 410 415

Leu Glu Arg Arg Met Glu Asn Leu Asn Lys Lys Val Asp Asp Gly Phe
420 425 430

Leu Asp Ile Trp Thr Tyr Asn Ala Glu Leu Leu Val Leu Leu Glu Asn
435 440 445

Gly Arg Thr Leu Asp Phe His Asp Ser Asn Val Lys Asn Leu Tyr Glu
450 455 460

Lys Val Lys Ser Gln Leu Lys Asn Asn Ala Lys Glu Ile Gly Asn Gly
465 470 475 480

Cys Phe Glu Phe Tyr His Lys Cys Asn Asn Glu Cys Met Glu Ser Val
485 490 495

Lys Asn Gly Thr Tyr Asp Tyr Pro Lys Tyr Ser Glu Glu Ser Lys Leu
500 505 510

Asn Arg Gly Lys Ile Asp Gly Val Lys Leu Glu Ser Met Gly Val Tyr
515 520 525

Gln Ile Leu Ala Ile Tyr Ser Thr Val Ala Ser Ser Leu Val Leu Leu
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 113
<211> LENGTH: 565
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 113

Met Lys Ala Lys Leu Leu Val Leu Leu Tyr Ala Phe Val Ala Thr Asp
1 5 10 15

Ala Asp Thr Ile Cys Ile Gly Tyr His Ala Asn Asn Ser Thr Asp Thr
20 25 30

Val Asp Thr Ile Phe Glu Lys Asn Val Ala Val Thr His Ser Val Asn
35 40 45

Leu Leu Glu Asp Arg His Asn Gly Lys Leu Cys Lys Leu Lys Gly Ile
50 55 60

Ala Pro Leu Gln Leu Gly Lys Cys Asn Ile Ile Gly Trp Leu Leu Gly
65 70 75 80

Asn Pro Glu Cys Asp Ser Leu Leu Pro Ala Arg Ser Trp Ser Tyr Ile
85 90 95

Val Glu Thr Pro Asn Ser Glu Asn Gly Ala Cys Tyr Pro Gly Asp Phe
100 105 110

Ile Asp Tyr Glu Glu Leu Arg Glu Gln Leu Ser Ser Val Ser Ser Leu
115 120 125

```
Glu Arg Phe Glu Ile Phe Pro Lys Glu Ser Ser Trp Pro Asn His Thr
    130                 135                 140

Phe Asn Gly Val Thr Ala Ser Cys Ser His Arg Gly Lys Ser Ser Phe
145                 150                 155                 160

Tyr Arg Asn Leu Leu Trp Leu Thr Lys Lys Gly Asp Ser Tyr Pro Lys
                165                 170                 175

Leu Thr Asn Ser Tyr Val Asn Asn Lys Gly Lys Glu Val Leu Val Leu
            180                 185                 190

Trp Gly Val His His Pro Ser Ser Ser Asp Glu Gln Gln Ser Leu Tyr
        195                 200                 205

Ser Asn Gly Asn Ala Tyr Val Ser Val Ala Ser Ser Asn Tyr Asn Arg
    210                 215                 220

Arg Phe Thr Pro Glu Ile Ala Ala Arg Pro Lys Val Lys Asp Gln His
225                 230                 235                 240

Gly Arg Met Asn Tyr Tyr Trp Thr Leu Leu Glu Pro Gly Asp Thr Ile
                245                 250                 255

Ile Phe Glu Ala Thr Gly Asn Leu Ile Ala Pro Trp Tyr Ala Phe Ala
            260                 265                 270

Leu Ser Arg Gly Phe Glu Ser Gly Ile Ile Thr Ser Asn Ala Ser Met
        275                 280                 285

His Glu Cys Asn Thr Lys Cys Gln Thr Pro Gln Gly Ser Ile Asn Ser
    290                 295                 300

Asn Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Tyr Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Ile Ile Glu
385                 390                 395                 400

Lys Met Asn Thr Gln Phe Thr Ala Val Gly Lys Glu Phe Asn Asn Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Gly
        435                 440                 445

Arg Thr Leu Asp Phe His Asp Leu Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540
```

Ser Leu Gly Ala Ile Ser Phe Trp Met Cys Ser Asn Gly Ser Leu Gln
545 550 555 560

Cys Arg Ile Cys Ile
565

<210> SEQ ID NO 114
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

Met Glu Ala Arg Leu Leu Val Leu Leu Cys Ala Phe Ala Ala Thr Asn
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Lys Leu Lys Gly Ile
50 55 60

Ala Pro Leu Gln Leu Gly Lys Cys Asn Ile Ala Gly Trp Leu Leu Gly
65 70 75 80

Asn Pro Glu Cys Asp Leu Leu Leu Thr Ala Ser Ser Trp Ser Tyr Ile
85 90 95

Val Glu Thr Ser Asn Ser Glu Asn Gly Thr Cys Tyr Pro Gly Asp Phe
100 105 110

Ile Asp Tyr Glu Glu Leu Arg Glu Gln Leu Ser Ser Val Ser Ser Phe
115 120 125

Glu Lys Phe Glu Ile Phe Pro Lys Thr Ser Ser Trp Pro Asn His Glu
130 135 140

Thr Thr Lys Gly Val Thr Ala Ala Cys Ser Tyr Ala Gly Ala Ser Ser
145 150 155 160

Phe Tyr Arg Asn Leu Leu Trp Leu Thr Lys Lys Gly Ser Ser Tyr Pro
165 170 175

Lys Leu Ser Lys Ser Tyr Val Asn Asn Lys Gly Lys Glu Val Leu Val
180 185 190

Leu Trp Gly Val His His Pro Pro Thr Gly Thr Asp Gln Gln Ser Leu
195 200 205

Tyr Gln Asn Ala Asp Ala Tyr Val Ser Val Gly Ser Ser Lys Tyr Asn
210 215 220

Arg Arg Phe Thr Pro Glu Ile Ala Ala Arg Pro Lys Val Arg Asp Gln
225 230 235 240

Ala Gly Arg Met Asn Tyr Tyr Trp Thr Leu Leu Glu Pro Gly Asp Thr
245 250 255

Ile Thr Phe Glu Ala Thr Gly Asn Leu Ile Ala Pro Trp Tyr Ala Phe
260 265 270

Ala Leu Asn Arg Gly Ser Gly Ser Gly Ile Ile Thr Ser Asp Ala Pro
275 280 285

Val His Asp Cys Asn Thr Lys Cys Gln Thr Pro His Gly Ala Ile Asn
290 295 300

Ser Ser Leu Pro Phe Gln Asn Ile His Pro Val Thr Ile Gly Glu Cys
305 310 315 320

Pro Lys Tyr Val Arg Ser Thr Lys Leu Arg Met Ala Thr Gly Leu Arg
325 330 335

Asn Ile Pro Ser Ile Gln Ser Arg Gly Leu Phe Gly Ala Ile Ala Gly
340 345 350

Phe Ile Glu Gly Gly Trp Thr Gly Met Ile Asp Gly Trp Tyr Gly Tyr
355 360 365

His His Gln Asn Glu Gln Gly Ser Gly Tyr Ala Ala Asp Gln Lys Ser
370 375 380

Thr Gln Asn Ala Ile Asp Gly Ile Thr Asn Lys Val Asn Ser Val Ile
385 390 395 400

Glu Lys Met Asn Thr Gln Phe Thr Ala Val Gly Lys Glu Phe Asn Asn
405 410 415

Leu Glu Arg Arg Ile Glu Asn Leu Asn Lys Lys Val Asp Asp Gly Phe
420 425 430

Leu Asp Ile Trp Thr Tyr Asn Ala Glu Leu Leu Val Leu Leu Glu Asn
435 440 445

Glu Arg Thr Leu Asp Phe His Asp Ser Asn Val Arg Asn Leu Tyr Glu
450 455 460

Lys Val Lys Ser Gln Leu Lys Asn Asn Ala Lys Glu Ile Gly Asn Gly
465 470 475 480

Cys Phe Glu Phe Tyr His Lys Cys Asp Asp Ala Cys Met Glu Ser Val
485 490 495

Arg Asn Gly Thr Tyr Asp Tyr Pro Lys Tyr Ser Glu Glu Ser Lys Leu
500 505 510

Asn Arg Glu Glu Ile Asp Gly Val Lys Leu Glu Ser Met Gly Val Tyr
515 520 525

Gln Ile Leu Ala Ile Tyr Ser Thr Val Ala Ser Ser Leu Val Leu Leu
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 115
<211> LENGTH: 566
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 115

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

Asn Pro Glu Cys Glu Ser Leu Ser Thr Ala Ser Ser Trp Ser Tyr Ile
85 90 95

Val Glu Thr Pro Ser Ser Asp Asn Gly Thr Cys Tyr Pro Gly Asp Phe
100 105 110

Ile Asp Tyr Glu Glu Leu Arg Glu Gln Leu Ser Ser Val Ser Ser Phe

-continued

```
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540
```

```
Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 116
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Arg Ser Leu Val Pro Arg Gly Ser Pro Gly Ser Gly Tyr Ile Pro Glu
1               5                   10                  15

Ala Pro Arg Asp Gly Gln Ala Tyr Val Arg Lys Asp Gly Glu Trp Val
            20                  25                  30

Leu Leu Ser Thr Phe Leu His His His His His His
        35                  40


<210> SEQ ID NO 117
<211> LENGTH: 274
<212> TYPE: PRT
<213> ORGANISM: Influenza A virus

<400> SEQUENCE: 117

Asn Thr Lys Cys Gln Thr Pro Leu Gly Ala Ile Asn Ser Ser Leu Pro
1               5                   10                  15

Tyr Gln Asn Ile His Pro Val Thr Ile Gly Glu Cys Pro Lys Tyr Val
            20                  25                  30

Arg Ser Ala Lys Leu Arg Met Val Thr Gly Leu Arg Asn Thr Pro Ser
        35                  40                  45

Ile Gln Ser Arg Gly Leu Phe Gly Ala Ile Ala Gly Phe Ile Glu Gly
    50                  55                  60

Gly Trp Thr Gly Met Ile Asp Gly Trp Tyr Gly Tyr His His Gln Asn
65                  70                  75                  80

Glu Gln Gly Ser Gly Tyr Ala Ala Asp Gln Lys Ser Thr Gln Asn Ala
                85                  90                  95

Ile Asn Gly Ile Thr Asn Lys Val Asn Thr Val Ile Glu Lys Met Asn
            100                 105                 110

Ile Gln Phe Thr Ala Val Gly Lys Glu Phe Asn Lys Leu Glu Lys Arg
        115                 120                 125

Met Glu Asn Leu Asn Lys Lys Val Asp Asp Gly Phe Leu Asp Ile Trp
    130                 135                 140

Thr Tyr Asn Ala Glu Leu Leu Val Leu Leu Glu Asn Glu Arg Thr Leu
145                 150                 155                 160

Asp Phe His Asp Ser Asn Val Lys Asn Leu Tyr Glu Lys Val Lys Ser
                165                 170                 175

Gln Leu Lys Asn Asn Ala Lys Glu Ile Gly Asn Gly Cys Phe Glu Phe
            180                 185                 190

Tyr His Lys Cys Asp Asn Glu Cys Met Glu Ser Val Arg Asn Gly Thr
        195                 200                 205

Tyr Asp Tyr Pro Lys Tyr Ser Glu Glu Ser Lys Leu Asn Arg Glu Lys
    210                 215                 220

Val Asp Gly Val Lys Leu Glu Ser Met Gly Ile Tyr Gln Ile Leu Ala
225                 230                 235                 240
```

-continued

```
Ile Tyr Ser Thr Val Ala Ser Ser Leu Val Leu Leu Val Ser Leu Gly
                245                 250                 255

Ala Ile Ser Phe Trp Met Cys Ser Asn Gly Ser Leu Gln Cys Arg Ile
            260                 265                 270

Cys Ile


<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 118

His His His His His His
1               5
```

INFLUENZA HEMAGGLUTININ PROTEINS AND METHODS OF USE THEREOF

CROSS-REFERENCE TO RELATED APPLICATIONS

This application claims the benefit of U.S. Provisional Patent Application No. 61/861,989, filed Aug. 3, 2013, the contents of which are hereby incorporated by reference.

SEQUENCE LISTING

The instant application contains a Sequence Listing which has been submitted electronically in ASCII format and is hereby incorporated by reference in its entirety. Said ASCII copy, created on Aug. 1, 2014, is named Avatar_006_US2_Sequence_Listing.txt and is 411,982 bytes in size.

COPYRIGHT AND INCORPORATION BY REFERENCE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

For the purposes of only those jurisdictions that permit incorporation by reference, the text of all documents cited herein is hereby incorporated by reference in its entirety.

BACKGROUND OF THE INVENTION

The US and world populations continue to be at risk of a pandemic influenza outbreak, analogous to the 1918 Spanish (H1N1) outbreak that killed more than 50 million people. Similarly, weaponized influenza virus remains a major biowarfare threat. Furthermore, antigenic drift requires individuals seeking protection against influenza to be vaccinated annually, and recent studies have shown that seasonal vaccine products are only weakly efficacious if a mismatch occurs between vaccination strains and circulating strains.

The development of an effective universal influenza vaccine that provides protection across strains of influenza virus would be of enormous value. Evidence that antibodies specific for the conserved stalk domain of the influenza HA protein can protect against infection has prompted a concerted effort to identify additional and better monoclonal antibodies, and to develop a protective vaccine to address this significant unmet medical and public health need.

SUMMARY OF THE INVENTION

Some aspects of the present invention are summarized below. Additional aspects are described in the Detailed Description of the Invention, the Examples, the Figures and the Claims sections of the present patent application.

The influenza HA protein is known to induce potent neutralizing antibodies that correlate with protection against influenza virus infection. Most existing influenza virus vaccines provide protection based on the generation of antibodies against the highly variable, immunodominant, head domain of the influenza HA protein. However, the head domain is often strain-specific so such vaccines are generally only effective against homologous influenza strains, and do not provide protection against other forms of influenza virus, such as homologous drift variants and heterologous strains. Recently it has been shown that the stalk domain of influenza HA can elicit antibodies that react across influenza virus subtypes, due to the more conserved structure of the stalk domain and the presence of epitopes presented on the conserved stalk. Also, potent neutralizing antibodies (nAbs) have been isolated that specifically bind to the native trimeric conformation of the stalk domain. However, the stalk domain becomes highly unstable and readily transitions to a non-native conformation or disassembles upon removal of the HA head domain—limiting usefulness of the stalk domain on its own (e.g. without the head domain) as a vaccine immunogen. An influenza HA protein having a stalk domain stabilized in its native trimeric conformation could be very valuable—providing a candidate influenza vaccine immunogen capable of providing protection across influenza virus strains. Similarly, such a stabilized influenza HA protein could also be useful for the generation of antibodies, such as diagnostic and therapeutic antibodies.

Based on an extensive analysis of the structure of the influenza HA protein, the present invention provides a variety of novel design strategies and novel constructs to stabilize or "lock" the stalk domain of the influenza HA protein in its native trimeric conformation. The present invention also provides a variety of engineered influenza HA polypeptides, proteins, and/or protein complexes, such as those that comprise one or more targeted cross-links (such as di-tyrosine cross-links), one or more to-tyrosine mutations, and/or one or more artificially-introduced protease cleavage sites/motifs. The engineered HA influenza HA polypeptides, proteins, and/or protein complexes of the invention can be made using any suitable influenza HA polypeptide or protein as a starting point. For example, an influenza HA sequence from any influenza type, sub-type, or strain can be used as a starting point for generation of the engineered products described herein. In many of the embodiments described herein, the influenza strain Puerto Rico/8/1934 or "PR8" (which is a strain of the H1N1 influenza subtype of influenza A) was used as the starting point. The amino acid sequence of a wild-type PR8 strain is provided in FIG. 9 (SEQ ID NO: 1). However, any other influenza HA sequence from any other influenza type, sub-type, or strain could equally be used. Non-limiting examples of other influenza HA sequences that can be used as the starting point for generating the engineered HA products described herein include, but are not limited to, those illustrated in FIGS. 55, 56, 57, 58, 59, and 60, and those having the sequences of SEQ ID NO:s 80, 81, 82, 83, 84, 85, 111, 112, 113, 114, and 115. Similarly, codon optimized versions of the nucleotide sequences that encode influenza HA proteins can be used as starting points for the generation of the engineered HA products described herein. Non-limiting examples of codon-optimized HA sequences from the PR8 influenza strain include those having the sequences of SEQ ID NO:s 63, 64, 65, 66, 67, and 68.

In some embodiments, the present invention provides influenza HA polypeptides, proteins, and/or protein complexes that comprise one or more targeted cross-links in their stalk domain which serve to stabilize or "lock" the stalk domain in its native trimeric conformation. In some embodiments such targeted cross-links are di-tyrosine cross-links. In some embodiments, the present invention provides an influenza HA protein complex comprising a trimeric stalk domain formed by the association of three protomers, wherein the stalk domain comprises one or more targeted cross-links, such as di-tyrosine cross-links, that stabilize the stalk domain in its native trimeric conformation. In some such embodiments, the influenza HA protein complex further comprises one or more cross-links in the influenza HA head domain. In some such embodiments, the influenza HA protein complex does not comprise an intact head domain. In embodiments where di-tyrosine cross-links are used, such cross-links can be made between two tyrosine residues that are naturally present in an HA polypeptide, protein, and/or protein complex, or between two tyrosine residues that have been introduced by mutation, or between a first tyrosine residue that is naturally present in an HA polypeptide, protein, and/or protein complex and a second tyrosine residue that has been introduced by mutation. In some embodiments, the present invention also provides influenza HA polypeptides, proteins, and/or protein complexes that comprise one or more "to-tyrosine" mutations in the HA stalk domain at locations that have been determined to be desirable locations for the formation of di-tyrosine cross-links to stabilize the stalk domain in its native trimeric conformation. In some embodiments, the influenza HA polypeptides, proteins, and/or protein complexes of the invention (whether containing targeted cross-links (such as di-tyrosine cross-links), or to-tyrosine mutations, or both) are full length HA proteins comprising both the HA stalk domain (with or without the signal peptide) and the HA head domain, and optionally also the HA transmembrane domain. In some embodiments the influenza HA polypeptides, proteins, and/or protein complexes of the invention lack one or more of the HA head domain, the transmembrane domain, and/or the signal peptide. In some embodiments the influenza HA polypeptides, proteins, and/or protein complexes of the invention comprise the HA stalk domain, or at least a portion of the HA stalk domain that is sufficient to assemble into, or form a part of, the normal trimeric stalk conformation. Thus, in some embodiments, it may be possible to remove, add, or substitute certain HA stalk domain amino acids without compromising the ability of the HA polypeptide or protein to assemble into its trimeric conformation.

In some embodiments the present invention provides influenza HA polypeptides, proteins, and/or protein complexes that comprise to-tyrosine mutations at one or more of amino acid positions 403, 406, 411, 422, 429, 432, 433, and 435, where such amino acid numbering is based upon the sequence shown in FIG. 9 (SEQ ID NO: 1), or at amino acid positions that correspond to such amino acid positions, for example as determined by alignment of an HA amino acid sequence to SEQ ID NO: 1. Non-limiting examples of influenza HA amino acid sequences that comprise one or more of such to-tyrosine mutations include SEQ ID NOs: 3, 4, 5, 6, 7, 8, 9, 10, 11, 12, 13, 14, 15, 16, 17, 86, 87, 88, 89, 90, 91, 92, 93, 96, 97, 98, 99, 100, 101, 102, 103, 104, 105, 106, 107, 108, 109 and 110. In some embodiments the present invention provides influenza HA polypeptides, proteins, and/or protein complexes that comprise di-tyrosine cross-links between one or more pairs of amino acids selected from the following amino acid positions: 308, 403, 406, 411, 422, 429, 432, 433, 435, and 437, where such amino acid numbering is based upon the sequence shown in FIG. 9 (SEQ ID NO: 1), or at amino acid positions that correspond to such amino acid positions, for example as determined by alignment of an HA amino acid sequence to SEQ ID NO: 1.

In some embodiments, the present invention provides influenza HA polypeptides, proteins, and/or protein complexes that comprise one or more artificially-introduced protease cleavage sites that can be used to proteolytically remove the head domain of an HA polypeptide, protein, and/or protein complex. In some embodiments the present invention provides influenza HA polypeptides, proteins, and/or protein complexes that comprise one or more artificially-introduced protease cleavage sites inserted after (e.g. immediately after) amino acid positions 48, 63, 228, 278, 282, 283, 286, and 291, where such amino acid numbering is based upon the sequence shown in SEQ ID NO: 1, or at amino acid positions that correspond to such amino acid positions, for example as determined by alignment of an HA amino acid sequence to sequence ID NO: 1. Non-limiting examples of influenza HA amino acid sequences that comprise one or more of such artificially-introduced protease cleavage sites include SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, and 30.

In some embodiments the present invention provides influenza HA polypeptides, proteins, and/or protein complexes that comprise at least one pair of artificially-introduced protease cleavage sites, such that cleavage at both of the pair of cleavage sites will result in removal of the HA head domain. Non-limiting examples of influenza HA amino acid sequences that comprise a pair of such artificially-introduced protease cleavage sites include SEQ ID NOs: 3, 4, 5, 6, 7, 8, 9, 10, 11, 12, 13, 14, 15, 16, 17, 26, 27, 28, 29, and 30. In some such embodiments, where there are a pair of artificially-introduced protease cleavage sites, the first such protease cleavage site is inserted after (e.g. immediately after) amino acid position 48 or 63, and the second such protease cleavage site is inserted after (e.g. immediately after) amino acid position 228, 278, 282, 283, 286, or 291, where such amino acid numbering is based upon the sequence shown in SEQ ID NO: 1, or at amino acid positions that correspond to such amino acid positions, for example as determined by alignment of an HA amino acid sequence to sequence ID NO: 1.

In some embodiments, the present invention also provides influenza HA stalk domain polypeptides, proteins, and/or protein complexes that do not comprise an intact HA head domain, such as those generated by proteolytic removal of the influenza HA head domain, for example by cleavage at one or more of the artificially-introduced protease cleavage sites described herein. The stalk domain sequences of influenza HA are discontinuous because the HA protein comprises an N-terminal region comprising stalk domain sequences, followed by a middle region comprising head domain sequences, followed by a C-terminal region comprising additional stalk domain sequences. Accordingly, in some embodiments, proteolytic cleavage/removal of the HA head domain results in the generation of two stalk domain polypeptide fragments—an N-terminal fragment and a C-terminal fragment. In some embodiments the present invention provides such N- and C-terminal stalk domain polypeptides, and/or polypeptides, proteins, or protein complexes that comprise such N- and C-terminal stalk domain polypeptides. In some embodiments such N- and C-terminal stalk domain polypeptides are present in an HA stalk domain protein complex having a native trimeric stalk domain conformation. Non-limiting examples of influenza HA N-terminal stalk domain polypeptides include SEQ ID NOs: 94 and 95. Non-limiting examples of influenza HA C-terminal stalk domain polypeptides include SEQ ID NOs: 96, 97, 98, 99, 100, 101, 102, 103, 104, 105, 106, 107, 108, 109, 110, and 117. A further non-limiting example of an influenza HA N-terminal stalk domain polypeptide is one that consists of, consists essentially of, or comprises, amino acids 1-228 of SEQ ID NO: 117, or amino acids 229 to 519 of SEQ ID NO: 1. In some embodiments the influenza HA N-terminal stalk domain polypeptide comprises one or more to-tyrosine mutations, for example at one or more of positions 403, 406, 411, 422, 429, 432, 433, or 435 of SEQ ID NO: 1, or positions corresponding thereto (for example as determined by alignment to SEQ ID NO: 1) or at one or more of positions 112, 115, 120, 131, 137, 141, 142, or 144 of SEQ ID NO: 117, or positions corresponding thereto (for example as determined by alignment to SEQ ID NO: 117).

In some embodiments, the present invention provides influenza HA polypeptides, proteins, and/or protein complexes that comprise both (a) one or more targeted cross-links, such as di-tyrosine cross-links in their stalk domain which serve to stabilize or "lock" the stalk domain in its native trimeric conformation, and/or one or more "to-tyrosine" mutations in the HA stalk domain at locations that have been determined to be desirable locations for the formation of di-tyrosine cross-links to stabilize the stalk domain in its native trimeric conformation, for example as described above and elsewhere throughout the present patent specification, and (b) one or more artificially-introduced protease cleavage sites that can be used to proteolytically remove the head domain of the HA polypeptide, protein, and/or protein complex, for example as described above and elsewhere throughout the present patent specification. In some embodiments, the present invention provides an influenza HA polypeptide, protein or protein complex that comprises: (a) a trimeric stalk domain that comprises one or more to-tyrosine mutations, and (b) a head domain that comprises one or more artificially-introduced protease recognition motifs. Non-limiting examples of influenza HA amino acid sequences that comprise both a to-tyrosine mutation and an artificially-introduced protease cleavage site include SEQ ID NOs: 3, 4, 5, 6, 7, 8, 9, 10, 11, 12, 13, 14, 15, 16, and 17. In addition, any of the to-tyrosine mutations and protease cleave site insertions described or illustrated herein can be combined in the same HA polypeptide, protein, or protein complex.

In some embodiments, the present invention provides an influenza HA protein complex that comprises: (a) a trimeric stalk domain formed by the association of three protomers, wherein the stalk domain comprises one or more artificially-introduced targeted cross links, such as di-tyrosine cross-links (for example, to stabilize the stalk domain in its native trimeric conformation), and (b) a head domain that comprises one or more artificially-introduced protease recognition motifs.

In some embodiments, the present invention provides a method of making a headless influenza HA polypeptide, protein or protein complex, the method comprising: (a) obtaining or expressing an influenza HA protein comprising (i) a stalk domain and (ii) a head domain containing one or more artificially-introduced protease recognition motifs, (b) allowing the soluble influenza HA protein obtained or expressed in step (a) to fold into its native conformation having a head domain and a trimeric stalk domain comprised of three protomers, (c) introducing one more targeted cross-links, such as di-tyrosine cross-links, into the trimeric stalk domain in order to stabilize the stalk domain in its native trimeric conformation, and (d) subsequently proteolytically cleaving the head domain at the one or more artificially-introduced protease recognition motifs, thereby producing a headless influenza HA protein complex. In some such methods the stalk domain comprises one or more "to-tyrosine" mutations and step (c) comprises introducing one or more di-tyrosine cross-links into the trimeric stalk domain. In some such methods, the locations of the di-tyrosine cross-links, to-tyrosine mutations, and/or artificially-introduced protease cleavage sites/motifs can be those specified above and/or elsewhere throughout the present patent specification. In some such methods, the influenza HA protein may be expressed in any suitable cell type, including, but not limited to, mammalian cells or insect cells.

In some embodiments the present invention provides influenza HA polypeptides, proteins, and/or protein complexes that are derived from, comprise, consist essentially of, or consist of any one of the influenza HA amino acid sequences presented herein, or any variants or fragments thereof, that have at least about 40% or 50% or 60% or 65% or 70% or 75% or 80% or 85% or 90% or 95% or 98% or 99% identity with such amino acid sequences presented herein, wherein the influenza HA polypeptides, proteins, and/or protein complexes comprise a to-tyrosine mutation at one or more of residues 403, 406, 411, 422, 429, 432, 433, and 435, where such amino acid numbering is based upon the sequence shown in FIG. 9 (SEQ ID NO: 1), or at amino acid positions that correspond to such amino acid positions, for example as determined by alignment of an HA amino acid sequence to sequence ID NO: 1.

In some embodiments the present invention provides influenza HA polypeptides, proteins, and/or protein complexes that are derived from, comprise, consist essentially of, or consist of any one of the influenza HA amino acid sequences presented herein, or any variants or fragments thereof, that have at least about 40% or 50% or 60% or 65% or 70% or 75% or 80% or 85% or 90% or 95% or 98% or 99% identity with such amino acid sequences presented herein, wherein the influenza HA polypeptides, proteins, and/or protein complexes comprise an artificially-introduced protease cleavage site inserted after, for example immediately after, one or more of the following residues: 48, 63, 228, 278, 282, 283, 286 and 291, where such amino acid numbering is based upon the sequence shown in FIG. 9 (SEQ ID NO: 1), or at amino acid positions that correspond to such amino acid positions, for example as determined by alignment of an HA amino acid sequence to sequence ID NO: 1.

In some embodiments the present invention provides influenza HA polypeptides, proteins, and/or protein complexes that are derived from, comprise, consist essentially of, or consist of any one of the influenza HA amino acid sequences presented herein, or any variants or fragments thereof, that have at least about 40% or 50% or 60% or 65% or 70% or 75% or 80% or 85% or 90% or 95% or 98% or 99% identity with such amino acid sequences presented herein, wherein the influenza HA polypeptides, proteins, and/or protein complexes comprise two artificially-introduced protease cleavage sites, the first such site introduced immediately after residue 48 or 63, and the second such site introduced immediately after residue 228, 278, 282, 283, 286 or 291, where such amino acid numbering is based upon the sequence shown in FIG. 9 (SEQ ID NO: 1), or at amino acid positions that correspond to such amino acid positions, for example as determined by alignment of an HA amino acid sequence to sequence ID NO: 1.

In some embodiments the present invention provides influenza HA polypeptides, proteins, and/or protein complexes that are derived from, comprise, consist essentially of, or consist of any one of the influenza HA amino acid sequences presented herein, or any variants or fragments thereof, that have at least about 40% or 50% or 60% or 65% or 70% or 75% or 80% or 85% or 90% or 95% or 98% or 99% identity with such amino acid sequences presented herein, wherein the influenza HA polypeptides, proteins, and/or protein complexes comprise both (a) a tyrosine residue (whether naturally occurring or arising from a mutation to-tyrosine), at one or more of residues 308, 403, 406, 411, 422, 429, 432, 433, 435, or 437, and (b) an artificially-introduced protease cleavage site inserted immediately after one or more of the following residues: 48, 63, 228, 278, 282, 283, 286 and 291, where such amino acid numbering is based upon the sequence shown in FIG. 9 (SEQ ID NO: 1), or at amino acid positions that correspond to such amino acid positions, for example as determined by alignment of an HA amino acid sequence to sequence ID NO: 1.

In some embodiments the present invention provides influenza HA polypeptides, proteins, and/or protein complexes that are derived from, comprise, consist essentially of, or consist of any one of the influenza HA amino acid sequences presented herein, or any variants or fragments thereof, that have at least about 40% or 50% or 60% or 65% or 70% or 75% or 80% or 85% or 90% or 95% or 98% or 99% identity with such amino acid sequences presented herein, wherein the influenza HA polypeptides, proteins, and/or protein complexes comprise both (a) a tyrosine residue (whether naturally occurring or arising from a mutation to-tyrosine), at one or more of residues 308, 403, 406, 411, 422, 429, 432, 433, 435, or 437, and (b) two artificially-introduced protease cleavage sites—the first such site introduced immediately after residue 48 or 63, and the second such site introduced immediately after residue 228, 278, 282, 283, 286 or 291, where such amino acid numbering is based upon the sequence shown in FIG. 9 (SEQ ID NO: 1), or at amino acid positions that correspond to such amino acid positions, for example as determined by alignment of an HA amino acid sequence to sequence ID NO: 1.

In some embodiments the present invention provides influenza HA polypeptides, proteins, and/or protein complexes that are derived from, comprise, consist essentially of, or consist of amino acid residues 229 to 519 of SEQ ID NO: 1, or 279 to 519 of SEQ ID NO: 1, or 283 to 519 of SEQ ID NO: 1, or 284 to 519 of SEQ ID NO: 1, or 287 to 519 of SEQ ID NO: 1, or 292 to 519 of SEQ ID NO: 1, or SEQ ID NO: 96, 97, 98, 99, 100, 101, 102, 103, 104, 105, 106, 107, 108, 109, 110, or 117, or amino acid residues 1-228 of SEQ ID NO: 117, or sequences that have at least about 40% or 50% or 60% or 65% or 70% or 75% or 80% or 85% or 90% or 95% or 98% or 99% identity with such amino acid sequences, wherein the influenza HA polypeptides, proteins, and/or protein complexes comprise a tyrosine residue or to-tyrosine mutation at one or more of residues 308, 403, 406, 411, 422, 429, 432, 433, 435, or 437, where such amino acid numbering is based upon the sequence shown in FIG. 9 (SEQ ID NO: 1), or at amino acid positions that correspond to such amino acid positions, for example as determined by alignment of an HA amino acid sequence to sequence ID NO: 1, or at one or more of residues 112, 115, 120, 131, 137, 141, 142, or 144, where such amino acid numbering is based upon the sequence shown in FIG. 89 (SEQ ID NO: 117), or at amino acid positions that correspond to such amino acid positions, for example as determined by alignment of an HA amino acid sequence to sequence ID NO: 117.

In some embodiments the present invention provides influenza HA polypeptides, proteins, and/or protein complexes that are derived from, comprise, consist essentially of, or consist of amino acid residues 1 to 47 of SEQ ID NO: 1, or 1 to 62 of SEQ ID NO: 1, or sequences that have at least about 40% or 50% or 60% or 65% or 70% or 75% or 80% or 85% or 90% or 95% or 98% or 99% identity with such amino acid sequences one or more of residues 308, 403, 406, 411, 422, 429, 432, 433, 435, and 437, where such amino acid numbering is based upon the sequence shown in FIG. 9 (SEQ ID NO: 1), or at amino acid positions that correspond to such amino acid positions, for example as determined by alignment of an HA amino acid sequence to sequence ID NO: 1.

In some embodiments the present invention provides compositions and/or influenza HA protein complexes that comprise, consist essentially of, or consist of a first and a second polypeptide, wherein (a) the first (C-terminal) polypeptide comprises, consists essentially of, or consists of amino acid residues 229 to 519 of SEQ ID NO: 1, or 279 to 519 of SEQ ID NO: 1, or 283 to 519 of SEQ ID NO: 1, or 284 to 519 of SEQ ID NO: 1, or 287 to 519 of SEQ ID NO: 1, or 292 to 519 of SEQ ID NO: 1, or SEQ ID NO: 96, 97, 98, 99, 100, 101, 102, 103, 104, 105, 106, 107, 108, 109, 110, or 117, or amino acid residues 1-228 of SEQ ID NO: 117, or sequences that have at least about 40% or 50% or 60% or 65% or 70% or 75% or 80% or 85% or 90% or 95% or 98% or 99% identity with such amino acid sequences, and wherein the influenza HA polypeptides, proteins, and/or protein complexes comprise a tyrosine residue or to-tyrosine mutation, at one or more of residues 308, 403, 406, 411, 422, 429, 432, 433, 435, or 437, such amino acid numbering is based upon the sequence shown in FIG. 9 (SEQ ID NO: 1), or at amino acid positions that correspond to such amino acid positions, for example as determined by alignment of an HA amino acid sequence to sequence ID NO: 1, or at one or more of residues 112, 115, 120, 131, 137, 141, 142, or 144, where such amino acid numbering is based upon the sequence shown in FIG. 89 (SEQ ID NO: 117), or at amino acid positions that correspond to such amino acid positions, for example as determined by alignment of an HA amino acid sequence to sequence ID NO: 117, and wherein (b) the second (N-terminal) polypeptide comprises, consists essentially of, or consists of amino acid residues 1 to 47 of SEQ ID NO: 1, or 1 to 62 of SEQ ID NO: 1, where such amino acid numbering is based upon the sequence shown in FIG. 9 (SEQ ID NO: 1), or at amino acid positions that correspond to such amino acid positions, for example as determined by alignment of an HA amino acid sequence to sequence ID NO: 1, or sequences that have at least about 40% or 50% or 60% or 65% or 70% or 75% or 80% or 85% or 90% or 95% or 98% or 99% identity with such amino acid sequences.

In some embodiments, the present invention provides an influenza hemagglutinin (HA) polypeptide, protein or protein complex comprising, consisting essentially of, or consisting of, an amino acid sequence having at least 50, 55, 60, 65, or 70% sequence identity to amino acid residues 229 to 519 of SEQ ID NO: 1, wherein the amino acid sequence comprises a point mutation to tyrosine at one or more of amino acid positions 403, 406, 411, 422, 429, 432, 433, and 435, where such amino acid numbering is based upon the sequence shown in FIG. 9 (SEQ ID NO: 1), or at amino acid positions that correspond to such amino acid positions, for example as determined by alignment of an HA amino acid sequence to sequence ID NO: 1. In some embodiments, the present invention provides an influenza hemagglutinin (HA) polypeptide, protein or protein complex comprising, consisting essentially of, or consisting of, an amino acid sequence having at least 50, 55, 60, 65, or 70% sequence identity to amino acid residues 1 to 228 of SEQ ID NO: 117, wherein the amino acid sequence comprises a point mutation to-tyrosine at one or more of amino acid positions 112, 115, 120, 131, 137, 141, 142, or 144, where such amino acid numbering is based upon the sequence shown in FIG. 89 (SEQ ID NO: 117), or at amino acid positions that correspond to such amino acid positions, for example as determined by alignment of an HA amino acid sequence to sequence ID NO: 117. In some such embodiments the influenza HA polypeptide, protein or protein complex forms a part of, and/or is folded into a protein complex having, or capable of forming, a trimeric stalk conformation, and that comprises at least one di-tyrosine cross-link, wherein one or both tyrosines of the at least one di-tyrosine cross-link originate from one of the to-tyrosine mutations. In some such embodiments, the influenza HA polypeptide, protein or protein complex comprises cross-links located between one or more paired tyrosine residues, wherein the paired tyrosine residues are selected from the group consisting of residues 403 and 433; 411 and 422, 403 and 429, 403 and 432, 433 and 435, and 406 and 433, where such amino acid numbering is based upon the sequence shown in FIG. 9 (SEQ ID NO: 1), or at amino acid positions that correspond to such amino acid positions, for example as determined by alignment of an HA amino acid sequence to sequence ID NO: 1.

In some embodiments the HA polypeptides, proteins or protein complexes described herein are capable of folding into a trimeric stalk conformation. In some such embodiments, the influenza HA polypeptides, proteins or protein complexes described herein further comprise one or more point mutations to cysteine. In some embodiments, the influenza HA polypeptides, proteins or protein complexes described herein further comprise a trimerization domain, such as a foldon domain.

Non-limiting examples of influenza HA polypeptides, proteins and/or protein complexes of the invention include, but are not limited to, those of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 86, 87, 88, 89, 90. 91, 92, 93, 94, 95, 96, 97, 98, 99, 100, 101, 102, 103, 104, 105, 106, 107, 108, 109, 110, and 117.

In some embodiments the influenza HA polypeptides, proteins or protein complexes described herein are capable of eliciting production of influenza HA-specific antibodies in a subject. In some embodiments, the influenza HA polypeptides, proteins or protein complexes described herein are capable of binding to an antibody that recognizes the trimeric stalk domain of influenza HA.

In some embodiments the present invention provides nucleic acid molecules encoding the influenza HA polypeptides, proteins or protein complexes described herein.

In some embodiments, the present invention provides compositions comprising the influenza HA polypeptides, proteins or protein complexes described herein, including, but not limited to, vaccine compositions. In some such embodiments, such compositions may further comprise an adjuvant, a carrier, an immunostimulatory agent, or any combination thereof.

In some embodiments the present invention provides a method of vaccinating a subject against influenza, the method comprising administering to a subject a composition comprising an effective amount of an influenza HA polypeptide, protein or protein complex as described herein.

These and other embodiments of the present invention are described throughout the present patent specification.

BRIEF DESCRIPTIONS OF THE DRAWINGS

FIG. 1. Schematic representation of a headless universal vaccine immunogen (PR8) presenting a QNE-bnAb complex (left), and the same bnAb neutralizing HA of (a) homologous PR8, (b) drift (NL09), (c) group 1 heterologous (VN04), and (d) group 2 heterologous (x31) virus on the right.

Figures 2A, 2B:
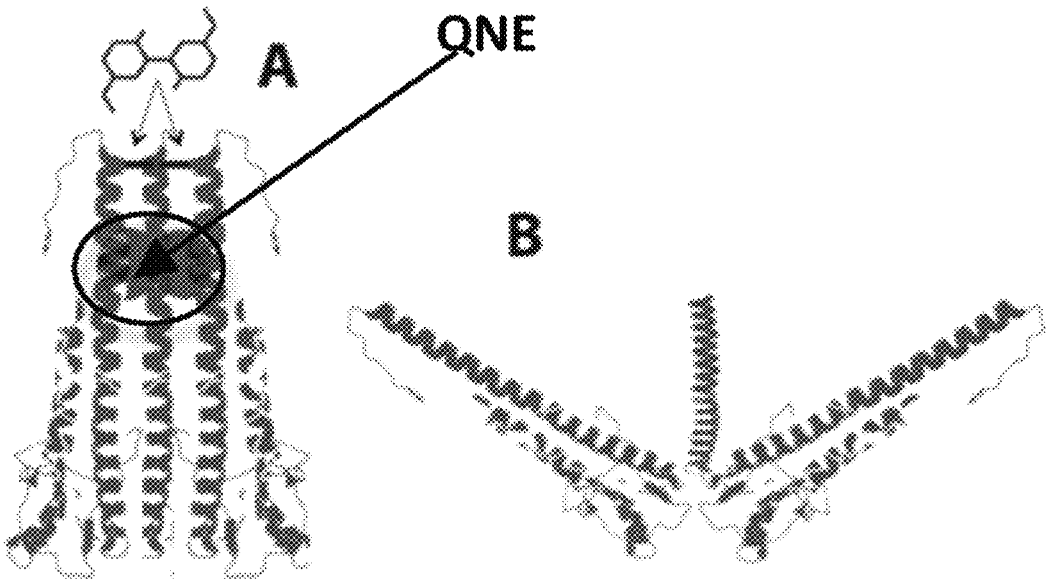

FIGS. 2A-2B. Schematic representation of DT-cross-links in headless HA stabilizing the stalk trimer. A. DT bonds (top in black) conformationally lock the stalk trimer. B. The stalk trimer has fallen apart without conformational locking. The QNE is lost.

Figure 3:
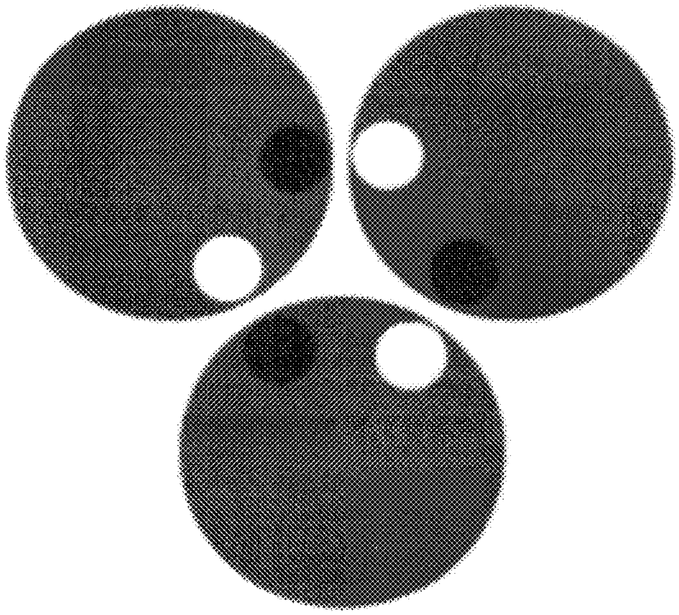

FIG. 3. Schematic diagram of a top-down view of the stalk, showing HA variant design: two amino acid substitutions per protomer (black and white circles).

FIGS. 4A-4B. (A) DT-specific fluorescence measurement at 405 nm or WT (negative control, left), four HA variants with two amino acid substitutions each, and insulin, as it forms DT bonds with high efficiency (positive control, right). (B) Relative fluorescence of dityrosine mutants. Data represents the average of four replicates with standard deviation indicated by the error bars.

Figure 5:
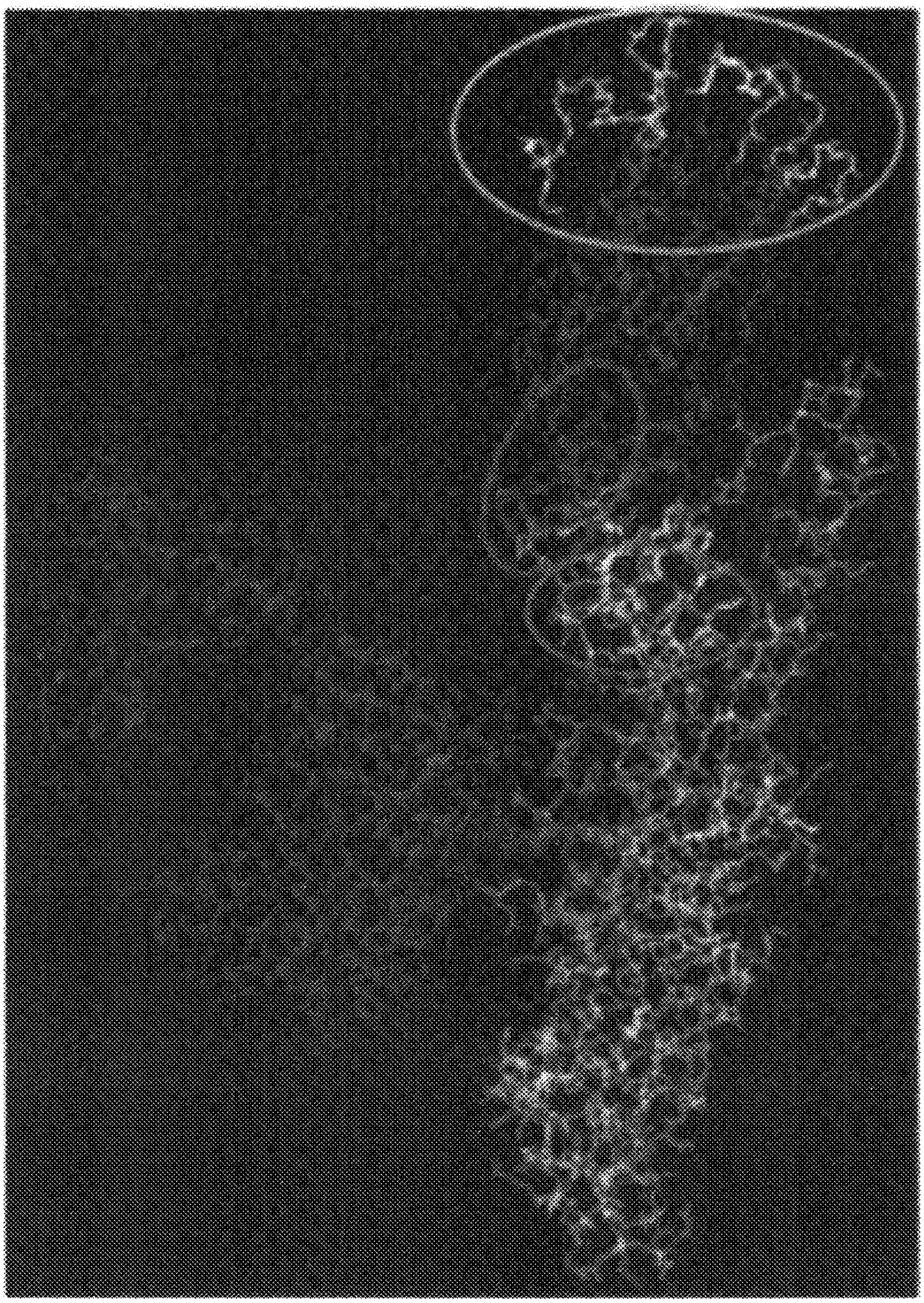

FIG. 5. Annotated crystal structure of HA bound to CRC261. The lower circle indicates the targeted area for DT bond formation, the middle circle indicates the targeted area for stalk-proximal proteolytic cleavage, and the upper circle indicates the targeted area for variable loop proteolysis designed to unravel the head to enable stalk-proximal cleavage site access.

Figure 6:
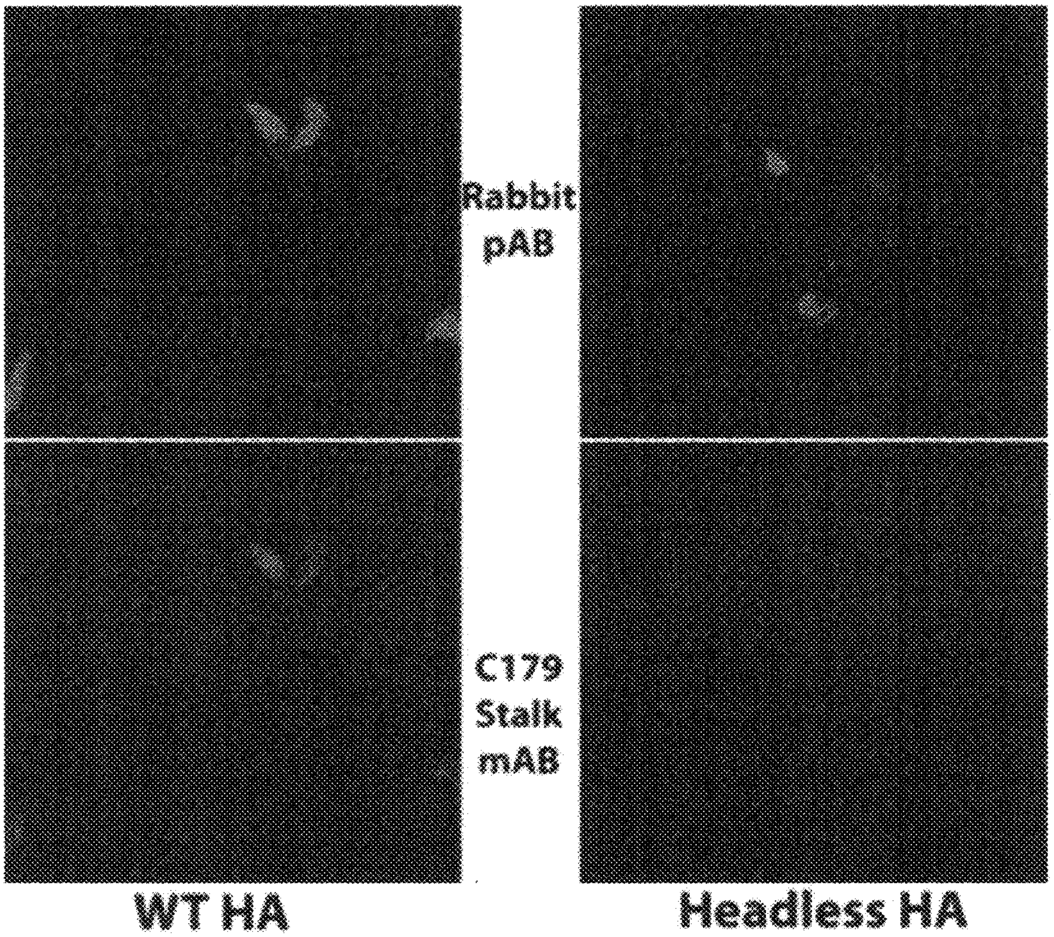

FIG. 6. Immunofluorescent staining of cells expressing WT and a headless HA protein without cross-linking to stabilize the stalk domain demonstrated that the non-stabilized headless HA protein dis not bind one of the most broadly reactive mAbs, C179. A549 cells were transfected with plasmids for the expression of either WT HA or a recombinantly-spliced headless construct without any cross-linking in the stalk domain. 24 hrs post transfection, cells were fixed, permeabilized, and the HA protein was detected with both rabbit polyclonal, pAB (general expression) (upper panels), and mAb C179 anti-stalk (conformational) (lower panels) primary Abs followed by anti-rabbit Alexa 555-conjugated and anti-mouse Alexa 488-conjugated secondary Abs.

Figures 7A, 7B:
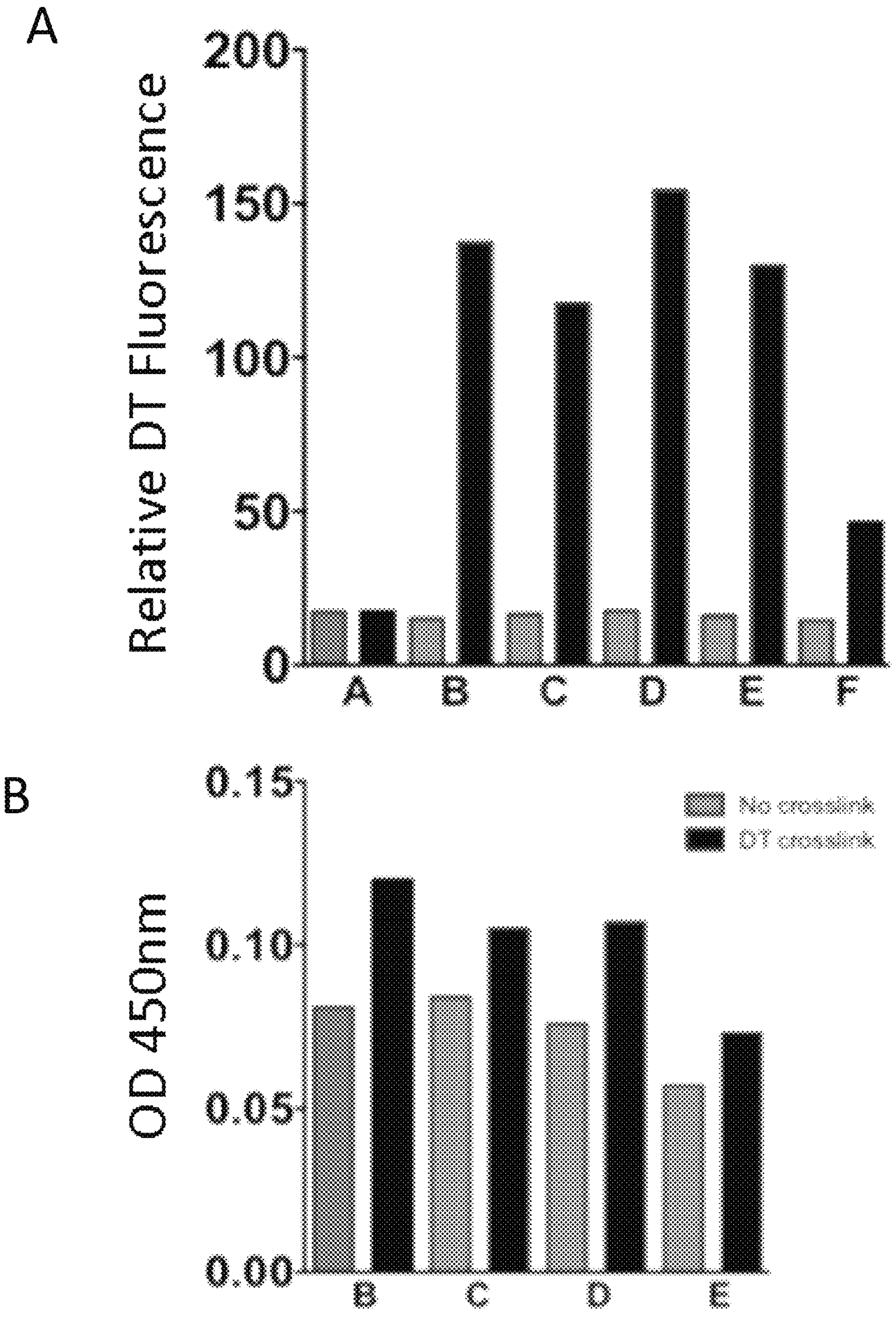

FIGS. 7A-7B. DT crosslinks form in the PR8 stalk efficiently, and C179 antigenicity is preserved before & after crosslinking. A. DT-specific fluorescence measurement at ex320/em405 nm of WT (neg. control, A), four HA variants with two amino acid substitutions each (to-Tyr substitutions), at residues 403 and 429 (B), 406 and 433 (C), 403 and 433 (D), and 403 and 432 (E) and insulin, which forms DT bonds with high efficiency (positive control, F). B. C179 binding to variants (B-E) before and after DT crosslinking, as measured by sandwich ELISA using goat polyclonal anti-HA antibody for capture (BEI catalog #NR-3148) and the C179 conformational Ab for detection.

Figures 8A, 8B, 8C:
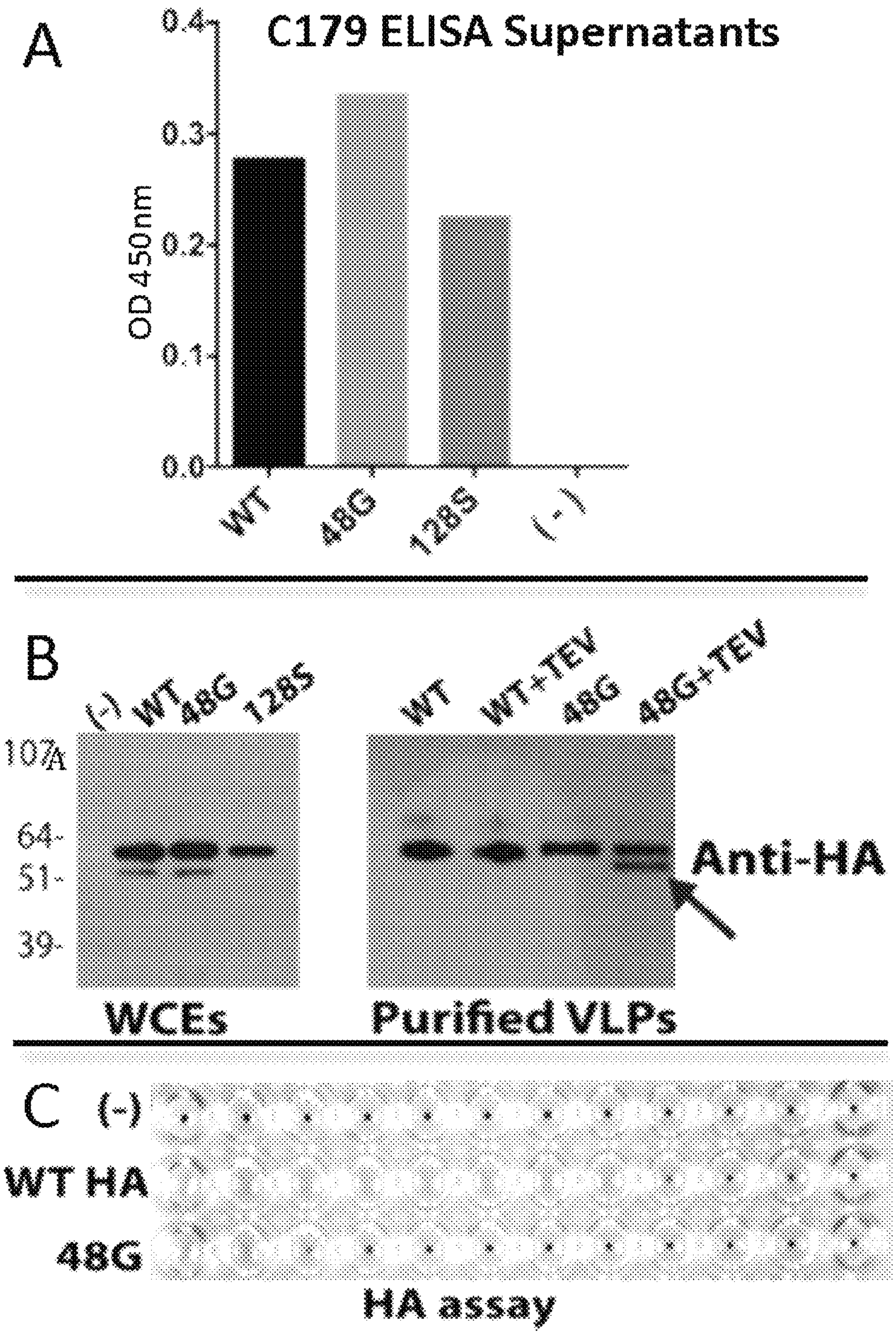

FIGS. 8A-8C. 293T cells were untransfected (−) or transfected with WT NA and the indicated HA plasmids. 72 hours post transfection, VLPs in supernatants and WCEs were analyzed by sandwich ELISA (A, BEI catalog #NR-3148 goat polyclonal anti-HA capture, C179 detection), western blot (B, left panel; PNGase treated WCE), and HA assay (C). Panel B, right. Cells were transfected as above as indicated with HA and NA. 72 hours post transfection, VLPs were purified over a 30% sucrose-NTE cushion, assayed for total protein, and either mock incubated (WT, 48G) or digested with TEV protease (WT+TEV, 48G+TEV) and PNGase treated. Percent cleavage was determined by western blot.

FIG. 9. Amino acid sequence (SEQ ID NO. 1) of HA protein from PR8 strain of H1N1 influenza virus. Amino acids 59 through 291 comprise the head domain, which may be proteolytically removed or disrupted in some embodiments. Amino acids 1 through 58 (or 18 to 58 without the signal peptide—which is located at residues 1-17) and 292 through 566 (or 292 through 529 without the transmembrane domain and cytoplasmic tail) comprise the stalk domain. The stalk domain is discontinuous and comprises both an N-terminal and a C-terminal portion of the HA protein. Amino acids 529 through 565 comprise the transmembrane region and cytoplasmic tail. The HA ectodomain (i.e. the outer exposed/non-membrane bound portion) comprises residues 1-528 (or 18 to 528 without the signal peptide).

FIG. 10. Nucleic acid sequence (SEQ ID NO. 2) of DNA encoding HA protein from PR8 strain of H1N1 influenza virus.

FIG. 11. Amino acid sequence of a modified PR8 influenza HA protein comprising inserted TEV protease cleavage sites at positions 63 and 278 (underlined), and to-tyrosine mutations at positions 403 (N403Y) and 433 (D433Y) (underlined) (SEQ ID NO:3). The boxed C-terminal sequence comprises the transmembrane region. The amino acid sequence of SEQ ID NO:3 is encoded by the nucleic acid sequence of SEQ ID NO:31 shown in FIG. 28.

FIG. 12. Amino acid sequence of a modified PR8 influenza HA protein comprising inserted TEV protease cleavage sites at positions 63 and 278 (underlined), and to-tyrosine mutations at positions 411 (K411Y) and 422 (N422Y) (underlined) (SEQ ID NO:4). The boxed C-terminal sequence comprises the transmembrane region. The amino acid sequence of SEQ ID NO:4 is encoded by the nucleic acid sequence of SEQ ID NO:32 shown in FIG. 29.

FIG. 13. Amino acid sequence of a modified PR8 influenza HA protein comprising inserted TEV protease cleavage sites at positions 63 and 278 (underlined), and to-tyrosine mutations at positions 403 (N403Y), 411 (K411Y), 422 (N422Y), and 433 (D433Y) (underlined) (SEQ ID NO:5). The boxed C-terminal sequence comprises the transmembrane region. The amino acid sequence of SEQ ID NO:5 is encoded by the nucleic acid sequence of SEQ ID NO:33 shown in FIG. 30.

FIG. 14. Amino acid sequence of a modified PR8 influenza HA protein comprising inserted TEV protease cleavage sites at positions 63 and 282 (underlined), and to-tyrosine mutations at positions 403 (N403Y) and 433 (D433Y) (underlined) (SEQ ID NO:6). The boxed C-terminal sequence comprises the transmembrane region. The amino acid sequence of SEQ ID NO:6 is encoded by the nucleic acid sequence of SEQ ID NO:34 shown in FIG. 31.

FIG. 15. Amino acid sequence of a modified PR8 influenza HA protein comprising inserted TEV protease cleavage sites at positions 63 and 282 (underlined), and to-tyrosine mutations at positions 411 (K411Y) and 422 (N422Y) (underlined) (SEQ ID NO:7). The boxed C-terminal sequence comprises the transmembrane region. The amino acid sequence of SEQ ID NO:7 is encoded by the nucleic acid sequence of SEQ ID NO:35 shown in FIG. 32.

FIG. 16. Amino acid sequence of a modified PR8 influenza HA protein comprising inserted TEV protease cleavage sites at positions 63 and 228 (underlined), and to-tyrosine mutations at positions 403 (N403Y), 411 (K411Y), 422 (N422Y), and 433 (D433Y) (underlined) (SEQ ID NO:8). The boxed C-terminal sequence comprises the transmembrane region. The amino acid sequence of SEQ ID NO:8 is encoded by the nucleic acid sequence of SEQ ID NO:36 shown in FIG. 33.

FIG. 17. Amino acid sequence of a modified PR8 influenza HA protein comprising inserted TEV protease cleavage sites at positions 63 and 283 (underlined), and to-tyrosine mutations at positions 403 (N403Y) and 433 (D433Y) (underlined) (SEQ ID NO:9). The boxed C-terminal sequence comprises the transmembrane region. The amino acid sequence of SEQ ID NO:9 is encoded by the nucleic acid sequence of SEQ ID NO:37 shown in FIG. 34.

FIG. 18. Amino acid sequence of a modified PR8 influenza HA protein comprising inserted TEV protease cleavage sites at positions 63 and 283 (underlined), and to-tyrosine mutations at positions 411 (K411Y) and 422 (N422Y) (underlined) (SEQ ID NO:10). The boxed C-terminal sequence comprises the transmembrane region. The amino acid sequence of SEQ ID NO:10 is encoded by the nucleic acid sequence of SEQ ID NO:38 shown in FIG. 35.

FIG. 19. Amino acid sequence of a modified PR8 influenza HA protein comprising inserted TEV protease cleavage sites at positions 63 and 283 (underlined), and to-tyrosine mutations at positions 403 (N403Y), 411 (K411Y), 422 (N422Y), and 433 (D433Y) (underlined) (SEQ ID NO:11). The boxed C-terminal sequence comprises the transmembrane region. The amino acid sequence of SEQ ID NO:11 is encoded by the nucleic acid sequence of SEQ ID NO:39 shown in FIG. 36.

FIG. 20. Amino acid sequence of a modified PR8 influenza HA protein comprising inserted TEV protease cleavage sites at positions 48 and 291 (underlined), and to-tyrosine mutations at positions 403 (N403Y) and 433 (D433Y) (underlined) (SEQ ID NO:12). The boxed C-terminal sequence comprises the transmembrane region. The amino acid sequence of SEQ ID NO:12 is encoded by the nucleic acid sequence of SEQ ID NO:43 shown in FIG. 40.

FIG. 21. Amino acid sequence of a modified PR8 influenza HA protein comprising inserted TEV protease cleavage sites at positions 48 and 291 (underlined), and to-tyrosine mutations at positions 411 (K411Y) and 422 (N422Y) (underlined) (SEQ ID NO:13). The boxed C-terminal sequence comprises the transmembrane region. The amino acid sequence of SEQ ID NO:13 is encoded by the nucleic acid sequence of SEQ ID NO:44 shown in FIG. 41.

FIG. 22. Amino acid sequence of a modified PR8 influenza HA protein comprising inserted TEV protease cleavage sites at positions 48 and 291 (underlined), and to-tyrosine mutations at positions 403 (N403Y), 411 (K411Y), 422 (N422Y), and 433 (D433Y) (underlined) (SEQ ID NO:14). The boxed C-terminal sequence comprises the transmembrane region. The amino acid sequence of SEQ ID NO:14 is encoded by the nucleic acid sequence of SEQ ID NO:45 shown in FIG. 42.

FIG. 23. Amino acid sequence of a modified PR8 influenza HA protein comprising inserted TEV protease cleavage sites at positions 48 and 291 (underlined), and to-tyrosine mutations at positions 403 (N403Y) and 433 (D433Y) (underlined) (SEQ ID NO:15). The boxed C-terminal sequence comprises the transmembrane region. The amino acid sequence of SEQ ID NO:15 is encoded by the nucleic acid sequence of SEQ ID NO:46 shown in FIG. 43.

FIG. 24. Amino acid sequence of a modified PR8 influenza HA protein comprising inserted TEV protease cleavage sites at positions 48 and 291 (underlined), and to-tyrosine mutations at positions 411 (K411Y) and 422 (N422Y) (underlined) (SEQ ID NO:16). The boxed C-terminal sequence comprises the transmembrane region. The amino acid sequence of SEQ ID NO:16 is encoded by the nucleic acid sequence of SEQ ID NO:47 shown in FIG. 44.

FIG. 25. Amino acid sequence of a modified PR8 influenza HA protein comprising inserted TEV protease cleavage sites at positions 48 and 291 (underlined), and to-tyrosine mutations at positions 403 (N403Y), 411 (K411Y), 422 (N422Y), and 433 (D433Y) (underlined) (SEQ ID NO:17). The boxed C-terminal sequence comprises the transmembrane region. The amino acid sequence of SEQ ID NO:17 is encoded by the nucleic acid sequence of SEQ ID NO:48 shown in FIG. 45.

FIGS. 26A-26B. Amino acid sequence alignment of modified PR8 influenza HA proteins comprising one inserted protease cleavage site, and the sequence of wild-type PR8 HA from the PR8 strain of influenza virus H1N1 (SEQ ID NO:1—identified as "PR8HA-WT" in the figure). Underlined amino acid residues indicate protease cleavage sites inserted into the wild-type sequence by substitution and/or replacement of amino acids in SEQ ID NO. 1. Protease cleavage sites are inserted immediately after the following amino acid residues: 291 (SEQ ID NO. 18 and SEQ ID NO. 19), 48 (SEQ ID NO. 20), 286 (SEQ ID NO. 21), 278 (SEQ ID NO. 22), 282, (SEQ ID NO. 23), 63 (SEQ ID NO. 24), or 283 (SEQ ID NO. 25). The inserted protease cleavage sites are TEV protease recognition sequences. The C-terminal sequences shown within the boxed portion of the alignment comprise the transmembrane regions of the influenza HA proteins. The amino acid sequences of SEQ ID NO. 18, 19, 20, 21, 22, 23, 24 and 25 are encoded by the nucleic acid sequences of SEQ ID NO. 49, 50, 52, 56, 53, 54, 51 and 55, respectively as shown in FIG. 46.

FIGS. 27A-27B. Amino acid sequence alignment of modified PR8 influenza HA proteins comprising two inserted protease cleavage sites, and the sequence of wild-type PR8 HA from the PR8 strain of influenza virus H1N1 (SEQ ID NO:1—identified as "PR8HA-WT" in the figure). Protease cleavage sites are inserted immediately after the following amino acid residues: 63 and 278 (SEQ ID NO. 26), 63 and 282 (SEQ ID NO. 27), 63 and 283 (SEQ ID NO. 28), 48 and 291 (SEQ ID NO. 29 and 30). The inserted protease cleavage sites are TEV protease recognition sequences. Underlined amino acid residues indicate the sequence located between the protease cleavage sites that would be removed from the HA sequence upon cleavage by a protease (here, TEV protease), for example to facilitate the production of a "headless" HA protein where the head domain is disrupted or removed. The C-terminal sequences shown within the boxed portion of the alignment comprise the transmembrane regions of the influenza HA proteins. Amino acid residues shown in bold (N403, F406, K411, N422, D429, L432, D433 and W435) illustrate positions where to-tyrosine mutations may be made so as to facilitate the formation of dityrosine bonds in the influenza HA stalk domain, as described herein. The amino acid sequences of SEQ ID NO. 26, 27, 28, 29 and 30 are encoded by the nucleic acid sequences of SEQ ID NO. 57, 58, 62, 60 and 61, respectively as shown in FIG. 47.

FIG. 28. Nucleic acid sequence (SEQ ID NO:31) encoding a modified PR8 influenza HA protein comprising inserted nucleic acid residues (shown in lower case) that encode TEV protease cleavage sites at positions 63 and 278 in the protein, and to-tyrosine mutations (shown in lower case) encoded at positions 403 (N403Y) and 433 (D433Y) in the protein. The boxed C-terminal sequence comprises the nucleic acid sequence that encodes the transmembrane region of the protein.

FIG. 29. Nucleic acid sequence (SEQ ID NO:32) encoding a modified PR8 influenza HA protein comprising inserted nucleic acid residues (shown in lower case) that encode TEV protease cleavage sites at positions 63 and 278 in the protein, and to-tyrosine mutations (shown in lower case) encoded at positions 411 (K411Y) and 422 (N422Y) in the protein. The boxed C-terminal sequence comprises the nucleic acid sequence that encodes the transmembrane region of the protein.

FIG. 30. Nucleic acid sequence (SEQ ID NO:33) encoding a modified PR8 influenza HA protein comprising inserted nucleic acid residues (shown in lower case) that encode TEV protease cleavage sites at positions 63 and 278 in the protein, and to-tyrosine mutations (shown in lower case) encoded at positions 403 (N403Y), 411 (K411Y), 422 (N422Y), and 433 (D433Y) in the protein. The boxed C-terminal sequence comprises the nucleic acid sequence that encodes the transmembrane region of the protein.

FIG. 31. Nucleic acid sequence (SEQ ID NO:34) encoding a modified PR8 influenza HA protein comprising inserted nucleic acid residues (shown in lower case) that encode TEV protease cleavage sites at positions 63 and 282 in the protein, and to-tyrosine mutations (shown in lower case) encoded at positions 403 (N403Y) and 433 (D433Y) in the protein. The boxed C-terminal sequence comprises the nucleic acid sequence that encodes the transmembrane region of the protein.

FIG. 32. Nucleic acid sequence (SEQ ID NO:34) encoding a modified PR8 influenza HA protein comprising inserted nucleic acid residues (shown in lower case) that encode TEV protease cleavage sites at positions 63 and 282 in the protein, and to-tyrosine mutations (shown in lower case) encoded at positions 411 (K411Y) and 422 (N422Y) in the protein. The boxed C-terminal sequence comprises the nucleic acid sequence that encodes the transmembrane region of the protein.

FIG. 33. Nucleic acid sequence (SEQ ID NO:36) encoding a modified PR8 influenza HA protein comprising inserted nucleic acid residues (shown in lower case) that encode TEV protease cleavage sites at positions 63 and 282 in the protein, and to-tyrosine mutations (shown in lower case) encoded at positions 403 (N403Y), 411 (K411Y), 422 (N422Y), and 433 (D433Y) in the protein. The boxed C-terminal sequence comprises the nucleic acid sequence that encodes the transmembrane region of the protein.

FIG. 34. Nucleic acid sequence (SEQ ID NO:37) encoding a modified PR8 influenza HA protein comprising inserted nucleic acid residues (shown in lower case) that encode TEV protease cleavage sites at positions 63 and 283 in the protein, and to-tyrosine mutations (shown in lower case) encoded at positions 403 (N403Y) and 433 (D433Y) in the protein. The boxed C-terminal sequence comprises the nucleic acid sequence that encodes the transmembrane region of the protein.

FIG. 35. Nucleic acid sequence (SEQ ID NO:38) encoding a modified PR8 influenza HA protein comprising inserted nucleic acid residues (shown in lower case) that encode TEV protease cleavage sites at positions 63 and 283 in the protein, and to-tyrosine mutations (shown in lower case) encoded at positions 411 (K411Y) and 422 (N422Y) in the protein. The boxed C-terminal sequence comprises the nucleic acid sequence that encodes the transmembrane region of the protein.

FIG. 36. Nucleic acid sequence (SEQ ID NO:39) encoding a modified PR8 influenza HA protein comprising inserted nucleic acid residues (shown in lower case) that encode TEV protease cleavage sites at positions 63 and 283 in the protein, and to-tyrosine mutations (shown in lower case) encoded at positions 403 (N403Y), 411 (K411Y), 422 (N422Y), and 433 (D433Y) in the protein. The boxed C-terminal sequence comprises the nucleic acid sequence that encodes the transmembrane region of the protein.

FIG. 37. Nucleic acid sequence (SEQ ID NO:40) encoding a modified PR8 influenza HA protein comprising inserted nucleic acid residues (shown in lower case) that encode TEV protease cleavage sites at positions 63 and 286 in the protein, and to-tyrosine mutations (shown in lower case) encoded at positions 403 (N403Y) and 433 (D433Y) in the protein. The boxed C-terminal sequence comprises the nucleic acid sequence that encodes the transmembrane region of the protein.

FIG. 38. Nucleic acid sequence (SEQ ID NO:41) encoding a modified PR8 influenza HA protein comprising inserted nucleic acid residues (shown in lower case) that encode TEV protease cleavage sites at positions 63 and 286 in the protein, and to-tyrosine mutations (shown in lower case) encoded at positions 411 (K411Y) and 422 (N422Y) in the protein. The boxed C-terminal sequence comprises the nucleic acid sequence that encodes the transmembrane region of the protein.

FIG. 39. Nucleic acid sequence (SEQ ID NO:42) encoding a modified PR8 influenza HA protein comprising inserted nucleic acid residues (shown in lower case) that encode TEV protease cleavage sites at positions 63 and 286 in the protein, and to-tyrosine mutations (shown in lower case) encoded at positions 403 (N403Y), 411 (K411Y), 422 (N422Y), and 433 (D433Y) in the protein. The boxed C-terminal sequence comprises the nucleic acid sequence that encodes the transmembrane region of the protein.

FIG. 40. Nucleic acid sequence (SEQ ID NO:43) encoding a modified PR8 influenza HA protein comprising inserted nucleic acid residues (shown in lower case) that encode TEV protease cleavage sites at positions 48 and 291 in the protein, and to-tyrosine mutations (shown in lower case) encoded at positions 403 (N403Y) and 433 (D433Y) in the protein. The boxed C-terminal sequence comprises the nucleic acid sequence that encodes the transmembrane region of the protein.

FIG. 41. Nucleic acid sequence (SEQ ID NO:44) encoding a modified PR8 influenza HA protein comprising inserted nucleic acid residues (shown in lower case) that encode TEV protease cleavage sites at positions 48 and 291 in the protein, and to-tyrosine mutations (shown in lower case) encoded at positions 411 (K411Y) and 422 (N422Y) in the protein. The boxed C-terminal sequence comprises the nucleic acid sequence that encodes the transmembrane region of the protein.

FIG. 42. Nucleic acid sequence (SEQ ID NO:45) encoding a modified PR8 influenza HA protein comprising inserted nucleic acid residues (shown in lower case) that encode TEV protease cleavage sites at positions 48 and 291 in the protein, and to-tyrosine mutations (shown in lower case) encoded at positions 403 (N403Y), 411 (K411Y), 422 (N422Y), and 433 (D433Y) in the protein. The boxed C-terminal sequence comprises the nucleic acid sequence that encodes the transmembrane region of the protein.

FIG. 43. Nucleic acid sequence (SEQ ID NO:46) encoding a modified PR8 influenza HA protein comprising inserted nucleic acid residues (shown in lower case) that encode TEV protease cleavage sites at positions 48 and 291 in the protein, and to-tyrosine mutations (shown in lower case) encoded at positions 403 (N403Y) and 433 (D433Y) in the protein. The boxed C-terminal sequence comprises the nucleic acid sequence that encodes the transmembrane region of the protein.

FIG. 44. Nucleic acid sequence (SEQ ID NO:47) encoding a modified PR8 influenza HA protein comprising inserted nucleic acid residues (shown in lower case) that encode TEV protease cleavage sites at positions 48 and 291 in the protein, and to-tyrosine mutations (shown in lower case) encoded at positions 411 (K411Y) and 422 (N422Y) in the protein. The boxed C-terminal sequence comprises the nucleic acid sequence that encodes the transmembrane region of the protein.

FIG. 45. Nucleic acid sequence (SEQ ID NO:48) encoding a modified PR8 influenza HA protein comprising inserted nucleic acid residues (shown in lower case) that encode TEV protease cleavage sites at positions 48 and 291 in the protein, and to-tyrosine mutations (shown in lower case) encoded at positions 403 (N403Y), 411 (K411Y), 422 (N422Y), and 433 (D433Y) in the protein. The boxed C-terminal sequence comprises the nucleic acid sequence that encodes the transmembrane region of the protein.

FIGS. 46A-46F. Alignment of nucleic acid sequences encoding modified PR8 influenza HA proteins comprising one inserted protease cleavage site, and the sequence of wild-type HA protein from the PR8 strain of influenza virus H1N1 (SEQ ID NO:2—identified as "RR8HA-WT" in the figure). Underlined nucleic acid residues encode TEV protease cleavage sites by substitution and/or replacement of nucleic acid residues of SEQ ID NO. 2. The nucleic acid residues are inserted into the nucleic acid sequence such that the encoded protein will have a protease cleavage site immediately after the following amino acid residues: 291 (SEQ ID NO. 49 and SEQ ID NO. 50), 48 (SEQ ID NO. 52), 286 (SEQ ID NO. 56), 278 (SEQ ID NO. 53), 282 (SEQ ID NO. 54), 63 (SEQ ID NO. 51), or 283 (SEQ ID NO. 55). The boxed C-terminal sequences comprise the sequence that encodes the transmembrane region of the protein.

FIGS. 47A-47E. Alignment of nucleic acid sequences encoding PR8 influenza HA proteins comprising two inserted protease cleavage sites, and the sequence of wild-type HA from the PR8 strain of influenza virus H1N1 (SEQ ID NO:2—identified as "PR8HA-WT" in the figure). Underlined nucleic acid residues encode TEV protease cleavage sites by substitution and/or replacement of nucleic acid residues of SEQ ID NO. 2. The nucleic acid residues are inserted into the nucleic acid sequence such that the encoded HA protein will have protease cleavage sites immediately after the following amino acid residues: 63 and 278 (SEQ ID NO. 57), 63 and 282 (SEQ ID NO. 58), 63 and 286 (SEQ ID NO. 59), 48 and 291 (SEQ ID NO. 60 and 61), and 63 and 283 (SEQ ID NO. 62). The boxed C-terminal sequences comprise the sequence that encodes the transmembrane region of the protein. Boxed nucleic acid residues (corresponding to amino acid positions N403, F406, K411, N422, D429, L432, D433 and W435 in the encoded HA protein) illustrate positions where to-tyrosine mutations may be made so as to facilitate the formation of dityrosine bonds in the stalk domain of the encoded influenza HA protein, as described herein.

FIG. 48. Nucleic acid sequence encoding HA protein of PR8 strain of influenza virus H1N1 with codon optimization for expression of the encoded HA protein in *Homo sapiens* (SEQ ID NO:63).

FIG. 49. Nucleic acid sequence encoding HA protein of PR8 strain of influenza virus H1N1 with codon optimization for expression of the encoded HA protein in *Cricetulus griseus* (SEQ ID NO:64).

FIG. 50. Nucleic acid sequence encoding HA protein of PR8 strain of influenza virus H1N1 with codon optimization for expression of the encoded HA protein in *Nicotiana benthamiana* (SEQ ID NO:65).

FIG. 51. Nucleic acid sequence encoding HA protein of PR8 strain of influenza virus H1N1 with codon optimization for expression of the encoded HA protein in *Pichia pastoris* (SEQ ID NO:66).

FIG. 52. Nucleic acid sequence encoding HA protein of PR8 strain of influenza virus H1N1 with codon optimization for expression of the encoded HA protein in *Saccharomyces cerevisiae* (SEQ ID NO:67).

FIG. 53. Nucleic acid sequence encoding HA protein of PR8 strain of influenza virus H1N1 with codon optimization for expression of the encoded HA protein in *Spodoptera frugiperda* (SEQ ID NO:68).

FIGS. 54A-54C. Alignment of amino acid sequences of full-length versions of HA proteins from various strains of influenza virus (Udorn 72 (SEQ ID NO:73), Hong Kong 68 (SEQ ID NO:74), Panama 99 (SEQ ID NO:75), Wisconsin 05 (SEQ ID NO:76), Shanghai 13 (SEQ ID NO:77), Singapore 57 (SEQ ID NO:78), Vietnam 04 (SEQ ID NO:79) and PR834 (SEQ ID NO:1), USSR 77 (SEQ ID NO:111), Texas 91 (SEQ ID NO:112), WSN 33 (SEQ ID NO:113), South Carolina 1918 (SEQ ID NO:114), and California 09 (SEQ ID NO:115)). Boxed amino acid residues (corresponding to amino acid positions 403, 406, 411, 422, 429, 432, 433 and 435 in the sequence of wild-type HA from the PR8 strain of influenza virus H1N1 (SEQ ID NO:1—identified as "WT-PR8-34" in the figure) represent positions where a mutation to a tyrosine residue is contemplated to facilitate the formation of dityrosine bonds in the stalk region of the HA protein. The italicized C-terminal sequences comprise the sequence that encodes the endogenous transmembrane region of the protein, and which can be removed or disrupted so as to generate a soluble version of influenza HA protein (see, for example, FIGS. 55-60).

FIG. 55. Amino acid sequence of a soluble version of HA protein from the PR8 strain of influenza virus (SEQ ID NO:80). Amino acids 520-565 of the endogenous transmembrane region (italicized C-terminal sequence of SEQ ID NO:1 in FIG. 54) have been replaced by an optional tag (underlined) comprising a thrombin cleavage domain, a T4 foldon trimerization motif, and a 6×His tag (SEQ ID NO: 118).

FIG. 56. Amino acid sequence of a soluble version of HA protein from the Hong Kong 68 strain of influenza virus (SEQ ID NO:81). Amino acids 521-566 of the endogenous transmembrane region (italicized C-terminal sequence of SEQ ID NO:74 in FIG. 54) have been replaced by an optional tag (underlined) comprising a thrombin cleavage domain, a T4 foldon trimerization motif, and a 6×His tag (SEQ ID NO: 118).

FIG. 57. Amino acid sequence of a soluble version of HA protein from the Wisconsin 05 strain of influenza virus (SEQ ID NO:82). Amino acids 521-566 of the endogenous transmembrane region (italicized C-terminal sequence of SEQ ID NO:76 in FIG. 54) have been replaced by an optional tag (underlined) comprising a thrombin cleavage domain, a T4 foldon trimerization motif, and a 6×His tag (SEQ ID NO: 118).

FIG. 58. Amino acid sequence of a soluble version of HA protein from the Vietnam 04 strain of influenza virus (SEQ ID NO:83). Amino acids 522-568 of the endogenous transmembrane region (italicized C-terminal sequence of SEQ ID NO:79 in FIG. 54) have been replaced by an optional tag (underlined) comprising a thrombin cleavage domain, a T4 foldon trimerization motif, and a 6×His tag (SEQ ID NO: 118).

FIG. 59. Amino acid sequence of a soluble version of HA protein from the Shanghai 13 strain of influenza virus (SEQ ID NO:84). Amino acids 515-560 of the endogenous transmembrane region (italicized C-terminal sequence of SEQ ID NO:77 in FIG. 54) have been replaced by an optional tag (underlined) comprising a thrombin cleavage domain, a T4 foldon trimerization motif, and a 6×His tag (SEQ ID NO: 118).

FIG. 60. Amino acid sequence of a soluble version of HA protein from the Singapore 57 strain of influenza virus (SEQ ID NO:85). Amino acids 516-562 of the endogenous transmembrane region (italicized C-terminal sequence of SEQ ID NO:78 in FIG. 54) have been replaced by an optional tag (underlined) comprising a thrombin cleavage domain, a T4 foldon trimerization motif, and a 6×His tag (SEQ ID NO: 118).

FIG. 61. Amino acid sequence of a modified PR8 influenza HA protein comprising to-tyrosine mutations at positions 403 (N403Y) and 429 (D429Y) (underlined) (SEQ ID NO:86).

FIG. 62. Amino acid sequence of a modified PR8 influenza HA protein comprising to-tyrosine mutations at positions 403 (N403Y) and 432 (L432Y) (underlined) (SEQ ID NO:87).

FIG. 63. Amino acid sequence of a modified PR8 influenza HA protein comprising one to-tyrosine mutations at position 403 (N403Y) (underlined) (SEQ ID NO:88).

FIG. 64. Amino acid sequence of a modified PR8 influenza HA protein comprising to-tyrosine mutations at positions 403 (N403Y) and 433 (D433Y) (underlined) (SEQ ID NO:89).

FIG. 65. Amino acid sequence of a modified PR8 influenza HA protein comprising to-tyrosine mutations at positions 433 (D433Y) and 435 (W435Y) (underlined) (SEQ ID NO:90).

FIG. 66. Amino acid sequence of a modified PR8 influenza HA protein comprising one to-tyrosine mutations at position 435 (W435Y) (underlined) (SEQ ID NO:91).

FIG. 67. Amino acid sequence of a modified PR8 influenza HA protein comprising to-tyrosine mutations at positions 406 (F406Y) and 433 (D433Y) (underlined) (SEQ ID NO:92).

FIG. 68. Amino acid sequence of a modified PR8 influenza HA protein comprising to-tyrosine mutations at positions 411 (K411Y) and 422 (N422Y) (underlined) (SEQ ID NO:93).

FIGS. 69A-69B. Amino acid sequence alignment of modified PR8 influenza HA proteins comprising one or more to-tyrosine mutations, and the sequence of wild-type PR8 HA from the PR8 strain of influenza virus H1N1 (SEQ ID NO:1—identified as "PR8HA-WT" in the figure). Dityrosine bonds may be introduced between various combinations of endogenous tyrosine residues (e.g. Y308 and Y437 of SEQ ID NO:1, shown in bold) and residues comprising to-tyrosine mutations (e.g. N403, F406, K411, N422, D429, L432, D433 and W435 of SEQ ID NO:1, shown as underlined), as described herein.

FIG. 70. Protein fragments comprising a 'headless' influenza HA protein generated after proteolysis at two protease cleavage sites (63G/278S) inserted into the full-length starting sequence (PR8 HA, SEQ ID NO:1). The first fragment (SEQ ID NO:94) is the N-terminal portion of the stalk domain and the second fragment (SEQ ID NO:96) is the C-terminal portion of the stalk domain comprising two to-tyrosine mutations at amino acid positions 120 and 150 (underlined; corresponding to amino acid positions 403 and 433, respectively, in SEQ ID NO:1).

FIG. 71. Protein fragments comprising a 'headless' influenza HA protein generated after proteolysis at two protease cleavage sites (63G/278S) inserted into the full-length starting sequence (PR8 HA, SEQ ID NO:1). The first fragment (SEQ ID NO:94) is the N-terminal portion of the stalk domain and the second fragment (SEQ ID NO:97) is the C-terminal portion of the stalk domain comprising two to-tyrosine mutations at amino acid positions 128 and 139 (underlined; corresponding to amino acid positions 411 and 422, respectively, in SEQ ID NO:1).

FIG. 72. Protein fragments comprising a 'headless' influenza HA protein generated after proteolysis at two protease cleavage sites (63G/278S) inserted into the full-length starting sequence (PR8 HA, SEQ ID NO:1). The first fragment (SEQ ID NO:94) is the N-terminal portion of the stalk domain and the second fragment (SEQ ID NO:98) is the C-terminal portion of the stalk domain comprising four to-tyrosine mutations at amino acid positions 120, 128, 139 and 150 (underlined; corresponding to amino acid positions 403, 411, 422 and 433, respectively, in SEQ ID NO:1).

FIG. 73. Protein fragments comprising a 'headless' influenza HA protein generated after proteolysis at two protease cleavage sites (63G/282S) inserted into the full-length starting sequence (PR8 HA, SEQ ID NO:1). The first fragment (SEQ ID NO:94) is the N-terminal portion of the stalk domain and the second fragment (SEQ ID NO:99) is the C-terminal portion of the stalk domain comprising two to-tyrosine mutations at amino acid positions 122 and 152 (underlined; corresponding to amino acid positions 403 and 433, respectively, in SEQ ID NO:1).

FIG. 74. Protein fragments comprising a 'headless' influenza HA protein generated after proteolysis at two protease cleavage sites (63G/282S) inserted into the full-length starting sequence (PR8 HA, SEQ ID NO:1). The first fragment (SEQ ID NO:94) is the N-terminal portion of the stalk domain and the second fragment (SEQ ID NO:100) is the C-terminal portion of the stalk domain comprising two to-tyrosine mutations at amino acid positions 130 and 141 (underlined; corresponding to amino acid positions 411 and 422, respectively, in SEQ ID NO:1).

FIG. 75. Protein fragments comprising a 'headless' influenza HA protein generated after proteolysis at two protease cleavage sites (63G/282S) inserted into the full-length starting sequence (PR8 HA, SEQ ID NO:1). The first fragment (SEQ ID NO:94) is the N-terminal portion of the stalk domain and the second fragment (SEQ ID NO:101) is the C-terminal portion of the stalk domain comprising four to-tyrosine mutations at amino acid positions 122, 130, 141 and 152 (underlined; corresponding to amino acid positions 403, 411, 422 and 433, respectively, in SEQ ID NO:1).

FIG. 76. Protein fragments comprising a 'headless' influenza HA protein generated after proteolysis at two protease cleavage sites (63G/283G) inserted into the full-length starting sequence (PR8 HA, SEQ ID NO:1). The first fragment (SEQ ID NO:94) is the N-terminal portion of the stalk domain and the second fragment (SEQ ID NO:102) is the C-terminal portion of the stalk domain comprising two to-tyrosine mutations at amino acid positions 121 and 151 (underlined; corresponding to amino acid positions 403 and 433, respectively, in SEQ ID NO:1).

FIG. 77. Protein fragments comprising a 'headless' influenza HA protein generated after proteolysis at two protease cleavage sites (63G/283G) inserted into the full-length starting sequence (PR8 HA, SEQ ID NO:1). The first fragment (SEQ ID NO:94) is the N-terminal portion of the stalk domain and the second fragment (SEQ ID NO:103) is the C-terminal portion of the stalk domain comprising two to-tyrosine mutations at amino acid positions 129 and 140 (underlined; corresponding to amino acid positions 411 and 422, respectively, in SEQ ID NO:1).

FIG. 78. Protein fragments comprising a 'headless' influenza HA protein generated after proteolysis at two protease cleavage sites (63G/283G) inserted into the full-length starting sequence (PR8 HA, SEQ ID NO:1). The first fragment (SEQ ID NO:94) is the N-terminal portion of the stalk domain and the second fragment (SEQ ID NO:104) is the C-terminal portion of the stalk domain comprising four to-tyrosine mutations at amino acid positions 121, 129, 140 and 151 (underlined; corresponding to amino acid positions 403, 411, 422 and 433, respectively, in SEQ ID NO:1).

FIG. 79. Protein fragments comprising a 'headless' influenza HA protein generated after proteolysis at two protease cleavage sites (48G/291G) inserted into the full-length starting sequence (PR8 HA, SEQ ID NO:1). The first fragment (SEQ ID NO:95) is the N-terminal portion of the stalk domain and the second fragment (SEQ ID NO:105) is the C-terminal portion of the stalk domain comprising two to-tyrosine mutations at amino acid positions 113 and 143 (underlined; corresponding to amino acid positions 403 and 433, respectively, in SEQ ID NO:1).

FIG. 80. Protein fragments comprising a 'headless' influenza HA protein generated after proteolysis at two protease cleavage sites (48G/291G) inserted into the full-length starting sequence (PR8 HA, SEQ ID NO:1). The first fragment (SEQ ID NO:95) is the N-terminal portion of the stalk domain and the second fragment (SEQ ID NO:106) is the C-terminal portion of the stalk domain comprising two to-tyrosine mutations at amino acid positions 121 and 132 (underlined; corresponding to amino acid positions 411 and 422, respectively, in SEQ ID NO:1).

FIG. 81. Protein fragments comprising a 'headless' influenza HA protein generated after proteolysis at two protease cleavage sites (48G/291G) inserted into the full-length starting sequence (PR8 HA, SEQ ID NO:1). The first fragment (SEQ ID NO:95) is the N-terminal portion of the stalk domain and the second fragment (SEQ ID NO:107) is the C-terminal portion of the stalk domain comprising four to-tyrosine mutations at amino acid positions 113, 121, 132 and 143 (underlined; corresponding to amino acid positions 403, 411, 422 and 433, respectively, in SEQ ID NO:1).

FIG. 82. Protein fragments comprising a 'headless' influenza HA protein generated after proteolysis at two protease cleavage sites (48G/291S) inserted into the full-length starting sequence (PR8 HA, SEQ ID NO:1). The first fragment (SEQ ID NO:95) is the N-terminal portion of the stalk domain and the second fragment (SEQ ID NO:108) is the C-terminal portion of the stalk domain comprising two to-tyrosine mutations at amino acid positions 113 and 143 (underlined; corresponding to amino acid positions 403 and 433, respectively, in SEQ ID NO:1).

FIG. 83. Protein fragments comprising a 'headless' influenza HA protein generated after proteolysis at two protease cleavage sites (48G/291S) inserted into the full-length starting sequence (PR8 HA, SEQ ID NO:1). The first fragment (SEQ ID NO:95) is the N-terminal portion of the stalk domain and the second fragment (SEQ ID NO:109) is the C-terminal portion of the stalk domain comprising two to-tyrosine mutations at amino acid positions 121 and 132 (underlined; corresponding to amino acid positions 411 and 422, respectively, in SEQ ID NO:1).

FIG. 84. Protein fragments comprising a 'headless' influenza HA protein generated after proteolysis at two protease cleavage sites (48G/291S) inserted into the full-length starting sequence (PR8 HA, SEQ ID NO:1). The first fragment (SEQ ID NO:95) is the N-terminal portion of the stalk domain and the second fragment (SEQ ID NO:110) is the C-terminal portion of the stalk domain comprising four to-tyrosine mutations at amino acid positions 113, 121, 132 and 143 (underlined; corresponding to amino acid positions 403, 411, 422 and 433, respectively, in SEQ ID NO:1).

Figure 85:
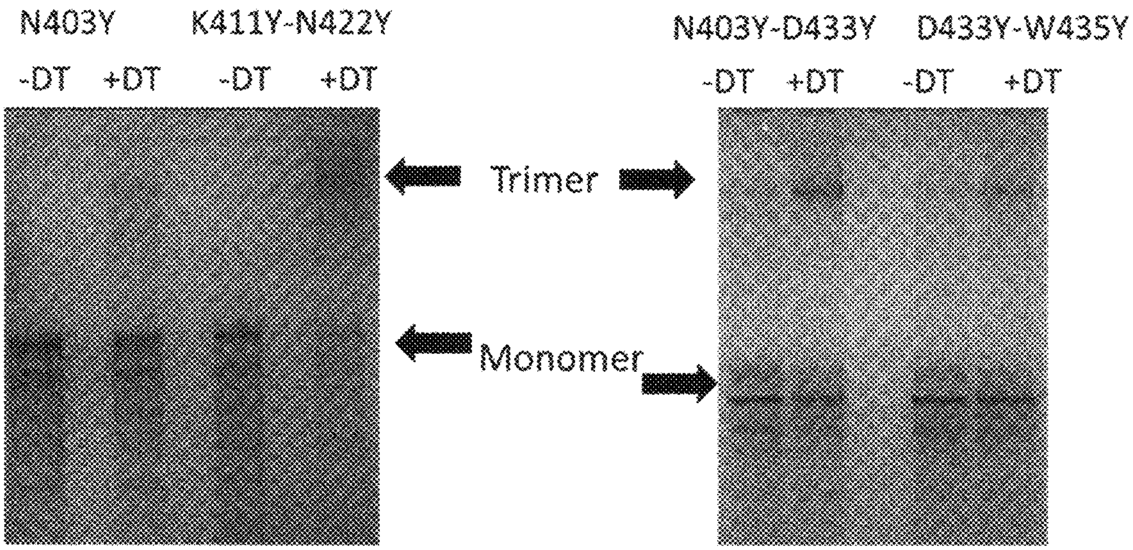
Figure 85B:
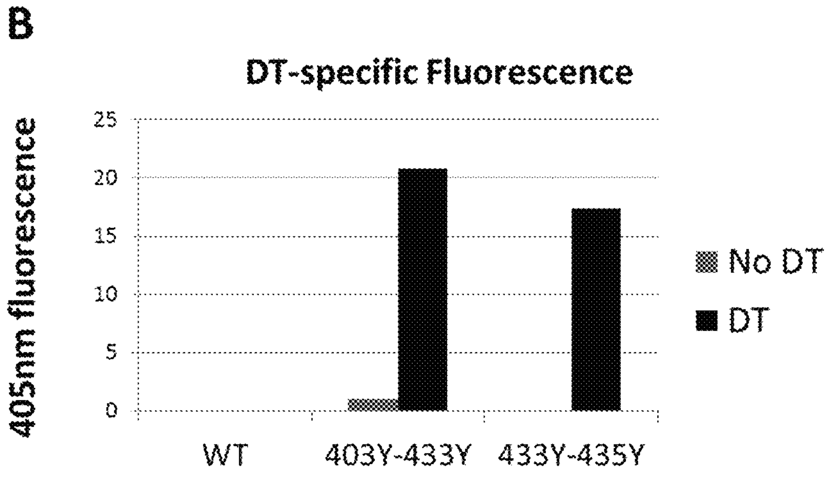
Figure 85C:
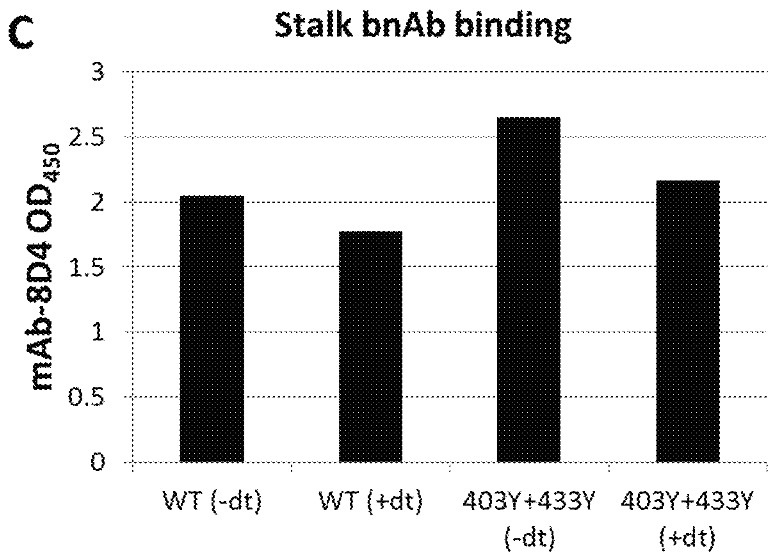

FIGS. 85A-85C. (A) 293T Cells were transfected with constructs for the expression of the indicated HA dityrosine mutants (403Y, 411Y-422Y, 403Y-433Y and 433Y-435Y) and soluble HA protein (with a C-terminal foldon domain) was purified from supernatants 72 hours post transfection by $Ni^{2+}$ affinity chromatography. Pure HA protein was then subjected to dityrosine crosslinking conditions in the presence (+) or absence (−) of the required ARP peroxidase enzyme and analyzed by reducing SDS-PAGE followed by Coomassie blue staining. The arrow marks the migration of the monomer and crosslinked trimer, as indicated. (B) To confirm the formation of Dityrosine crosslinks, the purified crosslinked and uncrosslinked samples, obtained as described in A, were analyzed for DT-specific fluorescence: excitation wavelength: 320 nm, emission wavelength: 405 nm. (C) Binding of the soluble 403Y-433Y HA mutant, before and after crosslinking, to the broadly neutralizing $V_H$1-69 stalk-specific mAb 8D4 by direct capture ELISA at 20 μg/ml of 8D4.

FIGS. 86A-86B. (A) 293T cells were transfected with plasmids for the expression of HA (WT and the indicated insertion mutants) and NA. Virus-like particles were analyzed by direct capture ELISA from transfected cell supernatants with a globular head antibody, PY-102. (B) VLPs obtained as described in A were purified over a 30% Sucrose-NTE cushion. 10 ug of total protein was then incubated in cleavage buffer in the presence (+) or absence (−) of TEV protease (Promega), according to the manufacturer's instructions. Cleavage efficiency was monitored by Western Blot using an anti-HA2 antibody. Arrows indicate the cleavage product of each of the indicated insertions (48G, 63G, and 278S).

Figure 87:
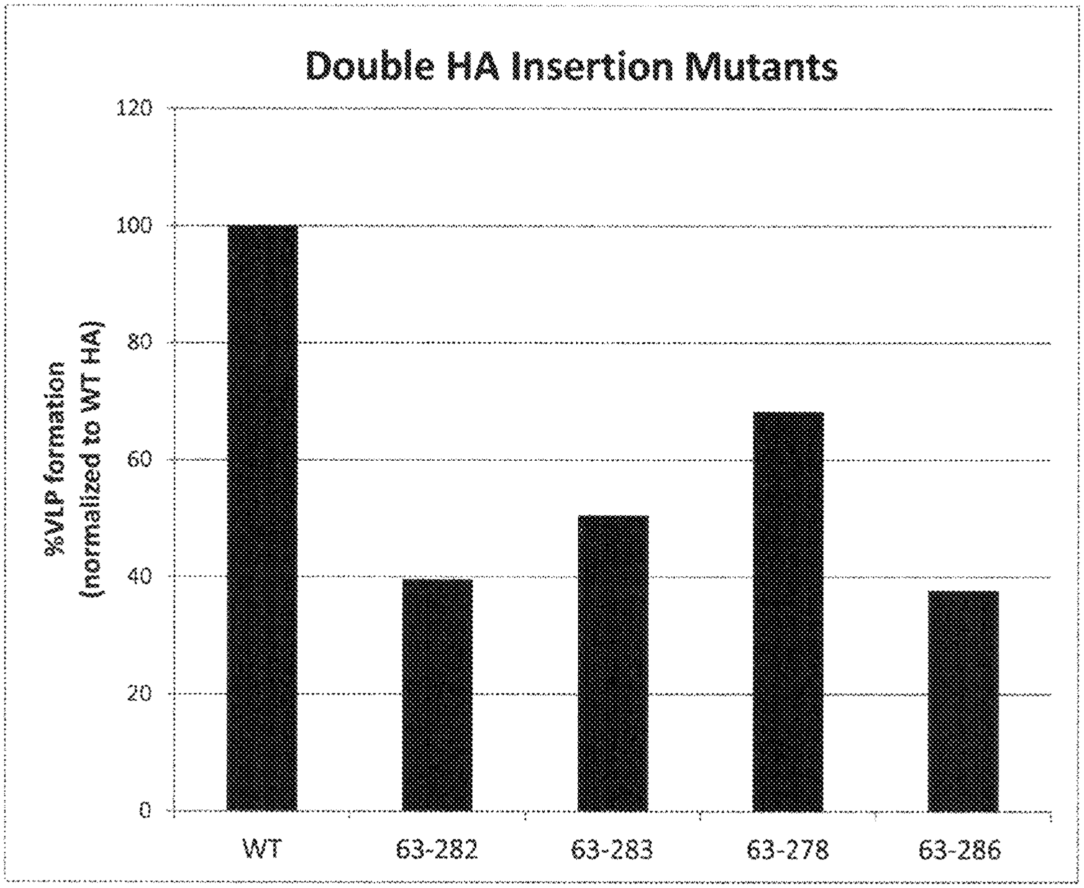
Figure 87:
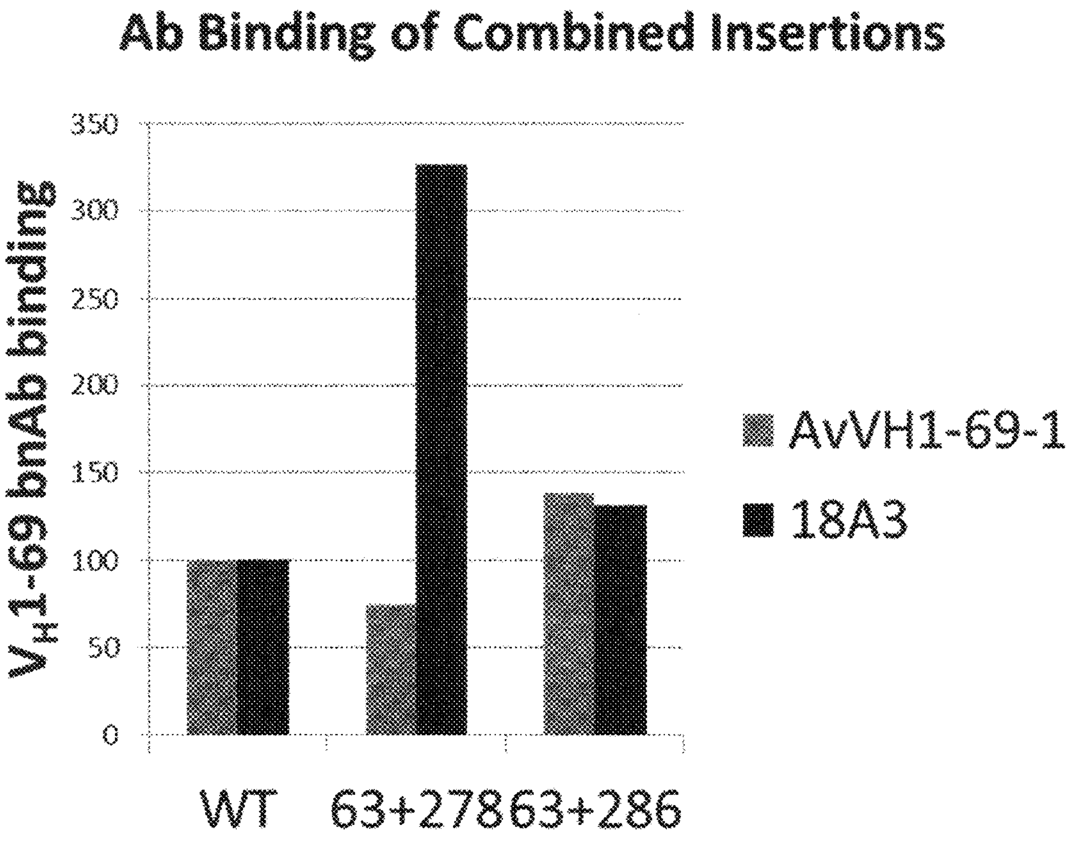

FIGS. 87A-87B. (A) 293T cells were transfected with plasmids for the expression of HA (WT and the indicated double-insertion mutants) and NA. Virus-like particles were analyzed by direct capture ELISA from transfected cell supernatants with a globular head antibody, PY-102. (B) Binding of the double-insertion HA mutants (insertions at positions 63+278, and 63+286) to two broadly neutralizing $V_H$1-69 stalk-specific mAb by direct capture ELISA at 50 μg/ml (normalized for HA presence in supernatants).

FIG. 88. Amino acid sequences of influenza HA C-terminal fragments generated following proteolysis at a protease cleavage site inserted at position 291 of the wild-type PR8 HA amino acid sequence (SEQ ID NO:1). The sequence of SEQ ID NO:108 comprises to-tyrosine mutations at positions 113 and 143 (underlined; corresponding to positions 403 and 433, respectively, of SEQ ID NO:1). The sequence of SEQ ID NO:109 comprises to-tyrosine mutations at positions 121 and 132 (underlined; corresponding to positions 411 and 422, respectively, of SEQ ID NO:1). The sequence of SEQ ID NO:110 comprises to-tyrosine mutations at positions 113, 121, 132 and 143 (underlined; corresponding to positions 403, 411, 422 and 433, respectively, of SEQ ID NO:1). The C-terminal transmembrane region is underlined in each sequence.

FIG. 89. Amino acid sequence of an influenza HA protein C-terminal fragment (SEQ ID NO: 117). This fragment is generated following proteolysis at a protease cleavage site inserted at position 291 of the wild-type PR8 HA amino acid sequence (SEQ ID NO:1). Underlined amino acid residues N112, F115, K120, N131, D137, L141, D142 and W144 illustrate positions in SEQ ID NO: 117 where to-tyrosine mutations can be made to facilitate the formation di-tyrosine bonds. The underlined residues correspond to positions N403, F406, K411, N422, D429, L432, D433 and W435 respectively, of SEQ ID NO:1. The C-terminal transmembrane region is underlined. In some embodiments the transmembrane region is absent (i.e. the fragment does not contain the last 46 amino acid residues (229-274 of SEQ ID NO: 117, but contains residues 1-228 of SEQ ID NO: 117). Tyrosine residues at positions 17 and 146 (shown in bold italic) are endogenous tyrosine residues that may be used in the formation of dityrosine bonds. These endogenous residues correspond to tyrosine residues at positions 308 and 437, respectively, of SEQ ID NO:1.

DETAILED DESCRIPTION OF THE INVENTION

The present invention provides, in part, influenza HA polypeptides, proteins and/or protein complexes (such as those that comprise a stalk domain having its native conformation and that may or may not comprise an intact head domain), methods of making such polypeptides, proteins and/or protein complexes, compositions (such as pharmaceutical compositions and vaccine compositions) comprising such polypeptides, proteins and/or protein complexes, and methods of use of such polypeptides, proteins and/or protein complexes, for example in vaccination methods, therapeutic methods and other methods. In some embodiments, the influenza HA polypeptides, proteins and/or protein complexes may be useful as immunogens, for example in influenza vaccines.

DEFINITIONS AND ABBREVIATIONS

As used in the present specification the terms "about" and "approximately," when used in relation to numerical values, mean within + or −20% of the stated value.

The abbreviation "HA" as used herein refers to a hemagglutinin protein. The abbreviation "Ab" as used herein refers to antibody. The abbreviation "bnAbs" as used herein refers to broadly neutralizing antibodies. The abbreviation "QNE" as used herein refers to quaternary neutralizing epitopes. The abbreviation "DT" as used herein refers to di-tyrosine. As used herein the phrase "full-length" when used in relation to an influenza HA protein or polypeptide does not require an HA protein or polypeptide that is as long as a wild-type influenza HA protein. Rather the term is used to refer to an influenza HA protein or polypeptide that comprises, at least, both a stalk domain and a head domain. Such stalk and head domains may or may not be as long as those found in a wild-type influenza HA protein or polypeptide. For example, an influenza HA protein or polypeptide that is missing the transmembrane domain found in a wild-type influenza HA protein or polypeptide may still be referred to as a "full-length" HA protein or polypeptide herein if it has a stalk domain and a head domain. In some embodiments, the phrase "full-length," when used in relation to an influenza HA protein or polypeptide, may refer to an influenza HA protein or polypeptide that, in addition to a stalk and head domain, also comprises a transmembrane domain. As used herein the phrase "soluble" when used in relation to an influenza HA protein or polypeptide refers to an influenza HA protein or polypeptide that does not comprise a transmembrane domain. Such soluble HA proteins or polypeptides may comprise either a stalk domain and a head domain, or stalk domain in the absence of a head domain.

As used herein the terms "protein" and "polypeptide" are used interchangeably, unless otherwise stated. As used herein the term "protein complex" refers to an assembly of two or more proteins or protein subunits, such as two or more monomers. Unless otherwise stated, all description herein that relates to proteins and/or polypeptides applies equally to protein complexes, and vice versa.

As used herein the terms "stabilized" and "locked" are used interchangeably, for example in relation to the effect of cross-linking in stabilizing or locking the stalk domain of an influenza HA protein, polypeptide, or protein complex in its native trimeric conformation. These terms do not require 100% stability. Rather these terms denote a degree of improved or increased stability. For example, in some embodiments, when the term "stabilized" is used in relation to a stalk domain cross-linked in its native trimeric conformation, the term denotes that the native trimeric conformation of the stalk domain has greater stability than it would have had prior to or without such cross-linking. Stability, and relative stability, may be measured in various ways as described in other sections of this application, for example based on the half-life of the native trimeric conformation of the stalk domain. The improvement or increase in stability may be to any degree that is useful or significant for the intended application. For example, in some embodiments stability may be increased by about 10%, 25%, 50%, 100%, 200% (i.e. 2-fold), 300% (i.e. 3-fold), 400% (i.e. 4-fold), 500% (i.e. 5-fold), 1000% (i.e. 10-fold), or more.

As used herein the terms "stem" and "stalk" are used interchangeably to refer to a stalk domain, or portion thereof, of an influenza HA protein or polypeptide.

As used herein the term "engineered" when used in relation to the influenza HA polypeptides, proteins and/or protein complexes of the invention refers generally to influenza HA polypeptides, proteins and/or protein complexes that have been altered in some way as compared to the wild-type versions of those polypeptides, proteins and/or protein complexes, for example, but not limited to, by way of removal or disruption of a particular portion or domain of the wild-type polypeptide, protein and/or protein complex (such as a transmembrane domain or a head domain) or by introduction of one or more point mutations (such as those introduced to facilitate formation of di-tyrosine bonds) or by way of introduction of one or more protease recognition motifs not ordinarily present in the wild-type polypeptide, protein and/or protein complex, or by any other modification of the polypeptide, protein and/or protein complex as compared to its wild-type form.

Other definitions and abbreviations are found throughout the specification.

Influenza and Influenza Viruses

Influenza, commonly known as "the flu", is an infectious disease of birds and mammals caused by RNA viruses of the family Orthomyxoviridae, the influenza viruses. Influenza spreads around the world in seasonal epidemics, resulting in about three to five million yearly cases of severe illness and about 250,000 to 500,000 yearly deaths, rising to millions in some pandemic years. In the 20th century three influenza pandemics occurred, each caused by the appearance of a new strain of the virus in humans, and killed tens of millions of people. Often, new influenza strains appear when an existing flu virus spreads to humans from another animal species, or when an existing human strain picks up new genes from a virus that usually infects birds or pigs.

There are three different types of influenza virus, type A, type B, and type C, with various subtypes and strains within those types.

Influenza type A viruses are the most virulent human pathogens among the three influenza types and cause the most severe disease. The influenza A virus can be subdivided into different subtypes or serotypes including, but not limited to H1N1 (which caused Spanish Flu in 1918, and Swine Flu in 2009), H2N2 (which caused Asian Flu in 1957), H3N2 (which caused Hong Kong Flu in 1968), H5N1 (which caused Bird Flu in 2004), H7N7, H1N2 (which is endemic in humans, pigs and birds), H9N2, H7N2, H7N3, H10N7, and H7N9. Wild aquatic birds are the natural hosts for a large variety of influenza A. However, domestic poultry, such as turkeys and chickens, can also become very sick and die from avian influenza, and some avian influenza A viruses also can cause serious disease and death in wild birds.

Influenza type B almost exclusively infects humans and is less common than influenza A. The only other animals known to be susceptible to influenza B infection are the seal and the ferret. Influenza type B mutates at a rate 2-3 times slower than type A and consequently is less genetically diverse, with only one influenza B serotype known. As a result of this lack of antigenic diversity, a degree of immunity to influenza B is usually acquired at an early age. However, influenza B mutates frequently enough that lasting immunity is not possible.

Influenza type C virus infects humans, dogs and pigs, sometimes causing both severe illness and local epidemics. However, influenza C is less common than the other types and usually only causes mild disease.

Influenza viruses A, B and C are very similar in their overall structure. They each comprise a viral envelope containing two main types of glycoproteins, and a central core containing the viral RNA genome and other viral proteins. Hemagglutinin ("HA") and neuraminidase ("NA") are the two large envelope glycoproteins. HA is a lectin that mediates binding of the virus to target cells and entry of the viral genome into the target cell. The various influenza A subtypes are classified based on their antibody responses to the HA and NA proteins. For example, an "H7N2 virus" designates an influenza A subtype that has an HA 7 protein and an NA 2 protein. Similarly an "H5N1" virus has an HA 5 protein and an NA 1 protein. There are currently around 17 known HA subtypes and around 10 known NA subtypes. Many different combinations of HA and NA proteins are possible. Influenza A subtypes H1N1, H1N2, and H3N2 are currently the main types in general circulation in the human population. There are also several prominent subtypes of the avian influenza A viruses that are known to infect both birds and humans—such as H5N1, H7N2, H7N7, H7N3, and H7N7 subtypes.

Within influenza type A, one can group the various different influenza subtypes in a variety of different ways, if desired. For example, influenza type A subtypes are frequently classified or grouped into different antigenic groups and antigenic subgroups based on their HA protein. Such groupings relate to the antigenicity and degree of HA sequence identity between the different subgroups. Influenza subtypes in the same antigenic group or antigenic subgroup are more similar to each other in terms of antigenicity and HA sequence than those in other antigenic groups. Antigenic group 1 consists of H1, H2, H5, H6, H8, H9, H11, H12, H13, and H16 influenza A subtypes. Antigenic group 2 consists of H3, H4, H14, H7, H10, and H15 influenza A subtypes. Within antigenic group 1, there are three antigenic subgroups, which will be referred to herein as antigenic subgroup 1A, 1B, and 1C. Antigenic subgroup 1A consists of H1, H2, H5 and H6 influenza A subtypes. Antigenic subgroup 1B consists of H11, H13 and H16 influenza A subtypes. Antigenic subgroup 1C consists of H8, H9, and H12 influenza A subtypes.

In some embodiments herein the HA polypeptides, proteins and protein complexes of the invention are generated from HA sequences from any influenza type—including type A, B, or C. In some embodiments herein the HA polypeptides, proteins and protein complexes of the invention are generated from HA sequences from influenza type A. In some embodiments herein the HA polypeptides, proteins and protein complexes of the invention are generated from HA sequences from influenza type A, antigenic group 1. In some embodiments herein the HA polypeptides, proteins and protein complexes of the invention are generated from HA sequences from influenza type A, antigenic group 1A.

In some embodiments herein the HA polypeptides, proteins and protein complexes of the invention can be used to vaccinate a subject, and provide protection against, any influenza type—including type A, B, or C. In some embodiments herein the HA polypeptides, proteins and protein complexes of the invention can be used to vaccinate a subject, and provide protection against, influenza type A. In some embodiments herein the HA polypeptides, proteins and protein complexes of the invention can be used to vaccinate a subject, and provide protection against, influenza type A, antigenic group 1. In some embodiments herein the HA polypeptides, proteins and protein complexes of the invention can be used to vaccinate a subject, and provide protection against, influenza type A, antigenic group 1A. In some embodiments herein the HA polypeptides, proteins and protein complexes of the invention can be used to vaccinate a subject, and provide protection against, influenza subtype H1. In some embodiments herein the HA polypeptides, proteins and protein complexes of the invention can be used to vaccinate a subject, and provide protection against, influenza subtypes H1 and H2. In some embodiments herein the HA polypeptides, proteins and protein complexes of the invention can be used to vaccinate a subject, and provide protection against, influenza subtypes H1, H2 and H5. In some embodiments herein the HA polypeptides, proteins and protein complexes of the invention can be used to vaccinate a subject, and provide protection against, influenza subtypes H1, H2, H5 and H6.

Tables A and B below provide some examples of the sequence identity between the HA protein of H1N1 strain PR8, or certain fragments of the HA protein, and corresponding proteins or fragments from other influenza subtypes and strains, including some from antigenic groups 1 and 2.

TABLE A

Percent identity of full-length influenza HA amino acid sequences to the PR8 amino acid sequence of SEQ ID NO: 1 (as illustrated in FIG. 54).

| Full-length influenza HA protein | % identity to SEQ ID NO: 1 |
|---|---|
| Antigenic group 1: | |
| HA-USSR-77.pro (SEQ ID NO: 111) (H1 subtype) | 90.1 |
| HA-Texas-91.pro (SEQ ID NO: 112) (H1 subtype) | 87.8 |
| HA-WSN-33.pro (SEQ ID NO: 113) (H1 subtype) | 90.1 |
| HA-SouthCarolina-1918.pro (SEQ ID NO: 114) (H1 subtype) | 88.2 |
| HA-California-09.pro (SEQ ID NO: 115) (H1 subtype) | 81.1 |
| HA-Singapore-57.pro (SEQ ID NO: 78) (H2 subtype) | 65.5 |
| HA-Vietnam-04.pro (SEQ ID NO: 79) (H5 subtype) | 63.8 |
| Antigenic group 2: | |
| HA-Udorn-72.pro (SEQ ID NO: 73) (H3 subtype) | 39.8 |
| HA-HongKong-68.pro (SEQ ID NO: 74) (H3 subtype) | 40.5 |
| HA-Panama-99.pro (SEQ ID NO: 75) (H3 subtype) | 39.2 |
| HA-Wisconsin-05.pro (SEQ ID NO: 76) (H3 subtype) | 38.7 |
| HA-Shanghai-13.pro (SEQ ID NO: 77) (H7 subtype) | 40.4 |

TABLE B

Percent identity of fragment that remains after cleavage of influenza HA protein at cleavage sites 48 and 291.

| Influenza HA protein C-terminal fragment | % identity to C-terminal fragment of SEQ ID NO: 1 |
|---|---|
| Antigenic group 1: | |
| HA-USSR-77 (H1 subtype) | 92.4 |
| HA-Texas-91 (H1 subtype) | 90.2 |
| HA-WSN-33 (H1 subtype) | 89.6 |
| HA-SouthCarolina-1918 (H1 subtype) | 89.6 |
| HA-California-09 (H1 subtype) | 85.4 |
| HA-Singapore-57 (H2 subtype) | 71.6 |
| HA-Vietnam-04 (H5 subtype) | 70.4 |
| Antigenic group 2: | |
| HA-Udorn-72 (H3 subtype) | 43.9 |
| HA-HongKong-68 (H3 subtype) | 44.5 |
| HA-Panama-99 (H3 subtype) | 43.3 |
| HA-Wisconsin-05 (H3 subtype) | 43.0 |
| HA-Shanghai-13 (H7 subtype) | 44.2 |

In addition to the sequence identities shown in the above table, the percent identity between PR8 (SEQ ID NO: 1) and sequences of H6, H9, H11, and H13 subtypes over a C-terminal fragment remaining after proteolytic cleavage of the influenza HA protein, was found to be 68.2%, 54.7%, 56.2%, and 50.5%, respectively.

Influenza HA Polypeptides, Proteins and Protein Complexes

In some embodiments the present invention provides engineered influenza HA polypeptides, proteins and/or protein complexes, compositions comprising such polypeptides, proteins and/or protein complexes, and methods of use of such polypeptides, proteins and/or protein complexes. Such proteins can be made using any suitable influenza virus HA protein as a starting point. For example, the proteins of the invention can be made using an influenza HA protein from any suitable influenza type (such as A, B, or C), subtype (including, but not limited to, H1N1, H1N2, and H3N2 subtypes) or strain (e.g. the H1N1 A/Puerto Rico/8/1934 ("PR8") strain (SEQ ID NO. 1)) of influenza virus as the starting point. One of the important features of the influenza HA polypeptides, proteins and/or protein complexes described herein is that they comprise the trimeric stalk domain of the HA protein which, unlike the highly variable head domain, is more conserved between influenza types, subtypes and strains. Accordingly, in addition to being useful as vaccine immunogens against homologous types, subtypes, and strains of influenza virus (i.e. against influenza viruses of the same type, subtype and/or strain as used as the starting point for making the influenza HA polypeptides, proteins and/or protein complexes described herein), the HA polypeptides, proteins and/or protein complexes of the invention may also be useful as vaccine immunogens against heterologous types, subtypes, and strains of influenza virus (i.e. against influenza viruses of a different type, subtype and/or strain to that used as the starting point for making the engineered HA polypeptides, proteins and/or protein complexes).

In some embodiments the present invention provides approaches for stabilizing the stalk domain of an influenza HA protein in its native trimeric conformation, including providing specific locations within the influenza HA protein that can be or should be cross-linked, and providing mutant forms of the HA protein that can facilitate the formation of such cross-links. Such cross-links and mutations can be used alone (e.g. in the context of a wild type HA protein or in the context of an HA protein that does not comprise any man-made mutations or other man-made modifications), or can be used in combination with one or more other man-made mutations, modifications, cross-links, or stabilization strategies. Thus, for example, the approaches described herein can be used in conjunction with the use of added foldon trimerization domains, stabilizing antibodies (such as 6F12, C179, CR6261, F10, A66 and D8), and/or other partially or potentially stabilizing modifications or mutations.

The present inventors have performed extensive analysis of the structure of the influenza HA protein and have developed a variety of novel design strategies and novel engineered influenza HA polypeptides, proteins, and/or protein complexes. The present invention also provides methods for making and using such influenza HA polypeptides, proteins, and/or protein complexes. In some embodiments, the present invention provides specific locations within the amino acid sequence of the influenza HA protein at which, or between which, targeted cross-links can be made in order to "lock" the stalk domain of the HA protein in its native trimeric conformation. In some embodiments, the targeted cross-links are di-tyrosine cross-links. Where di-tyrosine cross-links are used, the present invention provides specific amino acid residues (or pairs of amino acid residues) that either comprise a pre-existing tyrosine residue or can be or are mutated to a tyrosine residue such that di-tyrosine cross-links can be made.

The engineered influenza HA polypeptides, proteins and/or protein complexes described herein can be made based on the sequence of any suitable influenza HA polypeptide, protein and/or protein complex, such as a wild-type (WT) influenza HA protein or polypeptide, or mutant, homolog, derivative, analog, ortholog, or any other derivative of an influenza HA polypeptide, protein and/or protein complex, provided that the HA polypeptide, protein and/or protein complex has a stalk domain, or a portion of a stalk domain, that is capable of folding into, or forming a part of, an stalk domain having a native trimeric conformation and/or is capable of binding to one or more anti-stalk antibodies. Amino acid sequences of suitable influenza HA polypeptides, proteins and/or protein complexes, and nucleic acid sequences that encode such influenza HA polypeptides, proteins and/or protein complexes, are known in the art and any such amino acid or nucleic acid sequence may be used. Furthermore, amino acid sequences of several suitable influenza HA polypeptides, proteins and/or protein complexes, and nucleic acid sequences that encode such influenza HA polypeptides, proteins and/or protein complexes, are provided herein. While any suitable influenza virus HA protein can be used as a starting point for making the soluble influenza HA polypeptides, proteins and/or protein complexes described herein, such an HA protein should at least comprise a stalk domain, or a portion of a stalk domain, that is capable of folding into a native trimeric conformation and/or that is capable of binding to one or more anti-stalk antibodies, such as neutralizing anti-stalk antibodies. In some embodiments the HA protein used as a starting point is a full-length wild-type HA protein comprising a head domain and a stalk domain, and optionally also a transmembrane domain. In some embodiments the HA protein used lacks a transmembrane domain or lacks a functional or intact transmembrane domain. In some embodiments the HA protein comprises a T4 foldon trimerization motif. In some embodiments the HA proteins that are used as a starting point for making the influenza HA polypeptides, proteins and/or protein complexes described herein: (a) comprise a stalk domain, or a portion of a stalk domain, that is capable of folding into a native trimeric conformation and/or that is capable of binding to one or more neutralizing anti-stalk antibodies, (b) comprise a T4 foldon trimerization motif, and (c) lack a functional or intact transmembrane domain.

Throughout the present patent specification, when reference is made to specific amino acid residues or specific amino acid regions in the influenza HA protein by referring to their amino residue number or numbers (such as amino acid residues 403 and 422, for example), and unless otherwise stated, the numbering is based on the HA amino acid sequence provided herein in, FIG. 9 and SEQ ID NO: 1—which is an amino acid sequence of a wild-type HA protein from influenza strain PR8 (influenza type A—H1N1 subtype). However, it should be noted, and one of skill in the art will understand, that different HA sequences may have different numbering systems, for example, if there are additional amino acid residues added or removed as compared to SEQ ID NO: 1 (for example, as illustrated in FIGS. 26 and 27 and many of the other Figures and sequences herein). As such, it is to be understood that when specific amino acid residues are referred to by their number, the description is not limited to only amino acids located at precisely that numbered position when counting from the beginning of a given amino acid sequence, but rather that the equivalent/corresponding amino acid residue in any and all HA sequences is intended—even if that residue is not at the same precise numbered position, for example if the HA sequence is shorter or longer than SEQ ID NO. 1, or has insertions or deletions as compared to SEQ ID NO. 1. One of skill in the art can readily determine what is the corresponding/equivalent amino acid position to any of the specific numbered residues recited herein, for example by aligning a given HA sequence to SEQ ID NO. Thus, in embodiments where specific amino acid residues of the influenza HA protein are referred to, it is to be understood that the invention is not to be limited to sequences having the specified amino acid properties (e.g. presence of a tyrosine residue, a mutation, or an insertion of a protease recognition site, etc.) at only those precise numbered amino acid positions. Rather the specified amino acid properties may be located at any position in any influenza HA protein that is equivalent/corresponding to the numbered positions recited for the PR8 influenza HA protein of SEQ ID NO:1. This description applies equally where references are made to specific nucleic acid residues or specific nucleic acid regions in a nucleotide sequence encoding an influenza HA protein by referring to their nucleic acid residue number or numbers. Thus, unless otherwise stated, the numbering is based on the nucleotide sequence provided herein in FIG. 10 and SEQ ID NO. 2.

In some embodiments, the influenza HA polypeptides, proteins or protein complexes of the present invention can be derived from (or can comprise, consist essentially of, or consist of) the amino acid sequences of any suitable influenza HA polypeptide, protein or protein complex sequence known in the art, including, without limitation: the amino acid sequence of the PR8 strain of H1N1 influenza virus (for example, in a full-length form (SEQ ID NO:1) or a soluble form (SEQ ID NO:80; or amino acid residues 1-519 thereof), the amino acid sequence of the Udorn 72 strain of H3N2 influenza virus (for example, in a full-length form (SEQ ID NO:73) or a soluble form comprising amino acid residues 1-520 thereof), the amino acid sequence of the Hong Kong 68 strain of H3N2 influenza virus (for example, in a full-length form (SEQ ID NO:74) or a soluble form (SEQ ID NO:81; or amino acid residues 1-520 thereof)), the amino acid sequence of the Panama 99 strain of H3N2 influenza virus (for example, in a full-length form (SEQ ID NO:75) or a soluble form comprising amino acid residues 1-520 thereof), the amino acid sequence of the Wisconsin 05 strain of H3N2 influenza virus (for example, in a full-length form (SEQ ID NO:76) or a soluble form (SEQ ID NO:82; or amino acid residues 1-520 thereof)), the amino acid sequence of the Shanghai 13 strain of H7N9 influenza virus (for example, in a full-length form (SEQ ID NO:77) or a soluble form (SEQ ID NO:84; or amino acid residues 1-514 thereof)), the amino acid sequence of the Singapore 57 strain of H2N2 influenza virus (for example, in a full-length form (SEQ ID NO:78) or a soluble form (SEQ ID NO:85; or amino acid residues 1-515 thereof)), the amino acid sequence of the Vietnam 04 strain of H5N1 influenza virus (for example, in a full-length form (SEQ ID NO:79) or a soluble form (SEQ ID NO:83; or amino acid residues 1-521 thereof)), the amino acid sequence of the USSR 77 strain of H1N1 influenza virus (for example, in a full-length form (SEQ ID NO:111) or a soluble form comprising amino acid residues 1-519 thereof), the amino acid sequence of the Texas 91 strain of H1N1 influenza virus (for example, in a full-length form (SEQ ID NO:112) or a soluble form comprising amino acid residues 1-519 thereof), the amino acid sequence of the WSN 33 strain of H1N1 influenza virus (for example, in a full-length form (SEQ ID NO:113) or a soluble form comprising amino acid residues 1-518 thereof), the amino acid sequence of the South Carolina 1918 strain of H1N1 influenza virus (for example, in a full-length form (SEQ ID NO:114) or a soluble form comprising amino acids 1-519), the amino acid sequence of the California 09 strain of H1N1 influenza virus (for example, in a full-length form (SEQ ID NO:115) or a soluble form comprising amino acids 1-519), or any fragment thereof. In some embodiments, the influenza HA proteins and polypeptides of the present invention can be derived from (or can comprise, consist essentially of, or consist of) amino acid sequences that have at least about 40%, 50%, 60%, 65%, 70%, 75%, 80%, 85%, 90%, 95%, 98%, or 99% sequence identity to any known influenza HA sequences or to HA sequences from any known influenza groups, subgroups, families, subfamilies, types, subtypes, genera, species, strains, and/or clades, or any fragment thereof. Furthermore, in addition to the large number of specific amino acid and nucleotide molecules and sequences provided herein (including SEQ ID NO:s 1-110); the present invention also provides and encompasses amino acid and nucleotide molecules and sequences that have at least about 40%, 50%, 60%, 65%, 70%, 75%, 80%, 85%, 90%, 95%, 98%, or 99% sequence identity to any such molecules and sequences. Thus, for every embodiment herein that refers to a specific sequence or specific SEQ ID NO (such as SEQ ID NO:s 1-110), the present invention also includes variations of such embodiments that include amino acid and nucleotide molecules and sequences that have at least about 40%, 50%, 60%, 65%, 70%, 75%, 80%, 85%, 90%, 95%, 98%, or 99% sequence identity to such specific sequences or SEQ ID NOs.

In some embodiments the present invention provides engineered influenza HA polypeptides, proteins and/or protein complexes that comprise a stalk domain (for example, that has, or is capable of forming, its native trimeric conformation) and that do not comprise a head domain. Such polypeptides, proteins and/or protein complexes can be referred to as "headless" influenza HA polypeptides, proteins and/or protein complexes.

In some embodiments the present invention provides influenza HA polypeptides, proteins and/or protein complexes that comprise a stalk domain having its native trimeric conformation and a head domain. Such proteins may be referred to as "head-on" influenza HA polypeptides, proteins and/or protein complexes. In some embodiments such polypeptides, proteins and/or protein complexes may also comprise one or more engineered protease recognition motifs that can be used for proteolytic disruption and/or removal of the head domain. In some embodiments such head-on influenza HA polypeptides, proteins and/or protein complexes may be useful as, for example, intermediates in the production of "headless" influenza HA polypeptides, proteins and/or protein complexes—as described herein.

"Headless" HA variants can be obtained or generated by a variety of methods. For example in some embodiments, headless HA variants can be obtained by removal of all or part of the HA head domain, for example by proteolytic removal of the head domain, or by another other suitable means. In other embodiments headless HA variants can be obtained by expression of a nucleotide sequence encoding only the stalk domain. In some embodiments, "headless" HA variants can be generated by proteolytic cleavage of a full-length influenza HA protein at protease recognition motifs inserted into the protein such that following cleavage, the head domain sequence is cut out and at least two protein fragments comprising the stalk domain remain. FIG. 27 illustrates examples of protease cleavage motifs and shows intervening sequences of the head domain that are cut out following protease treatment. Thus, in some embodiments, for example as shown in FIG. 27, a "headless" influenza HA variant comprises at least two protein fragments—e.g. an N-terminal fragment and a C-terminal fragment—comprising the stalk domain. In some embodiments one or more fragments of a "headless" influenza protein comprise one or more to-tyrosine mutations, and/or one-or more dityrosine crosslinks. Such mutations and/or crosslinks will typically be present in the C-terminal fragment of the "headless" HA protein. (See for example SEQ ID NOs: 96-110 and 117). FIGS. 70-84 and 89 illustrate examples of some such HA peptides. In some embodiments such peptides (for example, SEQ ID NOs: 96-110 and 117) may be comprised within a larger HA molecule comprising a head domain, or they may be present in a "headless" HA protein. In some embodiments, several such peptides may associate to form an HA protein complex that is in, or is capable of forming, a trimeric stalk domain. In some embodiments an influenza HA polypeptide, protein and/or protein complex comprises the amino acid sequence of SEQ ID NO: 108, 109, 110. In some embodiments an influenza HA polypeptide, protein and/or protein complex comprises the amino acid sequence of SEQ ID NO:94 and SEQ ID NO:96, or the amino acid sequence of SEQ ID NO:94 and SEQ ID NO:97, or the amino acid sequence of SEQ ID NO:94 and SEQ ID NO:98, or the amino acid sequence of SEQ ID NO:94 and SEQ ID NO:99, or the amino acid sequence of SEQ ID NO:94 and SEQ ID NO:100, or the amino acid sequence of SEQ ID NO:94 and SEQ ID NO:101, or the amino acid sequence of SEQ ID NO:94 and SEQ ID NO:102, or the amino acid sequence of SEQ ID NO:94 and SEQ ID NO:103, or the amino acid sequence of SEQ ID NO:94 and SEQ ID NO:104, or the amino acid sequence of SEQ ID NO:95 and SEQ ID NO:106, or the amino acid sequence of SEQ ID NO:95 and SEQ ID NO:107, or the amino acid sequence of SEQ ID NO:95 and SEQ ID NO:108, or the amino acid sequence of SEQ ID NO:95 and SEQ ID NO:109, or the amino acid sequence of SEQ ID NO:95 and SEQ ID NO:110. In some embodiments an influenza HA polypeptide, protein and/or protein complex comprises an N-terminal HA peptide comprising, consisting essentially of, or consisting of, SEQ ID NO:94 or SEQ ID NO: 95, and a C-terminal HA peptide comprising, consisting essentially of, or consisting of, SEQ ID NO:96, 97, 98, 99, 100, 101, 102, 103, 104, 105, 106, 107, 108, 109 or 110, or a C-terminal HA peptide comprising, consisting essentially of, or consisting of, amino acid residues 229 to 519 of SEQ ID NO:1 wherein the amino acid sequence comprises a point mutation to tyrosine at one or more of amino acid positions 403, 406, 411, 422, 429, 432, 433, or 435, or a C-terminal HA peptide comprising, consisting essentially of, or consisting of, amino acid residues 1 to 228 of SEQ ID NO:117 wherein the amino acid sequence comprises a point mutation to tyrosine at one or more of amino acid positions 112, 115, 120, 131, 137, 141, 142, or 144.

It should be noted that amino acid residues 1 through 58 (or 18 to 58 without the signal peptide—which is located at residues 1-17) and 292 through 566 (or 292 through 529 without the transmembrane domain and cytoplasmic tail) of the PR8 HA amino acid sequence (SEQ ID NO. 1) represent the influenza HA stalk domain sequence. The stalk domain is discontinuous and comprises both an N-terminal and a C-terminal portion of the HA protein. The amino acid sequences provided here in may comprise additional domains that may be present or partially present or absent in some embodiments but not in others, for example the head domain (e.g. amino acid residues 59-291 of the PR8 HA amino acid sequence (SEQ ID NO. 1)), and/or the transmembrane and cytoplasmic region (e.g. amino acid residues 529 or 530 to 565 of the PR8 HA amino acid sequence (SEQ ID NO. 1)), and/or the signal peptide (e.g. amino acid residues 1-17 of the PR8 HA amino acid sequence (SEQ ID NO:1), and/or one or more optional exogenous (non-HA) sequences such as epitope tags, foldon domains, and the like. For example, in some embodiments an optional foldon trimerization domain, thrombin cleavage site, 6×His-tag (SEQ ID NO: 118), and/or a strep tag may be present. In some embodiments these additional sequences may be absent, modified, rearranged or replaced. For example, in some embodiments different trimerization domains may be used, or different epitope tags may be used.

In some embodiments these additional sequences may be absent, modified, rearranged or replaced, for example with different transmembrane or cytoplasmic domains.

In some embodiments the present invention provides influenza HA polypeptides, proteins, and/or protein complexes that are derived from, comprise, consist essentially of, or consist of any one of influenza HA amino acid sequences presented herein, or any variants or fragments thereof that have at least about 40% or 50% or 60% or 65% or 70% or 75% or 80% or 85% or 90% or 95% or 98% or 99% identity with such amino acid sequences presented herein, wherein the influenza HA polypeptides, proteins, and/or protein complexes comprise a tyrosine residue (whether naturally occurring or arising from a mutation to-tyrosine), at one or more of residues 308, 403, 406, 437, 411, 422, 429, 432, 433, and 435.

In some embodiments the present invention provides influenza HA polypeptides, proteins, and/or protein complexes that are derived from, comprise, consist essentially of, or consist of any one of influenza HA amino acid sequences presented herein, or any variants or fragments thereof that have at least about 40% or 50% or 60% or 65% or 70% or 75% or 80% or 85% or 90% or 95% or 98% or 99% identity with such amino acid sequences presented herein, wherein the influenza HA polypeptides, proteins, and/or protein complexes comprise an artificially-introduced protease cleavage site inserted immediately after one or more of the following residues: 48, 63, 228, 278, 282, 283, 286 and 291.

In some embodiments the present invention provides influenza HA polypeptides, proteins, and/or protein complexes that are derived from, comprise, consist essentially of, or consist of any one of influenza HA amino acid sequences presented herein, or any variants or fragments thereof that have at least about 40% or 50% or 60% or 65% or 70% or 75% or 80% or 85% or 90% or 95% or 98% or 99% identity with such amino acid sequences presented herein, wherein the influenza HA polypeptides, proteins, and/or protein complexes comprise two artificially-introduced protease cleavage sites, the first such site introduced immediately after residue 48 or 63, and the second such site introduced immediately after residue 228, 278, 282, 283, 286 or 291.

In some embodiments the present invention provides influenza HA polypeptides, proteins, and/or protein complexes that are derived from, comprise, consist essentially of, or consist of any one of influenza HA amino acid sequences presented herein, or any variants or fragments thereof that have at least about 40% or 50% or 60% or 65% or 70% or 75% or 80% or 85% or 90% or 95% or 98% or 99% identity with such amino acid sequences presented herein, wherein the influenza HA polypeptides, proteins, and/or protein complexes comprise both (a) a tyrosine residue (whether naturally occurring or arising from a mutation to-tyrosine), at one or more of residues 308, 403, 406, 437, 411, 422, 429, 432, 433, and 435, and (b) an artificially-introduced protease cleavage site inserted immediately after one or more of the following residues: 48, 63, 228, 278, 282, 283, 286 and 291.

In some embodiments the present invention provides influenza HA polypeptides, proteins, and/or protein complexes that are derived from, comprise, consist essentially of, or consist of any one of influenza HA amino acid sequences presented herein, or any variants or fragments thereof that have at least about 40% or 50% or 60% or 65% or 70% or 75% or 80% or 85% or 90% or 95% or 98% or 99% identity with such amino acid sequences presented herein, wherein the influenza HA polypeptides, proteins, and/or protein complexes comprise both (a) a tyrosine residue (whether naturally occurring or arising from a mutation to-tyrosine), at one or more of residues 308, 403, 406, 437, 411, 422, 429, 432, 433, and 435, and (b) two artificially-introduced protease cleavage sites—the first such site introduced immediately after residue 48 or 63, and the second such site introduced immediately after residue 228, 278, 282, 283, 286 or 291.

In some embodiments the present invention provides influenza HA polypeptides, proteins, and/or protein complexes that are derived from, comprise, consist essentially of, or consist of amino acid residues 229 to 519 of SEQ ID NO: 1, or 279 to 519 of SEQ ID NO: 1, or 283 to 519 of SEQ ID NO: 1, or 284 to 519 of SEQ ID NO: 1, or 287 to 519 of SEQ ID NO: 1, or 292 to 519 of SEQ ID NO: 1, or sequences that have at least about 40% or 50% or 60% or 65% or 70% or 75% or 80% or 85% or 90% or 95% or 98% or 99% identity with such amino acid sequences, wherein the influenza HA polypeptides, proteins, and/or protein complexes comprise a tyrosine residue (whether naturally occurring or arising from a mutation to-tyrosine), at one or more of residues 308, 403, 406, 437, 411, 422, 429, 432, 433, and 435.

In some embodiments the present invention provides influenza HA polypeptides, proteins, and/or protein complexes that are derived from, comprise, consist essentially of, or consist of amino acid residues 1 to 47 of SEQ ID NO: 1, or 1 to 62 of SEQ ID NO: 1, or sequences that have at least about 40% or 50% or 60% or 65% or 70% or 75% or 80% or 85% or 90% or 95% or 98% or 99% identity with such amino acid sequences.

In some embodiments the present invention provides compositions and/or influenza HA protein complexes that comprise, consist essentially of, or consist of a first and a second peptide, wherein (a) the first peptide comprises, consists essentially of, or consists of amino acid residues 229 to 519 of SEQ ID NO: 1, or 279 to 519 of SEQ ID NO: 1, or 283 to 519 of SEQ ID NO: 1, or 284 to 519 of SEQ ID NO: 1, or 287 to 519 of SEQ ID NO: 1, or 292 to 519 of SEQ ID NO: 1, or sequences that have at least about 40% or 50% or 60% or 65% or 70% or 75% or 80% or 85% or 90% or 95% or 98% or 99% identity with such amino acid sequences, and wherein the influenza HA polypeptides, proteins, and/or protein complexes comprise a tyrosine residue (whether naturally occurring or arising from a mutation to-tyrosine), at one or more of residues 308, 403, 406, 437, 411, 422, 429, 432, 433, and 435, and wherein (b) the second peptide comprises, consists essentially of, or consists of amino acid residues 1 to 47 of SEQ ID NO: 1, or 1 to 62 of SEQ ID NO: 1, or sequences that have at least about 40% or 50% or 60% or 65% or 70% or 75% or 80% or 85% or 90% or 95% or 98% or 99% identity with such amino acid sequences.

In some embodiments the present invention provides influenza HA polypeptides, proteins, and/or protein complexes that comprise one or more artificially-introduced cross-links, wherein at least one of the following amino acid residues within the influenza HA polypeptides, proteins, and/or protein complexes is artificially cross-linked to another amino acid residue in the influenza HA protein: Y308, N403, F406, Y437, K411, N422, D429, L432, D433, and W435 In some such embodiments, where the indicated position is not a tyrosine, that residue is mutated to tyrosine. In some such embodiments the cross-link is a di-tyrosine cross-link.

In some embodiments the present invention provides influenza HA polypeptides, proteins, and/or protein complexes that comprise one or more artificially-introduced cross-links, wherein such artificially introduced cross-links connect two of the following amino acid residues: Y308, N403, F406, K411, Y437, N422, D429, L432, D433, and W435. In some such embodiments, where the indicated position is not a tyrosine, that residue is mutated to tyrosine. In some such embodiment the cross-link is a di-tyrosine cross-link.

In some embodiments the present invention provides influenza HA polypeptides, proteins, and/or protein complexes in which the amino acid residues in one or more of the following pairs of amino residues are cross-linked to each other by an artificially introduced cross-link: 308/403, 308/435, 403/437, 403/429, 403/432, 403/433, 406/429, 406/433, 411/422, 422/433, 433/435 and 437/435. In some such embodiments, where the indicated position is not a tyrosine, that residue is mutated to tyrosine. In some such embodiments the cross-link is a di-tyrosine cross-link.

In some embodiments, the present invention contemplates the targeted introduction of one or more cross-links at any suitable position(s) in an influenza HA polypeptide, protein or protein complex, for example, in the stalk domain where the cross-link will or may stabilize the stalk domain in a native trimeric conformation or other conformation capable of binding anti-stalk antibodies, such as neutralizing or broadly neutralizing anti-stalk antibodies. Such stabilization may be achieved, for example, by introducing cross-links that stabilize interactions or folds within a stalk monomer or stalk protomer (intramolecular cross-link), and/or interactions between one or more stalk monomers or stalk protomers (intermolecular cross-link), or any combination of such crosslinks. In some such embodiments the cross-link is a di-tyrosine cross-link. For example, in some embodiments intermolecular di-tyrosine cross-links may be formed between tyrosine residues at positions 403 and 433, 411 and 422, or 433 and 435. Similarly, in some embodiments intermolecular di-tyrosine cross-links may be formed between a tyrosine at residue 403 and another tyrosine residue, and/or between a tyrosine at residue 433 and another residue, such as, in particular, any of the other residues described herein as potential sites for di-tyrosine cross-links, such as tyrosines (whether natural or mutated) located at residues 308, 403, 406, 411, 422, 429, 432, 433, 435, or 437.

In some embodiments the present invention provides influenza HA polypeptides, proteins, and/or protein complexes comprising an artificially introduced cross-link between two of the following regions: amino acid residues from about position 298 to about 318, amino acid residues from about position 393 to about position 413, amino acid residues from about position 396 to about position 416, amino acid residues from about position 401 to about position 421, amino acid residues from about position 412 to about position 432, amino acid residues from about position 419 to about position 439, amino acid residues from about position 422 to about position 442, amino acid residues from about position 423 to about position 443, amino acid residues from about position 425 to about position 445 and amino acid residues from about 427 to about 447. In some such embodiments the cross-link is a di-tyrosine cross-link.

In embodiments where the influenza HA polypeptides, proteins, and/or protein complexes of the invention comprise one or more di-tyrosine cross-links, di-tyrosine cross-links may be introduced between two endogenous tyrosine residues, between two tyrosine residues originating from "to-tyrosine" mutations, or between a tyrosine residue originating from a "to-tyrosine" mutation and an endogenous tyrosine residue. In some embodiments, more than one di-tyrosine cross-link is introduced into an influenza HA protein or polypeptide.

In embodiments where the influenza HA polypeptides, proteins, and/or protein complexes of the invention comprise one or more di-tyrosine cross-links, non-limiting examples of amino acid positions where a "to-tyrosine" mutation can be introduced include N403, F406, K411, N422, D429, L432, D433, W435, or any combination thereof.

In embodiments where the influenza HA polypeptides, proteins, and/or protein complexes of the invention comprise one or more di-tyrosine cross-links, non-limiting examples of preexisting or endogenous tyrosine residues that can be used to form a di-tyrosine cross-link include Y308 and Y437, or any combination thereof.

In embodiments where the influenza HA polypeptides, proteins, and/or protein complexes of the invention comprise one or more di-tyrosine cross-links, non-limiting examples of residue pairs between which a di-tyrosine cross-link can be introduced include 403/429, 403/432, 403/433, 406/429, 406/433, 411/422 and 433/435, or any combination thereof.

In embodiments where the influenza HA polypeptides, proteins, and/or protein complexes of the invention comprise one or more di-tyrosine cross-links, non-limiting examples of regions or secondary structures of the influenza HA protein from which amino acids may be selected for tyrosine substitution and/or di-tyrosine cross-linking include the stalk domain (e.g. amino acid residues 1 (with the signal peptide) or 18 (without the signal peptide) to 58, and 292 to 529 (without the transmembrane and cytoplasmic domain(s)) or 566 (with the transmembrane domain). In some embodiments the lower region of the stalk domain (comprising amino acid residues 18-46, 334-343, 344-390 and 449-503 of SEQ ID NO:1), and/or the head domain (e.g. amino acid residues 59 to 291 of SEQ ID NO:1), of the influenza HA polypeptides, proteins, and/or protein complexes of the invention may also comprise one or more di-tyrosine cross-links and/or one or more to-tyrosine mutations.

Non-limiting examples of other regions of influenza HA proteins from which one or more amino acids may be selected for tyrosine substitution and/or cross-linking include amino acid residues from about position 298 to about position 313, amino acid residues from about position 393 to about position 413, amino acid residues from about position 396 to about position 416, amino acid residues from about position 401 to about position 421, amino acid residues from about position 412 to about position 432, amino acid residues from about position 419 to about position 439, amino acid residues from about position 422 to about position 442, amino acid residues from about position 423 to about position 443, amino acid residues from about position 425 to about position 445, and amino acid residues from about position 427 to about position 447.

In some embodiments, the present invention provides influenza HA polypeptides, proteins, and/or protein complexes that are derived from, comprise, consist essentially of, or consist of, the amino acid sequence of SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 86, 87, 88, 89, 90, 91, 92, 93, 96, 97, 98, 99, 100, 101, 102, 103, 104, 105, 106, 107, 108, 109 or 110 (each of which are mutants of the influenza HA amino acid sequence that comprise one or more protease recognition sequences to facilitate proteolytic cleavage of the head domain of the HA protein, and/or one or more "to tyrosine" mutations to facilitate di-tyrosine cross-linking and to facilitate "locking" of the stalk domain of the influenza HA protein in a particular conformation, for example, in its native trimeric conformation), or any fragment thereof, such as fragments comprising amino acid the stalk domain of the influenza HA protein, or any other fragments of the influenza HA protein that may be generated proteolytically and/or that may be assembled into or form part of a functional influenza HA protein. In some embodiments, the present invention provides influenza HA polypeptides, proteins, and/or protein complexes that are derived from, comprise, consist essentially of, or consist of, an amino acid sequence having at least about 50%, 55%, 60%, 65%, 70%, 75%, 80%, 85%, 90%, 95%, 98%, or 99% sequence identity to SEQ ID NO: 3, 4, 5, 6, 7, 8, 9, 10, 11, 12, 13, 14, 15, 16, 17, 18, 19 20, 21, 22, 23, 24, 25, 26, 27, 28, 29, 30, 86, 87, 88, 89, 90, 91, 92, 93, 96, 97, 98, 99, 100, 101, 102, 103, 104, 105, 106, 107, 108, 109 or 110, or any fragment thereof.

Non-limiting examples of amino acid positions in an influenza HA protein or polypeptide to which di-tyrosine cross-links may be targeted include positions Y308 (pre-existing/endogenous Tyr residue) and N403Y (to-Tyr substitution), the positions Y308 (pre-existing/endogenous Tyr residue) and W435Y (to-Tyr substitution), the positions N403Y (to-Tyr substitution) and Y437 (pre-existing/endogenous Tyr residue), the positions N403Y (to-Tyr substitution) and D429Y (to-Tyr substitution), the positions N403Y (to-Tyr substitution) and L432Y (to-Tyr substitution), the positions N403Y (to-Tyr substitution) and D433Y (to-Tyr substitution), the positions N406Y (to-Tyr substitution) and D429Y (to-Tyr substitution), the positions N406Y (to-Tyr substitution) and D433Y (to-Tyr substitution), the positions D433Y (to-Tyr substitution) and W435Y (to-Tyr substitution), the positions K411Y (to-Tyr substitution) and W422Y (to-Tyr substitution), and the positions Y437 (pre-existing/endogenous Tyr residue) and W435Y (to-Tyr substitution). In some embodiments, the influenza HA polypeptides, proteins and/or protein complexes of the invention comprise one of the above listed di-tyrosine cross-links. In some embodiments, the influenza HA polypeptides, proteins and/or protein complexes of the invention comprise two of the above listed di-tyrosine cross-links (for example, SEQ ID NO: 5, 8, 11, 14, and 17). In some embodiments, the influenza HA polypeptides, proteins and/or protein complexes of the invention comprise three of the above listed di-tyrosine cross-links. In some embodiments, the influenza HA polypeptides, proteins and/or protein complexes of the invention comprise four of the above listed di-tyrosine cross-links. In some embodiments, the influenza HA polypeptides, proteins and/or protein complexes of the invention comprise five or more of the above listed di-tyrosine cross-links. In some embodiments, the influenza HA polypeptides, proteins and/or protein complexes of the invention comprise any combination or one or more of the above listed di-tyrosine cross-links.

Non-limiting examples of influenza HA polypeptides, proteins and/or protein complexes designed to have more than one di-tyrosine cross-link include influenza HA proteins with two "to-tyrosine" mutations, where each such tyrosine residue forms a crosslink with different endogenous/preexisting tyrosine residues, or influenza HA proteins with four "to-tyrosine" mutations, e.g. N403Y/K411Y/N422Y/D433Y, as illustrated by SEQ ID NOs: 5, 8, 11, 14 and 17 where the tyrosine at position 403 is designed to pair with the tyrosine at position 411, and the tyrosine at position 422 is designed to pair with the tyrosine at position 433, thus stabilizing the stalk domain of the HA protein by the formation of two di-tyrosine cross-links.

A bond between a first HA polypeptide and second HA polypeptide within the same protein complex (e.g. monomers that arrange to form a trimer) is an example of an inter-molecular bond. The invention provides exemplary influenza HA proteins and polypeptides comprising cross-links designed to stabilize inter-molecular interactions, as well as influenza HA polypeptides, proteins or protein complexes derived from such sequences and including the specific "to-tyrosine" mutations present in such sequences. For example, one introduced tyrosine in one monomer is designed to pair with the other introduced tyrosine on the adjacent monomer.

In some embodiments, an HA polypeptide is intra-molecularly cross-linked (e.g., both tyrosines of the cross-link are located within the same HA polypeptide). The invention provides exemplary influenza HA proteins and polypeptides comprising cross-links designed to stabilize intra-molecular interactions, including without limitation, SEQ ID NO:__________, as well as influenza HA polypeptides, proteins or protein complexes derived from such sequences and including the specific "to-tyrosine" mutations present in such sequences.

In some embodiments (including all of those described above, and those involving influenza HA polypeptides, proteins, and/or protein complexes having any of the specific amino acid sequences recited herein, and those involving variants or fragments of such influenza HA polypeptides, proteins, and/or protein complexes having less than 100% identity to the specific amino acid sequences provided herein), the influenza HA polypeptides, proteins, and/or protein complexes of the invention should have one or more desired properties, such as being capable of (1) forming a native trimeric conformation of the stalk domain, (2) having the stalk domain "locked" in a native trimeric conformation by cross-linking, (3) binding to an influenza HA stalk-specific antibody, (4) binding to a neutralizing antibody, (5) binding to a broadly neutralizing antibody, (6) binding to an antibody selected from the group consisting of 6F12, C179, CR6261, F10, A66, and D8, (7) binding to and/or activating a B cell receptor, (8) eliciting an antibody response in an animal, (9) eliciting a protective antibody response in an animal, (10) eliciting production of neutralizing antibodies in an animal, (11) eliciting production of broadly neutralizing antibodies in an animal, (12) eliciting production of antibodies that recognize quaternary neutralizing epitopes (QNEs) in an animal, and/or (13) eliciting a protective immune response in an animal. In some embodiments the influenza HA polypeptides, proteins, and/or protein complexes described herein are capable of eliciting a protective immune response against one or more influenza virus strains in an animal and/or capable of eliciting a protective immune response against both homologous and heterologous influenza virus strains in an animal.

Unless otherwise stated, all description herein that relates to specific influenza HA polypeptides, proteins, and protein complexes, relates equally to all homologs, orthologs, analogs, derivatives, mutant forms, fragments, chimeras, fusion proteins etc. thereof, such as those that have certain desired properties or features (for example those that have a stalk domain, or a portion of a stalk domain, that is capable of folding into a native trimeric conformation, or that have desired functional properties, including, but not limited to, being capable of binding to, or eliciting the production of, one or more anti-HA antibodies, such as antibodies that are specific to the influenza HA stalk domain).

Similarly, all description herein that relates to specific polypeptides, proteins, and/or protein complexes polypeptides, proteins, and/or protein complexes (e.g. those having specific amino acid sequences or those from a specific influenza type, subtype, or strain) relates equally to other related forms of such polypeptides, proteins, and/or protein complexes that may exist in nature (for example in different influenza types, subtypes or strains) or that are related to the specific sequences provides herein but have been altered artificially in some way, such as by recombinant means, chemical means, or any other means. The influenza HA polypeptides, proteins, and/or protein complexes described herein can have, or can be derived from, the nucleotide and/or amino acid sequences of any suitable influenza HA polypeptides, proteins, and/or protein complexes known in the art. In some embodiments, the influenza HA polypeptides, proteins, and/or protein complexes of the invention may be, or may be derived from, derivatives and/or analogs of specific influenza HA polypeptides, proteins, and/or protein complexes described herein or known in the art, including proteins that are substantially homologous to any such proteins, or fragments thereof (e.g., in various embodiments, those having at least about 50% or 55% or 60% or 65% or 70% or 75% or 80% or 85% or 90% or 95% or 98% or 99% identity with an amino acid or nucleic acid sequence of any specific influenza HA polypeptides, proteins, and/or protein complexes described herein or known in the art, when aligned using any suitable method known to one of ordinary skill in the art, such as, for example, using a computer homology program known in the art) or whose encoding nucleic acid is capable of hybridizing to a coding nucleic acid sequence of a protein of the invention, under high stringency, moderate stringency, or low stringency conditions.

In some embodiments, the invention provides fragments of the influenza HA polypeptides, proteins, and/or protein complexes described herein, such as those comprising, consisting essentially of, or consisting of, at least about 10 amino acids, 20 amino acids, 50 amino acids, 100 amino acids, 200 amino acids, or 500 amino acids.

In some embodiments one or more amino acid residues within a specific influenza HA polypeptide, protein, or protein complex as described herein, or as known in the art, can be deleted, added, or substituted with another amino acid. In embodiments where such mutations are introduced, the influenza HA polypeptides, proteins, or protein complexes can be micro-sequenced to determine a partial amino acid sequence. In other embodiments the nucleic acid molecules encoding the influenza HA polypeptides, proteins, and/or protein complexes can be sequenced to identify and/or confirm the introduction of mutations.

In some embodiments, one or more amino acid residues can be substituted by another amino acid having a similar polarity and that may acts as a functional equivalent, resulting in a silent alteration. In some embodiments substitutions for an amino acid within the sequence may be selected from other members of the class to which the amino acid belongs e.g. to create a conservative substitution. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In some embodiments artificial, synthetic, or non-classical amino acids or chemical amino acid analogs can be used to make the influenza HA polypeptides, proteins, and/or protein complexes of the invention. Non-classical amino acids include, but are not limited to, the D-isomers of the common amino acids, fluoro-amino acids, and "designer" amino acids such as β-methyl amino acids, Cγ-methyl amino acids, Nγ-methyl amino acids, and amino acid analogs in general. Additional non-limiting examples of non-classical amino acids include, but are not limited to: α-aminocaprylic acid, Acpa; (S)-2-aminoethyl-L-cysteine/HCl, Aecys; aminophenylacetate, Afa; 6-amino hexanoic acid, Ahx; γ-amino isobutyric acid and α-aminoisobytyric acid, Aiba; alloisoleucine, Aile; L-allylglycine, Alg; 2-amino butyric acid, 4-aminobutyric acid, and α-aminobutyric acid, Aba; p-aminophenylalanine, Aphe; b-alanine, Bal; p-bromophenylalaine, Brphe; cyclohexylalanine, Cha; citrulline, Cit; β-chloroalanine, Clala; cycloleucine, Cle; p-cholorphenylalanine, Clphe; cysteic acid, Cya; 2,4-diaminobutyric acid, Dab; 3-amino propionic acid and 2,3-diaminopropionic acid, Dap; 3,4-dehydroproline, Dhp; 3,4-dihydroxylphenylalanine, Dhphe; p-fluorophenylalanine, Fphe; D-glucoseaminic acid, Gaa; homoarginine, Hag; δ-hydroxylysine/HCl, Hlys; DL-β-hydroxynorvaline, Hnyl; homoglutamine, Hog; homophenylalanine, Hoph; homoserine, Hos; hydroxyproline, Hpr; p-iodophenylalanine, Iphe; isoserine, Ise; α-methylleucine, Mle; DL-methionine-S-methylsulfoniumchloide, Msmet; 3-(1-naphthyl) alanine, 1Nala; 3-(2-naphthyl) alanine, 2Nala; norleucine, Nle; N-methylalanine, Nmala; Norvaline, Nva; O-benzylserine, Obser; O-benzyltyrosine, Obtyr; O-ethyltyrosine, Oetyr; O-methylserine, Omser; O-methylthreonine, Omthr; O-methyltyrosine, Omtyr; Ornithine, Orn; phenylglycine; penicillamine, Pen; pyroglutamic acid, Pga; pipecolic acid, Pip; sarcosine, Sar; t-butylglycine; t-butylalanine; 3,3,3-trifluoroalanine, Tfa; 6-hydroxydopa, Thphe; L-vinylglycine, Vig; (−)-(2R)-2-amino-3-(2-aminoethylsulfonyl) propanoic acid dihydroxochloride, Aaspa; (2S)-2-amino-9-hydroxy-4,7-dioxanonanoic acid, Ahdna; (2S)-2-amino-6-hydroxy-4-oxahexanoic acid, Ahoha; (−)-(2R)-2-amino-3-(2-hydroxyethylsulfonyl) propanoic acid, Ahsopa; (−)-(2R)-2-amino-3-(2-hydroxyethylsulfanyl) propanoic acid, Ahspa; (2S)-2-amino-12-hydroxy-4,7,10-trioxadodecanoic acid, Ahtda; (2S)-2,9-diamino-4,7-dioxanonanoic acid, Dadna; (2S)-2,12-diamino-4,7,10-trioxadodecanoic acid, Datda; (S)-5,5-difluoronorleucine, Dfnl; (S)-4,4-difluoronorvaline, Dfnv; (3R)-1-1-dioxo-[1,4]thiaziane-3-carboxylic acid, Dtca; (S)-4,4,5,5,6,6,6-heptafluoronorleucine, Hfnl; (S)-5,5,6,6,6-pentafluoronorleucine, Pfnl; (S)-4,4,5,5,5-pentafluoronorvaline, Pfnv; and (3R)-1,4-thiazinane-3-carboxylic acid, Tca. Furthermore, the amino acid can be D (dextrorotary) or L (levorotary). For a review of classical and non-classical amino acids, see Sandberg et al., 1998 (Sandberg et al., 1998. New chemical descriptors relevant for the design of biologically active peptides. A multivariate characterization of 87 amino acids. J Med Chem 41(14): pp. 2481-91).

Nucleic Acids

In addition to providing certain influenza HA polypeptides, proteins, and/or protein complexes, as described herein, the present invention also provides nucleic acids encoding such influenza HA polypeptides, proteins, and/or protein complexes, and compositions and vectors comprising such nucleic acids. Such nucleic acids can be obtained or made using any suitable method known in the art. For example, nucleic acid molecules encoding influenza HA polypeptides, proteins, and/or protein complexes may be obtained from cloned DNA or made by chemical synthesis. In some embodiments the nucleic acids may be obtained by reverse transcribing RNA prepared by any of the methods known to one of ordinary skill in the art, such as random- or poly A-primed reverse transcription. Whatever the source, a nucleic acid molecule encoding an influenza HA polypeptide, protein, and/or protein complex of the present invention can be cloned into any suitable vector, such as those to be used for propagation of the nucleic acid molecule or those to be used for expression of the nucleic acid molecule. The nucleic acid may be cleaved at specific sites using various restriction enzymes, if needed. In embodiments requiring expression, the nucleic acid can be operatively linked to a promoter suitable for directing expression in the desired cell type, such as a mammalian cell or an insect cell, and may be incorporated into any suitable expression vector, such as a mammalian or insect expression vector. A nucleic acid molecule encoding an influenza HA polypeptide, protein, and/or protein complex of the present invention optimized by methods known in the art to improve expression levels of the protein expressed therefrom. For example, codon optimization may be used to minimize or eliminate variations in codon usage between species. In some embodiments an influenza HA polypeptide, protein, and/or protein complex of the present invention is derived from a nucleic acid molecule that has been codon optimized for expression in humans (see, for example, SEQ ID NO. 63 and FIG. 48), *Cricetulus griseus* (see, for example, SEQ ID NO. 64 and FIG. 49), *Nicotiana benthamiana* (see, for example, SEQ ID NO. 65 and FIG. 50), *Pichia pastoris* (see, for example, SEQ ID NO. 66 and FIG. 51), *Saccharomyces cerevisiae* (see, for example, SEQ ID NO. 67 and FIG. 52) or *Spodoptera frugiperda* (see, for example, SEQ ID NO. 68 and FIG. 53).

In some embodiments, the present invention provides nucleic acids that are derived from, comprise, consist essentially of, or consist of, the nucleic acid sequence of SEQ ID NO: 31, 32, 33, 34, 35, 36, 37, 38, 39, 40, 41, 42, 43, 44, 45, 50, 51, 52, 53, 54, 55, 56, 57, 58, 59, 60, 61, or 62 (each of which encodes a mutant of the influenza HA amino acid sequence that comprises one or more protease recognition sequences to facilitate proteolytic cleavage of the head domain of the HA protein, and/or one or more "to tyrosine" mutations to facilitate di-tyrosine cross-linking and to facilitate "locking" of the stalk domain of the influenza HA protein in a particular conformation, for example, in its native trimeric conformation), or any fragment thereof, such as fragments encoding the stalk domain of the influenza HA protein.

Furthermore, one or skill in the art can readily visualize, or make, nucleic acid molecules that comprise any one or more of the specific "to-tyrosine" mutations described herein, for example, by locating the nucleotide codon that encodes the specific amino acid residue to be mutated, and mutating the nucleotides at that codon as necessary to result in a tyrosine-encoding codon.

Cross-Linking

In some embodiments the influenza HA polypeptides and/or proteins of the invention are assembled into protein complexes having a desired conformational structure, such as the native trimeric conformation of the stalk domain, and are cross-linked in order to stabilize that conformation. Details of particular regions of the influenza HA protein that can be cross-linked, as well as particular influenza HA mutants designed to facilitate such cross-linking, are described in other sections of this application. In some embodiments the cross-links may be used to stabilize the tertiary and/or quarternary structures of the influenza HA protein. In some embodiments, the cross-linking may be intra- and/or intermolecular cross-linking. In some embodiments, the cross-links that are used are targeted cross-links. In some embodiments, the cross-links that are used are stable under physiological conditions. In some embodiments, the cross-links that are used do not lead to aggregate formation of the influenza HA protein, for example during expression and/or during storage (such as storage of compositions comprising high concentrations of the influenza HA protein). In some embodiments the introduction of such cross-links may enhance the effectiveness of the influenza HA polypeptides, proteins and proteins of the invention as immunogens, such as vaccine immunogens. In some embodiments the introduction of such cross-links may stabilize epitopes within the influenza HA protein, for example, epitopes in the stalk domain, such that the epitopes can be recognized by particular antibodies, elicit production of antibodies, and/or activate B cell receptors upon antibody binding.

In some embodiments targeted cross-linking can be used. A targeted cross-link is one that can be made to form at a particular position or positions within the influenza HA protein or protein complex. Several strategies may be used to target cross-links to specific locations in an influenza HA protein or polypeptide, such as the specific locations described herein. The present invention provides residue pairs within the influenza HA protein that, when cross-linked, can or may stabilize an influenza HA polypeptide, protein, or protein complex in a conformation that is capable of binding to, or eliciting the production of, neutralizing antibodies, and/or that is capable of generating a neutralizing antibody response in an animal. A targeted cross-link may be introduced at one or more of the locations or positions specified herein by exploiting the physical and/or chemical properties of certain amino acid side chains, for example by making use of enzymatic reactions that recognize specific amino acid sequences or three-dimensional structures, or by incorporating non-natural amino acids that have the ability to form cross-links in a folded protein or protein complex.

Cross-links or modifications may be targeted to specific sites in the structure of the influenza HA protein or polypeptide, for example the stalk domain, in order to achieve the desired outcome, e.g. stabilization of the stalk domain in its native trimeric conformation. The present invention contemplates the targeted introduction of one or more cross-links and/or other stabilizing modifications at any suitable position(s) in an influenza HA protein or polypeptide, preferably where the cross-link or modification stabilizes the stalk domain in its native trimeric conformation, or provides enhanced stabilization of the native trimeric conformation of the stalk domain. The invention contemplates that any influenza HA protein amino acid residue, residue pair, secondary structure or other region described herein for di-tyrosine cross-linking may also be used in the formation of other targeted cross-links or bonds or other modifications, including but not limited to amino acid positions Y308, N403, N406, K411, W422, D429, L432, D433, W435, and Y437 or any combination thereof; residue pairs 308/403, 308/435, 403/437, 403/429, 403/432, 403/433, 406/429, 406/433, 411/422, 433/435 and 437/435, or any combination thereof; regions or secondary structures including, for example the HA protein stalk domain or head domain; and other regions of influenza HA protein including the transmembrane domain or the lower region of the stalk domain.

In some embodiments the influenza HA polypeptides, proteins and protein complexes of the invention comprise cross-links in the stalk domain, such cross-links need not be located only in the stalk domain. In some embodiments cross-links may be located anywhere throughout the influenza HA polypeptide, protein or protein complex, including the head domain in "head-on" polypeptides, proteins and/or protein complexes, as desired. Preferably, an influenza HA polypeptide, protein and/or protein complex comprising cross-links in other regions (e.g. outside of the stalk domain) will retain one or more desired properties such as being capable of (1) forming a native trimeric conformation of the stalk domain, (2) having the stalk domain "locked" in a native trimeric conformation by cross-linking, (3) binding to an influenza HA stalk-specific antibody, (4) binding to a neutralizing antibody, (5) binding to a broadly neutralizing antibody, (6) binding to an antibody selected from the group consisting of 6F12, C179, CR6261, F10, A66, and D8, (7) binding to and/or activating a B cell receptor, (8) eliciting an antibody response in an animal, (9) eliciting a protective antibody response in an animal, (10) eliciting production of neutralizing antibodies in an animal, (11) eliciting production of broadly neutralizing antibodies in an animal, (12) eliciting production of antibodies that recognize quaternary neutralizing epitopes (QNEs) in an animal, and/or (13) eliciting a protective immune response in an animal.

A wide variety of methods of cross-linking proteins intra- and inter-molecularly are known in the art, including those having cross-links with varying lengths of spacer arms, and those with and without fluorescent and functional groups for purification. Such methods include, but are not limited to, the use of heterobifunctional cross-linkers (e.g. succinimidyl acetylthioacetate (SATA), trans-4-(maleimidylmethyl)cyclohexane-1-carboxylate (SMCC), and succinimidyl 3-(2-pyridyldithio)propionate (SPDP)), homobifunctional cross-linkers (e.g. succinimidyl 3-(2-pyridyldithio)propionate), photoreactive cross-linkers (e.g. 4-azido-2,3,5,6-tetrafluorobenzoic acid, STP ester, sodium salt (ATFB, STP ester), 4-azido-2,3,5,6-tetrafluorobenzoic acid, succinimidyl ester (ATFB, SE), 4-azido-2,3,5,6-tetrafluorobenzyl amine, hydrochloride, benzophenone-4-isothiocyanate, benzophenone-4-maleimide, 4-benzoylbenzoic acid, succinimidyl ester, N-((2-pyridyldithio)ethyl)-4-azidosalicylamide (PEAS; AET), thiol reactive cross-linkers (e.g. maleimides and iodoacetamides), amine reactive cross-linkers (e.g. glutaraldyde, bis(imido esters), bis(succinimidyl esters), diisocyanates and diacid chlorides). Because thiol groups are highly reactive and relatively rare in most proteins by comparison to amine groups, thiol-reactive cross-linking may be used in some embodiments. In cases where thiol groups are missing or not present at appropriate sites in the structures of influenza HA protein, they can be introduced using one of several thiolation methods. For example, Succinimidyl trans-4-(maleimidylmethyl)cyclohexane-1-carboxylate can be used to introduce thiol-reactive groups at amine sites.

Several oxidative cross-links are known, such as disulfide bonds (which form spontaneously and are pH and redox sensitive), and di-tyrosine bonds (which are highly stable, and irreversible under physiological conditions).

In some embodiments the cross-links stabilize the tertiary structure of an influenza HA protein. In some embodiments the cross-links stabilize the quaternary structure of an influenza HA protein. In some embodiments the cross-links stabilize both the tertiary and quaternary structure of an influenza HA protein.

In some embodiments an influenza HA polypeptide, protein and/or protein complex of the invention has cross-links that are thermostable. In some embodiments an influenza HA polypeptide, protein and/or protein complex of the invention has cross-links that are not toxic. In some embodiments an influenza HA polypeptide, protein and/or protein complex of the invention has cross-links that are targeted cross-links, or non-targeted cross-links, or reversible cross-links, or irreversible cross-links, or cross-links formed by use of homo-bifunctional cross-linking agents, or cross-links formed by use of hetero-bifunctional cross-linking agents, or cross-links formed by use of reagents that react with amine groups, or cross-links formed by use of reagents that react with thiol groups, or cross-links formed by use of reagents that are photoreactive, or cross-links formed between amino acid residues, or cross-links formed between mutated amino acid residues incorporated into the structure of the proteins or protein complexes, or oxidative cross-links, or di-tyrosine bonds, or glutaraldehyde cross-links, or any combination thereof. In some embodiments an influenza HA polypeptide, protein and/or protein complex of the invention does not have glutaraldehyde cross-links.

In some embodiments an influenza HA polypeptide, protein and/or protein complex of the invention does not have any artificially-introduced disulfide bonds, or if it does have such disulfide bonds, also has additional artificially-introduced cross-links. In some embodiments an influenza HA polypeptide, protein and/or protein complex of the invention does not have any artificially introduced disulfide bonds, but may have naturally occurring disulfide bonds. Disulfide bonds can be introduced artificially when cysteine side-chains are engineered by point mutation. Disulfide bonds are, however, known to be pH sensitive and to be dissolved under certain redox conditions, and the preventative and/or therapeutic utility of proteins and/or protein complexes engineered with disulfide cross-links, for example to be used as immunogens in vivo, may therefore be compromised. Furthermore, undesired disulfide bonds often form between proteins with free sulfhydryl groups that mediate aggregate formation (see, for example, Harris R J et al. 2004, Commercial manufacturing scale formulation and analytical characterization of therapeutic recombinant antibodies. Drug Dev Res 61 (3): 137-154; Costantino & Pikal (Eds.), 2004. Lyophilization of Biopharmaceuticals, editors Costantino & Pekal. Lyophilization of Biopharmaceuticals. Series: Biotechnology: Pharmaceutical Aspects II, see pages 453-454; Tracy et al., 2002, U.S. Pat. No. 6,465,425), which has also been reported as a problem with HIV gp120 and gp41 (Jeffs et al. 2004. Expression and characterization of recombinant oligomeric envelope glycoproteins derived from primary isolates of HIV-1. Vaccine 22:1032-1046; Schulke et al., 2002. Oligomeric and conformational properties of a proteolytically mature, disulfide-stabilized human immunodeficiency virus type 1 gp140 envelope glycoprotein. J Virol 76:7760-7776). Thus, in many embodiments it is preferred that disulfide bonding is not used, or is not used as the sole method of cross-linking.

If the structure and/or immunogenicity of an influenza HA polypeptide, protein and/or protein complex is compromised or altered by a cross-link, maintaining its overall structure and function can be achieved by controlling the availability of amino acid side-chains for the cross-linking reaction or by introducing additional cross-links or other stabilizing modifications. For example, in the case of DT cross-linking, tyrosyl side-chains that are available for reaction, but that lead to the distortion of the structure of the complex, and that compromise the immunogenicity/antigenicity of the influenza HA protein, can be removed by mutating such residues to another amino acid such as, for example, phenylalanine. Furthermore, point mutations may be introduced at positions where the amino acid side-chains will react with cross-linking agents or each other, such that the formation of the bond(s) causes the most beneficial outcome. These positions may also be identified as described herein.

When at a selected residue a reactive side-chain is not already present, a point mutation may be introduced, for example using molecular biological methods to introduce such a point mutation into the cDNA of a nucleic acid directing its expression, such that a reactive side-chain is present and available for the reaction.

Cross-links that may be used include, but are not limited to, reversible cross-links resulting from the use of homo- and hetero-bifunctional cross-linking agents that react with amine and/or thiol groups, photoreactive cross-link reagents, any cross-links that may form between non-classical amino acids incorporated into the structure of an influenza HA polypeptide, protein and/or protein complex, any oxidative cross-links, such as, but not limited to, di-tyrosine cross-links/bonds, heterobifunctional cross-linkers (e.g. succinimidyl acetylthioacetate (SATA), trans-4-(maleimidylmethyl)cyclohexane-1-carboxylate (SMCC), and succinimidyl 3-(2-pyridyldithio)propionate (SPDP)), homobifunctional cross-linkers (e.g. succinimidyl 3-(2-pyridyldithio)propionate), photoreactive cross-linkers (e.g. 4-azido-2,3,5,6-tetrafluorobenzoic acid, STP ester, sodium salt (ATFB, STP ester), 4-azido-2,3,5,6-tetrafluorobenzoic acid, succinimidyl ester (ATFB, SE), 4-azido-2,3,5,6-tetrafluorobenzyl amine, hydrochloride, benzophenone-4-isothiocyanate, benzophenone-4-maleimide, 4-benzoylbenzoic acid, succinimidyl ester, N-((2-pyridyldithio)ethyl)-4-azidosalicylamide (PEAS; AET), thiol reactive cross-linkers (e.g. maleimides and iodoacetamides), amine reactive cross-linkers (e.g. glutaraldyde, bis(imido esters), bis(succinimidyl esters), diisocyanates and diacid chlorides).

The present invention also contemplates the introduction of targeted non-covalent tyrosine-stacking interactions as "cross-links" to stabilize protein-protein interactions and/or desired protein or peptide conformations, such as the native trimeric conformation of a stalk domain of an influenza HA polypeptide, protein and/or protein complex. The cross-link comprises a targeted pi stacking interaction including but not limited to a T-shaped, sandwich, or parallel displaced pi stacking interaction between the aromatic side chains of an introduced/engineered tyrosine and an endogenous tyrosine, phenylalanine, histidine, or tryptophan within the influenza HA polypeptide, protein and/or protein complex, or between the aromatic side chain of an introduced/engineered tyrosine and a second introduced/engineered tyrosine within the influenza HA polypeptide, protein and/or protein complex.

Irreversible cross-links, as used in the context of this application, include those that are not significantly dissolved under physiologically relevant conditions. It is preferred that the type of cross-links used should not lead to aggregate formation during expression or when the influenza HA polypeptides, proteins and/or protein complexes of the invention are stored at high concentrations. Disulfide bonds are not irreversible cross-links. Rather they are reversible cross-links and may dissolve under physiologically relevant conditions and/or lead to aggregate formation during protein expression and/or production or when stored in high concentrations.

In some embodiments cross-links may be targeted to the specific regions of influenza HA polypeptides, proteins and/or protein complexes described herein in order to achieve the desired conformational stabilization and/or the desired immunogenic properties (e.g. the ability to maintain the stalk domain in its native trimeric conformation and/or to bind to broadly neutralizing antibodies). Alternatively, proteins with the cross-links at the locations specified herein may be isolated from a mixture of cross-linked and un-cross-linked proteins with and without desired modifications, for example based on chemical, physical, and/or functional characteristics. Such characteristics may include, for example, trimerization, the presence of a stalk domain having a native trimeric conformation, and/or any desired antigenic, immunogenic, or biochemical characteristics.

Alternatively, in some embodiments, cross-links may not be targeted, and proteins with the desired cross-links or properties may be isolated from a mixture of modified and unmodified proteins made using a non-targeted cross-linking system.

In embodiments where influenza HA polypeptides, proteins or protein complexes with the desired cross-links are to be isolated from a mixture of cross-linked and un-cross-linked proteins, such isolation or separation may be performed on the basis of one or more characteristics including, but not limited to, molecular weight, molecular volume, chromatographic properties, mobility in electrophoresis, antigenic and biochemical characteristics, fluorescence characteristics, solubility, binding to antibodies, structural characteristics, immunological characteristics, or any other suitable characteristics.

In addition to the specific cross-linking positions described herein, additional positions within influenza HA polypeptides, proteins or protein complexes can be identified at which further cross-links can be made, for example where a reactive side-chain would be able to form a bond with a reactive side-chain elsewhere on the influenza HA polypeptide, protein or protein complex. In some embodiments, such additional positions can be selected, for example, to maintain or improve the immunogenicity/antigenicity of the protein, polypeptide or protein complex. In some embodiments, such additional positions to be cross-linked can be selected in pairs.

Di-Tyrosine (DT) Cross-Linking

In some embodiments the present invention provides influenza HA polypeptides, proteins and/or protein complexes that comprise di-tyrosine (DT) cross-links, and methods of making such DT-cross-linked influenza HA polypeptides, proteins and/or protein complexes.

Di-tyrosine cross-linking introduces one or more covalent carbon-carbon bonds into proteins or protein complexes. This provides a method for stabilizing proteins, protein complexes, and conformations, by introduction of intra- and/or inter-polypeptide di-tyrosine bonds while maintaining their structural and functional integrity (See Marshall et al., U.S. Pat. Nos. 7,037,894 & 7,445,912, the contents of which are hereby incorporated by reference). The minimally altering, and zero-length DT cross-link is not hydrolyzed under physiological conditions, and has been demonstrated to maintain proteins' structural integrity by liquid chromatography/mass spectrometry (LC/MS). Di-tyrosine cross-links are known to be safe, as they form naturally in vivo, both in the context of proteins evolved to utilize their specific characteristics (e.g. Elvin C M et al. 2005, Nature 437:999-1002; Tenovuo J & Paunio K 1979, Arch Oral Biol.; 24(8):591-4), and as a consequence of non-specific protein oxidation (Giulivi et al. 2003, Amino Acids 25(3-4):227-32), and as they are present in large quantities in some of our most common foods: DT bonds form the structure of wheat gluten—the quarternary protein structure comprising the glutenin subunits—e.g. in bread dough during mixing and baking (Tilley et al. 2001, Agric. Food Chem 49, 2627). Di-tyrosine bonds do not form spontaneously in vitro. Rather, the enzymatic cross-link reaction is carried out under optimized conditions to preserve protein structure and function. Therefore, non-specific bonding/aggregation does not occur (unlike with disulfide bonding), and therefore large-scale manufacturing of a DT stabilized immunogen may be economically more feasible.

Tyrosyl side-chains are present in many redox enzymes, and catalysis of the enzyme-specific reactions often involves tyrosyl radicals that are long-lived and have comparatively low reactivity. Under optimized conditions radical formation is specific to tyrosyl side-chains. In close proximity, tyrosyl side chains undergo radical coupling and form a covalent, carbon-carbon bond. Tyrosyl radicals that do not react revert to non-radicalized tyrosyl side-chains (Malencik & Anderson, 2003. Di-tyrosine as a product of oxidative stress and fluorescent probe. Amino Acids 25: 233-247). Therefore, tyrosyl side-chains must be situated in close proximity to form DT bonds, either within a single folded polypeptide chain, or on closely interacting protein domains within a complex. Because a Cα-Cα separation of approximately 5-8 Å is a prerequisite to bond formation (Brown et al., 1998. Determining protein-protein interactions by oxidative cross-linking of a glycine-glycine-histidine fusion protein. Biochemistry 37, 4397-4406; Marshall et al. 2006, U.S. Pat. No. 7,037,894), and because no atom is added in the formation of these bonds, the resulting "staple" is "zero length" and non-disruptive to the protein structure.

Tyrosine residues to be cross-linked may be naturally present in the primary structure of the protein to be cross-linked or may be added by controlled point mutation. To form DT bonds, proteins with tyrosyl side chains can be subjected to reaction conditions that lead to the formation of DT bonds. Such conditions are, or become, oxidative reaction conditions, as the DT bond formation reaction is an oxidative cross-linking reaction. In some embodiments the DT cross-linking reaction conditions yield proteins that are otherwise not, or not detectably, modified. Such conditions may be obtained by use of enzymes that catalyze the formation of $H_2O_2$, such as peroxidases. DT bond formation may be monitored by spectrophotometry with an excitation wavelength of around 320 nm, and fluorescence measured at a wavelength of around 400 nm (see, for example, FIG. 4A), while loss of tyrosyl fluorescence is monitored also monitored by standard procedures. When loss of tyrosyl florescence is no longer stoichiometric with DT bond formation, the reaction may be stopped by any methods known to one skilled in the art, such as, for example, by the addition of a reducing agent and subsequent cooling (on ice) or freezing of the sample. Further details of how to perform DT cross-linking are known in the art and are described in, for example, Marshall et al. 2006, U.S. Pat. No. 7,037,894, the contents of which are hereby incorporated by reference.

The major advantages of di-tyrosine cross-linking in protein engineering include (i) the ability to target specific residues for cross-linking (based on the primary, secondary, tertiary, and/or quaternary structures of proteins and complexes), (ii) minimal structural modification, (iii) specificity of the reaction (tyrosine is the only amino acid known to form cross-links under specific cross-linking conditions); (iv) stability of the linkage, (v) zero length of the cross-link (no atom is added), and (vi) the scalability of the cross-linking chemistry.

In some embodiments, targeted DT cross-links may be introduced at one or more of the specific locations in the influenza HA protein that are recited herein. In other embodiments, additional positions within influenza HA polypeptides, proteins or protein complexes can be identified at which DT cross-links can be made. In some embodiments, di-tyrosine bonds or cross-links are targeted to specific residue pairs within the structure of an influenza HA polypeptide, protein and/or protein complex where DT bonds will, or are expected to, form due to, for example, their close proximity. In some embodiments tyrosyl side chains are already present at amino acid residues to be cross-linked. In some cases naturally occurring tyrosine residues may constitute either one or both of the paired tyrosine residues necessary for di-tyrosine bond formation. However, in other cases the influenza HA polypeptides, proteins and/or protein complexes of the invention are mutated or engineered to add one or more tyrosine residues, or to substitute one or more non-tyrosine residues for tyrosine residues. Such mutations are referred to herein as "to-tyrosine" mutations, and can be introduced at locations where it is desirable to form di-tyrosine cross-links/bonds. In some embodiments, the present invention provides mutant influenza HA polypeptides, proteins, and/or protein complexes in which tyrosyl side chains are introduced at desired cross-linking positions by introducing point mutations to tyrosine in a nucleic acid sequence encoding the influenza HA polypeptide, protein, or protein complex. Alternatively, in some embodiments influenza HA proteins, polypeptides or protein complexes, or portions thereof, may be synthesized to include tyrosine residues or amino acids having tyrosyl side chains at desired cross-linking positions. Conversely, in some embodiments the present invention provides mutant influenza HA polypeptides, proteins, and/or protein complexes in which tyrosyl side chains are removed at undesirable cross-linking positions by introducing point mutations from tyrosine in a nucleic acid sequence encoding the influenza HA polypeptide, protein, or protein complex, or influenza HA polypeptides, proteins, or protein complexes may be synthesized to exclude tyrosine residues or amino acids having tyrosyl side chains at positions where cross-linking is not desired. For example, at least one of the tyrosyl side chains can be replaced with another side chain, such as a phenylalanine side chain (see, for example, Marshall C P et al., U.S. Pat. No. 7,037,894, the contents of which are hereby incorporated by reference). Accordingly, the influenza HA polypeptides, proteins and protein complexes of the invention may comprise point mutations "to tyrosine" or "from tyrosine." Such mutations can be made by altering the nucleic acid sequences that encode the influenza HA polypeptides, proteins and/or protein complexes of the invention using any suitable mutagenesis methods known in the art. Alternatively, mutant influenza HA polypeptides, proteins and/or protein complexes may be synthesized, purified, and/or produced by any other suitable methods known in the art.

In some embodiments, the present invention contemplates the targeted introduction of one or more di-tyrosine cross-link at any suitable position(s) in an influenza HA polypeptide, protein or protein complex, for example, in the stalk domain where the cross-link will or may stabilize the stalk domain in a native trimeric conformation or other conformation capable of binding anti-stalk antibodies, such as neutralizing or broadly neutralizing anti-stalk antibodies. Such stabilization may be achieved, for example, by introducing cross-links that stabilize interactions or folds within a stalk monomer (intra-molecular cross-linking) and/or interactions between one or more stalk monomers that comprise that stalk trimer (inter-molecular cross-linking), or any combination of intra- and/or inter-molecular crosslinks.

Proteolytic Cleavage

In some embodiments of the invention the influenza HA polypeptides, proteins and/or protein complexes of the invention (and/or intermediates in the synthesis thereof), comprise one or more protease recognition motifs that can be used, for example, to facilitate proteolytic removal of the head domain. Any suitable protease recognition motifs known in the art can be used. Such engineered protease recognition sites can be located at any suitable location in the influenza HA polypeptide, protein, and/or protein complex in which they will be useful for the disruption and/or removal of the head domain but preferably will not disrupt the native trimeric conformation of (and/or conformation of neutralizing eptiopes in) the stalk domain. Such locations can be determined using methods known in the art, including, but not limited to, testing the effect of introducing engineered protease recognition sites in functional assays, antibody binding assays, antigenic assays, structural assays, and the like. In some embodiments such engineered protease recognition motifs may be located within a variable loop region—as such regions are known to tolerate variations in amino acid sequence without significantly altering the structure and/or function of the influenza HA protein. The influenza HA proteins of the invention can be engineered to introduce one or more protease recognition sequences by, for example, inserting one or more amino acids that comprise, or comprise part of, a protease recognition site (see for example SEQ ID NO. 18, 19, 21, 23 and 25), or by substituting one or more amino acids from the influenza HA protein with different amino acids that comprise, or comprise part or, a protease recognition site (see for example SEQ ID NO. 24), or by performing a combination of insertion and substitution of amino acids (see for example SEQ ID NO. 20 and 22) in order to generate a protease recognition sequence within the influenza HA protein sequence. The engineered protease recognition site will typically consist of up to about 20 amino acid residues. In some embodiments the influenza HA polypeptides, proteins and/or protein complexes described herein comprise an engineered protease recognition motif at one or more of the following primary head-removal sites: amino acid residues 53-67, amino acid residues 60-76, amino acid residues 269-277, and amino acid residues 277-290, and may optionally also comprise an engineered protease recognition motif at one or more of the following secondary head-removal sites: amino acid residues 142-146, and amino acid residues 155-164. In some embodiments the influenza HA polypeptides, proteins and/or protein complexes of the present invention comprise a protease recognition sequence that begins at an amino acid residue position within one of the following regions of the influenza HA protein: amino acid residues 40-68, amino acid residues 60-76, amino acid residues 77-114, amino acid residues 120-141, amino acid residues 142-146, amino acid residues 148-178, amino acid residues 182-188, amino acid residues 195-201, amino acid residues 209-242, amino acid residues 250-255, amino acid residues 260-285, amino acid residues 277-290, and amino acid residues 286-320. In some embodiments such protease recognition motifs may allow proteolytic cleavage at one or more of the Sa, Ca, Sb and Cb antigenic sites in the influenza HA head domain. In some embodiments the protease recognition motif is inserted into the influenza HA protein immediately following the amino acid at position 48, 63, 278, 282, 286, or 291. In some embodiments the protease recognition motif is inserted into the influenza HA protein within one or more of the following regions of the influenza HA protein: amino acid residues 38-58, amino acid residue 53-73, amino acid residues 268-288, amino acid residues 272-292, amino acid residues 276-296 and amino acid residues 281-301. In some embodiments the protease recognition motifs may comprise a PreScission Protease recognition sequence (for example, LEVLFQGP (SEQ ID NO. 69)) or TEV recognition sequence, (for example, ENLYFQG (SEQ ID NO. 70) or ENLYFQS (SEQ ID NO. 71)), or any combination thereof. Nucleotide sequences encoding such protease recognition sites can be engineered into the nucleic acids that encode the influenza HA polypeptides, proteins, and/or protein complexes of the invention using standard molecular biology techniques known in the art.

Making and Analyzing Influenza HA Polypeptides, Proteins, and Protein Complexes

In some embodiments the present invention provides methods for making the influenza HA polypeptides, proteins, and protein complexes of the invention. The influenza HA polypeptides, proteins, and protein complexes of the invention can be made by any suitable means known in the art. In some embodiments the influenza HA polypeptides, proteins, and/or protein complexes of the invention can be made by recombinant means. In some embodiments, the influenza HA polypeptides, proteins, and/or protein complexes of the invention, or any portion thereof, can be made by chemical synthesis means. For example, a peptide corresponding to a portion of a protein or protein complex as described herein can be synthesized by use of a peptide synthesizer.

Recombinant Production Methods

In embodiments where the influenza HA polypeptides, proteins and protein complexes of the invention are made by recombinant means, nucleic acids encoding the influenza HA polypeptides, proteins and protein complexes of the invention can be expressed in any suitable cell type, including, but not limited to mammalian cells, avian cells (such as EB66 duck cells) and insect cells (such as SF9 or Hi5 cells, using a baculovirus expression system). Methods for expressing polypeptides and proteins from nucleic acid molecules are routine and well known in the art, and any suitable methods, vectors, systems, and cell types known in the art can be used. For example, typically nucleic acid sequences encoding the influenza HA polypeptides, proteins and/or protein complexes of the invention will be placed into a suitable expression construct containing a suitable promoter, which will then be delivered to cells for expression.

Chimeric/Fusion Proteins & Oligomerization Domains

In some embodiments it may be desirable to add chimeric domains to the influenza HA polypeptides, proteins and/or protein complexes described herein, to produce chimeric proteins/fusion proteins, for example to facilitate the analysis and/or isolation and/or purification of the influenza HA polypeptides, proteins and/or protein complexes described herein. In some embodiments, the influenza HA polypeptides, proteins and protein complexes of the invention may comprise leader sequences, precursor polypeptide sequences, secretion signals, localization signals, epitope tags, protease cleavage sites, and the like. Epitope tags that can be used include, but are not limited to, FLAG tags, glutathione S-transferase (GST) tags, green fluorescent protein (GFP) tags, hemagglutinin A (HA) tags, histidine (His) tags, luciferase tags, maltose-binding protein (MBP) tags, c-Myc tags, protein A tags, protein G tags, streptavidin (strep) tags, and the like.

In some embodiments it may be desirable to add oligomerization domains to facilitate the assembly of influenza HA polypeptides, proteins and/or protein complexes as described herein, and/or to facilitate stabilization of stalk domain in a native trimeric conformation, and/or to stabilize other structural features of the influenza HA polypeptides, proteins and/or protein complexes. In some embodiments the oligomerization domains are trimerization motifs, including, but not limited to, the T4 foldon motif. There are a wide variety of trimerization domains in natural proteins that can be used for these purposes including, but not limited to, those described in Habazettl et al., 2009 (Habazettl et al., 2009. NMR Structure of a Monomeric Intermediate on the Evolutionarily Optimized Assembly Pathway of a Small Trimerization Domain. J. Mol. Biol.), Kammerer et al., 2005 (Kammerer et al., 2005. A conserved trimerization motif controls the topology of short coiled coils. Proc Natl Acad Sci USA 102 (39): 13891-13896), Innamorati et al., 2006 (Innamorati et al., 2006. An intracellular role for the Clq-globular domain. Cell signal 18(6): 761-770), and Schelling et al., 2007 (Schelling et al., 2007. The reovirus σ-1 aspartic acid sandwich: A trimerization motif poised for conformational change. Biol Chem 282 (15): 11582-11589). Stabilizing trimeric protein complexes can also be accomplished using the GCN4 and T4 fibrinitin motifs (Pancera et al., 2005. Soluble Mimetics of Human Immunodeficiency Virus Type 1 Viral Spikes Produced by Replacement of the Native Trimerization Domain with a Heterologous Trimerization Motif: Characterization and Ligand Binding Analysis. J Virol 79(15): 9954-9969; Guthe et al., 2004. Very fast folding and association of a trimerization domain from bacteriophage T4 fibritin. J. Mol. Biol. v337 pp. 905-15; Papanikolopoulou et al., 2008. Creation of hybrid nanorods from sequences of natural trimeric fibrous proteins using the fibritin trimerization motif. Methods Mol Biol 474: 15-33). Heterologous oligomerization motifs may be introduced by any recombinant methods known to one of ordinary skill in the art in order to stabilize the protein-protein interactions of the proteins of the present invention.

In some embodiments it may be desirable to add more than one additional domain and/or tag to the influenza polypeptides, proteins and/or protein complexes described herein, and any combination of suitable chimeric and/or oligomerization domains may be added to make desired influenza HA polypeptides, proteins and/or protein complexes. In some embodiments, the additional domains are engineered at or in the transmembrane region of an influenza HA protein, for example by insertion and/or substitution of one or more amino acids in the transmembrane region such that all or a portion of the transmembrane region is replaced by the additional domains. In some embodiments the additional domains comprise a thrombin cleavage site, a T4 foldon motif and a histidine tag (e.g. a 6×His tag (SEQ ID NO: 118)). In some embodiments the additional domains are encoded by a nucleic acid sequence comprising CGTTCTCTGGTTCCGCGTGGTTCTCCGGGTTCTGGTTACATCCCGGAAGCTCCGCGT GACGGTCAGGCTTACGTTCGTAAAGACGGTGAATGGGTTCTGCTGTC TACCTTCCTG CACCACCACCACCACCACTGA (SEQ ID NO. 72). In some embodiments the influenza HA polypeptides, proteins and/or protein complexes comprise a tag comprising, consisting of, or consisting essentially of the amino acid sequence RSLVPRGSPGSGYIPEAPRDGQAYVRKDGEWVLLSTFLHHHHHH (SEQ ID NO:116).

Chimeric influenza HA polypeptides, proteins and/or protein complexes can be made by any method known to one of ordinary skill in the art, and may comprise, for example, one or several influenza HA polypeptides, proteins and/or protein complexes of the invention, and/or any fragment, derivative, or analog thereof (for example, consisting of at least a domain of a polypeptide, protein, or protein complex of the invention, or at least 6, and preferably at least 10 amino acids of thereof) joined at its amino- or carboxy-terminus via a peptide bond to an amino acid sequence of another protein or other protein domain or motif. In some embodiments such chimeric proteins can be produced by any method known to one of ordinary skill in the art, including, but not limited to, recombinant expression of a nucleic acid encoding a chimeric protein (e.g. comprising a first coding sequence joined in-frame to a second coding sequence); ligating the appropriate nucleic acid sequences encoding the desired amino acid sequences to each other in the proper coding frame, and expressing the chimeric product.

Post-Translational Modifications

In some embodiments, the influenza HA polypeptides, proteins and protein complexes described herein may be altered by adding or removing post-translational modifications, by adding or removing chemical modifications or appendices, and/or by introducing any other modifications known to those of ordinary skill in the art. Included within the scope of the invention are influenza HA polypeptides, proteins and protein complexes that are modified during or after translation or synthesis, for example, by glycosylation (or deglycosylation), acetylation (or deacetylation), phosphorylation (or dephosphorylation), amidation (or deamidization), pegylation, derivatization by known protecting/blocking groups, proteolytic cleavage, or buy any other means known in the art. For example, in some embodiments the influenza HA polypeptides, proteins and/or protein complexes may be subjected to chemical cleavage by cyanogen bromide, trypsin, chymotrypsin, papain, V8 protease, NaBH4, acetylation, formylation, oxidation, reduction, metabolic synthesis in the presence of tunicamycin, etc. In some embodiments such post-translational modifications can be used to render the influenza HA polypeptides, proteins, and/or protein complexes of the present invention more immunogenic, more stable, and/or more capable of binding to, or eliciting the production of, neutralizing and broadly neutralizing antibodies.

Obtaining Influenza HA Protein in Desired Conformations

In some embodiments the influenza HA polypeptides and/or proteins of the invention are assembled into protein complexes having a desired conformational structure, such as the native trimeric structure of the stalk domain, and are cross-linked in order to stabilize that conformation. As described elsewhere in the present application, the influenza HA protein comprises a trimer formed from three monomers. In some embodiments, prior to and/or during the enzymatic cross-linking reaction, the influenza HA protein may be obtained in (and/or maintained in) the desired conformation, for example while cross-linking is performed. In some embodiments the influenza HA protein may be produced and/or isolated in such a way that most, or substantially all, of the influenza HA molecules have a stalk domain present in a native trimeric conformation. For example, when the HA protein is expressed or obtained in a form that still comprises the head domain, the stalk domain will typically assume its native trimeric stalk confirmation. In some embodiments influenza HA molecules in a desired conformation may be separated from a mixed population of influenza HA protein molecules comprising some that are in the desired conformation (e.g. native trimeric conformation of the stalk domain) and some that are in other conformations (e.g. stalk domain in a monomeric and/or dimeric conformation). In some embodiments, the influenza HA protein is expressed in cells (for example as its membrane bound or soluble form) and spontaneously assembles into its normal conformation (e.g. having a stalk domain in its native trimeric conformation). In some embodiments no additional stabilization may be necessary to retain stalk domain the influenza HA protein in its native trimeric form. In some embodiments the expressed and assembled/folded influenza HA protein may be kept under particular conditions, or in particular compositions, that favor formation and/or maintenance of the native trimeric conformation of the stalk domain. The influenza HA protein may be obtained and/or isolated and/or maintained in the desired conformation using any suitable method known in the art, including, but not limited to, standard protein purification methods, such as ion exchange chromatography, size exclusion chromatography, and/or affinity chromatography methods. In some embodiments the influenza HA protein may be expressed in the presence of, co-expressed with, or contacted with, molecules that bind to the influenza HA protein and stabilize it in its desired conformation, including, but not limited to, antibodies, small molecules, peptides, and/or peptidomimetics. Non-limiting examples of antibodies that bind to the stalk domain in its native trimeric conformation include 6F12, C179, CR6261, F10, A66, and D8. Other antibodies that can be used to characterize or stabilize the HA polypeptides, proteins and protein complexes of the invention include, but are not limited to, 18A3, 18C11, 18E7, 18E12, 18H9, 16B5, 10A14, 5K24, FI6v3, 6K14, 6J24, 8D4, anti-influenza human antibodies of the $V_H$1-69 heavy chain lineage, and anti-influenza human antibodies of the $V_H$3-30 heavy chain lineage. In some embodiments, the influenza HA protein may be obtained, isolated, or maintained in its desired conformation by controlling the ionic strength of the media/buffer in which the protein is present (such as by using high or low ionic strength media). In some embodiments the influenza HA protein may be obtained, isolated, or maintained at one or more temperatures that favor preservation of the desired conformation. In some embodiments the influenza HA protein may be obtained, isolated, or maintained over a period of time that diminishes the degree to which the desired conformation lost.

In some embodiments analysis may be performed to confirm that the desired conformation, such as the native trimeric conformation of the stalk domain, has been formed and/or maintained in the influenza HA protein. Such analysis may be performed prior to cross-linking, during the cross-linking process, after the cross-linking process, or at any combination of such stages. Such analysis may comprise any suitable methods known in the art for assessing the 3-dimensional structure of a protein or protein complex, including functional analysis, crystallographic analysis, and the like. In some embodiments such analysis may include assessing binding of the influenza HA protein to certain antibodies, such as those that are specific to the native trimeric conformation of the stalk domain and/or those that are known to bind to antigenic sites in the stalk domain or elsewhere in the influenza HA protein, as described elsewhere herein, including, but not limited to the 6F12, C179, CR6261, F10, A66, and D8 antibodies.

Protein Purification

In some embodiments the methods for making influenza HA polypeptides, proteins, and protein complexes of the invention may comprise purifying the influenza HA polypeptides, proteins, or protein complexes before, during, or after, one or more steps in the manufacturing process. For example, in some embodiments the influenza HA polypeptides, proteins, and/or protein complexes of the invention may be purified after completion of all of the manufacturing steps. In some embodiments the influenza HA polypeptides, proteins, and/or protein complexes of the invention may be purified before commencing the cross-linking process or after one or more of the intermediate method steps in the process, for example, after expression of an influenza HA polypeptide or protein, after assembly of a protein complex, after obtaining the influenza HA protein in a desired conformation, during or after performing a cross-linking reaction, or after removal of the head domain. The influenza HA polypeptides, proteins, and/or protein complexes of the invention may be isolated or purified using any suitable method known in the art. Such methods include, but are not limited to, chromatography (e.g. ion exchange, affinity, and/or sizing column chromatography), ammonium sulfate precipitation, centrifugation, differential solubility, or by any other technique for the purification of proteins known to one of ordinary skill in the art. In specific embodiments it may be necessary to separate the desirable influenza HA polypeptides, proteins, and/or protein complexes of the invention from those that were not sufficiently cross-linked, or those in which the head domain was not sufficiently removed. This can be done using any suitable system known in the art. For example, influenza HA proteins having a stalk domain in the native trimeric conformation can be separated from those that have a stalk domain that is not in the native trimeric conformation using antibody-based separation methods. The influenza HA polypeptides, proteins, and/or protein complexes of the invention may be purified from any source used to produce them. For example, the influenza HA polypeptides, proteins, and/or protein complexes of the invention may be purified from sources including insect, prokaryotic, eukaryotic, mono-cellular, multi-cellular, animal, plant, fungus, vertebrate, mammalian, human, porcine, bovine, feline, equine, canine, avian, or tissue culture cells, or any other source. The degree of purity may vary, but in various embodiments, the purified influenza HA polypeptides, proteins, and/or protein complexes of the invention are provided in a form in which they comprise more than about 10%, 20%, 50%, 70%, 75%, 80%, 85%, 90%, 95%, 98%, 99%, or 99.9% of the total protein in the final composition. In some embodiments the influenza HA polypeptides, proteins, and/or protein complexes of the invention may be isolated and purified from other proteins, or any other undesirable products (such as non-cross-linked products or products where removal of the head domain is insufficient or incomplete), by standard methods including, but not limited to, chromatography, glycerol gradients, affinity chromatography, centrifugation, ion exchange chromatography, size exclusion chromatography, and affinity chromatography, or by any other standard technique for the purification of proteins known in the art. The influenza HA polypeptides, proteins, and/or protein complexes to be isolated may be expressed in high or low ionic media, or isolated in high or low ionic buffers or solutions. The influenza HA polypeptides, proteins, and/or protein complexes of the invention may also be isolated at one or more temperatures that favor preservation of the desired conformation. They may also be isolated over a period of time that diminishes the degree to which a preparation would have lost the desired conformation. The degree to which a preparation of proteins retains one or more desired conformations (such as the native trimeric conformation of the stalk domain and/or conformations that favor binding to neutralizing antibodies, or other desired properties) may be assayed by any suitable method known in the art, including, for example, but not limited to, biochemical, biophysical, immunologic, and virologic analyses. Such assays include, for example, but are not limited to, immunoprecipation, enzyme-linked immunosorbent assays (ELISAs), or enzyme-linked immunosorbent spot (ELISPOT) assays, crystallographic analysis (including co-crystallization with antibodies), sedimentation, analytical ultracentrifugation, dynamic light scattering (DLS), electron microscopy (EM), cryo-EM tomography, calorimetry, surface plasmon resonance (SPR), fluorescence resonance energy transfer (FRET), circular dichroism analysis, and small angle x-ray scattering, neutralization assays, antibody-dependent cellular cytotoxicity assays, and/or virologic challenge studies in vivo.

The yield of the influenza HA polypeptides, proteins, and/or protein complexes of the invention can be determined by any means known in the art, for example, by comparing the amount of the final engineered proteins (such as cross-linked influenza HA proteins) as compared to the amount of the starting material, or as compared to the amount of the materials present in any preceding step of the production methods. Protein concentrations can determined by standard procedures, such as, for example, Bradford or Lowry protein assays. The Bradford assay is compatible with reducing agents and denaturing agents (Bradford, M, 1976. Anal. Biochem. 72: 248). The Lowry assay has better compatibility with detergents and the reaction is more linear with respect to protein concentrations and read-out (Lowry, O J, 1951. Biol. Chem. 193: 265).

Exemplary Production Methods

In some embodiments the present invention provides methods for making "headless" influenza HA polypeptides, proteins and/or protein complexes as described herein. In some embodiments methods for making "headless" influenza HA polypeptides, proteins and/or protein complexes comprise: (a) expressing an influenza HA protein having (i) both a stalk domain and a head domain, and (ii) one or more engineered protease recognition motifs in or near its head domain, (b) allowing the soluble influenza HA protein expressed in step (a) to fold into its native conformation having a trimeric stalk domain and a head domain, (c) introducing one more cross-links into the trimeric stalk domain, wherein the cross-links stabilize the stalk domain in its native trimeric conformation, and (d) subsequently proteolytically disrupting or removing the head domain, thereby producing a headless influenza HA protein. In some such embodiments the cross-links are targeted cross-links, such as di-tyrosine cross-links. In some embodiments the methods also involve first (at least prior to step (c)) identifying one or more regions in the HA protein in which the introduction of one or more cross-links in step (c) could stabilize the conformation of the stalk in its native trimeric conformation and/or stabilize the stalk in a conformation that allows binding of one or more broadly neutralizing anti-stalk antibodies. In some embodiments methods for making "headless" influenza HA polypeptides, proteins and/or protein complexes comprise: (a) expressing an influenza HA protein having: (i) both a stalk domain and a head domain, (ii) one or more "to-tyrosine mutations within its stalk domain, and (iii) one or more engineered protease recognition motifs within or close to its head domain, (b) allowing the influenza HA protein to fold into its native conformation having a trimeric stalk domain and a head domain, (c) introducing one or more di-tyrosine cross-links into the trimeric stalk domain, wherein the di-tyrosine cross-links are stable under physiological conditions and stabilize the stalk domain in its native trimeric conformation, and (d) subsequently proteolytically removing the head domain, thereby producing a soluble headless influenza HA protein. In some embodiments the method also involves identifying first (at least prior to step (c)) one or more regions in the HA protein in which the introduction of one or more DT cross-links in step (c) could stabilize the conformation of the stalk in its native trimeric conformation and/or stabilize the stalk in a conformation that allows binding of one or more broadly neutralizing anti-stalk antibodies. In such methods the soluble influenza HA protein will typically comprises one or more protease recognition motifs that can be used to facilitate proteolytic removal of the head domain, as described above and in other sections of this application.

In some embodiments the methods for making "headless" influenza HA polypeptides, proteins and/or protein complexes described herein may further comprise performing an analysis after commencement or completion of the proteolytic cleavage step(s) to confirm that the head domain of the influenza HA protein has been sufficiently disrupted or removed. In some such embodiments this analysis may comprise, for example, performing an SDS PAGE gel mobility shift assay or using a head-specific antibody.

In some embodiments the present invention provides methods for making "head-on" influenza HA polypeptides, proteins and/or protein complexes as described herein. In some embodiments methods for making "head-on" influenza HA polypeptides, proteins and/or protein complexes comprise: (a) expressing an influenza HA protein comprising a stalk domain and a head domain, (b) allowing the expressed influenza HA protein to fold into its native conformation having a trimeric stalk domain, and (c) introducing one more physiologically stable cross-links into the HA protein in the trimeric stalk domain and optionally also in the head domain, thereby producing an engineered "head-on" influenza HA protein having a cross-linked stalk domain. In some such embodiments the cross-links are targeted cross-links, such as di-tyrosine cross-links. In some embodiments methods for making "headless" influenza HA polypeptides, proteins and/or protein complexes comprise: (a) expressing an influenza HA protein having one or more "to-tyrosine" mutations at targeted positions within its stalk domain and optionally also in the head domain, (b) allowing the influenza HA protein to fold into its native conformation having a trimeric stalk domain and a head domain, and (c) performing a DT cross-linking reaction to cross-link tyrosine residues in the stalk domain and optionally also in the head domain, thereby producing an engineered "head-on" influenza HA protein having a DT-cross-linked stalk domain. In such methods the influenza HA protein may comprise one or more protease recognition motifs that could be used, if desired, to facilitate subsequent proteolytic removal of the head domain of the "head-on" protein to generate a "headless" influenza HA protein.

Properties of Influenza HA Polypeptides, Proteins and/or Protein Complexes

In some embodiments, the influenza HA polypeptides, proteins and/or protein complexes of the invention, including in particular those that are cross-linked as described herein, have certain structural, physical, functional, and/or biological properties. Such properties may include one or more of the following, or any combination of the following: presence or absence of a head domain, existence of the stalk domain in its native trimeric conformation; improved stability of the native trimeric conformation of the stalk domain (as compared to non-cross-linked influenza HA proteins); improved half-life of the influenza HA protein (as compared to non-cross-linked influenza HA proteins); improved thermostability (as compared to non-cross-linked influenza HA proteins); prolonged shelf-life (as compared to non-cross-linked influenza HA proteins); prolonged half-life inside the body of a subject (as compared to non-cross-linked influenza HA proteins); ability to be stored in solution without forming aggregates (including when present at a high concentration in solution); reduced aggregation in solution (as compared to non-cross-linked influenza HA proteins); binding to an antibody; binding to a neutralizing antibody; binding to a broadly neutralizing antibody; binding to a stalk-specific antibody; binding to a conformationally-specific antibody; binding to an antibody that recognizes a stalk domain epitope; binding to an antibody selected from the group consisting of 6F12, C179, CR6261, F10, A66, and D8; binding to a B cell receptor; activation of a B cell receptor; eliciting an antibody response in vivo; eliciting a protective antibody response in vivo; eliciting production of neutralizing antibodies in vivo; eliciting production of broadly neutralizing antibodies in vivo; eliciting production of antibodies that recognize quaternary neutralizing epitopes (QNEs) in vivo; eliciting a protective immune response in vivo; and/or eliciting a humoral immune response in vivo. In the case of binding to antibody molecules, in some embodiments the influenza HA polypeptides, proteins, and/or protein complexes of the invention bind to the antibodies (such as stalk-specific antibodies, and/or 6F12, C179, CR6261, F10, A66, and D8) with high specificity and/or with high affinity.

Assays for Properties

In some embodiments the influenza HA polypeptides, proteins, and/or protein complexes of the invention, or any intermediates in their manufacture, may be analyzed to confirm that they have desired properties, such as the desired structural, physical, functional, and/or biological properties—such as those properties listed above or identified elsewhere in this patent specification. For example, in some embodiments in vitro or in vivo assays can be performed to assess the influenza HA protein's conformational structure, stability (e.g. thermostability), half-life (e.g. inside the body of a subject), aggregation in solution, binding to an antibody (such as a neutralizing antibody, broadly neutralizing antibody; stalk-specific antibody; antibody that recognizes stalk domain epitopes, conformationally-specific antibody, 6F12, C179, CR6261, F10, A66, and Da), binding to a B cell receptor, activation of a B cell receptor, antigenicity, immunogenicity, ability to elicit an antibody response, ability to elicit a protective antibody/immune response, ability to elicit production of neutralizing antibodies, or ability to elicit production of broadly neutralizing antibodies. In embodiments where the influenza HA polypeptides, proteins, and/or protein complexes of the invention are tested in an animal in vivo, the animal may be any suitable animal species, including, but not limited to a mammal (such as a rodent species (e.g. a mouse or rat), a rabbit, a ferret, a porcine species, a bovine species, an equine species, an ovine species, or a primate species (e.g. a human or a non-human primate), or an avian species (such as a chicken)).

Assays for assessing a protein's conformational structure are well known in the art and any suitable assay can be used, including, but not limited to, crystallographic analysis (e.g. X-ray crystallography or electron crystallography), sedimentation analysis, analytical ultracentrifugation, electron microscopy (EM), cryo-electron microscopy (cryo-EM), cryo-EM tomography, nuclear magnetic resonance (NMR), small angle x-ray scattering, fluorescence resonance energy transfer (FRET) assays, and the like.

Assays for assessing a protein's stability are well known in the art and any suitable assay can be used, including, but not limited to, denaturing and non-denaturing electrophoresis, isothermal titration calorimetry, and time-course experiments in which proteins are incubated and analyzed over time at varying protein concentrations, temperatures, pHs or redox conditions. Proteins may also be analyzed for susceptibility to proteolytic degradation.

Assays for assessing binding of proteins to antibodies are well known in the art, and any suitable assay can be used, including, but not limited to, immunoprecipation assays, enzyme-linked immunosorbent assays (ELISAs), enzyme-linked immunosorbent spot assays (ELISPOTs), crystallographic assays (including co-crystallization with antibodies), surface plasmon resonance (SPR) assays, fluorescence resonance energy transfer (FRET) assays, and the like.

Assays for assessing neutralization activity are well known in the art, and any suitable assay can be used. For example, assays can be performed to determine the neutralizing activity of antibodies or antisera generated by vaccination/immunization of animals with the influenza HA polypeptides, proteins, and/or protein complexes of the invention. Neutralization assays known in the art include, but are not limited to, those described by Dey et al. 2007 (Dey et al., 2007, Characterization of Human Immunodeficiency Virus Type 1 Monomeric and Trimeric gp120 Glycoproteins Stabilized in the CD4-Bound State: Antigenicity, Biophysics, and Immunogenicity. J Virol 81(11): 5579-5593) and Beddows et al., 2006 (Beddows et al., 2007, A comparative immunogenicity study in rabbits of disulfide-stabilized proteolytically cleaved, soluble trimeric human immunodeficiency virus type 1 gp140, trimeric cleavage-defective gp140 and momomeric gp120. Virol 360: 329-340).

Assays for assessing whether a vaccine immunogen is capable of eliciting an immune response and/or providing protective immunity are well known in the art, and any suitable assay can be used. For example, assays can be performed to determine whether vaccination/immunization of animals with the influenza HA polypeptides, proteins, and/or protein complexes of the invention provide an immune response and/or protective immunity against infection with influenza virus. In some embodiments comparisons may be made between placebo and test vaccinated groups with regard to their rates of infection or sero-conversion or viral loads.

Assays for assessing a protein's pharmacokinetics and biodistribution are also well known in the art, and any suitable assay can be used to assess these properties of the influenza HA polypeptides, proteins, and/or protein complexes of the invention.

Compositions

In some embodiments the present invention provides compositions comprising any of the influenza HA polypeptides, proteins, and/or protein complexes described herein. In some embodiments such compositions may be immunogenic compositions, vaccine compositions and/or therapeutic compositions. In some embodiments, such compositions may be administered to subjects. In some embodiments the influenza HA polypeptides, proteins, and/or protein complexes described herein may be present in virus-like particles or "VLPs."

In some embodiments the influenza HA polypeptides, proteins, and/or protein complexes of the invention may be provided in a composition that comprises one or more additional active components, such as one or more additional vaccine immunogens or therapeutic agents. In some embodiments the influenza HA polypeptides, proteins, and/or protein complexes of the invention may be provided in a composition that comprises one or more other components, including, but not limited to, pharmaceutically acceptable carriers, adjuvants, wetting or emulsifying agents, pH buffering agents, preservatives, and/or any other components suitable for the intended use of the compositions. Such compositions can take the form of solutions, suspensions, emulsions and the like. The term "pharmaceutically acceptable carrier" includes various diluents, excipients and/or vehicles in which, or with which, the influenza HA polypeptides, proteins, and/or protein complexes of the invention can be provided. The term "pharmaceutically acceptable carrier" includes, but is not limited to, carriers known to be safe for delivery to human and/or other animal subjects, and/or approved by a regulatory agency of the Federal or a state government, and/or listed in the U.S. Pharmacopeia, and/or other generally recognized pharmacopeia, and/or receiving specific or individual approval from one or more generally recognized regulatory agencies for use in humans and/or other animals. Such pharmaceutically acceptable carriers, include, but are not limited to, water, aqueous solutions (such as saline solutions, buffers, and the like), organic solvents (such as certain alcohols and oils, including those of petroleum, animal, vegetable or synthetic origin, such as peanut oil, soybean oil, mineral oil, sesame oil), and the like. In some embodiments the compositions of the invention also comprise one or more adjuvants. Exemplary adjuvants include, but are not limited to, inorganic or organic adjuvants, oil-based adjuvants, virosomes, liposomes, lipopolysaccharide (LPS), molecular cages for antigens (such as immune-stimulating complexes ("ISCOMS")), Ag-modified saponin/cholesterol micelles that form stable cage-like structures that are transported to the draining lymph nodes), components of bacterial cell walls, endocytosed nucleic acids (such as double-stranded RNA (dsRNA), single-stranded DNA (ssDNA), and unmethylated CpG dinucleotide-containing DNA), AUM, aluminum phosphate, aluminum hydroxide, and Squalene. In some embodiments virosomes are used as the adjuvant. Additional commercially available adjuvants that can be used in accordance with the present invention include, but are not limited to, the Ribi Adjuvant System (RAS, an oil-in-water emulsion containing detoxified endotoxin (MPL) and mycobacterial cell wall components in 2% squalene (Sigma M6536)), TiterMax (a stable, metabolizable water-in-oil adjuvant (CytRx Corporation 150 Technology Parkway Technology Park/Atlanta Norcross, Ga. 30092)), Syntex Adjuvant Formulation (SAF, an oil-in-water emulsion stabilized by Tween 80 and pluronic polyoxyethlene/polyoxypropylene block copolymer L121 (Chiron Corporation, Emeryville, Calif.)), Freund's Complete Adjuvant, Freund's Incomplete Adjuvant, ALUM—aluminum hydroxide, Al(OH)3 (available as Alhydrogel, Accurate Chemical & Scientific Co, Westbury, N.Y.), SuperCarrier (Syntex Research 3401 Hillview Ave. P.O. Box 10850 Palo Alto, Calif. 94303), Elvax 40W1,2 (an ethylene-vinyl acetate copolymer (DuPont Chemical Co. Wilmington, Del.)), L-tyrosine co-precipitated with the antigen (available from numerous chemical companies); Montanide (a manide-oleate, ISA Seppic Fairfield, N.J.)), AdjuPrime (a carbohydrate polymer), Nitrocellulose-absorbed protein, Gerbu adjuvant (C—C Biotech, Poway, Calif.), and the like.

In some embodiments the compositions of the invention comprise an "effective amount" of an influenza HA polypeptide, protein, and/or protein complex of the invention. An "effective amount" is an amount required to achieve a desired end result. Examples of desired end results include, but are not limited to, the generation of a humoral immune response, the generation of a neutralizing antibody response, the generation of a broadly neutralizing antibody response, and the generation of protective immunity. The amount of an influenza HA polypeptide, protein, and/or protein complex of the invention that is effective to achieve the desired end result will depend on variety of factors including, but not limited to, the type, subtype, and strain of the influenza virus against which protection or some other therapeutic effect is sought, the species of the intended subject (e.g. whether a human or some other animal species), the age and/or sex of the intended subject, the planned route of administration, the planned dosing regimen, the seriousness of any ongoing influenza infection (e.g. in the case of therapeutic uses), and the like. The effective amount—which may be a range of effective amounts—can be determined by standard techniques without any undue experimentation, for example using in vitro assays and/or in vivo assays in the intended subject species or any suitable animal model species. Suitable assays include, but are not limited to, those that involve extrapolation from dose-response curves and/or other data derived from in vitro and/or in vivo model systems. In some embodiments the effective amount may be determined according to the judgment of a medical or veterinary practitioner based on the specific circumstances.

Uses of the Influenza HA Polypeptides, Proteins & Protein Complexes of the Invention In some embodiments, the influenza HA polypeptides, proteins, and protein complexes of the invention may be useful as research tools, as diagnostic tools, as therapeutic agents, as targets for the production of antibody reagents or therapeutic antibodies, and/or as vaccines or components of vaccine compositions. For example, in some embodiments the influenza HA polypeptides, proteins, and protein complexes of the invention are useful as vaccine immunogens in animal subjects, such as mammalian subject, including humans. These and other uses of the influenza HA polypeptides, proteins, and protein complexes of the invention are described more fully below. Those of skill in the art will appreciate that the influenza HA polypeptides, proteins, and protein complexes of the invention may be useful for a variety of other applications also, and all such applications and uses are intended to fall within the scope of this invention.

Tools for Studying Influenza HA Antibodies

In one embodiment, the influenza polypeptides, proteins, and protein complexes of the invention may be useful as analytes for assaying and/or measuring binding of, and/or titers of, anti-HA antibodies, for example in ELISA assays, Biacore/SPR binding assays, and/or any other assays for antibody binding known in the art. For example, the influenza HA polypeptides, proteins, and protein complexes of the invention could be used to analyze, and/or compare the efficacy of anti-HA antibodies.

Tools for Generation of Antibodies

The influenza HA polypeptides, proteins, and protein complexes of the invention (including any intermediates and/or variants produced during manufacture of the influenza HA polypeptides, proteins, and protein complexes) may also be useful for the generation of therapeutic antibodies and/or antibodies that can be used as research tools or for any other desired use. For example, the influenza HA polypeptides, proteins, and protein complexes of the invention can be used for immunizations to obtain antibodies to the influenza HA protein for use as research tools and/or as therapeutics. In some embodiments the influenza HA polypeptides, proteins, and protein complexes of the invention can be used to immunize a non-human animal, such as a vertebrate, including, but not limited to, a mouse, rat, guinea pig, rabbit, goat, non-human primate, etc. in order to generate antibodies. Such antibodies, which may be monoclonal or polyclonal, and/or cells that produce such antibodies, can then be obtained from the animal. For example, in some embodiments influenza HA polypeptides, proteins, and protein complexes of the invention may be used to immunize a mouse and to produce and obtain monoclonal antibodies, and/or hybridomas that produce such monoclonal antibodies. Such methods can be carried out using standard methods known in the art for the production of mouse monoclonal antibodies, including standard methods for hybridoma production. In some embodiments influenza HA polypeptides, proteins, and protein complexes of the invention may be used for the production of a chimeric (e.g. part-human), humanized, or fully-human antibody, for example using any of the methods currently known in the art for production of chimeric, humanized and fully human antibodies, including, but not limited to, CDR grafting methods, phage-display methods, transgenic mouse methods (e.g. using a mouse that has been genetically altered to allow for the production of fully human antibodies, such as the Xenomouse) and/or any other suitable method known in the art. Antibodies to the influenza HA polypeptides, proteins, and protein complexes of the invention made using such systems can be characterized antigenically using one or a set of several antigens, preferably including the influenza HA polypeptides, proteins, and protein complexes of the invention themselves. Additional characterization of such antibodies may be carried out by any standard methods known to one of ordinary skill in the art, including, but not limited to, ELISA-based methods, SPR-based methods, biochemical methods (such as, but not limited to, iso-electric point determination), and methods known in the art for studying biodistribution, safety, and efficacy of antibodies—for example in preclinical and clinical studies.

Administration to Subjects

In some embodiments, the present invention provides methods that comprise administering the influenza HA polypeptides, proteins and/or protein complexes of the invention (or compositions comprising such influenza HA polypeptides, proteins and/or protein complexes) to subjects. Such methods may comprise methods for treating individuals having influenza virus (i.e. therapeutic methods) and/or methods for protecting individuals against future influenza virus infection (i.e. prophylactic methods).

Subjects to which the influenza HA polypeptides, proteins and/or protein complexes of the invention, or compositions comprising such influenza HA polypeptides, proteins and/or protein complexes, can be administered (for example in the course of a method of treatment or a method of vaccination) include any and all animal species, including, in particular, those that are susceptible to influenza virus infection or that can provide model animal systems for the study of influenza virus infection. In some embodiments, the subjects are mammalian species. In some embodiments, the subjects are avian species. Mammalian subjects include, but are not limited to, humans, non-human primates, rodents, rabbits, and ferrets. Avian subjects include, but are not limited to chickens, such as those on poultry farms. In some embodiments the subjects to which the influenza HA polypeptides, proteins and/or protein complexes of the invention, or compositions comprising such influenza HA polypeptides, proteins and/or protein complexes are administered, either have influenza, or are at risk of influenza infection, for example due to the subject's age and/or underlying medical conditions. In some embodiments, the subject is immuno-compromised. In some embodiments, the subject has heart disease, lung disease, diabetes, renal disease, dementia, stroke and/or rheumatologic disease. In some embodiments, the subject is a human of greater than about 50 years in age, greater than about 55 years in age, greater than about 60 years in age, greater than about 65 years in age, greater than about 70 years in age, greater than about 75 years in age, greater than about 80 years in age, greater than about 85 years in age, or greater than about 90 years in age. In some embodiments, the subject is a human of less than about 1 month in age, less than about 2 months in age, less than about 3 months in age, less than about 4 months in age, less than about 5 months in age, less than about 6 months in age, less than about 7 months in age, less than about 8 months in age, less than about 9 months in age, less than about 10 months in age, less than about 11 months in age, less than about 12 months in age, less than about 13 months in age, less than about 14 months in age, less than about 15 months in age, less than about 16 months in age, less than about 17 months in age, less than about 18 months in age, less than about 19 months in age, less than about 20 months in age, less than about 21 months in age, less than about 22 months in age, less than about 23 months in age, or less than about 24 months in age.

Various delivery systems are known in the art and any suitable delivery systems can be used to administer the compositions of the present invention to subjects. Such delivery systems include, but are not limited to, intradermal, intramuscular, intraperitoneal, intravenous, subcutaneous, intranasal, epidural, and oral delivery systems. The compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In some embodiments it may be desirable to administer the pharmaceutical compositions of the invention locally to a tissue in which the influenza HA polypeptide, protein or protein complex may be most effective in generating a desirable outcome. This may be achieved by, for example, local infusion, injection, delivery using a catheter, or by means of an implant, such as a porous, non-porous, or gelatinous implant or an implant comprising one or more membranes (such as sialastic membranes) or fibers from or through which the protein or protein complexes may be released locally. In some embodiments a controlled release system may be used. In some embodiments a pump may be used (see Langer, supra; Sefton, 1987. CRC Crit. Ref. Biomed. Eng. 14: 201; Buchwald et al., 1980. Surgery 88: 507; Saudek et al., 1989. N. Engl. J. Med. 321: 574). In some embodiments polymeric materials may be used to facilitate and/or control release of the influenza HA polypeptide, protein and/or protein complex (see Medical Applications of Controlled Release, Langer and Wise (eds.), 1974. CRC Pres., Boca Raton, Fla.; Controlled Drug Bioavailability, 1984. Drug Product Design and Performance, Smolen and Ball (eds.), Wiley, New York; Ranger & Peppas, 1983 Macromol. Sci. Rev. Macromol. Chem. 23: 61; see also Levy et al., 1985. Science 228:190; During et al, 1989. Ann. Neurol. 25: 351; Howard et al., 1989. J. Neurosurg 71:105). In some embodiments a controlled release system can be placed in proximity to the tissue/organ to which the influenza HA polypeptide, protein and/or protein complex is to be delivered (see, e.g., Goodson, 1984. Medical Applications of Controlled Release, supra, vol. 2: 115-138). Some suitable controlled release systems that may be used in conjunction with the present invention are described Langer, 1990, Science; vol. 249: pp. 527-1533

In some embodiments, administration of the influenza HA polypeptide, protein and/or protein complex of the invention can be performed in conjunction with administration of one or more immunostimulatory agents. Non-limiting examples of such immunostimulatory agents include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory agents, such as macrophage inflammatory factor, Flt3 ligand, B7.1; B7.2. The immunostimulatory agents can be administered in the same formulation as the influenza HA protein or polypeptide, or can be administered separately.

In some embodiments, the influenza HA polypeptides, proteins, and/or protein complexes of the invention, or compositions comprising them, can be administered to subjects in a variety of different influenza virus vaccination methods or regimens. In some such embodiments, administration of a single dose is preferred. However, in other embodiments, additional dosages can be administered, by the same or different route, to achieve the desired prophylactic effect. In neonates and infants, for example, multiple administrations may be required to elicit sufficient levels of immunity. Administration can continue at intervals throughout childhood, as necessary to maintain sufficient levels of protection against influenza virus infection. Similarly, adults who are particularly susceptible to influenza virus infection, such as, for example, the elderly and immunocompromised individuals, may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

In some embodiments, dosing regimens may comprise a single administration/immunization. In other embodiments, dosing regimens may comprise multiple administrations/immunizations. For example, vaccines may be given as a primary immunization followed by one or more boosters. In some embodiments of the present invention such a "prime-boost" vaccination regimen may be used. For example, in some such prime-boost regimens a composition comprising an influenza HA polypeptide, protein or protein complex as described herein may be administered to an individual on multiple occasions (such as two, three, or even more occasions) separated in time, with the first administration being the "priming" administration and subsequent administrations being "booster" administrations. In other such prime-boost regimens a composition comprising an influenza HA polypeptide, protein or protein complex as described herein may be administered to an individual after first administering to the individual a composition comprising a viral or DNA vector encoding an influenza HA polypeptide, protein or protein complex as a "priming" administration, with one or more subsequent "booster" administrations of a composition comprising an influenza HA polypeptide, protein or protein complex as described herein. Boosters may be delivered via the same and/or different route as the primary immunization. Boosters are generally administered after a time period after the primary immunization or the previously administered booster. For example, a booster can be given about two weeks or more after a primary immunization, and/or a second booster can be given about two weeks or more after the first boosters. Boosters may be given repeatedly at time periods, for example, about two weeks or greater throughout up through the entirety of a subject's life. Boosters may be spaced, for example, about two weeks, about three weeks, about four weeks, about one month, about two months, about three months, about four months, about five months, about six months, about seven months, about eight months, about nine months, about ten months, about eleven months, about one year, about one and a half years, about two years, about two and a half years, about three years, about three and a half years, about four years, about four and a half years, about five years, or more after a primary immunization or after a previous booster.

Preferred unit dosage formulations are those containing a dose or unit (e.g. an effective amount), or an appropriate fraction thereof, of the influenza HA polypeptides, proteins, and/or protein complexes of the invention. In addition to such ingredients, formulations of the present invention may include other agents commonly used by one of ordinary skill in the art. Pharmaceutical compositions provided by the invention may be conveniently presented in preferred unit dosage formulations prepared using conventional pharmaceutical techniques. Such techniques include the step of bringing into association the active ingredient and the pharmaceutical carrier(s) or excipient(s) or other ingredients. In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Kits

The present invention further provides kits comprising influenza HA polypeptides, proteins or protein complexes of the invention, or compositions containing such polypeptides, proteins or protein complexes. To facilitate use of the methods and compositions of the invention, any of the components and/or compositions described herein, and additional components useful for experimental or therapeutic or vaccine purposes, can be packaged in the form of a kit. Typically, the kit contains, in addition to the above components, additional materials which can include, e.g., instructions for using the components, packaging material, a container, and/or a delivery device.

Various embodiments of the present invention may also be further described by the following non-limiting examples:

EXAMPLES

The numbers in square brackets/parentheses in the Examples section of the present application are citations to the numbered references provided as a reference list herein.

Example 1

The US and world populations continue to be at risk of a pandemic Influenza outbreak, and weaponized influenza virus remains a major bio-warfare/terrorism threat [23,24]. An influenza virus HA-based vaccine immunogen capable of eliciting Ab responses to the conserved stalk QNEs, instead of the immunodominant head of HA, is expected to give rise to broadly neutralizing antibodies that could protect from homologous (H1N1), as well as homologous drift variant, group 1 heterologous (H5N1), and group 2 heterologous challenge (H3N2). Thus, a single, universal immunogen could elicit protective immune responses against seasonal, pandemic, and weaponized influenza virus. Underscoring the commercial and public health impact that influenza virus has on the population is the fact that life insurance companies in the United States today are required to hold capital against a potential reoccurrence of the 1918 Spanish Flu pandemic (Oliver, Wyman, & Co, 2012 & [25]). The approach described herein has the potential to provide a broadly protective influenza vaccine that could enable stockpiling large amounts of vaccine product and eliminate real threats that derive from the ramp-up times in manufacturing required to address each new threat.

Current influenza virus vaccines protect mostly against homologous virus strains, requiring new trivalent vaccine cocktails to be matched seasonally to circulating strains. Protection is primarily due to high affinity antibodies to hemagglutinin (HA), and is often strain-specific due to a focusing of the immune response predominantly against the highly variable, immunodominant head domain of the HA protein. The HA stalk, however, is highly conserved across influenza strains, and considerable evidence now suggests that better responses to conserved regions of the stalk would provide broader protection [1-4]. Immunization with DNA coding for HA elicits predominantly stalk-specific Ab responses, and data showing limited heterosubtypic protection by vaccination with HA DNA by electroporation was recently described [5]. Furthermore, vaccination with a 'headless' HA protein based immunogen ("Headless HA", an HA construct from which the variable head domain is removed) results in the induction of Ab responses with significantly enhanced heterosubtypic binding activity [1,6]. A prime-boost combination of a viral or DNA vector encoding HA, followed by a Headless protein boost holds the promise of generating broadly heterospecific responses that yield long-lasting protection. However, good protection against heterologous challenges currently still remains elusive [7-10].

Significant attention has been focused on the identification and characterization of broadly neutralizing antibodies ("bnAbs") in order to reverse engineer an immunogen capable of eliciting similar antibody responses [9,11]. A number of these bnAbs have been described, and the most potent bind conserved, complex/conformation-specific epitopes that are presented on the conserved stalk of influenza HA trimers, but not on protomers of the same complex [7,12,13]. Isolation of these human Abs proves that a broadly protective vaccine is, in fact, an achievable goal (a "protomer" is a subunit of the trimer, that itself is a HA 1/HA2 heterodimer). These trimer/complex-specific epitopes are therefore called quaternary neutralizing epitopes (QNEs), and they are believed to represent key sites of vulnerability of influenza viruses since they have the potential to elicit potent quaternary bnAbs. [14,15]. Only the intact trimeric stalk exhibits the broadly protective QNE (see FIG. 2). A Headless construct that is locked in its trimeric, native conformation, and that binds the potent and broadly protective quaternary bnAbs could provide a universal influenza immunogen and could elicit potent bnAbs in vaccinated subjects.

Recently, a headless influenza hemagglutinin ("Headless HA") immunogen has been shown to elicit antibody ("Ab") responses focused on the highly conserved stalk region of influenza hemagglutinin (HA) that are broadly cross-reactive. It has also become clear that the most potent and broadly neutralizing/protective Abs (bnAbs) against the stalk region are trimer-specific (i.e. recognize the quaternary structure of the stalk), and that their corresponding quaternary epitopes are not displayed when the head of influenza HA is removed. In the absence of the head domain, the stalk trimer apparently falls apart. The present invention provides a Headless HA immunogen in which the trimeric conformation of the stalk region is stabilized or "conformationally locked"—for example by introduction of targeted cross-links—before the head is proteolytically removed. This Headless HA immunogen should retain binding to quaternary bnAbs and present quaternary neutralizing epitopes ("QNEs") as an influenza immunogen. Such a conformationally-locked Headless HA trimer may enable the long-sought goal of broad protection against influenza viruses from a single vaccination regimen.

Minimally modifying dityrosine ("DT") stabilization technology enzymatically introduces safe, targeted, zero-length, and irreversible DT bonds to lock proteins and complexes in native conformations. Application of this technology fully preserves protein structure and avoids aggregation because DT bonds do not form spontaneously. Bonds only form between Tyr side-chains in very close structural proximity, and are introduced after the protein has fully folded and is in its native state. Targeted DT crosslinking enables the design of an improved influenza vaccine immunogen by conformationally locking QNEs to maximize broad protection.

The methods described in the present example involve 3 steps. The first step involves expressing soluble, full-length influenza HA with "to-Tyr" substitutions at targeted positions within the stalk region. The second step involves introduction of stabilizing DT crosslinks. And the third step involves proteolytically removing the head domain of the influenza HA in order to focus the immune responses on the DT-Headless HA QNEs.

Preliminary studies using a recombinant, soluble HIV Env trimer have demonstrated that DT crosslinking can be used to conformationally-lock the Env immunogen in its native, trimeric conformation, so that it improves binding to the most potent HIV quaternary bnAbs, analogous to the flu quaternary anti-stalk bnAbs, demonstrating the feasibility of this approach. HIV Env and influenza virus Headless are highly analogous in that both are unstable trimers when expressed recombinantly; and in both, key QNEs are only presented in the native trimeric complex. In other preliminary studies targeted DT bonds have been successfully introduced into the influenza HA stalk.

DT crosslinking of a recombinant PR8 HA construct in its native, trimeric conformation can be performed to confirm binding to key bnAbs, and subsequently the "head" domain can be removed by engineering proteolytic cleavage sites, while maintaining the DT-locked, native antigenic conformation of the stalk trimer. The resulting Headless HA immunogen can be tested to confirm that it elicits broad protection in a C57BL/6 mouse model. Pre-clinical testing for efficacy can be performed in a highly predictive ferret lethal challenge model. Pre-clinical testing for safety can be performed in rabbits.

Targeted DT Cross-Linking

By generating native, soluble, and recombinant HA trimers and applying targeted dityrosine (DT) "staples" to covalently cross-link trimerizing interactions in the stalk of the trimer, DT-stabilized HA trimmers will be engineered with fully preserved antigenic profiles. Covalent stabilization of the trimer in the HA stalk region will be engineered to render stable the quaternary structure of the stalk, and this will allow subsequent proteolytic removal of the head while preserving the QNEs of the stalk. DT bonds are introduced to stabilize the complex after the protein/complex is fully folded, and therefore locks the native conformation, while maintaining structural functional integrity of the protein [16-18]. These safe, irreversible, and zero-length cross-links form only between Tyr residues in very close structural proximity, and do not distort the structure of the protein. Nor do they cause non-specific aggregate formation, as observed with disulfide bonds [17,19-22]. Targeted DT cross-linking technology can be applied to covalently stabilize a soluble HA trimer in its correctly folded conformation, and then one can determine whether it does, in fact, present key QNEs. Subsequently the immunodominant head can be removed by introducing sequence-specific protease cleavage sites—making use of variable loop tolerance for amino acid variation and information gathered from transposon-based mutagenesis analysis of HA. Presentation of QNEs on Headless HA is expected to improve upon the breadth of protection in lethal challenge studies with drift variant and heterologous viruses. The inventors' prior work in HIV shows that highly glycosylated multimers (e.g. HIV Env) can efficiently be locked together by DT cross-linking at various locations within the cleaved Env trimer—while maintaining the relevant quaternary structure and antigenicity.

Conformationally Locking the Influenza Virus HA Trimeric Complex

The HIV envelope spike is trimerized through well characterized interactions at its base as well as interactions at the spike's apex [33, 34]. In order to stabilize the trimerizing interactions at the apex of the spike, tyrosine substitutions were introduced, and the protein was expressed, purified, and DT cross-linked. By fluorescence, 7 variants were identified that form intermolecular, trimerizing cross-links with an average of 80%+ efficiency prior to any optimization, as quantified using DT-specific excitation (320 nm) and emission (405 nm) wavelengths. The ability of these constructs to bind conformational and trimer-specific bnAbs was assayed. DT crosslinking fully preserves binding of the anti-CD4 binding site bnAb b12, which binds both protomers and trimers, and the anti-V2 bnAb PG9, which preferentially binds trimers, but also binds monomers. In addition, conformational locking also significantly reduces binding to non-neutralizing mAbs, such as b6 & b13, in ELISA assays. The position of the DT bonds was confirmed by MS/MS of tryptic fragments of the DT-Env trimer. More importantly, a conformationally locked HIV Env trimer was found to bind significantly better to one of the most extremely broadly neutralizing and potent anti-HIV Env bnAbs, PG16, by comparison to the WT protomer; the PG16 epitope is only presented on the native/functional HIV envelope trimer [28]. Improved PG16 binding correlates with a significant reduction in binding to a poorly neutralizing anti-V2 mAb, CH58, that binds an α-helical conformer of an overlapping epitope that PG16 binds as a β-sheet. The next step with this DT-locked, soluble HIV Env trimer will be to test it in animal immunogenicity experiments.

Figure 4:
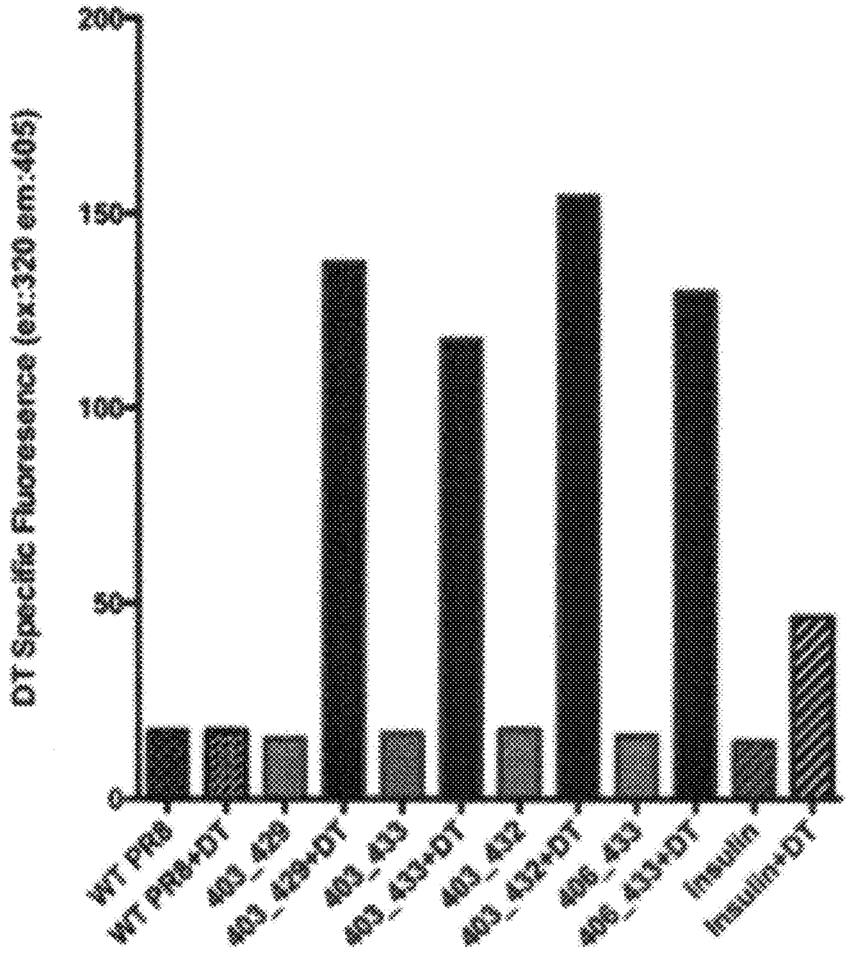
Figure 4:
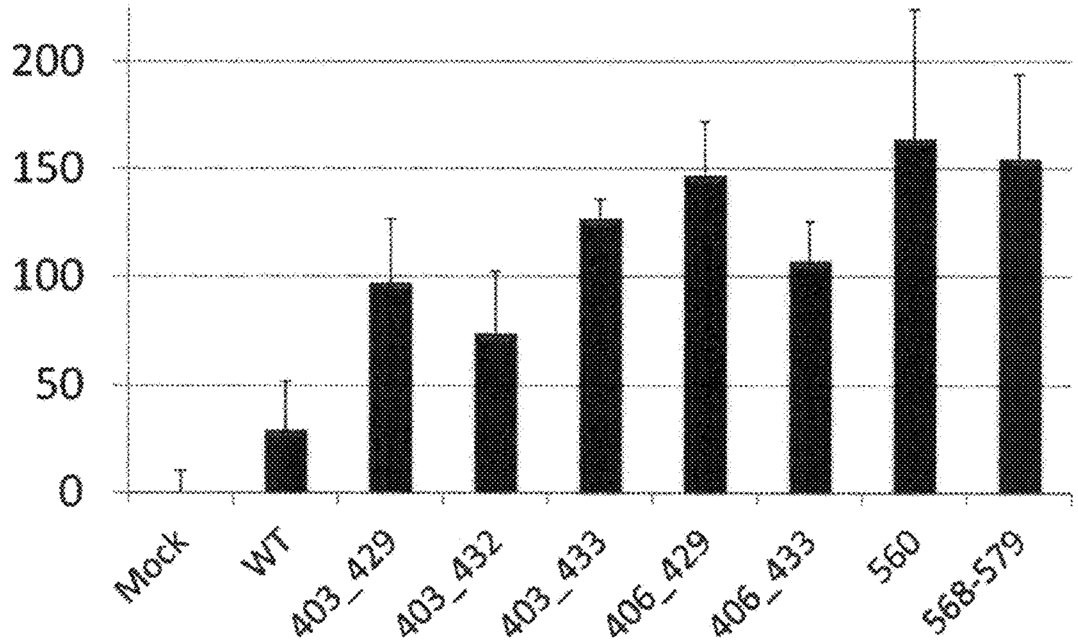

In influenza HA, the trimeric structure of the HA protein in complex with the CR6261 bnAb was analyzed. Five examples of possible HA variants (N403Y_D429Y; N403Y_L432Y; N403Y_D433Y; N406Y_D429Y; and N406Y_D433Y) were initially identified, each with two point mutations that were predicted to form intermolecular bonds and stabilize the stalk trimer at the membrane distal/head proximal end (see schematic for design in FIG. 3) without altering the CR6261 quaternary epitope. Expression vectors encoding four of these variants were generated, and the variants were expressed and subjected to cross-linking conditions. Spectrofluorometry was used to determine whether these variants were forming DT bonds using the DT-specific excitation and emission wavelengths at which DT bonds fluoresce powerfully in direct proportion to their molar concentration. All four variants, but not wild-type HA, formed DT bonds efficiently (FIG. 4). Based on comparison to the positive control (insulin) and a DT standard, cross-linking efficiency of >70% is estimated for all four of these constructs prior to any optimization [35].

Removing the HA Head from the Conformationally Locked HA

Proteolytic removal of the HA head domain from the DT-locked HA trimer requires engineering recognition motifs into the HA1 head domain for a substrate-specific protease (e.g. TEV). Using a transposon-based mutagenesis screen, four regions within the PR8 HA1 globular head have been identified that tolerate the insertion of foreign sequences approximately the same size as an engineered TEV protease site. Without further optimization, two of these regions (located at amino acid residues 128 and 223) would allow proteolytic cleavage of 3 of the 4 major antigenic sites in the PR8 globular head—the Sa, Ca, and Sb sites [36]. The remaining Cb site will also be removed. Viruses with insertions at these sites in HA1 remain capable of fusion, and the HA complex thus remains functionally intact. The proteolytic reaction will then be performed.

These data demonstrate that the approach of locking together the HA trimer in the stalk, and subsequently removing the immunodominant head domain, will preserve vaccine-relevant QNEs of headless HA, and will lock the immunogen in an antigenically favorable conformation. This, in turn, suggests that the DT-locked headless trimer(s) described herein are expected to induce broadly protective antibody responses in vivo.

Conformationally Locking the Influenza Virus HA Trimeric Complex

Experimental Design. Soluble forms (e.g. lacking the transmembrane domain and possessing the T4 foldon trimerization motif) of the WT HA and variants described above will be expressed in SF9 or Hi5 cells as secreted proteins and purified by well-established methods [37-38]. The antigenic effect of the to-Tyr substitutions and the DT cross-linking will be determined in ELISAs using a panel of anti-HA stalk broadly neutralizing mAbs (e.g. 6F12, C179, CR6261, F10, A66 and D8), as structural changes caused by to-Tyr substitutions may reduce or enhance binding to some of these antibodies. Methods: Full-curve binding assays will compare WT HA to the uncross-linked and cross-linked HA variants. Changes in binding will be determined using non-linear regression analysis (Graphpad software) of binding curves to calculate and compare EC50 values for each construct with each mAb. Intermolecular bond formation will be confirmed by gel-shift in reducing SDS-PAGE (Western blot/Coomassie; DT bonds are not reduced); DT cross-linking will be quantified by spectrofluorometry, as described above. Such methods can be used to produce HA variants that form intermolecular DT bonds, and that retain binding to key anti-stalk quaternary bnAbs equal to wild-type PR8 HA after cross-linking the engineered influenza immunogen.

Proteolytically Removing the HA Head from the Conformationally Locked HA

PreScission Protease recognition sequences (LEVLFQGP (SEQ ID NO:69) (cleavage between Q and G residues) and/or TEV recognition sequences (ENLYFQG (SEQ ID NO:70) (cleavage between Q and G residues) and ENLYFQS (SEQ ID NO:71) (cleavage between G and S residues)) can be inserted at defined (e.g. amino acid residues 128 and 223) or additional positions to remove most of the globular head of HA from the baculovirus expressed, purified, fully folded, DT-stabilized, soluble HA precursor. Following antigenic confirmation, amino acid analysis and mass spectrometry can be performed to characterize the cross-linked molecule biochemically.

Proteolysis of the head domain can be carried out by standard biochemical procedures and assayed by SDS-PAGE electro-mobility shift from a molecular weight corresponding to a complete DT-HA trimer (225 kD) to that of a headless trimer (135 kDa) (Coomassie stain, Western blot). Removal of the head from the DT cross-linked HA stalk can be confirmed with Head-specific Abs, for example in Western blots and ELISA. The same bnAbs and assays described above can be used to confirm preservation of the most relevant QNEs in DT-Headless HA.

Amino acid analysis can be performed to assess any non-specific changes to amino acid side chains, and to confirm the presence of DT bonds (the DT moiety itself can be specifically detected). In order to identify the position of the DT bonds in DT-Headless, LC-MS/MS analysis of deglycosylated tryptic digests can be performed, for example on a Thermo Scientific LTQ Mass Spectrometer with a Michrom Paradigm HPLC and Vacuum Spray ionization source.

Biochemical characterization can be performed to identify variants of DT-stabilized, Headless HAs that retain binding to key anti-stalk quaternary bnAbs equal to the wild-type soluble PR8 HA trimer. If necessary, additional cleavage sites can be engineered in order to first unravel the head, and thereby improve the efficiency of proteolytic cleavage. Similarly, PreScission and/or TEV proteases and their cleavage sites can be used as described above.

Testing Protection Against Challenge with Drift and Heterologous Viruses

A PR8 HA variant can be expressed in mg-quantities, DT crosslinked, proteolyzed, purified, and antigenically characterized. PR8, NL09, and VN04 HALO/PR8_6+2 mutant virus preparations can be made. To establish the LD50 for each of the challenge viruses, for each virus 4 groups of 4 C57BL/6 mice (female, 6- to 8-week-old (Charles River Laboratories) can be inoculated, using 10-fold dilutions of the indicated viruses for each group around the published LD50 for each virus. To establish the optimal dose of purified DT-locked Headless HA trimer immunogen that protects 80%+ of animals from 5× the LD50 dose of homologous (PR8) challenge, 4 groups of 5 C57BL/6 mice (female, 6- to 8-week-old (Charles River Laboratories) can be immunized with a prime-boost strategy consisting of consecutive injections of varying amounts of the purified DT-Headless HA immunogen with a fixed amount of Poly I/C adjuvant (10 μg). Briefly, each group can be immunized with 0 μg, 2.5 μg, 5 μg, and 10 μg of DT-locked Headless trimer formulated with Poly I/C as an adjuvant. Three weeks later, the mice can be boosted, each with an equivalent amount of the adjuvanted immunogen. Three weeks after the boost, they can be challenged intranasally with a 5×LD50 dose of homologous (PR8) influenza virus. Mice can be monitored and evaluated for morbidity and mortality for a suitable time, such as 14 days. Mice losing more than 25% of their initial weight can be sacrificed and scored as dead. Survival can be defined as <25% weight loss. To test immunized mice for protection against a drift variant and group 1 heterologous challenges, three groups of C57BL/6 mice can be immunized with 10 μg of Poly I/C adjuvant only (“Adjuvant Only” control groups) and the remaining three groups can be immunized according to the schedule described above with the optimal dose of adjuvanted DT-Headless HA immunogen identified above (“DT-locked Headless Trimer” groups).

Two weeks after the final immunization, one group of Adjuvant Only and one group immunized with the optimized dose of DT-locked Headless trimer each can be challenged intranasally with a lethal dose of homologous virus (PR8 H1N1), the mouse-adapted novel swine pandemic drift variant (NL/09, H1N1), and with heterosubtypic, group 1 influenza virus (VN04 HALO/PR8_6+2 mutant H5N1) (Table 1). Mice can be monitored and evaluated for morbidity and mortality for 10 days and scored as described above.

TABLE 1

Immunization groups to assess breadth of protection

| Immunogen | Adjuvant only (negative controls) | DT-locked Headless trimer |
|---|---|---|
| Challenge: homologous vs. drift variant vs. heterosubtypic | A. Homologous (PR8)<br>C. Drift variant (NL09)<br>E. Group 1 Heterosubtypic (VN04 HALO/PR8_6 + 2 mutant) | B. Homologous (PR8) (positive control)<br>D. Drift variant (NL09)<br>F. Group 1 Heterosubtypic (VN04 HALO/PR8_6 + 2 mutant) |

Statistical Considerations: In view of the fact that both the predictor (adjuvant only vs. adjuvant+DT Headless immunogen) and the outcome (death vs. survival) are dichotomous, the null hypothesis that the vaccine has no effect can be tested with Fisher’s Exact Test. To calculate the minimum number of animals per group (equal numbers in all groups) necessary to detect an effect at the 95% confidence level ($p<0.05$), the power can be set to 80% and an assumed effect size of 50% can be used (80% lethality in the control group, 30% lethality in the vaccinated groups). Accordingly, each analyte and control group should use a minimum of 15 animals.

All methods can be carried out according to standard procedures, for example as described in Steel et al. 2010 [1]. For example, in ELISA assays the antigen (PR8 HA) can be immobilized with an α-foldon mAb (e.g. 74550, Fibrogen Inc.) or an α-stalk mAb to a non-quaternary epitope in order to optimize presentation of its native structure. Antigen-specific Ig in serum can be detected using labeled α-mouse Abs.

It is expected that DT-Headless will successfully induce protection against drift virus (group D: NL09, H1N1), and/or a heterologous strain (group F: H5N1). If need be the immunogen can be reformulated with a different/additional adjuvant and/or the doses tested can be increased, and immunogen dose-calibration testing can be repeated. In addition, if need be the prime-boost regimen can be altered to include a third boost with purified DT-Headless HA antigen. The number of animals used in the final challenge study can be altered/increased to achieve an acceptable confidence level from homologous vs. drift and heterologous challenges.

References for Example 1

1. Steel, J. et al. Influenza virus vaccine based on the conserved hemagglutinin stalk domain. *MBio* 1, (2010).
2. Pica, N. et al. Hemagglutinin stalk antibodies elicited by the 2009 pandemic influenza virus as a mechanism for the extinction of seasonal H1N1 viruses. *Proc. Natl. Acad. Sci. U.S.A.* 109, 2573-2578 (2012).
3. Miller, M. S. et al. 1976 and 2009 H1N1 Influenza Virus Vaccines Boost Anti-Hemagglutinin Stalk Antibodies in Humans. *J. Infect. Dis*. (2012).doi:10.1093/infdis/jis652
4. Krammer, F., Pica, N., Hai, R., Tan, G. S. & Palese, P. Hemagglutinin Stalk-Reactive Antibodies Are Boosted following Sequential Infection with Seasonal and Pandemic H1N1 Influenza Virus in Mice. *J. Virol.* 86, 10302-10307 (2012).
5. Wei, C.-J. et al. Induction of broadly neutralizing H1N1 influenza antibodies by vaccination. *Science* 329, 1060-1064 (2010).
6. Sagawa, H., Ohshima, A., Kato, I., Okuno, Y. & Isegawa, Y. The immunological activity of a deletion mutant of influenza virus haemagglutinin lacking the globular region. *J. Gen. Virol.* 77 (Pt 7), 1483-1487 (1996).
7. Ekiert, D. C. et al. Antibody recognition of a highly conserved influenza virus epitope. *Science* 324, 246-251 (2009).
8. Wang, T. T. et al. Vaccination with a synthetic peptide from the influenza virus hemagglutinin provides protection against distinct viral subtypes. *Proc. Natl. Acad. Sci. U.S.A.* 107, 18979-18984 (2010).
9. Ekiert, D. C. & Wilson, I. A. Broadly neutralizing antibodies against influenza virus and prospects for universal therapies. *Curr Opin Virol* 2, 134-141 (2012).
10. Ekiert, D. C. et al. A highly conserved neutralizing epitope on group 2 influenza A viruses. *Science* 333, 843-850 (2011).
11. Julien, J.-P., Lee, P. S. & Wilson, I. A. Structural insights into key sites of vulnerability on HIV-1 Env and influenza HA. *Immunol. Rev.* 250, 180-198 (2012).
12. Dreyfus, C. et al. Highly conserved protective epitopes on influenza B viruses. *Science* 337, 1343-1348 (2012).
13. Corti, D. et al. A neutralizing antibody selected from plasma cells that binds to group 1 and group 2 influenza A hemagglutinins *Science* 333, 850-856 (2011).
14. Nabel, G. J. & Fauci, A. S. Induction of unnatural immunity: prospects for a broadly protective universal influenza vaccine. *Nat. Med.* 16, 1389-1391 (2010).
15. Burton, D. R., Poignard, P., Stanfield, R. L. & Wilson, I. A. Broadly neutralizing antibodies present new prospects to counter highly antigenically diverse viruses. *Science* 337, 183-186 (2012).
16. Helms, M. K., Malencik, D. A. & Anderson, S. R. Flexibility involving the intermolecular dityrosyl cross-links of enzymatically polymerized calmodulin. *Biochemistry* 37, 8378-8384 (1998).

17. Malencik, D. A., Sprouse, J. F., Swanson, C. A. & Anderson, S. R. Dityrosine: preparation, isolation, and analysis. *Anal. Biochem.* 242, 202-213 (1996).
18. Malencik, D. A. & Anderson, S. R. Dityrosine formation in calmodulin: cross-linking and polymerization catalyzed by *Arthromyces* peroxidase. *Biochemistry* 35, 4375-4386 (1996).
19. Rodriguez-Mateos, A., Millar, S. J., Bhandari, D. G. & Frazier, R. A. Formation of dityrosine cross-links during breadmaking *J. Agric. Food Chem.* 54, 2761-2766 (2006).
20. Horowitz, E. D., Finn, M. G. & Asokan, A. Tyrosine cross-linking reveals interfacial dynamics in adeno-associated viral capsids during infection. *ACS Chem. Biol.* 7, 1059-1066 (2012).
21. Elvin, C. M. et al. Synthesis and properties of crosslinked recombinant pro-resilin. *Nature* 437, 999-1002 (2005).
22. Wang, W. Protein aggregation and its inhibition in biopharmaceutics. *International Journal of Pharmaceutics* 289, 1-30 (2005).
23. Walker, L. M. et al. Broad and potent neutralizing antibodies from an African donor reveal a new HIV-1 vaccine target. *Science* 326, 285-289 (2009).
24. Pejchal, R. et al. Structure and function of broadly reactive antibody PG16 reveal an H3 subdomain that mediates potent neutralization of HIV-1. *Proc. Natl. Acad. Sci. U.S.A.* 107, 11483-11488 (2010).
25. Walker, L. M. et al. Broad neutralization coverage of HIV by multiple highly potent antibodies. *Nature* 477, 466-470 (2011).
26. Harris, A. et al. Trimeric HIV-1 glycoprotein gp140 immunogens and native HIV-1 envelope glycoproteins display the same closed and open quaternary molecular architectures. *Proc. Natl. Acad. Sci. U.S.A.* 108, 11440-11445 (2011).
27. Alff, P. J. & Marshall, C. et al., C. Conformational-Locking of Cleaved HIV-1 gp140 Trimers by Targeted Dityrosine Bonds. *Manuscript in Preparation*
28. Palese, P. Influenza: old and new threats. *Nat. Med.* 10, S82-7 (2004).
29. Madjid, M. & Casscells, W. Influenza as a bioterror threat: the need for global vaccination. *Expert Opin Biol Ther* 4, 265-267 (2004).
30. Osterholm, M. T. Preparing for the next pandemic. *N. Engl. J. Med.* 352, 1839-1842 (2005).
31. Avatar Medical, LLC Stabilized proteins. (2005).
32. Josefsberg, J. O. & Buckland, B. Vaccine process technology. *Biotechnol. Bioeng.* 109, 1443-1460 (2012).
33. Palese, P. Personal Communication. *Professor and Chair of Microbiology, Professor of Medicine, Infectious Disease—Mt. Sinal School of Medicine*
34. Aeschbach, R., Amadò, R. & Neukom, H. Formation of dityrosine cross-links in proteins by oxidation of tyrosine residues. *Biochim. Biophys. Acta* 439, 292-301 (1976).
35. Cox, M. M. J. Recombinant protein vaccines produced in insect cells. *Vaccine* 30, 1759-1766 (2012).
36. Cox, M. M. J. & Hollister, J. R. FluBlok, a next generation influenza vaccine manufactured in insect cells. *Biologicals* 37, 182-189 (2009).
37. Yondola, M. A. et al. Budding capability of the influenza virus neuraminidase can be modulated by tetherin. *J. Vivol.* 85, 2480-2491 (2011).
38. Crowe, J. E. Personal Communication. *Director, Vanderbilt Vaccine Center, Vanderbilt University Medical Center*

Example 2

Recombinant, soluble protein immunogens represent a significant opportunity in the fight against natural and weaponized pathogens. Broadly neutralizing antibodies (bnAbs) against many pathogens have been described in recent years, many of which bind quaternary structures only displayed by protein complexes—which themselves are often unstable. Therefore, an urgent need exists to "lock" protein-based vaccine immunogens into the same native quaternary conformation as they are presented by the pathogen itself.

The present example relates to a headless hemagglutinin-based universal flu vaccine made using a system that includes (i) performing site-directed mutagenesis at positions where resulting Tyr residues are predicted to be in close structural proximity, (ii) expressing and purifying the mutant protein, and (iii) subsequently enzymatically crosslinking/locking of the fully-folded protein complex. DT crosslinking is targeted and zero-length, DT bonds are irreversible and do not form spontaneously, and, most importantly, introduction of DT-bonds preserves protein structure and function, since it occurs once the protein is fully folded.

At present, a universal influenza vaccine immunogen is not available. Recently, however, headless HA constructs trimerized in the transmembrane domain were described that focus Ab responses on the highly conserved stalk, and that, indeed, elicit broadly protective responses. Soluble headless HA trimerized by a foldon motif, however misfolds, does not present key quaternary neutralizing epitopes (QNEs), and elicits insufficiently protective responses. The present invention provides an alternative system that involves (i) DT-crosslinking a soluble HA construct in its native, trimeric conformation, and (ii) removing the "head" domain by engineering and cutting proteolytic cleavage sites in the variable loops and at the base of the head. The interactions between the subunits of the HA soluble stem (lacking the transmembrane domain) can be locked by dityrosine crosslinking while maintaining the structural integrity of HA trimers. Based on crystal structures, constructs with Tyr side-chains in the stem and in close structural proximity can be made, while avoiding bnAb binding sites. These constructs can be expressed and the resulting proteins purified by His-tag affinity chromatography. Tests can be performed to determine whether the constructs form intermolecular DT crosslinks by screening for DT-specific fluorescence and by gel shift analyses (e.g. Western blots).

Using of a panel of anti-stem bnAbs, functional preservation of DT crosslinked HA trimer can be measured by ELISA using anti-stem bnAbs. Thermodynamic stabilization can be assayed to confirm the positions of DT bonds and the constructs' structural integrity after crosslinking biophysically. Constructs can be selected based on favorable antigenic and/or biochemical profiles. It is expected that binding to quaternary anti-stem bnAbs such as 6F12, C179, CR6261, F10, A66 and D8 will be fully maintained.

Proteolytic cleavage sites can be engineered to unravel and remove the head of native, DT-stabilized HA trimers. Fully folded HA constructs with 4 or more cleavage sites for 1 or 2 proteases can be designed, generated, expressed, and DT crosslinked, and then purified by His-tag affinity chromatography before digesting with protease(s) to remove the head. Antigenic and biochemical and biophysical analyses can be performed to confirm preservation/integrity of QNEs in DT-headless HA after proteolytic digestion and immunogenic analysis can be performed in mice.

Seasonal and pandemic influenza viruses remain a serious threat to human health, due to their ability to evade immune surveillance through rapid genetic drift and re-assortment. In the US alone, influenza causes seasonal epidemics that contribute to hundreds of thousands of hospitalizations and an average of 30,000 deaths annually, while creating a serious economic burden for individuals and the economy as a whole [1-3]. Pandemic outbreaks occur when a virulent strain of virus emerges that infects people with little or no immunity, and rapidly spreads across the globe, representing one of the most serious threats to human health. The 1918 Spanish Flu (H1N1) pandemic caused an estimated 50 million deaths; the 1957 Asian influenza (H2N2) pandemic and the 1968 Hong Kong (H3N2) pandemic each caused several million deaths [6]. Because influenza viruses are readily accessible and are easily transmitted by aerosol, the possibility for genetic engineering represents an enormous threat of weaponization, biowarfare, and bioterrorism [7,8]. Vaccines hold the greatest promise of providing protection in order to control infection.

Although highly effective when matched to circulating strains, current influenza virus vaccines protect mostly against homologous virus strains. Protection is primarily due to high-avidity antibodies against the highly variable, immunodominant head domain of the hemagglutinin (HA) protein, which is specific to each strain of influenza. Therefore, new trivalent vaccine cocktails must be tailored each year to the prevalent influenza strains in circulation. Conventional, egg-based influenza vaccine manufacturing requires that strains be selected 9 months before the start of the season. Unfortunately, predictions of the circulating strains are often inaccurate, resulting in vaccines that are poorly matched, and therefore poorly protective [9-11]. A multitude of development programs are underway to address this problem, many of them in advanced stages, but the approach proposed herein has the potential to move one or more programs beyond the safety and efficacy hurdles, and enable a truly long-term broadly protective vaccine product for both seasonal and pandemic influenza.

The stem of HA is highly conserved across a multitude of influenza strains, and considerable evidence now suggests that vaccination with a ‘headless’ HA consisting primarily of the HA stem results in the induction of antibody responses with significantly enhanced heterosubtypic binding activity and broad protection against lethal challenge [12-15, 16, 17]. As such, headless HA holds significant promise as a universal vaccine immunogen capable of protecting against all strains of influenza [16] [17]. Interestingly, immunization with DNA coding for HA has been observed to generate predominantly stalk-specific Ab responses, and data describing heterosubtypic protection by vaccination with HA DNA by electroporation was recently described [50]. A prime-boost combination of an expression vector encoding HA, followed by soluble headless protein boost holds the promise of generating broadly heterospecific responses that yield long-lasting protection.

The present invention provides a soluble ‘headless’ HA trimer covalently stabilized in its correctly folded conformation that presents key quaternary neutralizing epitopes (QNEs). Targeted dityrosine crosslinking technology is used to stabilize a full-length HA trimer, and subsequently the head is removed using sequence/substrate-specific proteases—making use of variable loop tolerance for amino acid variation.

Dityrosine (DT) crosslinking provides a method for stabilizing protein folds, complexes, and conformations by enzymatically introducing zero-length crosslinks, while maintaining structural and functional integrity of the protein [20,21]. Dityrosine bonds provide conformational stability and rigidity to protein structures and have been described in many diverse natural settings. DT crosslinks form naturally in vivo, both in the context of proteins evolved to utilize their specific characteristics [22-24], and as a consequence of protein oxidation [25]. DT bonds form the structure of wheat gluten—the quaternary protein structure comprising the glutenin subunits—and are present in large quantities in some of our most common foods [26]. No other amino acids form crosslinks or are modified when the reaction is carried out under mild conditions, though the tyrosyl side-chains themselves may oxidize if positioned too far apart, thus limiting the efficiency of the reaction, particularly under sub-optimal conditions. DT crosslinks are not hydrolyzed under normal physiological conditions, and do not form spontaneously in vitro. These features of the DT-crosslinking provide important advantages over conventional S—S chemistry; namely spontaneous and/or undesired protein products do not form and non-specific bonding/aggregation does not occur on maturation and processing. Because the reaction can be tightly controlled, development of a large-scale high-yield process can be relatively straight-forward, making the large-scale manufacturing a DT stabilized immunogen more feasible economically.

One of the key features of DT crosslinking is that it is highly dependent on the structural proximity of tyrosyl side-chains, which must therefore be engineered within the structure of a protein or protein complex. Because no carbons are added in the formation of the bond, the resulting “staples” are non-disruptive to the overall protein fold and, critically, specific sites within the protein structure can be targeted with high specificity. The necessary tyrosines may be present in the primary structure of the protein or added by “to tyrosine” point mutations, while Tyr residues that form undesirable DT bonds can be mutated (to Phe, for example) to reduce background.

Protein immunogens are folded chains of amino acid polypeptides, sometimes consisting of several polypeptide subunits. The rate of spontaneous unfolding, conformational transition, and dissociation determines a protein’s functional half-life. Covalent non-peptide bonds between non-adjacent amino acid side chains can dramatically affect the rate of unfolding, and thus the half-life of a protein or protein complex. At least two different chemistries have evolved to accomplish covalent cross-links in proteins in vivo to stabilize their conformations and/or retard unfolding: these are disulfide bonds and dityrosine (DT) bonds.

One major advantage of a directed DT cross-linking approach is that covalent bonds targeted to specific locations can reinforce particular 3-D arrangements of epitopes’ secondary, tertiary, and/or quaternary structures, thereby preventing undesirable conformational transitions, and have the potential to provide a high degree of thermodynamic stabilization and conformational locking without adversely affecting the antigenic properties of protein immunogens.

Disulfide bonds have been found in many eukaryotic proteins of diverse function. Intra-molecular S—S cross-links are often essential in stabilizing protein domains, and inter-molecular S—S bonds provide stability for the quaternary structure of protein complexes. These bonds can form spontaneously, and therefore do not require an additional manufacturing and purification process, but also reduce manufacturing yields due to free sulfhydryl-mediated aggregate formation. Furthermore, because they are formed as the protein is folding in the ER/Golgi apparatus, they can lead to structural distortions that would affect QNE presentation and the breadth of immunogenic protection.

The C—C bond created by DT-crosslinking is stable under virtually any physiological and/or operational conditions that are likely to be used in accordance with the present invention, including those used in the process of immunization and vaccination. DT bonds are “zero length”—i.e. no atom is added. The cross-linking catalyst simply initiates bond formation between two tyrosines and is not incorporated into the product. Thus, no undesirable chemical modification of the protein occurs. DT cross linking is also very specific—no amino acids other than tyrosines have been shown to form cross-links or to be modified when the reaction is carried out under mild conditions. In addition, there is a strict distance requirement between the tyrosine side-chains, with the bond forming only when the two are in very close proximity. Furthermore, DT crosslinks do not form spontaneously, and, as described above, form only between Tyr residues in close proximity. DT crosslinking a protein can therefore lock it in its pre-existing native/functional conformation. In the context of headless HA design, this allows one to (i) engineer headless in an antigenically/immunogenicaly favorable conformation, e.g. by introducing point mutations, and then (ii) lock it in this preferred conformation by DT crosslinking.

Dityrosine bonds (DT bonds) that have important biological functions have been identified in proteins of several species, presumably in environments where disulfide bonds would be unsuitable. Specific DT bonds have, for example, been described in the cuticlin protein of *Caenorhabditis elegans [*27], the cell wall proteins of bamboo shoots [28], and parchment collagen [29]. In all of these cases, the proteins have evolved such that specifically placed DT cross-links contribute to the structural rigidity underlying the proteins' functionality. The importance of such bonds is also evidenced by the fact that in yeast, for example, a metabolic pathway has been described that leads to the formation of DT bonds in specialized proteins [30].

Furthermore, due to the distinct fluorescent properties of DT bonds, in the absence of atomic level structures, their formation can easily be assayed using conventional 96- and 384-well fluorescence plate readers. This also makes optimization of cross-linking conditions simple and efficient.

The present methods involve (a) generating a DT stabilized full-length HA molecule that retains a stalk-specific antigenic profile equivalent to that of WT HA, (b) removing the head domain from the fully folded DT-HA by proteolytic cleavage while retaining the same 'stalk-specific' antigenic profile as WT HA. Immunogenicity may be confirmed in animal studies.

The present example utilizes HA from the H1N1 A/Puerto Rico/8/1934 ("PR8") strain of influenza as the starting point. The majority of influenza virus research in mice employs lab adapted PR8 or the A/WSN/1933 (H1N1) [WSN] influenza viruses. Immunogenicity and challenge studies can be carried out in BALB/c mice with homologous and heterologous H1N1 PR8 and H3N2X31 challenges. X31 is a reassortant virus carrying the HA and NA genes of A/Hong Kong/1/1968 (H3N2) in the background of PR8 [35].

To identify HA constructs which allow dityrosine bonds to form and stabilize the HA trimer, the trimeric HA crystal structure is analyzed (pdb file 3 GBN) and proximal residues are selected for tyr-substitution away from the binding sites of quaternary neutralizing antibodies (see FIG. 5). Once the in silico design of "to-tyr" point mutants (2T-HAs) is complete, cDNA encoding the ectodomain of wild-type HA (PR8) and to-tyr substitution mutants can be generated and cloned into a baculovirus transfer vector (pAcGP67A) using standard molecular biology techniques. WT and 2T-HA proteins can be expressed in SF9 or Hi5 cells and secreted HA can be purified over lectin-based glyco-affinity columns and MonoQ anion-exchange columns. Following purification, secreted HA trimmers can be isolated from monomers and high molecular weight aggregates by size exclusion chromatography (SEC) over a Superdex200 column.

To evaluate whether or not the designed 2T-HA constructs form intermolecular DT cross-links, the purified proteins can be analyzed before and after exposure to DT crosslinking conditions by gel-shift in reducing SDS-PAGE (Western blot and Coomassie stain) and for DT-specific fluorescence. Constructs capable forming DT cross-links with an efficiency of >50% can be taken forward for further characterization. Based on preliminary studies with HIV env trimers, it is believed that crosslinking efficiencies of greater than 80% are attainable without significant process optimization. Biochemical and biophysical analysis of DT-crosslinked HA trimers (DT-HA) be can be performed to compare their thermostability with that of uncrosslinked HA in normal human serum at 37° C. over a time-course of 1-30 days. Trimeric DT-HA and control (uncrosslinked) trimeric HA can be analyzed each day for the presence of retained trimer by Western blot. Likewise, a 60-day, 25° C. time course in PBS (pH 7.4) of purified, trimeric DT-HA and control (uncrosslinked) trimeric HA can be analyzed weekly by SEC. The proportion of total material in the trimeric and monomeric fractions can be quantified using standard peak-integration software and the ratio of trimer to monomer in the DT-HA and control samples can be determined. Given that DT-HA constructs can be identified based on their stability in reducing SDS-PAGE, it is expected that 100% of the DT crosslinked trimer will remain trimeric under the experimental conditions described above, while labile uncrosslinked HA trimers will dissociate into monomeric subunits throughout the duration of the time course.

A central advantage of DT crosslinking technology over other crosslinking methodologies is the ability to form covalent intermolecular crosslinks without disrupting the antigenic profile of vaccine immunogen candidates. The effect of the both the "to-tyr" mutations and the DT crosslinking can be determined by ELISA using a panel of anti-HA stem broadly neutralizing mAbs (e.g 6F12, C179, CR6261, F10, A66 and D8). Full-curve binding assays can be used to compare WT HA trimers to the 2T-HA mutant trimers (uncrosslinked) and to DT-HA trimers (crosslinked). Changes in binding following the introduction of to-tyr mutations as well as after DT crosslinking can be determined using non-linear regression analysis of binding curves to calculate and compare EC50 values for each construct with each mAb. The position of to-tyr mutations can be distal to and non-overlapping with amino acids involved in binding of the anti-stem bnAbs listed above. It is possible that structural changes caused by tyrosine substitutions may reduce or enhance binding to some of these antibodies. However, preliminary studies using HIV suggest that DT crosslinking fully preserves a protein candidate's antigenic profile and a similar degree of antigenic preservation is expected following DT crosslinking of influenza HA.

In order to assess non-specific changes to amino acid side chains throughout the entire crosslinked protein, comparative amino acid analysis (AAA) can be performed on uncrosslinked (control) and crosslinked constructs. Amino acid analysis can also be used to confirm the presence of DT bonds since dityrosine crosslinks withstand even the acid-hydrolysis used to prepare samples for AAA and dityrosine itself can be specifically detected in the analysis. In order to directly identify the position of the dityrosine bonds in DT-HA, mass spectrometry analysis of deglycosylated tryptic digests can be used, for example by performing LC-MS/MS on a Thermo Scientific LTQ Mass Spectrometer with a Michrom Paradigm HPLC and Michrom Vacuum Spray ionization source. Collectively these studies can be used to identify and characterize HA constructs capable of forming trimerizing DT bonds. Such constructs may, even prior to removal of the immune-dominant HA head domain, provide improved HA immunogens stably presenting stalk specific QNEs.

Previously reported recombinant headless HA constructs do not retain the fully native, quaternary structure of the HA stem and thus, these constructs do not bind known quaternary specific bnAbs. Following baculovirus expression and purification of DT-HA construct(s) as described above the head domain can be removed proteolytically—post-folding and after DT crosslinking—in order to generate a stable headless HA which retains binding to broadly protective, conformation-dependent quaternary antibodies. In order to enable the proteolytic removal of the globular head domain of HA, protease cleavage sites can be introduced into HA1. Head-removal sites can be introduced at, for example, positions 60-76 (N-terminal site) and 277-290 (c-terminal site) through standard molecular biology techniques [19]. Crystal structures of HA indicate that these positions are solvent-exposed and could be made further accessible to proteases by removing the structural constraints that may hamper efficient proteolysis through the introduction of additional cleavage sites into the HA1 variable loop domains (AA positions 142-146 and 155-164) [37]. Unraveling the head can be used to further improve protease substrate access, if required. Introduction of cleavage sites into the HA variable loops is not expected to alter the overall conformation of the HA trimer as these sites are highly tolerant of amino acid substitutions. Indeed, all of these amino acid positions (e.g. 142-146 and 155-164) have changed in infectious virus isolates collected from 1968 through 1999 [38]. Cleaving HA1 in the variable loops can be performed to destabilize the head's globular structure, allowing complete exposure and efficient cleavage at the primary head-removal sites (53-67 and 269-277). PreScission Protease (GE Healthcare Life Sciences) recognition sequences (LEVLFQGP (SEQ ID NO:69)) and TEV (Tobacco Etch Virus protease) recognition sequences ENLYFQG (SEQ ID NO:70) and ENLYFQS (SEQ ID NO:71)) can be used/introduced. TEV cleavage can be carried out at a substrate to enzyme ratio of 1:50-200 w/w in a 25 mM Tris-HCl buffer with 150-500 mM NaCl, and 14 mM (3-mercaptoethanol at pH 7.0. PreScission Protease cleavage can be performed in a 50 mM Tris-HCl buffer, with 150 mM NaCl, 1 mM EDTA and 1 mM dithiothreitol (DTT) at pH 7.0. Removal of the head can be assayed by electro-mobility shift from a molecular weight corresponding to a full-length DT-HA trimer (~225 kDa) to that of a headless trimer (~135 kDa) by SDS-PAGE, followed by coomassie stain and Western blot. Head-specific detection Abs can be used to confirm removal of the head from the DT crosslinked HA stem by Western blot and ELISA. If HA head-removal is incomplete, the positions of Prescission Protease and TEV sites can be swapped, or, only a single type of site can be introduced at all desired cleavage positions.

In order to test the immunogenicity of the DT-headless constructs, mouse immunogenicity studies can be performed. BALB/c mice (6-8 weeks old) can be anesthetized with isoflurane 3-5% and subsequently immunized in a prime-boost regime/schedule with two intramuscular injections 3 weeks apart, first with DNA comprising 37.5 μg of pGag-EGFP and 75 μg of pDZ_PR8_HA followed by electoporation pulsing (prime), and subsequently with 25 μg of WT HA, foldon/GCN4-stabilized HA trimers, or DT-headless protein (boost). Protein (boost) immunogens can be formulated with Alum (Aluminum phosphate, 300 μg/dose). Two weeks following the second injection (boost), serum can be collected and assayed for anti-HA responses relative to pre-immunization serum and adjuvant only controls. Overall anti-HA IgG and IgM titers for each group can be determined by ELISA. Heterosubtypic reactivity of antisera to 10 different purified group 1 and group 2 HAs can be determined Western blot and ELISA. Immunogens from each group are expected to elicit anti-HA antibody responses. In order to investigate the heterosubtypic neutralization capacity of anti-serum from each group, the ability of these sera to neutralize a panel of heterologous influenza viruses (HK/68 H3, Bris/07 H3, Neth/03 H7, Cal/09 H1, Sing/57 H2, Viet/04 H5, HK/97 H6, HK/99 H9) can be tested. Anti-serum can be serially diluted 2-fold, mixed with an equal volume of virus, and incubated for 2 h at 37° C. Virus-serum mixtures can be added to target cells (MDCK) in serum free media containing trypsin and incubated for 3 h prior to replacement of the media. Cells can be monitored for cytopathic effects 3-5 days following exposure to virus-serum mixtures.

A major objective of this immunogen design and development process is to generate a DT-headless immunogen capable of eliciting bnAbs and protecting against heterologous influenza challenge. To directly investigate the ability of DT-headless to elicit protective responses against influenza infection, 3 groups of 20 BALB/c mice can be immunized with WT HA, foldon/GCN4 headless, or DT-headless, compared to non/pre-immunized and adjuvant-only immunized controls (groups 4 and 5, 20 mice each), and challenged intranasally with a lethal dose of homologous (PR8) or heterologous (X31) virus—10 mice each—2 weeks following the second immunization (boost). Mice can be anesthetized with an intra-peritoneal injection of ketamine (75 mg/kg) and xylazine (15 mg/kg) prior to challenge, and body weight can be monitored daily. <20% weight loss can be used as a surrogate for survival. It is expected that each immunogen (WT HA, foldon/GCN4 headless, DT-headless) will provide some degree of protection against PR8 challenge. However, it is expected that immunization with a DT-headless immunogen will provide significantly improved protection against heterologous influenza challenge and that this protection will correlate with the titers of bnAbs recognizing conserved QNEs that presented on the native HA stem in its trimeric form.

The baculovirus expression vector system (BEVS) can be used for manufacturing of recombinant HA antigen as this system is well established and suitable production/purification protocols have been well described and validated [10]. Generally, such protocols involve harvesting infected cells by centrifugation, detergent-mediated protein solubilization, followed by purification involving two chromatographic (IE and HIC columns) steps [10]. Due to the large difference in MW of the trimeric stalk as compared to the monomeric head, and the enzymes used in processing, gel filtration can also be used. IE chromatography can also be used.

Two enzymes are used in the processes described herein—peroxidases to catalyze the formation of DT bonds and proteases to cleave off the HA head after cross-linking. Both are commercially available.

Purity of the finished immunogens can be ascertained by conventional gel electrophoresis and HPLC. Cross-linking can be assessed by a combination of gel electrophoresis under denaturing conditions, fluorescence measurements, and amino acid analysis. Immunogenicity can be assessed by profiling against a panel of selected antibodies as described above. HPLC-based assays can be used to identify and measure protein sugar compositions.

DT-Headless HA can be formulated with an adjuvant selected based on technical specifications and other considerations. Adjuvanted HA formulated with a variety of excipients and stabilizing agents/preservatives can be lyophilized, and following rehydration tested biophysically (dynamic light scattering) and antigenically. The effect of storage at room temperature, 4° C. and −20° C. can be tested to determine long-term storage conditions, stability, and potency.

Animal efficacy studies (e.g. conducted in ferrets) can be performed and acute and long-term animal safety studies can be performed. Ferrets are susceptible to human influenza viruses and develop some of the symptoms of influenza that are seen in humans; furthermore, they are large enough to monitor clinical parameters (e.g. temperature, pulse, and respiratory rate), and relatively large amounts of sera can be obtained for use in serologic and antigenic characterization.

References for Example 2

1. Bouvier N M, Palese P: The biology of influenza viruses. Vaccine 2008, 26 Suppl 4:D49-53.
2. Rappuoli R, Dormitzer P R: Influenza: options to improve pandemic preparation. Science, 336:1531-1533.
3. Palese P S M (Ed.). Orthomyxoviridae: The Viruses and their Replication.; 2007.
4. Liu J, Bartesaghi A, Borgnia M J, Sapiro G, Subramaniam S: Molecular architecture of native HIV-1 gp120 trimers. Nature 2008, 455:109-113.
5. McLellan J S, Pancera M, Carrico C, Gorman J, Julien J P, Khayat R, Louder R, Pejchal R, Sastry M, Dai K, et al: Structure of HIV-1 gp120 V1/V2 domain with broadly neutralizing antibody PG9. Nature 2011, 480:336-343.
6. Tumpey T M, Belser J A: Resurrected pandemic influenza viruses Annu Rev Microbiol 2009, 63:79-98.
7. Tripp R A, Tompkins S M: Animal models for evaluation of influenza vaccines. Curr Top Microbiol Immunol 2009, 333:397-412.
8. Bartlett J G, Borio L: Healthcare epidemiology: the current status of planning for pandemic influenza and implications for health care planning in the United States. Clin Infect Dis 2008, 46:919-925.
9. Fiore A E, Bridges C B, Cox N J: Seasonal influenza vaccines. Curr Top Microbiol Immunol 2009, 333:43-82.
10. Josefsberg J O, Buckland, B.: Vaccine Process Technology. Biotechnology and Bioengineering 2012, 109.
11. Greenberg M E, Lai M H, Hartel G F, Wichems C H, Gittleson C, Bennet J, Dawson G, Hu W, Leggio C, Washington D, Basser R L: Response to a monovalent 2009 influenza A (H1N1) vaccine. N Engl J Med 2009, 361: 2405-2413.
12. Ekiert D C, Bhabha G, Elsliger M A, Friesen R H, Jongeneelen M, Throsby M, Goudsmit J, Wilson I A: Antibody recognition of a highly conserved influenza virus epitope. Science 2009, 324:246-251.
13. Wang T T, Tan G S, Hai R, Pica N, Ngai L, Ekiert D C, Wilson I A, Garcia-Sastre A, Moran T M, Palese P: Vaccination with a synthetic peptide from the influenza virus hemagglutinin provides protection against distinct viral subtypes. Proc Natl Acad Sci USA, 107:18979-18984.
14. Ekiert D C, Wilson I A: Broadly neutralizing antibodies against influenza virus and prospects for universal therapies. Curr Opin Virol, 2:134-141.
15. Ekiert D C, Friesen R H, Bhabha G, Kwaks T, Jongeneelen M, Yu W, Ophorst C, Cox F, Korse H J, Brandenburg B, et al: A highly conserved neutralizing epitope on group 2 influenza A viruses. Science, 333:843-850.
16. Hu H, Voss J, Zhang G, Buchy P, Zuo T, Wang L, Wang F, Zhou F, Wang G, Tsai C, et al: A human antibody recognizing a conserved epitope of H5 hemagglutinin broadly neutralizes highly pathogenic avian influenza H5N1 viruses. J Virol, 86:2978-2989.
17. Corti D, Voss J, Gamblin S J, Codoni G, Macagno A, Jarrossay D, Vachieri S G, Pinna D, Minola A, Vanzetta F, et al: A neutralizing antibody selected from plasma cells that binds to group 1 and group 2 influenza A hemagglutinins Science, 333:850-856.
18. Steel J, Lowen A C, Wang T T, Yondola M, Gao Q, Haye K, Garcia-Sastre A, Palese P: Influenza virus vaccine based on the conserved hemagglutinin stalk domain. MBio 2010, 1.
19. Pica N, Hai R, Krammer F, Wang T T, Maamary J, Eggink D, Tan G S, Krause J C, Moran T, Stein C R, et al: Hemagglutinin stalk antibodies elicited by the 2009 pandemic influenza virus as a mechanism for the extinction of seasonal H1N1 viruses. Proc Natl Acad Sci USA, 109:2573-2578.
20. Malencik D A, Sprouse J F, Swanson C A, Anderson S R: Dityrosine: preparation, isolation, and analysis. Anal Biochem 1996, 242:202-213.
21. Malencik D A, Anderson S R: Dityrosine formation in calmodulin: cross-linking and polymerization catalyzed by *Arthromyces* peroxidase. Biochemistry 1996, 35:4375-4386.
22. Tenovuo J, Paunio K: Formation of dityrosine by human salivary lactoperoxidase in vitro. Acta Odontol Scand 1979, 37:147-152.
23. Tenovuo J, Paunio K: Peroxidase-catalysed formation of dityrosine, a protein cross-link, in human periodontal ligament collagen. Arch Oral Biol 1979, 24:591-594.
24. Elvin C M, Carr A G, Huson M, Maxwell J M, Pearson R D, Vuocolo T, Liyou N E, Wong D C, Merritt D J, Dixon N E: Synthesis and properties of crosslinked recombinant pro-resilin. Nature 2005, 13.
25. Giulivi C, Traaseth N J, Davies K J: Tyrosine oxidation products: analysis and biological relevance. Amino Acids 2003, 25:227-232.
26. Tilley K A, Benjamin R E, Bagorogoza K E, Okot-Kotber B M, Prakash O, Kwen H: Tyrosine cross-links: molecular basis of gluten structure and function. J Agric Food Chem 2001, 49:2627-2632.27. Lassandro F S M, Zei F, Bazzicalupo P.: The role of dityrosine formation in the crosslinking of CUT-2, the product of a second cuticlin gene of *Caenorhabditis elegans. Mol Biochem Parasitol* 1994, 65:147-159.
28. Totsune H N M, Inaba H.: Chemiluminescence from bamboo shoot cut. *Biochem Biophys Res Commun* 1993, 194:1025-1029.
29. Sobel H A H: Modification in amino acids of Dead Sea Scroll Parchments. *Free Radic Biol Med* 1992, 6:701-702.
30. Briza P K H, Pittenauer E, Allmaier G, Breitenbach M: N,N'-Bisformyl dityrosine is an in vivo precursor of the yeast ascospore wall. *Eur J Biochem* 1996, 239:124-131.
31. Walker L M, Phogat S K, Chan-Hui P Y, Wagner D, Phung P, Goss J L, Wrin T, Simek M D, Fling S, Mitcham J L, et al: Broad and potent neutralizing antibodies from an African donor reveal a new HIV-1 vaccine target. *Science* 2009, 326:285-289.
32. Kwong P D, Wilson I A: HIV-1 and influenza antibodies: seeing antigens in new ways. *Nat Immunol* 2009, 10:573-578.
33. Karlsson Hedestam G B, Fouchier R A, Phogat S, Burton D R, Sodroski J, Wyatt R T: The challenges of eliciting neutralizing antibodies to HIV-1 and to influenza virus. *Nat Rev Microbiol* 2008, 6:143-155.
34. Wu X, Yang Z Y, Li Y, Hogerkorp C M, Schief W R, Seaman M S, Zhou T, Schmidt S D, Wu L, Xu L, et al: Rational design of envelope identifies broadly neutralizing human monoclonal antibodies to HIV-1. *Science,* 329:856-861.

35. Bouvier N M, Lowen A C: Animal Models for Influenza Virus Pathogenesis and Transmission. *Viruses* 2010, 2:1530-1563.

36. Cox M M, Hollister J R: FluBlok, a next generation influenza vaccine manufactured in insect cells. *Biologicals* 2009, 37:182-189.

37. Skehel J J, Wiley D C: Receptor binding and membrane fusion in virus entry: the influenza hemagglutinin. *Annu Rev Biochem* 2000, 69:531-569.

38. Krashias G, Simon A K, Wegmann F, Kok W L, Ho L P, Stevens D, Skehel J, Heeney J L, Moghaddam A E, Sattentau Q J: Potent adaptive immune responses induced against HIV-1 gp140 and influenza virus HA by a polyanionic carbomer. *Vaccine,* 28:2482-2489.

39. Du L, Zhao G, Zhang X, Liu Z, Yu H, Zheng B J, Zhou Y, Jiang S: Development of a safe and convenient neutralization assay for rapid screening of influenza HA-specific neutralizing monoclonal antibodies. *Biochem Biophys Res Commun* 2010.

40. Yumiko Matsuoka E W L, Kanta Subbarao: The Ferret Model for Influenza. *Current Protocols in Microbiology* 2009, 15G.2.1-15G.2.29.

41. Osterhaus A, Fouchier R, Rimmelzwaan G: Towards universal influenza vaccines? *Philos Trans R Soc Lond B Biol Sci,* 366:2766-2773.

42. Medina R A, Manicassamy B, Stertz S, Seibert C W, Hai R, Belshe R B, Frey S E, Basler C F, Palese P, Garcia-Sastre A: Pandemic 2009 H1N1 vaccine protects against 1918 Spanish influenza virus. *Nat Commun,* 1:28.

43. Ross T M, Mahmood K, Crevar C J, Schneider-Ohrum K, Heaton P M, Bright R A: A trivalent virus-like particle vaccine elicits protective immune responses against seasonal influenza strains in mice and ferrets. *PLoS One* 2009, 4:e6032.

44. Settipane R A, Siri D, Bellanti J A: Egg allergy and influenza vaccination. *Allergy Asthma Proc* 2009, 30:660-665.

45. Schultz-Cherry S, Jones J C: Influenza vaccines: the good, the bad, and the eggs. *Adv Virus Res,* 77:63-84.

46. Wrammert J, Koutsonanos D, Li G M, Edupuganti S, Sui J, Morrissey M, McCausland M, Skountzou I, Hornig M, Lipkin W I, et al: Broadly cross-reactive antibodies dominate the human B cell response against 2009 pandemic H1N1 influenza virus infection. *J Exp Med,* 208:181-193.

47. Kaminski D A, Lee F E: Antibodies against conserved antigens provide opportunities for reform in influenza vaccine design. *Front Immunol,* 2:76.

48. Reisinger K S, Block S L, Izu A, Groth N, Holmes S J: Subunit influenza vaccines produced from cell culture or in embryonated chicken eggs: comparison of safety, reactogenicity, and immunogenicity. *J Infect Dis* 2009, 200:849-857.

49. Monto A S, Ohmit S E: Seasonal influenza vaccines: evolutions and future trends. *Expert Rev Vaccines* 2009, 8:383-389.

50. Wang T T, et al. Broadly protective monoclonal antibodies against H3 influenza viruses following sequential immunization with different hemagglutinins PLoS Pathog 6:e1000796

51. Steel J et al. Influenza Virus Vaccine Based on the Conserved Hemagglutinin Stalk Domain. mBio 1(1): e00018-10.

Example 3

Prior attempts at engineering headless HA have included expressing HA proteins in which the globular head region was recombinantly spliced out. Such prior headless HA constructs generated considerable excitement in the field, because they elicited improved, cross-reactive Ab responses. These Abs, however, were not cross protective and only protected against homologous challenge. These prior recombinant headless constructs do not bind the current repertoire of cross-protective, conformational stalk Abs, which suggests at least some degree of stalk mis-folding in the absence of the intact globular head. These prior observations were confirmed using one of the most broadly cross-reactive anti-stalk Abs, C179, by immunofluorescence analysis (see FIG. 6). Application of DT-based conformational locking will circumvent this shortcoming, by holding together the stalk trimer in its native conformation, prior to proteolytic removal of the head, and thus result in a DT-locked Headless HA immunogen that will focus Ab responses on the critical stalk QNEs.

Example 4

DT crosslinks were introduced into the PR8 HA stalk domain, and the DT-cross-linked HA trimer maintained native antigenicity. Based on the crystal structures of the 1918 H1N1 HA trimer in complex with the cr6261 bnAb (pdb file: 3 GBN) and of the PR8 HA (pdb file: 1RU7), to-tyrosine substitutions were successfully engineered into the HA stalk domain in order to enable DT crosslink formation, which should maintain quaternary antigenicity upon proteolytic removal of the globular head. 293T cells were subsequently transfected with secreted variants of the to-tyrosine mutants and measured at 405 nm fluorescence in transfected cell supernatants, to determine the formation of DT bonds. A large increase in 405 nm fluorescence (highly specific for DT bonds) demonstrates robust crosslinking in several to-tyrosine mutants (FIG. 7 A). Based on comparison to the positive control (insulin) and a DT standard, a cross-linking efficiency of >70% was confirmed for four of these constructs, prior to any optimization. As shown in FIG. 7B, C179 Ab binding is unchanged before and after the crosslinking reaction. These data show that the PR8 HA stalk can be cross-linked and that the key quaternary stalk epitope bound by one of the most broadly cross-reactive, conformational mAbs, C179 (2), is maintained.

Targeted protease cleavage sites were also successfully introduced and used to cleave the PR8 HA head domain. Extensive analysis of the PR8 HA structure and transposon-based mutagenesis studies revealed multiple locations within the globular head region that could tolerate insertion of proteolytic cleavage sites. Out of 20+ possible sites identified, two constructs that allow insertion were generated. One site is located at the base of the globular head domain ("48G"), while the other resides closer to the variable loops of the protein ("128S"). Both insertions express well as indicated by Western blot of whole cell extracts (FIG. 6B, left) and form virus-like particles (VLPs) in sufficient quantity for detection in transfected cell supernatants by C179 ELISA (FIG. 8A). Of the two constructs generated, the 48G insertion is predicted to be least accessible for the protease, yet would most completely remove the Head domain, due to its location close to the base of the head. In order to demonstrate that the 48G site is sufficiently accessible, TEV protease cleavage was performed on the HA 48G protein, using WT HA as a negative control. As shown in FIG. 8B, right, TEV protease cleavage of the HA 48G protein results in the removal of the first 48 AAs (6.5 kDa) of HA, but no cleavage occurs in the WT HA protein. Furthermore, HA 48G also maintains hemagglutination activity when assayed directly from transfected cell supernatants, suggesting that it remains folded in its functional conformation (FIG. 8C).

Example 5

Introduction: In designing a conformationally locked headless HA, the atomic structures of the 1918 HA:cr6261 complex (PDB:3 GBN) and PR8 HA (PDB:1RU7) were analyzed to identify positions that 1) enable dityrosine (DT) crosslinking in the stalk at a sufficient distance from the cr6261 epitope to maintain stalk bnAb binding; and 2) enable insertion of protease cleavage sites, that can be used to remove the head.

PR8 HA Trimers were Successfully Locked in their Native Trimeric Conformation Using DT Crosslinks at Several Locations in the HA Stalk; and these DT-Locked HAs Maintain Native Stalk Antigenicity Several tyrosine mutations were engineered into the stalk of PR8 HA that enable the trimers to be locked in their native prefusion state, at high efficiency. FIG. 85A demonstrates a clear shift to the trimeric state (reducing SDS-PAGE) following DT crosslinking; and FIG. 85B confirms that di-tyrosine bonds have formed by specific fluorescence at 405 nm. Densitometry of the cross-linked species demonstrates greater than 80% conversion to the trimeric state. Most importantly binding of 8D4, a stalk-specific bnAb, is fully maintained (FIG. 85C). Crystallographic analysis has shown that 8D4 binds the same epitope as cr6261. These data confirm that the PR8 HA can be cross-linked in its stalk while maintaining the native conformation of the key $V_H$1-69 quaternary stalk epitope.

Multiple C- and N-Terminal TEV Protease Recognition Sites have been Successfully Engineered into the Head of PR8 HA, Individually and in Combination Regions were identified in the head of PR8 HA into which TEV protease cleavage sites can be inserted without disrupting HA's function. For structure-based design, PR8 HA and TEV protease recognition site structural data were combined, and cleavage site insertions were specifically targeted into regions of HA's head based on the following criteria: i) proximity to the stalk apex, in order to maximize removal of the immune-dominant head; ii) similarity between the secondary structures of HA and the TEV cleavage site, to minimize structural perturbation; iii) regions identified as tolerant of insertion based on the transposon mutagenesis screen with data from a transposon-based mutagenesis screen (Heaton and Palese PNAS Vol. 110, No. 50; pp. 20248-53).

Figure 86:
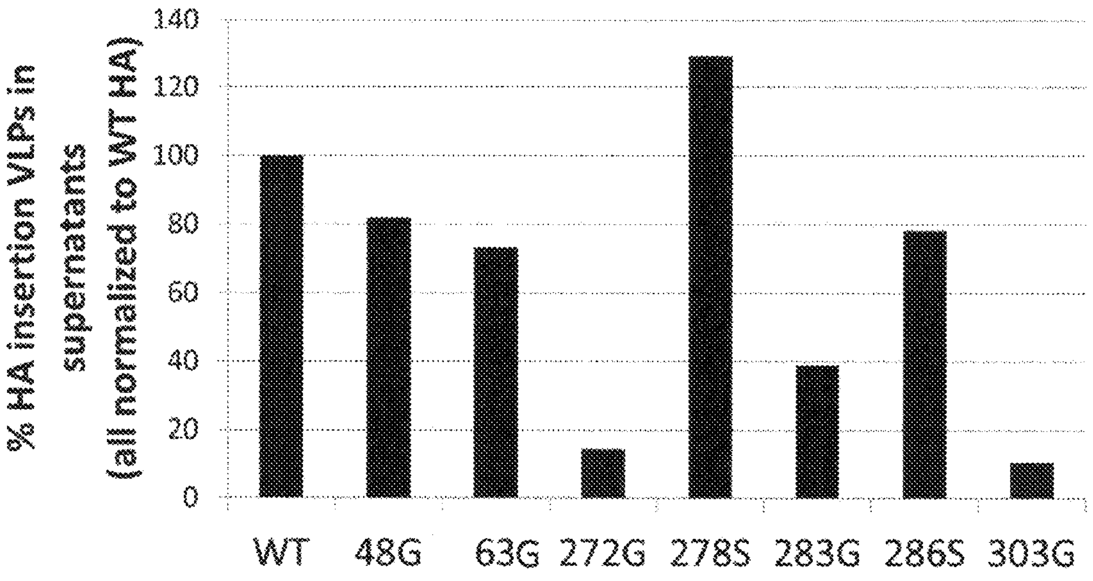
Figure 86:
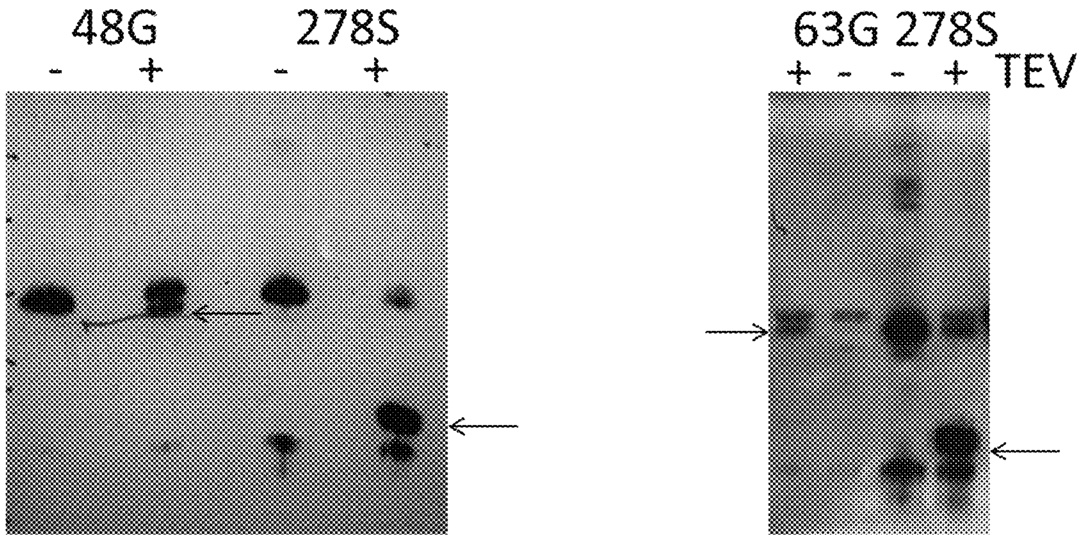

In total, approximately 50 insertion sites were screened individually, and assayed for their ability to be incorporated into VLPs by expressing only HA (WT or with insertion) and NA. This assay encompasses several of HA's functional attributes, including expression, cell surface accumulation, membrane microdomain localization, and particle formation, and was therefore performed with full length HA proteins. This approach identified several C-terminal (e.g. at positions 278, 282, 283, 286, and 291) and 2 N-terminal (positions 48 and 63) where TEV insertions maintain the function of WT HA in the VLP formation assay (FIG. 86 A). Several of these also maintain stalk bnAb binding, and cleave efficiently (FIG. 86 B). The single insertion HA mutants (insertion at positions 63, 278, and 286) bound to a broadly neutralizing $V_H$1-69 stalk-specific mAb by direct capture ELISA at 50 μg/ml (normalized for HA presence in supernatants). Two C-terminal insertions (positions 278 and 286) and 1 N-terminal insertion (position 63) were prioritized for further analysis and testing in combination. A second N-terminal insertion (position 48), binds well to certain anti-stalk $V_H$1-69 bnAbs (e.g. 18A3), but less well to others, and therefore could nonetheless provide a reasonable alternative to the insertion at position 63.

Some of the prioritized insertion sites have been tested in various combinations (e.g. 63-278 and 63-286) and have shown that both of the combinations of insertions also maintain efficient VLP formation (FIG. 87A) and bind well to stalk bnAbs (FIG. 87B).

Going forward both components (to-tyrosine mutations and proteolytic cleavage site insertions) can be introduced into a single HA molecule. DT crosslinking can then be applied to lock the stalk of HA in its trimeric, prefusion conformation, and following this the head can be removed proteolytically to generate a fully native, headless HA.

While the foregoing invention has been described in some detail for purposes of clarity and understanding, it will be clear to one skilled in the art from a reading of this disclosure that various changes in form and detail can be made without departing from the true scope of the invention. The invention may also be further defined in terms of the following claims.

The invention claimed is:

1. An influenza hemagglutinin (HA) polypeptide, protein or protein complex comprising an amino acid sequence having at least 65% sequence identity to amino acid residues 229 to 519 of SEQ ID NO: 1, wherein the amino acid sequence comprises a point mutation to tyrosine at one or more of amino acid positions 403, 406, 429, 432, 433, and 435, or an amino acid residue corresponding thereto.

2. An influenza hemagglutinin (HA) polypeptide, protein or protein complex according to claim 1, wherein the amino acid sequence comprises point mutations to tyrosine at two or more of amino acid positions 403, 406, 411, 422, 429, 432, 433, and 435, or amino acid residues corresponding thereto.

3. A headless influenza hemagglutinin (HA) polypeptide, protein or protein complex that comprises an amino acid sequence having at least 65% sequence identity to amino acid residues 229 to 519 of SEQ ID NO: 1, wherein the amino acid sequence comprises a point mutation to tyrosine at one or more of amino acid positions 403, 406, 411, 422, 429, 432, 433, and 435, or an amino acid residue corresponding thereto.

4. An influenza HA polypeptide, protein or protein complex according to claim 1 or claim 2, wherein the polypeptide, protein or protein complex is within, or comprises, an influenza HA trimeric stalk complex comprising at least one di-tyrosine cross-link, wherein one or both tyrosines of the at least one di-tyrosine cross-link originate from a point mutation to tyrosine.

5. A headless influenza HA polypeptide according to claim 3, wherein the polypeptide is comprised within an influenza HA trimeric stalk complex comprising at least one di-tyrosine cross-link, wherein one or both tyrosines of the at least one di-tyrosine cross-link originates from a point mutation to tyrosine.

6. An influenza HA polypeptide, protein or protein complex according to claim 4, wherein the cross-links are located between one or more paired tyrosine residues, wherein the paired tyrosine residues are selected from the group consisting of residues 403 and 433; 411 and 422, 403 and 429, 403 and 432, 433 and 435, and 406 and 433.

7. A headless influenza HA polypeptide, protein, or protein complex according to claim 5, wherein the cross-links are located between one or more paired tyrosine residues, wherein the paired tyrosine residues are selected from the group consisting of residues 403 and 433; 411 and 422, 403 and 429, 403 and 432, 433 and 435, and 406 and 433.

8. An influenza HA polypeptide, protein or protein complex according to claim 1, wherein the influenza HA polypeptide, protein or protein complex comprises the amino acid sequence of SEQ ID NO: 3, 4, 5, 6, 7, 8, 9, 10, 11, 12, 13, 14, 15, 16, 17, 86, 87, 88, 89, 90, 91, 92, 93, 96, 97, 98, 99, 100, 101, 102, 103, 104, 105, 106, 107, 108, 109, or 110, or an amino acid sequence having 65% or greater sequence identity to any of such sequences.

9. An influenza HA polypeptide, protein or protein complex according to claim 1, claim 2, or claim 3, wherein the polypeptide, protein or protein complex is capable of binding to an HA-stalk-specific antibody.

10. An influenza HA polypeptide, protein or protein complex according to claim 9, wherein the polypeptide, protein or protein complex is capable of binding to antibody C179.

11. An influenza HA polypeptide, protein or protein complex according to claim 1, claim 2, or claim 3, wherein the polypeptide, protein or protein complex is capable of folding into a trimeric stalk conformation.

12. An influenza HA polypeptide, protein or protein complex according to claim 1, claim 2, or claim 3, wherein the polypeptide, protein or protein complex further comprises a trimerization domain.

13. An influenza HA polypeptide, protein or protein complex according to claim 12, wherein the trimerization domain is a foldon domain.

14. A nucleic acid molecule encoding an influenza HA polypeptide, protein or protein complex according to claim 1, claim 2, or claim 3.

15. A composition comprising an influenza HA polypeptide, protein or protein complex according to claim 1, claim 2, or claim 3.

16. The composition of claim 15, wherein the composition is a vaccine composition.

17. The composition of claim 16, wherein the composition further comprises an adjuvant, a carrier, an immunostimulatory agent, or any combination thereof.

18. A composition comprising an influenza HA polypeptide according to claim 2 and a headless influenza HA polypeptide comprising an amino sequence having at least 65% sequence identity to SEQ ID NO: 94 or SEQ ID NO: 95.

19. A headless influenza hemagglutinin (HA) polypeptide according to claim 3, wherein the amino acid sequence comprises point mutations to tyrosine at two or more of amino acid positions 403, 406, 411, 422, 429, 432, 433, and 435, or amino acid residues corresponding thereto.

20. An influenza HA polypeptide, protein or protein complex according to claim 1, wherein the influenza HA polypeptide, protein or protein complex consists of the amino acid sequence of SEQ ID NO: 3, 4, 5, 6, 7, 8, 9, 10, 11, 12, 13, 14, 15, 16, 17, 86, 87, 88, 89, 90, 91, 92, 93, 96, 97, 98, 99, 100, 101, 102, 103, 104, 105, 106, 107, 108, 109, or 110, or an amino acid sequence having 65% or greater sequence identity to any of such sequences.

21. A headless influenza HA polypeptide, protein or protein complex according to claim 3, wherein the influenza HA polypeptide, protein or protein complex comprises the amino acid sequence of SEQ ID NO: 3, 4, 5, 6, 7, 8, 9, 10, 11, 12, 13, 14, 15, 16, 17, 86, 87, 88, 89, 90, 91, 92, 93, 96, 97, 98, 99, 100, 101, 102, 103, 104, 105, 106, 107, 108, 109, or 110, or an amino acid sequence having 65% or greater sequence identity to any of such sequences.

22. A headless influenza HA polypeptide, protein or protein complex according to claim 3, wherein the influenza HA polypeptide, protein or protein complex consists of the amino acid sequence of SEQ ID NO: 3, 4, 5, 6, 7, 8, 9, 10, 11, 12, 13, 14, 15, 16, 17, 86, 87, 88, 89, 90, 91, 92, 93, 96, 97, 98, 99, 100, 101, 102, 103, 104, 105, 106, 107, 108, 109, or 110, or comprising an amino acid sequence having 65% or greater sequence identity to any of such sequences.

* * * * *